US011524968B2

(12) United States Patent
Lee et al.

(10) Patent No.: US 11,524,968 B2
(45) Date of Patent: Dec. 13, 2022

(54) HETEROCYCLIC COMPOUND AS A PROTEIN KINASE INHIBITOR

(71) Applicant: HK inno.N Corporation, Seoul (KR)

(72) Inventors: Hyuk Woo Lee, Gyeonggi-do (KR); Mi Kyung Ji, Seoul (KR); Seung Chan Kim, Gyeonggi-do (KR); Ha Na Yu, Gyeonggi-do (KR); Soo Yeon Jung, Seoul (KR); Ji-Yeon Park, Jeollanam-do (KR); Ye-Lim Lee, Gyeongsangnam-do (KR); Ho-Youl Lee, Gyeonggi-do (KR); So Young Ki, Gyeonggi-do (KR); Dongkyu Kim, Gyeonggi-do (KR); Myeongjoong Kim, Gyeonggi-do (KR)

(73) Assignee: HK inno.N Corporation, Seoul (KR)

( * ) Notice: Subject to any disclaimer, the term of this patent is extended or adjusted under 35 U.S.C. 154(b) by 0 days.

(21) Appl. No.: 16/757,182

(22) PCT Filed: Oct. 17, 2018

(86) PCT No.: PCT/KR2018/012270
§ 371 (c)(1),
(2) Date: Apr. 17, 2020

(87) PCT Pub. No.: WO2019/078619
PCT Pub. Date: Apr. 25, 2019

(65) Prior Publication Data
US 2021/0171544 A1  Jun. 10, 2021

(30) Foreign Application Priority Data
Oct. 18, 2017  (KR) ......................... 10-2017-0135515

(51) Int. Cl.
*C07D 471/04* (2006.01)
*C07D 519/00* (2006.01)
*C07D 473/34* (2006.01)
*C07D 487/04* (2006.01)

(52) U.S. Cl.
CPC ......... *C07D 519/00* (2013.01); *C07D 471/04* (2013.01); *C07D 473/34* (2013.01); *C07D 487/04* (2013.01)

(58) Field of Classification Search
CPC .................................................. C07D 471/04
See application file for complete search history.

(56) References Cited

U.S. PATENT DOCUMENTS

| 7,098,333 B2 * | 8/2006 | Gillespie ................ A61P 25/04 544/280 |
| 2004/0127538 A1 | 7/2004 | Oinuma et al. |
| 2008/0146565 A1 | 6/2008 | Dunn et al. |
| 2014/0302010 A1 | 10/2014 | Klar et al. |
| 2016/0289207 A1 | 10/2016 | DeMong et al. |
| 2018/0244654 A1 | 8/2018 | Schiltz et al. |
| 2022/0009902 A1 | 1/2022 | Park |

FOREIGN PATENT DOCUMENTS

| CA | 2319275 | 8/1999 |
| CA | 2404594 | 10/2001 |
| CA | 2424303 | 4/2002 |
| CA | 2537731 | 3/2005 |
| CA | 2539548 | 3/2005 |
| CA | 2575808 | 2/2006 |
| CA | 2588627 | 7/2006 |
| CA | 2610828 | 12/2006 |
| CA | 2625442 | 4/2007 |
| CA | 2358998 | 11/2007 |
| CA | 2672172 | 7/2008 |
| CA | 2686903 | 11/2008 |
| CA | 2709883 | 6/2009 |
| CA | 2709806 | 7/2009 |
| CA | 2718727 | 10/2009 |
| CA | 2728559 | 1/2010 |
| CA | 2729552 | 1/2010 |
| CA | 2736522 | 3/2010 |
| CA | 2561950 | 4/2010 |
| CA | 2738348 | 4/2010 |
| CA | 2746221 | 7/2010 |
| CA | 2407593 | 1/2011 |
| CA | 2767079 | 1/2011 |
| CA | 2496842 | 2/2011 |
| CA | 2770155 | 2/2011 |

(Continued)

OTHER PUBLICATIONS

PubChem CID 11020179, National Center for Biotechnology Information. PubChem Compound Summary for CID 11020179, 6-Phenyl-7H-purin-2-amine. https://pubchem.ncbi.nlm.nih.gov/compound/6-Phenyl-7H-purin-2-amine. Accessed Jun. 21, 2021, create date Oct. 26, 2006. (Year: 2006).*
Pala et al., ACS Medicinal Chemistry Letters (2015), 6(8), 866-871 and the Supporting Information—pp. 1-11. (Year: 2015).*
Rituraj et al., International Journal of Pharmaceutical Sciences and Research (May 1, 2017), 8(5), 2122-2133. (Year: 2017).*
Golub et al., Science, vol. 286, Oct. 15, 1999, pp. 531-537. (Year: 1999).*
Belikov et al., "The Relationship Between the Structure of Molecules of Substances and their Effect on the Body", Pharmaceutical Chemistry, Chapter 2.2, 1993, pp. 43-47.

(Continued)

*Primary Examiner* — Laura L Stockton
(74) *Attorney, Agent, or Firm* — Fish & Richardson P.C.

(57) ABSTRACT

The present invention provides a novel compound having a protein kinase inhibition activity, a stereoisomer thereof or a pharmaceutically acceptable salt thereof.

The compound, the stereoisomer thereof or the pharmaceutically acceptable salt thereof according to the present invention show a protein kinase inhibition activity, thus being effective in preventing or treating diseases related to protein kinase, such as cancer, autoimmune disease, neurological disease, metabolic disease, infection or the like.

12 Claims, No Drawings

(56) References Cited

FOREIGN PATENT DOCUMENTS

| | | |
|---|---|---|
| CA | 2781056 | 5/2011 |
| CA | 2786950 | 6/2011 |
| CA | 2799156 | 11/2011 |
| CA | 2804347 | 1/2012 |
| CA | 2804845 | 1/2012 |
| CA | 2809911 | 3/2012 |
| CA | 2834548 | 11/2012 |
| CA | 2839767 | 12/2012 |
| CA | 2849340 | 3/2013 |
| CA | 2857193 | 6/2013 |
| CA | 2854093 | 7/2013 |
| CA | 2878412 | 1/2014 |
| CA | 2879448 | 1/2014 |
| CA | 2901929 | 10/2014 |
| CA | 2904048 | 10/2014 |
| CA | 2918910 | 1/2015 |
| CA | 2926340 | 4/2015 |
| CA | 2935329 | 7/2015 |
| CA | 2940666 | 9/2015 |
| CA | 2942957 | 10/2015 |
| CA | 2949163 | 11/2015 |
| CA | 2952083 | 1/2016 |
| CA | 2958966 | 3/2016 |
| CA | 2982493 | 11/2016 |
| CA | 2999937 | 4/2017 |
| CA | 3002558 | 5/2017 |
| CA | 3003930 | 5/2017 |
| CA | 3016196 | 9/2017 |
| CA | 3020778 | 10/2017 |
| CA | 2794153 | 1/2018 |
| CA | 3036987 | 3/2018 |
| CA | 3048217 | 6/2018 |
| CA | 3050770 | 6/2018 |
| CA | 3047212 | 8/2018 |
| CA | 2803156 | 1/2019 |
| CA | 3071024 | 2/2019 |
| CA | 3071900 | 2/2019 |
| CA | 3077238 | 4/2019 |
| CA | 3079292 | 4/2019 |
| CA | 3082156 | 4/2019 |
| CA | 3080806 | 5/2019 |
| CA | 3083374 | 5/2019 |
| CA | 3084058 | 6/2019 |
| CA | 3085427 | 6/2019 |
| CA | 3088025 | 8/2019 |
| CA | 3101223 | 11/2019 |
| CA | 3101368 | 11/2019 |
| CA | 3102598 | 12/2019 |
| CA | 3109192 | 2/2020 |
| CA | 3107426 | 3/2020 |
| CA | 3107624 | 3/2020 |
| CN | 102574857 | 7/2012 |
| CN | 105263930 | 1/2016 |
| CN | 106478651 | 3/2017 |
| CN | 108084153 | 5/2018 |
| JP | 2003523942 | 8/2003 |
| JP | 2005524621 | 8/2005 |
| JP | 2006199617 | 8/2006 |
| JP | 2009521504 | 6/2009 |
| JP | 2010511655 | 4/2010 |
| JP | 2012532152 | 12/2012 |
| JP | 2014509625 | 4/2014 |
| JP | 2016516791 | 6/2016 |
| JP | 2018529770 | 10/2018 |
| RU | 2485106 C2 | 6/2006 |
| RU | 2016104388 | 8/2017 |
| WO | WO200100213 | 1/2001 |
| WO | WO2001000213 | 1/2001 |
| WO | WO2002055084 | 7/2002 |
| WO | WO2002083648 | 10/2002 |
| WO | WO 2007/004944 | 1/2007 |
| WO | WO2008079907 | 7/2008 |
| WO | WO2008135785 | 11/2008 |
| WO | WO2009027732 | 3/2009 |
| WO | 2010-068806 A1 | 6/2010 |
| WO | WO 2010/068806 | 6/2010 |
| WO | WO 2011/003418 | 1/2011 |
| WO | WO2011005119 | 1/2011 |
| WO | WO2011163424 | 12/2011 |
| WO | WO2012020787 | 2/2012 |
| WO | WO2013020369 | 2/2013 |
| WO | WO2014137728 | 9/2014 |
| WO | 2014-170248 A1 | 10/2014 |
| WO | WO2015006754 | 1/2015 |
| WO | WO 2015/192119 | 12/2015 |
| WO | WO2015187684 | 12/2015 |
| WO | WO2016183094 | 11/2016 |
| WO | WO2017050938 | 3/2017 |
| WO | 2017-087905 A1 | 5/2017 |
| WO | 2017-098467 A1 | 6/2017 |
| WO | WO2017161004 | 9/2017 |
| WO | WO-2018/154578 A1 * | 8/2018 ........... C07D 409/12 |

OTHER PUBLICATIONS

Durnov et al., "Pediatric Oncology", Second Edition Medicina, 2003, p. 139.

Dyson et al., "Chemistry of Synthetic Drug Substances", MIR, 1964, pp. 12-19, with English Abstract.

JP Office Action in Japanese Appln. No. 2020-521905, dated Apr. 27, 2021, 15 pages with English Translation.

Kasatkina et al., "Protein Kinases: Variety and Classification", Transduction of Hormonal Signal, Research Work, 2014.

KR Office Action for App No. KR 10-2018-0140578, dated Mar. 25, 2020 (with English Translation) 11 pages.

RU Office Action in Russian Appln. No. 2020115890/04(026059), dated Apr. 29, 2021, 29 pages with English Translation.

Tyukavkina et al., BioOrganic Chemistry, published by "Drofa", Moscow, 2005, pp. 83-85.

International Search Report for PCT/KR2018/012270 dated Feb. 1, 2019. 4 pages.

Lucas, X et al., "4-Acyl Pyrroles: Mimicking Acetylated Lysines in Histone Code Reading". Angew. Chem. Int. Ed. 2013, vol. 52, pp. 14055-14059.

Lacroix, C. et al., "Identification of Novel Smoothened Ligands Using Structure-Based Docking", PLOS ONE, Aug. 4, 2016, vol. 11, No. 8, e0160365, Internal pp. 1-20.

KR Office Action for App No. KR 10-2019-0098472, dated May 4, 2020 (English translation) (5 pages).

KR Office Action for App No. KR 10-2019-0064740, dated Jul. 1, 2020 (English translation) (5 pages).

RU Office Action for App No. RU2020115890/04, dated Oct. 15, 2020 (English translation) (25 pages).

RU Search Report for App No. RU2020115890/04, dated Oct. 8, 2020 (English translation) (5 pages).

Stepkowski et al., Selective inhibitor of Janus tyrosine kinase 3, PNU156804, prolongs allograft survival and acts synergistically with cyclosporine but additively with rapamycin, Blood, 2002, 99(2): p. 680-689.

PCT International Search Report in International Appln. No. PCT/KR2019/015516, dated Mar. 9, 2020, 3 pages.

KR Office Action for App No. KR 10-2017-0135515, dated Nov. 1, 2018 (with English translation) (21 pages).

KR Office Action for App No. KR 10-2019-0064740, dated Jan. 2, 2020 (English translation) (15 pages).

CA Examination Report in Canadian Appln. No. 3082156, dated Jun. 11, 2021, 6 pages.

IN Examination Report in Indian Appln No. 202137026444, dated Aug. 13, 2021, 5 pages with English Translation.

Gurzov et al., "The JAK/STAT Pathway in Obesity and Diabetes", The FEBS Journal, 2016, 283:3002-3015.

JP Office Action in Japanese Appln. No. 2020-521905, dated Nov. 2, 2021, 8 pages with English Translation.

Kontzias et al. "Jakinibs: A New Class of Kinase Inhibitors in Cancer and Autoimmune Disease", Current Opinion in Pharmacology, 2012, 12:464-470.

Nicolas et al., "The Role of JAK-STAT Signaling Within the CNS" Landes Bioscience, 2013, 2(1):122925.

Tsirigotis et al., "Treatment of Experimental Candia Sepsis with a

(56) References Cited

OTHER PUBLICATIONS

Janus Kinase Inhibitor Controls Inflammation and Prolongs Survival", Antimicrobial Agents and Chemotherapy, Dec. 2015, 59(12):7367-7373.

AU Examination Report No. 1 in Australian Appln. No. 2018353759, dated Jun. 23, 2021, 8 pages.

AU Office Action in Australian Appln. No. 2018353759, dated Apr. 26, 2022, 10 pages.

Belikov et al., "The Relationship Between a Chemical Structure and Properties of Substances and their Action to Organism," Pharmaceutical Chemistry, Moscow Publishing House, MEDpress-inform, 2007, Section 2.6, pp. 27-29.

CN Office Action in Chinese Appln. No. 201880067864.1, dated Jan. 11, 2022, 19 pages (with English Translation).

EP Search Report in a European Appln. No. 19885184.2, dated Jun. 24, 2022, 7 pages.

ID Office Action in Indonesian Appln. No. P00202003535, dated Jun. 30, 2022, 4 pages (with English Translation).

ID Office Action in Indonesian Appln. No. P00202104463, dated Jul. 18, 2022, 6 pages (with English Translation).

IN Hearing Notice in Indian Appln. No. 202137026444, dated Mar. 25, 2022, 3 pages (with English Translation).

Jones et al., "Design and Synthesis of a pan-Janus Kinase Inhibitor Clinical Candidate (PF-06263276) Suitable for Inhaled and Topical Delivery for the Treatment of Inflammatory Diseases of the Lungs and Skin," Just-Accepted Manuscript, Journal of Medicinal Chemistry, 2016, 63 pages, DOI:10.1021/acs.jmedchem.6b01634.

JP Office Action in Japanese Appln. No. 2021-526602, dated Jun. 7, 2022, 5 pages (with English Translation).

Li et al., "Design and optimization of (3-aryl-1H-indazol-6-yl)spiro[cyclopropane-1,3'-indolin]-2'-ones as potent PLK4 inhibitors with oral antitumor efficacy," Bioorganic & Medicinal Chemistry Letters, 2016, 26(19):4625-4630, DOI:10.1016/j.bmcl.2016.08.063.

MX Office Action in Mexican Appln. No. MX/a/2020/003868, dated Jun. 21, 2022, 18 pages (with English Translation).

RU Office Action in Russian Appln. No. 2021117137/04(036124), dated Mar. 17, 2022, 22 pages (with English Translation).

Shahani et al., "A 2,6,9-hetero-trisubstituted purine inhibitor exhibits potent biological effects against multiple myeloma cells," Bioorganic & Medicinal Chemistry, 2013, 21:5618-5628.

\* cited by examiner

HETEROCYCLIC COMPOUND AS A PROTEIN KINASE INHIBITOR

TECHNICAL FIELD

The present invention relates to a novel compound, which inhibits a protein kinase activity so as to prevent or treat diseases related to such protein kinase activity, as well as to a use thereof.

BACKGROUND

A protein kinase is an enzyme, which controls various intracellular processes by phosphorating other proteins and adjusting their activity, positions and functions. The abnormal control functions of such protein kinase are closely associated with mechanisms of diseases such as cancer, autoimmune disease, neurological disease, metabolic disease, infection or the like.

Janus Kinase (hereinafter JAK) is a protein consisting of about 1,150 amino acids and having an approximate molecular weight of 120-130 KDa, wherein the JAK is classified into four types—JAK1, JAK2, JAK3 and TYK2. The JAK is located in an intracellular receptor of an inflammatory cytokine, wherein the inflammatory cytokine (IL-2, IL-4, IL-6, IL-7, IL-9, IL15, IL-21, GM-CSF, G-CSF, EPO, TPO, IFN-a, IFN-b, IFN-g, etc.) is bound to the receptor, and then phosphorylated, after that the JAK transfers an inflammatory cytokine signal to a cell through an action with STAT molecules. Excessive activation of the signal transfer through such various inflammatory cytokines causes the result that an immune system of our body attacks the human body, which results in the autoimmune disease. Thus, it is expected that the development of a drug for inhibiting a receptor kinase of such inflammatory cytokines in the autoimmune disease will show a therapeutic effect more improved than existing therapeutic agents.

SUMMARY OF THE INVENTION

Technical Problem

The objective of the present invention is to provide a novel compound showing a protein kinase inhibition activity, a stereoisomer thereof or a pharmaceutically acceptable salt thereof.

Further, the objective of the present invention is to provide a method for preparing a compound according to the present invention, a stereoisomer thereof or a pharmaceutically acceptable salt thereof.

The objective of the present invention is to provide a pharmaceutical composition for treating or preventing diseases related to protein kinase, wherein it contains the compound according to the present invention, the stereoisomer thereof or the pharmaceutically acceptable salt thereof as an effective component.

Furthermore, the objective of the present invention is to provide a method for treating or preventing the diseases related to protein kinase, wherein the method comprises administering a therapeutically effective dose of the compound according to the present invention, the stereoisomer thereof or the pharmaceutically acceptable salt thereof.

Moreover, the objective of the present invention is to provide a use of the compound according to the present invention, the stereoisomer thereof or the pharmaceutically acceptable salt thereof, for preparing a drug for preventing or treating the diseases related to protein kinase.

Technical Solution

Protein Kinase Inhibitor Compound

In order to solve the aforementioned problems, the present invention provides a compound having a following formula 1, a stereoisomer thereof or a pharmaceutically acceptable salt thereof:

[Formula 1]

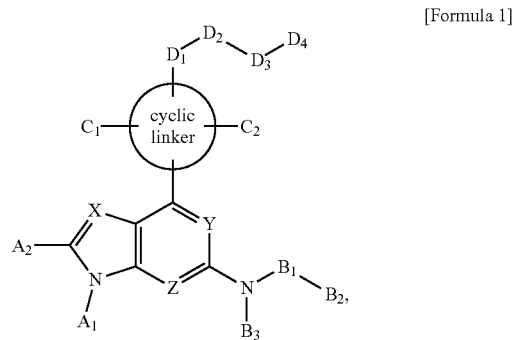

wherein

X is C-$A_3$ or N;

Y is C-$A_4$ or N;

Z is N or N—O;

$A_1$ to $A_4$ are each independently H or C1-C6 alkyl, C1-C6 alkoxy, C1-C6 hydroxyalkyl, C1-C6 haloalkyl, C1-C6 cyanoalkyl, C(=O)—OH, C(=O)—O—C1-C6 alkyl, S(=O)$_2$—C1-C6 alkyl, aryl or heteroaryl;

$B_1$ is —(CH$_2$)$_m$—, —C(=O)—, —C(=S)—, —C(=NR$_1$)—, —C(=O)—NR$_1$—, —S(=O)$_2$— or null, wherein at least one H of —(CH$_2$)$_m$— may be substituted with C1-C6 alkyl, halogen or cyano, or may be linked to each other along with at least one carbon atom to form a ring;

$B_2$ is H, C1-C6 alkyl, C3-C7 cycloalkyl, 5-6 membered heterocycloalkyl, aryl, heteroaryl, C1-C6 alkyl-aryl or C1-C6 alkyl-heteroaryl, wherein at least one H of C3-C7 cycloalkyl, 5-6 membered heterocycloalkyl, aryl, heteroaryl, C1-C6 alkyl-aryl or C1-C6 alkyl-heteroaryl may be substituted with C1-C6 alkyl, hydroxy or halogen;

$B_3$ is H or C1-C6 alkyl;

Cyclic linker is C3-C7 cycloalkyl, C3-C7 cycloalkenyl, 5-6 membered heterocycloalkyl, 5-6 membered heterocycloalkenyl, aryl or heteroaryl;

$C_1$ and $C_2$ are each independently H, C1-C6 alkyl, C1-C6 alkoxy, C1-C6 hydroxyalkyl, C1-C6 cyanoalkyl, C1-C6 haloalkyl, hydroxy, cyano, halogen, C(=O)—OH, C(=O)—O—C1-C6 alkyl, S(=O)$_2$—C1-C6 alkyl, aryl or heteroaryl, or $C_1$ and $C_2$ may be linked to each other through at least one carbon atom to make a bicyclic ring or spiro ring;

$D_1$ is —(CH$_2$)$_m$—, —(CH$_2$)$_m$—NR$_1$—, —NR$_1$—, —O—,

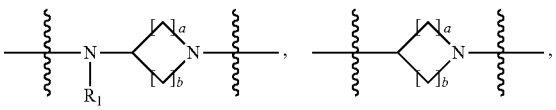

-continued

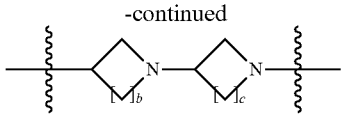

or null, wherein at least one H of —(CH$_2$)$_m$— or —(CH$_2$)$_m$—NR$_1$— may be substituted with C1-C6 alkyl, halogen or cyano, or may be linked to each other along with at least one carbon atom to form a ring; and at least one H of

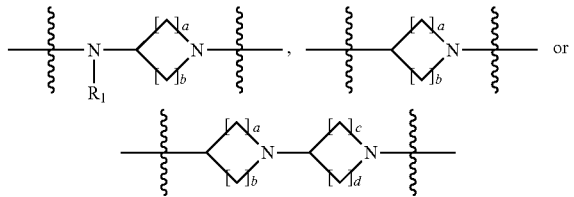

may be substituted with C1-C6 alkyl, C1-C6 hydroxyalkyl, C1-C6 haloalkyl or C1-C6 cyanoalkyl;

D$_2$ is —C(=O)—, —C(=O)—CH$_2$—C(=O)—, —C(=S)—, —S(=O)$_2$— or null, wherein at least one H of —C(=O)—CH$_2$—C(=O)— may be substituted with C1-C6 alkyl or halogen;

D$_3$ is —(CH$_2$)$_m$—, —(CH$_2$)$_m$—NR$_1$—, —NR$_1$—, —O—,

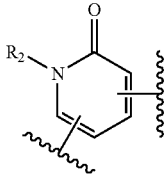

or null, wherein at least one H of —(CH$_2$)$_m$— or —(CH$_2$)$_m$—NR$_1$— may be substituted with C1-C6 alkyl, halogen or cyano, or may be linked to each other along with at least one carbon atom to form a ring;

D$_4$ is H, C1-C6 alkyl, C1-C6 alkenyl, C1-C6 alkoxyalkyl, C1-C6 hydroxyalkyl, C1-C6 haloalkyl, C1-C6 cyanoalkyl, S(=O)$_2$—C1-C6 alkyl, C3-C7 cycloalkyl,

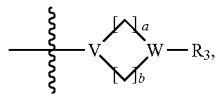

aryl or heteroaryl,
wherein at least one H of C1-C6 alkyl, C1-C6 alkenyl, C1-C6 alkoxyalkyl, C1-C6 hydroxyalkyl, C1-C6 haloalkyl or C1-C6 cyanoalkyl may be substituted with C3-C7 cycloalkyl;
at least one H of C3-C7 cycloalkyl or

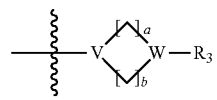

may be substituted with C1-C6 alkyl, C1-C6 haloalkyl, C1-C6 cyanoalkyl, cyano, halogen, —C(=O)—R$_4$ or —C(=O)—O—R$_4$; and
at least one H of aryl or heteroaryl may be substituted with C1-C6 alkyl, C1-C6 alkoxy, C1-C6 haloalkyl, C1-C6 hydroxyalkyl, C1-C6 cyanoalkyl, C1-C6 thioalkyl, hydroxy, cyano, nitro, halogen, —C(=O)—R$_4$, —C(=O)—NR$_1$—R$_4$, —S(=O)$_2$—R$_4$, —S(=O)$_2$—NR$_1$—R$_4$, —NR$_1$—R$_5$,

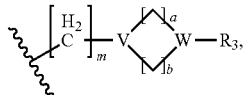

aryl or heteroaryl, wherein, at this time, at least one H of

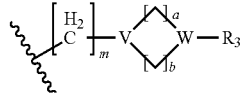

may be substituted with C1-C6 alkyl or (=O));
R$_1$ and R$_2$ are each independently H or C1-C6 alkyl;
R$_3$ is H, C1-C6 alkyl, —C(=O)—R$_4$, —C(=O)—O—R$_4$, —S(=O)$_2$—R$_4$ or —S(=O)$_2$—NR$_1$—R$_4$, wherein, in case W is —O—, —C(=O)— or —S(=O)$_2$—, R$_3$ is null;
R$_4$ is H, C1-C6 alkyl or C1-C6 haloalkyl;
R$_5$ is H, C1-C6 alkyl,

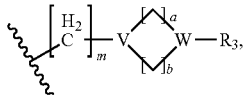

aryl or heteroaryl, wherein at least one H of

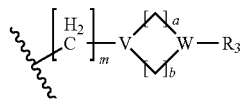

may be substituted with C1-C6 alkyl or (=O); and at least one H of aryl or heteroaryl may be substituted with C1-C6 alkyl or halogen;
V is —CH— or —N—;
W is —CH—, —N—, —O—, —S—, —C(=O)—, —S(=O)— or —S(=O)$_2$—, wherein, in case V is —CH—, W is not —CH—;
a to d are each independently 1, 2 or 3; and
m is 1, 2 or 3.

According to one specific embodiment of the present invention, it may be provided that
X is C-A$_3$ or N;
Y is C-A$_4$ or N;
Z is N or N—O;
A$_1$ to A$_4$ are each independently H or C1-C6 alkyl or C1-C6 cyanoalkyl;
B$_1$ is —(CH$_2$)$_m$—, —C(=O)—, —C(=S)—, —C(=NR$_1$)—, —C(=O)—NR$_1$—, —S(=O)$_2$— or null, wherein at least one H of —(CH$_2$)$_m$— may be substituted with C1-C6 alkyl, halogen or cyano, or may be linked to each other along with at least one carbon atom to form a ring;

B₂ is H, C1-C6 alkyl, C3-C7 cycloalkyl, aryl, heteroaryl or C1-C6 alkyl-aryl, wherein at least one H of C3-C7 cycloalkyl, aryl, heteroaryl or C1-C6 alkyl-aryl may be substituted with C1-C6 alkyl;

B₃ is H or C1-C6 alkyl;

Cyclic linker is C3-C7 cycloalkyl, C3-C7 cycloalkenyl, 5-6 membered heterocycloalkyl, 5-6 membered heterocycloalkenyl, aryl or heteroaryl;

C₁ and C₂ are each independently H, C1-C6 alkyl, C1-C6 haloalkyl, hydroxy, cyano, halogen, C(=O)—OH, C(=O)—O—C1-C6 alkyl or aryl, or C₁ and C₂ may be linked to each other through at least one carbon atom to make a bicyclic ring or spiro ring;

D₁ is —(CH₂)ₘ—, —(CH₂)ₘ—NR₁—, —NR₁—, —O—,

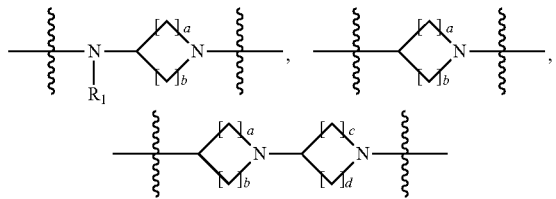

or null, wherein at least one H of —(CH₂)ₘ— or —(CH₂)ₘ—NR₁— may be substituted with C1-C6 alkyl or halogen, or may be linked to each other along with at least one carbon atom to form a ring; and at least one H of

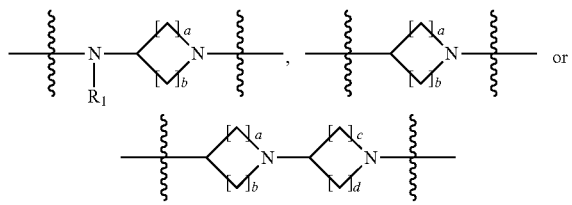

may be substituted with C1-C6 alkyl or C1-C6 cyanoalkyl;

D₂ is —C(=O)—, —C(=O)—CH₂—C(=O)—, —C(=S)—, —S(=O)₂— or null, wherein at least one H of —C(=O)—CH₂—C(=O)— may be substituted with C1-C6 alkyl;

D₃ is —(CH₂)ₘ—, —(CH₂)ₘ—NR₁—, —NR₁—, —O—,

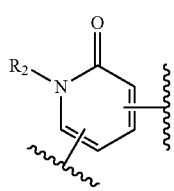

or null, wherein at least one H of —(CH₂)ₘ— or —(CH₂)ₘ—NR₁— may be substituted with cyano;

D₄ is H, C1-C6 alkyl, C1-C6 alkenyl, C1-C6 alkoxyalkyl, C1-C6 hydroxyalkyl, C1-C6 haloalkyl, C1-C6 cyanoalkyl, S(=O)₂—C1-C6 alkyl, C3-C7 cycloalkyl,

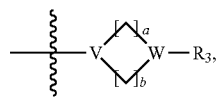

aryl or heteroaryl, wherein at least one H of C1-C6 alkyl, C1-C6 alkenyl, C1-C6 alkoxyalkyl, C1-C6 hydroxyalkyl, C1-C6 haloalkyl or C1-C6 cyanoalkyl may be substituted with C3-C7 cycloalkyl;

at least one H of C3-C7 cycloalkyl or

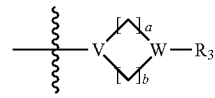

may be substituted with C1-C6 alkyl, C1-C6 haloalkyl, C1-C6 cyanoalkyl, cyano, halogen or —C(=O)—O—R₄; and at least one H of aryl or heteroaryl may be substituted with C1-C6 alkyl, C1-C6 alkoxy, C1-C6 haloalkyl, C1-C6 thioalkyl, hydroxy, cyano, nitro, halogen, —C(=O)—R₄, —C(=O)—NR₁—R₄, —S(=O)₂—R₄, —S(=O)₂—NR₁—R₄, —NR₁—R₅ or

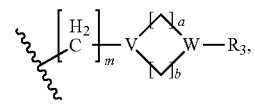

wherein, at this time, at least one H of

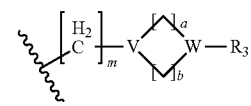

b may be substituted with (=O));

R₁ and R₂ are each independently H or C1-C6 alkyl;

R₃ is H, C1-C6 alkyl, —C(=O)—R₄, —C(=O)—O—R₄, —S(=O)₂—R₄ or —S(=O)₂—NR₁—R₄, wherein in case W is —O—, —C(=O)— or —S(=O)₂—, R₃ is null;

R₄ is H, C1-C6 alkyl or C1-C6 haloalkyl;

R₅ is H,

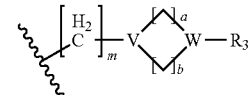

or aryl, wherein at least one H of

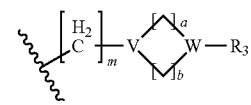

may be substituted with (=O); and at least one H of aryl or heteroaryl may be substituted with C1-C6 alkyl or halogen;

V is —CH— or —N—;

W is —CH—, —N—, —O—, —S—, —C(=O)—, —S(=O)— or —S(=O)$_2$—, wherein in case V is —CH—, W is not —CH—;

a to d are each independently 1, 2 or 3; and m is 1 or 2.

Compound, a stereoisomer thereof or a pharmaceutically acceptable salt thereof.

According to other specific embodiment of the present invention, it may be provided that X is C-A$_3$;

Y is C-A$_4$;

Z is N or N—O;

A$_1$ to A$_4$ are each independently H or C1-C6 alkyl or C1-C6 cyanoalkyl;

B$_1$ is —(CH$_2$)$_m$—, —C(=O)—, —C(=S)—, —C(=NR$_1$)—, —C(=O)—NR$_1$—, —S(=O)$_2$— or null;

B$_2$ is H, C1-C6 alkyl, C3-C7 cycloalkyl, aryl, heteroaryl or C1-C6 alkyl-aryl, wherein at least one H of C3-C7 cycloalkyl, aryl, heteroaryl or C1-C6 alkyl-aryl may be substituted with C1-C6 alkyl-;

B$_3$ is H;

Cyclic linker is C3-C7 cycloalkyl, C3-C7 cycloalkenyl, 5-6 membered heterocycloalkyl, 5-6 membered heterocycloalkenyl, aryl or heteroaryl;

C$_1$ and C$_2$ are each independently H, C1-C6 alkyl, C1-C6 haloalkyl, hydroxy, cyano, halogen, C(=O)—OH, C(=O)—O—C1-C6 alkyl or aryl, or C$_1$ and C$_2$ may be linked to each other through at least one carbon atom to make a bicyclic ring or spiro ring;

D$_1$ is —(CH$_2$)$_m$—, —(CH$_2$)$_m$—NR$_1$—, —NR$_1$—, —O—,

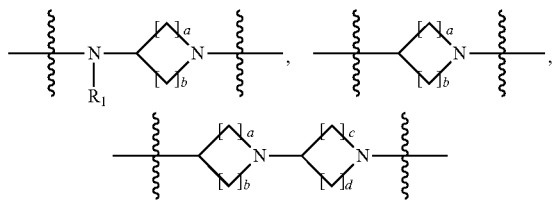

or null, wherein at least one H of —(CH$_2$)$_m$— or —(CH$_2$)$_m$—NR$_1$— may be substituted with C1-C6 alkyl or halogen, or may be linked to each other along with at least one carbon atom to form a ring; and at least one H of

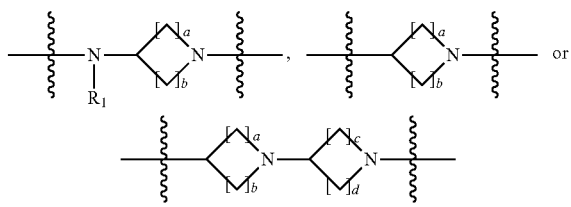

may be substituted with C1-C6 alkyl or C1-C6 cyanoalkyl;

D$_2$ is —C(=O)—, —C(=O)—CH$_2$—C(=O)—, —C(=S)—, —S(=O)$_2$— or null, wherein at least one H of —C(=O)—CH$_2$—C(=O)— may be substituted with C1-C6 alkyl;

D$_3$ is —(CH$_2$)$_m$—, —(CH$_2$)$_m$—NR$_1$—, —NR$_1$—, —O—,

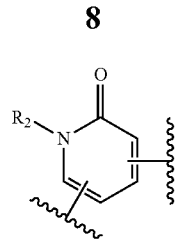

or null, wherein at least one H of —(CH$_2$)$_m$— or —(CH$_2$)$_m$—NR$_1$— may be substituted with cyano;

D$_4$ is H, C1-C6 alkyl, C1-C6 alkenyl, C1-C6 alkoxyalkyl, C1-C6 haloalkyl, C1-C6 cyanoalkyl, S(=O)$_2$—C1-C6 alkyl, C3-C7 cycloalkyl,

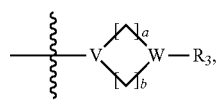

aryl or heteroaryl, wherein at least one H of C1-C6 alkyl, C1-C6 alkenyl, C1-C6 alkoxyalkyl, C1-C6 haloalkyl or C1-C6 cyanoalkyl may be substituted with C3-C7 cycloalkyl;

at least one H of C3-C7 cycloalkyl or

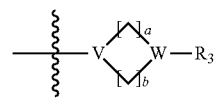

may be substituted with C1-C6 alkyl, C1-C6 haloalkyl, C1-C6 cyanoalkyl, cyano, halogen or —C(=O)—O—R$_4$; and at least one H of aryl or heteroaryl may be substituted with C1-C6 alkyl, C1-C6 alkoxy, C1-C6 haloalkyl, C1-C6 thioalkyl, hydroxy, cyano, nitro, halogen, —C(=O)—R$_4$, —C(=O)—NR$_1$—R$_4$, —S(=O)$_2$—R$_4$, —S(=O)$_2$—NR$_1$—R$_4$, —NR$_1$—R$_5$ or

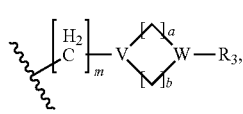

wherein, at this time, at least one H of

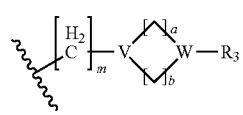

may be substituted with (=O));

R$_1$ and R$_2$ are each independently H or C1-C6 alkyl;

R$_3$ is H, C1-C6 alkyl, —C(=O)—R$_4$, —C(=O)—O—R$_4$, —S(=O)$_2$—R$_4$ or —S(=O)$_2$—NR$_1$—R$_4$, wherein in case W is —O—, —C(=O)— or —S(=O)$_2$—, R$_3$ is null;

R$_4$ is H, C1-C6 alkyl or C1-C6 haloalkyl;

R$_5$ is H,

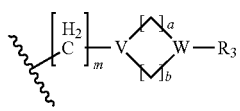

or aryl, wherein at least one H of

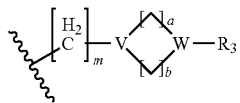

may be substituted with (=O), and at least one H of aryl or heteroaryl may be substituted with C1-C6 alkyl or halogen;
V is —CH— or —N—;
W is —CH—, —N—, —O—, —S—, —C(=O)—, —S(=O)— or —S(=O)$_2$—, wherein in case V is —CH—, W is not —CH—;
a to d are each independently 1, 2 or 3; and
m is 1 or 2.

According to another specific embodiment of the present invention, it may be provided that
X is C-A$_3$;
Y is N;
Z is N;
A$_1$ to A$_3$ are each independently H or C1-C6 alkyl;
B$_1$ is —C(=O)—;
B$_2$ is C3-C7 cycloalkyl or aryl—here, at least one H of C3-C7 cycloalkyl or aryl may be substituted with C1-C6 alkyl-;
B$_3$ is H or C1-C6 alkyl;
Cyclic linker is 5-6 membered heterocycloalkyl, 5-6 membered heterocycloalkenyl, aryl or heteroaryl;
C$_1$ and C$_2$ are each independently H, C1-C6 alkyl or halogen,
or C$_1$ and C$_2$ may be linked to each other through at least one carbon atom to make a bicyclic ring;
D$_1$ is —(CH$_2$)$_m$—, —NR$_1$— or null;
D$_2$ is —C(=O)—, —C(=S)—, —S(=O)$_2$— or null;
D$_3$ is —(CH$_2$)$_m$—, —NR$_1$—, —O— or null;
D$_4$ is C1-C6 alkyl, C1-C6 alkenyl, C1-C6 hydroxyalkyl, C1-C6 haloalkyl, C1-C6 cyanoalkyl, C3-C7 cycloalkyl,

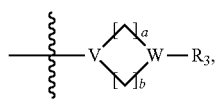

aryl or heteroaryl,
wherein at least one H of C3-C7 cycloalkyl or

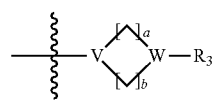

may be substituted with C1-C6 alkyl or cyano; and
at least one H of aryl or heteroaryl may be substituted with C1-C6 alkyl, cyano, halogen or —C(=O)—NR$_1$—R$_4$;
R$_1$ is H or C1-C6 alkyl;
R$_4$ is H;
V is —CH— or —N—;

W is —O— or —S(=O)$_2$—;
a and b are each independently 1, 2 or 3; and
m is 1 or 2.

According to another specific embodiment of the present invention, it may be provided that
X is N;
Y is C-A$_4$;
Z is N;
A$_1$, A$_2$ and A$_4$ are each independently H or C1-C6 alkyl;
B$_1$ is —C(=O)—;
B$_2$ is C3-C7 cycloalkyl, wherein at least one H of C3-C7 cycloalkyl may be substituted with C1-C6 alkyl;
B$_3$ is H;
Cyclic linker is aryl;
C$_1$ and C$_2$ are each independently H, C1-C6 alkyl or halogen;
D$_1$ is —(CH$_2$)$_m$ or —NR$_1$—;
D$_2$ is —S(=O)$_2$— or null;
D$_3$ is null;
D$_4$ is C1-C6 alkyl, C1-C6 haloalkyl or heteroaryl,
wherein at least one H of C1-C6 alkyl or C1-C6 haloalkyl may be substituted with C3-C7 cycloalkyl; and
at least one H of heteroaryl may be substituted with C1-C6 alkyl;
R$_1$ is H; and
m is 1 or 2.

According to another specific embodiment of the present invention, it may be provided that
X is N;
Y is N;
Z is N;
A$_1$ and A$_2$ are each independently H or C1-C6 alkyl;
B$_1$ is —C(=O)—;
B$_2$ is C3-C7 cycloalkyl, wherein at least one H of C3-C7 cycloalkyl may be substituted with C1-C6 alkyl;
B$_3$ is H;
Cyclic linker is aryl;
C$_1$ and C$_2$ are each independently H, C1-C6 alkyl or halogen;
D$_1$ is —(CH$_2$)$_m$, —NR$_1$—, —NR$_1$— or —O—;
D$_2$ is —S(=O)$_2$— or null;
D$_3$ is null;
D$_4$ is C1-C6 alkyl, C1-C6 haloalkyl,

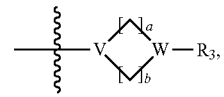

aryl or heteroaryl,
wherein at least one H of C1-C6 alkyl or C1-C6 haloalkyl may be substituted with C3-C7 cycloalkyl; and
at least one H of aryl or heteroaryl may be substituted with cyano or halogen};
R$_1$ is H;
V is —N—;
W is —O— or —S(=O)$_2$—;
a and b are each independently 1, 2 or 3; and
m is 1 or 2.

The concepts used for defining a compound of a formula 1 throughout the present specification are as follows. Following definitions are also applied to the terms used either individually or as a part of a larger group thereof, throughout the present specification, unless otherwise particularly indicated:

A term "alkyl" means a linear, branched or cyclic hydrocarbon radical respectively, when used alone or in a combined way, e.g., "heteroalkyl," wherein each carbon atom may be arbitrarily substituted with at least one cyano, hydroxy, alkoxy, oxo, halogen, carbonyl, sulfonyl, cyanyl, etc.

A term "alkoxy" refers to —O-alkyl, wherein alkyl is as defined above.

A term "heteroalkyl" means alkyl including at least one heteroatom selected from N, O and S.

A term "aryl" means an aromatic group including phenyl, naphthyl, etc., and may be arbitrarily substituted with at least one alkyl, alkoxy, halogen, hydroxy, carbonyl, sulfonyl, cyanyl, etc.

A term "heterocycle" includes 1 to 4 heteroatoms selected from N, O and S, and refers to a saturated or partially saturated or aromatic form, which may be arbitrarily fused with benzo or cycloalkyl.

A term "halo(gen)" means a substitution product selected from fluoro, chloro, bromo and iodo.

Other terms and abbreviations used in the present specification have their original meanings, unless otherwise defined.

In the present invention, representative examples of the compound represented by the formula 1 above are as follows.

1) N-(4-(4-(ethylsulfonamido)-3-fluorophenyl)-1H-pyrrolo[2,3-b]pyridin-6-yl)cyclopropanecarboxamide
2) N-(4-(4-((3,4-difluorophenyl)sulfonamido)phenyl)-1H-pyrrolo[2,3-b]pyridin-6-yl)cyclopropanecarboxamide
3) N-(4-(4-((3-fluoropropyl)sulfonamido)phenyl)-1H-pyrrolo[2,3-b]pyridin-6-yl)cyclopropanecarboxamide
4) N-(4-(4-(ethylsulfonamido)phenyl)-1H-pyrrolo[2,3-b]pyridin-6-yl)cyclopropanecarboxamide
5) N-(4-(4-(propylsulfonamido)phenyl)-1H-pyrrolo[2,3-b]pyridin-6-yl)cyclopropanecarboxamide
6) N-(4-(4-(butylsulfonamido)phenyl)-1H-pyrrolo[2,3-b]pyridin-6-yl)cyclopropanecarboxamide
7) N-(4-(4-(cyclohexanesulfonamido)phenyl)-1H-pyrrolo[2,3-b]pyridin-6-yl)cyclopropanecarboxamide
8) N-(4-(4-((2-fluoroethyl)sulfonamido)phenyl)-1H-pyrrolo[2,3-b]pyridin-6-yl)cyclopropanecarboxamide
9) N-(4-(4-((1,1-dioxidotetrahydro-2H-thiopyran)-4-sulfonamido)phenyl)-1H-pyrrolo[2,3-b]pyridin-6-yl)cyclopropanecarboxamide
10) N-(4-(4-((1,1-dioxidotetrahydrothiophene)-3-sulfonamido)phenyl)-1H-pyrrolo[2,3-b]pyridin-6-yl)cyclopropanecarboxamide
11) N-(4-(4-((1,1-dioxidothietane)-3-sulfonamido)phenyl)-1H-pyrrolo[2,3-b]pyridin-6-yl)cyclopropanecarboxamide
12) N-(4-(4-((6-chloropyridine)-3-sulfonamido)phenyl)-1H-pyrrolo[2,3-b]pyridin-6-yl)cyclopropanecarboxamide
13) N-(4-(4-((4-fluorophenyl)sulfonamido)phenyl)-1H-pyrrolo[2,3-b]pyridin-6-yl)cyclopropanecarboxamide
14) N-(4-(4-((4-chlorophenyl)sulfonamido)phenyl)-1H-pyrrolo[2,3-b]pyridin-6-yl)cyclopropanecarboxamide
15) N-(4-(4-((1-methyl-1H-imidazole)-5-sulfonamido)phenyl)-1H-pyrrolo[2,3-b]pyridin-6-yl)cyclopropanecarboxamide
16) N-(4-(4-((1-methyl-1Hpyrazole)-4-sulfonamido)phenyl)-1H-pyrrolo[2,3-b]pyridin-6-yl)cyclopropanecarboxamide
17) 4-(N-(4-(6-(cyclopropanecarboxamido)-1H-pyrrolo[2,3-b]pyridin-4-yl)phenyl)sulfamoyl)benzamide
18) N-(4-(4-((1-acetylpiperidine)-4-sulfonamido)phenyl)-1H-pyrrolo[2,3-b]pyridin-6-yl)cyclopropanecarboxamide
19) N-(4-(4-((4-isopropoxyphenyl)sulfonamido)phenyl)-1H-pyrrolo[2,3-b] pyridin-6-yl)cyclopropanecarboxamide
20) N-(4-(4-((4-bromophenyl)sulfonamido)phenyl)-1H-pyrrolo[2,3-b]pyridin-6-yl)cyclopropanecarboxamide
21) N-(4-(4-((4-cyanophenyl)sulfonamido)phenyl)-1H-pyrrolo[2,3-b]pyridin-6-yl)cyclopropanecarboxamide
22) N-(4-(4-((2,3-dihydrobenzofuran)-5-sulfonamido)phenyl)-1H-pyrrolo[2,3-b] pyridin-6-yl)cyclopropanecarboxamide
23) N-(4-(4-((6-methoxypyridine)-3-sulfonamido)phenyl)-1H-pyrrolo[2,3-b]pyridin-6-yl)cyclopropanecarboxamide
24) N-(4-(4-(phenylsulfonamido)phenyl)-1H-pyrrolo[2,3-b]pyridin-6-yl)cyclopropanecarboxamide
25) N-(4-(4-((3-fluorophenyl)sulfonamido)phenyl)-1H-pyrrolo[2,3-b]pyridin-6-yl)cyclopropanecarboxamide
26) N-(4-(4-((3-chlorophenyl)sulfonamido)phenyl)-1H-pyrrolo[2,3-b]pyridin-6-yl)cyclopropanecarboxamide
27) N-(4-(4-((4-methylphenyl)sulfonamido)phenyl)-1H-pyrrolo[2,3-b]pyridin-6-yl)cyclopropanecarboxamide
28) N-(4-(4-((4-(methylthio)phenyl)sulfonamido)phenyl)-1H-pyrrolo[2,3-b]pyridin-6-yl)cyclopropanecarboxamide
29) N-(4-(4-(ethylsulfonamido)-2-methylphenyl)-1H-pyrrolo[2,3-b]pyridin-6-yl)cyclopropanecarboxamide
30) N-(4-(4-(ethylsulfonamido)-2-fluorophenyl)-1H-pyrrolo[2,3-b]pyridin-6-yl)cyclopropanecarboxamide
31) N-(4-(4-((4-bromo-3-fluorophenyl)sulfonamido)phenyl)-1H-pyrrolo[2,3-b]pyridin-6-yl)cyclopropanecarboxamide -continued 32) N-(4-(4-((4-bromo-2-fluorophenyl)sulfonamido)phenyl)-1H-pyrrolo[2,3-b]pyridin-6-yl)cyclopropanecarboxamide
33) N-(4-(4-((4-chloro-3-(trifluoromethyl)phenyl)sulfonamido)phenyl)-1H-pyrrolo[2,3-b]pyridin-6-yl)cyclopropanecarboxamide
34) N-(4-(4-(benzo[d][1,3]dioxole-5-sulfonamido)phenyl)-1H-pyrrolo[2,3-b]pyridin-6-yl)cyclopropanecarboxamide
35) N-(4-(4-(ethylsulfonamido)phenyl)-1H-pyrrolo[2,3-b] pyridin-6-yl)-2-methylcyclopropane-1-carboxamide
36) N-(4-(4-(((4-fluorophenyl)methyl)sulfonamido)phenyl)-1H-pyrrolo[2,3-b]pyridin-6-yl)cyclopropanecarboxamide
37) N-(4-(4-((4-(N,N-dimethylsulfamoyl)phenyl)sulfonamido)phenyl)-1H-pyrrolo[2,3-b]pyridin-6-yl)cyclopropanecarboxamide
38) N-(4-(4-((2,3-dihydrobenzo[b][1,4]dioxine)-6-sulfonamido)phenyl)-1H-pyrrolo[2,3-b]pyridin-6-yl)cyclopropanecarboxamide
39) N-(4-(4-((4-(1H-tetrazol-1-yl)phenyl)sulfonamido)phenyl)-1H-pyrrolo[2,3-b]pyridin-6-yl)cyclopropanecarboxamide
40) N-(4-(4-((6-cyanopyridine)-3-sulfonamido)phenyl)-1H-pyrrolo[2,3-b]pyridin-6-yl)cyclopropanecarboxamide
41) N-(4-(4-((1-methylethyl)sulfonamido)phenyl)-1H-pyrrolo[2,3-b]pyridin-6-yl)cyclopropanecarboxamide
42) N-(4-(4-((1-ethylpropyl)sulfonamido)phenyl)-1H-pyrrolo[2,3-b]pyridin-6-yl)cyclopropanecarboxamide
43) N-(4-(4-((2-methylpropyl)sulfonamido)phenyl)-1H-pyrrolo[2,3-b]pyridin-6-yl)cyclopropanecarboxamide
44) N-(4-(4-((2,2-dimethylpropyl)sulfonamido)phenyl)-1H-pyrrolo[2,3-b]pyridin-6-yl)cyclopropanecarboxamide
45) N-(4-(4-((3-methylbutyl)sulfonamido)phenyl)-1H-pyrrolo[2,3-b]pyridin-6-yl)cyclopropanecarboxamide
46) N-(4-(4-((cyclopropylmethyl)sulfonamido)phenyl)-1H-pyrrolo[2,3-b]pyridin-6-yl)cyclopropanecarboxamide
47) N-(4-(4-((cyclohexylmethyl)sulfonamido)phenyl)-1H-pyrrolo[2,3-b]pyridin-6-yl)cyclopropanecarboxamide
48) N-(4-(4-(allylsulfonamido)phenyl)-1H-pyrrolo[2,3-b]pyridin-6-yl)cyclopropanecarboxamide
49) N-(4-(4-((fluoromethyl)sulfonamido)phenyl)-1H-pyrrolo[2,3-b]pyridin-6-yl)cyclopropanecarboxamide
50) N-(4-(4-((difluoromethyl)sulfonamido)phenyl)-1H-pyrrolo[2,3-b]pyridin-6-yl)cyclopropanecarboxamide
51) N-(4-(4-((2,2-difluoroethyl)sulfonamido)phenyl)-1H-pyrrolo[2,3-b]pyridin-6-yl)cyclopropanecarboxamide
52) N-(4-(4-((3-cyanopropyl)sulfonamido)phenyl)-1H-pyrrolo[2,3-b]pyridin-6-yl)cyclopropanecarboxamide
53) N-(4-(4-((2-ethoxyethyl)sulfonamido)phenyl)-1H-pyrrolo[2,3-b]pyridin-6-yl)cyclopropanecarboxamide
54) N-(4-(4-(((tetrahydrofuran-3-yl)methyl)sulfonamido)phenyl)-1H-pyrrolo[2,3-b]pyridin-6-yl)cyclopropanecarboxamide
55) N-(4-(4-(((tetrahydro-2H-pyran-4-yl)methyl)sulfonamido)phenyl)-1H-pyrrolo[2,3-b]pyridin-6-yl)cyclopropanecarboxamide
56) N-(4-(4-((2-(methylsulfonyl)ethyl)sulfonamido)phenyl)-1H-pyrrolo[2,3-b]pyridin-6-yl)cyclopropanecarboxamide
57) N-(4-(4-(cyclopropanesulfonamido)phenyl)-1H-pyrrolo[2,3-b]pyridin-6-yl)cyclopropanecarboxamide
58) N-(4-(4-(cyclobutanesulfonamido)phenyl)-1H-pyrrolo[2,3-b]pyridin-6-yl)cyclopropanecarboxamide
59) N-(4-(3-cyano-4-(ethylsulfonamido)phenyl)-1H-pyrrolo[2,3-b]pyridin-6-yl)cyclopropanecarboxamide
60) N-(4-(4-(ethylsulfonamido)-3-fluorophenyl)-1-methyl-1H-pyrrolo[2,3-b]pyridin-6-yl)cyclopropanecarboxamide
61) N-(4-(4-(ethylsulfonamido)-3-fluorophenyl)-1-propyl-1H-pyrrolo[2,3-b]pyridin-6-yl)cyclopropanecarboxamide
62) N-(1-(cyanomethyl)-4-(4-(ethylsulfonamido)-3-fluorophenyl)-1H-pyrrolo[2,3-b]pyridin-6-yl)cyclopropanecarboxamide
63) N-(4-(3-chloro-4-(propylsulfonamido)phenyl)-1H-pyrrolo[2,3-b]pyridin-6-yl)cyclopropanecarboxamide
64) N-(4-(4-(ethylsulfonamido)-3-methylphenyl)-1H-pyrrolo[2,3-b]pyridin-6-yl)cyclopropanecarboxamide
65) N-(4-(3-methyl-4-(propylsulfonamido)phenyl)-1H-pyrrolo[2,3-b]pyridin-6-yl)cyclopropanecarboxamide
66) N-(4-(3-fluoro-4-(propylsulfonamido)phenyl)-1H-pyrrolo[2,3-b]pyridin-6-yl)cyclopropanecarboxamide
67) N-(4-(4-(butylsulfonamido)-3-fluorophenyl)-1H-pyrrolo[2,3-b]pyridin-6-yl)cyclopropanecarboxamide
68) N-(4-(4-(cyclohexanesulfonamido)-3-fluorophenyl)-1H-pyrrolo[2,3-b]pyridin-6-yl)cyclopropanecarboxamide
69) N-(4-(4-(cyclopropanesulfonamido)-3-fluorophenyl)-1H-pyrrolo[2,3-b]pyridin-6-yl)cyclopropanecarboxamide
70) N-(4-(4-((cyclohexylmethyl)sulfonamido)-3-fluorophenyl)-1H-pyrrolo[2,3-b]pyridin-6-yl)cyclopropanecarboxamide

| | |
|---|---|
| 71) | N-(4-(4-(allylsulfonamido)-3-fluorophenyl)-1H-pyrrolo[2,3-b]pyridin-6-yl)cyclopropanecarboxamide |
| 72) | N-(4-(3-fluoro-4-(((tetrahydrofuran-3-yl)methyl)sulfonamido)phenyl)-1H-pyrrolo[2,3-b]pyridin-6-yl)cyclopropanecarboxamide |
| 73) | N-(4-(3-fluoro-4-(((tetrahydro-2H-pyran-4-yl)methyl)sulfonamido)phenyl)-1H-pyrrolo[2,3-b]pyridin-6-yl)cyclopropanecarboxamide |
| 74) | N-(4-(4-(ethylsulfonamido)phenyl)-2-methyl-1H-pyrrolo[2,3-b]pyridin-6-yl)cyclopropanecarboxamide |
| 75) | N-(4-(3-fluoro-4-((2-methylpropyl)sulfonamido)phenyl)-1H-pyrrolo[2,3-b]pyridin-6-yl)cyclopropanecarboxamide |
| 76) | N-(4-(3-fluoro-4-((3-fluoropropyl)sulfonamido)phenyl)-1H-pyrrolo[2,3-b]pyridin-6-yl)cyclopropanecarboxamide |
| 77) | N-(4-(4-((3-cyanopropyl)sulfonamido)-3-fluorophenyl)-1H-pyrrolo[2,3-b]pyridin-6-yl)cyclopropanecarboxamide |
| 78) | N-(4-(4-(cyclobutanesulfonamido)-3-fluorophenyl)-1H-pyrrolo[2,3-b]pyridin-6-yl)cyclopropanecarboxamide |
| 79) | N-(4-(4-((2,2-dimethylpropyl)sulfonamido)-3-fluorophenyl)-1H-pyrrolo[2,3-b]pyridin-6-yl)cyclopropanecarboxamide |
| 80) | N-(4-(4-((cyclopropylmethyl)sulfonamido)-3-fluorophenyl)-1H-pyrrolo[2,3-b]pyridin-6-yl)cyclopropanecarboxamide |
| 81) | N-(4-(4-(ethylsulfonamido)-3,5-difluorophenyl)-1H-pyrrolo[2,3-b]pyridin-6-yl)cyclopropanecarboxamide |
| 82) | N-(4-(3,5-difluoro-4-(propylsulfonamido)phenyl)-1H-pyrrolo[2,3-b]pyridin-6-yl)cyclopropanecarboxamide |
| 83) | N-(4-(4-(ethylsulfonamido)-2,5-difluorophenyl)-1H-pyrrolo[2,3-b]pyridin-6-yl)cyclopropanecarboxamide |
| 84) | N-(4-(2,5-difluoro-4-(propylsulfonamido)phenyl)-1H-pyrrolo[2,3-b]pyridin-6-yl)cyclopropanecarboxamide |
| 85) | N-(4-(4-(((1-cyanocyclopropyl)methyl)sulfonamido)-3-fluorophenyl)-1H-pyrrolo[2,3-b]pyridin-6-yl)cyclopropanecarboxamide |
| 86) | N-(4-(4-(((1-(cyanomethyl)cyclopropyl)methyl)sulfonamido)-3-fluorophenyl)-1H-pyrrolo[2,3-b]pyridin-6-yl)cyclopropanecarboxamide |
| 87) | N-(4-(4-((3-cyano-3-methylbutyl)sulfonamido)-3-fluorophenyl)-1H-pyrrolo[2,3-b]pyridin-6-yl)cyclopropanecarboxamide |
| 88) | N-(4-(4-(((1-cyanocyclopropyl)methyl)sulfonamido)phenyl)-1H-pyrrolo[2,3-b]pyridin-6-yl)cyclopropanecarboxamide |
| 89) | N-(4-(4-(((1-(cyanomethyl)cyclopropyl)methyl)sulfonamido)phenyl)-1H-pyrrolo[2,3-b]pyridin-6-yl)cyclopropanecarboxamide |
| 90) | N-(4-(4-(cyclopropanesulfonamido)-2-methylphenyl)-1H-pyrrolo[2,3-b]pyridin-6-yl)cyclopropanecarboxamide |
| 91) | N-(4-(4-(cyclobutanesulfonamido)-2-methylphenyl)-1H-pyrrolo[2,3-b]pyridin-6-yl)cyclopropanecarboxamide |
| 92) | N-(4-(4-((cyclopropylmethyl)sulfonamido)-2-methylphenyl)-1H-pyrrolo[2,3-b]pyridin-6-yl)cyclopropanecarboxamide |
| 93) | N-(4-(4-(ethylsulfonamido)phenyl)-3-methyl-1H-pyrrolo[2,3-b]pyridin-6-yl)cyclopropanecarboxamide |
| 94) | N-(3-methyl-4-(4-(propylsulfonamido)phenyl)-1H-pyrrolo[2,3-b]pyridin-6-yl)cyclopropanecarboxamide |
| 95) | N-(4-(2-methyl-4-(propylsulfonamido)phenyl)-1H-pyrrolo[2,3-b]pyridin-6-yl)cyclopropanecarboxamide |
| 96) | N-(4-(4-((3-cyanopropyl)sulfonamido)-2-methylphenyl)-1H-pyrrolo[2,3-b]pyridin-6-yl)cyclopropanecarboxamide |
| 97) | 6-(cyclopropanecarboxamido)-4-(4-(ethylsulfonamido)-3-fluorophenyl)-1H-pyrrolo[2,3-b]pyridine 7-oxide |
| 98) | N-(4-(4-(ethylsulfonamido)-3-(trifluoromethyl)phenyl)-1H-pyrrolo[2,3-b]pyridin-6-yl)cyclopropanecarboxamide |
| 99) | N-(4-(2-ethyl-4-(ethylsulfonamido)phenyl)-1H-pyrrolo[2,3-b]pyridin-6-yl)cyclopropanecarboxamide |
| 100) | N-(4-(3-fluoro-2-methyl-4-(propylsulfonamido)phenyl)-1H-pyrrolo[2,3-b]pyridin-6-yl)cyclopropanecarboxamide |
| 101) | N-(4-(4-(ethylsulfonamido)-3-fluoro-2-methylphenyl)-1H-pyrrolo[2,3-b]pyridin-6-yl)cyclopropanecarboxamide |
| 102) | N-(4-(4-(((1-cyanocyclopropyl)methyl)sulfonamido)-2-methylphenyl)-1H-pyrrolo[2,3-b]pyridin-6-yl)cyclopropanecarboxamide |
| 103) | N-(4-(4-(((1-(cyanomethyl)cyclopropyl)methyl)sulfonamido)-2-methylphenyl)-1H-pyrrolo[2,3-b]pyridin-6-yl)cyclopropanecarboxamide |
| 104) | N-(4-(4-((3-cyanopropyl)sulfonamido)-2,5-difluorophenyl)-1H-pyrrolo[2,3-b]pyridin-6-yl)cyclopropanecarboxamide |
| 105) | N-(4-(4-(((1-cyanocyclopropyl)methyl)sulfonamido)-2,5-difluorophenyl)-1H-pyrrolo[2,3-b]pyridin-6-yl)cyclopropanecarboxamide |
| 106) | N-(4-(4-(((1-(cyanomethyl)cyclopropyl)methyl)sulfonamido)-2,5-difluorophenyl)-1H-pyrrolo[2,3-b]pyridin-6-yl)cyclopropanecarboxamide |
| 107) | N-(4-(4-(((1-cyanocyclopropyl)methyl)sulfonamido)-3,5-difluorophenyl)-1H-pyrrolo[2,3-b]pyridin-6-yl)cyclopropanecarboxamide |
| 108) | N-(4-(4-(((1-(cyanomethyl)cyclopropyl)methyl)sulfonamido)-3,5-difluorophenyl)-1H-pyrrolo[2,3-b]pyridin-6-yl)cyclopropanecarboxamide |
| 109) | N-(4-(4-(((1-cyanocyclopropyl)methyl)sulfonamido)-2-ethylphenyl)-1H-pyrrolo[2,3-b]pyridin-6-yl)cyclopropanecarboxamide |

| | |
|---|---|
| 110) | N-(4-(4-(((1-(cyanomethyl)cyclopropyl)methyl)sulfonamido)-2-ethylphenyl)-1H-pyrrolo[2,3-b]pyridin-6-yl)cyclopropanecarboxamide |
| 111) | N-(4-(4-((3-cyanopropyl)sulfonamido)-2-ethylphenyl)-1H-pyrrolo[2,3-b]pyridin-6-yl)cyclopropanecarboxamide |
| 112) | N-(4-(4-(cyclohexanesulfonamido)-2-ethylphenyl)-1H-pyrrolo[2,3-b]pyridin-6-yl)cyclopropanecarboxamide |
| 113) | N-(4-(4-(cyclopropanesulfonamido)-2-ethylphenyl)-1H-pyrrolo[2,3-b]pyridin-6-yl)cyclopropanecarboxamide |
| 114) | N-(4-(4-(cyclobutanesulfonamido)-2-ethylphenyl)-1H-pyrrolo[2,3-b]pyridin-6-yl)cyclopropanecarboxamide |
| 115) | N-(4-(2-ethyl-4-(propylsulfonamido)phenyl)-1H-pyrrolo[2,3-b]pyridin-6-yl)cyclopropanecarboxamide |
| 116) | N-(4-(4-(butylsulfonamido)-2-ethylphenyl)-1H-pyrrolo[2,3-b]pyridin-6-yl)cyclopropanecarboxamide |
| 117) | N-(4-(2-methyl-4-((4,4,4-trifluorobutyl)sulfonamido)phenyl)-1H-pyrrolo[2,3-b]pyridin-6-yl)cyclopropanecarboxamide |
| 118) | N-(4-(4-(cyclopropanesulfonamido)-2-(trifluoromethyl)phenyl)-1H-pyrrolo[2,3-b]pyridin-6-yl)cyclopropanecarboxamide |
| 119) | N-(4-(4-(propylsulfonamido)-2-(trifluoromethyl)phenyl)-1H-pyrrolo[2,3-b]pyridin-6-yl)cyclopropanecarboxamide |
| 120) | N-(4-(4-(cyclobutanesulfonamido)-2-(trifluoromethyl)phenyl)-1H-pyrrolo[2,3-b]pyridin-6-yl)cyclopropanecarboxamide |
| 121) | N-(4-(4-((3,4-difluorophenyl)sulfonamido)-2-(trifluoromethyl)phenyl)-1H-pyrrolo[2,3-b]pyridin-6-yl)cyclopropanecarboxamide |
| 122) | N-(4-(4-((3-fluorophenyl)sulfonamido)-2-(trifluoromethyl)phenyl)-1H-pyrrolo[2,3-b]pyridin-6-yl)cyclopropanecarboxamide |
| 123) | N-(4-(4-(((1-cyanocyclopropyl)methyl)sulfonamido)-3-ethylphenyl)-1H-pyrrolo[2,3-b]pyridin-6-yl)cyclopropanecarboxamide |
| 124) | N-(4-(3-ethyl-4-(ethylsulfonamido)phenyl)-1H-pyrrolo[2,3-b]pyridin-6-yl)cyclopropanecarboxamide |
| 125) | N-(4-(4-(cyclopropanesulfonamido)-3-ethylphenyl)-1H-pyrrolo[2,3-b]pyridin-6-yl)cyclopropanecarboxamide |
| 126) | N-(4-(3-ethyl-4-(propylsulfonamido)phenyl)-1H-pyrrolo[2,3-b]pyridin-6-yl)cyclopropanecarboxamide |
| 127) | N-(4-(4-(butylsulfonamido)-3-ethylphenyl)-1H-pyrrolo[2,3-b]pyridin-6-yl)cyclopropanecarboxamide |
| 128) | N-(4-(4-(cyclobutanesulfonamido)-3-ethylphenyl)-1H-pyrrolo[2,3-b]pyridin-6-yl)cyclopropanecarboxamide |
| 129) | N-(4-(6-(methylsulfonamido)-[1,1'-biphenyl]-3-yl)-1H-pyrrolo[2,3-b]pyridin-6-yl)cyclopropanecarboxamide |
| 130) | N-(4-(6-(cyclopropanesulfonamido)-[1,1'-biphenyl]-3-yl)-1H-pyrrolo[2,3-b]pyridin-6-yl)cyclopropanecarboxamide |
| 131) | N-(4-(4-(ethylsulfonamido)-2,3-dimethylphenyl)-1H-pyrrolo[2,3-b]pyridin-6-yl)cyclopropanecarboxamide |
| 132) | N-(4-(2,3-dimethyl-4-(propylsulfonamido)phenyl)-1H-pyrrolo[2,3-b]pyridin-6-yl)cyclopropanecarboxamide |
| 133) | N-(4-(4-(cyclopropanesulfonamido)-2,3-dimethylphenyl)-1H-pyrrolo[2,3-b]pyridin-6-yl)cyclopropanecarboxamide |
| 134) | 6-(cyclopropanecarboxamido)-4-(4-(ethylsulfonamido)-2-methylphenyl)-1H-pyrrolo[2,3-b]pyridine 7-oxide |
| 135) | 6-(cyclopropanecarboxamido)-4-(3-ethyl-4-(ethylsulfonamido)phenyl)-1H-pyrrolo[2,3-b]pyridine 7-oxide |
| 136) | 6-(cyclopropanecarboxamido)-4-(4-(cyclopropanesulfonamido)-2,3-dimethylphenyl)-1H-pyrrolo[2,3-b]pyridine 7-oxide |
| 137) | 4-(4-(((1-cyanocyclopropyl)methyl)sulfonamido)-2-ethylphenyl)-6-(cyclopropanecarboxamido)-1H-pyrrolo[2,3-b]pyridine 7-oxide |
| 138) | N-(4-(4-(((1-cyanocyclopropyl)methyl)sulfonamido)-3,5-diethylphenyl)-1H-pyrrolo[2,3-b]pyridin-6-yl)cyclopropanecarboxamide |
| 139) | N-(4-(4-((3,4-difluorophenyl)sulfonamido)-3,5-diethylphenyl)-1H-pyrrolo[2,3-b]pyridin-6-yl)cyclopropanecarboxamide |
| 140) | methyl 2-(6-(cyclopropanecarboxamido)-1H-pyrrolo[2,3-b]pyridin-4-yl)-5-(ethylsulfonamido)benzoate |
| 141) | methyl 2-(6-(cyclopropanecarboxamido)-1H-pyrrolo[2,3-b]pyridin-4-yl)-5-(propylsulfonamido)benzoate |
| 142) | methyl 5-(((1-cyanocyclopropyl)methyl)sulfonamido)-2-(6-(cyclopropanecarboxamido)-1H-pyrrolo[2,3-b]pyridin-4-yl)benzoate |
| 143) | 5-(((1-cyanocyclopropyl)methyl)sulfonamido)-2-(6-(cyclopropanecarboxamido)-1H-pyrrolo[2,3-b]pyridin-4-yl)benzoic acid |
| 144) | N-(4-(2-cyano-4-(ethylsulfonamido)phenyl)-1H-pyrrolo[2,3-b]pyridin-6-yl)cyclopropanecarboxamide |
| 145) | N-(4-(2-cyano-4-(propylsulfonamido)phenyl)-1H-pyrrolo[2,3-b]pyridin-6-yl)cyclopropanecarboxamide |
| 146) | N-(4-(2-cyano-4-((3,4-difluorophenyl)sulfonamido)phenyl)-1H-pyrrolo[2,3-b]pyridin-6-yl)cyclopropanecarboxamide |
| 147) | N-(4-(2-cyano-4-(((1-cyanocyclopropyl)methyl)sulfonamido)phenyl)-1H-pyrrolo[2,3-b]pyridin-6-yl)cyclopropanecarboxamide |
| 148) | N-(4-(6-(ethylsulfonamido)pyridin-3-yl)-1H-pyrrolo[2,3-b]pyridin-6-yl)cyclopropanecarboxamide |

| | |
|---|---|
| 149) | N-(4-(5-(ethylsulfonamido)-6-fluoropyridin-2-yl)-1H-pyrrolo[2,3-b]pyridin-6-yl)cyclopropanecarboxamide |
| 150) | N-(4-(6-fluoro-5-(propylsulfonamido)pyridin-2-yl)-1H-pyrrolo[2,3-b]pyridin-6-yl)cyclopropanecarboxamide |
| 151) | N-(4-(4-(ethylsulfonamido)cyclohex-1-en-1-yl)-1H-pyrrolo[2,3-b]pyridin-6-yl)cyclopropanecarboxamide |
| 152) | N-(4-(4-(propylsulfonamido)cyclohex-1-en-1-yl)-1H-pyrrolo[2,3-b]pyridin-6-yl)cyclopropanecarboxamide |
| 153) | N-(4-(4-((trifluoromethyl)sulfonamido)cyclohex-1-en-1-yl)-1H-pyrrolo[2,3-b]pyridin-6-yl)cyclopropanecarboxamide |
| 154) | N-(4-(4-(cyclopropanesulfonamido)cyclohex-1-en-1-yl)-1H-pyrrolo[2,3-b]pyridin-6-yl)cyclopropanecarboxamide |
| 155) | N-(4-(4-((2-cyanoethyl)sulfonamido)cyclohex-1-en-1-yl)-1H-pyrrolo[2,3-b]pyridin-6-yl)cyclopropanecarboxamide |
| 156) | N-(4-(4-(((1-(cyanomethyl)cyclopropyl)methyl)sulfonamido)cyclohex-1-en-1-yl)-1H-pyrrolo[2,3-b]pyridin-6-yl)cyclopropanecarboxamide |
| 157) | N-(4-(4-(((1-cyanocyclopropyl)methyl)sulfonamido)cyclohex-1-en-1-yl)-1H-pyrrolo[2,3-b]pyridin-6-yl)cyclopropanecarboxamide |
| 158) | N-(4-(4-((3-cyanopropyl)sulfonamido)cyclohex-1-en-1-yl)-1H-pyrrolo[2,3-b]pyridin-6-yl)cyclopropanecarboxamide |
| 159) | N-(4-(4-((3-fluoropropyl)sulfonamido)cyclohex-1-en-1-yl)-1H-pyrrolo[2,3-b]pyridin-6-yl)cyclopropanecarboxamide |
| 160) | N-(4-(4-(allylsulfonamido)cyclohex-1-en-1-yl)-1H-pyrrolo[2,3-b]pyridin-6-yl)cyclopropanecarboxamide |
| 161) | N-(4-(4-((cyclopropylmethyl)sulfonamido)cyclohex-1-en-1-yl)-1H-pyrrolo[2,3-b]pyridin-6-yl)cyclopropanecarboxamide |
| 162) | N-(4-(4-((3,4-difluorophenyl)sulfonamido)cyclohex-1-en-1-yl)-1H-pyrrolo[2,3-b]pyridin-6-yl)cyclopropanecarboxamide |
| 163) | N-(4-(4-((3-fluorophenyl)sulfonamido)cyclohex-1-en-1-yl)-1H-pyrrolo[2,3-b]pyridin-6-yl)cyclopropanecarboxamide |
| 164) | N-(4-(4-((4-cyanophenyl)sulfonamido)cyclohex-1-en-1-yl)-1H-pyrrolo[2,3-b]pyridin-6-yl)cyclopropanecarboxamide |
| 165) | N-(4-(4-(cyclobutanesulfonamido)cyclohex-1-en-1-yl)-1H-pyrrolo[2,3-b]pyridin-6-yl)cyclopropanecarboxamide |
| 166) | N-(4-(1-(ethylsulfonyl)-1,2,3,6-tetrahydropyridin-4-yl)-1H-pyrrolo[2,3-b]pyridin-6-yl)cyclopropanecarboxamide |
| 167) | N-(4-(1-((3-fluoropropyl)sulfonyl)-1,2,3,6-tetrahydropyridin-4-yl)-1H-pyrrolo[2,3-b]pyridin-6-yl)cyclopropanecarboxamide |
| 168) | N-(4-(1-(cyclopropylsulfonyl)-1,2,3,6-tetrahydropyridin-4-yl)-1H-pyrrolo[2,3-b]pyridin-6-yl)cyclopropanecarboxamide |
| 169) | N-(4-(1-(((tetrahydro-2H-pyran-4-yl)methyl)sulfonyl)-1,2,3,6-tetrahydropyridin-4-yl)-1H-pyrrolo[2,3-b]pyridin-6-yl)cyclopropanecarboxamide |
| 170) | N-(4-(1-((3-cyanopropyl)sulfonyl)-1,2,3,6-tetrahydropyridin-4-yl)-1H-pyrrolo[2,3-b]pyridin-6-yl)cyclopropanecarboxamide |
| 171) | N-(4-(1-(((1-(cyanomethyl)cyclopropyl)methyl)sulfonyl)-1,2,3,6-tetrahydropyridin-4-yl)-1H-pyrrolo[2,3-b]pyridin-6-yl)cyclopropanecarboxamide |
| 172) | N-(4-(1-(((1-cyanocyclopropyl)methyl)sulfonyl)-1,2,3,6-tetrahydropyridin-4-yl)-1H-pyrrolo[2,3-b]pyridin-6-yl)cyclopropanecarboxamide |
| 173) | N-(4-(1-((3,4-difluorophenyl)sulfonyl)-1,2,3,6-tetrahydropyridin-4-yl)-1H-pyrrolo[2,3-b]pyridin-6-yl)cyclopropanecarboxamide |
| 174) | N-(4-(8-(ethylsulfonyl)-8-azabicyclo[3.2.1]oct-2-en-3-yl)-1H-pyrrolo[2,3-b]pyridin-6-yl)cyclopropanecarboxamide |
| 175) | N-(4-(8-((3-fluoropropyl)sulfonyl)-8-azabicyclo[3.2.1]oct-2-en-3-yl)-1H-pyrrolo[2,3-b]pyridin-6-yl)cyclopropanecarboxamide |
| 176) | N-(4-(8-(propylsulfonyl)-8-azabicyclo[3.2.1]oct-2-en-3-yl)-1H-pyrrolo[2,3-b]pyridin-6-yl)cyclopropanecarboxamide |
| 177) | N-(4-(8-(cyclopropylsulfonyl)-8-azabicyclo[3.2.1]oct-2-en-3-yl)-1H-pyrrolo[2,3-b]pyridin-6-yl)cyclopropanecarboxamide |
| 178) | N-(4-(8-((3,4-difluorophenyl)sulfonyl)-8-azabicyclo[3.2.1]oct-2-en-3-yl)-1H-pyrrolo[2,3-b]pyridin-6-yl)cyclopropanecarboxamide |
| 179) | N-(4-(1-(ethylsulfonyl)-3,3-dimethyl-1,2,3,6-tetrahydropyridin-4-yl)-1H-pyrrolo[2,3-b]pyridin-6-yl)cyclopropanecarboxamide |
| 180) | N-(4-(1-((3-cyanopropyl)sulfonyl)-3,3-dimethyl-1,2,3,6-tetrahydropyridin-4-yl)-1H-pyrrolo[2,3-b]pyridin-6-yl)cyclopropanecarboxamide |
| 181) | N-(4-(4-((3,4-difluorophenyl)sulfonamido)phenyl)-7H-pyrrolo[2,3-d]pyrimidin-2-yl)cyclopropanecarboxamide |
| 182) | N-(4-(4-(ethylsulfonamido)phenyl)-7H-pyrrolo[2,3-d]pyrimidin-2-yl)cyclopropanecarboxamide |
| 183) | N-(4-(4-(cyclohexanesulfonamido)phenyl)-7H-pyrrolo[2,3-d]pyrimidin-2-yl)cyclopropanecarboxamide |
| 184) | N-(4-(4-((4,4,4-trifluorobutyl)sulfonamido)phenyl)-7H-pyrrolo[2,3-d]pyrimidin-2-yl)cyclopropanecarboxamide |
| 185) | N-(4-(4-((3-fluoropropyl)sulfonamido)phenyl)-7H-pyrrolo[2,3-d]pyrimidin-2-yl)cyclopropanecarboxamide |
| 186) | N-(4-(4-((3-cyanopropyl)sulfonamido)phenyl)-7H-pyrrolo[2,3-d]pyrimidin-2-yl)cyclopropanecarboxamide |

| | |
|---|---|
| 187) | N-(4-(4-((4-chlorophenyl)sulfonamido)phenyl)-7H-pyrrolo[2,3-d]pyrimidin-2-yl)cyclopropanecarboxamide |
| 188) | N-(4-(4-((4-fluorophenyl)sulfonamido)phenyl)-7H-pyrrolo[2,3-d]pyrimidin-2-yl)cyclopropanecarboxamide |
| 189) | N-(4-(4-((4-bromophenyl)sulfonamido)phenyl)-7H-pyrrolo[2,3-d]pyrimidin-2-yl)cyclopropanecarboxamide |
| 190) | N-(4-(4-(propylsulfonamido)phenyl)-7H-pyrrolo[2,3-d]pyrimidin-2-yl)cyclopropanecarboxamide |
| 191) | N-(4-(4-(butylsulfonamido)phenyl)-7H-pyrrolo[2,3-d]pyrimidin-2-yl)cyclopropanecarboxamide |
| 192) | N-(4-(4-((3-fluorophenyl)sulfonamido)phenyl)-7H-pyrrolo[2,3-d]pyrimidin-2-yl)cyclopropanecarboxamide |
| 193) | N-(4-(4-(3,4-difluoro-N-methylphenylsulfonamido)phenyl)-7H-pyrrolo[2,3-d]pyrimidin-2-yl)cyclopropanecarboxamide |
| 194) | N-(4-(4-((3,3,3-trifluoropropyl)sulfonamido)phenyl)-7H-pyrrolo[2,3-d]pyrimidin-2-yl)cyclopropanecarboxamide |
| 195) | N-(4-(4-((1,1-dioxidotetrahydro-2H-thiopyran)-4-sulfonamido)phenyl)-7H-pyrrolo[2,3-d]pyrimidin-2-yl)cyclopropanecarboxamide |
| 196) | N-(4-(4-((1,1-dioxidotetrahydrothiophene)-3-sulfonamido)phenyl)-7H-pyrrolo[2,3-d]pyrimidin-2-yl)cyclopropanecarboxamide |
| 197) | N-(4-(4-((6-cyanopyridine)-3-sulfonamido)phenyl)-7H-pyrrolo[2,3-d]pyrimidin-2-yl)cyclopropanecarboxamide |
| 198) | N-(4-(4-((1-methyl-1H-imidazole)-5-sulfonamido)phenyl)-7H-pyrrolo[2,3-d]pyrimidin-2-yl)cyclopropanecarboxamide |
| 199) | N-(4-(4-((1-methyl-1H-pyrazole)-4-sulfonamido)phenyl)-7H-pyrrolo[2,3-d]pyrimidin-2-yl)cyclopropanecarboxamide |
| 200) | 4-(N-(4-(2-(cyclopropanecarboxamido)-7H-pyrrolo[2,3-d]pyrimidin-4-yl)phenyl)sulfamoyl)benzamide |
| 201) | N-(4-(3-fluoro-4-(methylsulfonamido)phenyl)-7H-pyrrolo[2,3-d]pyrimidin-2-yl)cyclopropanecarboxamide |
| 202) | N-(4-(4-(ethylsulfonamido)-3-fluorophenyl)-7H-pyrrolo[2,3-d]pyrimidin-2-yl)cyclopropanecarboxamide |
| 203) | N-(4-(3-fluoro-4-((3-fluoropropyl)sulfonamido)phenyl)-7H-pyrrolo[2,3-d]pyrimidin-2-yl)cyclopropanecarboxamide |
| 204) | N-(4-(4-((3-cyanopropyl)sulfonamido)-3-fluorophenyl)-7H-pyrrolo[2,3-d]pyrimidin-2-yl)cyclopropanecarboxamide |
| 205) | N-(4-(4-((3,4-difluorophenyl)sulfonamido)-3-fluorophenyl)-7H-pyrrolo[2,3-d]pyrimidin-2-yl)cyclopropanecarboxamide |
| 206) | N-(4-(3-fluoro-4-(propylsulfonamido)phenyl)-7H-pyrrolo[2,3-d]pyrimidin-2-yl)cyclopropanecarboxamide |
| 207) | N-(7-(4-(ethylsulfonamido)phenyl)-3H-imidazo[4,5-b]pyridin-5-yl)cyclopropanecarboxamide |
| 208) | N-(6-(4-((3,4-difluorophenyl)sulfonamido)phenyl)-9H-purin-2-yl)cyclopropanecarboxamide |
| 209) | N-(6-(4-(ethylsulfonamido)phenyl)-9H-purin-2-yl)cyclopropanecarboxamide |
| 210) | N-(6-(4-((3-cyanopropyl)sulfonamido)phenyl)-9H-purin-2-yl)cyclopropanecarboxamide |
| 211) | N-(6-(4-((4,4,4-trifluorobutyl)sulfonamido)phenyl)-9H-purin-2-yl)cyclopropanecarboxamide |
| 212) | N-(4-(1-(propylsulfonyl)-2,5-dihydro-1H-pyrrol-3-yl)-1H-pyrrolo[2,3-b]pyridin-6-yl)cyclopropanecarboxamide |
| 213) | N-(4-(1-(((1-cyanocyclopropyl)methyl)sulfonyl)-2,5-dihydro-1H-pyrrol-3-yl)-1H-pyrrolo[2,3-b]pyridin-6-yl)cyclopropanecarboxamide |
| 214) | N-(4-(4-(morpholine-4-sulfonamido)phenyl)-1H-pyrrolo[2,3-b]pyridin-6-yl)cyclopropanecarboxamide |
| 215) | N-(4-(4-((N-ethyl-N-methylsulfamoyl)amino)phenyl)-1H-pyrrolo[2,3-b]pyridin-6-yl)cyclopropanecarboxamide |
| 216) | N-(4-(4-((N,N-diethylsulfamoyl)amino)phenyl)-1H-pyrrolo[2,3-b]pyridin-6-yl)cyclopropanecarboxamide |
| 217) | N-(4-(4-((N-cyclopropyl-N-methylsulfamoyl)amino)phenyl)-1H-pyrrolo[2,3-b]pyridin-6-yl)cyclopropanecarboxamide |
| 218) | N-(4-(4-(pyrrolidine-1-sulfonamido)phenyl)-1H-pyrrolo[2,3-b]pyridin-6-yl)cyclopropanecarboxamide |
| 219) | N-(4-(4-(piperidine-1-sulfonamido)phenyl)-1H-pyrrolo[2,3-b]pyridin-6-yl)cyclopropanecarboxamide |
| 220) | N-(4-(4-((2,6-dimethylmorpholine)-4-sulfonamido)phenyl)-1H-pyrrolo[2,3-b]pyridin-6-yl)cyclopropanecarboxamide |
| 221) | N-(4-(4-((3-cyanoazetidine)-1-sulfonamido)phenyl)-1H-pyrrolo[2,3-b]pyridin-6-yl)cyclopropanecarboxamide |
| 222) | N-(4-(4-((N-isopropyl-N-methylsulfamoyl)amino)phenyl)-1H-pyrrolo[2,3-b]pyridin-6-yl)cyclopropanecarboxamide |
| 223) | N-(4-(4-((N-(2-methoxyethyl)-N-methylsulfamoyl)amino)phenyl)-1H-pyrrolo[2,3-b]pyridin-6-yl)cyclopropanecarboxamide |
| 224) | N-(4-(3-fluoro-4-(piperidine-1-sulfonamido)phenyl)-1H-pyrrolo[2,3-b]pyridin-6-yl)cyclopropanecarboxamide |

-continued

225) N-(4-(3-fluoro-4-(pyrrolidine-1-sulfonamido)phenyl)-1H-pyrrolo[2,3-b]pyridin-6-yl)cyclopropanecarboxamide
226) N-(4-(3-fluoro-4-(morpholine-4-sulfonamido)phenyl)-1H-pyrrolo[2,3-b]pyridin-6-yl)cyclopropanecarboxamide
227) N-(4-(2-methyl-4-((N-(2,2,2-trifluoroethyl)sulfamoyl)amino)phenyl)-1H-pyrrolo[2,3-b]pyridin-6-yl)cyclopropanecarboxamide
228) N-(4-(2-methyl-4-((N-methyl-N-(2,2,2-trifluoroethyl)sulfamoyl)amino)phenyl)-1H-pyrrolo[2,3-b]pyridin-6-yl)cyclopropanecarboxamide
229) N-(4-(4-((1,1-dioxidothiomorpholine)-4-sulfonamido)phenyl)-1H-pyrrolo[2,3-b]pyridin-6-yl)cyclopropanecarboxamide
230) N-(4-(4-((4-(methylsulfonyl)piperazine)-1-sulfonamido)phenyl)-1H-pyrrolo[2,3-b]pyridin-6-yl)cyclopropanecarboxamide
231) N-(4-(4-(morpholine-4-sulfonamido)cyclohex-1-en-1-yl)-1H-pyrrolo[2,3-b]pyridin-6-yl)cyclopropanecarboxamide
232) N-(4-(1-(N-(2,2,2-trifluoroethyl)sulfamoyl)-1,2,3,6-tetrahydropyridin-4-yl)-1H-pyrrolo[2,3-b]pyridin-6-yl)cyclopropanecarboxamide
233) N-(4-(1-(N-methyl-N-(2,2,2-trifluoroethyl)sulfamoyl)-1,2,3,6-tetrahydropyridin-4-yl)-1H-pyrrolo[2,3-b]pyridin-6-yl)cyclopropanecarboxamide
234) N-(4-(1-(morpholinosulfonyl)-1,2,3,6-tetrahydropyridin-4-yl)-1H-pyrrolo[2,3-b]pyridin-6-yl)cyclopropanecarboxamide
235) N-(4-(4-(morpholine-4-sulfonamido)phenyl)-7H-pyrrolo[2,3-d]pyrimidin-2-yl)cyclopropanecarboxamide
236) N-(4-(4-((N,N-dimethylsulfamoyl)amino)phenyl)-7H-pyrrolo[2,3-d]pyrimidin-2-yl)cyclopropanecarboxamide
237) N-(4-(4-((2,6-dimethylmorpholine)-4-sulfonamido)phenyl)-7H-pyrrolo[2,3-d]pyrimidin-2-yl)cyclopropanecarboxamide
238) N-(6-(4-(morpholine-4-sulfonamido)phenyl)-9H-purin-2-yl)cyclopropanecarboxamide
239) N-(4-(4-(2-cyanoacetamido)phenyl)-1H-pyrrolo[2,3-b]pyridin-6-yl)cyclopropanecarboxamide
240) N-(4-(4-(2-cyanoacetamido)-2-methylphenyl)-1H-pyrrolo[2,3-b]pyridin-6-yl)cyclopropanecarboxamide
241) N-(4-(4-(2-(1-cyanocyclopropyl)acetamido)phenyl)-1H-pyrrolo[2,3-b]pyridin-6-yl)cyclopropanecarboxamide
242) N-(4-(4-propionamidocyclohex-1-en-1-yl)-1H-pyrrolo[2,3-b]pyridin-6-yl)cyclopropanecarboxamide
243) N-(4-(6-(cyclopropanecarboxamido)-1H-pyrrolo[2,3-b]pyridin-4-yl)cyclohex-3-en-1-yl)benzamide
244) N-(4-(6-(cyclopropanecarboxamido)-1H-pyrrolo[2,3-b]pyridin-4-yl)cyclohex-3-en-1-yl)-2-methylcyclopropane-1-carboxamide
245) N-(4-(6-(cyclopropanecarboxamido)-1H-pyrrolo[2,3-b]pyridin-4-yl)cyclohex-3-en-1-yl)cyclopentanecarboxamide
246) N-(4-(6-(cyclopropanecarboxamido)-1H-pyrrolo[2,3-b]pyridin-4-yl)cyclohex-3-en-1-yl)cyclopropanecarboxamide
247) N-(4-(4-(2-cyanoacetamido)cyclohex-1-en-1-yl)-1H-pyrrolo[2,3-b]pyridin-6-yl)cyclopropanecarboxamide
248) N-(4-(4-(4,4,4-trifluorobutanamido)cyclohex-1-en-1-yl)-1H-pyrrolo[2,3-b]pyridin-6-yl)cyclopropanecarboxamide
249) N-(4-(1-(1,1-dioxidotetrahydro-2H-thiopyran-4-carbonyl)-1,2,3,6-tetrahydropyridin-4-yl)-1H-pyrrolo[2,3-b]pyridin-6-yl)cyclopropanecarboxamide
250) N-(4-(1-(2-cyanoacetyl)-1,2,3,6-tetrahydropyridin-4-yl)-1H-pyrrolo[2,3-b]pyridin-6-yl)cyclopropanecarboxamide
251) N-(4-(1-(2-(1,1-dioxidothiomorpholino)acetyl)-1,2,3,6-tetrahydropyridin-4-yl)-1H-pyrrolo[2,3-b]pyridin-6-yl)cyclopropanecarboxamide
252) N-(4-(1-(3-cyanopropanoyl)-1,2,3,6-tetrahydropyridin-4-yl)-1H-pyrrolo[2,3-b]pyridin-6-yl)cyclopropanecarboxamide
253) N-(4-(1-(3,3,3-trifluoropropanoyl)-1,2,3,6-tetrahydropyridin-4-yl)-1H-pyrrolo[2,3-b]pyridin-6-yl)cyclopropanecarboxamide
254) N-(4-(1-(4,4,4-trifluorobutanoyl)-1,2,3,6-tetrahydropyridin-4-yl)-1H-pyrrolo[2,3-b]pyridin-6-yl)cyclopropanecarboxamide
255) N-(4-(8-(3-cyanopropanoyl)-8-azabicyclo[3.2.1]oct-2-en-3-yl)-1H-pyrrolo[2,3-b]pyridin-6-yl)cyclopropanecarboxamide
256) N-(4-(8-(cyclopropanecarbonyl)-8-azabicyclo[3.2.1]oct-2-en-3-yl)-1H-pyrrolo[2,3-b]pyridin-6-yl)cyclopropanecarboxamide
257) N-(4-(8-(2-cyanoacetyl)-8-azabicyclo[3.2.1]oct-2-en-3-yl)-1H-pyrrolo[2,3-b]pyridin-6-yl)cyclopropanecarboxamide
258) N-(4-(8-(4,4,4-trifluorobutanoyl)-8-azabicyclo[3.2.1]oct-2-en-3-yl)-1H-pyrrolo[2,3-b]pyridin-6-yl)cyclopropanecarboxamide
259) N-(4-(1-(1-cyanocyclopropane-1-carbonyl)-1,2,3,6-tetrahydropyridin-4-yl)-1H-pyrrolo[2,3-b]pyridin-6-yl)cyclopropanecarboxamide
260) N-(4-(1-(3,3-difluorocyclobutane-1-carbonyl)-1,2,3,6-tetrahydropyridin-4-yl)-1H-pyrrolo[2,3-b]pyridin-6-yl)cyclopropanecarboxamide
261) N-(4-(8-(3,3,3-trifluoropropanoyl)-8-azabicyclo[3.2.1]oct-2-en-3-yl)-1H-pyrrolo[2,3-b]pyridin-6-yl)cyclopropanecarboxamide
262) N-(4-((1S,5R)-8-(2-cyanoacetyl)-8-azabicyclo[3.2.1]oct-2-en-3-yl)-1H-pyrrolo[2,3-b]pyridin-6-yl)cyclopropanecarboxamide -continued 263) N-(4-(1-(2,2-difluorocyclopropane-1-carbonyl)-1,2,3,6-tetrahydropyridin-4-yl)-1H-pyrrolo[2,3-b]pyridin-6-yl)cyclopropanecarboxamide
264) N-(4-(1-(cyclopropanecarbonyl)-1,2,3,6-tetrahydropyridin-4-yl)-1H-pyrrolo[2,3-b]pyridin-6-yl)cyclopropanecarboxamide
265) N-(4-(1-(4-cyanobutanoyl)-1,2,3,6-tetrahydropyridin-4-yl)-1H-pyrrolo[2,3-b]pyridin-6-yl)cyclopropanecarboxamide
266) N-(4-(1-acryloyl-1,2,3,6-tetrahydropyridin-4-yl)-1H-pyrrolo[2,3-b]pyridin-6-yl)cyclopropanecarboxamide
267) N-(4-(1-((1S,2S)-2-cyanocyclopropane-1-carbonyl)-1,2,3,6-tetrahydropyridin-4-yl)-1H-pyrrolo[2,3-b]pyridin-6-yl)cyclopropanecarboxamide
268) N-(4-(1-(2-(1-cyanocyclopropyl)acetyl)-1,2,3,6-tetrahydropyridin-4-yl)-1H-pyrrolo[2,3-b]pyridin-6-yl)cyclopropanecarboxamide
269) N-(4-(1-(2-cyanopropanoyl)-1,2,3,6-tetrahydropyridin-4-yl)-1H-pyrrolo[2,3-b]pyridin-6-yl)cyclopropanecarboxamide
270) N-(4-(1-(but-3-enoyl)-1,2,3,6-tetrahydropyridin-4-yl)-1H-pyrrolo[2,3-b]pyridin-6-yl)cyclopropanecarboxamide
271) N-(4-(1-(2-cyanobutanoyl)-1,2,3,6-tetrahydropyridin-4-yl)-1H-pyrrolo[2,3-b]pyridin-6-yl)cyclopropanecarboxamide
272) N-(4-(1-(2,2,2-trifluoroacetyl)-1,2,3,6-tetrahydropyridin-4-yl)-1H-pyrrolo[2,3-b]pyridin-6-yl)cyclopropanecarboxamide
273) N-(4-(1-(2-methylcyclopropane-1-carbonyl)-1,2,3,6-tetrahydropyridin-4-yl)-1H-pyrrolo[2,3-b]pyridin-6-yl)cyclopropanecarboxamide
274) N-(4-(1-(2-fluorocyclopropane-1-carbonyl)-1,2,3,6-tetrahydropyridin-4-yl)-1H-pyrrolo[2,3-b]pyridin-6-yl)cyclopropanecarboxamide
275) 4-(1-(2-cyanoacetyl)-1,2,3,6-tetrahydropyridin-4-yl)-6-(cyclopropanecarboxamido)-1H-pyrrolo[2,3-b]pyridine 7-oxide
276) N-(4-(1-(2-(3,4-difluorophenyl)acetyl)-1,2,3,6-tetrahydropyridin-4-yl)-1H-pyrrolo[2,3-b]pyridin-6-yl)cyclopropanecarboxamide
277) N-(4-(1-isonicotinoyl-1,2,3,6-tetrahydropyridin-4-yl)-1H-pyrrolo[2,3-b]pyridin-6-yl)cyclopropanecarboxamide
278) N-(4-(1-(furan-3-carbonyl)-1,2,3,6-tetrahydropyridin-4-yl)-1H-pyrrolo[2,3-b]pyridin-6-yl)cyclopropanecarboxamide
279) N-(4-(1-(4-fluorobenzoyl)-1,2,3,6-tetrahydropyridin-4-yl)-1H-pyrrolo[2,3-b]pyridin-6-yl)cyclopropanecarboxamide
280) N-(4-(1-(1-methylpyrrolidine-3-carbonyl)-1,2,3,6-tetrahydropyridin-4-yl)-1H-pyrrolo[2,3-b]pyridin-6-yl)cyclopropanecarboxamide
281) N-(4-(1-(dimethylglycyl)-1,2,3,6-tetrahydropyridin-4-yl)-1H-pyrrolo[2,3-b]pyridin-6-yl)cyclopropanecarboxamide
282) N-(4-(1-(2-(trifluoromethyl)cyclopropane-1-carbonyl)-1,2,3,6-tetrahydropyridin-4-yl)-1H-pyrrolo[2,3-b]pyridin-6-yl)cyclopropanecarboxamide
283) N-(4-(1-(2-cyanoacetyl)-3-methyl-1,2,3,6-tetrahydropyridin-4-yl)-1H-pyrrolo[2,3-b]pyridin-6-yl)cyclopropanecarboxamide
284) N-(4-(1-(3-cyanopropanoyl)-3-methyl-1,2,3,6-tetrahydropyridin-4-yl)-1H-pyrrolo[2,3-b]pyridin-6-yl)cyclopropanecarboxamide
285) N-(4-(1-(4-cyanobutanoyl)-3-methyl-1,2,3,6-tetrahydropyridin-4-yl)-1H-pyrrolo[2,3-b]pyridin-6-yl)cyclopropanecarboxamide
286) N-(4-(1-(1,2,5-oxadiazole-3-carbonyl)-1,2,3,6-tetrahydropyridin-4-yl)-1H-pyrrolo[2,3-b]pyridin-6-yl)cyclopropanecarboxamide
287) N-(4-(1-(isoxazole-4-carbonyl)-1,2,3,6-tetrahydropyridin-4-yl)-1H-pyrrolo[2,3-b]pyridin-6-yl)cyclopropanecarboxamide
288) N-(4-(1-(isoxazole-5-carbonyl)-1,2,3,6-tetrahydropyridin-4-yl)-1H-pyrrolo[2,3-b]pyridin-6-yl)cyclopropanecarboxamide
289) N-(4-(1-(2-cyanoacetyl)-1,2,3,6-tetrahydropyridin-4-yl)-5-methyl-1H-pyrrolo[2,3-b]pyridin-6-yl)cyclopropanecarboxamide
290) N-(5-methyl-4-(1-(3,3,3-trifluoropropanoyl)-1,2,3,6-tetrahydropyridin-4-yl)-1H-pyrrolo[2,3-b]pyridin-6-yl)cyclopropanecarboxamide
291) N-(4-(1-(thiazole-4-carbonyl)-1,2,3,6-tetrahydropyridin-4-yl)-1H-pyrrolo[2,3-b]pyridin-6-yl)cyclopropanecarboxamide
292) N-(4-(1-(isothiazole-4-carbonyl)-1,2,3,6-tetrahydropyridin-4-yl)-1H-pyrrolo[2,3-b]pyridin-6-yl)cyclopropanecarboxamide
293) N-(4-(1-(4-cyanobenzoyl)-1,2,3,6-tetrahydropyridin-4-yl)-1H-pyrrolo[2,3-b]pyridin-6-yl)cyclopropanecarboxamide
294) N-(4-(1-(2-cyanoacetyl)-3-ethyl-1,2,3,6-tetrahydropyridin-4-yl)-1H-pyrrolo[2,3-b]pyridin-6-yl)cyclopropanecarboxamide
295) N-(4-(1-(3-cyanopropanoyl)-3-ethyl-1,2,3,6-tetrahydropyridin-4-yl)-1H-pyrrolo[2,3-b]pyridin-6-yl)cyclopropanecarboxamide
296) N-(4-(1-(2-cyanoacetyl)-5-methyl-1,2,3,6-tetrahydropyridin-4-yl)-1H-pyrrolo[2,3-b]pyridin-6-yl)cyclopropanecarboxamide
297) N-(4-(1-(2-bromoacetyl)-1,2,3,6-tetrahydropyridin-4-yl)-1H-pyrrolo[2,3-b]pyridin-6-yl)cyclopropanecarboxamide
298) N-(4-(1-(2-chloroacetyl)-1,2,3,6-tetrahydropyridin-4-yl)-1H-pyrrolo[2,3-b]pyridin-6-yl)cyclopropanecarboxamide
299) N-(4-(1-(2-cyanoacetyl)-3,3-dimethyl-1,2,3,6-tetrahydropyridin-4-yl)-1H-pyrrolo[2,3-b]pyridin-6-yl)cyclopropanecarboxamide
300) N-(4-(1-(3-cyanopropanoyl)-3,3-dimethyl-1,2,3,6-tetrahydropyridin-4-yl)-1H-pyrrolo[2,3-b]pyridin-6-yl)cyclopropanecarboxamide

| | |
|---|---|
| 301) | N-(4-(1-(2-cyanoacetyl)-1,2,3,6-tetrahydropyridin-4-yl)-1H-pyrrolo[2,3-b]pyridin-6-yl)furan-2-carboxamide |
| 302) | N-(4-(5-(3-cyanopropanoyl)-5-azaspiro[2.5]oct-7-en-8-yl)-1H-pyrrolo[2,3-b]pyridin-6-yl)cyclopropanecarboxamide |
| 303) | N-(4-(5-(2-cyanoacetyl)-5-azaspiro[2.5]oct-7-en-8-yl)-1H-pyrrolo[2,3-b]pyridin-6-yl)cyclopropanecarboxamide |
| 304) | (S)-N-(4-(1-(2-cyanoacetyl)-3-methyl-1,2,3,6-tetrahydropyridin-4-yl)-1H-pyrrolo[2,3-b]pyridin-6-yl)cyclopropanecarboxamide |
| 305) | (R)-N-(4-(1-(2-cyanoacetyl)-3-methyl-1,2,3,6-tetrahydropyridin-4-yl)-1H-pyrrolo[2,3-b]pyridin-6-yl)cyclopropanecarboxamide |
| 306) | N-(4-(3-methyl-1-(2-methylthiazole-5-carbonyl)-1,2,3,6-tetrahydropyridin-4-yl)-1H-pyrrolo[2,3-b]pyridin-6-yl)cyclopropanecarboxamide |
| 307) | N-(4-(1-(2,4-dimethylthiazole-5-carbonyl)-3-methyl-1,2,3,6-tetrahydropyridin-4-yl)-1H-pyrrolo[2,3-b]pyridin-6-yl)cyclopropanecarboxamide |
| 308) | N-(4-(3-methyl-1-(4-methylthiazole-5-carbonyl)-1,2,3,6-tetrahydropyridin-4-yl)-1H-pyrrolo[2,3-b]pyridin-6-yl)cyclopropanecarboxamide |
| 309) | N-(4-(1-(2-fluoroisonicotinoyl)-3-methyl-1,2,3,6-tetrahydropyridin-4-yl)-1H-pyrrolo[2,3-b]pyridin-6-yl)cyclopropanecarboxamide |
| 310) | N-(4-(1-(2-chloroisonicotinoyl)-3-methyl-1,2,3,6-tetrahydropyridin-4-yl)-1H-pyrrolo[2,3-b]pyridin-6-yl)cyclopropanecarboxamide |
| 311) | N-(4-(1-(3,4-difluorobenzoyl)-3-methyl-1,2,3,6-tetrahydropyridin-4-yl)-1H-pyrrolo[2,3-b]pyridin-6-yl)cyclopropanecarboxamide |
| 312) | N-(4-(1-(3-fluoro-4-methoxybenzoyl)-3-methyl-1,2,3,6-tetrahydropyridin-4-yl)-1H-pyrrolo[2,3-b]pyridin-6-yl)cyclopropanecarboxamide |
| 313) | N-(4-(3-methyl-1-(1H-pyrrole-2-carbonyl)-1,2,3,6-tetrahydropyridin-4-yl)-1H-pyrrolo[2,3-b]pyridin-6-yl)cyclopropanecarboxamide |
| 314) | N-(4-(1-(3-fluoroisonicotinoyl)-3-methyl-1,2,3,6-tetrahydropyridin-4-yl)-1H-pyrrolo[2,3-b]pyridin-6-yl)cyclopropanecarboxamide |
| 315) | N-(4-(1-(3-(2-(3,5-dioxomorpholino)ethyl)benzoyl)-3-methyl-1,2,3,6-tetrahydropyridin-4-yl)-1H-pyrrolo[2,3-b]pyridin-6-yl)cyclopropanecarboxamide |
| 316) | N-(4-(3-methyl-1-(3-(phenylamino)benzoyl)-1,2,3,6-tetrahydropyridin-4-yl)-1H-pyrrolo[2,3-b]pyridin-6-yl)cyclopropanecarboxamide |
| 317) | N-(4-(1-(6-(2,4-difluorophenyl)-2-oxo-1,2-dihydropyridine-3-carbonyl)-3-methyl-1,2,3,6-tetrahydropyridin-4-yl)-1H-pyrrolo[2,3-b]pyridin-6-yl)cyclopropanecarboxamide |
| 318) | methyl 1-(4-(6-(cyclopropanecarboxamido)-1H-pyrrolo[2,3-b]pyridin-4-yl)-3-methyl-1,2,3,6-tetrahydropyridine-1-carbonyl)cyclobutane-1-carboxylate |
| 319) | methyl 1-(4-(6-(cyclopropanecarboxamido)-1H-pyrrolo[2,3-b]pyridin-4-yl)-3-methyl-1,2,3,6-tetrahydropyridine-1-carbonyl)cyclopropane-1-carboxylate |
| 320) | methyl 3-(4-(6-(cyclopropanecarboxamido)-1H-pyrrolo[2,3-b]pyridin-4-yl)-3-methyl-3,6-dihydropyridin-1(2H)-yl)-2-methyl-3-oxopropanoate |
| 321) | N-(4-(1-(6-(tert-butyl)-2-oxo-1,2-dihydropyridine-3-carbonyl)-3-methyl-1,2,3,6-tetrahydropyridin-4-yl)-1H-pyrrolo[2,3-b]pyridin-6-yl)cyclopropanecarboxamide |
| 322) | N-(4-(1-(6-(4-fluorophenyl)-2-oxo-1,2-dihydropyridine-3-carbonyl)-3-methyl-1,2,3,6-tetrahydropyridin-4-yl)-1H-pyrrolo[2,3-b]pyridin-6-yl)cyclopropanecarboxamide |
| 323) | N-(4-(1-(3-fluoro-4-((2-morpholinoethyl)amino)benzoyl)-3-methyl-1,2,3,6-tetrahydropyridin-4-yl)-1H-pyrrolo[2,3-b]pyridin-6-yl)cyclopropanecarboxamide |
| 324) | N-(4-(1-(5-bromonicotinoyl)-3-methyl-1,2,3,6-tetrahydropyridin-4-yl)-1H-pyrrolo[2,3-b]pyridin-6-yl)cyclopropanecarboxamide |
| 325) | N-(4-(1-(2,3-dihydrobenzo[b][1,4]dioxine-6-carbonyl)-3-methyl-1,2,3,6-tetrahydropyridin-4-yl)-1H-pyrrolo[2,3-b]pyridin-6-yl)cyclopropanecarboxamide |
| 326) | N-(4-(1-(benzo[d][1,3]dioxole-5-carbonyl)-3-methyl-1,2,3,6-tetrahydropyridin-4-yl)-1H-pyrrolo[2,3-b]pyridin-6-yl)cyclopropanecarboxamide |
| 327) | N-(4-(1-(1H-indole-6-carbonyl)-3-methyl-1,2,3,6-tetrahydropyridin-4-yl)-1H-pyrrolo[2,3-b]pyridin-6-yl)cyclopropanecarboxamide |
| 328) | N-(4-(3-methyl-1-(1H-pyrrolo[2,3-b]pyridine-4-carbonyl)-1,2,3,6-tetrahydropyridin-4-yl)-1H-pyrrolo[2,3-b]pyridin-6-yl)cyclopropanecarboxamide |
| 329) | N-(4-(1-(3,4-dimethoxybenzoyl)-3-methyl-1,2,3,6-tetrahydropyridin-4-yl)-1H-pyrrolo[2,3-b]pyridin-6-yl)cyclopropanecarboxamide |
| 330) | N-(4-(1-(3-methoxybenzoyl)-3-methyl-1,2,3,6-tetrahydropyridin-4-yl)-1H-pyrrolo[2,3-b]pyridin-6-yl)cyclopropanecarboxamide |
| 331) | N-(4-(3-methyl-1-(4-nitrobenzoyl)-1,2,3,6-tetrahydropyridin-4-yl)-1H-pyrrolo[2,3-b]pyridin-6-yl)cyclopropanecarboxamide |
| 332) | N-(4-(1-(3-acetylbenzoyl)-3-methyl-1,2,3,6-tetrahydropyridin-4-yl)-1H-pyrrolo[2,3-b]pyridin-6-yl)cyclopropanecarboxamide |

| | |
|---|---|
| 333) | N-(4-(1-(4-chlorobenzoyl)-3-methyl-1,2,3,6-tetrahydropyridin-4-yl)-1H-pyrrolo[2,3-b]pyridin-6-yl)cyclopropanecarboxamide |
| 334) | N-(4-(1-(3-bromobenzoyl)-3-methyl-1,2,3,6-tetrahydropyridin-4-yl)-1H-pyrrolo[2,3-b]pyridin-6-yl)cyclopropanecarboxamide |
| 335) | N-(4-(1-(6-chloronicotinoyl)-3-methyl-1,2,3,6-tetrahydropyridin-4-yl)-1H-pyrrolo[2,3-b]pyridin-6-yl)cyclopropanecarboxamide |
| 336) | N-(4-(1-isonicotinoyl-3-methyl-1,2,3,6-tetrahydropyridin-4-yl)-1H-pyrrolo[2,3-b]pyridin-6-yl)cyclopropanecarboxannide |
| 337) | N-(4-(1-(6-bromopicolinoyl)-3-methyl-1,2,3,6-tetrahydropyridin-4-yl)-1H-pyrrolo[2,3-b]pyridin-6-yl)cyclopropanecarboxamide |
| 338) | N-(4-(1-(3-bromobutanoyl)-3-methyl-1,2,3,6-tetrahydropyridin-4-yl)-1H-pyrrolo[2,3-b]pyridin-6-yl)cyclopropanecarboxamide |
| 339) | (E)-N-(4-(1-(5-bromopent-2-enoyl)-3-methyl-1,2,3,6-tetrahydropyridin-4-yl)-1H-pyrrolo[2,3-b]pyridin-6-yl)cyclopropanecarboxamide |
| 340) | N-(4-(1-(2-cyclopentylacetyl)-3-methyl-1,2,3,6-tetrahydropyridin-4-yl)-1H-pyrrolo[2,3-b]pyridin-6-yl)cyclopropanecarboxamide |
| 341) | N-(4-(1-(2-(4-methoxyphenyl)acetyl)-3-methyl-1,2,3,6-tetrahydropyridin-4-yl)-1H-pyrrolo[2,3-b]pyridin-6-yl)cyclopropanecarboxamide |
| 342) | N-(4-(3-methyl-1-(3-methylthiophene-2-carbonyl)-1,2,3,6-tetrahydropyridin-4-yl)-1H-pyrrolo[2,3-b]pyridin-6-yl)cyclopropanecarboxamide |
| 343) | N-(4-(3-methyl-1-(pyrazine-2-carbonyl)-1,2,3,6-tetrahydropyridin-4-yl)-1H-pyrrolo[2,3-b]pyridin-6-yl)cyclopropanecarboxamide |
| 344) | N-(4-(3-methyl-1-(5-methylpyrazine-2-carbonyl)-1,2,3,6-tetrahydropyridin-4-yl)-1H-pyrrolo[2,3-b]pyridin-6-yl)cyclopropanecarboxamide |
| 345) | N-(4-(3-methyl-1-(2-(thiophen-2-yl)acetyl)-1,2,3,6-tetrahydropyridin-4-yl)-1H-pyrrolo[2,3-b]pyridin-6-yl)cyclopropanecarboxamide |
| 346) | N-(4-(1-(2-(3-fluorophenyl)acetyl)-3-methyl-1,2,3,6-tetrahydropyridin-4-yl)-1H-pyrrolo[2,3-b]pyridin-6-yl)cyclopropanecarboxamide |
| 347) | N-(4-(1-(2-(3-bromophenyl)acetyl)-3-methyl-1,2,3,6-tetrahydropyridin-4-yl)-1H-pyrrolo[2,3-b]pyridin-6-yl)cyclopropanecarboxamide |
| 348) | N-(4-(1-(2-chloroacetyl)-3-methyl-1,2,3,6-tetrahydropyridin-4-yl)-1H-pyrrolo[2,3-b]pyridin-6-yl)cyclopropanecarboxamide |
| 349) | N-(4-(1-(2-chloronicotinoyl)-3-methyl-1,2,3,6-tetrahydropyridin-4-yl)-1H-pyrrolo[2,3-b]pyridin-6-yl)cyclopropanecarboxamide |
| 350) | N-(4-(1-(4-hydroxybenzoyl)-3-methyl-1,2,3,6-tetrahydropyridin-4-yl)-1H-pyrrolo[2,3-b]pyridin-6-yl)cyclopropanecarboxamide |
| 351) | N-(4-(1-(3,5-dichloro-2-hydroxybenzoyl)-3-methyl-1,2,3,6-tetrahydropyridin-4-yl)-1H-pyrrolo[2,3-b]pyridin-6-yl)cyclopropanecarboxamide |
| 352) | N-(4-(1-(benzofuran-2-carbonyl)-3-methyl-1,2,3,6-tetrahydropyridin-4-yl)-1H-pyrrolo[2,3-b]pyridin-6-yl)cyclopropanecarboxamide |
| 353) | N-(4-(1-(3,4-dichlorobenzoyl)-3-methyl-1,2,3,6-tetrahydropyridin-4-yl)-1H-pyrrolo[2,3-b]pyridin-6-yl)cyclopropanecarboxamide |
| 354) | N-(4-(3-methyl-1-(4-(methylsulfonyl)benzoyl)-1,2,3,6-tetrahydropyridin-4-yl)-1H-pyrrolo[2,3-b]pyridin-6-yl)cyclopropanecarboxamide |
| 355) | N-(4-(1-(2-chloro-4-fluorobenzoyl)-3-methyl-1,2,3,6-tetrahydropyridin-4-yl)-1H-pyrrolo[2,3-b]pyridin-6-yl)cyclopropanecarboxamide |
| 356) | N-(4-(1-(2,4-dimethoxybenzoyl)-3-methyl-1,2,3,6-tetrahydropyridin-4-yl)-1H-pyrrolo[2,3-b]pyridin-6-yl)cyclopropanecarboxamide |
| 357) | N-(4-(3-methyl-1-(2-(methylthio)benzoyl)-1,2,3,6-tetrahydropyridin-4-yl)-1H-pyrrolo[2,3-b]pyridin-6-yl)cyclopropanecarboxamide |
| 358) | N-(4-(1-(3,5-difluorobenzoyl)-3-methyl-1,2,3,6-tetrahydropyridin-4-yl)-1H-pyrrolo[2,3-b]pyridin-6-yl)cyclopropanecarboxamide |
| 359) | N-(4-(1-(2-cyano-3-(4-fluorophenyl)propanoyl)-3-methyl-1,2,3,6-tetrahydropyridin-4-yl)-1H-pyrrolo[2,3-b]pyridin-6-yl)cyclopropanecarboxamide |
| 360) | N-(4-(1-(2-cyano-3-phenylpropanoyl)-3-methyl-1,2,3,6-tetrahydropyridin-4-yl)-1H-pyrrolo[2,3-b]pyridin-6-yl)cyclopropanecarboxamide |
| 361) | N-(4-(1-(1-cyanocyclopentane-1-carbonyl)-3-methyl-1,2,3,6-tetrahydropyridin-4-yl)-1H-pyrrolo[2,3-b]pyridin-6-yl)cyclopropanecarboxamide |
| 362) | N-(4-(3-methyl-1-(3-morpholino-3-oxopropanoyl)-1,2,3,6-tetrahydropyridin-4-yl)-1H-pyrrolo[2,3-b]pyridin-6-yl)cyclopropanecarboxamide |
| 363) | N-(4-(1-(2-cyanoacetyl)-2-methyl-1,2,3,6-tetrahydropyridin-4-yl)-1H-pyrrolo[2,3-b]pyridin-6-yl)cyclopropanecarboxamide |
| 365) | N-(4-(3-methyl-1-(2-phenylacetyl)-1,2,3,6-tetrahydropyridin-4-yl)-1H-pyrrolo[2,3-b]pyridin-6-yl)cyclopropanecarboxamide |
| 366) | N-(4-(9-(2-fluoroisonicotinoyl)-9-azabicyclo[3.3.1]non-2-en-3-yl)-1H-pyrrolo[2,3-b]pyridin-6-yl)cyclopropanecarboxamide |
| 367) | N-(4-(9-(2-chloroisonicotinoyl)-9-azabicyclo[3.3.1]non-2-en-3-yl)-1H-pyrrolo[2,3-b]pyridin-6-yl)cyclopropanecarboxamide |
| 368) | N-(4-(9-(6-chloronicotinoyl)-9-azabicyclo[3.3.1]non-2-en-3-yl)-1H-pyrrolo[2,3-b]pyridin-6-yl)cyclopropanecarboxamide |
| 369) | N-(4-(9-(3-fluoroisonicotinoyl)-9-azabicyclo[3.3.1]non-2-en-3-yl)-1H-pyrrolo[2,3-b]pyridin-6-yl)cyclopropanecarboxamide |

| | |
|---|---|
| 370) | N-(4-(9-(4-nitrobenzoyl)-9-azabicyclo[3.3.1]non-2-en-3-yl)-1H-pyrrolo[2,3-b]pyridin-6-yl)cyclopropanecarboxamide |
| 371) | N-(4-(9-(3-bromobenzoyl)-9-azabicyclo[3.3.1]non-2-en-3-yl)-1H-pyrrolo[2,3-b]pyridin-6-yl)cyclopropanecarboxamide |
| 372) | N-(4-(1-(2,6-dichloroisonicotinoyl)-3-methyl-1,2,3,6-tetrahydropyridin-4-yl)-1H-pyrrolo[2,3-b]pyridin-6-yl)cyclopropanecarboxamide |
| 373) | N-(4-(1-(2,5-dichloroisonicotinoyl)-3-methyl-1,2,3,6-tetrahydropyridin-4-yl)-1H-pyrrolo[2,3-b]pyridin-6-yl)cyclopropanecarboxamide |
| 374) | N-(4-(1-(3,5-dichloroisonicotinoyl)-3-methyl-1,2,3,6-tetrahydropyridin-4-yl)-1H-pyrrolo[2,3-b]pyridin-6-yl)cyclopropanecarboxamide |
| 375) | N-(4-(1-(2-chloro-6-methylisonicotinoyl)-3-methyl-1,2,3,6-tetrahydropyridin-4-yl)-1H-pyrrolo[2,3-b]pyridin-6-yl)cyclopropanecarboxamide |
| 376) | N-(4-(1-(3-chloroisonicotinoyl)-3-methyl-1,2,3,6-tetrahydropyridin-4-yl)-1H-pyrrolo[2,3-b]pyridin-6-yl)cyclopropanecarboxamide |
| 377) | N-(4-(1-(3-hydroxyisonicotinoyl)-3-methyl-1,2,3,6-tetrahydropyridin-4-yl)-1H-pyrrolo[2,3-b]pyridin-6-yl)cyclopropanecarboxamide |
| 378) | N-(4-(1-(2,3-difluorobenzoyl)-3-methyl-1,2,3,6-tetrahydropyridin-4-yl)-1H-pyrrolo[2,3-b]pyridin-6-yl)cyclopropanecarboxamide |
| 379) | N-(4-(3-methyl-1-(2-methylisonicotinoyl)-1,2,3,6-tetrahydropyridin-4-yl)-1H-pyrrolo[2,3-b]pyridin-6-yl)cyclopropanecarboxamide |
| 380) | N-(4-(1-(6-methoxynicotinoyl)-3-methyl-1,2,3,6-tetrahydropyridin-4-yl)-1H-pyrrolo[2,3-b]pyridin-6-yl)cyclopropanecarboxamide |
| 381) | N-(4-(1-(2-aminoisonicotinoyl)-3-methyl-1,2,3,6-tetrahydropyridin-4-yl)-1H-pyrrolo[2,3-b]pyridin-6-yl)cyclopropanecarboxamide |
| 382) | N-(4-(1-(2-bromoisonicotinoyl)-3-methyl-1,2,3,6-tetrahydropyridin-4-yl)-1H-pyrrolo[2,3-b]pyridin-6-yl)cyclopropanecarboxamide |
| 383) | N-(4-(1-(2-hydroxyisonicotinoyl)-3-methyl-1,2,3,6-tetrahydropyridin-4-yl)-1H-pyrrolo[2,3-b]pyridin-6-yl)cyclopropanecarboxamide |
| 384) | N-(4-(3-methyl-1-(2-(trifluoromethyl)isonicotinoyl)-1,2,3,6-tetrahydropyridin-4-yl)-1H-pyrrolo[2,3-b]pyridin-6-yl)cyclopropanecarboxamide |
| 385) | N-(4-(1-(2-fluoroisonicotinoyl)-2,2-dimethyl-1,2,3,6-tetrahydropyridin-4-yl)-1H-pyrrolo[2,3-b]pyridin-6-yl)cyclopropanecarboxamide |
| 386) | N-(4-(1-(2-chloroisonicotinoyl)-2,2-dimethyl-1,2,3,6-tetrahydropyridin-4-yl)-1H-pyrrolo[2,3-b]pyridin-6-yl)cyclopropanecarboxamide |
| 387) | N-(4-(1-(2-cyanoacetyl)-2,2-dimethyl-1,2,3,6-tetrahydropyridin-4-yl)-1H-pyrrolo[2,3-b]pyridin-6-yl)cyclopropanecarboxamide |
| 388) | (R)-N-(4-(1-(2-cyanoacetyl)-6-methyl-1,2,3,6-tetrahydropyridin-4-yl)-1H-pyrrolo[2,3-b]pyridin-6-yl)cyclopropanecarboxamide |
| 389) | (R)-N-(4-(1-(2-cyanoacetyl)-2-methyl-1,2,3,6-tetrahydropyridin-4-yl)-1H-pyrrolo[2,3-b]pyridin-6-yl)cyclopropanecarboxamide |
| 390) | (S)-N-(4-(1-(2-cyanoacetyl)-6-methyl-1,2,3,6-tetrahydropyridin-4-yl)-1H-pyrrolo[2,3-b]pyridin-6-yl)cyclopropanecarboxamide |
| 391) | (S)-N-(4-(1-(2-cyanoacetyl)-2-methyl-1,2,3,6-tetrahydropyridin-4-yl)-1H-pyrrolo[2,3-b]pyridin-6-yl)cyclopropanecarboxamide |
| 392) | N-(4-(1-(2-cyanoisonicotinoyl)-3-methyl-1,2,3,6-tetrahydropyridin-4-yl)-1H-pyrrolo[2,3-b]pyridin-6-yl)cyclopropanecarboxamide |
| 393) | N-(4-(1-(2-cyanoacetyl)-2-(trifluoromethyl)-1,2,3,6-tetrahydropyridin-4-yl)-1H-pyrrolo[2,3-b]pyridin-6-yl)cyclopropanecarboxamide |
| 394) | N-(4-(9-(2-cyanoacetyl)-9-azabicyclo[3.3.1]non-2-en-3-yl)-1H-pyrrolo[2,3-b]pyridin-6-yl)cyclopropanecarboxamide |
| 395) | (S)-N-(4-(1-(2-fluoroisonicotinoyl)-3-methyl-1,2,3,6-tetrahydropyridin-4-yl)-1H-pyrrolo[2,3-b]pyridin-6-yl)cyclopropanecarboxamide |
| 396) | (S)-N-(4-(1-(2,3-difluoroisonicotinoyl)-3-methyl-1,2,3,6-tetrahydropyridin-4-yl)-1H-pyrrolo[2,3-b]pyridin-6-yl)cyclopropanecarboxamide |
| 397) | (S)-N-(4-(1-(3-bromobenzoyl)-3-methyl-1,2,3,6-tetrahydropyridin-4-yl)-1H-pyrrolo[2,3-b]pyridin-6-yl)cyclopropanecarboxamide |
| 398) | (S)-N-(4-(3-methyl-1-(4-nitrobenzoyl)-1,2,3,6-tetrahydropyridin-4-yl)-1H-pyrrolo[2,3-b]pyridin-6-yl)cyclopropanecarboxamide |
| 399) | (S)-N-(4-(1-(2-chloroisonicotinoyl)-3-methyl-1,2,3,6-tetrahydropyridin-4-yl)-1H-pyrrolo[2,3-b]pyridin-6-yl)cyclopropanecarboxamide |
| 400) | (S)-N-(4-(1-(6-chloronicotinoyl)-3-methyl-1,2,3,6-tetrahydropyridin-4-yl)-1H-pyrrolo[2,3-b]pyridin-6-yl)cyclopropanecarboxamide |
| 401) | (S)-N-(4-(1-(2-chloroacetyl)-3-methyl-1,2,3,6-tetrahydropyridin-4-yl)-1H-pyrrolo[2,3-b]pyridin-6-yl)cyclopropanecarboxamide |
| 402) | (S)-N-(4-(1-(3-fluoroisonicotinoyl)-3-methyl-1,2,3,6-tetrahydropyridin-4-yl)-1H-pyrrolo[2,3-b]pyridin-6-yl)cyclopropanecarboxamide |
| 403) | (S)-N-(4-(1-(2-cyano-3-(thiophen-2-yl)acryloyl)-3-methyl-1,2,3,6-tetrahydropyridin-4-yl)-1H-pyrrolo[2,3-b]pyridin-6-yl)cyclopropanecarboxamide |
| 404) | (S)-N-(4-(1-(2-(cyanomethyl)-3-phenylacryloyl)-3-methyl-1,2,3,6-tetrahydropyridin-4-yl)-1H-pyrrolo[2,3-b]pyridin-6-yl)cyclopropanecarboxamide |
| 405) | (S)-N-(4-(3-methyl-1-(1-methyl-2-oxo-1,2-dihydropyridine-3-carbonyl)-1,2,3,6-tetrahydropyridin-4-yl)-1H-pyrrolo[2,3-b]pyridin-6-yl)cyclopropanecarboxamide |

| | |
|---|---|
| 406) | (S)-N-(4-(1-(2-(1-cyanocyclohexyl)acetyl)-3-methyl-1,2,3,6-tetrahydropyridin-4-yl)-1H-pyrrolo[2,3-b]pyridin-6-yl)cyclopropanecarboxamide |
| 407) | (S)-N-(4-(1-(4-cyanotetrahydro-2H-pyran-4-carbonyl)-3-methyl-1,2,3,6-tetrahydropyridin-4-yl)-1H-pyrrolo[2,3-b]pyridin-6-yl)cyclopropanecarboxamide |
| 408) | (S)-N-(4-(1-(2-cyano-3-methylbut-2-enoyl)-3-methyl-1,2,3,6-tetrahydropyridin-4-yl)-1H-pyrrolo[2,3-b]pyridin-6-yl)cyclopropanecarboxamide |
| 409) | N-(4-(1-(2-cyanoacetyl)-2,6-diethyl-1,2,3,6-tetrahydropyridin-4-yl)-1H-pyrrolo[2,3-b]pyridin-6-yl)cyclopropanecarboxamide |
| 410) | N-(4-(1-(2-cyanoacetyl)-2-isopropyl-1,2,3,6-tetrahydropyridin-4-yl)-1H-pyrrolo[2,3-b]pyridin-6-yl)cyclopropanecarboxamide |
| 411) | N-(4-(1-(2-cyanoacetyl)-6-propyl-1,2,3,6-tetrahydropyridin-4-yl)-1H-pyrrolo[2,3-b]pyridin-6-yl)cyclopropanecarboxamide |
| 412) | N-(4-(6-(tert-butyl)-1-(2-cyanoacetyl)-1,2,3,6-tetrahydropyridin-4-yl)-1H-pyrrolo[2,3-b]pyridin-6-yl)cyclopropanecarboxamide |
| 413) | N-(4-(1-(2-cyanoacetyl)-2-ethyl-1,2,3,6-tetrahydropyridin-4-yl)-1H-pyrrolo[2,3-b]pyridin-6-yl)cyclopropanecarboxamide |
| 414) | N-(4-(5-(2-cyanoacetyl)-5-azaspiro[3.5]non-7-en-8-yl)-1H-pyrrolo[2,3-b]pyridin-6-yl)cyclopropanecarboxamide |
| 415) | (S)-N-(4-(1-(2-(1-cyanocyclopropyl)acetyl)-3-methyl-1,2,3,6-tetrahydropyridin-4-yl)-1H-pyrrolo[2,3-b]pyridin-6-yl)cyclopropanecarboxamide |
| 416) | (R)-N-(4-(1-(2-cyanoacetyl)-6-ethyl-1,2,3,6-tetrahydropyridin-4-yl)-1H-pyrrolo[2,3-b]pyridin-6-yl)cyclopropanecarboxamide |
| 417) | (R)-N-(4-(1-(2-cyanoacetyl)-2-ethyl-1,2,3,6-tetrahydropyridin-4-yl)-1H-pyrrolo[2,3-b]pyridin-6-yl)cyclopropanecarboxamide |
| 418) | N-(4-(1-(3-cyanopropanoyl)-1,4,5,6-tetrahydropyridin-3-yl)-1H-pyrrolo[2,3-b]pyridin-6-yl)cyclopropanecarboxamide |
| 419) | N-(4-(1-(2-cyanoacetyl)-1,4,5,6-tetrahydropyridin-3-yl)-1H-pyrrolo[2,3-b]pyridin-6-yl)cyclopropanecarboxamide |
| 420) | N-(4-(1-(2-cyanoacetyl)-1,2,5,6-tetrahydropyridin-3-yl)-1H-pyrrolo[2,3-b]pyridin-6-yl)cyclopropanecarboxamide |
| 421) | N-(4-(1-(3-cyanopropanoyl)-1,2,5,6-tetrahydropyridin-3-yl)-1H-pyrrolo[2,3-b]pyridin-6-yl)cyclopropanecarboxamide |
| 422) | N-(4-(1-(2-cyanoacetyl)-2,5,6,7-tetrahydro-1H-azepin-4-yl)-1H-pyrrolo[2,3-b]pyridin-6-yl)cyclopropanecarboxamide |
| 423) | N-(4-(1-(2-fluoroisonicotinoyl)-2,5,6,7-tetrahydro-1H-azepin-4-yl)-1H-pyrrolo[2,3-b]pyridin-6-yl)cyclopropanecarboxamide |
| 424) | N-(4-(1-(2,3-difluoroisonicotinoyl)-2,5,6,7-tetrahydro-1H-azepin-4-yl)-1H-pyrrolo[2,3-b]pyridin-6-yl)cyclopropanecarboxamide |
| 425) | N-(4-(1-(2-cyanoacetyl)-1,2,3,6-tetrahydropyridin-4-yl)-7H-pyrrolo[2,3-d]pyrimidin-2-yl)cyclopropanecarboxamide |
| 426) | N-(4-(1-(2-cyanoacetyl)-2,5-dihydro-1H-pyrrol-3-yl)-1H-pyrrolo[2,3-b]pyridin-6-yl)cyclopropanecarboxamide |
| 427) | N-(4-(1-(3-cyanopropanoyl)-2,5-dihydro-1H-pyrrol-3-yl)-1H-pyrrolo[2,3-b]pyridin-6-yl)cyclopropanecarboxamide |
| 428) | N-(4-(1-(3,3,3-trifluoropropanoyl)-2,5-dihydro-1H-pyrrol-3-yl)-1H-pyrrolo[2,3-b]pyridin-6-yl)cyclopropanecarboxamide |
| 429) | N-(4-(1-(4,4,4-trifluorobutanoyl)-2,5-dihydro-1H-pyrrol-3 -yl)-1H-pyrrolo[2,3-b]pyridin-6-yl)cyclopropanecarboxamide |
| 430) | N-(4-(1-(1-cyanocyclopropane-1-carbonyl)-2,5-dihydro-1H-pyrrol-3-yl)-1H-pyrrolo[2,3-b]pyridin-6-yl)cyclopropanecarboxamide |
| 431) | N-(4-(4-(3-ethylureido)phenyl)-1H-pyrrolo[2,3-b]pyridin-6-yl)cyclopropanecarboxamide |
| 432) | N-(4-(6-(cyclopropanecarboxamido)-1H-pyrrolo[2,3-b]pyridin-4-yl)phenyl)morpholine-4-carboxamide |
| 433) | N-(4-(4-(3-butylureido)phenyl)-1H-pyrrolo[2,3-b]pyridin-6-yl)cyclopropanecarboxamide |
| 434) | N-(4-(4-(3-(4-fluorophenyl)ureido)phenyl)-1H-pyrrolo[2,3-b]pyridin-6-yl)cyclopropanecarboxamide |
| 435) | N-(4-(4-(3-(2,2,2-trifluoroethyl)ureido)phenyl)-1H-pyrrolo[2,3-b]pyridin-6-yl)cyclopropanecarboxamide |
| 436) | N-(4-(2-methyl-4-(3-(2,2,2-trifluoroethyl)ureido)phenyl)-1H-pyrrolo[2,3-b]pyridin-6-yl)cyclopropanecarboxamide |
| 437) | N-(4-(4-(3-cyclopropylureido)phenyl)-7H-pyrrolo[2,3-d]pyrimidin-2-yl)cyclopropanecarboxamide |
| 438) | N-(4-(4-(3-ethylureido)phenyl)-7H-pyrrolo[2,3-d]pyrimidin-2-yl)cyclopropanecarboxamide |
| 439) | N-(4-(4-(3-butylureido)phenyl)-7H-pyrrolo[2,3-d]pyrimidin-2-yl)cyclopropanecarboxamide |
| 440) | N-(4-(4-(3-(3,4-difluorophenyl)ureido)phenyl)-7H-pyrrolo[2,3-d]pyrimidin-2-yl)cyclopropanecarboxamide |
| 441) | N-(4-(4-(3-(4-fluorophenyl)ureido)phenyl)-7H-pyrrolo[2,3-d]pyrimidin-2-yl)cyclopropanecarboxamide |
| 442) | N-(4-(4-(3-(2,2,2-trifluoroethyl)ureido)cyclohex-1-en-1-yl)-1H-pyrrolo[2,3-b]pyridin-6-yl)cyclopropanecarboxamide |

| | |
|---|---|
| 443) | 4-(6-(cyclopropanecarboxamido)-1H-pyrrolo[2,3-b]pyridin-4-yl)-N-(2,2,2-trifluoroethyl)-3,6-dihydropyridine-1(2H)-carboxamide |
| 444) | N-butyl-4-(6-(cyclopropanecarboxamido)-1H-pyrrolo[2,3-b]pyridin-4-yl)-3,6-dihydropyridine-1(2H)-carboxamide |
| 445) | N-(4-(1-(1,1-dioxidothiomorpholine-4-carbonyl)-1,2,3,6-tetrahydropyridin-4-yl)-1H-pyrrolo[2,3-b]pyridin-6-yl)cyclopropanecarboxamide |
| 446) | N-(4-(1-(morpholine-4-carbonyl)-1,2,3,6-tetrahydropyridin-4-yl)-1H-pyrrolo[2,3-b]pyridin-6-yl)cyclopropanecarboxamide |
| 447) | N-(cyanomethyl)-4-(6-(cyclopropanecarboxamido)-1H-pyrrolo[2,3-b]pyridin-4-yl)-3,6-dihydropyridine-1(2H)-carboxamide |
| 448) | 3-(6-(cyclopropanecarboxamido)-1H-pyrrolo[2,3-b]pyridin-4-yl)-N-(2,2,2-trifluoroethyl)-8-azabicyclo[3.2.1]oct-2-ene-8-carboxamide |
| 449) | N-butyl-3-(6-(cyclopropanecarboxamido)-1H-pyrrolo[2,3-b]pyridin-4-yl)-8-azabicyclo[3.2.1]oct-2-ene-8-carboxamide |
| 450) | 4-(6-(cyclopropanecarboxamido)-1H-pyrrolo[2,3-b]pyridin-4-yl)-N-(1-cyclopropyl-2,2,2-trifluoroethyl)-3,6-dihydropyridine-1(2H)-carboxamide |
| 451) | N-(4-(1-(1H-imidazole-1-carbonyl)-1,2,3,6-tetrahydropyridin-4-yl)-1H-pyrrolo[2,3-b]pyridin-6-yl)cyclopropanecarboxamide |
| 452) | N-(4-(1-(1H-imidazole-1-carbonyl)-3-methyl-1,2,3,6-tetrahydropyridin-4-yl)-1H-pyrrolo[2,3-b]pyridin-6-yl)cyclopropanecarboxamide |
| 453) | 4-(6-(cyclopropanecarboxamido)-1H-pyrrolo[2,3-b]pyridin-4-yl)-3-methyl-N-(2,2,2-trifluoroethyl)-3,6-dihydropyridine-1(2H)-carboxamide |
| 454) | tert-butyl 4-(6-(cyclopropanecarboxamido)-1H-pyrrolo[2,3-b]pyridin-4-yl)-3,6-dihydropyridine-1(2H)-carboxylate |
| 455) | cyanomethyl 4-(6-(cyclopropanecarboxamido)-1H-pyrrolo[2,3-b]pyridin-4-yl)-3,6-dihydropyridine-1(2H)-carboxylate |
| 456) | tert-butyl 4-(6-(cyclopropanecarboxamido)-1H-pyrrolo[2,3-b]pyridin-4-yl)-3-methyl-3,6-dihydropyridine-1(2H)-carboxylate |
| 457) | tert-butyl 4-(6-(cyclopropanecarboxamido)-5-methyl-1H-pyrrolo[2,3-b]pyridin-4-yl)-3,6-dihydropyridine-1(2H)-carboxylate |
| 458) | tert-butyl 4-(6-(cyclopropanecarboxamido)-1H-pyrrolo[2,3-b]pyridin-4-yl)-3-ethyl-3,6-dihydropyridine-1(2H)-carboxylate |
| 459) | tert-butyl 5-(6-(cyclopropanecarboxamido)-1H-pyrrolo[2,3-b]pyridin-4-yl)-3,4-dihydropyridine-1(2H)-carboxylate |
| 460) | tert-butyl 5-(6-(cyclopropanecarboxamido)-1H-pyrrolo[2,3-b]pyridin-4-yl)-3,6-dihydropyridine-1(2H)-carboxylate |
| 461) | tert-butyl 3-(6-(cyclopropanecarboxamido)-1H-pyrrolo[2,3-b]pyridin-4-yl)-2,5-dihydro-1H-pyrrole-1-carboxylate |
| 462) | N-(4-(4-(3-ethylthioureido)phenyl)-1H-pyrrolo[2,3-b]pyridin-6-yl)cyclopropanecarboxamide |
| 463) | N-(4-(4-(3-butylthioureido)phenyl)-1H-pyrrolo[2,3-b]pyridin-6-yl)cyclopropanecarboxamide |
| 464) | N-(4-(4-(3-cyclohexylthioureido)phenyl)-7H-pyrrolo[2,3-d]pyrimidin-2-yl)cyclopropanecarboxamide |
| 465) | N-(4-(4-(3-butylthioureido)phenyl)-7H-pyrrolo[2,3-d]pyrimidin-2-yl)cyclopropanecarboxamide |
| 466) | N-(4-(4-(3-ethylthioureido)phenyl)-7H-pyrrolo[2,3-d]pyrimidin-2-yl)cyclopropanecarboxamide |
| 467) | N-(4-(4-(3-propylthioureido)phenyl)-7H-pyrrolo[2,3-d]pyrimidin-2-yl)cyclopropanecarboxamide |
| 468) | N-(4-(1-(ethylcarbamothioyl)-1,2,3,6-tetrahydropyridin-4-yl)-1H-pyrrolo[2,3-b]pyridin-6-yl)cyclopropanecarboxamide |
| 469) | N-(4-(8-(ethylcarbamothioyl)-8-azabicyclo[3.2.1]oct-2-en-3-yl)-1H-pyrrolo[2,3-b]pyridin-6-yl)cyclopropanecarboxamide |
| 470) | N-(4-(4-((cyclopropylmethyl)amino)phenyl)-1H-pyrrolo[2,3-b]pyridin-6-yl)cyclopropanecarboxamide |
| 471) | N-(4-(4-((cyclohexylmethyl)amino)phenyl)-1H-pyrrolo[2,3-b]pyridin-6-yl)cyclopropanecarboxamide |
| 472) | N-(4-(4-(benzylamino)phenyl)-1H-pyrrolo[2,3-b]pyridin-6-yl)cyclopropanecarboxamide |
| 473) | N-(4-(4-((4-fluorobenzyl)amino)phenyl)-7H-pyrrolo[2,3-d]pyrimidin-2-yl)cyclopropanecarboxamide |
| 474) | N-(4-(4-((3-fluorobenzyl)amino)phenyl)-7H-pyrrolo[2,3-d]pyrimidin-2-yl)cyclopropanecarboxamide |
| 475) | N-(4-(4-((4-chlorobenzyl)amino)phenyl)-7H-pyrrolo[2,3-d]pyrimidin-2-yl)cyclopropanecarboxamide |
| 476) | N-(4-(4-((3-hydroxypropyl)amino)phenyl)-7H-pyrrolo[2,3-d]pyrimidin-2-yl)cyclopropanecarboxamide |
| 477) | N-(4-(1-(2-cyanoethyl)-1H-pyrazol-4-yl)-1H-pyrrolo[2,3-b]pyridin-6-yl)cyclopropanecarboxamide |
| 478) | N-(4-(1-(cyclopropylmethyl)-1H-pyrazol-4-yl)-1H-pyrrolo[2,3-b]pyridin-6-yl)cyclopropanecarboxamide |
| 479) | N-(4-(1-benzyl-1H-pyrazol-4-yl)-1H-pyrrolo[2,3-b]pyridin-6-yl)cyclopropanecarboxamide |
| 480) | N-(4-(1-(2-cyanoethyl)-3,5-dimethyl-1H-pyrazol-4-yl)-1H-pyrrolo[2,3-b]pyridin-6-yl)cyclopropanecarboxamide |
| 481) | N-(4-(1-benzyl-1H-1,2,3-triazol-4-yl)-1H-pyrrolo[2,3-b]pyridin-6-yl)cyclopropanecarboxamide |

| | |
|---|---|
| 482) | N-(4-(1-((6-cyanopyridin-3-yl)methyl)-1H-pyrazol-4-yl)-7H-pyrrolo[2,3-d]pyrimidin-2-yl)cyclopropanecarboxamide |
| 483) | N-(4-(1-(2-cyanoethyl)-1H-pyrrol-3-yl)-1H-pyrrolo[2,3-b]pyridin-6-yl)cyclopropanecarboxamide |
| 484) | N-(4-(1-(2-morpholinoethyl)-2,5-dihydro-1H-pyrrol-3-yl)-1H-pyrrolo[2,3-b]pyridin-6-yl)cyclopropanecarboxamide |
| 485) | N-(4-(1-(2-cyanoethyl)-2,5-dihydro-1H-pyrro-3-yl)-1H-pyrrolo[2,3-b]pyridin-6-yl)cyclopropanecarboxamide |
| 486) | N-(4-(1-(2-cyanoethyl)-1,2,3,6-tetrahydropyridin-4-yl)-1H-pyrrolo[2,3-b]pyridin-6-yl)cyclopropanecarboxamide |
| 487) | N-(4-(1-((3-methyloxetan-3-yl)methyl)-1,2,3,6-tetrahydropyridin-4-yl)-1H-pyrrolo[2,3-b]pyridin-6-yl)cyclopropanecarboxamide |
| 488) | N-(4-(1-(isothiazol-5-ylmethyl)-1,2,3,6-tetrahydropyridin-4-yl)-1H-pyrrolo[2,3-b]pyridin-6-yl)cyclopropanecarboxamide |
| 489) | N-(4-(1-((2,2-difluorocyclopropyl)methyl)-1,2,3,6-tetrahydropyridin-4-yl)-1H-pyrrolo[2,3-b]pyridin-6-yl)cyclopropanecarboxamide |
| 490) | N-(4-(1-(3-cyanocyclobutyl)-1,2,3,6-tetrahydropyridin-4-yl)-1H-pyrrolo[2,3-b]pyridin-6-yl)cyclopropanecarboxamide |
| 491) | N-(4-(4-((1-(3,5-difluorobenzoyl)piperidin-4-yl)amino)cyclohex-1-en-1-yl)-1H-pyrrolo[2,3-b]pyridin-6-yl)cyclopropanecarboxamide |
| 492) | N-(4-(4-((1-(cyclohexanecarbonyl)piperidin-4-yl)amino)cyclohex-1-en-1-yl)-1H-pyrrolo[2,3-b]pyridin-6-yl)cyclopropanecarboxamide |
| 493) | N-(4-(4-((1-(2-fluoroisonicotinoyl)piperidin-4-yl)amino)cyclohex-1-en-1-yl)-1H-pyrrolo[2,3-b]pyridin-6-yl)cyclopropanecarboxamide |
| 494) | N-(4-(4-((1-(4-nitrobenzoyl)piperidin-4-yl)amino)cyclohex-1-en-1-yl)-1H-pyrrolo[2,3-b]pyridin-6-yl)cyclopropanecarboxamide |
| 495) | N-(4-(4-((1-(3,5-difluorobenzoyl)azetidin-3-yl)amino)cyclohex-1-en-1-yl)-1H-pyrrolo[2,3-b]pyridin-6-yl)cyclopropanecarboxamide |
| 496) | N-(4-(4-((1-(2-fluoroisonicotinoyl)azetidin-3-yl)amino)cyclohex-1-en-1-yl)-1H-pyrrolo[2,3-b]pyridin-6-yl)cyclopropanecarboxamide |
| 497) | N-(4-(4-((1-(2-methoxyisonicotinoyl)azetidin-3-yl)amino)cyclohex-1-en-1-yl)-1H-pyrrolo[2,3-b]pyridin-6-yl)cyclopropanecarboxamide |
| 498) | 4-((4-(6-(cyclopropanecarboxamido)-1H-pyrrolo[2,3-b]pyridin-4-yl)-2-fluorophenyl)amino)-N-phenylpiperidine-1-carboxamide |
| 499) | N-(4-(4-((1-(3,5-difluorobenzoyl)piperidin-4-yl)amino)-3-fluorophenyl)-1H-pyrrolo[2,3-b]pyridin-6-yl)cyclopropanecarboxamide |
| 500) | N-(4-(3-fluoro-4-((1-(2-fluoroisonicotinoyl)piperidin-4-yl)amino)phenyl)-1H-pyrrolo[2,3-b]pyridin-6-yl)cyclopropanecarboxamide |
| 501) | 4-((4-(6-(cyclopropanecarboxamido)-1H-pyrrolo[2,3-b]pyridin-4-yl)-2-fluorophenyl)amino)-N-(2,4-difluorophenyl)piperidine-1-carboxamide |
| 502) | N-(4-(4-(((2S)-1-(3,5-difluorobenzoyl)-2-methylpiperidin-4-yl)amino)phenyl)-1H-pyrrolo[2,3-b]pyridin-6-yl)cyclopropanecarboxamide |
| 503) | N-(4-(4-(((2S)-1-(2-fluoroisonicotinoyl)-2-methylpiperidin-4-yl)amino)phenyl)-1H-pyrrolo[2,3-b]pyridin-6-yl)cyclopropanecarboxamide |
| 504) | (2S)-4-((4-(6-(cyclopropanecarboxamido)-1H-pyrrolo[2,3-b]pyridin-4-yl)phenyl)amino)-2-methyl-N-(2,2,2-trifluoroethyl)piperidine-1-carboxamide |
| 505) | 4-((4-(6-(cyclopropanecarboxamido)-1H-pyrrolo[2,3-b]pyridin-4-yl)-2-fluorophenyl)amino)-N-(2,2,2-trifluoroethyl)piperidine-1-carboxamide |
| 506) | (2S)-4-((4-(6-(cyclopropanecarboxamido)-1H-pyrrolo[2,3-b]pyridin-4-yl)phenyl)amino)-N-(2,4-difluorophenyl)-2-methylpiperidine-1-carboxamide |
| 507) | N-(4-(4-((1-isonicotinoylpiperidin-4-yl)amino)phenyl)-1H-pyrrolo[2,3-b]pyridin-6-yl)cyclopropanecarboxamide |
| 508) | N-(4-(4-((1-(3,5-difluorobenzoyl)piperidin-4-yl)amino)phenyl)-1H-pyrrolo[2,3-b]pyridin-6-yl)cyclopropanecarboxamide |
| 509) | N-(4-(4-((1-(2-fluoroisonicotinoyl)piperidin-4-yl)amino)phenyl)-1H-pyrrolo[2,3-b]pyridin-6-yl)cyclopropanecarboxamide |
| 510) | N-(4-(4-((1-(3,5-difluorobenzoyl)azetidin-3-yl)amino)phenyl)-1H-pyrrolo[2,3-b]pyridin-6-yl)cyclopropanecarboxamide |
| 511) | 4-((4-(6-(cyclopropanecarboxamido)-1H-pyrrolo[2,3-b]pyridin-4-yl)phenyl)amino)-N-(2,4-difluorophenyl)piperidine-1-carboxamide |
| 512) | 4-((4-(6-(cyclopropanecarboxamido)-1H-pyrrolo[2,3-b]pyridin-4-yl)phenyl)amino)-N-(2,2,2-trifluoroethyl)piperidine-1-carboxamide |
| 513) | 3-((4-(6-(cyclopropanecarboxamido)-1H-pyrrolo[2,3-b]pyridin-4-yl)phenyl)amino)-N-(2,4-difluorophenyl)azetidine-1-carboxamide |
| 514) | 3-((4-(6-(cyclopropanecarboxamido)-1H-pyrrolo[2,3-b]pyridin-4-yl)phenyl)amino)-N-(2,2,2-trifluoroethyl)azetidine-1-carboxamide |
| 515) | N-(4-(4-((1-(2-cyanoacetyl)azetidin-3-yl)amino)phenyl)-1H-pyrrolo[2,3-b]pyridin-6-yl)cyclopropanecarboxamide |
| 516) | N-(4-(4-((1-(2-cyanoacetyl)piperidin-4-yl)amino)phenyl)-1H-pyrrolo[2,3-b]pyridin-6-yl)cyclopropanecarboxamide |
| 517) | N-(4-(4-((1-(3,3,3-trifluoropropanoyl)azetidin-3-yl)amino)phenyl)-1H-pyrrolo[2,3-b]pyridin-6-yl)cyclopropanecarboxamide |
| 518) | N-(4-(4-((1-(3,3,3-trifluoropropanoyl)piperidin-4-yl)amino)phenyl)-1H-pyrrolo[2,3-b]pyridin-6-yl)cyclopropanecarboxamide |

| | |
|---|---|
| 519) | N-(4-(4-(2-cyanoacetyl)phenyl)-1H-pyrrolo[2,3-b]pyridin-6-yl)cyclopropanecarboxamide |
| 520) | N-(4-(4-(1,1-dioxidothiomorpholine-4-carbonyl)phenyl)-1H-pyrrolo[2,3-b]pyridin-6-yl)cyclopropanecarboxamide |
| 521) | N-(4-(4-(thiomorpholine-4-carbonyl)phenyl)-1H-pyrrolo[2,3-b]pyridin-6-yl)cyclopropanecarboxamide |
| 522) | N-(4-(2-methyl-4-(morpholine-4-carbonyl)phenyl)-1H-pyrrolo[2,3-b]pyridin-6-yl)cyclopropanecarboxamide |
| 523) | N-(cyanomethyl)-4-(6-(cyclopropanecarboxamido)-1H-pyrrolo[2,3-b]pyridin-4-yl)benzamide |
| 524) | 4-(6-(cyclopropanecarboxamido)-1H-pyrrolo[2,3-b]pyridin-4-yl)-N-(2,2,2-trifluoroethyl)benzamide |
| 525) | 4-(6-(cyclopropanecarboxamido)-1H-pyrrolo[2,3-b]pyridin-4-yl)-3-methyl-N-(2,2,2-trifluoroethyl)benzamide |
| 526) | N-(cyanomethyl)-4-(6-(cyclopropanecarboxamido)-1H-pyrrolo[2,3-b]pyridin-4-yl)-3-methylbenzamide |
| 527) | N-(cyanomethyl)-4-(6-(cyclopropanecarboxamido)-1H-pyrrolo[2,3-b]pyridin-4-yl)-N,3-dimethylbenzamide |
| 528) | N-(cyanomethyl)-4-(6-(cyclopropanecarboxamido)-1H-pyrrolo[2,3-b]pyridin-4-yl)-2-fluorobenzamide |
| 529) | N-(cyanomethyl)-4-(6-(cyclopropanecarboxamido)-1H-pyrrolo[2,3-b]pyridin-4-yl)-2,6-difluorobenzamide |
| 530) | N-(cyanomethyl)-4-(6-(cyclopropanecarboxamido)-1H-pyrrolo[2,3-b]pyridin-4-yl)cyclohex-3-ene-1-carboxamide |
| 531) | 4-(6-(cyclopropanecarboxamido)-1H-pyrrolo[2,3-b]pyridin-4-yl)-N-(2,2,2-trifluoroethyl)cyclohex-3-ene-1-carboxamide |
| 532) | N-(2-cyanoethyl)-4-(6-(cyclopropanecarboxamido)-1H-pyrrolo[2,3-b]pyridin-4-yl)cyclohex-3-ene-1-carboxamide |
| 533) | N-(4-(4-((N-methylsulfamoyl)methyl)phenyl)-1H-pyrrolo[2,3-b]pyridin-6-yl)cyclopropanecarboxamide |
| 534) | N-(4-(4-((morpholinosulfonyl)methyl)phenyl)-1H-pyrrolo[2,3-b]pyridin-6-yl)cyclopropanecarboxamide |
| 535) | N-(4-(4-(2-(1,1-dioxidothiomorpholino)-2-oxoethyl)phenyl)-1H-pyrrolo[2,3-b]pyridin-6-yl)cyclopropanecarboxamide |
| 536) | N-(4-(4-(2-morpholino-2-oxoethyl)phenyl)-1H-pyrrolo[2,3-b]pyridin-6-yl)cyclopropanecarboxamide |
| 537) | N-(4-(4-(2-oxo-2-((2,2,2-trifluoroethyl)amino)ethyl)phenyl)-1H-pyrrolo[2,3-b]pyridin-6-yl)cyclopropanecarboxamide |
| 538) | N-(4-(4-(2-((1,1-dioxidotetrahydrothiophen-3-yl)amino)-2-oxoethyl)phenyl)-1H-pyrrolo[2,3-b]pyridin-6-yl)cyclopropanecarboxamide |
| 539) | N-(4-(4-(2-(methylamino)-2-oxoethyl)phenyl)-1H-pyrrolo[2,3-b]pyridin-6-yl)cyclopropanecarboxamide |
| 540) | N-(4-(4-(2-(dimethylamino)-2-oxoethyl)phenyl)-1H-pyrrolo[2,3-b]pyridin-6-yl)cyclopropanecarboxamide |
| 541) | N-(4-(4-(2-(ethylamino)-2-oxoethyl)phenyl)-1H-pyrrolo[2,3-b]pyridin-6-yl)cyclopropanecarboxamide |
| 542) | N-(4-(4-(2-(4-(methylsulfonyl)piperazin-1-yl)-2-oxoethyl)phenyl)-1H-pyrrolo[2,3-b]pyridin-6-yl)cyclopropanecarboxamide |
| 543) | N-(4-(4-(2-(4-acetylpiperazin-1-yl)-2-oxoethyl)phenyl)-1H-pyrrolo[2,3-b]pyridin-6-yl)cyclopropanecarboxamide |
| 544) | N-(4-(4-(2-(isoxazol-3-ylamino)-2-oxoethyl)phenyl)-1H-pyrrolo[2,3-b]pyridin-6-yl)cyclopropanecarboxamide |
| 545) | N-(4-(4-(2-(1,1-dioxidothiomorpholino)-2-oxoethyl)-2-methylphenyl)-1H-pyrrolo[2,3-b]pyridin-6-yl)cyclopropanecarboxamide |
| 546) | N-(4-(4-(2-(azetidin-1-yl)-2-oxoethyl)phenyl)-1H-pyrrolo[2,3-b]pyridin-6-yl)cyclopropanecarboxamide |
| 547) | N-(4-(4-(2-oxo-2-(pyrrolidin-1-yl)ethyl)phenyl)-1H-pyrrolo[2,3-b]pyridin-6-yl)cyclopropanecarboxamide |
| 548) | N-(4-(4-(2-(4-cyanopiperidin-1-yl)-2-oxoethyl)phenyl)-1H-pyrrolo[2,3-b]pyridin-6-yl)cyclopropanecarboxamide |
| 549) | N-(4-(4-(2-oxo-2-(4-oxopiperidin-1-yl)ethyl)phenyl)-1H-pyrrolo[2,3-b]pyridin-6-yl)cyclopropanecarboxamide |
| 550) | N-(4-(4-(2-(4-methylpiperazin-1-yl)-2-oxoethyl)phenyl)-1H-pyrrolo[2,3-b]pyridin-6-yl)cyclopropanecarboxamide |
| 551) | N-(4-(4-(2-(4-ethylpiperazin-1-yl)-2-oxoethyl)phenyl)-1H-pyrrolo[2,3-b]pyridin-6-yl)cyclopropanecarboxamide |
| 552) | N-(4-(4-(2-(4-isopropylpiperazin-1-yl)-2-oxoethyl)phenyl)-1H-pyrrolo[2,3-b]pyridin-6-yl)cyclopropanecarboxamide |
| 553) | N-(4-(4-(2-((2-cyanoethyl)amino)-2-oxoethyl)phenyl)-1H-pyrrolo[2,3-b]pyridin-6-yl)cyclopropanecarboxamide |
| 554) | tert-butyl 4-(2-(4-(6-(cyclopropanecarboxamido)-1H-pyrrolo[2,3-b]pyridin-4-yl)phenyl)acetyl)piperazine-1-carboxylate |
| 555) | tert-butyl 3-(2-(4-(6-(cyclopropanecarboxamido)-1H-pyrrolo[2,3-b]pyridin-4-yl)phenyl)acetamido)piperidine-1-carboxylate |
| 556) | N-(4-(4-(2-((1-methyl-1H-pyrazol-3-yl)amino)-2-oxoethyl)phenyl)-1H-pyrrolo[2,3-b]pyridin-6-yl)cyclopropanecarboxamide |
| 557) | N-(4-(4-(2-oxo-2-(piperidin-1-yl)ethyl)phenyl)-1H-pyrrolo[2,3-b]pyridin-6-yl)cyclopropanecarboxamide |

| | |
|---|---|
| 558) | N-(4-(4-(2-oxo-2-(piperazin-1-yl)ethyl)phenyl)-1H-pyrrolo[2,3-b]pyridin-6-yl)cyclopropanecarboxamide |
| 559) | N-(4-(4-(2-(1,1-dioxidothiomorpholino)-2-oxoethyl)-3-fluorophenyl)-1H-pyrrolo[2,3-b]pyridin-6-yl)cyclopropanecarboxamide |
| 560) | N-(4-(4-(2-oxo-2-thiomorpholinoethyl)phenyl)-1H-pyrrolo[2,3-b]pyridin-6-yl)cyclopropanecarboxamide |
| 561) | N-(4-(4-(2-(4,4-difluoropiperidin-1-yl)-2-oxoethyl)phenyl)-1H-pyrrolo[2,3-b]pyridin-6-yl)cyclopropanecarboxamide |
| 562) | N-(4-(4-(2-oxo-2-(4-(trifluoromethylsulfonyl)piperazin-1-yl)ethyl)phenyl)-1H-pyrrolo[2,3-b]pyridin-6-yl)cyclopropanecarboxamide |
| 563) | N-(4-(4-(2-(4-(ethylsulfonyl)piperazin-1-yl)-2-oxoethyl)phenyl)-1H-pyrrolo[2,3-b]pyridin-6-yl)cyclopropanecarboxamide |
| 564) | N-(4-(4-(2-oxo-2-(4-(propylsulfonyl)piperazin-1-yl)ethyl)phenyl)-1H-pyrrolo[2,3-b]pyridin-6-yl)cyclopropanecarboxamide |
| 565) | ethyl 4-(2-(4-(6-(cyclopropanecarboxamido)-1H-pyrrolo[2,3-b]pyridin-4-yl)phenyl)acetyl)piperazine-1-carboxylate |
| 566) | N-(4-(4-(2-oxo-2-(4-(N-(2,2,2-trifluoroethyl)sulfamoyl)piperazin-1-yl)ethyl)phenyl)-1H-pyrrolo[2,3-b]pyridin-6-yl)cyclopropanecarboxamide |
| 567) | N-(4-(4-(2-(3-cyanopyrrolidin-1-yl)-2-oxoethyl)phenyl)-1H-pyrrolo[2,3-b]pyridin-6-yl)cyclopropanecarboxamide |
| 568) | N-(4-(4-(2-(3-cyanoazetidin-1-yl)-2-oxoethyl)phenyl)-1H-pyrrolo[2,3-b]pyridin-6-yl)cyclopropanecarboxamide |
| 569) | N-(4-(4-(2-(3,3-difluoropyrrolidin-1-yl)-2-oxoethyl)phenyl)-1H-pyrrolo[2,3-b]pyridin-6-yl)cyclopropanecarboxamide |
| 570) | N-(4-(4-(2-oxo-2-(4-(trifluoromethyl)piperidin-1-yl)ethyl)phenyl)-1H-pyrrolo[2,3-b]pyridin-6-yl)cyclopropanecarboxamide |
| 571) | N-(4-(4-(2-(1,1-dioxidothiomorpholino)-1,1-difluoro-2-oxoethyl)phenyl)-1H-pyrrolo[2,3-b]pyridin-6-yl)cyclopropanecarboxamide |
| 572) | N-(4-(4-(1,1-difluoro-2-morpholino-2-oxoethyl)phenyl)-1H-pyrrolo[2,3-b]pyridin-6-yl)cyclopropanecarboxamide |
| 573) | N-(4-(4-(2-((cyanomethyl)(methyl)amino)-2-oxoethyl)phenyl)-1H-pyrrolo[2,3-b]pyridin-6-yl)cyclopropanecarboxamide |
| 574) | N-(4-(4-(2-(1-oxidothiomorpholino)-2-oxoethyl)phenyl)-1H-pyrrolo[2,3-b]pyridin-6-yl)cyclopropanecarboxamide |
| 575) | N-(4-(4-(2-(4-cyanopiperidin-1-yl)-1,1-difluoro-2-oxoethyl)phenyl)-1H-pyrrolo[2,3-b]pyridin-6-yl)cyclopropanecarboxamide |
| 576) | N-(4-(4-(2-(3-cyanomorpholino)-2-oxoethyl)phenyl)-1H-pyrrolo[2,3-b]pyridin-6-yl)cyclopropanecarboxamide |
| 577) | N-(4-(4-(1-(1,1-dioxidothiomorpholine-4-carbonyl)cyclopropyl)phenyl)-1H-pyrrolo[2,3-b]pyridin-6-yl)cyclopropanecarboxamide |
| 578) | N-(4-(1-(2-(1,1-dioxidothiomorpholino)-2-oxoethyl)-1,2,3,6-tetrahydropyridin-4-yl)-1H-pyrrolo[2,3-b]pyridin-6-yl)cyclopropanecarboxamide |
| 579) | N-(4-(6-(cyclopropanecarboxamido)-1H-pyrrolo[2,3-b]pyridin-4-yl)benzyl)morpholine-4-carboxamide |
| 580) | N-(4-(6-(cyclopropanecarboxamido)-1H-pyrrolo[2,3-b]pyridin-4-yl)benzyl)thiomorpholine-4-carboxamide 1,1-dioxide |
| 581) | N-(4-(4-((3-(2,2,2-trifluoroethyl)ureido)methyl)phenyl)-1H-pyrrolo[2,3-b]pyridin-6-yl)cyclopropanecarboxamide |
| 582) | N-(4-(4-(((3,4-difluorophenyl)sulfonamido)methyl)phenyl)-1H-pyrrolo[2,3-b]pyridin-6-yl)cyclopropanecarboxamide |
| 583) | N-(4-(4-(propylsulfonamidomethyl)phenyl)-1H-pyrrolo[2,3-b]pyridin-6-yl)cyclopropanecarboxamide |
| 584) | N-(4-(4-((1,1-dioxidothiomorpholino)methyl)phenyl)-1H-pyrrolo[2,3-b]pyridin-6-yl)cyclopropanecarboxamide |
| 585) | N-(4-(4-((4-oxopiperidin-1-yl)methyl)phenyl)-1H-pyrrolo[2,3-b]pyridin-6-yl)cyclopropanecarboxamide |
| 586) | N-(4-(4-((3-cyanoazetidin-1-yl)methyl)phenyl)-1H-pyrrolo[2,3-b]pyridin-6-yl)cyclopropanecarboxamide |
| 587) | N-(4-(4-((4-(methylsulfonyl)piperazin-1-yl)methyl)phenyl)-1H-pyrrolo[2,3-b]pyridin-6-yl)cyclopropanecarboxamide |
| 588) | N-(4-(4-((1,1-dioxidothiomorpholino)methyl)phenyl)-1H-pyrrolo[2,3-b]pyridin-6-yl)-2-methylcyclopropane-1-carboxamide |
| 589) | N-(4-(4-(1-(1,1-dioxidothiomorpholino)ethyl)phenyl)-1H-pyrrolo[2,3-b]pyridin-6-yl)cyclopropanecarboxamide |
| 590) | N-(4-(3,5-difluoro-4-(morpholinomethyl)phenyl)-1H-pyrrolo[2,3-b]pyridin-6-yl)cyclopropanecarboxamide |
| 591) | N-(4-(4-(2-(1,1-dioxidothiomorpholino)ethyl)phenyl)-1H-pyrrolo[2,3-b]pyridin-6-yl)cyclopropanecarboxamide |
| 592) | N-(6-(4-((1,1-dioxidothiomorpholino)methyl)phenyl)-9H-purin-2-yl)cyclopropanecarboxamide |
| 593) | N-(7-(4-((5-methyl-2H-tetrazol-2-yl)methyl)phenyl)-3H-imidazo[4,5-b]pyridin-5-yl)cyclopropanecarboxamide |
| 594) | N-(7-(4-((5-methyl-1H-tetrazol-1-yl)methyl)phenyl)-3H-imidazo[4,5-b]pyridin-5-yl)cyclopropanecarboxamide |
| 595) | N-(4-(4-(((1,1-dioxidotetrahydrothiophen-3-yl)amino)methyl)phenyl)-1H-pyrrolo[2,3-b]pyridin-6-yl)cyclopropanecarboxamide |

| | |
|---|---|
| 596) | N-(4-(4-(((1,1-dioxidotetrahydro-2H-thiopyran-4-yl)amino)methyl)phenyl)-1H-pyrrolo[2,3-b]pyridin-6-yl)cyclopropanecarboxamide |
| 597) | N-(6-(4-(((4-fluorophenyl)amino)methyl)phenyl)-9H-purin-2-yl)cyclopropanecarboxamide |
| 598) | N-(6-(4-(((3-fluorophenyl)amino)methyl)phenyl)-9H-purin-2-yl)cyclopropanecarboxamide |
| 599) | N-(4-(1-(1-((trifluoromethyl)sulfonyl)azetidin-3-yl)-1H-pyrazol-4-yl)-1H-pyrrolo[2,3-b]pyridin-6-yl)cyclopropanecarboxamide |
| 600) | N-(4-(1-(azetidin-3-yl)-1H-pyrazol-4-yl)-1H-pyrrolo[2,3-b]pyridin-6-yl)cyclopropanecarboxamide |
| 601) | N-(4-(1-(1-(ethylsulfonyl)azetidin-3-yl)-1H-pyrazol-4-yl)-1H-pyrrolo[2,3-b]pyridin-6-yl)cyclopropanecarboxamide |
| 602) | N-(4-(1-(1-(butylsulfonyl)azetidin-3-yl)-1H-pyrazol-4-yl)-1H-pyrrolo[2,3-b]pyridin-6-yl)cyclopropanecarboxamide |
| 603) | N-(4-(1-(1-(methylsulfonyl)azetidin-3-yl)-1H-pyrazol-4-yl)-1H-pyrrolo[2,3-b]pyridin-6-yl)cyclopropanecarboxamide |
| 604) | N-(4-(1-(1-(phenylsulfonyl)azetidin-3-yl)-1H-pyrazol-4-yl)-1H-pyrrolo[2,3-b]pyridin-6-yl)cyclopropanecarboxamide |
| 605) | N-(4-(1-(1-((3,4-difluorophenyl)sulfonyl)azetidin-3-yl)-1H-pyrazol-4-yl)-1H-pyrrolo[2,3-b]pyridin-6-yl)cyclopropanecarboxamide |
| 606) | N-(4-(1-(1-(cyclohexylsulfonyl)azetidin-3-yl)-1H-pyrazol-4-yl)-1H-pyrrolo[2,3-b]pyridin-6-yl)cyclopropanecarboxamide |
| 607) | N-(4-(1-(1-(methylsulfonyl)piperidin-4-yl)-1H-pyrazol-4-yl)-1H-pyrrolo[2,3-b]pyridin-6-yl)cyclopropanecarboxamide |
| 608) | N-(4-(1-(1-(ethylsulfonyl)piperidin-4-yl)-1H-pyrazol-4-yl)-1H-pyrrolo[2,3-b]pyridin-6-yl)cyclopropanecarboxamide |
| 609) | N-(4-(1-(1-((trifluoromethyl)sulfonyl)piperidin-4-yl)-1H-pyrazol-4-yl)-1H-pyrrolo[2,3-b]pyridin-6-yl)cyclopropanecarboxamide |
| 610) | N-(4-(1-(1-(2-cyanoacetyl)azetidin-3-yl)-1H-pyrazol-4-yl)-1H-pyrrolo[2,3-b]pyridin-6-yl)cyclopropanecarboxamide |
| 611) | N-(4-(1-(1-(cyanomethyl)piperidin-4-yl)-1H-pyrazol-4-yl)-1H-pyrrolo[2,3-b]pyridin-6-yl)cyclopropanecarboxamide |
| 612) | N-(4-(1-(3-(cyanomethyl)oxetan-3-yl)-1,2,3,6-tetrahydropyridin-4-yl)-1H-pyrrolo[2,3-b]pyridin-6-yl)cyclopropanecarboxamide |
| 613) | N-(4-(1-(3-(cyanomethyl)oxetan-3-yl)-3-methyl-1,2,3,6-tetrahydropyridin-4-yl)-1H-pyrrolo[2,3-b]pyridin-6-yl)cyclopropanecarboxamide |
| 614) | tert-butyl 3-(cyanomethyl)-3-(4-(6-(cyclopropanecarboxamido)-1H-pyrrolo[2,3-b]pyridin-4-yl)-3,6-dihydropyridin-1(2H)-yl)azetidine-1-carboxylate |
| 615) | N-(4-(1-(3-(cyanomethyl)azetidin-3-yl)-1,2,3,6-tetrahydropyridin-4-yl)-1H-pyrrolo[2,3-b]pyridin-6-yl)cyclopropanecarboxamide |
| 616) | N-(4-(1-(3-(cyanomethyl)-1-(ethylsulfonyl)azetidin-3-yl)-1,2,3,6-tetrahydropyridin-4-yl)-1H-pyrrolo[2,3-b]pyridin-6-yl)cyclopropanecarboxamide |
| 617) | N-(4-(1-(3-(cyanomethyl)-1-(isopropylsulfonyl)azetidin-3-yl)-1,2,3,6-tetrahydropyridin-4-yl)-1H-pyrrolo[2,3-b]pyridin-6-yl)cyclopropanecarboxamide |
| 618) | N-(4-(1-(3-(cyanomethyl)-1-((3-cyanopropyl)sulfonyl)azetidin-3-yl)-1,2,3,6-tetrahydropyridin-4-yl)-1H-pyrrolo[2,3-b]pyridin-6-yl)cyclopropanecarboxamide |
| 619) | N-(4-(1-(3-(cyanomethyl)-1-((trifluoromethyl)sulfonyl)azetidin-3-yl)-1,2,3,6-tetrahydropyridin-4-yl)-1H-pyrrolo[2,3-b]pyridin-6-yl)cyclopropanecarboxamide |
| 620) | N-(4-(1-(3-(cyanomethyl)-1-(piperidin-4-yl)azetidin-3 -yl)-1,2,3,6-tetrahydropyridin-4-yl)-1H-pyrrolo[2,3-b]pyridin-6-yl)cyclopropanecarboxamide |
| 621) | N-(4-(1-(3-(cyanomethyl)-1-(1-(4-(trifluoromethyl)thiazole-2-carbonyl)piperidin-4-yl)azetidin-3-yl)-1,2,3,6-tetrahydropyridin-4-yl)-1H-pyrrolo[2,3-b]pyridin-6-yl)cyclopropanecarboxamide |
| 622) | N-(4-(1-(1-(1-(2-cyanoacetyl)piperidin-4-yl)-3-(cyanomethyl)azetidin-3-yl)-1,2,3,6-tetrahydropyridin-4-yl)-1H-pyrrolo[2,3-b]pyridin-6-yl)cyclopropanecarboxamide |
| 623) | N-(4-(1-(3-(cyanomethyl)-1-((4-fluorophenyl)sulfonyl)azetidin-3-yl)-1,2,3,6-tetrahydropyridin-4-yl)-1H-pyrrolo[2,3-b]pyridin-6-yl)cyclopropanecarboxamide |
| 624) | 3-(cyanomethyl)-3-(4-(6-(cyclopropanecarboxamido)-1H-pyrrolo[2,3-b]pyridin-4-yl)-3,6-dihydropyridin-1(2H)-yl)-N-(2,2,2-trifluoroethyl)azetidine-1-carboxamide |
| 625) | N-(4-(1-(3-(cyanomethyl)-1-(3,3,3-trifluoropropanoyl)azetidin-3-yl)-1,2,3,6-tetrahydropyridin-4-yl)-1H-pyrrolo[2,3-b]pyridin-6-yl)cyclopropanecarboxamide |
| 626) | N-(4-(1-(3-(cyanomethyl)-1-(ethylsulfonyl)azetidin-3-yl)-3-methyl-1,2,3,6-tetrahydropyridin-4-yl)-1H-pyrrolo[2,3-b]pyridin-6-yl)cyclopropanecarboxamide |
| 627) | (S)-N-(4-(1-(3-(cyanomethyl)-1-(ethylsulfonyl)azetidin-3-yl)-3-methyl-1,2,3,6-tetrahydropyridin-4-yl)-1H-pyrrolo[2,3-b]pyridin-6-yl)cyclopropanecarboxamide |

| | |
|---|---|
| 628) | (S)-N-(4-(1-(3-(cyanomethyl)-1-((trifluoromethyl)sulfonyl)azetidin-3-yl)-3-methyl-1,2,3,6-tetrahydropyridin-4-yl)-1H-pyrrolo[2,3-b]pyridin-6-yl)cyclopropanecarboxamide |
| 629) | 4-(6-(cyclopropanecarboxamido)-1H-pyrrolo[2,3-b]pyridin-4-yl)phenyl ethanesulfonate |
| 630) | 4-(6-(cyclopropanecarboxamido)-1H-pyrrolo[2,3-b]pyridin-4-yl)phenyl 4-fluorobenzenesulfonate |
| 631) | 4-(6-(cyclopropanecarboxamido)-1H-pyrrolo[2,3-b]pyridin-4-yl)phenyl propane-1-sulfonate |
| 632) | 4-(6-(cyclopropanecarboxamido)-1H-pyrrolo[2,3-b]pyridin-4-yl)phenyl butane-1-sulfonate |
| 633) | 4-(6-(cyclopropanecarboxamido)-1H-pyrrolo[2,3-b]pyridin-4-yl)phenyl propane-2-sulfonate |
| 634) | 4-(6-(cyclopropanecarboxamido)-1H-pyrrolo[2,3-b]pyridin-4-yl)phenyl cyclohexanesulfonate |
| 635) | 4-(6-(cyclopropanecarboxamido)-1H-pyrrolo[2,3-b]pyridin-4-yl)phenyl 3-fluoropropane-1-sulfonate |
| 636) | 4-(6-(cyclopropanecarboxamido)-1H-pyrrolo[2,3-b]pyridin-4-yl)phenyl prop-2-ene-1-sulfonate |
| 637) | 4-(6-(cyclopropanecarboxamido)-1H-pyrrolo[2,3-b]pyridin-4-yl)phenyl cyclohexylmethanesulfonate |
| 638) | 4-(6-(cyclopropanecarboxamido)-1H-pyrrolo[2,3-b]pyridin-4-yl)phenyl (tetrahydrofuran-3-yl)methanesulfonate |
| 639) | 4-(6-(cyclopropanecarboxamido)-1H-pyrrolo[2,3-b]pyridin-4-yl)phenyl 3-cyanopropane-1-sulfonate |
| 640) | 4-(1-(3-cyanopropyl)-6-(cyclopropanecarboxamido)-1H-pyrrolo[2,3-b]pyridin-4-yl)phenyl 3-cyanopropane-1-sulfonate |
| 641) | N-(4-(4-((4-fluorobenzyl)oxy)phenyl)-1H-pyrrolo[2,3-b]pyridin-6-yl)cyclopropanecarboxamide |
| 642) | N-(4-(4-(2-morpholinoethoxy)phenyl)-1H-pyrrolo[2,3-b]pyridin-6-yl)cyclopropanecarboxamide |
| 643) | N-(4-(4-butoxyphenyl)-1H-pyrrolo[2,3-b]pyridin-6-yl)cyclopropanecarboxamide |
| 644) | N-(6-(4-((6-cyanopyridin-3-yl)methoxy)phenyl)-9H-purin-2-yl)cyclopropanecarboxamide |
| 645) | N-(4-(4-(ethylsulfonamido)cyclohexyl)-1H-pyrrolo[2,3-b]pyridin-6-yl)cyclopropanecarboxamide |
| 646) | N-(4-(8-(ethylsulfonyl)-8-azabicyclo[3.2.1]octan-3-yl)-1H-pyrrolo[2,3-b]pyridin-6-yl)cyclopropanecarboxamide |
| 647) | N-(4-(8-(cyclopropylsulfonyl)-8-azabicyclo[3.2.1]octan-3-yl)-1H-pyrrolo[2,3-b]pyridin-6-yl)cyclopropanecarboxamide |
| 648) | N-(4-(8-((3-fluoropropyl)sulfonyl)-8-azabicyclo[3.2.1]octan-3-yl)-1H-pyrrolo[2,3-b]pyridin-6-yl)cyclopropanecarboxamide |
| 649) | N-(4-(8-((3,4-difluorophenyl)sulfonyl)-8-azabicyclo[3.2.1]octan-3-yl)-1H-pyrrolo[2,3-b]pyridin-6-yl)cyclopropanecarboxamide |
| 650) | N-(4-(8-(cyclopropanecarbonyl)-8-azabicyclo[3.2.1]octan-3-yl)-1H-pyrrolo[2,3-b]pyridin-6-yl)cyclopropanecarboxamide |
| 651) | N-(4-(8-pentanoyl-8-azabicyclo[3.2.1]octan-3-yl)-1H-pyrrolo[2,3-b]pyridin-6-yl)cyclopropanecarboxamide |
| 652) | N-(4-(1-(2-cyanoacetyl)piperidin-4-yl)-1H-pyrrolo[2,3-b]pyridin-6-yl)cyclopropanecarboxamide |
| 653) | N-butyl-4-(6-(cyclopropanecarboxamido)-1H-pyrrolo[2,3-b]pyridin-4-yl)piperidine-1-carboxamide |
| 654) | 4-(6-(cyclopropanecarboxamido)-1H-pyrrolo[2,3-b]pyridin-4-yl)-N-(2,2,2-trifluoroethyl)piperidine-1-carboxamide |
| 655) | tert-butyl 4-(6-(cyclopropanecarboxamido)-1H-pyrrolo[2,3-b]pyridin-4-yl)-3-hydroxypiperidine-1-carboxylate |
| 656) | tert-butyl 4-(6-(cyclopropanecarboxamido)-1H-pyrrolo[2,3-b]pyridin-4-yl)-3-fluoropiperidine-1-carboxylate |
| 657) | N-(4-(8-(ethylcarbamothioyl)-8-azabicyclo[3.2.1]octan-3-yl)-1H-pyrrolo[2,3-b]pyridin-6-yl)cyclopropanecarboxamide |
| 658) | N-(4-(1-(ethylcarbamothioyl)piperidin-4-yl)-1H-pyrrolo[2,3-b]pyridin-6-yl)cyclopropanecarboxamide |
| 659) | N-(4-(1-(butylcarbamothioyl)piperidin-4-yl)-1H-pyrrolo[2,3-b]pyridin-6-yl)cyclopropanecarboxamide |
| 660) | N-(4-(4-(methylsulfonyl)piperazin-1-yl)-1H-pyrrolo[2,3-b]pyridin-6-yl)cyclopropanecarboxamide |
| 661) | N-(4-(8-(methylsulfonyl)-3,8-diazabicyclo[3.2.1]octan-3-yl)-1H-pyrrolo[2,3-b]pyridin-6-yl)cyclopropanecarboxamide |
| 662) | N-(4-(4-(((1-cyanocyclopropyl)methyl)sulfonyl)piperazin-1-yl)-1H-pyrrolo[2,3-b]pyridin-6-yl)cyclopropanecarboxamide |
| 663) | N-(4-(4-((3-fluoropropyl)sulfonyl)piperazin-1-yl)-1H-pyrrolo[2,3-b]pyridin-6-yl)cyclopropanecarboxamide |
| 664) | N-(4-(8-((3-cyanopropyl)sulfonyl)-3,8-diazabicyclo[3.2.1]octan-3-yl)-1H-pyrrolo[2,3-b]pyridin-6-yl)cyclopropanecarboxamide |
| 665) | N-(4-(8-(((1-(cyanomethyl)cyclopropyl)methyl)sulfonyl)-3,8-diazabicyclo[3.2.1]octan-3-yl)-1H-pyrrolo[2,3-b]pyridin-6-yl)cyclopropanecarboxamide |

| | |
|---|---|
| 666) | N-(4-(8-((4,4,4-trifluorobutyl)sulfonyl)-3,8-diazabicyclo[3.2.1]octan-3-yl)-1H-pyrrolo[2,3-b]pyridin-6-yl)cyclopropanecarboxamide |
| 667) | N-(4-(8-(((1-cyanocyclopropyl)methyl)sulfonyl)-3,8-diazabicyclo[3.2.1]octan-3-yl)-1H-pyrrolo[2,3-b]pyridin-6-yl)cyclopropanecarboxamide |
| 668) | N-(4-(4-(propylsulfonyl)piperazin-1-yl)-7H-pyrrolo[2,3-d]pyrimidin-2-yl)cyclopropanecarboxamide |
| 669) | N-(4-(8-(ethylsulfonyl)-3,8-diazabicyclo[3.2.1]octan-3-yl)-7H-pyrrolo[2,3-d]pyrimidin-2-yl)cyclopropanecarboxamide |
| 670) | (S)-N-(4-(3-(propylsulfonamido)pyrrolidin-1-yl)-7H-pyrrolo[2,3-d]pyrimidin-2-yl)cyclopropanecarboxamide |
| 671) | (S)-N-(4-(3-(allylsulfonamido)pyrrolidin-1-yl)-7H-pyrrolo[2,3-d]pyrimidin-2-yl)cyclopropanecarboxamide |
| 672) | (S)-N-(4-(3-(N-methylethylsulfonamido)pyrrolidin-1-yl)-1H-pyrrolo[2,3-b]pyridin-6-yl)cyclopropanecarboxamide |
| 673) | N-(4-(4-(morpholinosulfonyl)piperazin-1-yl)-1H-pyrrolo[2,3-b]pyridin-6-yl)cyclopropanecarboxamide |
| 674) | N-(4-(4-(N,N-dimethylsulfamoyl)piperazin-1-yl)-1H-pyrrolo[2,3-b]pyridin-6-yl)cyclopropanecarboxamide |
| 675) | N-(4-(4-(2-cyanoacetamido)piperidin-1-yl)-1H-pyrrolo[2,3-b]pyridin-6-yl)cyclopropanecarboxamide |
| 676) | N-(4-(4-(2-cyanoacetyl)piperazin-1-yl)-1H-pyrrolo[2,3-b]pyridin-6-yl)cyclopropanecarboxamide |
| 677) | N-(4-(8-(2-cyanoacetyl)-3,8-diazabicyclo[3.2.1]octan-3-yl)-1H-pyrrolo[2,3-b]pyridin-6-yl)cyclopropanecarboxamide |
| 678) | N-(4-(3-(2-cyanoacetyl)-3,8-diazabicyclo[3.2.1]octan-8-yl)-1H-pyrrolo[2,3-b]pyridin-6-yl)cyclopropanecarboxamide |
| 679) | N-(4-((1S,4S)-5-(2-cyanoacetyl)-2,5-diazabicyclo[2.2.1]heptan-2-yl)-1H-pyrrolo[2,3-b]pyridin-6-yl)cyclopropanecarboxamide |
| 680) | N-(4-((1S,4S)-5-(3-cyanopropanoyl)-2,5-diazabicyclo[2.2.1]heptan-2-yl)-1H-pyrrolo[2,3-b]pyridin-6-yl)cyclopropanecarboxamide |
| 681) | N-(4-((1R,4R)-5-(2-cyanoacetyl)-2,5-diazabicyclo[2.2.1]heptan-2-yl)-1H-pyrrolo[2,3-b]pyridin-6-yl)cyclopropanecarboxamide |
| 682) | N-(4-((1R,4R)-5-(3-cyanopropanoyl)-2,5-diazabicyclo[2.2.1]heptan-2-yl)-1H-pyrrolo[2,3-b]pyridin-6-yl)cyclopropanecarboxamide |
| 683) | N-(4-(4-(2-(1-cyanocyclopropyl)acetyl)piperazin-1-yl)-1H-pyrrolo[2,3-b]pyridin-6-yl)cyclopropanecarboxamide |
| 684) | N-(4-(4-(3-cyanopropanoyl)piperazin-1-yl)-1H-pyrrolo[2,3-b]pyridin-6-yl)cyclopropanecarboxamide |
| 685) | N-(4-(6-(2-cyanoacetyl)-3,6-diazabicyclo[3.1.1]heptan-3-yl)-1H-pyrrolo[2,3-b]pyridin-6-yl)cyclopropanecarboxamide |
| 686) | N-(4-(8-(3-cyanobenzoyl)-3,8-diazabicyclo[3.2.1]octan-3-yl)-1H-pyrrolo[2,3-b]pyridin-6-yl)cyclopropanecarboxamide |
| 687) | N-(4-(4-(2-cyanoacetyl)piperazin-1-yl)-7H-pyrrolo[2,3-d]pyrimidin-2-yl)cyclopropanecarboxamide |
| 688) | N-(4-(8-(2-cyanoacetyl)-3,8-diazabicyclo[3.2.1]octan-3-yl)-7H-pyrrolo[2,3-d]pyrimidin-2-yl)cyclopropanecarboxamide |
| 689) | N-(4-(8-(2-(1-cyanocyclopropyl)acetyl)-3,8-diazabicyclo[3.2.1]octan-3-yl)-7H-pyrrolo[2,3-d]pyrimidin-2-yl)cyclopropanecarboxamide |
| 690) | 4-(6-(cyclopropanecarboxamido)-1H-pyrrolo[2,3-b]pyridin-4-yl)-N-(2,2,2-trifluoroethyl)piperazine-1-carboxamide |
| 691) | 3-(6-(cyclopropanecarboxamido)-1H-pyrrolo[2,3-b]pyridin-4-yl)-N-(2,2,2-trifluoroethyl)-3,8-diazabicyclo[3.2.1]octane-8-carboxamide |
| 692) | tert-butyl 4-(6-(cyclopropanecarboxamido)-1H-pyrrolo[2,3-b]pyridine-4-yl)piperazin-1-carboxylate |
| 693) | tert-butyl 3-(6-(cyclopropanecarboxamido)-1H-pyrrolo[2,3-b]pyridin-4-yl)-3,8-diazabicyclo[3.2.1]octane-8-carboxylate |
| 694) | tert-butyl 8-(6-(cyclopropanecarboxamido)-1H-pyrrolo[2,3-b]pyridin-4-yl)-3,8-diazabicyclo[3.2.1]octane-3-carboxylate |
| 695) | tert-butyl 3-(2-(cyclopropanecarboxamido)-7H-pyrrolo[2,3-d]pyrimidin-4-yl)-3,8-diazabicyclo[3.2.1]octane-8-carboxylate |
| 696) | tert-butyl (S)-(1-(2-(cyclopropanecarboxamido)-7H-pyrrolo[2,3-d]pyrimidin-4-yl)pyrrolidin-3-yl)carbamate |
| 697) | tert-butyl (S)-(1-(6-(cyclopropanecarboxamido)-1H-pyrrolo[2,3-b]pyridin-4-yl)pyrrolidin-3-yl)carbamate |
| 698) | N-(4-(4-(isothiazol-5-ylmethyl)piperazin-1-yl)-1H-pyrrolo[2,3-b]pyridin-6-yl)cyclopropanecarboxamide |
| 699) | (S)-N-(4-(4-((2,2-difluorocyclopropyl)methyl)piperazin-1-yl)-1H-pyrrolo[2,3-b]pyridin-6-yl)cyclopropanecarboxamide |
| 700) | N-(4-(4-(3-(cyanomethyl)-1-(ethylsulfonyl)azetidin-3-yl)piperazin-1-yl)-1H-pyrrolo[2,3-b]pyridin-6-yl)cyclopropanecarboxamide |
| 701) | N-(4-(8-(3-(cyanomethyl)-1-(ethylsulfonyl)azetidin-3-yl)-3,8-diazabicyclo[3.2.1]octan-3-yl)-1H-pyrrolo[2,3-b]pyridin-6-yl)cyclopropanecarboxamide |
| 702) | N-(4-(4-(2-(1,1-dioxidothiomorpholino)-2-oxoethyl)piperazin-1-yl)-1H-pyrrolo[2,3-b]pyridin-6-yl)cyclopropanecarboxamide |
| 703) | N-(4-(8-(2-((R)-2-cyanopyrrolidin-1-yl)-2-oxoethyl)-3,8-diazabicyclo[3.2.1]octan-3-yl)-1H-pyrrolo[2,3-b]pyridin-6-yl)cyclopropanecarboxamide |

| | |
|---|---|
| 704) | N-(4-(8-(2-(1,1-dioxidothiomorpholino)-2-oxoethyl)-3,8-diazabicyclo[3.2.1]octan-3-yl)-7H-pyrrolo[2,3-d]pyrimidin-2-yl)cyclopropanecarboxamide |
| 705) | (S)-3-(4-(6-amino-1H-pyrrolo[2,3-b]pyridin-4-yl)-3-methyl-3,6-dihydropyridin-1(2H)-yl)-3-oxopropanenitrile |
| 706) | N-(4-(4-(ethylsulfonamido)-3-fluorophenyl)-1H-pyrrolo[2,3-b]pyridin-6-yl)cyclopentanecarboxamide |
| 707) | N-(4-(4-(ethylsulfonamido)-3-fluorophenyl)-1H-pyrrolo[2,3-b]pyridin-6-yl)cyclohexanecarboxamide |
| 708) | N-(4-(4-(ethylsulfonamido)-3-fluorophenyl)-1H-pyrrolo[2,3-b]pyridin-6-yl)propionamide |
| 709) | N-(4-(4-(ethylsulfonamido)-3-fluorophenyl)-1H-pyrrolo[2,3-b]pyridin-6-yl)-2-phenylacetamide |
| 710) | N-(4-(4-(ethylsulfonamido)-3-fluorophenyl)-1H-pyrrolo[2,3-b]pyridin-6-yl)acetamide |
| 711) | N-(4-(4-(ethylsulfonamido)-3-fluorophenyl)-1H-pyrrolo[2,3-b]pyridin-6-yl)isobutyramide |
| 712) | N-(4-(4-(ethylsulfonamido)-3-fluorophenyl)-1H-pyrrolo[2,3-b]pyridin-6-yl)butyramide |
| 713) | N-(4-(6-((cyclopropylmethyl)amino)-1H-pyrrolo[2,3-b]pyridin-4-yl)-2-fluorophenyl)ethanesulfonamide |
| 714) | (Z)-N-(4-(4-(ethylsulfonamido)phenyl)-1H-pyrrolo[2,3-b]pyridin-6-yl)-N'-methylcyclopropanecarboximidamide |
| 715) | N-(4-(4-(ethylsulfonamido)phenyl)-1H-pyrrolo[2,3-b]pyridin-6-yl)cyclopropanecarbothioamide |
| 716) | N-(4-(4-(ethylsulfonamido)-3-fluorophenyl)-1H-pyrrolo[2,3-b]pyridin-6-yl)cyclopropanesulfonamide |
| 717) | 1-cyclopropyl-3-(4-(4-((1,1-dioxidothiomorpholino)methyl)phenyl)-1H-pyrrolo[2,3-b]pyridin-6-yl)urea |
| 718) | N-(4-(2-(dimethylamino)-7H-pyrrolo[2,3-d]pyrimidin-4-yl)phenyl)-3,4-difluorobenzenesulfonamide |
| 719) | N-(2-fluoro-4-(2-(phenylamino)-7H-pyrrolo[2,3-d]pyrimidin-4-yl)phenyl)ethanesulfonamide |
| 720) | N-(4-(2-(phenylamino)-7H-pyrrolo[2,3-d]pyrimidin-4-yl)phenyl)ethanesulfonamide |
| 721) | 3-oxo-3-(3-(2-(phenylamino)-7H-pyrrolo[2,3-d]pyrimidin-4-yl)-3,8-diazabicyclo[3.2.1]octan-8-yl)propanenitrile |

Hereinafter, unless otherwise indicated for convenience, the compound of the formula 1 comprises and refers to all of a compound of the formula 1 according to the present invention, a stereoisomer thereof and a pharmaceutically acceptable salt thereof.

The compound according to the present invention may form a pharmaceutically acceptable salt. Such pharmaceutically acceptable salt includes an acid-addition salt, wherein the acid forms a nontoxic acid-addition salt, for example, an acid-addition salt formed by means of an inorganic acid such as hydrochloric acid, sulfuric acid, nitric acid, phosphoric acid, hydrobromic acid, hydriodic acid, etc.; an organic carbonic acid such as tartaric acid, formic acid, citric acid, acetic acid, trichloroacetic acid, trifluoroacetic acid, gluconic acid, benzoic acid, lactic acid, fumaric acid, maleic acid, etc.; a sulphonic acid such as methanesulfonic acid, benzenesulfonic acid, p-toluenesulfonic acid, naphthalenesulfonic acid or the like; etc. The compound of the formula 1 according to the present invention may be converted into salt thereof by means of a conventional method.

Meanwhile, the compounds according to the present invention may have asymmetric carbons, and may exist as an R or S isomer, a racemate, a diastereomer mixture and an individual diastereomer, wherein all the isomers and mixtures are included in the scope of the present invention. In other words, in caseasymmetric carbon(s) is included in a structure of the formula 1, it should be understood that all the stereoisomers are included therein, unless its direction is separately described.

Method for Preparing Compound of Formula 1

The present invention also provides a method for preparing a compound of a formula 1. Hereinafter, a method for preparing the compound of the formula 1 is described based on illustrative reaction formulas for better understanding of the present invention, but it should be understood that those skilled in the art, to which the present invention pertains, may prepare the compound of the formula 1 by means of various methods based on a structure of the formula 1, wherein such methods are all included in the scope of the present invention. In other words, it should be understood that it is possible to prepare the compound of the formula 1 by arbitrarily combining the several synthesis methods either described in the present specification or disclosed in prior art, wherein such preparation falls in the scope of the present invention. In reaction formulas below, all of the substituents are as defined above, unless otherwise indicated.

In case of acid, base and reaction solvent used in the compounds of the present invention, those generally used in the art may be used without limitation. For example, as acid, an inorganic acid such as hydrochloric acid, sulfuric acid, nitric acid, phosphoric acid, hydrobromic acid, hydriodic acid, etc.; an organic carbonic acid such as tartaric acid, formic acid, citric acid, acetic acid, adipic acid, trichloroacetic acid, trifluoroacetic acid, gluconic acid, benzoic acid, lactic acid, fumaric acid, maleic acid, etc.; and a sulphonic acid such as methanesulfonic acid, benzenesulfonic acid, p-toluenesulfonic acid, naphthalenesulfonic acid or the like may be used. As base, NaH, $K_2CO_3$, $Na_2CO_3$, $NaHCO_3$, $K_3PO_4$, KOH, NaOH, LiOH, n-BuLi, sec-BuLi, LiHMDS, etc. may be used. As reaction solvent, DCM, THF, dioxane, MeOH, EtOH, hexane, EtOAC, ether, DMF, DMSO, toluene, xylene, etc., or mixed solvents thereof, etc., may be used.

A synthesis method for the compound of the formula 1 above according to the present invention may be indicated as an example such as a following a reaction formula 1 or 2:

[Reaction Formula 1]

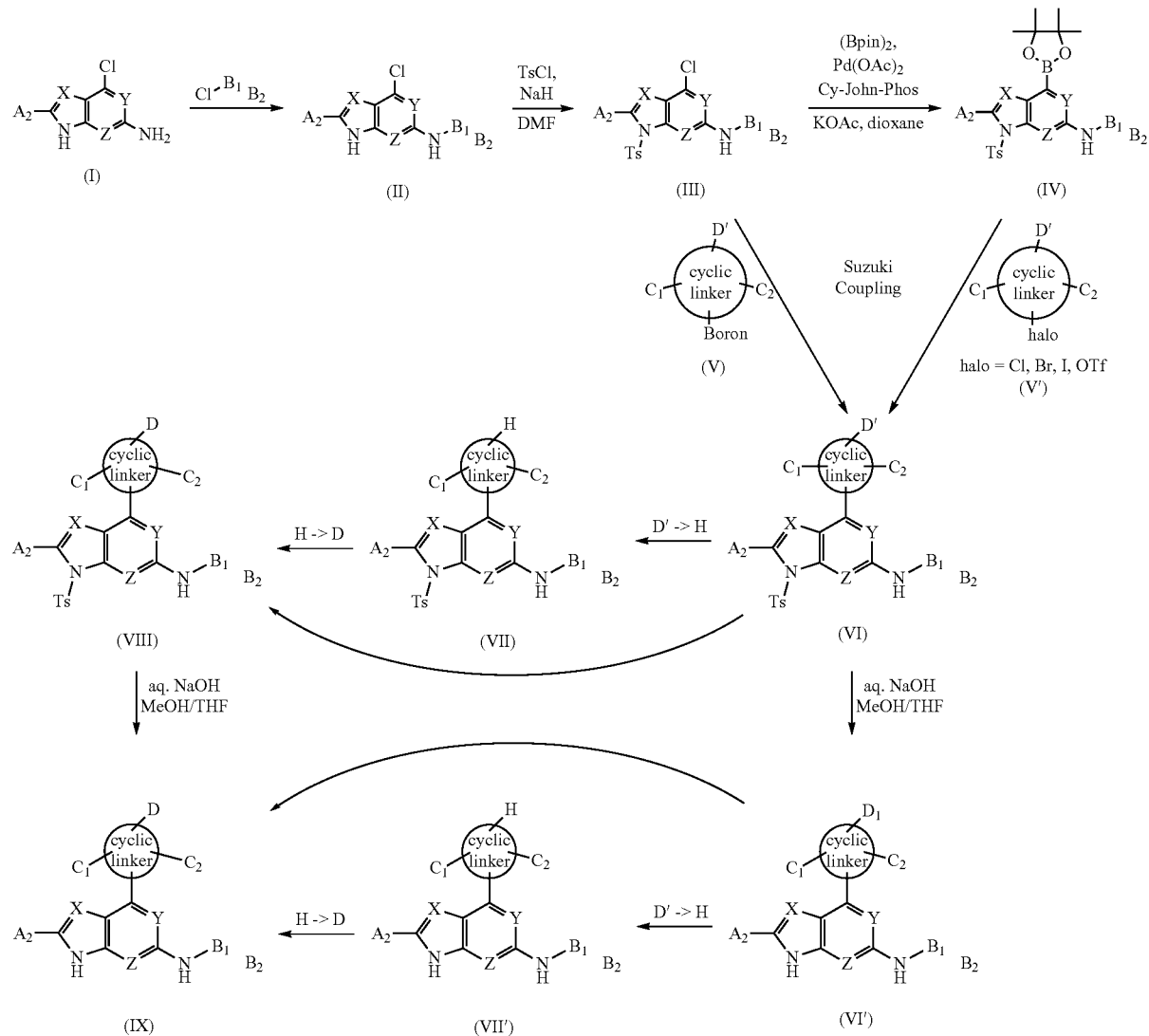

wherein
A2, B1, B2, C1, C2, X, Y, Z and cyclic linker are as defined in the formula 1; and D and D' are analogues for introducing D1-D2-D3-D4 defined in the formula 1 or D1-D2-D3-D4 themselves.

In the reaction formula 1 above, in case of halo=OTf, an intermediate compound

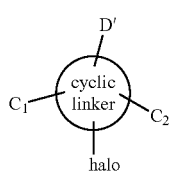

may be synthesized through a method of a following reaction formula 1-1:

[Reaction Formula 1-1]

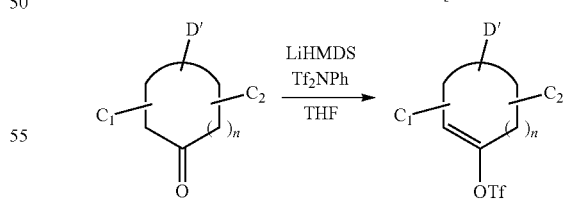

wherein
C1, C2 and D' are respectively identical to those defined in the reaction formula 1 above; and ( )n represents a polygonal cyclic compound.

Besides the method of the reaction formula 1 above, the synthesis may be also performed through a following reaction formula 2:

[Reaction Formula 2]

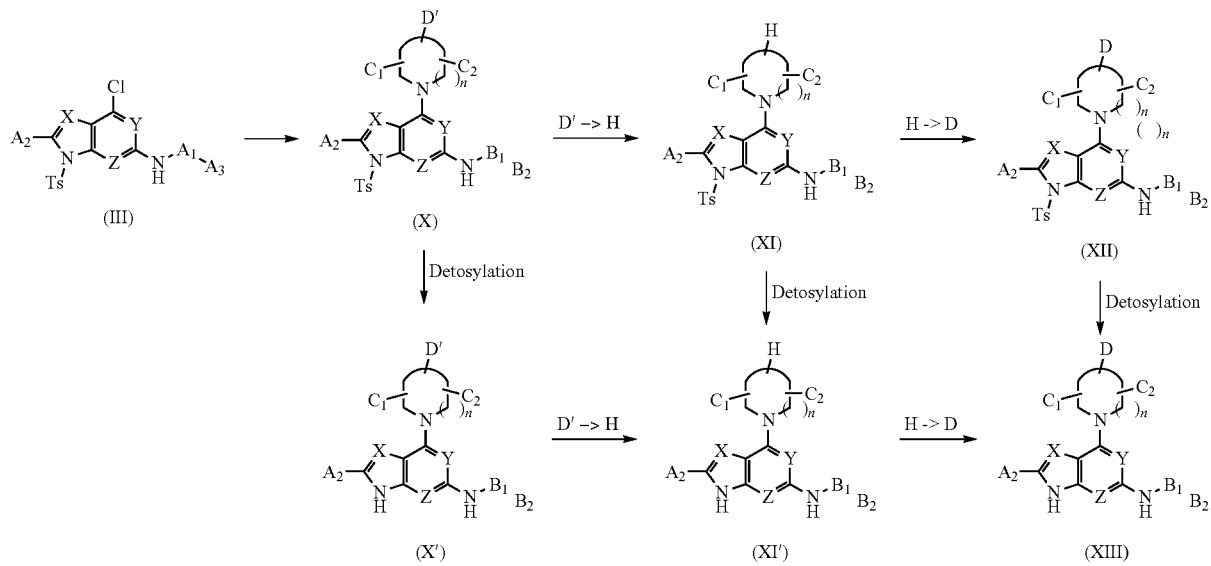

wherein

A compound (III) corresponds to compound (III) of the reaction formula 1.

A2, B1, B2, C1, C2, X, Y, Z and cyclic linker are as defined in the formula 1; and D and D' are analogues for introducing D1-D2-D3-D4 defined in the formula 1 or D1-D2-D3-D4 themselves.

In the reaction formula 1 above, a compound (I) may be conventionally purchased or synthesized.

The compound of the formula 1 according to the present invention may be separated or purified from products of the reaction formulas 1 and 2 above by means of several methods such as crystallization, silica gel column chromatography, etc. In this way, the compound according to the present invention, as well as an initiation, an intermediate, etc., for preparing the same may be synthesized by means of various methods, and it should be understood that such methods are included in the scope of the present invention with regard to a preparation for the compound of the formula 1.

Medical Use of Compound of Formula 1

The present invention provides a medical use of a compound represented by a following formula 1, a stereoisomer thereof, or a pharmaceutically acceptable salt thereof:

[Formula 1]

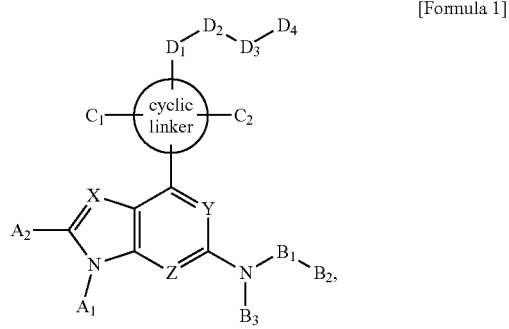

wherein the formula 1 above is as defined above.

According to one specific embodiment of the present invention, the present invention provides a pharmaceutical composition for treating or preventing diseases related to protein kinase, wherein it comprises a compound represented by the formula 1 above, a stereoisomer thereof or a pharmaceutically acceptable salt thereof as an effective component.

According to other specific embodiment of the present invention, the present invention provides a use of the compound of the formula 1 above, the stereoisomer thereof or the pharmaceutically acceptable salt thereof, for preparing a drug for treating cancer, autoimmune disease, neurological disease, metabolic disease or infection.

According to another specific embodiment of the present invention, the present invention provides a method for treating cancer, autoimmune disease, neurological disease, metabolic disease or infection, wherein the method comprises administering a therapeutically effective dose of the compound of the formula 1 above, the stereoisomer thereof or the pharmaceutically acceptable salt thereof.

According to another specific embodiment of the present invention, the present invention also provides a method for inhibiting a protein kinase, wherein the method comprises administering a therapeutically effective dose of the compound of the formula 1 above, the stereoisomer thereof or the pharmaceutically acceptable salt thereof.

The compound of the formula 1 according to the present invention, the stereoisomer thereof or the pharmaceutically acceptable salt thereof show a protein kinase inhibition activity, thus achieving a remarkable effect of preventing or treating diseases related to protein kinase.

In the present invention, the said diseases related to protein kinase comprise cancer, autoimmune disease, neurological disease, metabolic disease or infection.

Advantageous Effects

A compound represented by a formula 1 according to the present invention, a stereoisomer thereof or a pharmaceutically acceptable salt thereof have a protein kinase inhibition activity, thus achieving a remarkably excellent effect of preventing or treating diseases related to protein kinase.

MODE FOR INVENTION

Hereinafter, preferred Examples will be suggested for better understanding of the present invention. However, the following Examples are provided only for the purpose of illustrating the present invention, and thus the present invention is not limited thereto.

Various synthesis methods of a starting material for synthesizing a compound according to the present invention have been known. If the said starting material is available on the market, it may be purchased from its supplier and then used. As a reagent supplier, there are companies such as Sigma-Aldrich, TCI, Wako, Kanto, Fluorchem, Acros, Alfa, Fluka, Combi-Blocks, Dae-Jung, etc., but not limited thereto. Also, except as otherwise specified, all the materials available on the market may be used without any additional purification.

Hereinafter, the following Examples may be appropriately changed and modified by those skilled in the art within the scope of the present invention.

Preparing Example: Synthesis of N-(4-(4,4,5,5-tetramethyl-1,3,2-dioxaborolan-2-yl)-1-tosyl-1H-pyrrolo[2,3-b]pyridine-6-yl)cyclopropanecarboxamide

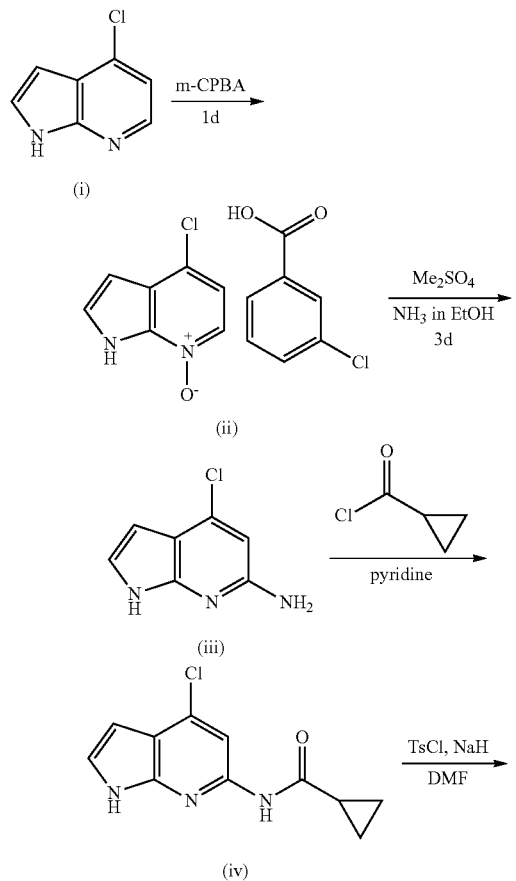

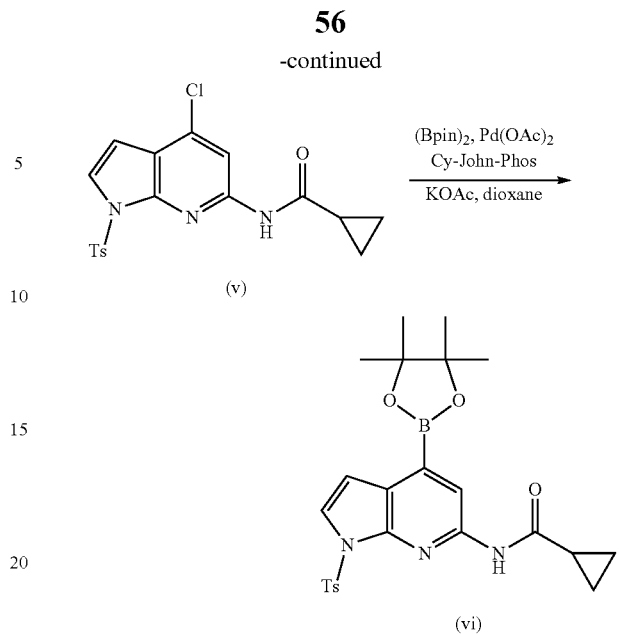

[Step 1] Synthesis of 4-chloro-1H-pyrrolo[2,3-b]pyridine 7-oxide 3-chlorobenzoate

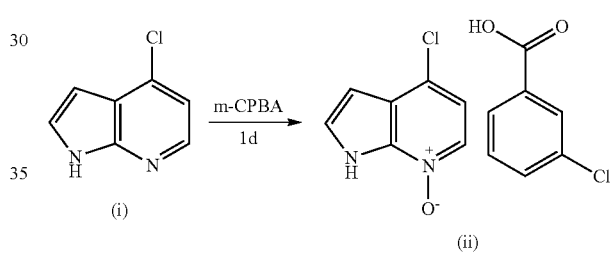

4-chloro-7-azaindole (15.0 g, 98.3 mmol) was dissolved in 800 ml of n-butyl acetate/n-heptane=3/5 (v/v), and then m-chloroperoxybenzoic acid (77%, 24.2 g, 108.1 mmol) was slowly added dropwise thereto at 0° C. and stirred at room temperature for 12 hours. A produced solid was filtered out and dried under reduced pressure. Finally, the title compound (30 g, 94%) was accordingly obtained.

$^1$H NMR (400 MHz, DMSO-$d_6$) δ 13.37 (br s, 1H), 12.90 (br s, 1H), 8.15 (d, J=6.6 Hz, 1H), 7.89 (m, 2H) 7.68 (d, J=8.0 Hz, 1H), 7.56 (d, J=3.1 Hz, 1H), 7.52 (t, J=8.1 Hz, 1H), 7.20 (d, J=6.6 Hz, 1H), 6.58 (d, J=3.1 Hz, 1H).

MS (ESI+) m/z 169, 171 (M+H)$^+$

[Step 2] Synthesis of 4-chloro-1H-pyrrolo[2,3-b]pyridine-6-amine

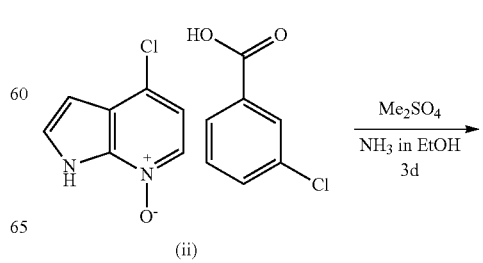

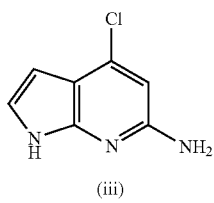

(iii)

The compound (30 g, 92.3 mmol) obtained in the step 1 was suspended in acetonitrile (300 ml), and then dimethyl sulfate (9.6 ml, 101.5 mmol) was added dropwise thereto at room temperature, then warmed up to 55° C., and then stirred for 12 hours.

The reaction mixture was cooled down to 0° C., and then an excessive amount of ammonia ethanol solution was added thereto, then warmed up to 45° C., and then stirred for 3 days. After that, the resulting mixture was cooled down to room temperature, and then an insoluble solid was filtered out and removed. After that, the remaining solution was concentrated under reduced pressure, then dissolved in dichloromethane (1 L), then washed by means of 10% sodium carbonate aqueous solution, and then dried by means of magnesium sulfate anhydrous. After that, the remaining filtered solution was concentrated under reduced pressure. The resulting concentrate was separated via column chromatography, from which the title compound (10 g, 42.4 mmol) was accordingly obtained.

$^1$H NMR (400 MHz, DMSO-d$_6$) δ 11.16 (s, 1H), 7.00 (s, 1H), 6.33 (s, 1H), 6.19 (s, 1H), 5.83 (s, 2H)

MS (ESI+) m/z 168, 170 (M+H)$^+$

[Step 3] Synthesis of N-(4-chloro-1H-pyrrolo[2,3-b]pyridine-6-yl)cyclopropanecarboxamide

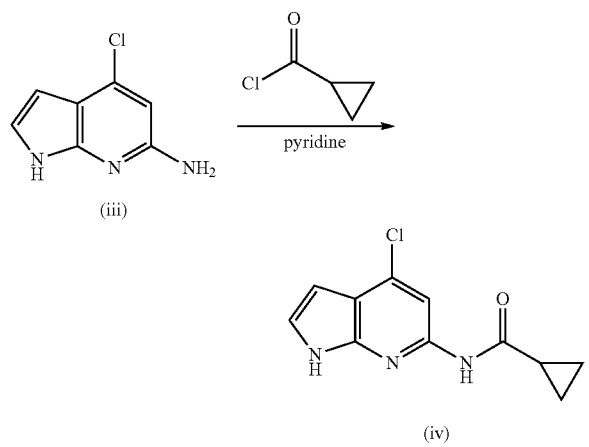

The compound (11.0 g, 65.6 mmol) obtained in the step 2 was dissolved in pyridine (100 ml), and then cyclopropanecarbonylchloride (7.5 g, 72.2 mmol) was slowly added dropwise thereto at 0° C. and stirred at the same temperature for 1 hour. The reaction mixture was added to water (350 ml), and then a produced solid was filtered out and dried under reduced pressure. Finally, the title compound (12.7 g, 53.9 mmol) was accordingly obtained.

$^1$H NMR (400 MHz, DMSO-d$^6$) δ 11.77 (s, 1H), 10.79 (s, 1H), 8.02 (s, 1H), 7.44 (d, 1H), 6.25 (d, 1H), 2.00 (m, 1H), 0.88 (m, 4H)

MS (ESI+) m/z 236, 238 (M+H)$^+$

[Step 4] Synthesis of N-(4-chloro-1-tosyl-1H-pyrrolo[2,3-b]pyridine-6-yl)cyclopropanecarboxamide

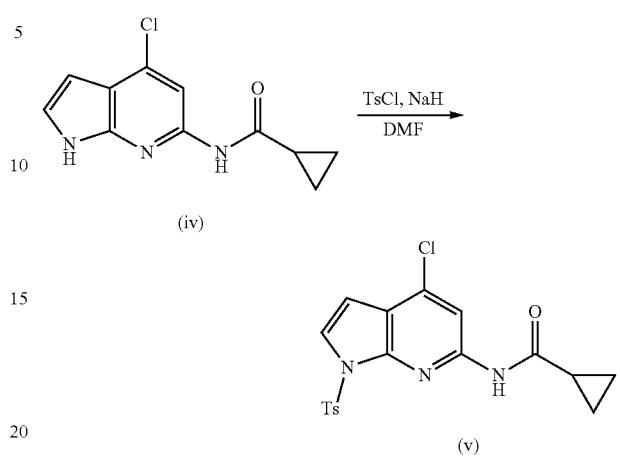

The compound (12.7 g, 53.9 mmol) obtained in the step 3 was dissolved in dimethylformamide (100 ml), then sodium hydride (3.2 g, 80.8 mmol) was slowly added dropwise thereto at 0° C., and then tosyl chloride (11.3 g, 59.3 mmol) was slowly added dropwise thereto and stirred for 30 minutes. Ethyl acetate (300 ml) was added to the resulting mixture, then washed by means of water (300 ml, twice), and then dried by means of magnesium sulfate anhydrous. After that, the remaining filtered solution was distilled under reduced pressure and separated via column chromatography, from which the title compound (13.0 g, 33.3 mmol) was accordingly obtained.

$^1$H NMR (400 MHz, DMSO-d$_6$) δ 11.13 (s, 1H), 8.16 (m, 3H), 7.80 (s, 1H), 7.42 (m, 2H), 6.74 (s, 1H), 2.34 (s, 3H), 2.08 (m, 1H), 0.87 (m, 4H)

MS (ESI+) m/z 390, 392 (M+H)$^+$

[Step 5] Synthesis of N-(4-(4,4,5,5-tetramethyl-1,3,2-dioxaborolan-2-yl)-1-tosyl-1H-pyrrolo[2,3-b]pyridine-6-yl)cyclopropanecarboxamide

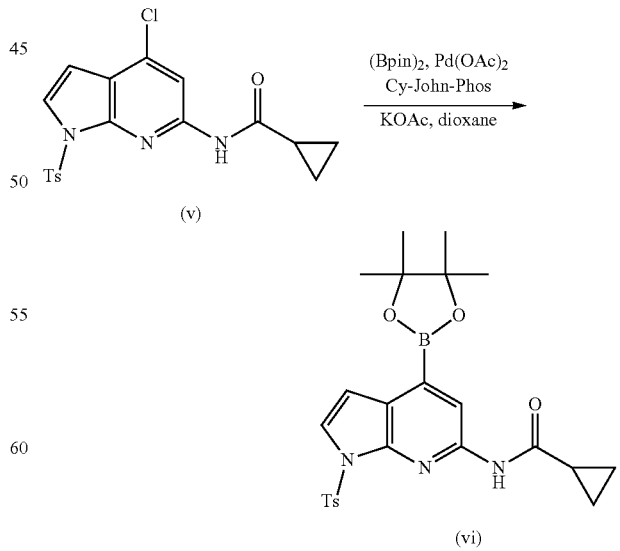

The compound (20.0 g, 51.3 mmol) obtained in the step 4 as well as bis(pinacolato)diboron (26.0 g, 102.6 mmol), palladium acetate (0.2 g, 1.02 mmol), 2-(dicyclohexyl)phosphinobiphenyl (0.7 g, 2.05 mmol) and potassium acetate (10.1 g, 102.6 mmol) were added to dioxane (200 ml) and warmed at 100° C. for 2 hours. The resulting mixture was cooled down to room temperature and distilled under reduced pressure. After that, dichloromethane (300 ml) was added thereto and washed by means of distilled water (300 ml, twice). A separated organic layer was dried by means of magnesium sulfate anhydrous, and then the remaining filtered solution was distilled under reduced pressure and separated via column chromatography, from which the title compound (24.0 g, 49.8 mmol) was accordingly obtained.

$^1$H NMR (400 MHz, DMSO-d$_6$) δ 10.75 (s, 1H), 8.34 (s, 1H), 8.16 (d, 2H), 7.74 (d, 1H), 7.41 (d, 2H), 6.82 (d, 1H), 2.33 (s, 3H), 2.15 (m, 1H), 1.30 (s, 12H), 0.87 (m, 4H)

Example 1: Synthesis of N-(4-(4-(ethylsulfonamido)-3-fluorophenyl)-1H-pyrrolo[2,3-b]pyridin-6-yl)cyclopropanecarboxamide

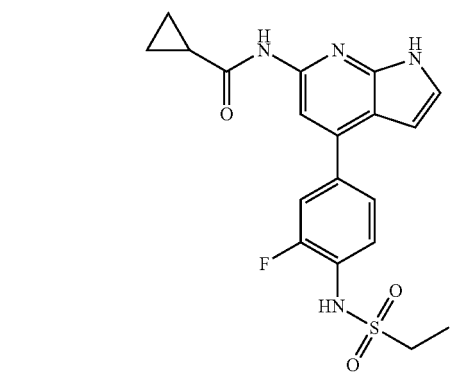 [SMILES: CCS(=O)(=O)Nc1ccc(-c2cc(NC(=O)C3CC3)nc3[nH]ccc23)cc1F]

[Step 1]

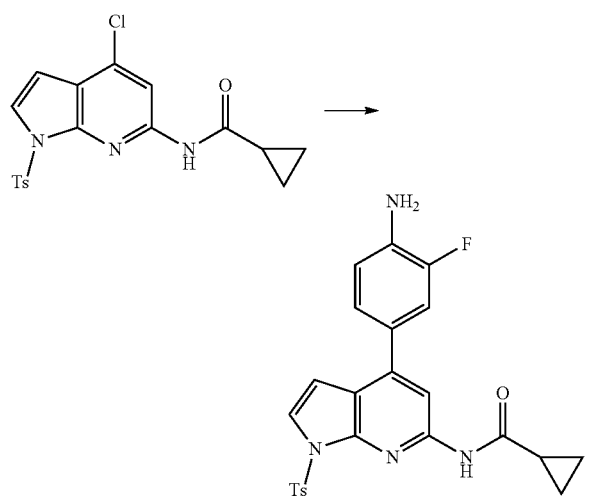

4.0 g (10.3 mmol) of N-(4-chloro-1-tosyl-1H-pyrrolo[2,3-b]pyridine-6-yl)cyclopropanecarboxamide prepared from the reaction formula 3 above was dissolved in DMF/H$_2$O=2:1 solution, and then 2.7 g (12.4 mmol) of 2-fluoro-4-(4,4,5,5-tetramethyl-1,3,2-dioxaborolan-2-yl)aniline, 1.3 g (1.5 mmol) of Pd(dppf)Cl$_2$ and 2.6 g (12.4 mmol) of K$_3$PO$_4$ were inserted thereinto and stirred at 80-90° C. for 1 hour. Once the reaction was completed, the said mixture was cooled down at room temperature, then water was added thereto, and then an extraction using ethyl acetate was performed. After that, a solution extracted therefrom was dried by means of magnesium sulfate anhydrous and concentrated under reduced pressure, from which a residue was accordingly obtained. The residue was separated via silica gel column chromatography (n-hexane/ethyl acetate=2:1), from which N-(4-(4-amino-3-fluorophenyl)-1-tosyl-1H-pyrrolo[2,3-b]pyridine-6-yl)cyclopropanecarboxamide was accordingly obtained.

MS(ESI+) m/z 465 (M+H)$^+$

[Step 2]

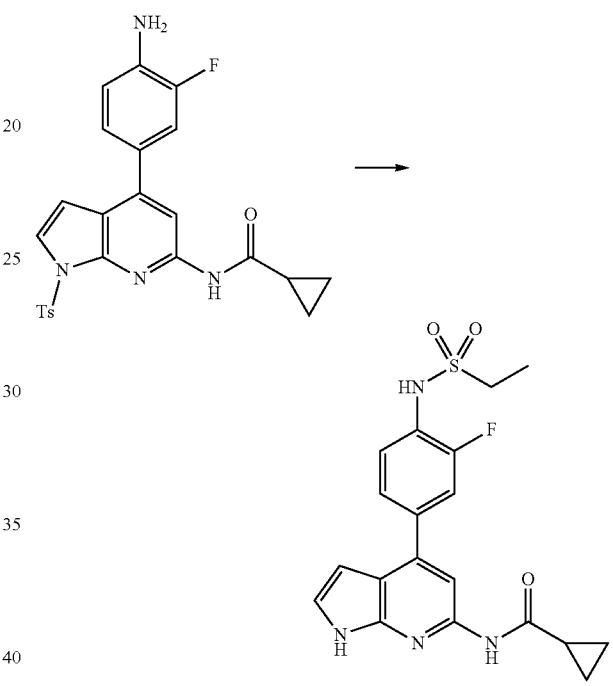

N-(4-(4-amino-3-fluorophenyl)-1-tosyl-1H-pyrrolo[2,3-b]pyridine-6-yl)cyclopropanecarboxamide (100 mg) obtained in the step 1 above was inserted into dichloromethane, and then 3 equivalent of Et$_3$N was added thereto. 2 equivalent of ethanesulfonyl chloride was inserted into the said mixture and stirred at room temperature. Once the reaction was completed, d-HCl was added to the said mixture, then an extraction using dichloromethane was performed, and then an organic layer was separated. After concentrating the mixture, the resulting concentrate was dissolved in MeOH/THF (1:1) solution, and then 2N sodium hydroxide aqueous solution was added thereto and stirred at 30-40° C. for 4 hours. Once the reaction was completed, the said mixture was cooled down to room temperature, and saturated NH$_4$Cl aqueous solution was added thereto while being stirred. A produced solid was filtered out, from which N-(4-(4-(4-(ethylsulfonamido)-3-fluorophenyl)-1H-pyrrolo[2,3-b]pyridine-6-yl)cyclopropanecarboxamide was accordingly obtained.

$^1$H NMR (400 MHz, DMSO-d$_6$) δ 11.60 (s, 1H), 10.66 (s, 1H), 9.82 (s, 1H), 8.02 (s, 1H), 7.64-7.52 (m, 3H), 7.49-7.41 (m, 1H), 6.61-6.53 (m, 1H), 3.18 (q, J=7.2 Hz, 2H), 2.04 (dd, J=5.0, 10.1 Hz, 1H), 1.29 (t, J=7.3 Hz, 3H), 0.89-0.78 (m, 4H).

MS(ESI+) m/z 403 (M+H)$^+$

Examples 2 to 213

Hereinafter, in Examples 2 to 213, a corresponding compound was synthesized by means of the same method as shown in Example 1 or prepared by means of an appropriate reactant under the consideration of the reaction formula 1 as well as a structure of the compound to be prepared.

Example 2: Synthesis of N-(4-(4-((3,4-difluorophenyl)sulfonamido)phenyl)-1H-pyrrolo[2,3-b]pyridin-6-yl)cyclopropanecarboxamide

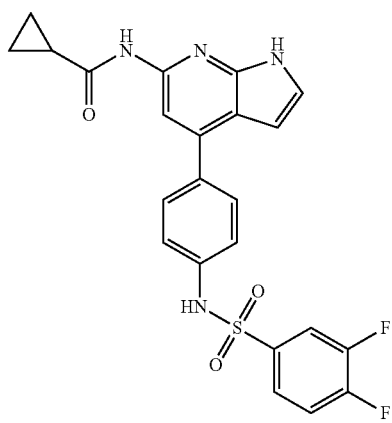 [SMILES: O=C(Nc1cc(-c2ccc(NS(=O)(=O)c3ccc(F)c(F)c3)cc2)c2cc[nH]c2n1)C1CC1]

MS(ESI+) m/z 469 (M+H)$^+$

Example 3: Synthesis of N-(4-(4-((3-fluoropropyl)sulfonamido)phenyl)-1H-pyrrolo[2,3-b]pyridin-6-yl)cyclopropanecarboxamide

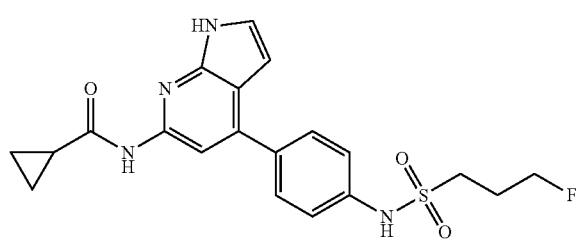 [SMILES: O=C(Nc1cc(-c2ccc(NS(=O)(=O)CCCF)cc2)c2cc[nH]c2n1)C1CC1]

$^1$H NMR (400 MHz, Methanol-d$_4$) δ 7.89 (s, 1H), 7.82-7.74 (m, 2H), 7.48-7.37 (m, 2H), 7.32 (d, J=3.6 Hz, 1H), 6.60 (d, J=3.6 Hz, 1H), 4.59 (s, 1H), 4.47 (s, 1H), 3.27 (d, J=5.6 Hz, 1H), 2.32-2.10 (m, 2H), 1.12 (d, J=6.1 Hz, 1H), 0.95 (ddt, J=3.1, 8.1, 40.7 Hz, 5H).

MS(ESI+) m/z 417 (M+H)$^+$

Example 4: Synthesis of N-(4-(4-(ethylsulfonamido)phenyl)-1H-pyrrolo[2,3-b]pyridin-6-yl)cyclopropanecarboxamide

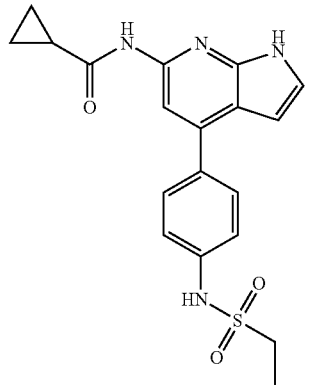

$^1$H NMR (400 MHz, DMSO-d$_6$) δ 11.51 (s, 1H), 10.59 (s, 1H), 10.01 (s, 1H), 7.99 (s, 1H), 7.75-7.63 (m, 2H), 7.46-7.29 (m, 3H), 6.54 (dd, J=1.9, 3.5 Hz, 1H), 3.17 (d, J=7.4 Hz, 2H), 2.06 (d, J=16.6 Hz, 1H), 1.23 (t, J=7.3 Hz, 4H), 0.89-0.75 (m, 4H).

MS(ESI+) m/z 385 (M+H)$^+$

Example 5: Synthesis of N-(4-(4-(propylsulfonamido)phenyl)-1H-pyrrolo[2,3-b]pyridin-6-yl)cyclopropanecarboxamide

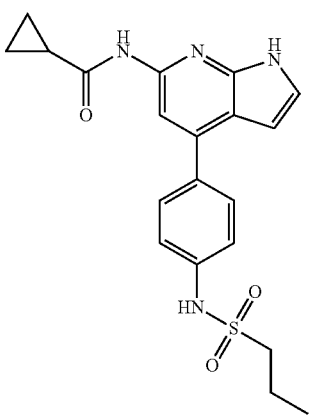

$^1$H NMR (400 MHz, DMSO-d$_6$) δ 11.51 (s, 1H), 10.60 (s, 1H), 10.00 (s, 1H), 8.00 (s, 1H), 7.81-7.64 (m, 2H), 7.38 (ddd, J=2.4, 6.2, 8.6 Hz, 3H), 6.54 (dd, J=1.9, 3.5 Hz, 1H), 3.22-3.05 (m, 2H), 2.06 (d, J=16.5 Hz, 1H), 1.72 (td, J=6.2, 8.3, 8.8 Hz, 2H), 0.96 (t, J=7.4 Hz, 4H), 0.81 (ddd, J=2.6, 6.4, 10.6 Hz, 5H).

MS(ESI+) m/z 399 (M+H)$^+$

Example 6: Synthesis of N-(4-(4-(butylsulfonamido)phenyl)-1H-pyrrolo[2,3-b]pyridin-6-yl)cyclopropanecarboxamide

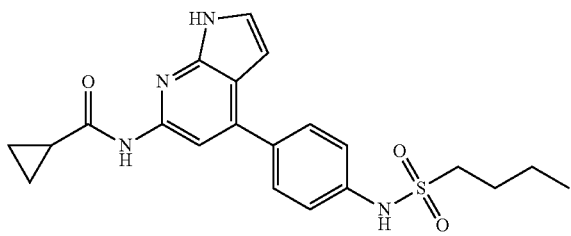 [SMILES: CCCCS(=O)(=O)Nc1ccc(-c2cc(NC(=O)C3CC3)nc3[nH]ccc23)cc1]

$^1$H NMR (400 MHz, DMSO-$d_6$) δ 11.50 (s, 1H), 10.59 (s, 1H), 10.13-9.90 (m, 1H), 7.99 (s, 1H), 7.72-7.64 (m, 2H), 7.42-7.30 (m, 3H), 6.54 (dd, J=1.8, 3.5 Hz, 1H), 3.21-3.10 (m, 2H), 2.09-1.99 (m, 1H), 1.73-1.61 (m, 2H), 1.38 (dt, J=7.5, 15.0 Hz, 2H), 0.89-0.75 (m, 7H).

MS(ESI+) m/z 413 (M+H)$^+$

Example 7: Synthesis of N-(4-(4-(cyclohexanesulfonamido)phenyl)-1H-pyrrolo[2,3-b]pyridin-6-yl)cyclopropanecarboxamide

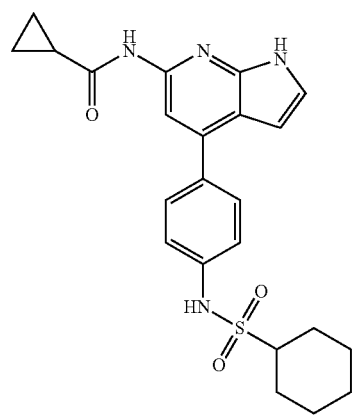 [SMILES: O=C(Nc1cc(-c2ccc(NS(=O)(=O)C3CCCCC3)cc2)c2cc[nH]c2n1)C1CC1]

MS(ESI+) m/z 439 (M+H)$^+$

Example 8: Synthesis of N-(4-(4-((2-fluoroethyl)sulfonamido)phenyl)-1H-pyrrolo[2,3-b]pyridin-6-yl)cyclopropanecarboxamide

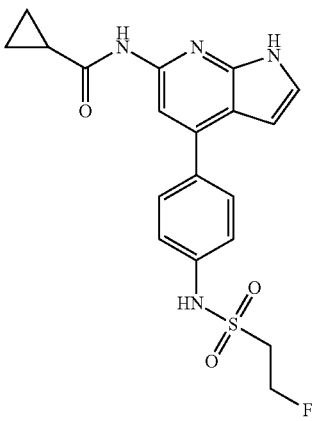 [SMILES: O=C(Nc1cc(-c2ccc(NS(=O)(=O)CCF)cc2)c2cc[nH]c2n1)C1CC1]

$^1$H NMR (400 MHz, DMSO-$d_6$) δ 11.45 (s, 1H), 10.73 (s, 1H), 7.86 (s, 1H), 7.61 (d, J=8.1 Hz, 2H), 7.42 (d, J=8.5 Hz, 1H), 7.37 (t, J=2.9 Hz, 1H), 6.89 (d, J=8.8 Hz, 2H), 6.60 (s, 1H), 2.74 (t, J=7.0 Hz, 2H), 2.02 (d, J=7.9 Hz, 1H), 1.24 (s, 2H), 0.93-0.76 (m, 4H).

MS(ESI+) m/z 403 (M+H)$^+$

Example 9: Synthesis of N-(4-(4-((1,1-dioxidotetrahydro-2H-thiopyran)-4-sulfonamido)phenyl)-1H-pyrrolo[2,3-b]pyridin-6-yl)cyclopropanecarboxamide

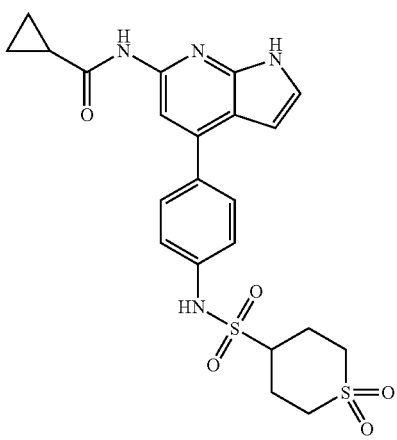

MS(ESI+) m/z 489 (M+H)$^+$

Example 10: Synthesis of N-(4-(4-((1,1-dioxidotetrahydrothiophene)-3-sulfonamido)phenyl)-1H-pyrrolo[2,3-b]pyridin-6-yl)cyclopropanecarboxamide

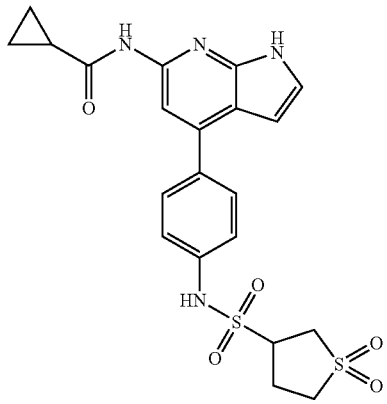 [SMILES: O=C(Nc1cc(-c2ccc(NS(=O)(=O)C3CCS(=O)(=O)C3)cc2)c2cc[nH]c2n1)C1CC1]

¹H NMR (400 MHz, DMSO-d₆) δ 11.53 (s, 1H), 10.61 (s, 1H), 10.41 (s, 1H), 8.00 (s, 1H), 7.75-7.66 (m, 2H), 7.44-7.34 (m, 3H), 6.54 (dd, J=1.9, 3.7 Hz, 1H), 4.30-4.19 (m, 1H), 3.52 (dd, J=9.4, 14.0 Hz, 1H), 3.27-3.18 (m, 2H), 2.43-2.33 (m, 1H), 2.03 (d, J=7.4 Hz, 1H), 0.81 (dt, J=4.3, 9.9 Hz, 4H).

MS(ESI+) m/z 475 (M+H)⁺

Example 11: Synthesis of N-(4-(4-((1,1-dioxidothietane)-3-sulfonamido)phenyl)-1H-pyrrolo[2,3-b]pyridin-6-yl)cyclopropanecarboxamide

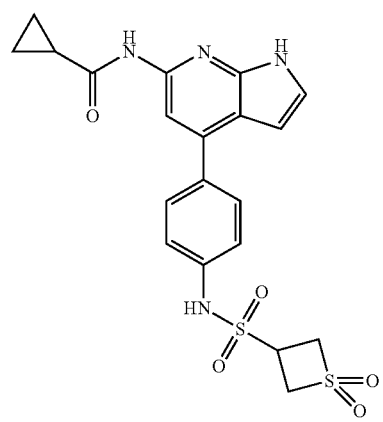 [SMILES: O=C(Nc1cc(-c2ccc(NS(=O)(=O)C3CS(=O)(=O)C3)cc2)c2cc[nH]c2n1)C1CC1]

¹H NMR (400 MHz, DMSO-d₆) δ 11.53 (s, 1H), 10.62 (d, J=6.0 Hz, 1H), 10.49 (d, J=13.3 Hz, 1H), 8.01 (d, J=3.0 Hz, 1H), 7.78-7.69 (m, 2H), 7.46-7.36 (m, 3H), 6.58-6.48 (m, 2H), 4.68-4.57 (m, 2H), 4.52-4.40 (m, 2H), 2.03 (s, 2H), 0.83-0.76 (m, 4H).

MS(ESI+) m/z 461 (M+H)⁺

Example 12: Synthesis of N-(4-(4-((6-chloropyridine)-3-sulfonamido)phenyl)-1H-pyrrolo[2,3-b]pyridin-6-yl)cyclopropanecarboxamide

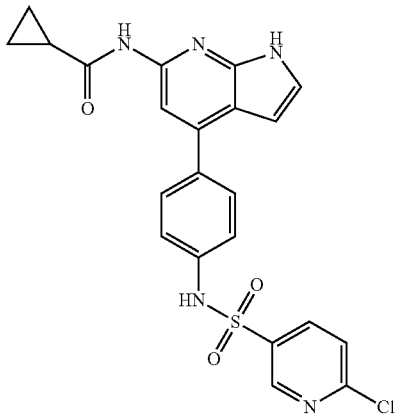 [SMILES: O=C(Nc1cc(-c2ccc(NS(=O)(=O)c3ccc(Cl)nc3)cc2)c2cc[nH]c2n1)C1CC1]

¹H NMR (400 MHz, DMSO-d₆) δ 11.51 (s, 1H), 10.78 (s, 1H), 10.59 (s, 1H), 8.79 (d, J=2.6 Hz, 1H), 8.19 (dd, J=2.6, 8.5 Hz, 1H), 7.96 (s, 1H), 7.76 (d, J=8.5 Hz, 1H), 7.64 (d, J=8.1 Hz, 2H), 7.38 (t, J=3.0 Hz, 1H), 7.28 (d, J=8.3 Hz, 2H), 6.49 (d, J=3.4 Hz, 1H), 2.03 (s, 1H), 0.86-0.75 (m, 4H).

MS(ESI+) m/z 468, 480 (M+H)⁺

Example 13: Synthesis of N-(4-(4-((4-fluorophenyl)sulfonamido)phenyl)-1H-pyrrolo[2,3-b]pyridin-6-yl)cyclopropanecarboxamide

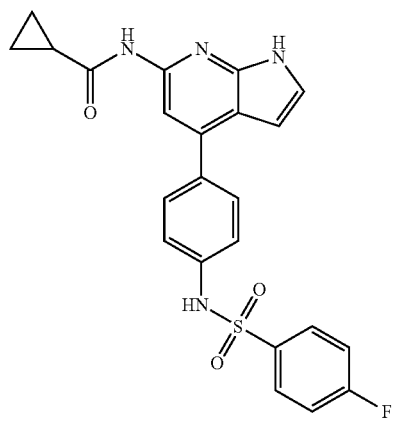 [SMILES: O=C(Nc1cc(-c2ccc(NS(=O)(=O)c3ccc(F)cc3)cc2)c2cc[nH]c2n1)C1CC1]

¹H NMR (400 MHz, DMSO-d₆) δ 11.49 (s, 1H), 10.56 (d, J=15.6 Hz, 2H), 7.94 (s, 1H), 7.92-7.83 (m, 2H), 7.60 (d, J=8.3 Hz, 2H), 7.46-7.34 (m, 3H), 7.25 (d, J=8.5 Hz, 2H), 6.48 (dd, J=1.9, 3.7 Hz, 1H), 2.02 (d, J=8.7 Hz, 1H), 0.80 (q, J=5.9, 8.6 Hz, 4H).

MS(ESI+) m/z 451 (M+H)⁺

Example 14: Synthesis of N-(4-(4-((4-chlorophenyl)sulfonamido)phenyl)-1H-pyrrolo[2,3-b]pyridin-6-yl)cyclopropanecarboxamide

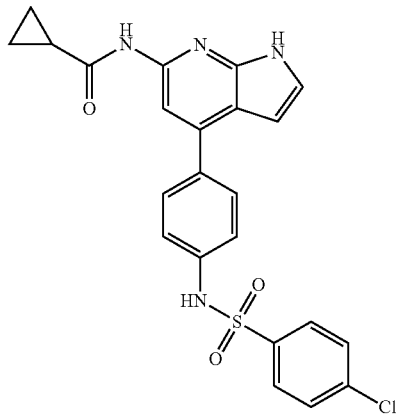

¹H NMR (400 MHz, DMSO-d₆) δ 11.49 (s, 1H), 10.58 (s, 2H), 7.94 (s, 1H), 7.87-7.75 (m, 2H), 7.62 (dd, J=8.2, 18.3 Hz, 4H), 7.37 (t, J=3.1 Hz, 1H), 7.24 (d, J=8.2 Hz, 2H), 6.48 (dd, J=1.9, 3.6 Hz, 1H), 2.02 (d, J=9.2 Hz, 1H), 0.79 (t, J=7.2 Hz, 4H).

MS(ESI+) m/z 467, 469 (M+H)⁺

Example 15: Synthesis of N-(4-(4-((1-methyl-1H-imidazole)-5-sulfonamido)phenyl)-1H-pyrrolo[2,3-b]pyridin-6-yl)cyclopropanecarboxamide

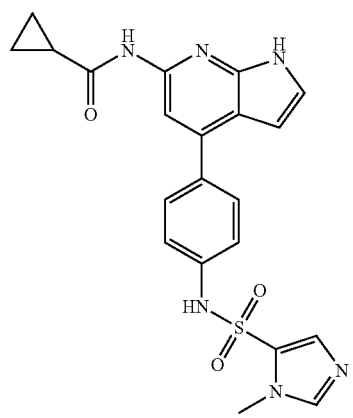 [SMILES: Cn1cncc1S(=O)(=O)Nc1ccc(-c2cc(NC(=O)C3CC3)nc3[nH]ccc23)cc1]

¹H NMR (400 MHz, DMSO-d₆) δ 11.49 (s, 1H), 10.58 (s, 1H), 10.45 (s, 1H), 7.92 (d, J=22.8 Hz, 2H), 7.75 (s, 1H), 7.59 (d, J=8.4 Hz, 2H), 7.37 (t, J=3.0 Hz, 1H), 7.31 (d, J=8.2 Hz, 2H), 6.50 (s, 1H), 3.67 (s, 3H), 2.03 (s, 1H), 0.85-0.76 (m, 4H).

MS(ESI+) m/z 437 (M+H)⁺

Example 16: Synthesis of N-(4-(4-((1-methyl-1H-pyrazole)-4-sulfonamido)phenyl)-1H-pyrrolo[2,3-b]pyridin-6-yl)cyclopropanecarboxamide

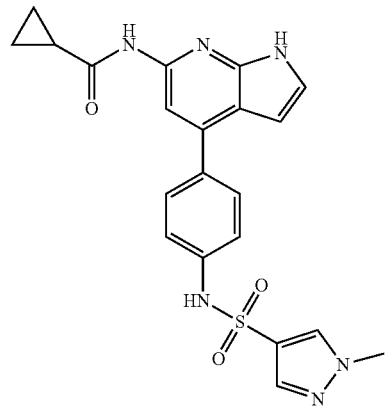 [SMILES: Cn1cc(S(=O)(=O)Nc2ccc(-c3cc(NC(=O)C4CC4)nc4[nH]ccc34)cc2)cn1]

¹H NMR (400 MHz, DMSO-d₆) δ 11.50 (s, 1H), 10.59 (s, 1H), 10.36 (s, 1H), 8.29 (s, 1H), 7.97 (s, 1H), 7.75 (s, 1H), 7.63 (d, J=8.3 Hz, 2H), 7.38 (t, J=3.0 Hz, 1H), 7.34-7.25 (m, 2H), 6.51 (dd, J=1.9, 3.7 Hz, 1H), 3.84 (s, 3H), 2.04 (d, J=7.0 Hz, 1H), 0.80 (tt, J=3.8, 10.6 Hz, 4H).

MS(ESI+) m/z 437 (M+H)⁺

Example 17: Synthesis of 4-(N-(4-(6-(cyclopropanecarboxamido)-1H-pyrrolo[2,3-b]pyridin-4-yl)phenyl)sulfamoyl)benzamide

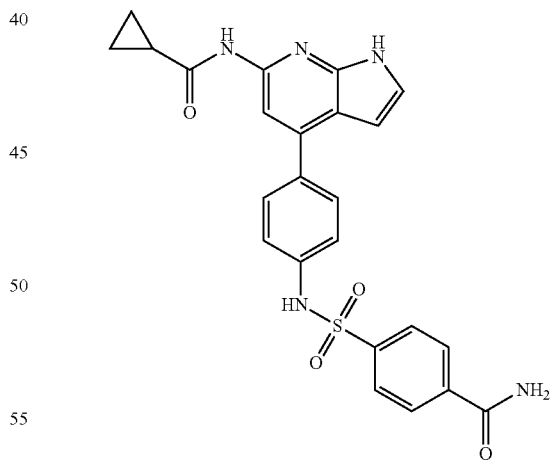

¹H NMR (400 MHz, DMSO-d₆) δ 11.50 (s, 1H), 10.62 (s, 1H), 10.59 (s, 1H), 8.11 (s, 1H), 7.99 (d, J=8.2 Hz, 2H), 7.93 (s, 1H), 7.89 (d, J=8.1 Hz, 2H), 7.61 (d, J=8.5 Hz, 2H), 7.57 (s, 1H), 7.39-7.34 (m, 1H), 7.28 (d, J=8.3 Hz, 2H), 6.47 (d, J=3.0 Hz, 1H), 2.03 (s, 1H), 0.84-0.76 (m, 4H).

MS(ESI+) m/z 476 (M+H)⁺

Example 18: Synthesis of N-(4-(4-((1-acetylpiperidine)-4-sulfonamido)phenyl)-1H-pyrrolo[2,3-b]pyridin-6-yl)cyclopropanecarboxamide

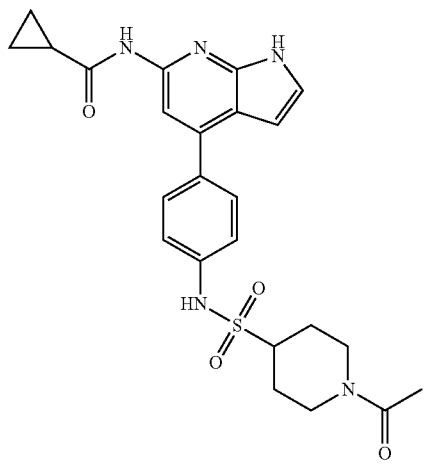 [SMILES: CC(=O)N1CCC(S(=O)(=O)Nc2ccc(-c3cc(NC(=O)C4CC4)nc4[nH]ccc34)cc2)CC1]

$^1$H NMR (400 MHz, CDCl$_3$) δ 8.55 (s, 1H), 8.26 (s, 1H), 8.17 (s, 1H), 7.73 (d, J=8.1 Hz, 2H), 7.34 (d, J=8.2 Hz, 2H), 6.81 (s, 1H), 6.62 (d, J=3.1 Hz, 1H), 4.72 (d, J=12.9 Hz, 1H), 3.93 (d, J=14.0 Hz, 1H), 3.49 (s, 3H), 3.28 (d, J=12.3 Hz, 1H), 3.06 (t, J=12.9 Hz, 1H), 2.55 (t, J=12.5 Hz, 1H), 2.15 (d, J=9.9 Hz, 2H), 2.09 (s, 3H), 1.85 (d, J=12.2 Hz, 2H), 1.13 (d, J=3.9 Hz, 3H), 0.95-0.78 (m, 9H).

MS(ESI+) m/z 482 (M+H)$^+$

Example 19: Synthesis of N-(4-(4-((4-isopropoxyphenyl)sulfonamido)phenyl)-1H-pyrrolo[2,3-b]pyridin-6-yl)cyclopropanecarboxamide

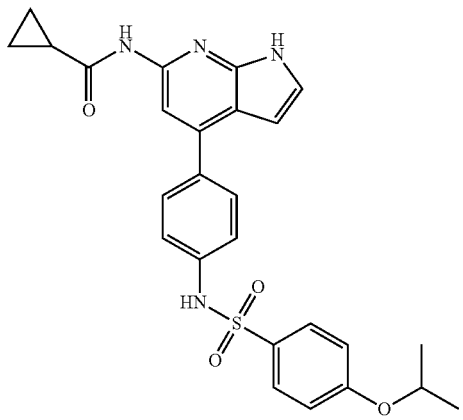 [SMILES: CC(C)Oc1ccc(S(=O)(=O)Nc2ccc(-c3cc(NC(=O)C4CC4)nc4[nH]ccc34)cc2)cc1]

$^1$H NMR (400 MHz, DMSO-d$_6$) δ 11.49 (s, 1H), 10.58 (s, 2H), 7.95-7.84 (m, 3H), 7.59 (d, J=8.2 Hz, 2H), 7.39-7.19 (m, 6H), 6.54-6.38 (m, 1H), 2.03 (s, 1H), 0.85-0.77 (m, 4H).

MS(ESI+) m/z 491 (M+H)$^+$

Example 20: Synthesis of N-(4-(4-((4-bromophenyl)sulfonamido)phenyl)-1H-pyrrolo[2,3-b]pyridin-6-yl)cyclopropanecarboxamide

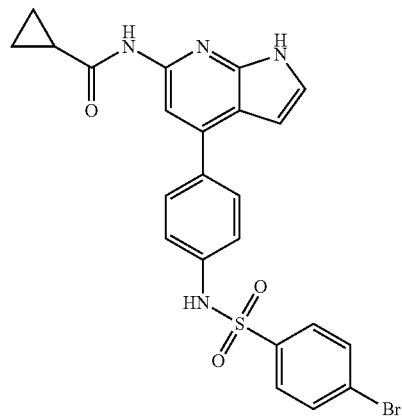 [SMILES: O=C(Nc1cc(-c2ccc(NS(=O)(=O)c3ccc(Br)cc3)cc2)c2cc[nH]c2n1)C1CC1]

$^1$H NMR (400 MHz, DMSO-d$_6$) δ 11.46 (s, 1H), 10.56 (s, 1H), 7.93 (s, 1H), 7.72 (dd, J=8.0, 5.5 Hz, 4H), 7.55 (d, J=8.5 Hz, 2H), 7.39-7.33 (m, 1H), 7.18 (d, J=8.6 Hz, 2H), 6.53-6.44 (m, 1H), 2.03 (s, 1H), 0.86-0.74 (m, 4H).

MS(ESI+) m/z 512 (M+H)$^+$

Example 21: Synthesis of N-(4-(4-((4-cyanophenyl)sulfonamido)phenyl)-1H-pyrrolo[2,3-b]pyridin-6-yl)cyclopropanecarboxamide

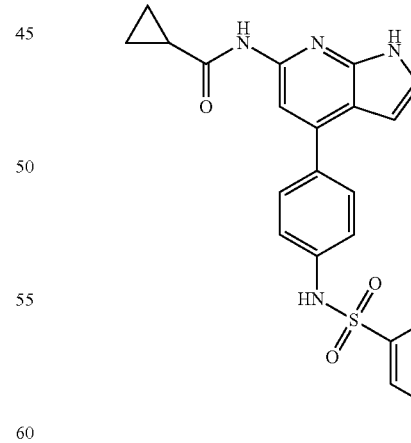

$^1$H NMR (400 MHz, DMSO-d$_6$) δ 11.50 (s, 1H), 10.67 (s, 1H), 10.59 (s, 1H), 8.03-7.84 (m, 5H), 7.61 (d, J=8.3 Hz, 2H), 7.39-7.23 (m, 3H), 6.48 (s, 1H), 2.03 (s, 1H), 0.82-0.75 (m, 4H).

MS(ESI+) m/z 458 (M+H)$^+$

Example 22: Synthesis of N-(4-(4-((2,3-dihydrobenzofuran)-5-sulfonamido)phenyl)-1H-pyrrolo[2,3-b]pyridin-6-yl)cyclopropanecarboxamide

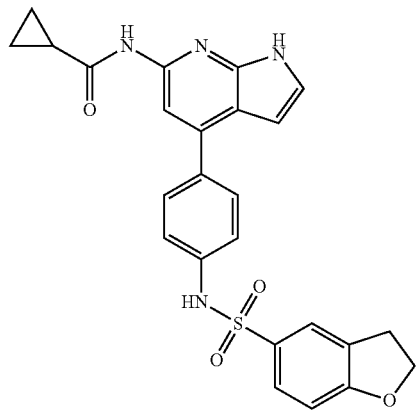 [SMILES: O=C(Nc1cc(-c2ccc(NS(=O)(=O)c3ccc4c(c3)CCO4)cc2)c2cc[nH]c2n1)C1CC1]

$^1$H NMR (400 MHz, DMSO-d$_6$) δ 11.49 (s, 1H), 10.58 (s, 1H), 10.36 (s, 1H), 7.94 (s, 1H), 7.68 (s, 1H), 7.63-7.55 (m, 3H), 7.40-7.32 (m, 1H), 7.29-7.21 (m, 2H), 6.88 (d, J=8.4 Hz, 1H), 6.52-6.43 (m, 1H), 4.60 (t, J=8.7 Hz, 2H), 3.22 (t, J=8.8 Hz, 2H), 2.03 (s, 1H), 0.84-0.74 (m, 4H).

MS(ESI+) m/z 475 (M+H)$^+$

Example 23: Synthesis of N-(4-(4-((6-methoxypyridine)-3-sulfonamido)phenyl)-1H-pyrrolo[2,3-b]pyridin-6-yl)cyclopropanecarboxamide

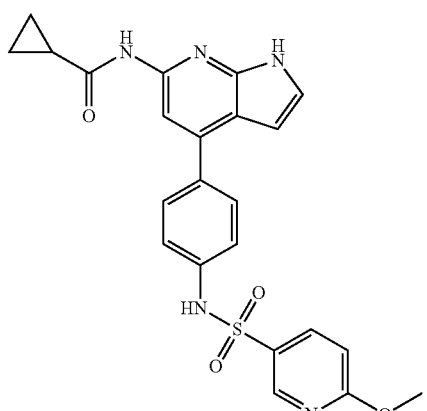

$^1$H NMR (400 MHz, DMSO-d$_6$) δ 11.50 (s, 1H), 10.59 (s, 2H), 8.64-8.54 (m, 1H), 8.07-7.92 (m, 2H), 7.63 (d, J=8.1 Hz, 2H), 7.39-7.26 (m, 3H), 7.00 (d, J=8.6 Hz, 1H), 6.49 (s, 1H), 3.89 (s, 4H), 2.03 (s, 1H), 0.82-0.75 (m, 4H).

MS(ESI+) m/z 464 (M+H)$^+$

Example 24: Synthesis of N-(4-(4-(phenylsulfonamido)phenyl)-1H-pyrrolo[2,3-b]pyridin-6-yl)cyclopropanecarboxamide

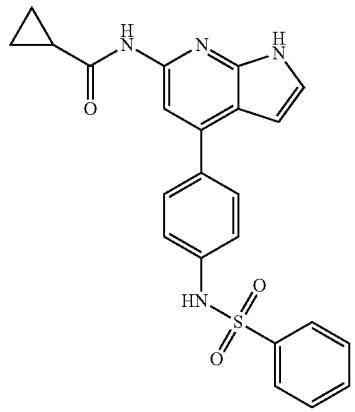 [SMILES: O=C(Nc1cc(-c2ccc(NS(=O)(=O)c3ccccc3)cc2)c2cc[nH]c2n1)C1CC1]

$^1$H NMR (400 MHz, DMSO-d$_6$) δ 11.50 (d, J=7.6 Hz, 1H), 10.55 (d, J=22.8 Hz, 2H), 7.93 (s, 1H), 7.89-7.80 (m, 2H), 7.69-7.54 (m, 5H), 7.40-7.34 (m, 1H), 7.27 (d, J=8.7 Hz, 2H), 6.53-6.38 (m, 1H), 2.02 (d, J=8.1 Hz, 1H), 0.80 (q, J=8.4, 6.4 Hz, 4H).

MS(ESI+) m/z 433 (M+H)$^+$

Example 25: Synthesis of N-(4-(4-((3-fluorophenyl)sulfonamido)phenyl)-1H-pyrrolo[2,3-b]pyridin-6-yl)cyclopropanecarboxamide

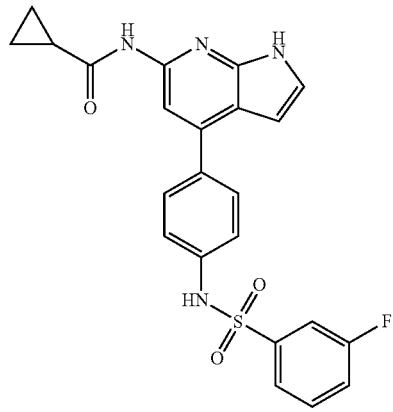 [SMILES: O=C(Nc1cc(-c2ccc(NS(=O)(=O)c3cccc(F)c3)cc2)c2cc[nH]c2n1)C1CC1]

$^1$H NMR (400 MHz, DMSO-d$_6$) δ 11.49 (s, 1H), 10.60 (d, J=19.3 Hz, 2H), 7.94 (s, 1H), 7.71-7.57 (m, 5H), 7.49 (t, J=7.5 Hz, 1H), 7.41-7.33 (m, 1H), 7.31-7.16 (m, 2H), 6.56-6.43 (m, 1H), 2.03 (d, J=9.3 Hz, 1H), 0.87-0.65 (m, 4H).

MS(ESI+) m/z 451 (M+H)$^+$

Example 26: Synthesis of N-(4-(4-((3-chlorophenyl)sulfonamido)phenyl)-1H-pyrrolo[2,3-b]pyridin-6-yl)cyclopropanecarboxamide

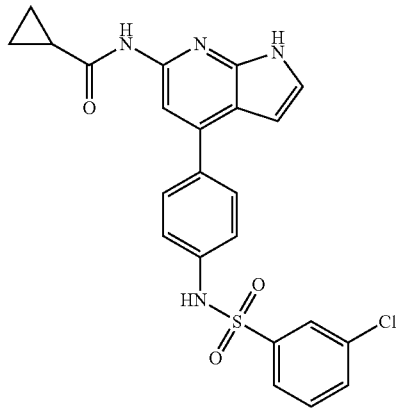 [SMILES: O=C(Nc1cc(-c2ccc(NS(=O)(=O)c3cccc(Cl)c3)cc2)c2cc[nH]c2n1)C1CC1]

$^1$H NMR (400 MHz, Chloroform-d) δ 7.94-7.77 (m, 2H), 7.68 (d, J=7.8 Hz, 1H), 7.58 (dd, J=6.6, 4.3 Hz, 2H), 7.51-7.43 (m, 1H), 7.36 (t, J=7.9 Hz, 1H), 7.28-7.18 (m, 4H), 6.58 (d, J=3.6 Hz, 1H), 1.89 (tt, J=8.6, 4.6 Hz, 1H), 1.09-1.01 (m, 3H), 0.92 (dq, J=7.8, 4.1 Hz, 2H), 0.87-0.72 (m, 4H).

MS(ESI+) m/z 467, 469 (M+H)$^+$

Example 27: Synthesis of N-(4-(4-((4-methylphenyl)sulfonamido)phenyl)-1H-pyrrolo[2,3-b]pyridin-6-yl)cyclopropanecarboxamide

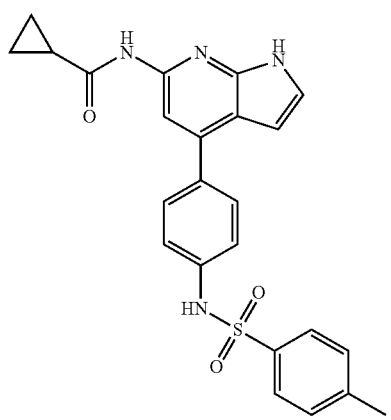 [SMILES: Cc1ccc(S(=O)(=O)Nc2ccc(-c3cc(NC(=O)C4CC4)nc4[nH]ccc34)cc2)cc1]

$^1$H NMR (400 MHz, DMSO-d$_6$) δ 11.33 (s, 1H), 10.46 (s, 1H), 7.87 (s, 1H), 7.62 (d, J=7.9 Hz, 2H), 7.32 (dd, J=19.4, 5.6 Hz, 3H), 7.18 (d, J=7.9 Hz, 2H), 6.94 (d, J=8.3 Hz, 2H), 6.56-6.44 (m, 1H), 2.29 (s, 3H), 2.00 (d, J=11.3 Hz, 1H), 0.88-0.66 (m, 4H).

MS(ESI+) m/z 447 (M+H)$^+$

Example 28: Synthesis of N-(4-(4-((4-(methylthio)phenyl)sulfonamido)phenyl)-1H-pyrrolo[2,3-b]pyridin-6-yl)cyclopropanecarboxamide

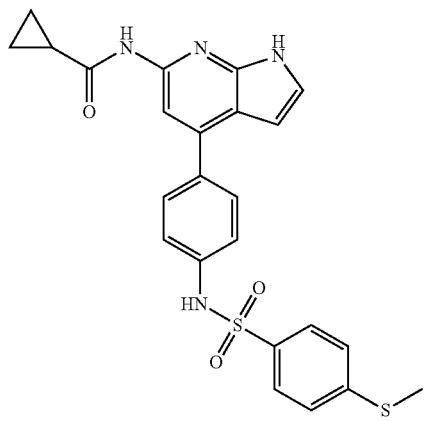 [SMILES: CSc1ccc(S(=O)(=O)Nc2ccc(-c3cc(NC(=O)C4CC4)nc4[nH]ccc34)cc2)cc1]

$^1$H NMR (400 MHz, DMSO-d$_6$) δ 11.31 (s, 1H), 10.44 (s, 1H), 7.86 (s, 1H), 7.74-7.55 (m, 2H), 7.30 (dd, J=14.1, 5.6 Hz, 3H), 7.26-7.15 (m, 2H), 6.90 (d, J=8.4 Hz, 2H), 6.64-6.31 (m, 1H), 2.02 (s, 1H), 0.89-0.68 (m, 4H).

MS(ESI+) m/z 479 (M+H)$^+$

Example 29: Synthesis of N-(4-(4-(ethylsulfonamido)-2-methylphenyl)-1H-pyrrolo[2,3-b]pyridin-6-yl)cyclopropanecarboxamide

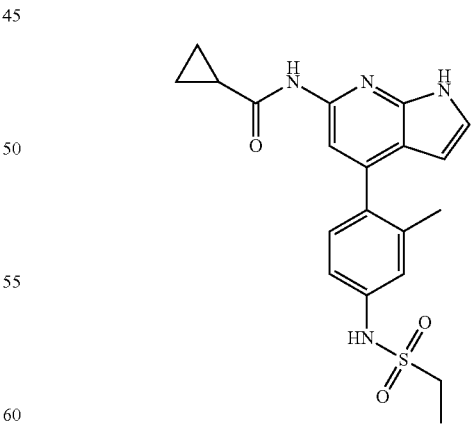

$^1$H NMR (400 MHz, DMSO-d6) δ 11.48 (s, 1H), 10.63 (s, 1H), 9.86 (s, 1H), 7.75 (s, 1H), 7.54-7.06 (m, 6H), 6.09 (s, 1H), 3.16 (q, J=7.6 Hz, 3H), 2.14 (s, 3H), 2.04 (s, 1H), 1.23 (t, J=7.5 Hz, 4H), 0.78 (d, J=9.5 Hz, 4H).

MS(ESI+) m/z 399 (M+H)$^+$

Example 30: Synthesis of N-(4-(4-(ethylsulfonamido)-2-fluorophenyl)-1H-pyrrolo[2,3-b]pyridin-6-yl)cyclopropanecarboxamide

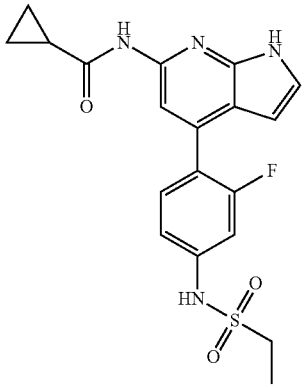 [SMILES: CCS(=O)(=O)Nc1ccc(-c2cc(NC(=O)C3CC3)nc3[nH]ccc23)c(F)c1]

$^1$H NMR (400 MHz, DMSO-d$_6$) δ 11.52 (s, 1H), 10.63 (s, 1H), 10.26 (s, 1H), 7.94 (s, 1H), 7.56 (t, J=8.4 Hz, 1H), 7.45-7.32 (m, 1H), 7.17 (d, J=11.3 Hz, 2H), 6.38-6.26 (m, 1H), 3.23 (q, J=7.2 Hz, 2H), 2.04 (s, 1H), 1.23 (t, J=7.2 Hz, 3H), 0.92-0.71 (m, 4H).

MS(ESI+) m/z 403 (M+H)$^+$

Example 31: Synthesis of N-(4-(4-((4-bromo-3-fluorophenyl)sulfonamido)phenyl)-1H-pyrrolo[2,3-b]pyridin-6-yl)cyclopropanecarboxamide

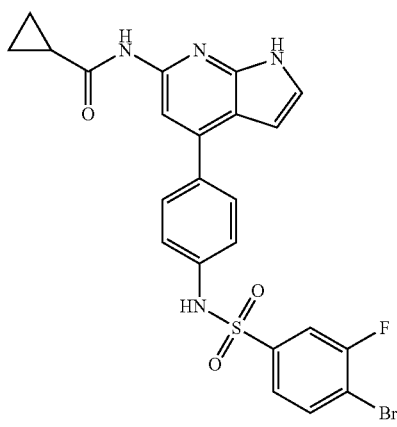 [SMILES: O=C(Nc1cc(-c2ccc(NS(=O)(=O)c3ccc(Br)c(F)c3)cc2)c2cc[nH]c2n1)C1CC1]

$^1$H NMR (400 MHz, DMSO-d$_6$) δ 11.41 (s, 1H), 10.52 (s, 1H), 7.91 (s, 1H), 7.83 (t, J=7.6 Hz, 1H), 7.65 (dd, J=2.0, 8.5 Hz, 1H), 7.57-7.44 (m, 3H), 7.33 (t, J=2.9 Hz, 1H), 7.10 (d, J=8.4 Hz, 2H), 6.56-6.44 (m, 1H), 2.02 (s, 1H), 0.86-0.72 (m, 4H).

MS(ESI+) m/z 529, 531 (M+H)$^+$

Example 32: Synthesis of N-(4-(4-((4-bromo-2-fluorophenyl)sulfonamido)phenyl)-1H-pyrrolo[2,3-b]pyridin-6-yl)cyclopropanecarboxamide

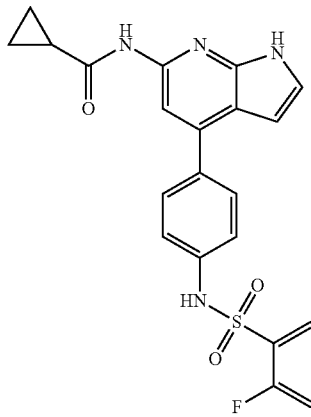

$^1$H NMR (400 MHz, DMSO-d$_6$) δ 11.32 (s, 1H), 10.45 (s, 1H), 7.87 (s, 1H), 7.69 (t, J=8.0 Hz, 1H), 7.54-7.42 (m, 1H), 7.42-7.24 (m, 4H), 6.96-6.82 (m, 2H), 6.57-6.42 (m, 1H), 2.00 (d, J=12.5 Hz, 1H), 0.87-0.68 (m, 4H).

MS(ESI+) m/z 529, 531 (M+H)$^+$

Example 33: Synthesis of N-(4-(4-((4-chloro-3-(trifluoromethyl)phenyl)sulfonamido)phenyl)-1H-pyrrolo[2,3-b]pyridin-6-yl)cyclopropanecarboxamide

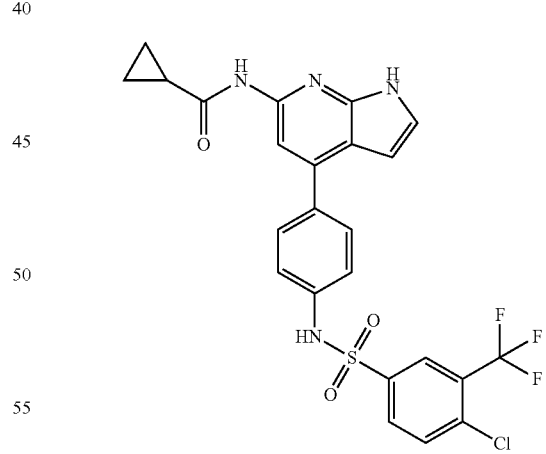

$^1$H NMR (400 MHz, DMSO-d$_6$) δ 11.51 (s, 1H), 10.70 (s, 1H), 10.59 (s, 1H), 8.13 (d, J=2.3 Hz, 1H), 8.10-8.03 (m, 1H), 7.96 (d, J=7.7 Hz, 2H), 7.64 (d, J=8.2 Hz, 2H), 7.49-7.35 (m, 1H), 7.27 (d, J=8.3 Hz, 2H), 6.53-6.40 (m, 1H), 2.02 (d, J=8.5 Hz, 1H), 0.85-0.70 (m, 4H).

MS(ESI+) m/z 535, 537 (M+H)$^+$

Example 34: Synthesis of N-(4-(4-(benzo[d][1,3]dioxole-5-sulfonamido)phenyl)-1H-pyrrolo[2,3-b]pyridin-6-yl)cyclopropanecarboxamide

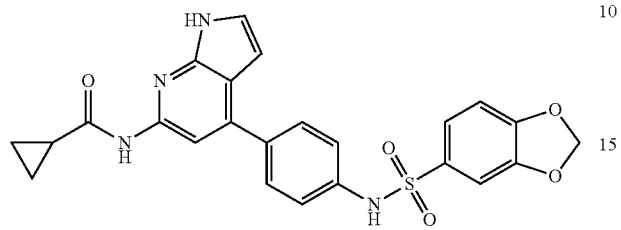

¹H NMR (400 MHz, DMSO-d₆) δ 11.50 (s, 1H), 10.59 (s, 1H), 10.40 (s, 1H), 7.94 (s, 1H), 7.61 (d, J=8.3 Hz, 2H), 7.37 (dd, J=5.7, 2.7 Hz, 2H), 7.27 (dd, J=5.3, 3.2 Hz, 3H), 7.05 (d, J=7.8 Hz, 1H), 6.49 (s, 1H), 6.14 (s, 2H), 2.10-1.92 (m, 2H), 1.24 (s, 5H), 0.86-0.70 (m, 5H).

MS(ESI+) m/z 477 (M+H)⁺

Example 35: Synthesis of N-(4-(4-(ethylsulfonamido)phenyl)-1H-pyrrolo[2,3-b]pyridin-6-yl)-2-methylcyclopropane-1-carboxamide

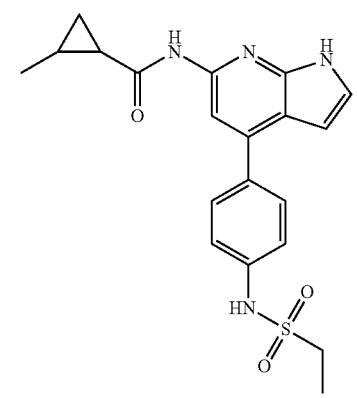 [SMILES: CCS(=O)(=O)Nc1ccc(-c2cc(NC(=O)C3CC3C)nc3[nH]ccc23)cc1]

¹H NMR (400 MHz, DMSO-d₆) δ 11.52 (s, 1H), 10.59 (s, 1H), 10.02 (s, 1H), 7.96 (d, J=5.8 Hz, 1H), 7.69 (dd, J=4.1, 8.6 Hz, 2H), 7.47 (d, J=7.8 Hz, 1H), 7.39 (dd, J=4.4, 7.5 Hz, 3H), 7.11 (d, J=7.9 Hz, 1H), 6.63-6.49 (m, 1H), 3.17 (q, J=7.3 Hz, 2H), 1.86-1.74 (m, 1H), 1.34-1.17 (m, 5H), 1.17-0.93 (m, 4H).

MS(ESI+) m/z 399 (M+H)⁺

Example 36: Synthesis of N-(4-(4-(((4-fluorophenyl)methyl)sulfonamido)phenyl)-1H-pyrrolo[2,3-b]pyridin-6-yl)cyclopropanecarboxamide

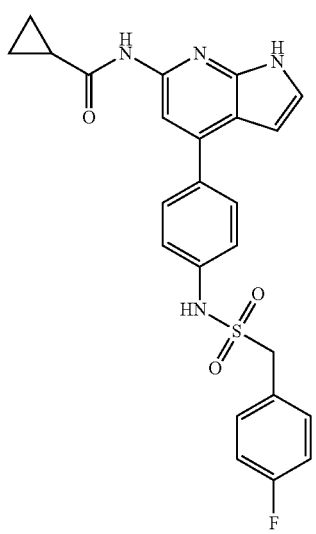 [SMILES: O=C(Nc1cc(-c2ccc(NS(=O)(=O)Cc3ccc(F)cc3)cc2)c2cc[nH]c2n1)C1CC1]

MS(ESI+) m/z 465 (M+H)⁺

Example 37: Synthesis of N-(4-(4-((4-(N,N-dimethylsulfamoyl)phenyl)sulfonamido)phenyl)-1H-pyrrolo[2,3-b]pyridin-6-yl)cyclopropanecarboxamide

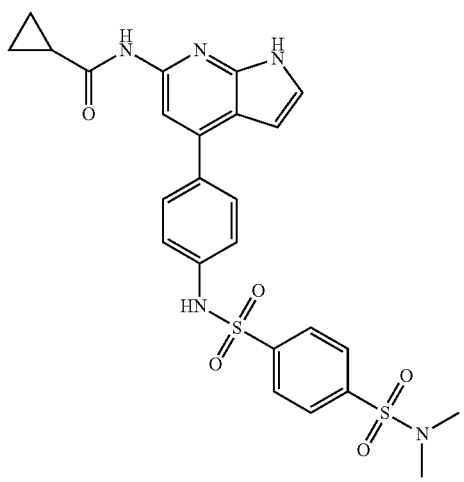 [SMILES: CN(C)S(=O)(=O)c1ccc(S(=O)(=O)Nc2ccc(-c3cc(NC(=O)C4CC4)nc4[nH]ccc34)cc2)cc1]

MS(ESI+) m/z 540 (M+H)⁺

Example 38: Synthesis of N-(4-(4-((2,3-dihydrobenzo[b][1,4]dioxine)-6-sulfonamido)phenyl)-1H-pyrrolo[2,3-b]pyridin-6-yl)cyclopropanecarboxamide

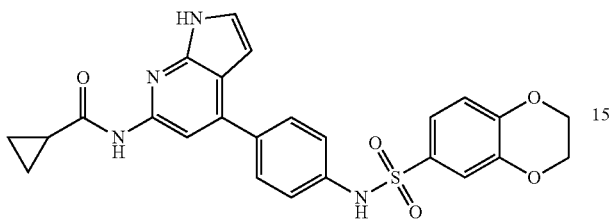

$^1$H NMR (400 MHz, DMSO-d$_6$) δ 11.49 (s, 1H), 10.58 (s, 1H), 7.94 (s, 1H), 7.60 (s, 2H), 7.27 (s, 5H), 7.01 (s, 2H), 6.49 (s, 1H), 4.28 (s, 4H), 2.03 (s, 1H), 0.80 (s, 4H).
MS(ESI+) m/z 491 (M+H)$^+$

Example 39: Synthesis of N-(4-(4-((4-(1H-tetrazol-1-yl)phenyl)sulfonamido)phenyl)-1H-pyrrolo[2,3-b]pyridin-6-yl)cyclopropanecarboxamide

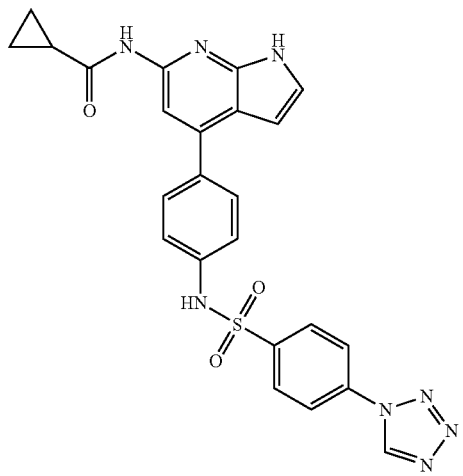 [SMILES: O=C(Nc1cc(-c2ccc(NS(=O)(=O)c3ccc(-n4cnnn4)cc3)cc2)c2cc[nH]c2n1)C1CC1]

$^1$H NMR (400 MHz, DMSO-d$_6$) δ 11.50 (s, 1H), 10.58 (s, 1H), 10.39 (s, 1H), 8.12 (d, J=21.2 Hz, 1H), 7.94 (s, 1H), 7.74 (d, J=8.7 Hz, 1H), 7.61 (t, J=9.0 Hz, 2H), 7.39-7.00 (m, 6H), 6.48 (s, 1H), 2.03 (s, 1H), 0.80 (s, 4H).
MS(ESI+) m/z 501 (M+H)$^+$

Example 40: Synthesis of N-(4-(4-((6-cyanopyridine)-3-sulfonamido)phenyl)-1H-pyrrolo[2,3-b]pyridin-6-yl)cyclopropanecarboxamide

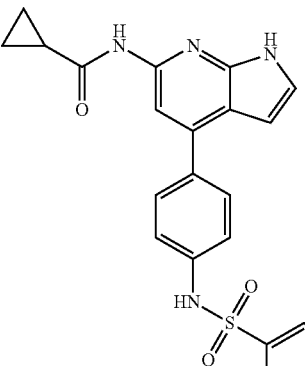

$^1$H NMR (400 MHz, DMSO-d$_6$) δ 11.47 (d, J=19.4 Hz, 1H), 10.56 (d, J=12.4 Hz, 1H), 9.00 (d, J=55.6 Hz, 1H), 8.46-7.81 (m, 4H), 7.56 (d, J=37.7 Hz, 2H), 7.41-7.11 (m, 3H), 6.48 (d, J=8.3 Hz, 1H), 2.02 (s, 1H), 0.79 (s, 4H).
MS(ESI+) m/z 459 (M+H)$^+$

Example 41: Synthesis of N-(4-(4-((1-methylethyl)sulfonamido)phenyl)-1H-pyrrolo[2,3-b]pyridin-6-yl)cyclopropanecarboxamide

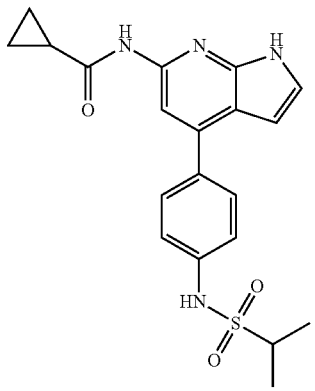 [SMILES: CC(C)S(=O)(=O)Nc1ccc(-c2cc(NC(=O)C3CC3)nc3[nH]ccc23)cc1]

$^1$H NMR (400 MHz, DMSO-d$_6$) δ 11.51 (s, 1H), 10.60 (s, 1H), 9.96 (s, 1H), 7.99 (s, 1H), 7.67 (d, J=8.2 Hz, 2H), 7.39 (d, J=6.8 Hz, 3H), 6.54 (s, 1H), 2.04 (s, 1H), 1.30-1.24 (m, 6H), 0.81 (s, 4H).
MS(ESI+) m/z 399 (M+H)$^+$

Example 42: Synthesis of N-(4-(4-((1-ethylpropyl)sulfonamido)phenyl)-1H-pyrrolo[2,3-b]pyridin-6-yl)cyclopropanecarboxamide

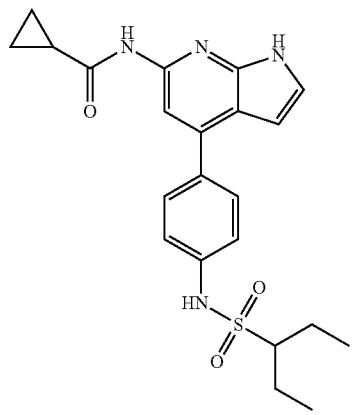 [SMILES: CCC(CC)S(=O)(=O)Nc1ccc(-c2cc(NC(=O)C3CC3)nc3[nH]ccc23)cc1]

¹H NMR (400 MHz, DMSO-d$_6$) δ 11.52 (s, 1H), 10.62 (s, 1H), 10.04 (s, 1H), 7.99 (s, 1H), 7.70-7.62 (m, 2H), 7.41-7.34 (m, 3H), 6.54 (dd, J=3.5, 1.8 Hz, 1H), 2.97 (dd, J=8.7, 3.7 Hz, 1H), 2.03 (d, J=5.0 Hz, 1H), 1.87 (ddd, J=14.7, 7.6, 5.1 Hz, 2H), 1.70 (dt, J=14.3, 7.2 Hz, 2H), 0.96 (t, J=7.5 Hz, 6H), 0.80 (t, J=5.5 Hz, 4H).

MS(ESI+) m/z 427 (M+H)⁺

Example 43: Synthesis of N-(4-(4-((2-methylpropyl)sulfonamido)phenyl)-1H-pyrrolo[2,3-b]pyridin-6-yl)cyclopropanecarboxamide

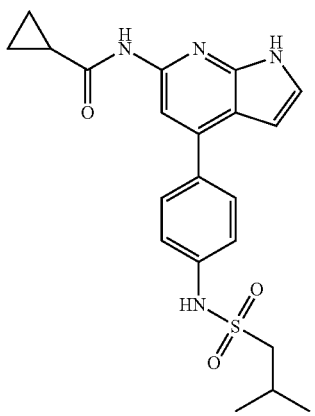 [SMILES: CC(C)CS(=O)(=O)Nc1ccc(-c2cc(NC(=O)C3CC3)nc3[nH]ccc23)cc1]

¹H NMR (400 MHz, DMSO-d$_6$) δ 11.51 (s, 1H), 10.60 (s, 1H), 10.00 (s, 1H), 8.00 (s, 1H), 7.69 (d, J=8.7 Hz, 2H), 7.37 (t, J=9.9 Hz, 3H), 6.55 (s, 1H), 3.06 (d, J=6.8 Hz, 2H), 2.17 (s, 1H), 2.04 (s, 1H), 1.05-0.95 (m, 6H), 0.81 (s, 4H).

MS(ESI+) m/z 413 (M+H)⁺

Example 44: Synthesis of N-(4-(4-((2,2-dimethylpropyl)sulfonamido)phenyl)-1H-pyrrolo[2,3-b]pyridin-6-yl)cyclopropanecarboxamide

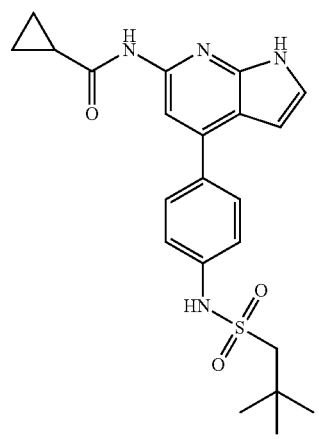 [SMILES: CC(C)(C)CS(=O)(=O)Nc1ccc(-c2cc(NC(=O)C3CC3)nc3[nH]ccc23)cc1]

¹H NMR (400 MHz, DMSO-d$_6$) δ 11.51 (s, 1H), 10.60 (s, 1H), 9.99 (s, 1H), 8.00 (s, 1H), 7.69 (d, J=6.8 Hz, 2H), 7.44-7.29 (m, 3H), 6.55 (s, 1H), 3.11 (s, 2H), 2.04 (s, 1H), 1.11 (q, J=7.5, 5.8 Hz, 9H), 0.81 (s, 4H).

MS(ESI+) m/z 427 (M+H)⁺

Example 45: Synthesis of N-(4-(4-((3-methylbutyl)sulfonamido)phenyl)-1H-pyrrolo[2,3-b]pyridin-6-yl)cyclopropanecarboxamide

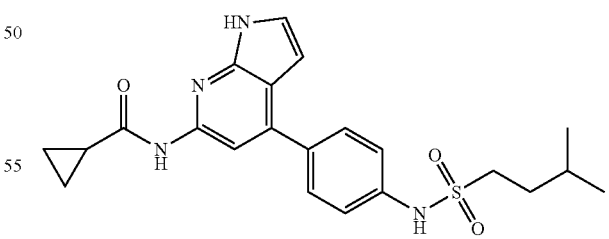

¹H NMR (400 MHz, DMSO-d$_6$) δ 11.51 (s, 1H), 10.60 (s, 1H), 10.00 (s, 1H), 8.00 (s, 1H), 7.69 (d, J=8.4 Hz, 2H), 7.37 (d, J=9.7 Hz, 3H), 6.53 (s, 1H), 3.14 (d, J=8.8 Hz, 2H), 2.04 (s, 1H), 1.60 (s, 3H), 0.82 (s, 10H).

MS(ESI+) m/z 427 (M+H)⁺

Example 46: Synthesis of N-(4-(4-(((cyclopropylmethyl)sulfonamido)phenyl)-1H-pyrrolo[2,3-b]pyridin-6-yl)cyclopropanecarboxamide

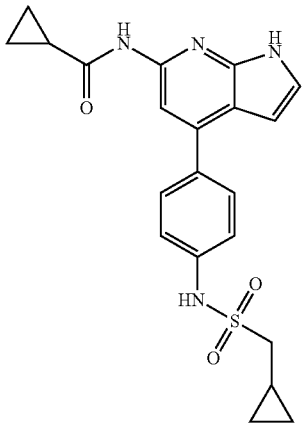 [SMILES: O=C(Nc1cc(-c2ccc(NS(=O)(=O)CC3CC3)cc2)c2cc[nH]c2n1)C1CC1]

¹H NMR (400 MHz, DMSO-d₆) δ 11.51 (s, 1H), 10.60 (s, 1H), 10.06 (s, 1H), 7.99 (s, 1H), 7.74-7.61 (m, 2H), 7.38 (d, J=8.9 Hz, 3H), 6.54 (s, 1H), 3.21-3.07 (m, 2H), 2.04 (s, 1H), 1.02 (s, 1H), 0.81 (s, 4H), 0.56 (s, 2H), 0.27 (s, 2H).

MS(ESI+) m/z 411 (M+H)⁺

Example 47: Synthesis of N-(4-(4-(((cyclohexylmethyl)sulfonamido)phenyl)-1H-pyrrolo[2,3-b]pyridin-6-yl)cyclopropanecarboxamide

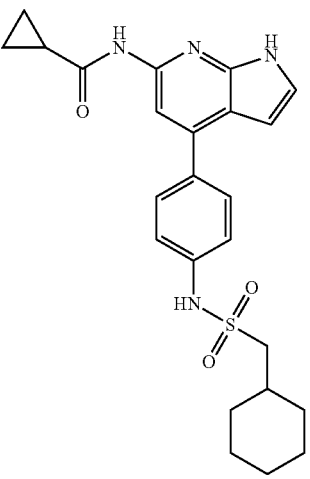 [SMILES: O=C(Nc1cc(-c2ccc(NS(=O)(=O)CC3CCCCC3)cc2)c2cc[nH]c2n1)C1CC1]

¹H NMR (400 MHz, DMSO-d₆) δ 11.51 (s, 1H), 10.60 (s, 1H), 10.01 (s, 1H), 8.00 (s, 1H), 7.68 (d, J=7.9 Hz, 2H), 7.37 (t, J=10.1 Hz, 3H), 6.54 (s, 1H), 3.11-2.99 (m, 2H), 2.03 (s, 1H), 1.85 (s, 2H), 1.63 (s, 2H), 1.24 (s, 2H), 1.06 (s, 2H), 0.81 (s, 4H).

MS(ESI+) m/z 453 (M+H)⁺

Example 48: Synthesis of N-(4-(4-(allylsulfonamido)phenyl)-1H-pyrrolo[2,3-b]pyridin-6-yl)cyclopropanecarboxamide

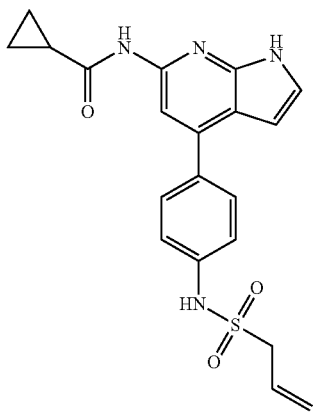 [SMILES: C=CCS(=O)(=O)Nc1ccc(-c2cc(NC(=O)C3CC3)nc3[nH]ccc23)cc1]

¹H NMR (400 MHz, DMSO-d₆) δ 11.53 (s, 1H), 10.63 (s, 1H), 10.12 (s, 1H), 8.00 (s, 1H), 7.69 (d, J=8.3 Hz, 2H), 7.38 (dd, J=8.2, 5.6 Hz, 3H), 6.55 (dd, J=3.7, 1.9 Hz, 1H), 5.81 (ddd, J=17.2, 10.1, 7.3 Hz, 1H), 5.36 (dd, J=19.3, 13.6 Hz, 2H), 3.98 (d, J=7.2 Hz, 2H), 2.04 (s, 1H), 0.85-0.76 (m, 4H).

MS(ESI+) m/z 397 (M+H)⁺

Example 49: Synthesis of N-(4-(4-(((fluoromethyl)sulfonamido)phenyl)-1H-pyrrolo[2,3-b]pyridin-6-yl)cyclopropanecarboxamide

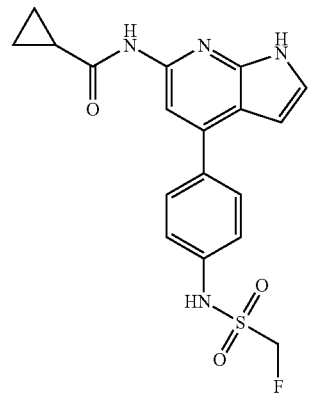 [SMILES: O=C(Nc1cc(-c2ccc(NS(=O)(=O)CF)cc2)c2cc[nH]c2n1)C1CC1]

¹H NMR (400 MHz, DMSO-d₆) δ 11.52 (s, 1H), 10.61 (s, 2H), 8.00 (s, 1H), 7.69 (d, J=8.1 Hz, 2H), 7.38 (d, J=11.9 Hz, 3H), 6.54 (s, 1H), 5.59 (s, 1H), 5.48 (s, 1H), 2.05 (s, 1H), 0.81 (s, 4H).

MS(ESI+) m/z 389 (M+H)⁺

Example 50: Synthesis of N-(4-(4-((difluoromethyl)sulfonamido)phenyl)-1H-pyrrolo[2,3-b]pyridin-6-yl)cyclopropanecarboxamide

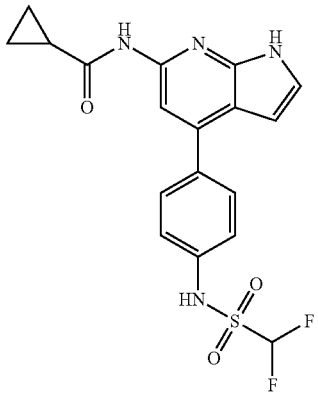 [SMILES: O=C(Nc1cc(-c2ccc(NS(=O)(=O)C(F)F)cc2)c2cc[nH]c2n1)C1CC1]

¹H NMR (400 MHz, DMSO-d₆) δ 11.55 (s, 1H), 11.16 (s, 1H), 10.62 (s, 1H), 8.01 (s, 1H), 7.72 (d, J=8.6 Hz, 2H), 7.50-7.30 (m, 3H), 7.14 (d, J=51.5 Hz, 1H), 6.53 (s, 1H), 2.05 (s, 1H), 0.92-0.71 (m, 4H).

MS(ESI+) m/z 407 (M+H)⁺

Example 51: Synthesis of N-(4-(4-((2,2-difluoroethyl)sulfonamido)phenyl)-1H-pyrrolo[2,3-b]pyridin-6-yl)cyclopropanecarboxamide

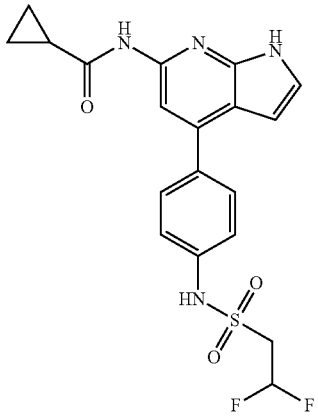 [SMILES: O=C(Nc1cc(-c2ccc(NS(=O)(=O)CC(F)F)cc2)c2cc[nH]c2n1)C1CC1]

¹H NMR (400 MHz, DMSO-d₆) δ 11.36 (s, 1H), 10.48 (s, 1H), 7.92 (s, 1H), 7.44 (s, 2H), 7.32 (s, 1H), 6.70 (s, 2H), 6.54 (s, 1H), 5.40 (s, 2H), 4.03 (s, 1H), 2.03 (s, 1H), 0.79 (d, J=14.6 Hz, 4H).

MS(ESI+) m/z 421 (M+H)⁺

Example 52: Synthesis of N-(4-(4-((3-cyanopropyl)sulfonamido)phenyl)-1H-pyrrolo[2,3-b]pyridin-6-yl)cyclopropanecarboxamide

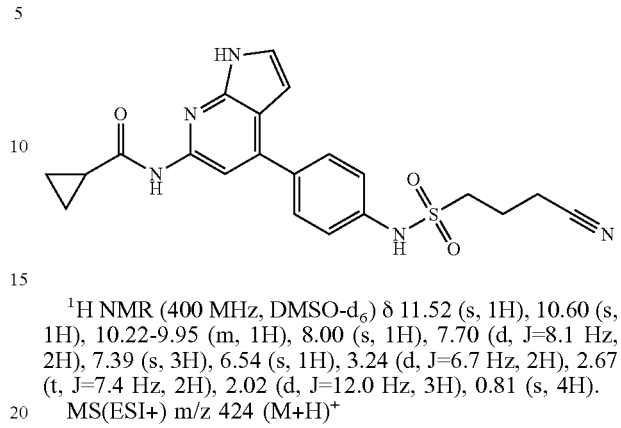

¹H NMR (400 MHz, DMSO-d₆) δ 11.52 (s, 1H), 10.60 (s, 1H), 10.22-9.95 (m, 1H), 8.00 (s, 1H), 7.70 (d, J=8.1 Hz, 2H), 7.39 (s, 3H), 6.54 (s, 1H), 3.24 (d, J=6.7 Hz, 2H), 2.67 (t, J=7.4 Hz, 2H), 2.02 (d, J=12.0 Hz, 3H), 0.81 (s, 4H).

MS(ESI+) m/z 424 (M+H)⁺

Example 53: Synthesis of N-(4-(4-((2-ethoxyethyl)sulfonamido)phenyl)-1H-pyrrolo[2,3-b]pyridin-6-yl)cyclopropanecarboxamide

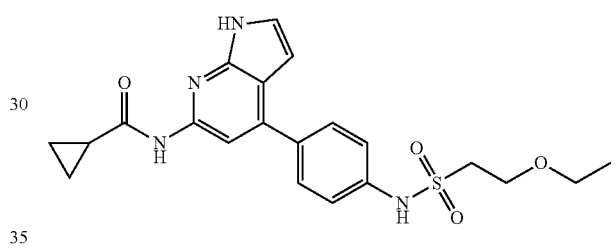

¹H NMR (400 MHz, DMSO-d₆) δ 11.51 (s, 1H), 10.60 (s, 1H), 9.89 (s, 1H), 8.01 (d, J=15.2 Hz, 1H), 7.68 (d, J=8.9 Hz, 2H), 7.48-7.29 (m, 3H), 6.54 (s, 1H), 3.83-3.68 (m, 2H), 3.49-3.39 (m, 4H), 2.05 (s, 1H), 1.13-0.98 (m, 3H), 0.91-0.73 (m, 4H).

MS(ESI+) m/z 429 (M+H)⁺

Example 54: Synthesis of N-(4-(4-(((tetrahydrofuran-3-yl)methyl)sulfonamido)phenyl)-1H-pyrrolo[2,3-b]pyridin-6-yl)cyclopropanecarboxamide

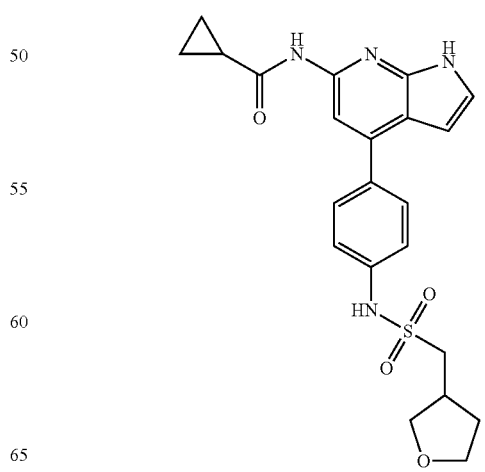

¹H NMR (400 MHz, DMSO-d₆) δ 11.52 (s, 1H), 10.61 (s, 1H), 9.93 (s, 1H), 8.00 (s, 1H), 7.80-7.63 (m, 2H), 7.38 (d, J=11.3 Hz, 3H), 6.55 (s, 1H), 3.89 (d, J=10.3 Hz, 1H), 3.66 (d, J=29.1 Hz, 2H), 2.09 (d, J=20.8 Hz, 2H), 1.64 (d, J=12.5 Hz, 1H), 0.82 (s, 4H).

MS(ESI+) m/z 441 (M+H)⁺

Example 55: Synthesis of N-(4-(4-(((tetrahydro-2H-pyran-4-yl)methyl)sulfonamido)phenyl)-1H-pyrrolo[2,3-b]pyridin-6-yl)cyclopropanecarboxamide

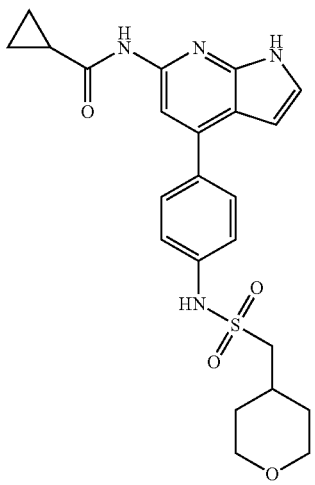 [SMILES: O=C(Nc1cc(-c2ccc(NS(=O)(=O)CC3CCOCC3)cc2)c2cc[nH]c2n1)C1CC1]

¹H NMR (400 MHz, DMSO-d₆) δ 11.52 (s, 1H), 10.62 (d, J=12.6 Hz, 1H), 9.93 (s, 1H), 8.00 (s, 1H), 7.68 (d, J=9.5 Hz, 2H), 7.51-7.22 (m, 3H), 6.55 (d, J=11.0 Hz, 1H), 3.81 (s, 2H), 3.14 (q, J=6.7 Hz, 2H), 2.09 (d, J=30.9 Hz, 2H), 1.76 (s, 2H), 1.32 (s, 2H), 0.82 (s, 4H).

MS(ESI+) m/z 455 (M+H)⁺

Example 56: Synthesis of N-(4-(4-((2-(methylsulfonyl)ethyl)sulfonamido)phenyl)-1H-pyrrolo[2,3-b]pyridin-6-yl)cyclopropanecarboxamide

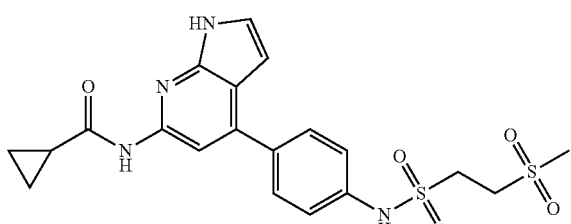

MS(ESI+) m/z 463 (M+H)⁺

Example 57: Synthesis of N-(4-(4-(cyclopropanesulfonamido)phenyl)-1H-pyrrolo[2,3-b]pyridin-6-yl)cyclopropanecarboxamide

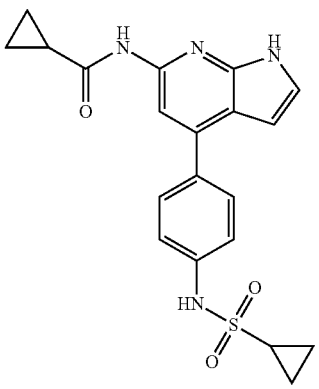 [SMILES: O=C(Nc1cc(-c2ccc(NS(=O)(=O)C3CC3)cc2)c2cc[nH]c2n1)C1CC1]

¹H NMR (400 MHz, DMSO-d₆) δ 11.51 (s, 1H), 10.60 (s, 1H), 9.94 (s, 1H), 8.00 (s, 1H), 7.68 (dd, J=11.1, 4.7 Hz, 2H), 7.40 (d, J=8.1 Hz, 3H), 6.54 (s, 1H), 2.71 (s, 1H), 2.04 (s, 1H), 0.97 (d, J=9.6 Hz, 4H), 0.80 (d, J=12.4 Hz, 4H).

MS(ESI+) m/z 397 (M+H)⁺

Example 58: Synthesis of N-(4-(4-(cyclobutanesulfonamido)phenyl)-1H-pyrrolo[2,3-b]pyridin-6-yl)cyclopropanecarboxamide

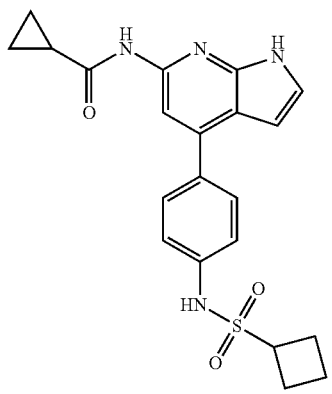 [SMILES: O=C(Nc1cc(-c2ccc(NS(=O)(=O)C3CCC3)cc2)c2cc[nH]c2n1)C1CC1]

¹H NMR (400 MHz, DMSO-d₆) δ 11.53 (s, 1H), 10.62 (s, 1H), 9.93 (s, 1H), 7.99 (s, 1H), 7.70-7.64 (m, 2H), 7.39 (dd, J=3.5, 2.5 Hz, 1H), 7.35 (d, J=8.6 Hz, 2H), 6.53 (dd, J=3.6, 1.9 Hz, 1H), 3.99 (p, J=8.0 Hz, 1H), 2.32 (d, J=18.7 Hz, 2H), 2.20 (dt, J=8.4, 4.4 Hz, 2H), 2.02 (d, J=13.0 Hz, 1H), 1.95-1.82 (m, 2H), 0.81 (d, J=4.4 Hz, 4H).

MS(ESI+) m/z 411 (M+H)⁺

Example 59: Synthesis of N-(4-(3-cyano-4-(ethylsulfonamido)phenyl)-1H-pyrrolo[2,3-b]pyridin-6-yl)cyclopropanecarboxamide

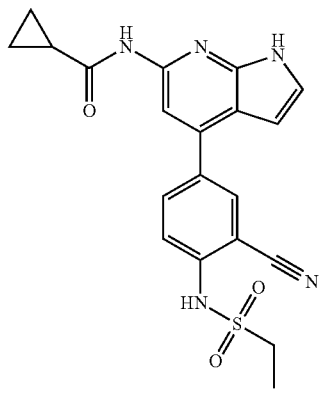 [SMILES: CCS(=O)(=O)Nc1ccc(-c2cc(NC(=O)C3CC3)nc3[nH]ccc23)cc1C#N]

MS(ESI+) m/z 410 (M+H)+

Example 60: Synthesis of N-(4-(4-(ethylsulfonamido)-3-fluorophenyl)-1-methyl-1H-pyrrolo[2,3-b]pyridin-6-yl)cyclopropanecarboxamide

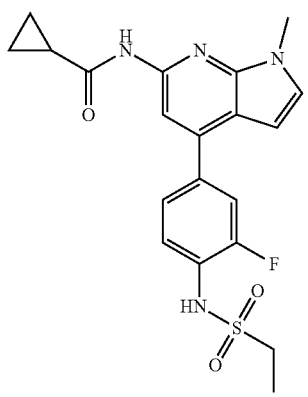 [SMILES: CCS(=O)(=O)Nc1ccc(-c2cc(NC(=O)C3CC3)nc3c2ccn3C)cc1F]

$^1$H NMR (400 MHz, DMSO-d$_6$) δ 10.77 (d, J=19.2 Hz, 1H), 8.06 (d, J=14.7 Hz, 1H), 7.69-7.46 (m, 4H), 6.57 (dd, J=3.7, 1.8 Hz, 1H), 3.82 (d, J=4.9 Hz, 3H), 2.08 (s, 1H), 1.27 (dt, J=18.9, 7.1 Hz, 5H), 0.86-0.80 (m, 4H).

MS(ESI+) m/z 417 (M+H)+

Example 61: Synthesis of N-(4-(4-(ethylsulfonamido)-3-fluorophenyl)-1-propyl-1H-pyrrolo[2,3-b]pyridin-6-yl)cyclopropanecarboxamide

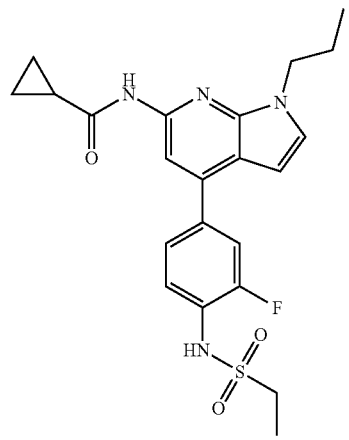 [SMILES: CCCn1ccc2c(-c3ccc(NS(=O)(=O)CC)c(F)c3)cc(NC(=O)C3CC3)nc21]

$^1$H NMR (400 MHz, DMSO-d$_6$) δ 10.72 (s, 1H), 8.07 (s, 1H), 7.68-7.50 (m, 4H), 6.59 (d, J=3.6 Hz, 1H), 4.20 (t, J=7.3 Hz, 2H), 3.60 (t, J=7.0 Hz, 3H), 2.10 (s, 1H), 1.84 (q, J=7.2 Hz, 2H), 1.42 (q, J=7.5 Hz, 2H), 1.31-1.27 (m, 3H), 0.84-0.78 (m, 4H).

MS(ESI+) m/z 445 (M+H)+

Example 62: Synthesis of N-(1-(cyanomethyl)-4-(4-(ethylsulfonamido)-3-fluorophenyl)-1H-pyrrolo[2,3-b]pyridin-6-yl)cyclopropanecarboxamide

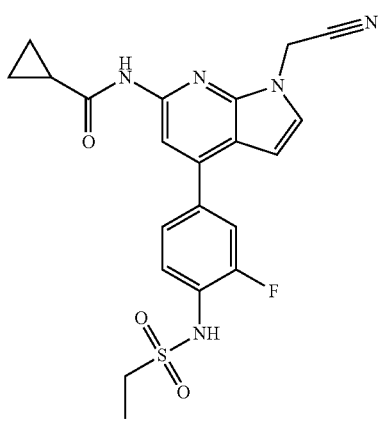 [SMILES: CCS(=O)(=O)Nc1ccc(-c2cc(NC(=O)C3CC3)nc3c2ccn3CC#N)cc1F]

$^1$H NMR (400 MHz, DMSO-d$_6$) δ 10.88 (d, J=15.7 Hz, 1H), 9.86 (s, 1H), 8.14 (d, J=12.2 Hz, 1H), 7.70-7.48 (m, 4H), 6.70 (d, J=3.8 Hz, 1H), 5.43 (d, J=4.2 Hz, 2H), 2.12 (s, 1H), 1.28 (d, J=6.7 Hz, 3H), 1.23 (s, 2H), 0.85-0.81 (m, 4H).

MS(ESI+) m/z 442 (M+H)+

Example 63: Synthesis of N-(4-(3-chloro-4-(propylsulfonamido)phenyl)-1H-pyrrolo[2,3-b]pyridin-6-yl)cyclopropanecarboxamide

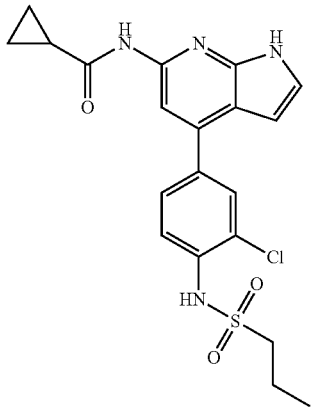

$^1$H NMR (400 MHz, DMSO-d$_6$) δ 11.63 (s, 1H), 10.70 (s, 1H), 9.65 (s, 1H), 8.02 (s, 1H), 7.76 (d, J=2.0 Hz, 1H), 7.70 (dd, J=2.0, 8.4 Hz, 1H), 7.63 (d, J=8.4 Hz, 1H), 7.45 (dd, J=2.5, 3.6 Hz, 1H), 6.53 (dd, J=1.8, 3.5 Hz, 1H), 3.20-3.12 (m, 2H), 2.03 (q, J=5.9, 7.3 Hz, 1H), 1.84-1.74 (m, 2H), 0.99 (t, J=7.4 Hz, 3H), 0.85-0.75 (m, 4H).

MS(ESI+) m/z 433, 435 (M+H)$^+$

Example 64: Synthesis of N-(4-(4-(ethylsulfonamido)-3-methylphenyl)-1H-pyrrolo[2,3-b]pyridin-6-yl)cyclopropanecarboxamide

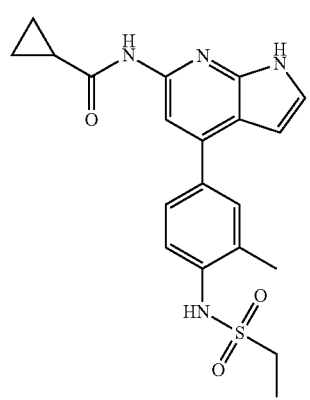 [SMILES: CCS(=O)(=O)Nc1ccc(-c2cc(NC(=O)C3CC3)nc3[nH]ccc23)cc1C]

$^1$H NMR (400 MHz, DMSO-d$_6$) δ 11.56 (s, 1H), 10.65 (s, 1H), 9.21 (s, 1H), 8.00 (s, 1H), 7.58-7.50 (m, 2H), 7.50-7.38 (m, 2H), 6.54 (dd, J=1.9, 3.5 Hz, 1H), 3.15 (q, J=7.3 Hz, 2H), 2.41 (s, 3H), 2.08-1.97 (m, 1H), 1.28 (t, J=7.3 Hz, 3H), 0.89-0.74 (m, 4H).

MS(ESI+) m/z 399 (M+H)$^+$

Example 65: Synthesis of N-(4-(3-methyl-4-(propylsulfonamido)phenyl)-1H-pyrrolo[2,3-b]pyridin-6-yl)cyclopropanecarboxamide

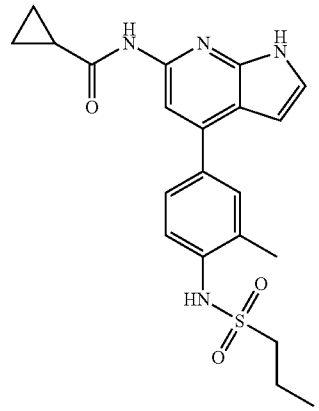

$^1$H NMR (400 MHz, DMSO-d$_6$) δ 11.54 (s, 1H), 10.64 (s, 1H), 9.11 (s, 1H), 8.00 (s, 1H), 7.58-7.50 (m, 2H), 7.47-7.37 (m, 2H), 6.54 (dd, J=1.9, 3.5 Hz, 1H), 3.16-3.06 (m, 2H), 2.39 (s, 3H), 2.09-1.99 (m, 1H), 1.76 (q, J=7.5 Hz, 2H), 0.99 (t, J=7.4 Hz, 3H), 0.87-0.75 (m, 4H).

MS(ESI+) m/z 413 (M+H)$^+$

Example 66: Synthesis of N-(4-(3-fluoro-4-(propylsulfonamido)phenyl)-1H-pyrrolo[2,3-b]pyridin-6-yl)cyclopropanecarboxamide

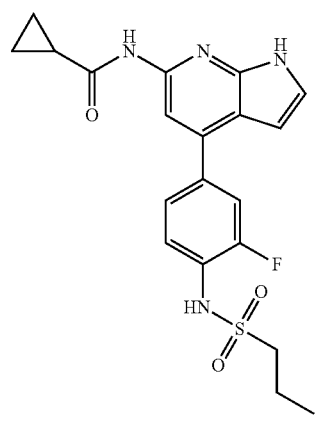 [SMILES: CCCS(=O)(=O)Nc1ccc(-c2cc(NC(=O)C3CC3)nc3[nH]ccc23)cc1F]

$^1$H NMR (400 MHz, DMSO-d$_6$) δ 11.61 (s, 1H), 10.68 (s, 1H), 9.84 (s, 1H), 8.02 (s, 1H), 7.62-7.52 (m, 3H), 7.49-7.40 (m, 1H), 6.56 (dd, J=3.5, 1.8 Hz, 1H), 3.23-3.10 (m, 2H), 2.08-1.97 (m, 1H), 1.84-1.71 (m, 2H), 0.99 (t, J=7.4 Hz, 3H), 0.80 (dd, J=10.1, 3.5 Hz, 4H).

MS(ESI+) m/z 417 (M+H)$^+$

Example 67: Synthesis of N-(4-(4-(butylsulfonamido)-3-fluorophenyl)-1H-pyrrolo[2,3-b]pyridin-6-yl)cyclopropanecarboxamide

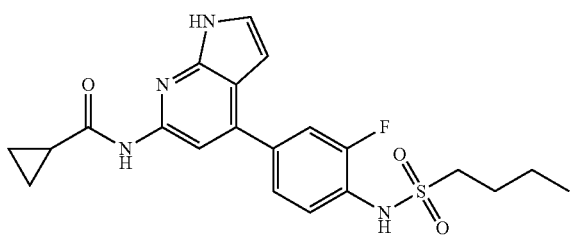 [SMILES: CCCCS(=O)(=O)Nc1ccc(-c2cc(NC(=O)C3CC3)nc3[nH]ccc23)cc1F]

$^1$H NMR (400 MHz, Chloroform-d) δ 11.59 (s, 1H), 10.65 (s, 1H), 9.82 (s, 1H), 8.02 (s, 1H), 7.62-7.53 (m, 3H), 7.43 (t, J=3.0 Hz, 1H), 6.56 (dd, J=3.5, 1.8 Hz, 1H), 3.21-3.13 (m, 2H), 2.11-1.98 (m, 1H), 1.73 (p, J=7.7 Hz, 2H), 1.41 (q, J=7.4 Hz, 2H), 0.89 (d, J=7.3 Hz, 3H), 0.83-0.76 (m, 4H).

MS(ESI+) m/z 431 (M+H)$^+$

Example 68: Synthesis of N-(4-(4-(cyclohexanesulfonamido)-3-fluorophenyl)-1H-pyrrolo[2,3-b]pyridin-6-yl)cyclopropanecarboxamide

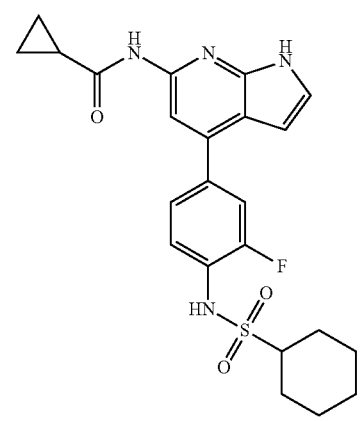 [SMILES: O=C(Nc1cc(-c2ccc(NS(=O)(=O)C3CCCCC3)c(F)c2)c2cc[nH]c2n1)C1CC1]

$^1$H NMR (400 MHz, Chloroform-d) δ 11.59 (s, 1H), 10.65 (s, 1H), 9.78 (s, 1H), 8.02 (s, 1H), 7.60 (t, J=8.4 Hz, 1H), 7.54 (dd, J=8.7, 4.7 Hz, 2H), 7.43 (d, J=5.8 Hz, 1H), 6.56 (dd, J=3.4, 1.7 Hz, 1H), 3.06 (t, J=11.8 Hz, 1H), 2.12 (d, J=12.3 Hz, 2H), 2.05 (s, 1H), 1.79 (d, J=12.7 Hz, 2H), 1.62 (d, J=13.0 Hz, 1H), 1.44 (q, J=12.4 Hz, 2H), 1.34-1.25 (m, 2H), 1.15 (t, J=12.7 Hz, 1H), 0.84-0.77 (m, 4H).

MS(ESI+) m/z 457 (M+H)$^+$

Example 69: Synthesis of N-(4-(4-(cyclopropanesulfonamido)-3-fluorophenyl)-1H-pyrrolo[2,3-b]pyridin-6-yl)cyclopropanecarboxamide

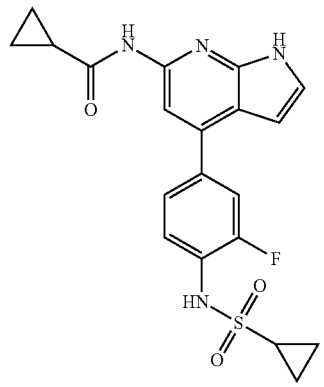 [SMILES: O=C(Nc1cc(-c2ccc(NS(=O)(=O)C3CC3)c(F)c2)c2cc[nH]c2n1)C1CC1]

$^1$H NMR (400 MHz, Chloroform-d) δ 11.59 (s, 1H), 10.65 (s, 1H), 9.80 (s, 1H), 8.01 (s, 1H), 7.58 (dt, J=11.8, 6.9 Hz, 3H), 7.43 (d, J=5.9 Hz, 1H), 6.56 (dd, J=3.5, 1.8 Hz, 1H), 2.74 (td, J=7.8, 3.8 Hz, 1H), 2.08-1.98 (m, 1H), 1.01-0.93 (m, 4H), 0.83-0.79 (m, 4H).

MS(ESI+) m/z 415 (M+H)$^+$

Example 70: Synthesis of N-(4-(4-((cyclohexylmethyl)sulfonamido)-3-fluorophenyl)-1H-pyrrolo[2,3-b]pyridin-6-yl)cyclopropanecarboxamide

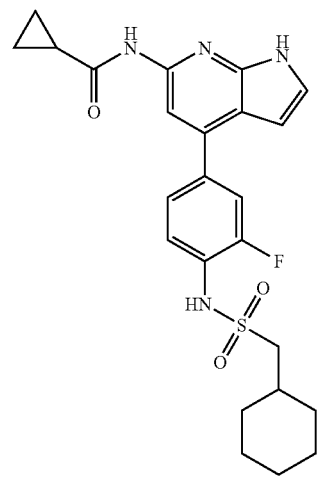 [SMILES: O=C(Nc1cc(-c2ccc(NS(=O)(=O)CC3CCCCC3)c(F)c2)c2cc[nH]c2n1)C1CC1]

$^1$H NMR (400 MHz, DMSO-d$_6$) δ 11.62 (s, 1H), 10.69 (s, 1H), 9.87 (s, 1H), 8.02 (s, 1H), 7.60-7.52 (m, 3H), 7.44 (t, J=3.1 Hz, 1H), 6.56 (dd, J=3.6, 1.8 Hz, 1H), 3.07 (d, J=6.0 Hz, 2H), 2.04 (s, 1H), 1.89 (t, J=14.8 Hz, 3H), 1.62 (dd, J=27.0, 12.4 Hz, 3H), 1.30-0.97 (m, 7H), 0.86-0.75 (m, 4H).

MS(ESI+) m/z 471 (M+H)$^+$

Example 71: Synthesis of N-(4-(4-(allylsulfonamido)-3-fluorophenyl)-1H-pyrrolo[2,3-b]pyridin-6-yl)cyclopropanecarboxamide

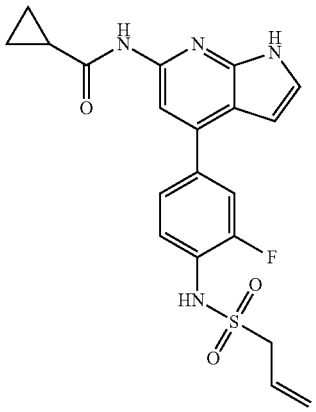 [SMILES: C=CCS(=O)(=O)Nc1ccc(-c2cc(NC(=O)C3CC3)nc3[nH]ccc23)cc1F]

¹H NMR (400 MHz, DMSO-d₆) δ 11.62 (s, 1H), 10.69 (s, 1H), 9.92 (s, 1H), 8.02 (s, 1H), 7.58 (dd, J=16.4, 8.0 Hz, 3H), 7.44 (t, J=2.9 Hz, 1H), 6.56 (d, J=4.7 Hz, 1H), 5.86 (td, J=17.1, 7.2 Hz, 1H), 5.50-5.37 (m, 2H), 3.99 (d, J=7.2 Hz, 2H), 2.06-1.99 (m, 1H), 0.81 (d, J=4.8 Hz, 4H).

MS(ESI+) m/z 415 (M+H)⁺

Example 72: Synthesis of N-(4-(3-fluoro-4-(((tetrahydrofuran-3-yl)methyl)sulfonamido)phenyl)-1H-pyrrolo[2,3-b]pyridin-6-yl)cyclopropanecarboxamide

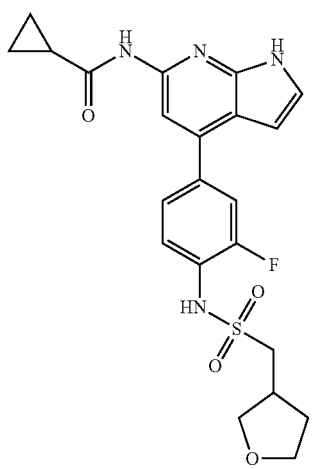 [SMILES: O=C(Nc1cc(-c2ccc(NS(=O)(=O)CC3CCOC3)c(F)c2)c2cc[nH]c2n1)C1CC1]

¹H NMR (400 MHz, DMSO-d₆) δ 11.61 (s, 1H), 10.68 (s, 1H), 9.96 (s, 1H), 8.02 (s, 1H), 7.64-7.52 (m, 3H), 7.44 (dd, J=3.5, 2.5 Hz, 1H), 6.56 (dd, J=3.6, 1.8 Hz, 1H), 3.88 (dd, J=8.6, 7.2 Hz, 1H), 3.72 (td, J=8.3, 5.0 Hz, 1H), 3.63 (d, J=7.8 Hz, 1H), 2.70-2.61 (m, 1H), 2.17-2.07 (m, 1H), 2.06-1.97 (m, 1H), 1.68 (dq, J=12.3, 7.7 Hz, 1H), 0.83-0.78 (m, 4H).

MS(ESI+) m/z 459 (M+H)⁺

Example 73: Synthesis of N-(4-(3-fluoro-4-(((tetrahydro-2H-pyran-4-yl)methyl)sulfonamido)phenyl)-1H-pyrrolo[2,3-b]pyridin-6-yl)cyclopropanecarboxamide

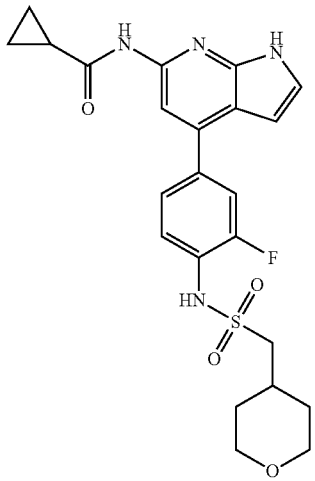 [SMILES: O=C(Nc1cc(-c2ccc(NS(=O)(=O)CC3CCOCC3)c(F)c2)c2cc[nH]c2n1)C1CC1]

¹H NMR (400 MHz, DMSO-d₆) δ 11.62 (s, 1H), 10.69 (s, 1H), 9.91 (s, 1H), 8.03 (s, 1H), 7.62-7.53 (m, 3H), 7.46-7.41 (m, 1H), 6.56 (dd, J=3.5, 1.8 Hz, 1H), 3.85-3.76 (m, 2H), 3.28 (dd, J=11.7, 2.0 Hz, 2H), 3.16 (d, J=6.4 Hz, 2H), 2.18 (q, J=6.0, 4.1 Hz, 1H), 2.03 (d, J=8.7 Hz, 1H), 1.78 (d, J=13.0 Hz, 2H), 1.35 (qd, J=12.2, 4.4 Hz, 2H), 0.84-0.75 (m, 4H).

MS(ESI+) m/z 473 (M+H)⁺

Example 74: Synthesis of N-(4-(4-(ethylsulfonamido)phenyl)-2-methyl-1H-pyrrolo[2,3-b]pyridin-6-yl)cyclopropanecarboxamide

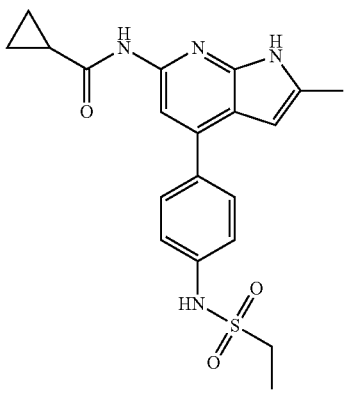 [SMILES: CCS(=O)(=O)Nc1ccc(-c2cc(NC(=O)C3CC3)nc3[nH]c(C)cc23)cc1]

MS(ESI+) m/z 399 (M+H)⁺

Example 75: Synthesis of N-(4-(3-fluoro-4-((2-methylpropyl)sulfonamido)phenyl)-1H-pyrrolo[2,3-b]pyridin-6-yl)cyclopropanecarboxamide

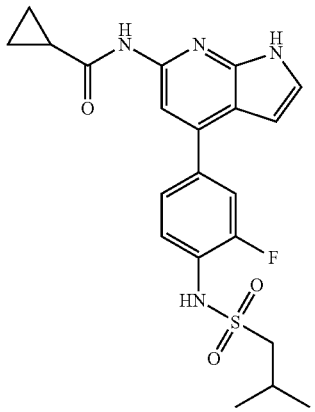 [SMILES: CC(C)CS(=O)(=O)Nc1ccc(-c2cc(NC(=O)C3CC3)nc3[nH]ccc23)cc1F]

¹H NMR (400 MHz, DMSO-d₆) δ 11.61 (s, 1H), 10.68 (s, 1H), 8.02 (s, 1H), 7.62-7.50 (m, 3H), 7.44 (dd, J=3.5, 2.5 Hz, 1H), 6.56 (dd, J=3.5, 1.8 Hz, 1H), 3.08 (d, J=6.4 Hz, 2H), 2.21 (dq, J=13.3, 6.6 Hz, 1H), 2.04 (h, J=6.2, 5.4 Hz, 1H), 1.04 (d, J=6.7 Hz, 6H), 0.83-0.78 (m, 4H).
MS(ESI+) m/z 431 (M+H)⁺

Example 76: Synthesis of N-(4-(3-fluoro-4-((3-fluoropropyl)sulfonamido)phenyl)-1H-pyrrolo[2,3-b]pyridin-6-yl)cyclopropanecarboxamide

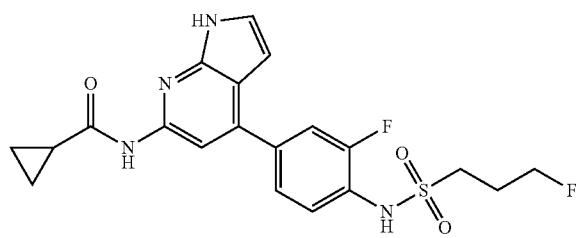 [SMILES: O=C(Nc1cc(-c2ccc(NS(=O)(=O)CCCF)c(F)c2)c2cc[nH]c2n1)C1CC1]

¹H NMR (400 MHz, DMSO-d₆) δ 11.62 (s, 1H), 10.68 (s, 1H), 9.98 (s, 1H), 8.02 (s, 1H), 7.61-7.54 (m, 3H), 7.44 (t, J=3.0 Hz, 1H), 6.56 (dd, J=3.6, 1.8 Hz, 1H), 4.62 (t, J=5.9 Hz, 1H), 4.50 (t, J=6.0 Hz, 1H), 3.28 (d, J=15.4 Hz, 2H), 2.12 (ddd, J=33.0, 16.5, 9.7 Hz, 3H), 0.83-0.78 (m, 4H).
MS(ESI+) m/z 435 (M+H)⁺

Example 77: Synthesis of N-(4-(4-((3-cyanopropyl)sulfonamido)-3-fluorophenyl)-1H-pyrrolo[2,3-b]pyridin-6-yl)cyclopropanecarboxamide

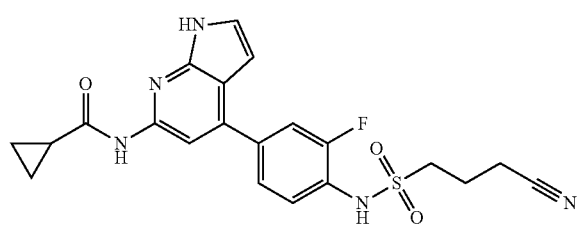 [SMILES: N#CCCCS(=O)(=O)Nc1ccc(-c2cc(NC(=O)C3CC3)nc3[nH]ccc23)cc1F]

¹H NMR (400 MHz, DMSO-d₆) δ 11.62 (s, 1H), 10.68 (s, 1H), 10.03 (s, 1H), 8.02 (s, 1H), 7.61-7.55 (m, 3H), 7.44 (dd, J=3.5, 2.5 Hz, 1H), 6.56 (dd, J=3.5, 1.8 Hz, 1H), 3.30-3.24 (m, 2H), 2.70 (t, J=7.3 Hz, 2H), 2.06 (p, J=7.2 Hz, 3H), 0.85-0.77 (m, 4H).
MS(ESI+) m/z 442 (M+H)⁺

Example 78: Synthesis of N-(4-(4-(cyclobutanesulfonamido)-3-fluorophenyl)-1H-pyrrolo[2,3-b]pyridin-6-yl)cyclopropanecarboxamide

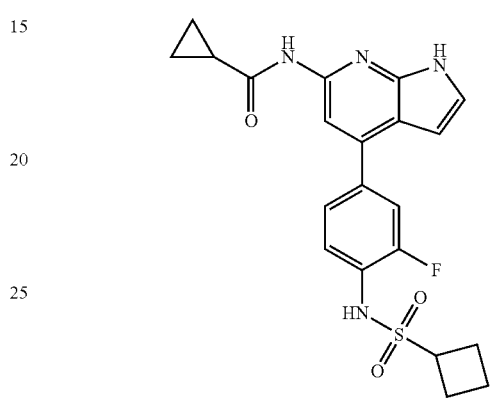

¹H NMR (400 MHz, DMSO-d₆) δ 11.61 (s, 1H), 10.68 (s, 1H), 9.77 (s, 1H), 8.02 (s, 1H), 7.62-7.50 (m, 3H), 7.44 (t, J=3.0 Hz, 1H), 6.55 (t, J=2.5 Hz, 1H), 4.00 (t, J=8.1 Hz, 1H), 2.42-1.82 (m, 6H), 0.81 (t, J=6.5 Hz, 4H).
MS(ESI+) m/z 429 (M+H)⁺

Example 79: Synthesis of N-(4-(4-((2,2-dimethylpropyl)sulfonamido)-3-fluorophenyl)-1H-pyrrolo[2,3-b]pyridin-6-yl)cyclopropanecarboxamide

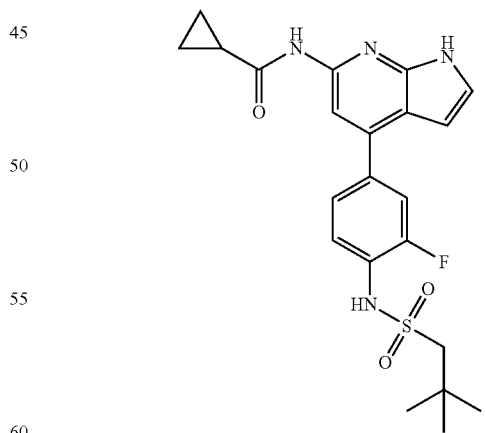

¹H NMR (400 MHz, DMSO-d₆) δ 11.61 (s, 1H), 10.68 (s, 1H), 8.02 (s, 1H), 7.62-7.51 (m, 3H), 7.44 (t, J=2.8 Hz, 1H), 6.57 (s, 1H), 3.14 (s, 2H), 2.03 (d, J=12.4 Hz, 1H), 1.11 (s, 9H), 0.81 (d, J=4.6 Hz, 4H).
MS(ESI+) m/z 445 (M+H)⁺

Example 80: Synthesis of N-(4-(4-((cyclopropylmethyl)sulfonamido)-3-fluorophenyl)-1H-pyrrolo[2,3-b]pyridin-6-yl)cyclopropanecarboxamide

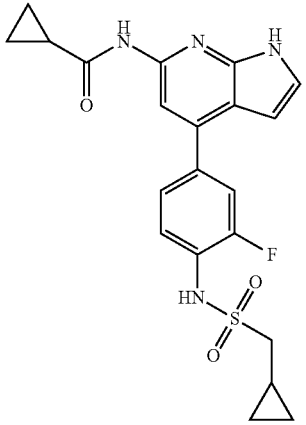 [SMILES: O=C(Nc1cc(-c2ccc(NS(=O)(=O)CC3CC3)c(F)c2)c2cc[nH]c2n1)C1CC1]

$^1$H NMR (400 MHz, DMSO-d$_6$) δ 11.60 (s, 1H), 10.67 (s, 1H), 9.88 (s, 1H), 8.01 (s, 1H), 7.60 (t, J=8.4 Hz, 1H), 7.53 (t, J=8.4 Hz, 2H), 7.43 (t, J=3.0 Hz, 1H), 6.56 (d, J=3.2 Hz, 1H), 3.14 (d, J=7.0 Hz, 2H), 2.04 (s, 1H), 1.08 (s, 1H), 0.87-0.74 (m, 4H), 0.56 (q, J=5.8 Hz, 2H), 0.34 (q, J=5.1 Hz, 2H).

MS(ESI+) m/z 429 (M+H)$^+$

Example 81: Synthesis of N-(4-(4-(ethylsulfonamido)-3,5-difluorophenyl)-1H-pyrrolo[2,3-b]pyridin-6-yl)cyclopropanecarboxamide

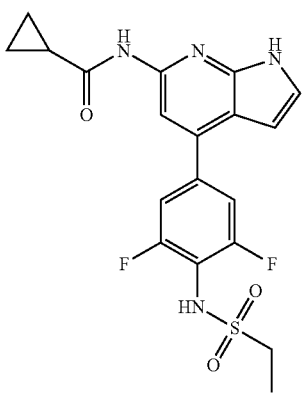 [SMILES: CCS(=O)(=O)Nc1c(F)cc(-c2cc(NC(=O)C3CC3)nc3[nH]ccc23)cc1F]

$^1$H NMR (400 MHz, DMSO-d$_6$) δ 11.69 (s, 1H), 10.73 (s, 1H), 9.64 (s, 1H), 8.03 (s, 1H), 7.53-7.42 (m, 3H), 6.58 (dd, J=1.8, 3.5 Hz, 1H), 3.19 (q, J=7.4 Hz, 2H), 2.09-1.99 (m, 1H), 1.34 (t, J=7.3 Hz, 3H), 0.83-0.77 (m, 4H).

MS(ESI+) m/z 421 (M+H)$^+$

Example 82: Synthesis of N-(4-(3,5-difluoro-4-(propylsulfonamido)phenyl)-1H-pyrrolo[2,3-b]pyridin-6-yl)cyclopropanecarboxamide

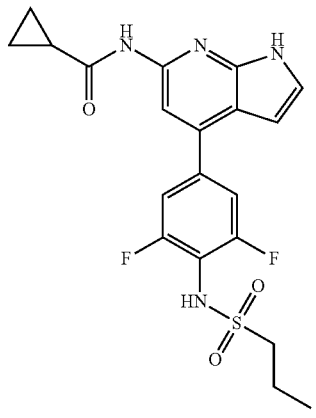 [SMILES: CCCS(=O)(=O)Nc1c(F)cc(-c2cc(NC(=O)C3CC3)nc3[nH]ccc23)cc1F]

$^1$H NMR (400 MHz, DMSO-d$_6$) δ 11.68 (s, 1H), 10.73 (s, 1H), 9.64 (s, 1H), 8.03 (s, 1H), 7.51-7.45 (m, 3H), 6.58 (dd, J=1.8, 3.6 Hz, 1H), 3.21-3.12 (m, 2H), 2.04 (dd, J=5.7, 11.3 Hz, 1H), 1.83 (q, J=7.6 Hz, 2H), 1.02 (t, J=7.4 Hz, 3H), 0.86-0.78 (m, 4H).

MS(ESI+) m/z 435 (M+H)$^+$

Example 83: Synthesis of N-(4-(4-(ethylsulfonamido)-2,5-difluorophenyl)-1H-pyrrolo[2,3-b]pyridin-6-yl)cyclopropanecarboxamide

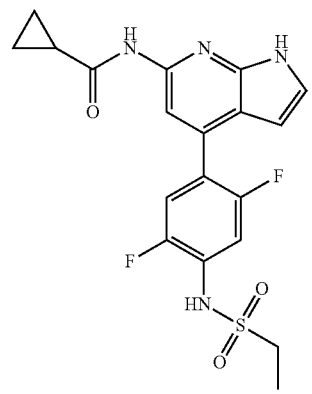 [SMILES: CCS(=O)(=O)Nc1cc(F)c(-c2cc(NC(=O)C3CC3)nc3[nH]ccc23)cc1F]

$^1$H NMR (400 MHz, DMSO-d$_6$) δ 11.59 (s, 1H), 10.69 (s, 1H), 10.12 (s, 1H), 7.96 (s, 1H), 7.54-7.46 (m, 1H), 7.45-7.38 (m, 2H), 6.32 (d, J=2.1 Hz, 1H), 3.23 (q, J=7.3 Hz, 2H), 2.03 (d, J=5.8 Hz, 1H), 1.26 (q, J=7.8, 8.3 Hz, 4H), 0.84-0.75 (m, 4H).

MS(ESI+) m/z 421 (M+H)$^+$

Example 84: Synthesis of N-(4-(2,5-difluoro-4-(propylsulfonamido)phenyl)-1H-pyrrolo[2,3-b]pyridin-6-yl)cyclopropanecarboxamide

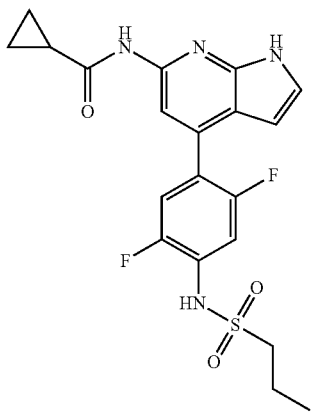 [SMILES: CCCS(=O)(=O)Nc1cc(F)c(-c2cc(NC(=O)C3CC3)nc3[nH]ccc23)cc1F]

¹H NMR (400 MHz, DMSO-d₆) δ 11.60 (s, 1H), 10.70 (s, 1H), 10.12 (s, 1H), 7.97 (s, 1H), 7.50 (dd, J=6.7, 10.6 Hz, 1H), 7.46-7.37 (m, 2H), 6.32 (d, J=2.6 Hz, 1H), 3.25-3.17 (m, 2H), 2.09-1.98 (m, 1H), 1.75 (dt, J=7.6, 15.2 Hz, 2H), 0.99 (t, J=7.4 Hz, 3H), 0.85-0.78 (m, 4H).

MS(ESI+) m/z 435 (M+H)⁺

Example 85: Synthesis of N-(4-(4-(((1-cyanocyclopropyl)methyl)sulfonamido)-3-fluorophenyl)-1H-pyrrolo[2,3-b]pyridin-6-yl)cyclopropanecarboxamide

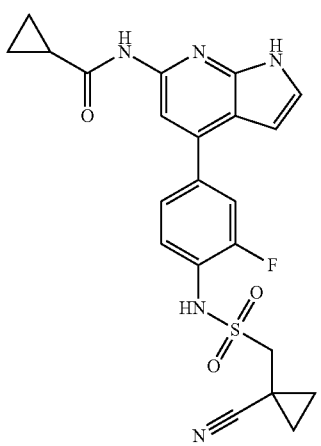 [SMILES: N#CC1(CS(=O)(=O)Nc2ccc(-c3cc(NC(=O)C4CC4)nc4[nH]ccc34)cc2F)CC1]

¹H NMR (400 MHz, DMSO-d₆) δ 11.60 (s, 1H), 10.67 (s, 1H), 10.18 (s, 1H), 8.01 (s, 1H), 7.56 (d, J=13.3 Hz, 3H), 7.43 (s, 1H), 6.55 (s, 1H), 2.02 (s, 1H), 1.33 (d, J=42.9 Hz, 2H), 1.23 (s, 2H), 0.81 (s, 4H).

MS(ESI+) m/z 454 (M+H)⁺

Example 86: Synthesis of N-(4-(4-(((1-(cyanomethyl)cyclopropyl)methyl)sulfonamido)-3-fluorophenyl)-1H-pyrrolo[2,3-b]pyridin-6-yl)cyclopropanecarboxamide

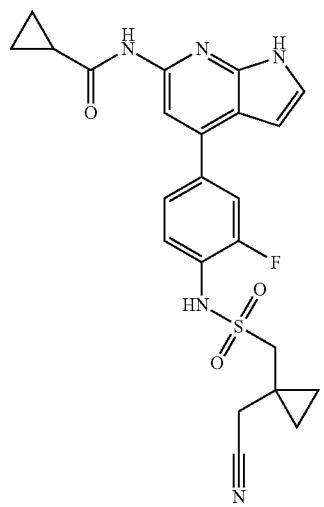 [SMILES: N#CCC1(CS(=O)(=O)Nc2ccc(-c3cc(NC(=O)C4CC4)nc4[nH]ccc34)cc2F)CC1]

MS(ESI+) m/z 468 (M+H)⁺

Example 87: Synthesis of N-(4-(4-((3-cyano-3-methylbutyl)sulfonamido)-3-fluorophenyl)-1H-pyrrolo[2,3-b]pyridin-6-yl)cyclopropanecarboxamide

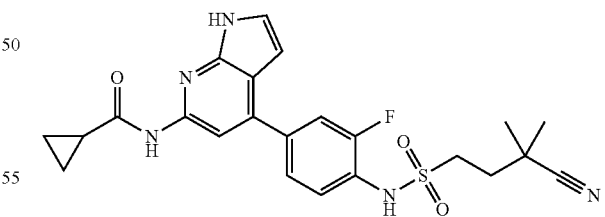

¹H NMR (400 MHz, DMSO-d₆) δ 11.61 (s, 1H), 10.68 (s, 1H), 10.03 (s, 1H), 8.02 (s, 1H), 7.57 (t, J=5.9 Hz, 3H), 7.44 (s, 1H), 6.59-6.49 (m, 1H), 2.06 (d, J=12.8 Hz, 5H), 1.23 (s, 6H), 0.85-0.77 (m, 4H).

MS(ESI+) m/z 470 (M+H)⁺

Example 88: Synthesis of N-(4-(4-(((1-cyanocyclopropyl)methyl)sulfonamido)phenyl)-1H-pyrrolo[2,3-b]pyridin-6-yl)cyclopropanecarboxamide

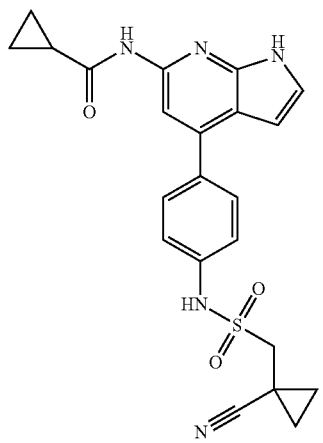 [SMILES: N#CC1(CS(=O)(=O)Nc2ccc(-c3cc(NC(=O)C4CC4)nc4[nH]ccc34)cc2)CC1]

$^1$H NMR (400 MHz, DMSO-d$_6$) δ 11.52 (s, 1H), 10.62 (s, 1H), 7.99 (s, 1H), 7.68 (d, J=8.5 Hz, 2H), 7.41-7.32 (m, 3H), 6.53 (dd, J=3.5, 1.8 Hz, 1H), 3.54 (s, 2H), 2.06-1.94 (m, 2H), 1.36 (q, J=4.9 Hz, 2H), 1.20-1.14 (m, 2H), 0.83-0.75 (m, 4H).

MS(ESI+) m/z 436 (M+H)$^+$

Example 89: Synthesis of N-(4-(4-(((1-(cyanomethyl)cyclopropyl)methyl)sulfonamido)phenyl)-1H-pyrrolo[2,3-b]pyridin-6-yl)cyclopropanecarboxamide

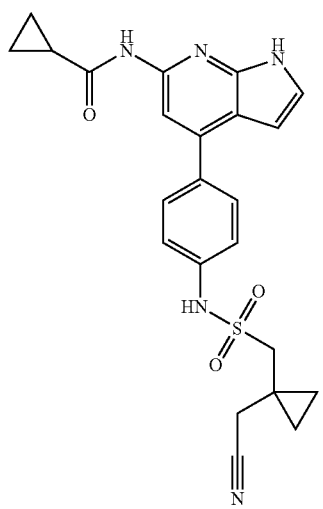 [SMILES: N#CCC1(CS(=O)(=O)Nc2ccc(-c3cc(NC(=O)C4CC4)nc4[nH]ccc34)cc2)CC1]

$^1$H NMR (400 MHz, Methanol-d$_4$) δ 11.52 (s, 1H), 10.62 (s, 1H), 10.23 (s, 1H), 7.99 (s, 1H), 7.69 (d, J=8.5 Hz, 2H), 7.42-7.31 (m, 3H), 6.54 (dd, J=3.6, 1.8 Hz, 1H), 3.30 (s, 2H), 2.86 (s, 2H), 2.09-1.92 (m, 1H), 0.80 (td, J=7.9, 2.9 Hz, 4H), 0.75-0.63 (m, 4H).

MS(ESI+) m/z 450 (M+H)$^+$

Example 90: Synthesis of N-(4-(4-(cyclopropanesulfonamido)-2-methylphenyl)-1H-pyrrolo[2,3-b]pyridin-6-yl)cyclopropanecarboxamide

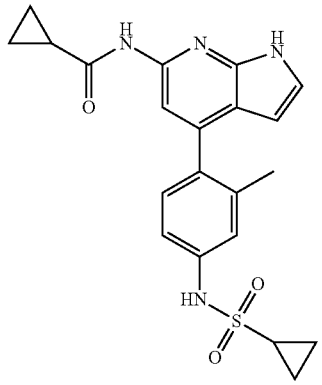 [SMILES: Cc1cc(NS(=O)(=O)C2CC2)ccc1-c1cc(NC(=O)C2CC2)nc2[nH]ccc12]

$^1$H NMR (400 MHz, Chloroform-d) δ 11.47 (s, 1H), 10.62 (s, 1H), 9.80 (s, 1H), 7.77 (s, 1H), 7.33 (dd, J=3.5, 2.4 Hz, 1H), 7.26-7.15 (m, 3H), 6.08 (dd, J=3.5, 1.9 Hz, 1H), 2.15 (s, 3H), 2.06-2.00 (m, 1H), 0.99-0.96 (m, 4H), 0.82-0.74 (m, 4H).

MS(ESI+) m/z 411 (M+H)$^+$

Example 91: Synthesis of N-(4-(4-(cyclobutanesulfonamido)-2-methylphenyl)-1H-pyrrolo[2,3-b]pyridin-6-yl)cyclopropanecarboxamide

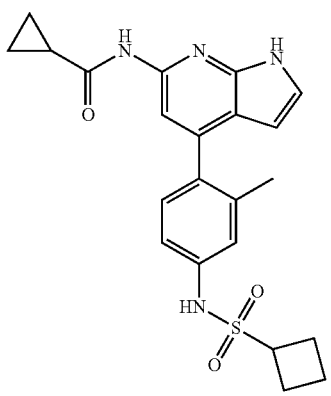 [SMILES: Cc1cc(NS(=O)(=O)C2CCC2)ccc1-c1cc(NC(=O)C2CC2)nc2[nH]ccc12]

$^1$H NMR (400 MHz, Chloroform-d) δ 11.47 (s, 1H), 10.62 (s, 1H), 9.77 (s, 1H), 7.76 (s, 1H), 7.33 (dd, J=3.5, 2.5 Hz, 1H), 7.25-7.09 (m, 3H), 6.07 (dd, J=3.5, 1.9 Hz, 1H), 3.99 (p, J=8.1 Hz, 1H), 2.36 (dd, J=19.7, 9.4 Hz, 2H), 2.23-2.17 (m, 2H), 2.13 (s, 3H), 2.03 (s, 1H), 1.95-1.84 (m, 2H), 0.82-0.74 (m, 4H).

MS(ESI+) m/z 425 (M+H)$^+$

Example 92: Synthesis of N-(4-(4-((cyclopropylmethyl)sulfonamido)-2-methylphenyl)-1H-pyrrolo[2,3-b]pyridin-6-yl)cyclopropanecarboxamide

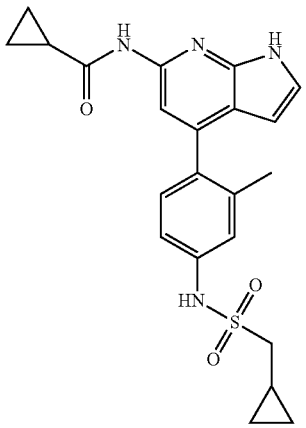 [SMILES: Cc1cc(NS(=O)(=O)CC2CC2)ccc1-c1cc(NC(=O)C2CC2)nc2[nH]ccc12]

¹H NMR (400 MHz, Chloroform-d) δ 11.47 (s, 1H), 10.61 (s, 1H), 9.91 (s, 1H), 7.76 (s, 1H), 7.33 (d, J=2.4 Hz, 1H), 7.28-7.10 (m, 3H), 6.08 (dd, J=3.5, 1.9 Hz, 1H), 3.13 (d, J=7.1 Hz, 2H), 2.14 (s, 3H), 2.07-1.94 (m, 1H), 1.02 (td, J=7.5, 3.8 Hz, 1H), 0.78 (dd, J=8.4, 2.5 Hz, 4H), 0.58-0.53 (m, 2H), 0.28 (dt, J=6.3, 4.5 Hz, 2H).

MS(ESI+) m/z 425 (M+H)⁺

Example 93: Synthesis of N-(4-(4-(ethylsulfonamido)phenyl)-3-methyl-1H-pyrrolo[2,3-b]pyridin-6-yl)cyclopropanecarboxamide

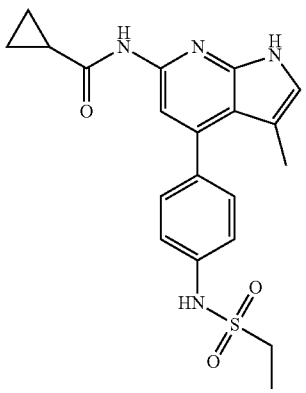 [SMILES: CCS(=O)(=O)Nc1ccc(-c2cc(NC(=O)C3CC3)nc3[nH]cc(C)c23)cc1]

¹H NMR (400 MHz, Chloroform-d) δ 11.17 (s, 1H), 10.56 (s, 1H), 7.72 (s, 1H), 7.42-7.38 (m, 2H), 7.31 (d, J=6.8 Hz, 2H), 7.10 (s, 1H), 3.15 (q, J=7.2 Hz, 2H), 2.03 (s, 1H), 1.87 (s, 3H), 1.24-1.20 (m, 5H), 0.81-0.74 (m, 4H).

MS(ESI+) m/z 399 (M+H)⁺

Example 94: Synthesis of N-(3-methyl-4-(4-(propylsulfonamido)phenyl)-1H-pyrrolo[2,3-b]pyridin-6-yl)cyclopropanecarboxamide

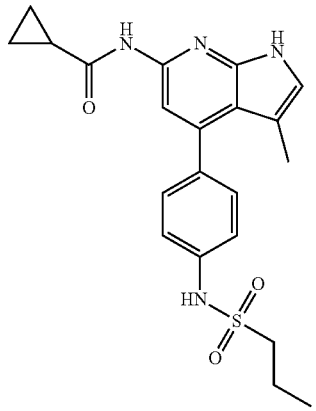 [SMILES: CCCS(=O)(=O)Nc1ccc(-c2cc(NC(=O)C3CC3)nc3[nH]cc(C)c23)cc1]

¹H NMR (400 MHz, Chloroform-d) δ 11.17 (d, J=2.4 Hz, 1H), 10.57 (s, 1H), 7.72 (s, 1H), 7.39 (d, J=8.5 Hz, 2H), 7.34-7.28 (m, 3H), 7.10 (d, J=2.1 Hz, 1H), 3.12 (t, J=2.1 Hz, 2H), 2.02 (d, J=2.1 Hz, 1H), 1.86 (s, 3H), 1.74-1.70 (m, 2H), 0.95 (d, J=7.5 Hz, 3H), 0.81-0.73 (m, 4H).

MS(ESI+) m/z 413 (M+H)⁺

Example 95: Synthesis of N-(4-(2-methyl-4-(propylsulfonamido)phenyl)-1H-pyrrolo[2,3-b]pyridin-6-yl)cyclopropanecarboxamide ¹H NMR (400 MHz, Chloroform-d) δ 11.48 (s, 1H), 10.62 (s, 1H), 9.84 (s, 1H), 7.77 (s, 1H), 7.33 (dd, J=3.5, 2.5 Hz, 1H), 7.23 (s, 1H), 7.19-7.10 (m, 2H), 6.08 (dd, J=3.5, 1.8 Hz, 1H), 3.16-3.11 (m, 2H), 2.14 (s, 3H), 2.09-2.01 (m, 1H), 1.72 (h, J=7.5 Hz, 2H), 0.97 (t, J=7.4 Hz, 3H), 0.83-0.73 (m, 4H).

MS(ESI+) m/z 413 (M+H)⁺

Example 96: Synthesis of N-(4-(4-((3-cyanopropyl)sulfonamido)-2-methylphenyl)-1H-pyrrolo[2,3-b]pyridin-6-yl)cyclopropanecarboxamide

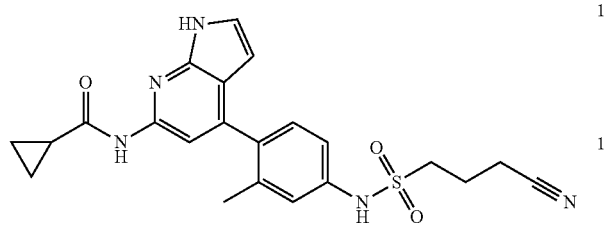

$^1$H NMR (400 MHz, Chloroform-d) δ 11.47 (s, 1H), 10.62 (s, 1H), 7.76 (s, 1H), 7.37-7.31 (m, 1H), 7.24 (t, J=7.1 Hz, 1H), 7.20-7.14 (m, 2H), 6.11-6.04 (m, 1H), 3.25 (dd, J=8.5, 6.6 Hz, 2H), 2.68 (t, J=7.3 Hz, 2H), 2.14 (s, 3H), 2.04-1.98 (m, 2H), 1.92 (d, J=8.2 Hz, 1H), 0.82-0.74 (m, 4H).

MS(ESI+) m/z 438 (M+H)$^+$

Example 97: Synthesis of 6-(cyclopropanecarboxamido)-4-(4-(ethylsulfonamido)-3-fluorophenyl)-1H-pyrrolo[2,3-b]pyridine 7-oxide

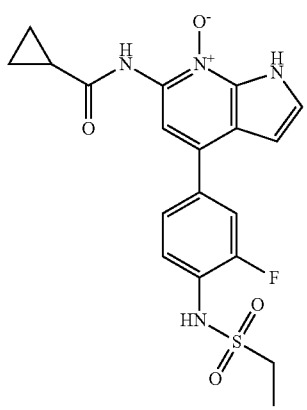 [SMILES: CCS(=O)(=O)Nc1ccc(-c2cc(NC(=O)C3CC3)[n+]([O-])c3[nH]ccc23)cc1F]

$^1$H NMR (400 MHz, DMSO-d$_6$) δ 12.54 (s, 1H), 10.78 (s, 1H), 9.84 (s, 1H), 8.16 (s, 1H), 7.61-7.50 (m, 3H), 7.46 (t, J=2.8 Hz, 1H), 6.71 (dd, J=3.5, 1.8 Hz, 1H), 3.18 (q, J=7.2 Hz, 2H), 2.41 (q, J=6.5, 5.3 Hz, 1H), 1.28 (t, J=7.3 Hz, 3H), 0.89 (d, J=7.9 Hz, 4H).

MS(ESI+) m/z 419 (M+H)$^+$

Example 98: Synthesis of N-(4-(4-(ethylsulfonamido)-3-(trifluoromethyl)phenyl)-1H-pyrrolo[2,3-b]pyridin-6-yl)cyclopropanecarboxamide

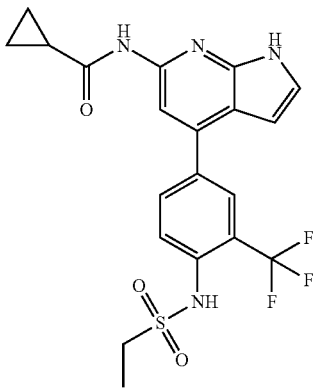 [SMILES: CCS(=O)(=O)Nc1ccc(-c2cc(NC(=O)C3CC3)nc3[nH]ccc23)cc1C(F)(F)F]

$^1$H NMR (400 MHz, DMSO-d$_6$) δ 11.53 (s, 1H), 10.64 (s, 1H), 10.32 (s, 1H), 7.82 (s, 1H), 7.67 (d, J=2.2 Hz, 1H), 7.60-7.52 (m, 1H), 7.43 (d, J=8.4 Hz, 1H), 7.34-7.26 (m, 1H), 6.01 (dd, J=3.6, 1.8 Hz, 1H), 3.24 (d, J=7.4 Hz, 2H), 2.07-1.98 (m, 1H), 1.25 (t, J=7.3 Hz, 3H), 0.81-0.72 (m, 4H).

MS(ESI+) m/z 453 (M+H)$^+$

Example 99: Synthesis of N-(4-(2-ethyl-4-(ethylsulfonamido)phenyl)-1H-pyrrolo[2,3-b]pyridin-6-yl)cyclopropanecarboxamide

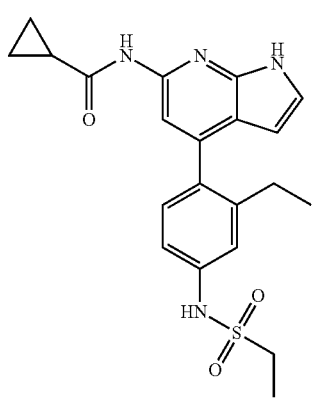 [SMILES: CCc1cc(NS(=O)(=O)CC)ccc1-c1cc(NC(=O)C2CC2)nc2[nH]ccc12]

$^1$H NMR (400 MHz, DMSO-d$_6$) δ 11.47 (s, 1H), 10.61 (s, 1H), 9.85 (s, 1H), 7.77 (s, 1H), 7.32 (dd, J=3.5, 2.4 Hz, 1H), 7.24-7.12 (m, 3H), 6.05 (dd, J=3.5, 1.9 Hz, 1H), 3.16 (q, J=7.3 Hz, 2H), 2.46 (d, J=7.6 Hz, 2H), 2.11-1.97 (m, 1H), 1.23 (t, J=7.3 Hz, 3H), 0.95 (t, J=7.5 Hz, 3H), 0.81-0.72 (m, 4H).

MS(ESI+) m/z 413 (M+H)$^+$

Example 100: Synthesis of N-(4-(3-fluoro-2-methyl-4-(propylsulfonamido)phenyl)-1H-pyrrolo[2,3-b]pyridin-6-yl)cyclopropanecarboxamide

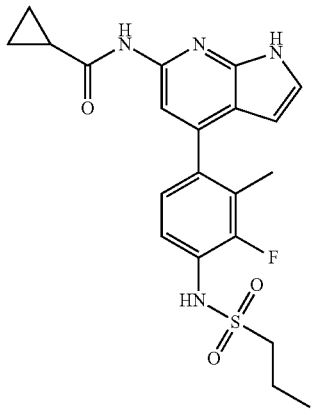

¹H NMR (400 MHz, DMSO-d₆) δ 11.54 (s, 1H), 10.66 (s, 1H), 9.70 (s, 1H), 7.79 (s, 1H), 7.36 (dd, J=5.4, 2.5 Hz, 2H), 7.12 (d, J=8.4 Hz, 1H), 6.16-6.08 (m, 1H), 3.19-3.09 (m, 2H), 2.08 (d, J=2.6 Hz, 3H), 2.05-2.01 (m, 1H), 1.83-1.73 (m, 2H), 1.00 (t, J=7.2 Hz, 3H), 0.84-0.74 (m, 4H).

MS(ESI+) m/z 431 (M+H)⁺

Example 101: Synthesis of N-(4-(4-(ethylsulfonamido)-3-fluoro-2-methylphenyl)-1H-pyrrolo[2,3-b]pyridin-6-yl)cyclopropanecarboxamide

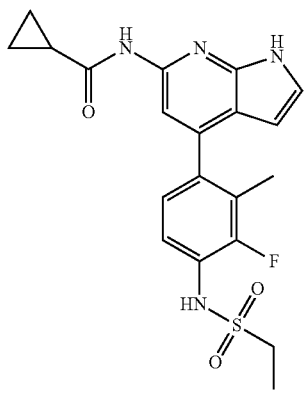 [SMILES: CCS(=O)(=O)Nc1ccc(-c2cc(NC(=O)C3CC3)nc3[nH]ccc23)c(C)c1F]

¹H NMR (400 MHz, DMSO-d₆) δ 11.54 (s, 1H), 10.66 (s, 1H), 9.71 (s, 1H), 7.79 (s, 1H), 7.40-7.30 (m, 2H), 7.18-7.06 (m, 1H), 6.11 (dd, J=3.5, 1.9 Hz, 1H), 3.16 (t, J=7.3 Hz, 2H), 2.08 (d, J=2.7 Hz, 3H), 2.03-1.95 (m, 1H), 1.29 (t, J=7.3 Hz, 3H), 0.82-0.73 (m, 4H).

MS(ESI+) m/z 417 (M+H)⁺

Example 102: Synthesis of N-(4-(4-(((1-cyanocyclopropyl)methyl)sulfonamido)-2-methylphenyl)-1H-pyrrolo[2,3-b]pyridin-6-yl)cyclopropanecarboxamide

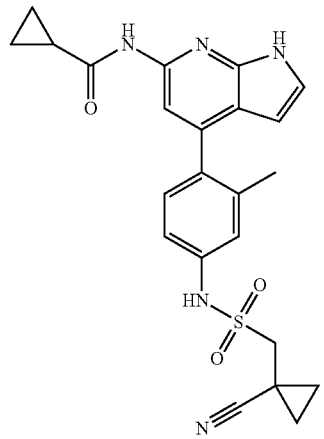 [SMILES: Cc1cc(NS(=O)(=O)CC2(C#N)CC2)ccc1-c1cc(NC(=O)C2CC2)nc2[nH]ccc12]

¹H NMR (400 MHz, DMSO-d₆) δ 11.47 (s, 1H), 10.61 (s, 1H), 9.91 (s, 1H), 7.76 (s, 1H), 7.33 (dd, J=3.5, 2.4 Hz, 1H), 7.23 (d, J=8.3 Hz, 1H), 7.18 (d, J=2.2 Hz, 1H), 7.14 (dd, J=8.1, 2.3 Hz, 1H), 6.07 (dd, J=3.5, 1.9 Hz, 1H), 3.52 (s, 2H), 2.14 (s, 3H), 1.99 (dt, J=14.0, 7.8 Hz, 2H), 1.38-1.33 (m, 2H), 1.22-1.16 (m, 2H), 0.80-0.74 (m, 4H).

MS(ESI+) m/z 450 (M+H)⁺

Example 103: Synthesis of N-(4-(4-(((1-(cyanomethyl)cyclopropyl)methyl)sulfonamido)-2-methylphenyl)-1H-pyrrolo[2,3-b]pyridin-6-yl)cyclopropanecarboxamide

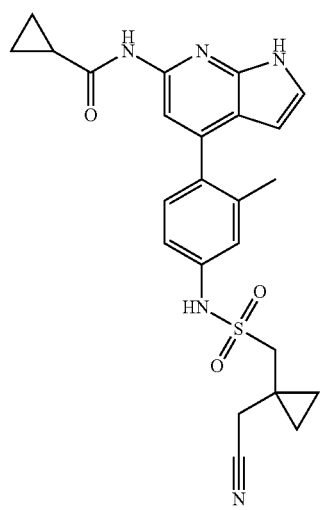 [SMILES: Cc1cc(NS(=O)(=O)CC2(CC#N)CC2)ccc1-c1cc(NC(=O)C2CC2)nc2[nH]ccc12]

¹H NMR (400 MHz, DMSO-d₆) δ 11.47 (s, 1H), 10.61 (s, 1H), 7.76 (s, 1H), 7.32 (dd, J=3.4, 2.4 Hz, 1H), 7.24 (d, J=8.3 Hz, 1H), 7.17-7.11 (m, 2H), 2.86 (s, 2H), 2.14 (s, 3H), 2.05-1.95 (m, 2H), 0.79 (d, J=3.8 Hz, 2H), 0.75-0.65 (m, 4H).

MS(ESI+) m/z 464 (M+H)⁺

Example 104: Synthesis of N-(4-(4-((3-cyanopropyl)sulfonamido)-2,5-difluorophenyl)-1H-pyrrolo[2,3-b]pyridin-6-yl)cyclopropanecarboxamide

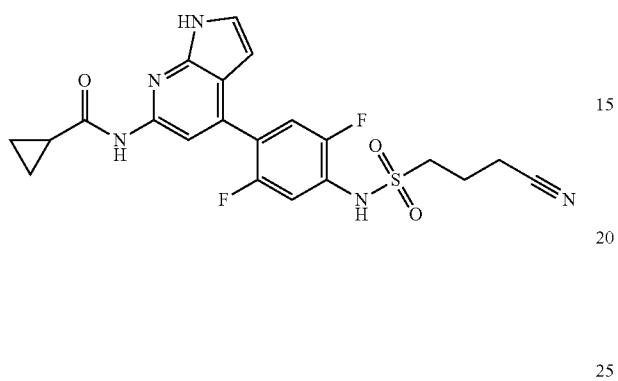

$^1$H NMR (400 MHz, DMSO-d$_6$) δ 11.64 (s, 1H), 10.69 (s, 1H), 7.96 (d, J=1.2 Hz, 1H), 7.52 (dd, J=6.6, 10.6 Hz, 1H), 7.47-7.39 (m, 4H), 6.31 (dt, J=2.0, 3.9 Hz, 1H), 3.37 (s, 2H), 2.70 (t, J=7.3 Hz, 2H), 2.11-1.99 (m, 3H), 0.85-0.76 (m, 4H).

MS(ESI+) m/z 460 (M+H)$^+$

Example 105: Synthesis of N-(4-(4-(((1-cyanocyclopropyl)methyl)sulfonamido)-2,5-difluorophenyl)-1H-pyrrolo[2,3-b]pyridin-6-yl)cyclopropanecarboxamide

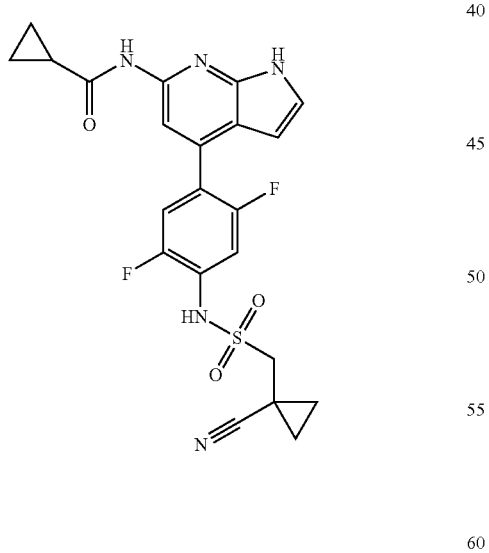

$^1$H NMR (400 MHz, DMSO-d$_6$) δ 11.58 (s, 1H), 10.67 (s, 1H), 7.96 (s, 1H), 7.47 (ddd, J=6.8, 11.0, 15.3 Hz, 2H), 7.40 (dd, J=2.5, 3.5 Hz, 1H), 6.31 (dd, J=1.9, 3.6 Hz, 1H), 3.62 (s, 2H), 2.07-2.00 (m, 1H), 1.38 (q, J=4.1, 4.8 Hz, 2H), 1.30-1.22 (m, 2H), 0.84-0.75 (m, 4H).

MS(ESI+) m/z 472 (M+H)$^+$

Example 106: Synthesis of N-(4-(4-(((1-(cyanomethyl)cyclopropyl)methyl)sulfonamido)-2,5-difluorophenyl)-1H-pyrrolo[2,3-b]pyridin-6-yl)cyclopropanecarboxamide

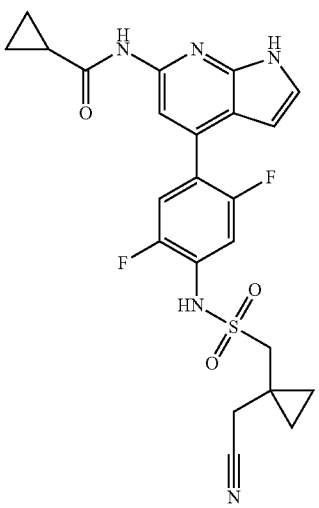 [SMILES: N#CCC1(CS(=O)(=O)Nc2cc(F)c(-c3cc(NC(=O)C4CC4)nc4[nH]ccc34)cc2F)CC1]

MS(ESI+) m/z 486 (M+H)$^+$

Example 107: Synthesis of N-(4-(4-(((1-cyanocyclopropyl)methyl)sulfonamido)-3,5-difluorophenyl)-1H-pyrrolo[2,3-b]pyridin-6-yl)cyclopropanecarboxamide

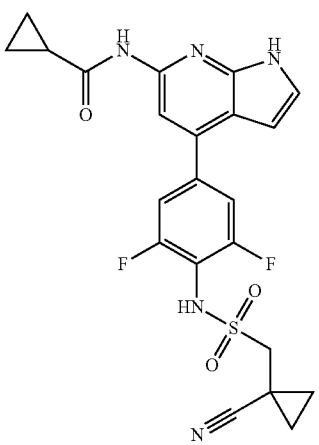 [SMILES: N#CC1(CS(=O)(=O)Nc2c(F)cc(-c3cc(NC(=O)C4CC4)nc4[nH]ccc34)cc2F)CC1]

MS(ESI+) m/z 472 (M+H)$^+$

Example 108: Synthesis of N-(4-(4-(((1-(cyanomethyl)cyclopropyl)methyl)sulfonamido)-3,5-difluorophenyl)-1H-pyrrolo[2,3-b]pyridin-6-yl)cyclopropanecarboxamide

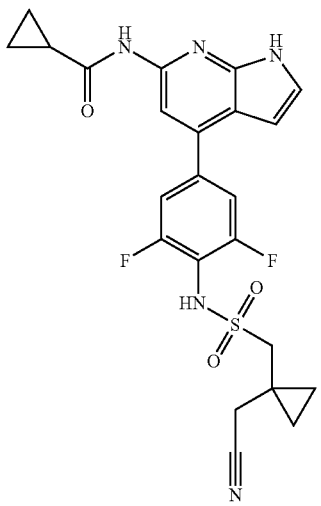 [SMILES: N#CCC1(CS(=O)(=O)Nc2c(F)cc(-c3cc(NC(=O)C4CC4)nc4[nH]ccc34)cc2F)CC1]

¹H NMR (400 MHz, DMSO-d₆) δ 11.68 (s, 1H), 10.71 (s, 1H), 8.03 (s, 1H), 7.52-7.44 (m, 3H), 6.58 (dd, J=1.8, 3.5 Hz, 1H), 3.38 (s, 2H), 2.86 (s, 2H), 2.04 (td, J=3.8, 7.4, 7.8 Hz, 1H), 0.93-0.87 (m, 2H), 0.82 (ddd, J=2.3, 6.2, 9.5 Hz, 4H), 0.74-0.68 (m, 2H).

MS(ESI+) m/z 486 (M+H)⁺

Example 109: Synthesis of N-(4-(4-(((1-cyanocyclopropyl)methyl)sulfonamido)-2-ethylphenyl)-1H-pyrrolo[2,3-b]pyridin-6-yl)cyclopropanecarboxamide

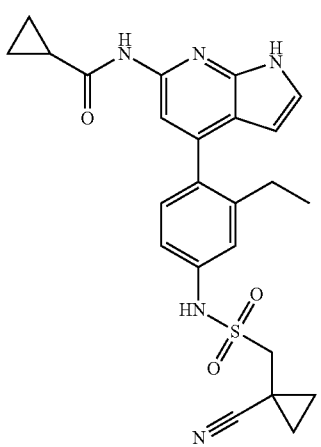 [SMILES: CCc1cc(NS(=O)(=O)CC2(C#N)CC2)ccc1-c1cc(NC(=O)C2CC2)nc2[nH]ccc12]

¹H NMR (400 MHz, DMSO-d₆) δ 11.49 (s, 1H), 10.63 (s, 1H), 10.23 (s, 1H), 7.77 (s, 1H), 7.32 (s, 1H), 7.25-7.09 (m, 3H), 6.04 (d, J=3.2 Hz, 1H), 3.52 (s, 2H), 2.04 (d, J=14.3 Hz, 1H), 1.36 (s, 2H), 1.20 (d, J=5.2 Hz, 2H), 0.95 (t, J=7.6 Hz, 3H), 0.77 (d, J=7.3 Hz, 4H).

MS(ESI+) m/z 464 (M+H)⁺

Example 110: Synthesis of N-(4-(4-(((1-(cyanomethyl)cyclopropyl)methyl)sulfonamido)-2-ethylphenyl)-1H-pyrrolo[2,3-b]pyridin-6-yl)cyclopropanecarboxamide

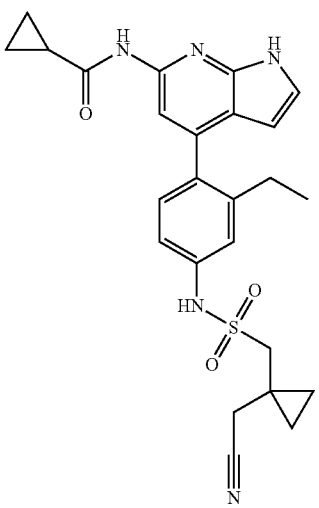 [SMILES: CCc1cc(NS(=O)(=O)CC2(CC#N)CC2)ccc1-c1cc(NC(=O)C2CC2)nc2[nH]ccc12]

¹H NMR (400 MHz, DMSO-d₆) δ 11.48 (s, 1H), 10.63 (s, 1H), 10.08 (s, 1H), 7.77 (s, 1H), 7.32 (s, 1H), 7.19 (d, J=10.0 Hz, 2H), 7.12 (d, J=8.6 Hz, 1H), 6.04 (s, 1H), 2.85 (s, 2H), 2.03 (s, 1H), 0.95 (t, J=7.6 Hz, 3H), 0.78 (s, 4H), 0.73 (s, 2H), 0.66 (s, 2H).

MS(ESI+) m/z 478 (M+H)⁺

Example 111: Synthesis of N-(4-(4-((3-cyanopropyl)sulfonamido)-2-ethylphenyl)-1H-pyrrolo[2,3-b]pyridin-6-yl)cyclopropanecarboxamide

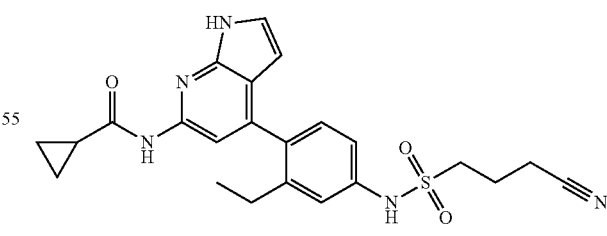

¹H NMR (400 MHz, DMSO-d₆) δ 11.49 (s, 1H), 10.64 (s, 1H), 10.01 (s, 1H), 7.78 (s, 1H), 7.32 (s, 1H), 7.18 (dd, J=23.0, 9.1 Hz, 3H), 6.05 (s, 1H), 3.25 (t, J=7.9 Hz, 2H), 2.68 (t, J=7.3 Hz, 2H), 2.02 (q, J=7.5 Hz, 3H), 0.96 (t, J=7.5 Hz, 3H), 0.77 (d, J=7.7 Hz, 4H).

MS(ESI+) m/z 452 (M+H)⁺

Example 112: Synthesis of N-(4-(4-(cyclohexane-sulfonamido)-2-ethylphenyl)-1H-pyrrolo[2,3-b]pyridin-6-yl)cyclopropanecarboxamide

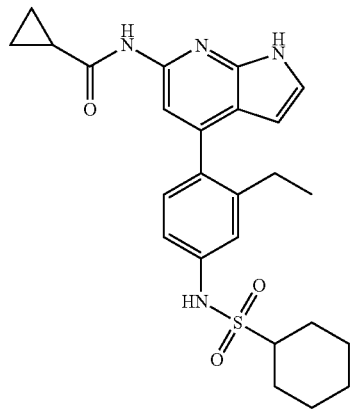 [SMILES: CCc1cc(NS(=O)(=O)C2CCCCC2)ccc1-c1cc(NC(=O)C2CC2)nc2[nH]ccc12]

¹H NMR (400 MHz, DMSO-d₆) δ 11.50 (s, 1H), 10.65 (s, 1H), 9.86 (d, J=13.7 Hz, 1H), 7.79 (s, 1H), 7.41-7.07 (m, 4H), 6.05 (s, 1H), 3.06 (s, 1H), 2.06 (s, 3H), 1.77 (s, 2H), 1.59 (s, 1H), 1.34 (d, J=77.0 Hz, 3H), 1.17-1.05 (m, 1H), 0.93-0.81 (m, 5H).

MS(ESI+) m/z 467 (M+H)⁺

Example 113: Synthesis of N-(4-(4-(cyclopropane-sulfonamido)-2-ethylphenyl)-1H-pyrrolo[2,3-b]pyridin-6-yl)cyclopropanecarboxamide

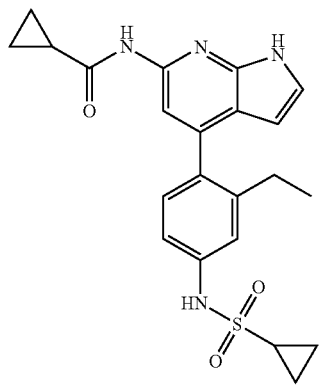 [SMILES: CCc1cc(NS(=O)(=O)C2CC2)ccc1-c1cc(NC(=O)C2CC2)nc2[nH]ccc12]

¹H NMR (400 MHz, DMSO-d₆) δ 11.49 (s, 1H), 10.64 (s, 1H), 9.82 (s, 1H), 7.78 (s, 1H), 7.32 (d, J=3.1 Hz, 1H), 7.25 (s, 1H), 7.18 (s, 2H), 6.04 (d, J=3.0 Hz, 1H), 3.38 (d, J=6.4 Hz, 1H), 2.74-2.65 (m, 1H), 2.04 (d, J=6.9 Hz, 1H), 1.09 (t, J=7.2 Hz, 1H), 0.97 (d, J=7.2 Hz, 7H), 0.82-0.74 (m, 4H).

MS(ESI+) m/z 425 (M+H)⁺

Example 114: Synthesis of N-(4-(4-(cyclobutane-sulfonamido)-2-ethylphenyl)-1H-pyrrolo[2,3-b]pyridin-6-yl)cyclopropanecarboxamide

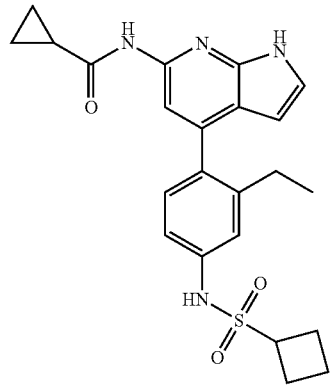 [SMILES: CCc1cc(NS(=O)(=O)C2CCC2)ccc1-c1cc(NC(=O)C2CC2)nc2[nH]ccc12]

¹H NMR (400 MHz, DMSO-d₆) δ 11.49 (s, 1H), 10.64 (s, 1H), 9.78 (s, 1H), 7.77 (s, 1H), 7.32 (s, 1H), 7.14 (dd, J=24.3, 10.7 Hz, 3H), 6.04 (s, 1H), 4.06-3.91 (m, 1H), 2.46 (s, 2H), 2.39-2.30 (m, 2H), 2.20 (s, 2H), 2.07-1.98 (m, 1H), 1.93 (dd, J=19.3, 10.2 Hz, 2H), 0.94 (t, J=7.6 Hz, 3H), 0.82-0.73 (m, 4H).

MS(ESI+) m/z 439 (M+H)⁺

Example 115: Synthesis of N-(4-(2-ethyl-4-(propylsulfonamido)phenyl)-1H-pyrrolo[2,3-b]pyridin-6-yl)cyclopropanecarboxamide

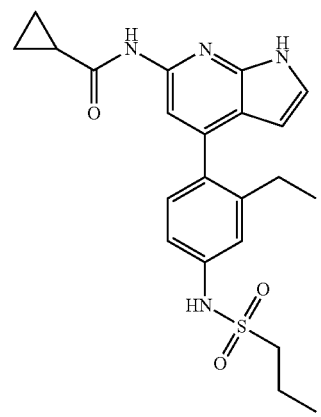 [SMILES: CCCS(=O)(=O)Nc1ccc(-c2cc(NC(=O)C3CC3)nc3[nH]ccc23)c(CC)c1]

¹H NMR (400 MHz, DMSO-d₆) δ 11.49 (s, 1H), 10.64 (s, 1H), 9.87 (s, 1H), 7.78 (s, 1H), 7.32 (s, 1H), 7.16 (dd, J=22.3, 9.1 Hz, 3H), 6.05 (s, 1H), 3.13 (t, J=7.4 Hz, 2H), 2.42 (s, 2H), 2.02 (d, J=7.2 Hz, 1H), 1.72 (q, J=7.7 Hz, 2H), 0.96 (q, J=7.8, 7.1 Hz, 6H), 0.82-0.74 (m, 4H).

MS(ESI+) m/z 427 (M+H)⁺

Example 116: Synthesis of N-(4-(4-(butylsulfonamido)-2-ethylphenyl)-1H-pyrrolo[2,3-b]pyridin-6-yl)cyclopropanecarboxamide

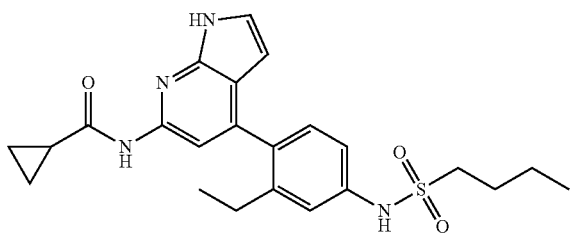 [SMILES: CCCCS(=O)(=O)Nc1ccc(-c2cc(NC(=O)C3CC3)nc3[nH]ccc23)c(CC)c1]

¹H NMR (400 MHz, DMSO-d₆) δ 11.49 (s, 1H), 10.63 (s, 1H), 9.87 (s, 1H), 7.78 (s, 1H), 7.32 (d, J=3.1 Hz, 1H), 7.16 (dd, J=22.4, 9.6 Hz, 3H), 6.04 (d, J=2.9 Hz, 1H), 3.14 (t, J=7.9 Hz, 2H), 2.42 (t, J=7.3 Hz, 2H), 2.04 (d, J=5.7 Hz, 1H), 1.69 (q, J=8.0 Hz, 2H), 1.38 (q, J=7.6 Hz, 2H), 0.94 (q, J=6.1, 4.6 Hz, 3H), 0.84 (t, J=7.4 Hz, 3H), 0.81-0.75 (m, 4H).

MS(ESI+) m/z 441 (M+H)⁺

Example 117: Synthesis of N-(4-(2-methyl-4-((4,4,4-trifluorobutyl)sulfonamido)phenyl)-1H-pyrrolo[2,3-b]pyridin-6-yl)cyclopropanecarboxamide

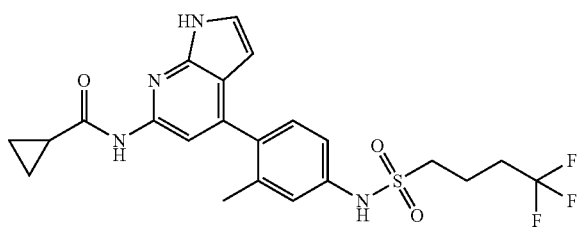 [SMILES: Cc1cc(NS(=O)(=O)CCCC(F)(F)F)ccc1-c1cc(NC(=O)C2CC2)nc2[nH]ccc12]

¹H NMR (400 MHz, DMSO-d₆) δ 11.50 (s, 1H), 10.64 (s, 1H), 7.77 (s, 1H), 7.38-7.29 (m, 1H), 7.25 (d, J=8.2 Hz, 1H), 7.21-7.11 (m, 2H), 6.07 (dd, J=1.8, 3.5 Hz, 1H), 3.28 (t, J=7.7 Hz, 2H), 2.47-2.35 (m, 2H), 2.14 (s, 3H), 1.99 (d, J=33.4 Hz, 1H), 1.91 (dd, J=5.7, 8.6 Hz, 2H), 0.83-0.74 (m, 4H).

MS(ESI+) m/z 481 (M+H)⁺

Example 118: Synthesis of N-(4-(4-(cyclopropanesulfonamido)-2-(trifluoromethyl)phenyl)-1H-pyrrolo[2,3-b]pyridin-6-yl)cyclopropanecarboxamide

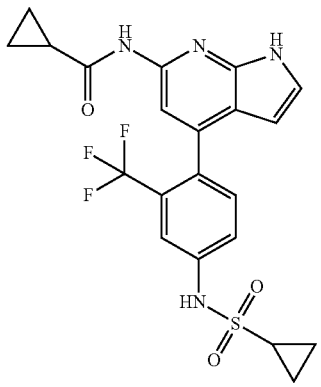 [SMILES: O=C(Nc1cc(-c2ccc(NS(=O)(=O)C3CC3)cc2C(F)(F)F)c2cc[nH]c2n1)C1CC1]

¹H NMR (400 MHz, DMSO-d₆) δ 11.55 (s, 1H), 10.67 (s, 1H), 10.30 (s, 1H), 7.83 (s, 1H), 7.69 (t, J=1.7 Hz, 1H), 7.59 (d, J=8.4 Hz, 1H), 7.44 (d, J=8.4 Hz, 1H), 7.33 (t, J=2.6 Hz, 1H), 6.00 (dt, J=3.4, 1.6 Hz, 1H), 2.80 (p, J=6.5 Hz, 1H), 2.06-1.96 (m, 1H), 1.04-0.95 (m, 4H), 0.77 (d, J=6.5 Hz, 4H).

MS(ESI+) m/z 465 (M+H)⁺

Example 119: Synthesis of N-(4-(4-(propylsulfonamido)-2-(trifluoromethyl)phenyl)-1H-pyrrolo[2,3-b]pyridin-6-yl)cyclopropanecarboxamide

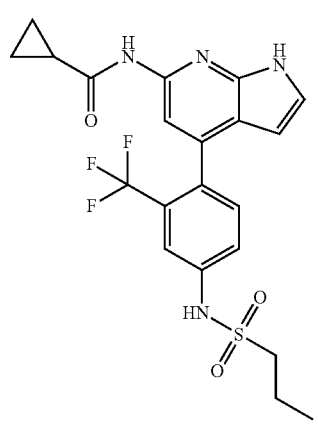 [SMILES: CCCS(=O)(=O)Nc1ccc(-c2cc(NC(=O)C3CC3)nc3[nH]ccc23)c(C(F)(F)F)c1]

¹H NMR (400 MHz, DMSO-d₆) δ 11.55 (s, 1H), 10.67 (s, 1H), 10.34 (s, 1H), 7.83 (s, 1H), 7.65 (s, 1H), 7.56 (d, J=8.5 Hz, 1H), 7.43 (d, J=8.4 Hz, 1H), 7.32 (d, J=2.5 Hz, 1H), 6.04-5.98 (m, 1H), 3.22 (t, J=7.6 Hz, 2H), 2.05-1.98 (m, 1H), 1.73 (q, J=7.7 Hz, 2H), 1.02-0.91 (m, 3H), 0.77 (d, J=6.4 Hz, 4H).

MS(ESI+) m/z 467 (M+H)⁺

Example 120: Synthesis of N-(4-(4-(cyclobutane-sulfonamido)-2-(trifluoromethyl)phenyl)-1H-pyrrolo[2,3-b]pyridin-6-yl)cyclopropanecarboxamide

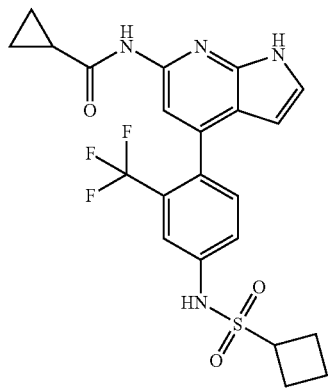 [SMILES: O=C(Nc1cc(-c2ccc(NS(=O)(=O)C3CCC3)cc2C(F)(F)F)c2cc[nH]c2n1)C1CC1]

$^1$H NMR (400 MHz, DMSO-d$_6$) δ 11.55 (s, 1H), 10.67 (s, 1H), 10.26 (s, 1H), 7.82 (s, 1H), 7.65 (s, 1H), 7.54 (d, J=8.3 Hz, 1H), 7.42 (d, J=8.3 Hz, 1H), 7.33 (d, J=3.3 Hz, 1H), 6.00 (t, J=2.2 Hz, 1H), 4.08 (p, J=8.2 Hz, 1H), 2.35 (p, J=9.7 Hz, 2H), 2.22 (s, 2H), 2.02 (d, J=6.4 Hz, 1H), 1.98-1.83 (m, 2H), 0.77 (d, J=6.3 Hz, 4H).

MS(ESI+) m/z 479 (M+H)$^+$

Example 121: Synthesis of N-(4-(4-((3,4-difluorophenyl)sulfonamido)-2-(trifluoromethyl)phenyl)-1H-pyrrolo[2,3-b]pyridin-6-yl)cyclopropanecarboxamide

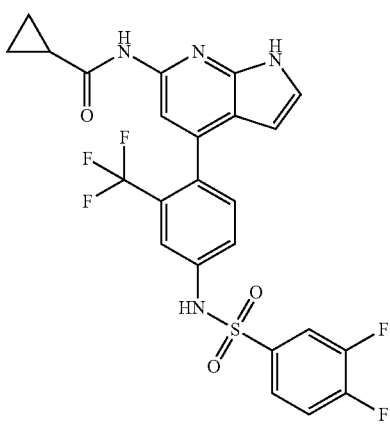 [SMILES: O=C(Nc1cc(-c2ccc(NS(=O)(=O)c3ccc(F)c(F)c3)cc2C(F)(F)F)c2cc[nH]c2n1)C1CC1]

$^1$H NMR (400 MHz, DMSO-d$_6$) δ 11.51 (s, 1H), 10.63 (s, 1H), 7.84 (s, 1H), 7.76 (s, 1H), 7.67 (s, 2H), 7.46 (s, 1H), 7.30 (s, 3H), 5.93 (s, 1H), 2.01 (s, 1H), 0.77 (s, 4H).

MS(ESI+) m/z 537 (M+H)$^+$

Example 122: Synthesis of N-(4-(4-((3-fluorophenyl)sulfonamido)-2-(trifluoromethyl)phenyl)-1H-pyrrolo[2,3-b]pyridin-6-yl)cyclopropanecarboxamide

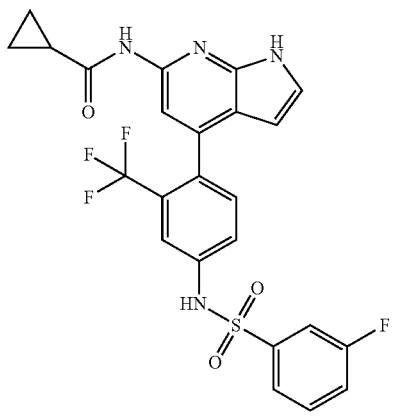 [SMILES: O=C(Nc1cc(-c2ccc(NS(=O)(=O)c3cccc(F)c3)cc2C(F)(F)F)c2cc[nH]c2n1)C1CC1]

$^1$H NMR (400 MHz, DMSO-d$_6$) δ 11.54 (s, 1H), 10.97 (s, 1H), 10.65 (s, 1H), 7.76 (s, 1H), 7.68 (s, 2H), 7.63 (d, J=8.6 Hz, 1H), 7.57 (d, J=8.8 Hz, 1H), 7.53 (s, 1H), 7.46 (d, J=8.6 Hz, 1H), 7.38 (d, J=8.3 Hz, 1H), 7.31 (d, J=3.2 Hz, 1H), 5.90 (s, 1H), 2.06-1.95 (m, 1H), 0.81-0.73 (m, 4H).

MS(ESI+) m/z 519 (M+H)$^+$

Example 123: Synthesis of N-(4-(4-(((1-cyanocyclopropyl)methyl)sulfonamido)-3-ethylphenyl)-1H-pyrrolo[2,3-b]pyridin-6-yl)cyclopropanecarboxamide

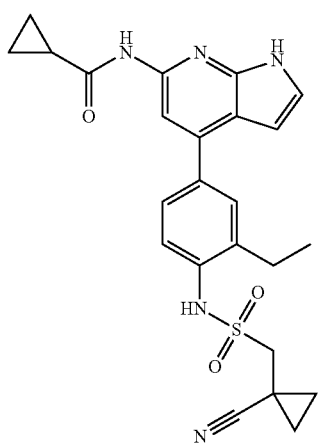 [SMILES: CCc1cc(-c2cc(NC(=O)C3CC3)nc3[nH]ccc23)ccc1NS(=O)(=O)CC1(C#N)CC1]

$^1$H NMR (400 MHz, DMSO-d$_6$) δ 11.56 (s, 1H), 10.64 (s, 1H), 9.47 (s, 1H), 8.01 (s, 1H), 7.59 (d, J=2.0 Hz, 1H), 7.52 (dd, J=8.3, 2.1 Hz, 1H), 7.45 (d, J=8.2 Hz, 1H), 7.41 (t, J=3.0 Hz, 1H), 6.52 (dd, J=3.6, 1.8 Hz, 1H), 3.54 (s, 2H), 2.81 (q, J=7.5 Hz, 2H), 2.09-1.98 (m, 1H), 1.40 (q, J=4.8, 3.9 Hz, 2H), 1.29 (t, J=3.7 Hz, 2H), 1.22 (t, J=7.5 Hz, 3H), 0.86-0.73 (m, 4H).

MS(ESI+) m/z 464 (M+H)$^+$

Example 124: Synthesis of N-(4-(3-ethyl-4-(ethylsulfonamido)phenyl)-1H-pyrrolo[2,3-b]pyridin-6-yl)cyclopropanecarboxamide

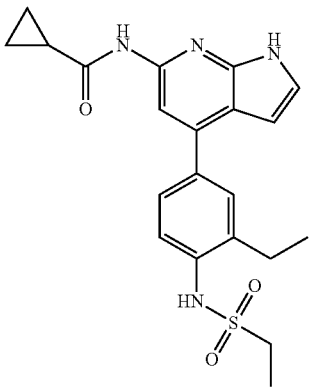 [SMILES: CCc1cc(-c2cc(NC(=O)C3CC3)nc3[nH]ccc23)ccc1NS(=O)(=O)CC]

$^1$H NMR (400 MHz, DMSO-d$_6$) δ 11.55 (s, 1H), 10.64 (s, 1H), 9.18 (s, 1H), 8.01 (s, 1H), 7.59 (d, J=2.1 Hz, 1H), 7.53 (dd, J=8.2, 2.1 Hz, 1H), 7.45-7.39 (m, 2H), 6.52 (dd, J=3.5, 1.8 Hz, 1H), 3.17 (q, J=7.3 Hz, 2H), 2.81 (q, J=7.5 Hz, 2H), 2.04 (d, J=7.0 Hz, 1H), 1.30 (t, J=7.3 Hz, 3H), 1.22 (t, J=7.5 Hz, 3H), 0.83-0.78 (m, 4H).

MS(ESI+) m/z 413 (M+H)$^+$

Example 125: Synthesis of N-(4-(4-(cyclopropanesulfonamido)-3-ethylphenyl)-1H-pyrrolo[2,3-b]pyridin-6-yl)cyclopropanecarboxamide

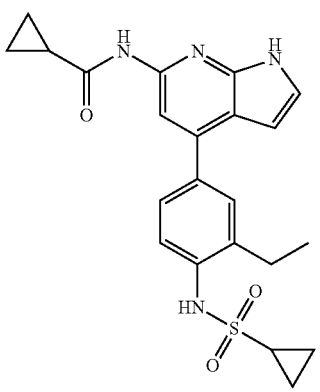 [SMILES: CCc1cc(-c2cc(NC(=O)C3CC3)nc3[nH]ccc23)ccc1NS(=O)(=O)C1CC1]

$^1$H NMR (400 MHz, DMSO-d$_6$) δ 11.55 (s, 1H), 10.64 (s, 1H), 9.22 (s, 1H), 8.02 (s, 1H), 7.59 (d, J=2.0 Hz, 1H), 7.55-7.47 (m, 2H), 7.41 (dd, J=3.5, 2.5 Hz, 1H), 6.53 (dd, J=3.6, 1.9 Hz, 1H), 2.84 (q, J=7.5 Hz, 2H), 2.72-2.67 (m, 1H), 2.03 (t, J=6.5 Hz, 1H), 1.22 (t, J=7.5 Hz, 3H), 1.03-0.95 (m, 2H), 0.94-0.89 (m, 2H), 0.84-0.76 (m, 4H).

MS(ESI+) m/z 425 (M+H)$^+$

Example 126: Synthesis of N-(4-(3-ethyl-4-(propylsulfonamido)phenyl)-1H-pyrrolo[2,3-b]pyridin-6-yl)cyclopropanecarboxamide

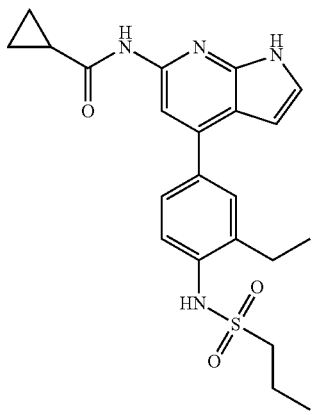 [SMILES: CCCS(=O)(=O)Nc1ccc(-c2cc(NC(=O)C3CC3)nc3[nH]ccc23)cc1CC]

$^1$H NMR (400 MHz, DMSO-d$_6$) δ 11.55 (s, 1H), 10.64 (s, 1H), 9.19 (s, 1H), 8.01 (s, 1H), 7.59 (d, J=2.1 Hz, 1H), 7.55-7.50 (m, 1H), 7.46-7.38 (m, 2H), 6.53 (dd, J=3.5, 1.8 Hz, 1H), 3.17-3.09 (m, 2H), 2.81 (q, J=7.5 Hz, 2H), 2.04 (s, 1H), 1.78 (h, J=7.4 Hz, 2H), 1.21 (t, J=7.5 Hz, 3H), 1.01 (t, J=7.5 Hz, 3H), 0.85-0.76 (m, 4H).

MS(ESI+) m/z 427 (M+H)$^+$

Example 127: Synthesis of N-(4-(4-(butylsulfonamido)-3-ethylphenyl)-1H-pyrrolo[2,3-b]pyridin-6-yl)cyclopropanecarboxamide $^1$H NMR (400 MHz, DMSO-d$_6$) δ 11.55 (s, 1H), 10.64 (s, 1H), 9.19 (s, 1H), 8.01 (s, 1H), 7.58 (d, J=2.1 Hz, 1H), 7.53 (d, J=8.1 Hz, 1H), 7.45-7.36 (m, 2H), 6.52 (dd, J=3.5, 1.9 Hz, 1H), 3.18-3.12 (m, 2H), 2.81 (q, J=7.5 Hz, 2H), 2.04 (s, 1H), 1.72 (q, J=7.7 Hz, 2H), 1.43 (h, J=7.3 Hz, 2H), 1.21 (t, J=7.5 Hz, 3H), 0.89 (t, J=7.4 Hz, 3H), 0.84-0.76 (m, 4H).

MS(ESI+) m/z 441 (M+H)$^+$

Example 128: Synthesis of N-(4-(4-(cyclobutanesulfonamido)-3-ethylphenyl)-1H-pyrrolo[2,3-b]pyridin-6-yl)cyclopropanecarboxamide

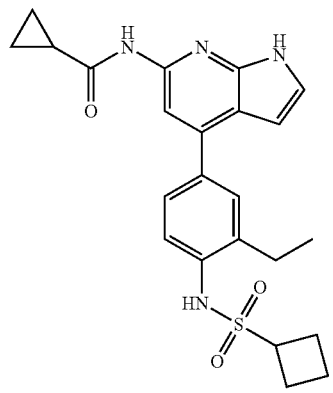 [SMILES: CCc1cc(-c2cc(NC(=O)C3CC3)nc3[nH]ccc23)ccc1NS(=O)(=O)C1CCC1]

¹H NMR (400 MHz, DMSO-d$_6$) δ 11.55 (s, 1H), 10.64 (s, 1H), 9.15 (s, 1H), 8.01 (s, 1H), 7.57 (d, J=2.0 Hz, 1H), 7.51 (dd, J=8.2, 2.2 Hz, 1H), 7.44-7.34 (m, 2H), 6.52 (dd, J=3.5, 1.8 Hz, 1H), 3.97 (p, J=8.2 Hz, 1H), 2.79 (q, J=7.5 Hz, 2H), 2.38-2.23 (m, 4H), 2.03 (d, J=4.8 Hz, 1H), 1.97-1.86 (m, 2H), 1.21 (t, J=7.5 Hz, 3H), 0.84-0.76 (m, 4H).

MS(ESI+) m/z 439 (M+H)⁺

Example 129: Synthesis of N-(4-(6-(methylsulfonamido)-[1,1'-biphenyl]-3-yl)-1H-pyrrolo[2,3-b]pyridin-6-yl)cyclopropanecarboxamide

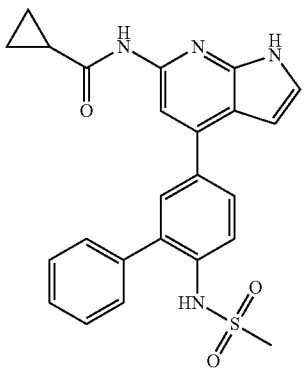 [SMILES: CS(=O)(=O)Nc1ccc(-c2cc(NC(=O)C3CC3)nc3[nH]ccc23)cc1-c1ccccc1]

¹H NMR (400 MHz, DMSO-d$_6$) δ 11.25 (s, 1H), 10.47 (d, J=3.2 Hz, 1H), 10.04 (t, J=2.8 Hz, 1H), 7.68 (d, J=3.2 Hz, 1H), 7.42-7.28 (m, 3H), 7.17-7.04 (m, 6H), 5.86 (s, 1H), 3.22 (d, J=6.5 Hz, 2H), 1.98 (d, J=7.2 Hz, 1H), 1.25 (q, J=7.0, 5.7 Hz, 3H), 0.74 (d, J=5.9 Hz, 4H).

MS(ESI+) m/z 447 (M+H)⁺

Example 130: Synthesis of N-(4-(6-(cyclopropanesulfonamido)-[1,1'-biphenyl]-3-yl)-1H-pyrrolo[2,3-b]pyridin-6-yl)cyclopropanecarboxamide

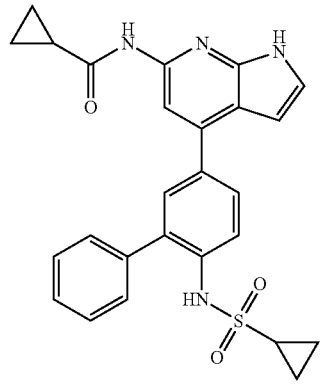 [SMILES: O=C(Nc1cc(-c2ccc(NS(=O)(=O)C3CC3)c(-c3ccccc3)c2)c2cc[nH]c2n1)C1CC1]

¹H NMR (400 MHz, DMSO-d$_6$) δ 11.25 (s, 1H), 10.48 (s, 1H), 9.98 (s, 1H), 7.69 (s, 1H), 7.41-7.30 (m, 3H), 7.19-7.07 (m, 6H), 5.85 (s, 1H), 2.78 (d, J=7.9 Hz, 1H), 1.98 (d, J=7.5 Hz, 1H), 1.01 (t, J=4.6 Hz, 4H), 0.75 (d, J=6.1 Hz, 4H).

MS(ESI+) m/z 473 (M+H)⁺

Example 131: Synthesis of N-(4-(4-(ethylsulfonamido)-2,3-dimethylphenyl)-1H-pyrrolo[2,3-b]pyridin-6-yl)cyclopropanecarboxamide

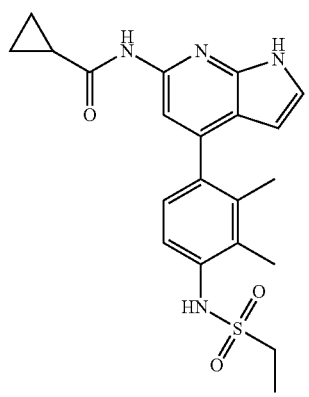 [SMILES: CCS(=O)(=O)Nc1ccc(-c2cc(NC(=O)C3CC3)nc3[nH]ccc23)c(C)c1C]

¹H NMR (400 MHz, DMSO-d$_6$) δ 11.48 (s, 1H), 10.63 (s, 1H), 9.15 (d, J=4.1 Hz, 1H), 7.75 (d, J=4.2 Hz, 1H), 7.33 (s, 1H), 7.28-7.00 (m, 2H), 6.04 (s, 1H), 3.11 (p, J=7.4 Hz, 2H), 2.31 (t, J=2.9 Hz, 3H), 2.07 (t, J=2.9 Hz, 3H), 2.03 (s, 1H), 1.29 (dt, J=11.0, 5.8 Hz, 3H), 0.77 (d, J=8.2 Hz, 4H).

MS(ESI+) m/z 413 (M+H)⁺

Example 132: Synthesis of N-(4-(2,3-dimethyl-4-(propylsulfonamido)phenyl)-1H-pyrrolo[2,3-b]pyridin-6-yl)cyclopropanecarboxamide

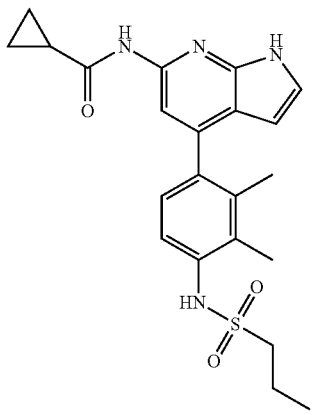 [SMILES: CCCS(=O)(=O)Nc1ccc(-c2cc(NC(=O)C3CC3)nc3[nH]ccc23)c(C)c1C]

$^1$H NMR (400 MHz, DMSO-d$_6$) δ 11.48 (s, 1H), 10.63 (s, 1H), 9.15 (d, J=4.4 Hz, 1H), 7.76 (t, J=3.2 Hz, 1H), 7.33 (s, 1H), 7.22 (d, J=7.8 Hz, 1H), 7.10 (t, J=6.4 Hz, 1H), 6.04 (s, 1H), 3.08 (q, J=6.4, 4.8 Hz, 2H), 2.30 (d, J=4.4 Hz, 3H), 2.06 (d, J=4.1 Hz, 3H), 2.03 (s, 1H), 1.78 (q, J=7.4 Hz, 2H), 1.01 (t, J=7.0 Hz, 3H), 0.82-0.76 (m, 4H).

MS(ESI+) m/z 427 (M+H)$^+$

Example 133: Synthesis of N-(4-(4-(cyclopropanesulfonamido)-2,3-dimethylphenyl)-1H-pyrrolo[2,3-b]pyridin-6-yl)cyclopropanecarboxamide

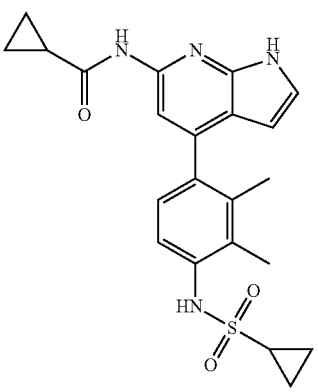 [SMILES: Cc1c(NS(=O)(=O)C2CC2)ccc(-c2cc(NC(=O)C3CC3)nc3[nH]ccc23)c1C]

$^1$H NMR (400 MHz, DMSO-d$_6$) δ 11.48 (s, 1H), 10.63 (d, J=3.3 Hz, 1H), 9.18 (d, J=3.1 Hz, 1H), 7.76 (d, J=3.5 Hz, 1H), 7.33 (s, 1H), 7.25 (d, J=4.5 Hz, 1H), 7.09 (d, J=8.9 Hz, 1H), 6.03 (s, 1H), 2.64 (s, 1H), 2.34 (d, J=2.9 Hz, 3H), 2.07 (d, J=4.8 Hz, 3H), 0.93 (d, J=29.3 Hz, 4H), 0.82-0.74 (m, 4H).

MS(ESI+) m/z 425 (M+H)$^+$

Example 134: Synthesis of 6-(cyclopropanecarboxamido)-4-(4-(ethylsulfonamido)-2-methylphenyl)-1H-pyrrolo[2,3-b]pyridine 7-oxide

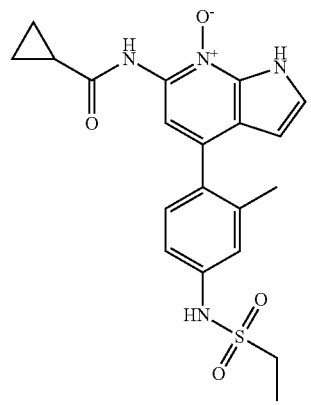 [SMILES: CCS(=O)(=O)Nc1ccc(-c2cc(NC(=O)C3CC3)[n+]([O-])c3[nH]ccc23)c(C)c1]

MS(ESI+) m/z 415 (M+H)$^+$

Example 135: Synthesis of 6-(cyclopropanecarboxamido)-4-(3-ethyl-4-(ethylsulfonamido)phenyl)-1H-pyrrolo[2,3-b]pyridine 7-oxide

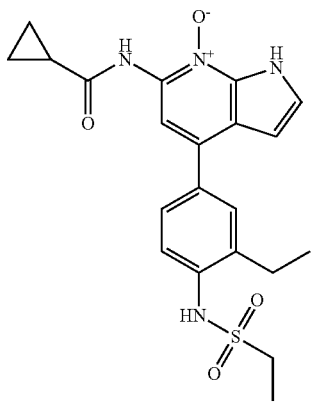 [SMILES: CCc1cc(-c2cc(NC(=O)C3CC3)[n+]([O-])c3[nH]ccc23)ccc1NS(=O)(=O)CC]

MS(ESI+) m/z 429 (M+H)$^+$

Example 136: Synthesis of 6-(cyclopropanecarboxamido)-4-(4-(cyclopropanesulfonamido)-2,3-dimethylphenyl)-1H-pyrrolo[2,3-b]pyridine 7-oxide

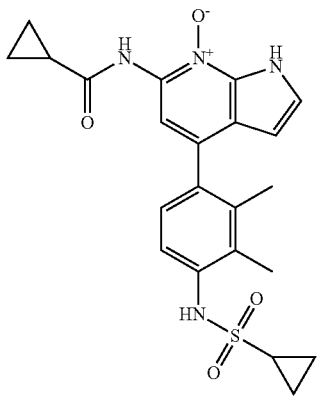 [SMILES: Cc1c(NS(=O)(=O)C2CC2)ccc(-c2cc(NC(=O)C3CC3)[n+]([O-])c3[nH]ccc23)c1C]

MS(ESI+) m/z 441 (M+H)⁺

Example 137: Synthesis of 4-(4-(((1-cyanocyclopropyl)methyl)sulfonamido)-2-ethylphenyl)-6-(cyclopropanecarboxamido)-1H-pyrrolo[2,3-b]pyridine 7-oxide

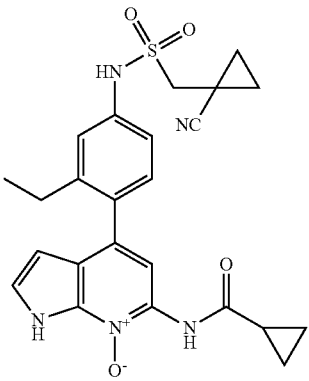 [SMILES: CCc1cc(NS(=O)(=O)CC2(C#N)CC2)ccc1-c1cc(NC(=O)C2CC2)[n+]([O-])c2[nH]ccc12]

MS(ESI+) m/z 480 (M+H)⁺

Example 138: Synthesis of N-(4-(4-(((1-cyanocyclopropyl)methyl)sulfonamido)-3,5-diethylphenyl)-1H-pyrrolo[2,3-b]pyridin-6-yl)cyclopropanecarboxamide

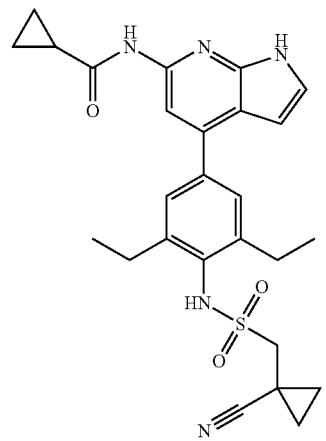 [SMILES: CCc1cc(-c2cc(NC(=O)C3CC3)nc3[nH]ccc23)cc(CC)c1NS(=O)(=O)CC1(C#N)CC1]

¹H NMR (400 MHz, DMSO-d$_6$) δ 11.57 (s, 1H), 10.97 (s, 1H), 10.65 (s, 1H), 8.23 (s, 1H), 7.53 (s, 2H), 7.11 (d, J=7.8 Hz, 1H), 6.58-6.47 (m, 1H), 3.06 (s, 2H), 2.60 (q, J=7.5 Hz, 4H), 2.05 (s, 1H), 1.40 (d, J=10.4 Hz, 4H), 1.19 (t, J=7.5 Hz, 6H), 0.85-0.74 (m, 4H).

MS(ESI+) m/z 492 (M+H)⁺

Example 139: Synthesis of N-(4-(4-((3,4-difluorophenyl)sulfonamido)-3,5-diethylphenyl)-1H-pyrrolo[2,3-b]pyridin-6-yl)cyclopropanecarboxamide

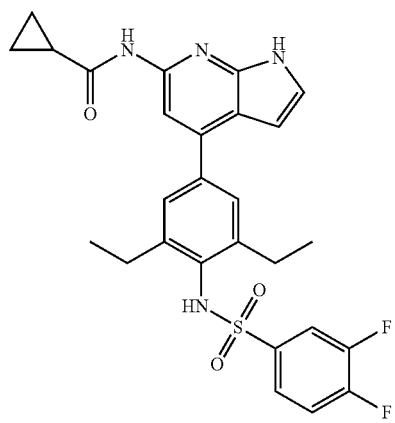 [SMILES: CCc1cc(-c2cc(NC(=O)C3CC3)nc3[nH]ccc23)cc(CC)c1NS(=O)(=O)c1ccc(F)c(F)c1]

¹H NMR (400 MHz, DMSO-d$_6$) δ 11.55 (s, 1H), 10.62 (s, 1H), 9.73 (s, 1H), 8.00 (s, 1H), 7.84-7.67 (m, 2H), 7.63 (d, J=9.6 Hz, 1H), 7.41 (s, 3H), 6.48 (dd, J=3.6, 1.9 Hz, 1H), 2.05 (d, J=5.8 Hz, 1H), 1.05 (t, J=7.5 Hz, 6H), 0.85-0.74 (m, 4H).

MS(ESI+) m/z 525 (M+H)⁺

Example 140: Synthesis of methyl 2-(6-(cyclopropanecarboxamido)-1H-pyrrolo[2,3-b]pyridin-4-yl)-5-(ethylsulfonamido)benzoate

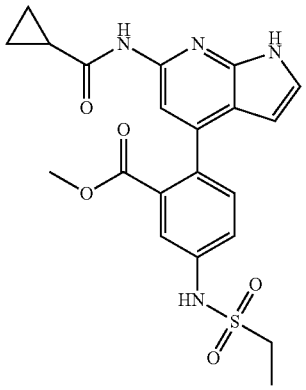 [SMILES: CCS(=O)(=O)Nc1ccc(-c2cc(NC(=O)C3CC3)nc3[nH]ccc23)c(C(=O)OC)c1]

¹H NMR (400 MHz, DMSO-d₆) δ 11.46 (s, 1H), 10.60 (s, 1H), 10.19 (s, 1H), 7.79 (s, 1H), 7.66 (s, 1H), 7.50 (s, 2H), 7.33 (s, 1H), 6.09 (s, 1H), 3.46 (s, 3H), 3.21 (q, J=7.3 Hz, 2H), 2.04 (s, 1H), 1.23 (t, J=7.3 Hz, 3H), 0.82-0.75 (m, 4H).
MS(ESI+) m/z 443 (M+H)⁺

Example 141: Synthesis of methyl 2-(6-(cyclopropanecarboxamido)-1H-pyrrolo[2,3-b]pyridin-4-yl)-5-(propylsulfonamido)benzoate

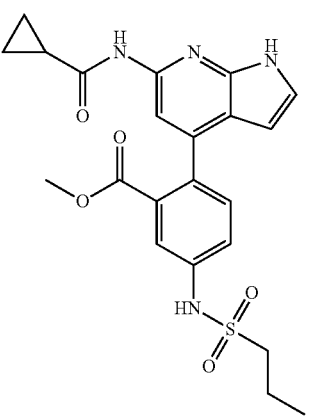 [SMILES: CCCS(=O)(=O)Nc1ccc(-c2cc(NC(=O)C3CC3)nc3[nH]ccc23)c(C(=O)OC)c1]

¹H NMR (400 MHz, DMSO-d₆) δ 11.46 (s, 1H), 10.60 (s, 1H), 10.19 (s, 1H), 7.79 (s, 1H), 7.65 (t, J=1.5 Hz, 1H), 7.50 (d, J=1.5 Hz, 2H), 7.33 (dd, J=3.5, 2.4 Hz, 1H), 6.09 (dd, J=3.6, 1.9 Hz, 1H), 3.46 (s, 3H), 3.23-3.10 (m, 2H), 2.08-1.99 (m, 1H), 1.78-1.61 (m, 2H), 0.97 (t, J=7.4 Hz, 3H), 0.83-0.72 (m, 4H).
MS(ESI+) m/z 457 (M+H)⁺

Example 142: Synthesis of methyl 5-(((1-cyanocyclopropyl)methyl)sulfonamido)-2-(6-(cyclopropanecarboxamido)-1H-pyrrolo[2,3-b]pyridin-4-yl)benzoate

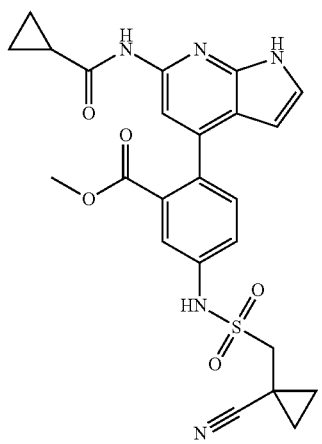 [SMILES: COC(=O)c1cc(NS(=O)(=O)CC2(C#N)CC2)ccc1-c1cc(NC(=O)C2CC2)nc2[nH]ccc12]

¹H NMR (400 MHz, DMSO-d₆) δ 11.46 (s, 1H), 10.60 (s, 1H), 7.79 (s, 1H), 7.66 (d, J=1.5 Hz, 1H), 7.49 (d, J=1.5 Hz, 2H), 7.32 (t, J=3.0 Hz, 1H), 6.07 (dd, J=3.5, 1.9 Hz, 1H), 3.59 (s, 2H), 3.45 (s, 3H), 2.03 (s, 1H), 1.37 (q, J=4.8 Hz, 2H), 1.20 (q, J=5.3, 4.9 Hz, 2H), 0.81-0.70 (m, 4H).
MS(ESI+) m/z 494 (M+H)⁺

Example 143: Synthesis of cyanocyclopropyl)methyl)sulfonamido)-2-(6-(cyclopropanecarboxamido)-1H-pyrrolo[2,3-b]pyridin-4-yl)benzoic acid

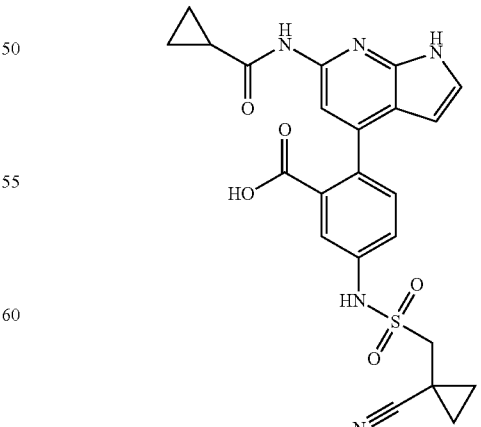

MS(ESI+) m/z 480 (M+H)⁺

Example 144: Synthesis of N-(4-(2-cyano-4-(ethylsulfonamido)phenyl)-1H-pyrrolo[2,3-b]pyridin-6-yl)cyclopropanecarboxamide

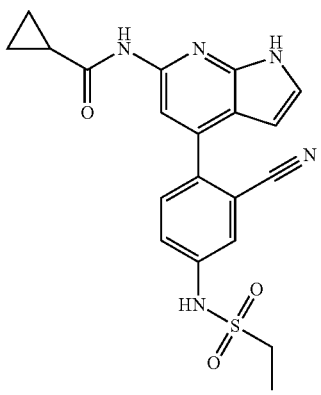 [SMILES: CCS(=O)(=O)Nc1ccc(-c2cc(NC(=O)C3CC3)nc3[nH]ccc23)c(C#N)c1]

$^1$H NMR (400 MHz, DMSO-d$_6$) δ 11.64 (s, 1H), 10.72 (s, 1H), 10.40 (s, 1H), 7.98 (s, 1H), 7.75-7.59 (m, 3H), 7.42 (t, J=3.0 Hz, 1H), 6.27 (dd, J=3.6, 1.8 Hz, 1H), 3.29 (q, J=7.3 Hz, 2H), 2.10-1.98 (m, 1H), 1.25 (t, J=7.3 Hz, 3H), 0.85-0.70 (m, 4H).

MS(ESI+) m/z 410 (M+H)$^+$

Example 145: Synthesis of N-(4-(2-cyano-4-(propylsulfonamido)phenyl)-1H-pyrrolo[2,3-b]pyridin-6-yl)cyclopropanecarboxamide

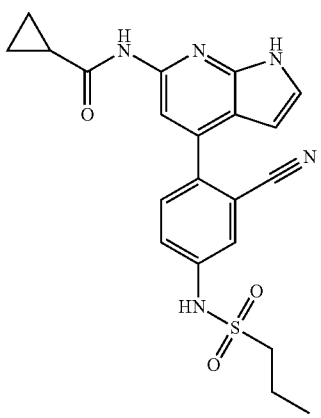 [SMILES: CCCS(=O)(=O)Nc1ccc(-c2cc(NC(=O)C3CC3)nc3[nH]ccc23)c(C#N)c1]

$^1$H NMR (400 MHz, DMSO-d$_6$) δ 11.64 (s, 1H), 10.72 (s, 1H), 10.39 (s, 1H), 7.98 (s, 1H), 7.70-7.57 (m, 3H), 7.42 (t, J=3.0 Hz, 1H), 6.27 (dd, J=3.5, 1.7 Hz, 1H), 3.30-3.23 (m, 2H), 2.10-1.97 (m, 1H), 1.73 (h, J=7.5 Hz, 2H), 0.98 (t, J=7.4 Hz, 3H), 0.88-0.68 (m, 4H).

MS(ESI+) m/z 424 (M+H)$^+$

Example 146: Synthesis of N-(4-(2-cyano-4-((3,4-difluorophenyl)sulfonamido)phenyl)-1H-pyrrolo[2,3-b]pyridin-6-yl)cyclopropanecarboxamide

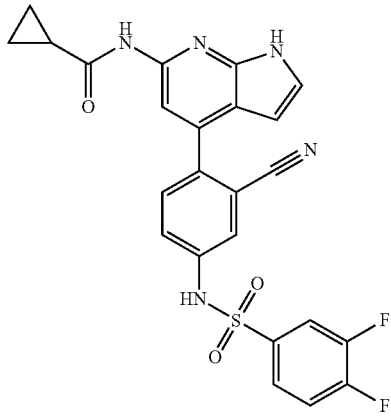 [SMILES: N#Cc1cc(NS(=O)(=O)c2ccc(F)c(F)c2)ccc1-c1cc(NC(=O)C2CC2)nc2[nH]ccc12]

$^1$H NMR (400 MHz, DMSO-d$_6$) δ 11.64 (s, 1H), 11.04 (s, 1H), 10.71 (s, 1H), 7.97 (d, J=8.3 Hz, 1H), 7.93 (s, 1H), 7.73 (d, J=3.5 Hz, 1H), 7.72-7.67 (m, 1H), 7.64-7.60 (m, 2H), 7.54 (dd, J=8.5, 2.3 Hz, 1H), 7.41 (t, J=3.0 Hz, 1H), 6.20 (dd, J=3.6, 1.8 Hz, 1H), 2.09-1.97 (m, 1H), 0.85-0.76 (m, 4H).

MS(ESI+) m/z 494 (M+H)$^+$

Example 147: Synthesis of N-(4-(2-cyano-4-(((1-cyanocyclopropyl)methyl)sulfonamido)phenyl)-1H-pyrrolo[2,3-b]pyridin-6-yl)cyclopropanecarboxamide

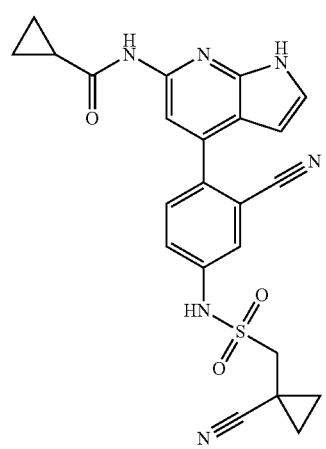 [SMILES: N#Cc1cc(NS(=O)(=O)CC2(C#N)CC2)ccc1-c1cc(NC(=O)C2CC2)nc2[nH]ccc12]

$^1$H NMR (400 MHz, DMSO-d$_6$) δ 11.64 (s, 1H), 10.78 (s, 1H), 10.72 (s, 1H), 7.98 (s, 1H), 7.70-7.57 (m, 3H), 7.42 (t, J=3.0 Hz, 1H), 6.25 (t, J=2.6 Hz, 1H), 3.70 (s, 2H), 2.09-1.98 (m, 1H), 1.09 (t, J=7.0 Hz, 4H), 0.83-0.77 (m, 4H).

MS(ESI+) m/z 461 (M+H)$^+$

Example 148: Synthesis of N-(4-(6-(ethylsulfonamido)pyridin-3-yl)-1H-pyrrolo[2,3-b]pyridin-6-yl)cyclopropanecarboxamide

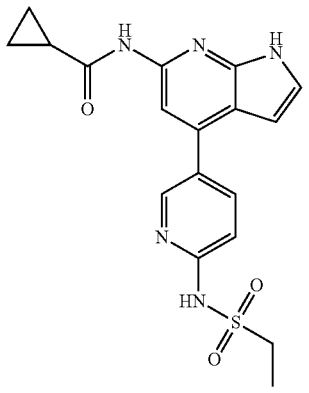 [SMILES: CCS(=O)(=O)Nc1ccc(-c2cc(NC(=O)C3CC3)nc3[nH]ccc23)cn1]

$^1$H NMR (400 MHz, DMSO-d$_6$) δ 11.61 (s, 1H), 10.78 (s, 1H), 10.68 (s, 1H), 8.57 (s, 1H), 8.08 (dd, J=2.5, 8.6 Hz, 1H), 8.01 (s, 1H), 7.43 (dd, J=2.5, 3.5 Hz, 1H), 7.16 (d, J=8.6 Hz, 1H), 6.54 (dd, J=1.9, 3.5 Hz, 1H), 3.52 (s, 2H), 2.04 (t, J=5.0 Hz, 1H), 1.25 (t, J=7.3 Hz, 4H), 0.85-0.73 (m, 4H).

MS(ESI+) m/z 386 (M+H)$^+$

Example 149: Synthesis of N-(4-(5-(ethylsulfonamido)-6-fluoropyridin-2-yl)-1H-pyrrolo[2,3-b]pyridin-6-yl)cyclopropanecarboxamide

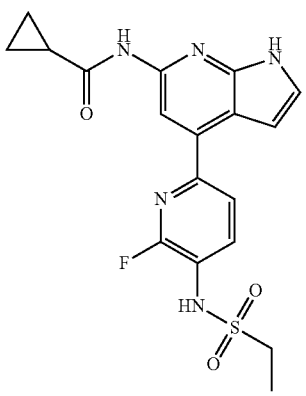 [SMILES: CCS(=O)(=O)Nc1ccc(-c2cc(NC(=O)C3CC3)nc3[nH]ccc23)nc1F]

$^1$H NMR (400 MHz, DMSO-d$_6$) δ 11.60 (s, 1H), 10.67 (s, 1H), 8.39 (s, 1H), 8.01 (d, J=9.7 Hz, 1H), 7.92 (d, J=8.3 Hz, 1H), 7.47 (t, J=3.0 Hz, 1H), 6.89 (dd, J=1.9, 3.5 Hz, 1H), 3.20 (d, J=7.4 Hz, 2H), 2.10-1.97 (m, 1H), 1.28-1.22 (m, 3H), 0.87-0.76 (m, 4H).

MS(ESI+) m/z 404 (M+H)$^+$

Example 150: Synthesis of N-(4-(6-fluoro-5-(propylsulfonamido)pyridin-2-yl)-1H-pyrrolo[2,3-b]pyridin-6-yl)cyclopropanecarboxamide

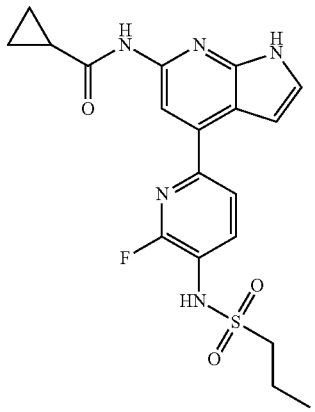 [SMILES: CCCS(=O)(=O)Nc1ccc(-c2cc(NC(=O)C3CC3)nc3[nH]ccc23)nc1F]

$^1$H NMR (400 MHz, DMSO-d$_6$) δ 11.62 (s, 1H), 10.68 (s, 1H), 10.14 (s, 1H), 8.40 (s, 1H), 8.12-8.01 (m, 1H), 7.94 (d, J=8.1 Hz, 1H), 7.48 (dd, J=2.6, 3.5 Hz, 1H), 6.89 (dd, J=1.9, 3.5 Hz, 1H), 3.26-3.16 (m, 2H), 2.04 (t, J=3.9 Hz, 1H), 1.76 (h, J=7.5 Hz, 2H), 0.99 (t, J=7.4 Hz, 3H), 0.89-0.78 (m, 4H).

MS(ESI+) m/z 418 (M+H)$^+$

Example 151: Synthesis of N-(4-(4-(ethylsulfonamido)cyclohex-1-en-1-yl)-1H-pyrrolo[2,3-b]pyridin-6-yl)cyclopropanecarboxamide

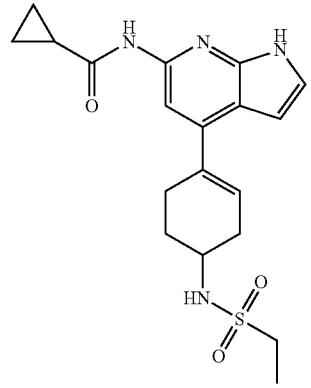 [SMILES: CCS(=O)(=O)NC1CC=C(c2cc(NC(=O)C3CC3)nc3[nH]ccc23)CC1]

$^1$H NMR (400 MHz, DMSO-d$_6$) δ 11.39 (s, 1H), 10.52 (s, 1H), 7.83 (s, 1H), 7.31 (t, J=3.0 Hz, 1H), 7.22 (d, J=7.3 Hz, 1H), 6.50 (d, J=3.4 Hz, 1H), 6.18 (s, 1H), 3.06 (q, J=7.3 Hz, 2H), 2.24 (d, J=9.8 Hz, 2H), 2.01 (s, 2H), 1.76-1.61 (m, 1H), 1.21 (d, J=7.4 Hz, 3H), 0.82-0.74 (m, 4H).

MS(ESI+) m/z 389 (M+H)$^+$

Example 152: Synthesis of N-(4-(4-(propylsulfona-mido)cyclohex-1-en-1-yl)-1H-pyrrolo[2,3-b]pyridin-6-yl)cyclopropanecarboxamide

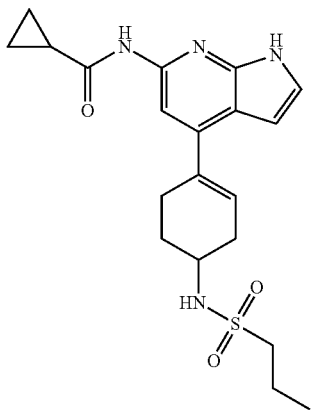 [SMILES: CCCS(=O)(=O)NC1CC=C(c2cc(NC(=O)C3CC3)nc3[nH]ccc23)CC1]

$^1$H NMR (400 MHz, Chloroform-d) δ 11.39 (s, 1H), 10.52 (s, 1H), 7.83 (s, 1H), 7.31 (t, J=2.9 Hz, 1H), 7.21 (d, J=7.4 Hz, 1H), 6.51 (dd, J=1.8, 3.5 Hz, 1H), 6.18 (s, 1H), 3.11-2.99 (m, 2H), 2.22 (dd, J=9.0, 17.2 Hz, 1H), 2.01 (s, 2H), 1.76-1.63 (m, 3H), 0.99 (t, J=7.4 Hz, 3H), 0.81-0.72 (m, 4H).

MS(ESI+) m/z 403 (M+H)$^+$

Example 153: Synthesis of N-(4-(4-((trifluorom-ethyl)sulfonamido)cyclohex-1-en-1-yl)-1H-pyrrolo[2,3-b]pyridin-6-yl)cyclopropanecarboxamide

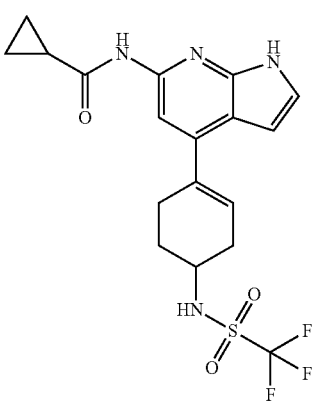 [SMILES: O=C(Nc1cc(C2=CCC(NS(=O)(=O)C(F)(F)F)CC2)c2cc[nH]c2n1)C1CC1]

$^1$H NMR (400 MHz, DMSO-d$_6$) δ 11.41 (s, 1H), 10.56 (s, 1H), 9.62 (d, J=7.9 Hz, 1H), 7.82 (s, 1H), 7.32 (t, J=3.0 Hz, 1H), 6.53 (dd, J=1.8, 3.5 Hz, 1H), 6.18 (s, 1H), 3.71 (s, 2H), 2.70-2.55 (m, 5H), 2.34 (d, J=8.2 Hz, 1H), 2.02 (s, 2H), 1.82 (s, 1H), 0.84-0.76 (m, 4H).

MS(ESI+) m/z 429 (M+H)$^+$

Example 154: Synthesis of N-(4-(4-(cyclopropane-sulfonamido)cyclohex-1-en-1-yl)-1H-pyrrolo[2,3-b]pyridin-6-yl)cyclopropanecarboxamide

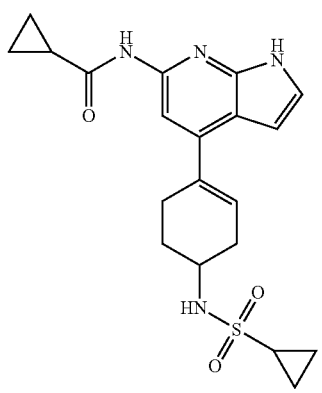 [SMILES: O=C(Nc1cc(C2=CCC(NS(=O)(=O)C3CC3)CC2)c2cc[nH]c2n1)C1CC1]

$^1$H NMR (400 MHz, Chloroform-d) δ 11.37 (s, 1H), 10.49 (s, 1H), 7.83 (s, 1H), 7.31 (dd, J=2.4, 3.5 Hz, 1H), 7.22 (d, J=7.5 Hz, 1H), 6.51 (dd, J=1.9, 3.5 Hz, 1H), 6.19 (s, 1H), 3.54 (d, J=3.3 Hz, 1H), 2.68-2.55 (m, 4H), 2.30-2.19 (m, 1H), 2.08 (d, J=13.3 Hz, 1H), 2.00 (dt, J=4.8, 8.4 Hz, 1H), 1.72 (ddt, J=5.7, 10.1, 15.5 Hz, 1H), 0.98-0.93 (m, 4H), 0.84-0.75 (m, 4H).

MS(ESI+) m/z 401 (M+H)$^+$

Example 155: Synthesis of N-(4-(4-((2-cyanoethyl)sulfonamido)cyclohex-1-en-1-yl)-1H-pyrrolo[2,3-b]pyridin-6-yl)cyclopropanecarboxamide

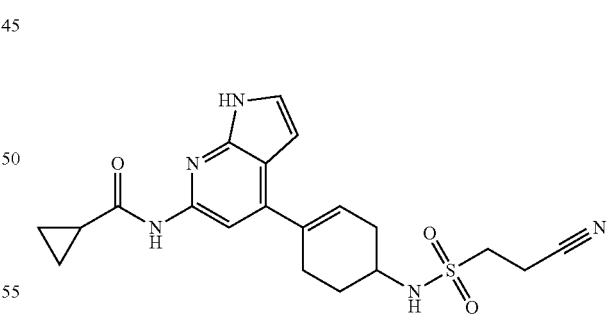

$^1$H NMR (400 MHz, DMSO-d$_6$) δ 11.37 (s, 1H), 10.49 (s, 1H), 7.83 (s, 1H), 7.33-7.27 (m, 1H), 6.50 (dd, J=1.4, 3.5 Hz, 1H), 6.18 (t, J=3.4 Hz, 1H), 3.49 (q, J=9.4, 10.2 Hz, 2H), 3.20-3.14 (m, 2H), 2.68 (t, J=7.2 Hz, 2H), 2.58 (d, J=18.9 Hz, 3H), 2.28-2.17 (m, 1H), 2.06-1.96 (m, 4H), 1.77-1.64 (m, 1H), 0.85-0.76 (m, 4H).

MS(ESI+) m/z 414 (M+H)$^+$

Example 156: Synthesis of N-(4-(4-(((1-(cyanomethyl)cyclopropyl)methyl)sulfonamido)cyclohex-1-en-1-yl)-1H-pyrrolo[2,3-b]pyridin-6-yl)cyclopropanecarboxamide

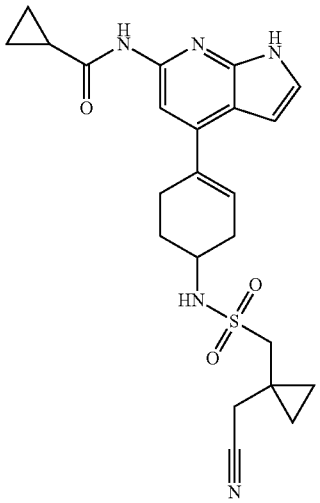 [SMILES: N#CCC1(CS(=O)(=O)NC2CC=C(c3cc(NC(=O)C4CC4)nc4[nH]ccc34)CC2)CC1]

$^1$H NMR (400 MHz, DMSO-d$_6$) δ 11.37 (s, 1H), 10.49 (s, 1H), 7.83 (s, 1H), 7.39 (d, J=6.9 Hz, 1H), 7.31 (dd, J=2.5, 3.5 Hz, 1H), 6.50 (dd, J=1.9, 3.5 Hz, 1H), 6.18 (s, 1H), 3.51 (s, 1H), 3.18 (s, 2H), 2.83 (s, 2H), 2.58 (d, J=22.9 Hz, 3H), 2.23 (dd, J=12.2, 23.6 Hz, 1H), 2.01 (s, 2H), 1.78-1.63 (m, 1H), 0.84-0.79 (m, 4H), 0.79-0.73 (m, 2H), 0.71-0.65 (m, 2H).

MS(ESI+) m/z 454 (M+H)$^+$

Example 157: Synthesis of N-(4-(4-(((1-cyanocyclopropyl)methyl)sulfonamido)cyclohex-1-en-1-yl)-1H-pyrrolo[2,3-b]pyridin-6-yl)cyclopropanecarboxamide

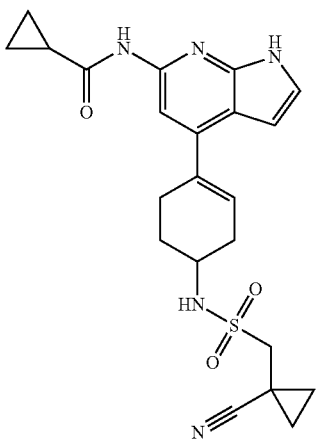 [SMILES: N#CC1(CS(=O)(=O)NC2CC=C(c3cc(NC(=O)C4CC4)nc4[nH]ccc34)CC2)CC1]

$^1$H NMR (400 MHz, DMSO-d$_6$) δ 11.37 (s, 1H), 10.49 (s, 1H), 7.83 (s, 1H), 7.51 (s, 1H), 7.31 (dd, J=2.5, 3.5 Hz, 1H), 6.50 (dd, J=1.9, 3.5 Hz, 1H), 6.18 (s, 1H), 3.52 (d, J=16.4 Hz, 1H), 3.37 (s, 2H), 2.59 (d, J=29.8 Hz, 3H), 2.24 (dd, J=9.4, 16.1 Hz, 1H), 2.12-1.97 (m, 2H), 1.78-1.63 (m, 1H), 1.36 (t, J=3.5 Hz, 2H), 1.29-1.23 (m, 2H), 0.86-0.74 (m, 4H).

MS(ESI+) m/z 440 (M+H)$^+$

Example 158: Synthesis of N-(4-(4-((3-cyanopropyl)sulfonamido)cyclohex-1-en-1-yl)-1H-pyrrolo[2,3-b]pyridin-6-yl)cyclopropanecarboxamide

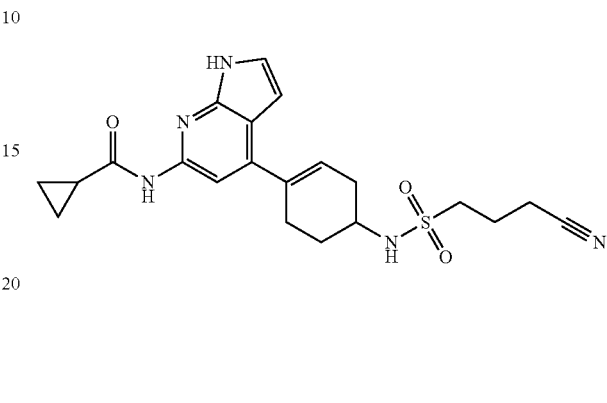

$^1$H NMR (400 MHz, DMSO-d$_6$) δ 11.37 (s, 1H), 10.49 (s, 1H), 7.83 (s, 1H), 7.40 (d, J=6.4 Hz, 1H), 7.31 (dd, J=2.4, 3.5 Hz, 1H), 6.50 (dd, J=1.8, 3.5 Hz, 1H), 6.18 (s, 1H), 3.49 (s, 2H), 3.17 (dd, J=6.4, 8.7 Hz, 2H), 2.68 (t, J=7.3 Hz, 2H), 2.58 (d, J=18.3 Hz, 3H), 2.23 (dd, J=8.9, 17.2 Hz, 1H), 2.00 (h, J=6.2, 7.3 Hz, 4H), 1.76-1.63 (m, 1H), 0.83-0.75 (m, 4H).

MS(ESI+) m/z 428 (M+H)$^+$

Example 159: Synthesis of N-(4-(4-((3-fluoropropyl)sulfonamido)cyclohex-1-en-1-yl)-1H-pyrrolo[2,3-b]pyridin-6-yl)cyclopropanecarboxamide

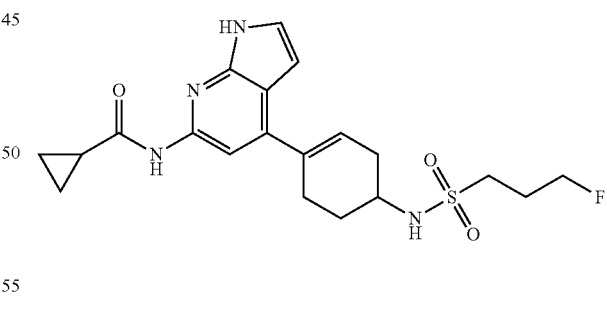

$^1$H NMR (400 MHz, DMSO-d$_6$) δ 11.39 (s, 1H), 10.52 (s, 1H), 7.83 (s, 1H), 7.36 (d, J=7.3 Hz, 1H), 7.31 (dd, J=2.5, 3.5 Hz, 1H), 6.51 (dd, J=1.9, 3.5 Hz, 1H), 6.18 (d, J=4.3 Hz, 1H), 4.62 (t, J=6.0 Hz, 1H), 4.51 (t, J=6.0 Hz, 1H), 3.50 (s, 1H), 3.24-3.11 (m, 2H), 2.55 (s, 3H), 2.23 (dd, J=8.8, 15.7 Hz, 1H), 2.13-1.98 (m, 4H), 1.71 (tt, J=8.0, 15.8 Hz, 1H), 0.83-0.74 (m, 4H).

MS(ESI+) m/z 421 (M+H)$^+$

Example 160: Synthesis of N-(4-(4-(allylsulfona-mido)cyclohex-1-en-1-yl)-1H-pyrrolo[2,3-b]pyridin-6-yl)cyclopropanecarboxamide

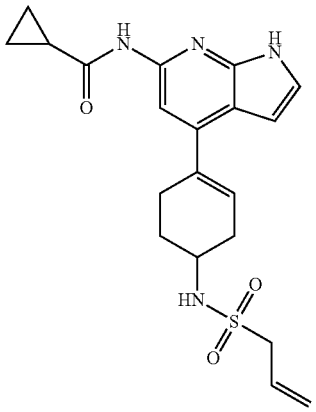 [SMILES: C=CCS(=O)(=O)NC1CC=C(c2cc(NC(=O)C3CC3)nc3[nH]ccc23)CC1]

¹H NMR (400 MHz, DMSO-d₆) δ 11.39 (s, 1H), 10.52 (s, 1H), 7.83 (d, J=3.0 Hz, 1H), 7.34-7.26 (m, 2H), 6.50 (dt, J=1.6, 3.2 Hz, 1H), 6.17 (s, 1H), 5.45-5.36 (m, 1H), 3.87 (d, J=7.2 Hz, 1H), 2.57 (d, J=23.0 Hz, 2H), 2.23 (d, J=7.5 Hz, 1H), 2.01 (s, 2H), 1.87 (dd, J=1.5, 6.7 Hz, 1H), 1.77-1.60 (m, 1H), 0.83-0.75 (m, 4H).

MS(ESI+) m/z 401 (M+H)⁺

Example 161: Synthesis of N-(4-(4-((cyclopropylm-ethyl)sulfonamido)cyclohex-1-en-1-yl)-1H-pyrrolo[2,3-b]pyridin-6-yl)cyclopropanecarboxamide

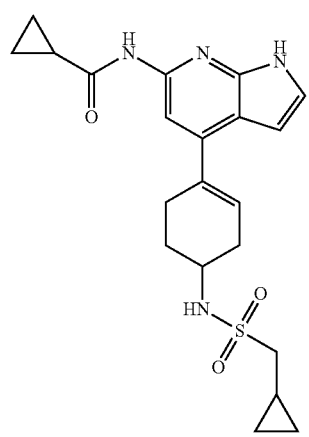 [SMILES: O=C(Nc1cc(C2=CCC(NS(=O)(=O)CC3CC3)CC2)c2cc[nH]c2n1)C1CC1]

¹H NMR (400 MHz, DMSO-d₆) δ 11.39 (s, 1H), 10.52 (s, 1H), 7.83 (s, 1H), 7.31 (dd, J=2.3, 3.5 Hz, 1H), 7.21 (d, J=6.1 Hz, 1H), 6.50 (dd, J=1.6, 3.5 Hz, 1H), 6.18 (s, 1H), 3.51 (s, 1H), 3.01 (d, J=6.9 Hz, 2H), 2.58 (d, J=20.5 Hz, 3H), 2.23 (dd, J=9.2, 16.8 Hz, 1H), 2.02 (s, 2H), 1.79-1.63 (m, 1H), 1.12-0.98 (m, 1H), 0.84-0.74 (m, 4H).

MS(ESI+) m/z 415 (M+H)⁺

Example 162: Synthesis of N-(4-(4-((3,4-difluoro-phenyl)sulfonamido)cyclohex-1-en-1-yl)-1H-pyrrolo[2,3-b]pyridin-6-yl)cyclopropanecarboxamide

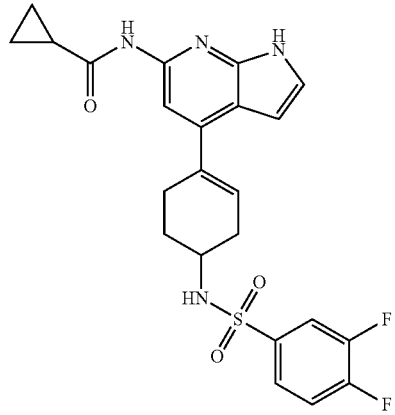 [SMILES: O=C(Nc1cc(C2=CCC(NS(=O)(=O)c3ccc(F)c(F)c3)CC2)c2cc[nH]c2n1)C1CC1]

¹H NMR (400 MHz, DMSO-d₆) δ 11.38 (s, 1H), 10.51 (s, 1H), 7.92 (ddd, J=2.2, 7.4, 9.8 Hz, 1H), 7.80 (s, 1H), 7.78-7.61 (m, 2H), 7.29 (dd, J=2.2, 3.5 Hz, 1H), 6.47 (dd, J=1.5, 3.5 Hz, 1H), 6.15-6.07 (m, 1H), 3.42-3.36 (m, 2H), 2.40-2.28 (m, 1H), 2.12 (ddd, J=3.1, 8.3, 18.0 Hz, 1H), 2.00 (tt, J=4.9, 7.8 Hz, 1H), 1.85-1.77 (m, 1H), 1.68-1.53 (m, 1H), 0.82-0.73 (m, 4H).

MS(ESI+) m/z 473 (M+H)⁺

Example 163: Synthesis of N-(4-(4-((3-fluorophe-nyl)sulfonamido)cyclohex-1-en-1-yl)-1H-pyrrolo[2,3-b]pyridin-6-yl)cyclopropanecarboxamide

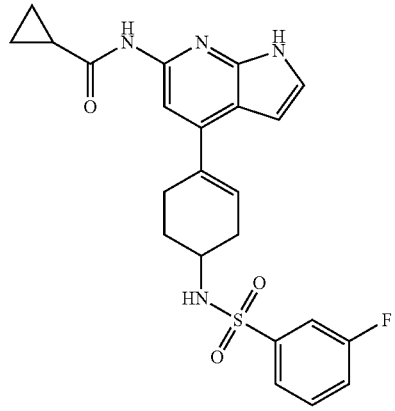 [SMILES: O=C(Nc1cc(C2=CCC(NS(=O)(=O)c3cccc(F)c3)CC2)c2cc[nH]c2n1)C1CC1]

¹H NMR (400 MHz, DMSO-d₆) δ 11.37 (s, 1H), 10.50 (s, 1H), 7.79 (s, 1H), 7.75-7.63 (m, 3H), 7.56-7.48 (m, 1H), 7.29 (dd, J=2.2, 3.5 Hz, 1H), 6.47 (dd, J=1.5, 3.5 Hz, 1H), 6.09 (d, J=4.1 Hz, 1H), 2.49 (s, 3H), 2.39-2.25 (m, 1H), 2.12 (ddd, J=3.0, 8.5, 18.1 Hz, 1H), 1.99 (dt, J=4.9, 7.5 Hz, 1H), 1.83-1.73 (m, 1H), 1.69-1.54 (m, 1H), 0.77 (tdd, J=4.0, 6.4, 9.9 Hz, 4H).

MS(ESI+) m/z 455 (M+H)⁺

Example 164: Synthesis of N-(4-(4-((4-cyanophenyl)sulfonamido)cyclohex-1-en-1-yl)-1H-pyrrolo[2,3-b]pyridin-6-yl)cyclopropanecarboxamide

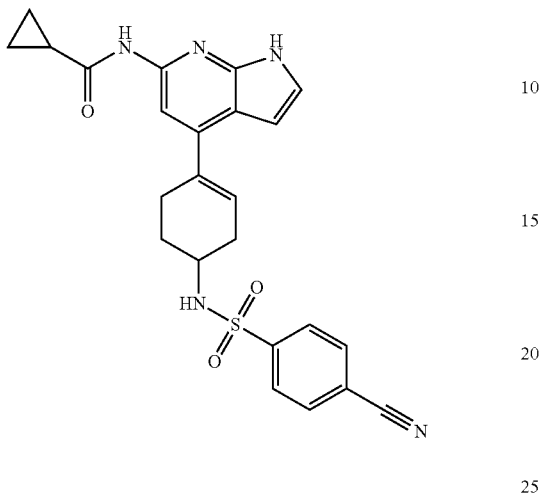

$^1$H NMR (400 MHz, DMSO-$d_6$) δ 11.38 (s, 1H), 10.51 (s, 1H), 8.21-8.15 (m, 1H), 8.13-8.07 (m, 2H), 8.07-8.01 (m, 2H), 7.79 (s, 1H), 7.29 (dd, J=2.5, 3.5 Hz, 1H), 6.47 (dd, J=1.9, 3.5 Hz, 1H), 6.09 (t, J=3.7 Hz, 1H), 3.40 (s, 2H), 3.17 (d, J=3.2 Hz, 1H), 2.36-2.29 (m, 1H), 2.16-2.05 (m, 1H), 2.04-1.95 (m, 1H), 1.80 (d, J=12.2 Hz, 1H), 1.63 (td, J=5.8, 10.8, 11.7 Hz, 1H), 0.80-0.73 (m, 4H).

MS(ESI+) m/z 462 (M+H)$^+$

Example 165: Synthesis of N-(4-(4-(cyclobutanesulfonamido)cyclohex-1-en-1-yl)-1H-pyrrolo[2,3-b]pyridin-6-yl)cyclopropanecarboxamide

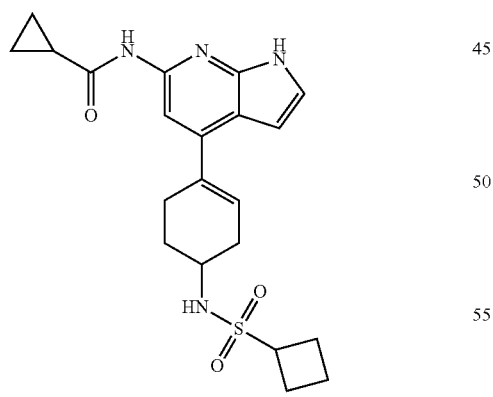

$^1$H NMR (400 MHz, DMSO-$d_6$) δ 11.38 (s, 1H), 10.51 (s, 1H), 7.82 (s, 1H), 7.31 (dd, J=2.5, 3.5 Hz, 1H), 7.18 (d, J=7.7 Hz, 1H), 6.50 (dd, J=1.8, 3.5 Hz, 1H), 6.17 (s, 1H), 3.94 (p, J=8.2 Hz, 1H), 3.65-3.54 (m, 1H), 2.37-2.14 (m, 5H), 2.06-1.80 (m, 4H), 1.69 (dd, J=6.2, 11.5 Hz, 1H), 0.85-0.75 (m, 4H).

MS(ESI+) m/z 415 (M+H)$^+$

Example 166: Synthesis of N-(4-(1-(ethylsulfonyl)-1,2,3,6-tetrahydropyridin-4-yl)-1H-pyrrolo[2,3-b]pyridin-6-yl)cyclopropanecarboxamide

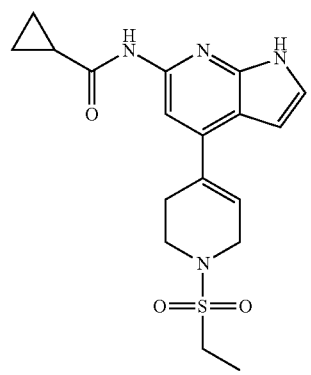 [SMILES: CCS(=O)(=O)N1CC=C(c2cc(NC(=O)C3CC3)nc3[nH]ccc23)CC1]

$^1$H NMR (400 MHz, DMSO-$d_6$) δ 11.46 (s, 1H), 10.56 (s, 1H), 7.87 (s, 1H), 7.35 (t, J=2.9 Hz, 1H), 6.57 (dd, J=1.7, 3.6 Hz, 1H), 6.35 (d, J=3.8 Hz, 1H), 4.00 (q, J=2.9 Hz, 2H), 3.49 (t, J=5.7 Hz, 4H), 3.14 (q, J=7.3 Hz, 2H), 2.62 (s, 2H), 2.07-1.95 (m, 1H), 1.24 (t, J=7.3 Hz, 3H), 0.84-0.77 (m, 4H).

MS(ESI+) m/z 375 (M+H)$^+$

Example 167: Synthesis of N-(4-(1-((3-fluoropropyl)sulfonyl)-1,2,3,6-tetrahydropyridin-4-yl)-1H-pyrrolo[2,3-b]pyridin-6-yl)cyclopropanecarboxamide

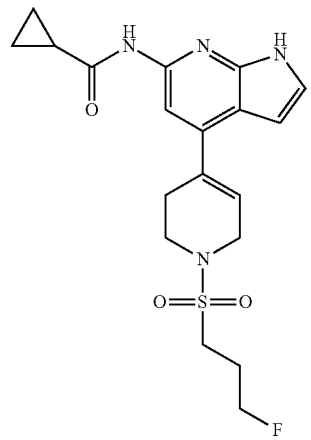 [SMILES: O=C(Nc1cc(C2=CCN(S(=O)(=O)CCCF)CC2)c2cc[nH]c2n1)C1CC1]

MS(ESI+) m/z 407 (M+H)$^+$

Example 168: Synthesis of N-(4-(1-(cyclopropylsulfonyl)-1,2,3,6-tetrahydropyridin-4-yl)-1H-pyrrolo[2,3-b]pyridin-6-yl)cyclopropanecarboxamide

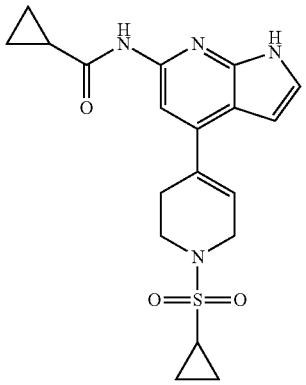 [SMILES: O=C(Nc1cc(C2=CCN(S(=O)(=O)C3CC3)CC2)c2cc[nH]c2n1)C1CC1]

MS(ESI+) m/z 387 (M+H)$^+$

Example 169: Synthesis of N-(4-(1-(((tetrahydro-2H-pyran-4-yl)methyl)sulfonyl)-1,2,3,6-tetrahydropyridin-4-yl)-1H-pyrrolo[2,3-b]pyridin-6-yl)cyclopropanecarboxamide

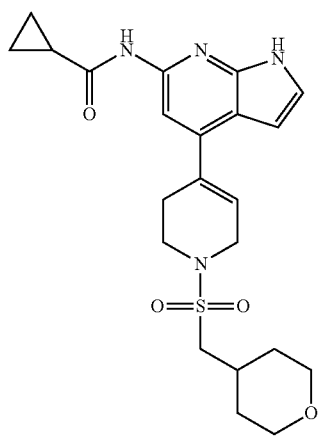 [SMILES: O=C(Nc1cc(C2=CCN(S(=O)(=O)CC3CCOCC3)CC2)c2cc[nH]c2n1)C1CC1]

MS(ESI+) m/z 445 (M+H)$^+$

Example 170: Synthesis of N-(4-(1-((3-cyanopropyl)sulfonyl)-1,2,3,6-tetrahydropyridin-4-yl)-1H-pyrrolo[2,3-b]pyridin-6-yl)cyclopropanecarboxamide

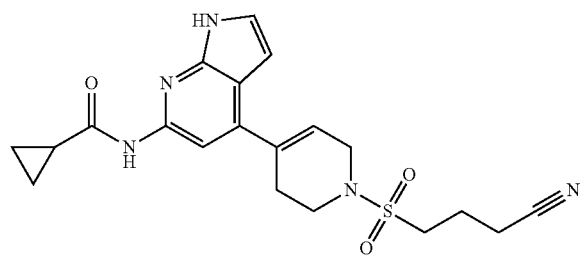 [SMILES: N#CCCCS(=O)(=O)N1CC=C(c2cc(NC(=O)C3CC3)nc3[nH]ccc23)CC1]

MS(ESI+) m/z 414 (M+H)$^+$

Example 171: Synthesis of N-(4-(1-(((1-(cyanomethyl)cyclopropyl)methyl)sulfonyl)-1,2,3,6-tetrahydropyridin-4-yl)-1H-pyrrolo[2,3-b]pyridin-6-yl)cyclopropanecarboxamide

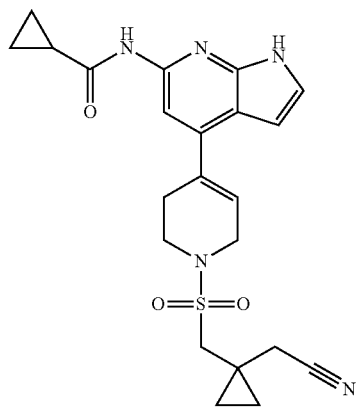 [SMILES: N#CCC1(CS(=O)(=O)N2CC=C(c3cc(NC(=O)C4CC4)nc4[nH]ccc34)CC2)CC1]

MS(ESI+) m/z 440 (M+H)$^+$

Example 172: Synthesis of N-(4-(1-(((1-cyanocyclopropyl)methyl)sulfonyl)-1,2,3,6-tetrahydropyridin-4-yl)-1H-pyrrolo[2,3-b]pyridin-6-yl)cyclopropanecarboxamide

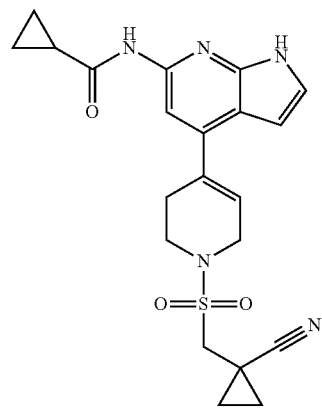 [SMILES: N#CC1(CS(=O)(=O)N2CC=C(c3cc(NC(=O)C4CC4)nc4[nH]ccc34)CC2)CC1]

MS(ESI+) m/z 426 (M+H)$^+$

Example 173: Synthesis of N-(4-(1-((3,4-difluorophenyl)sulfonyl)-1,2,3,6-tetrahydropyridin-4-yl)-1H-pyrrolo[2,3-b]pyridin-6-yl)cyclopropanecarboxamide

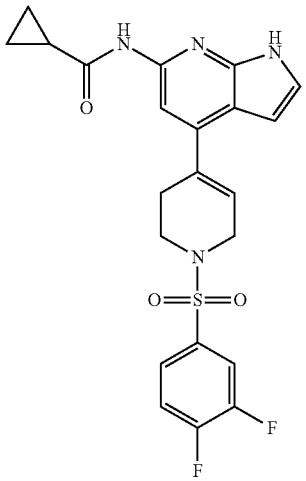 [SMILES: O=C(Nc1cc(C2=CCN(S(=O)(=O)c3ccc(F)c(F)c3)CC2)c2cc[nH]c2n1)C1CC1]

MS(ESI+) m/z 459 (M+H)+

Example 174: Synthesis of N-(4-(8-(ethylsulfonyl)-8-azabicyclo[3.2.1]oct-2-en-3-yl)-1H-pyrrolo[2,3-b]pyridin-6-yl)cyclopropanecarboxamide

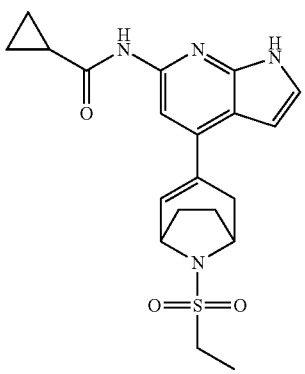 [SMILES: CCS(=O)(=O)N1C2C=C(c3cc(NC(=O)C4CC4)nc4[nH]ccc34)CC1CC2]

MS(ESI+) m/z 401 (M+H)+

Example 175: Synthesis of N-(4-(8-((3-fluoropropyl)sulfonyl)-8-azabicyclo[3.2.1]oct-2-en-3-yl)-1H-pyrrolo[2,3-b]pyridin-6-yl)cyclopropanecarboxamide

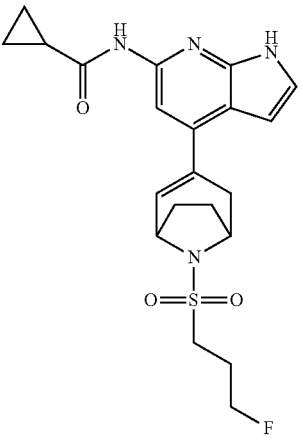 [SMILES: O=C(Nc1cc(C2=CC3CCC(C2)N3S(=O)(=O)CCCF)c2cc[nH]c2n1)C1CC1]

MS(ESI+) m/z 433 (M+H)+

Example 176: Synthesis of N-(4-(8-(propylsulfonyl)-8-azabicyclo[3.2.1]oct-2-en-3-yl)-1H-pyrrolo[2,3-b]pyridin-6-yl)cyclopropanecarboxamide

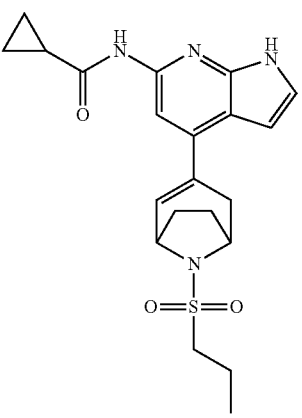 [SMILES: CCCS(=O)(=O)N1C2C=C(c3cc(NC(=O)C4CC4)nc4[nH]ccc34)CC1CC2]

MS(ESI+) m/z 415 (M+H)+

Example 177: Synthesis of N-(4-(8-(cyclopropylsulfonyl)-8-azabicyclo[3.2.1]oct-2-en-3-yl)-1H-pyrrolo[2,3-b]pyridin-6-yl)cyclopropanecarboxamide

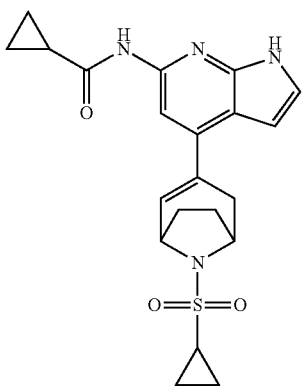 [SMILES: O=C(Nc1cc(C2=CC3CCC(C2)N3S(=O)(=O)C2CC2)c2cc[nH]c2n1)C1CC1]

MS(ESI+) m/z 413 (M+H)+

Example 178: Synthesis of N-(4-(8-((3,4-difluorophenyl)sulfonyl)-8-azabicyclo[3.2.1]oct-2-en-3-yl)-1H-pyrrolo[2,3-b]pyridin-6-yl)cyclopropanecarboxamide

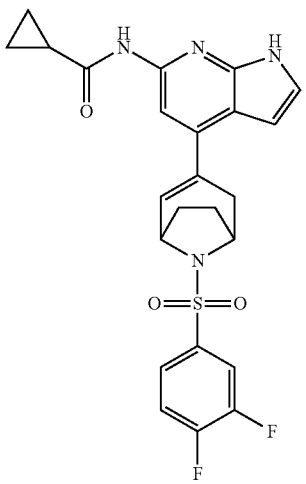 [SMILES: O=C(Nc1cc(C2=CC3CCC(C2)N3S(=O)(=O)c2ccc(F)c(F)c2)c2cc[nH]c2n1)C1CC1]

MS(ESI+) m/z 485 (M+H)+

Example 179: Synthesis of N-(4-(1-(ethylsulfonyl)-3,3-dimethyl-1,2,3,6-tetrahydropyridin-4-yl)-1H-pyrrolo[2,3-b]pyridin-6-yl)cyclopropanecarboxamide

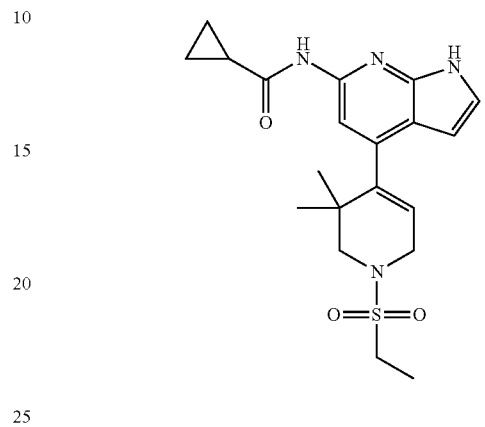

$^1$H NMR (400 MHz, DMSO-d$_6$) δ 11.37 (s, 1H), 10.53 (s, 1H), 7.74 (s, 1H), 7.28 (dd, J=2.4, 3.5 Hz, 1H), 6.28 (dd, J=1.9, 3.5 Hz, 1H), 5.62 (t, J=3.2 Hz, 1H), 3.89 (d, J=3.2 Hz, 2H), 3.19 (s, 2H), 3.15 (t, J=7.3 Hz, 2H), 2.01 (s, 1H), 1.27 (t, J=7.4 Hz, 3H), 1.04 (s, 6H), 0.82-0.75 (m, 4H).

MS(ESI+) m/z 403 (M+H)+

Example 180: Synthesis of N-(4-(1-((3-cyanopropyl)sulfonyl)-3,3-dimethyl-1,2,3,6-tetrahydropyridin-4-yl)-1H-pyrrolo[2,3-b]pyridin-6-yl)cyclopropanecarboxamide

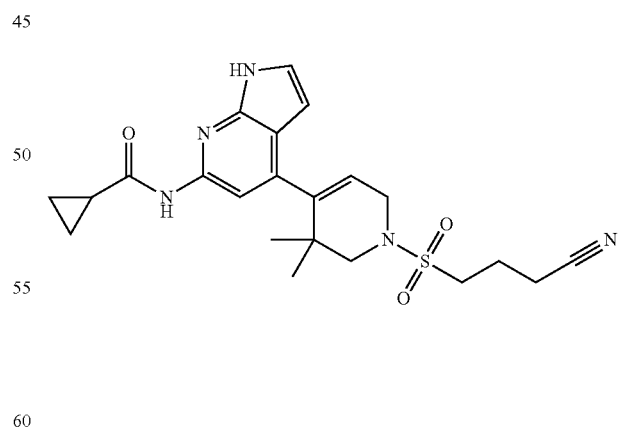

$^1$H NMR (400 MHz, DMSO-d$_6$) δ 11.37 (s, 1H), 10.54 (s, 1H), 7.74 (s, 1H), 7.29 (dd, J=2.4, 3.5 Hz, 1H), 6.28 (dd, J=1.9, 3.5 Hz, 1H), 5.62 (t, J=3.2 Hz, 1H), 3.90 (d, J=3.2 Hz, 2H), 3.28-3.18 (m, 4H), 2.68 (t, J=7.2 Hz, 2H), 2.03 (q, J=7.5 Hz, 3H), 1.05 (s, 6H), 0.82-0.76 (m, 4H).

MS(ESI+) m/z 442 (M+H)+

Example 181: Synthesis of N-(4-(4-((3,4-difluorophenyl)sulfonamido)phenyl)-7H-pyrrolo[2,3-d]pyrimidin-2-yl)cyclopropanecarboxamide

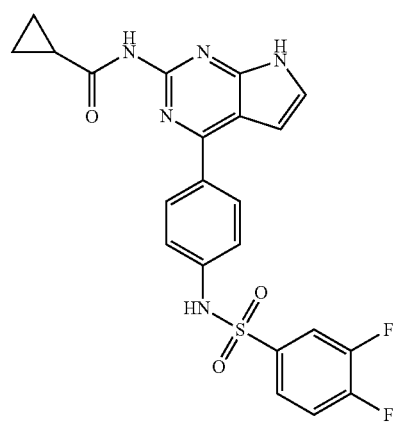

MS(ESI+) m/z 470 (M+H)+

Example 182: Synthesis of N-(4-(4-(ethylsulfonamido)phenyl)-7H-pyrrolo[2,3-d]pyrimidin-2-yl)cyclopropanecarboxamide

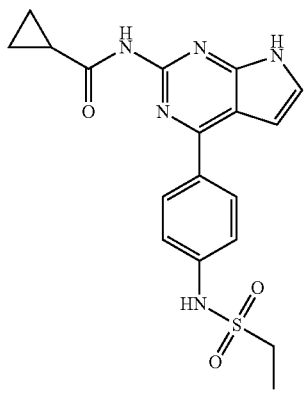

MS(ESI+) m/z 386 (M+H)+

Example 183: Synthesis of N-(4-(4-(cyclohexanesulfonamido)phenyl)-7H-pyrrolo[2,3-d]pyrimidin-2-yl)cyclopropanecarboxamide

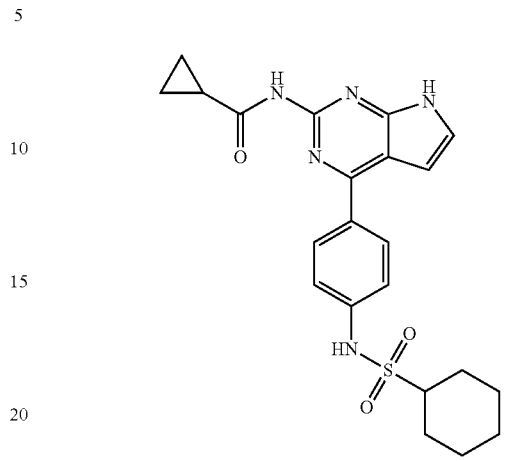

MS(ESI+) m/z 440 (M+H)+

Example 184: Synthesis of N-(4-(4-((4,4,4-trifluorobutyl)sulfonamido)phenyl)-7H-pyrrolo[2,3-d]pyrimidin-2-yl)cyclopropanecarboxamide

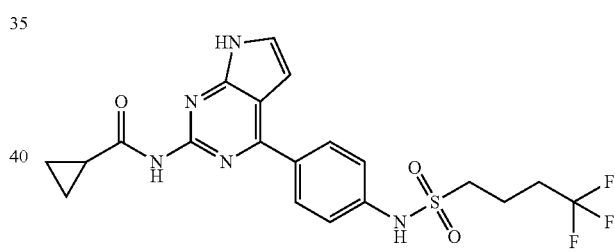

MS(ESI+) m/z 468 (M+H)+

Example 185: Synthesis of N-(4-(4-((3-fluoropropyl)sulfonamido)phenyl)-7H-pyrrolo[2,3-d]pyrimidin-2-yl)cyclopropanecarboxamide

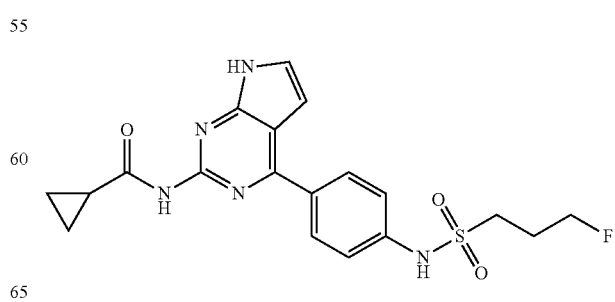

MS(ESI+) m/z 418 (M+H)+

Example 186: Synthesis of N-(4-(4-((3-cyanopropyl)sulfonamido)phenyl)-7H-pyrrolo[2,3-d]pyrimidin-2-yl)cyclopropanecarboxamide

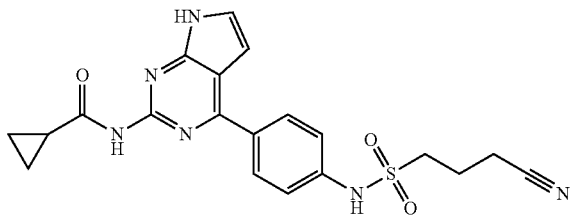

MS(ESI+) m/z 425 (M+H)+

Example 187: Synthesis of N-(4-(4-((4-chlorophenyl)sulfonamido)phenyl)-7H-pyrrolo[2,3-d]pyrimidin-2-yl)cyclopropanecarboxamide

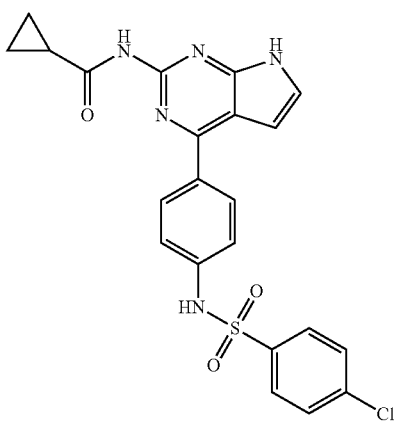 [SMILES: O=C(Nc1nc(-c2ccc(NS(=O)(=O)c3ccc(Cl)cc3)cc2)c2cc[nH]c2n1)C1CC1]

MS(ESI+) m/z 468, 470 (M+H)+

Example 188: Synthesis of N-(4-(4-((4-fluorophenyl)sulfonamido)phenyl)-7H-pyrrolo[2,3-d]pyrimidin-2-yl)cyclopropanecarboxamide

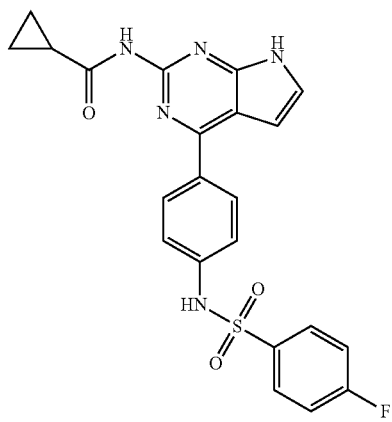 [SMILES: O=C(Nc1nc(-c2ccc(NS(=O)(=O)c3ccc(F)cc3)cc2)c2cc[nH]c2n1)C1CC1]

MS(ESI+) m/z 452 (M+H)+

Example 189: Synthesis of N-(4-(4-((4-bromophenyl)sulfonamido)phenyl)-7H-pyrrolo[2,3-d]pyrimidin-2-yl)cyclopropanecarboxamide

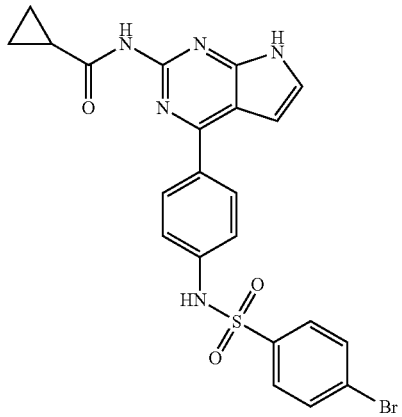

MS(ESI+) m/z 512, 514 (M+H)+

Example 190: Synthesis of N-(4-(4-(propylsulfonamido)phenyl)-7H-pyrrolo[2,3-d]pyrimidin-2-yl)cyclopropanecarboxamide

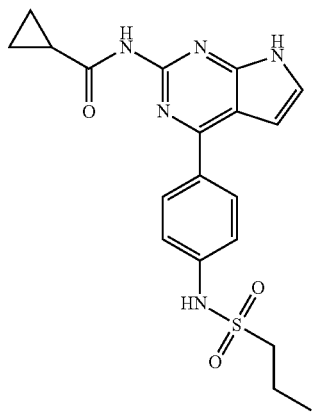

MS(ESI+) m/z 400 (M+H)+

Example 191: Synthesis of N-(4-(4-(butylsulfonamido)phenyl)-7H-pyrrolo[2,3-d]pyrimidin-2-yl)cyclopropanecarboxamide

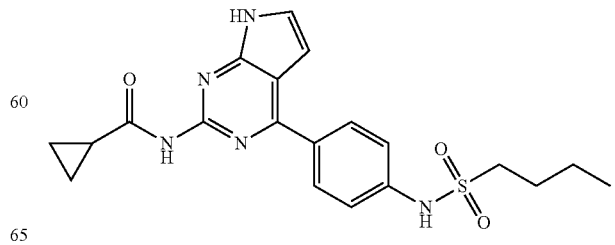

MS(ESI+) m/z 414 (M+H)+

Example 192: Synthesis of N-(4-(4-((3-fluorophenyl)sulfonamido)phenyl)-7H-pyrrolo[2,3-d]pyrimidin-2-yl)cyclopropanecarboxamide

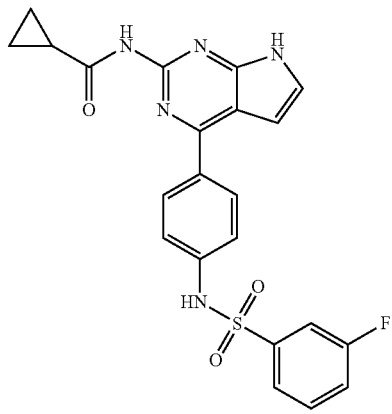

MS(ESI+) m/z 452 (M+H)+

Example 193: Synthesis of N-(4-(4-((3,4-difluoro-N-methylphenyl)sulfonamido)phenyl)-7H-pyrrolo[2,3-d]pyrimidin-2-yl)cyclopropanecarboxamide

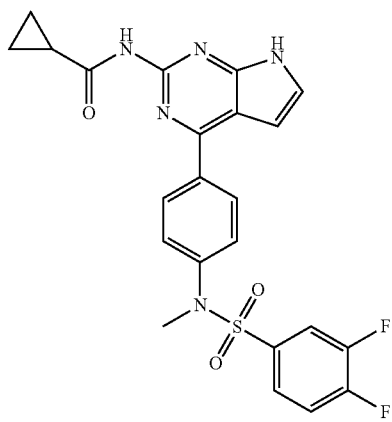 [SMILES: CN(c1ccc(-c2nc(NC(=O)C3CC3)nc3[nH]ccc23)cc1)S(=O)(=O)c1ccc(F)c(F)c1]

MS(ESI+) m/z 484 (M+H)+

Example 194: Synthesis of N-(4-(4-((3,3,3-trifluoropropyl)sulfonamido)phenyl)-7H-pyrrolo[2,3-d]pyrimidin-2-yl)cyclopropanecarboxamide

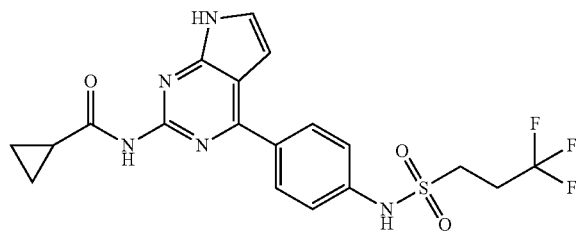 [SMILES: O=C(Nc1nc(-c2ccc(NS(=O)(=O)CCC(F)(F)F)cc2)c2cc[nH]c2n1)C1CC1]

MS(ESI+) m/z 454 (M+H)+

Example 195: Synthesis of N-(4-(4-((1,1-dioxido-tetrahydro-2H-thiopyran)-4-sulfonamido)phenyl)-7H-pyrrolo[2,3-d]pyrimidin-2-yl)cyclopropanecarboxamide

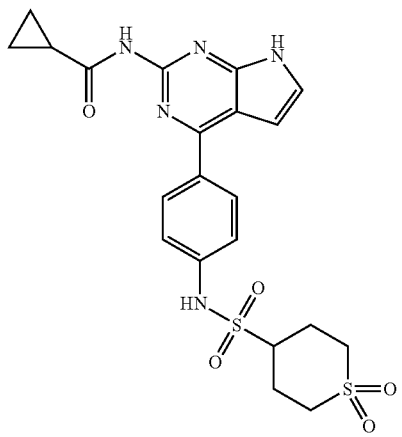

MS(ESI+) m/z 490 (M+H)+

Example 196: Synthesis of N-(4-(4-((1,1-dioxido-tetrahydrothiophene)-3-sulfonamido)phenyl)-7H-pyrrolo[2,3-d]pyrimidin-2-yl)cyclopropanecarboxamide

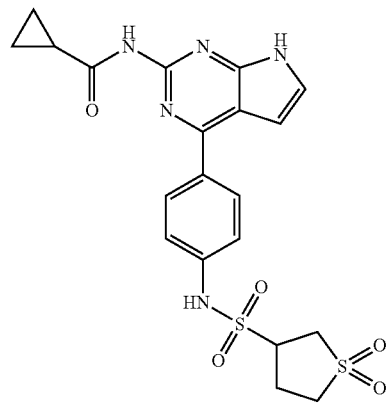 [SMILES: O=C(Nc1nc(-c2ccc(NS(=O)(=O)C3CCS(=O)(=O)C3)cc2)c2cc[nH]c2n1)C1CC1]

MS(ESI+) m/z 476 (M+H)+

Example 197: Synthesis of N-(4-(4-((6-cyanopyridine)-3-sulfonamido)phenyl)-7H-pyrrolo[2,3-d]pyrimidin-2-yl)cyclopropanecarboxamide

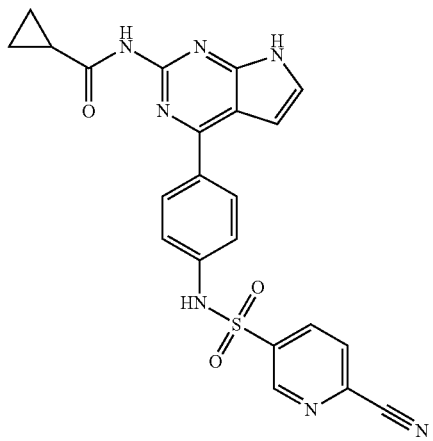 [SMILES: N#Cc1ccc(S(=O)(=O)Nc2ccc(-c3nc(NC(=O)C4CC4)nc4[nH]ccc34)cc2)cn1]

MS(ESI+) m/z 460 (M+H)+

Example 198: Synthesis of N-(4-(4-((1-methyl-1H-imidazole)-5-sulfonamido)phenyl)-7H-pyrrolo[2,3-d]pyrimidin-2-yl)cyclopropanecarboxamide

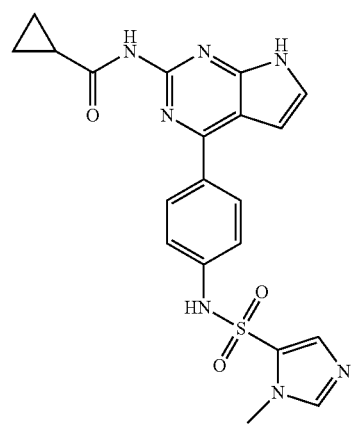 [SMILES: Cn1cncc1S(=O)(=O)Nc1ccc(-c2nc(NC(=O)C3CC3)nc3[nH]ccc23)cc1]

MS(ESI+) m/z 438 (M+H)+

Example 199: Synthesis of N-(4-(4-((1-methyl-1H-pyrazole)-4-sulfonamido)phenyl)-7H-pyrrolo[2,3-d]pyrimidin-2-yl)cyclopropanecarboxamide

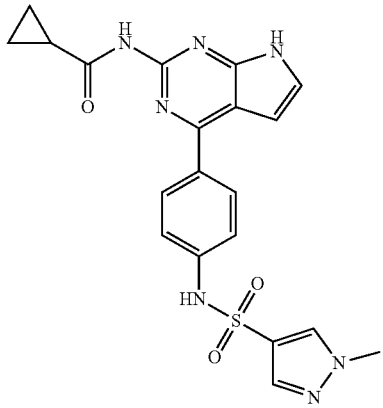 [SMILES: Cn1cc(S(=O)(=O)Nc2ccc(-c3nc(NC(=O)C4CC4)nc4[nH]ccc34)cc2)cn1]

MS(ESI+) m/z 438 (M+H)+

Example 200: Synthesis of 4-(N-(4-(2-(cyclopropanecarboxamido)-7H-pyrrolo[2,3-d]pyrimidin-4-yl)phenyl)sulfamoyl)benzamide

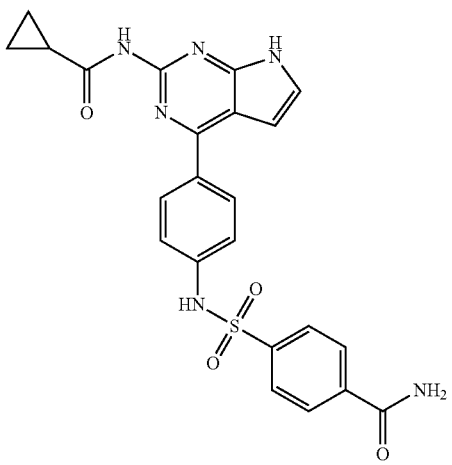 [SMILES: NC(=O)c1ccc(S(=O)(=O)Nc2ccc(-c3nc(NC(=O)C4CC4)nc4[nH]ccc34)cc2)cc1]

MS(ESI+) m/z 477 (M+H)+

Example 201: Synthesis of N-(4-(3-fluoro-4-(methylsulfonamido)phenyl)-7H-pyrrolo[2,3-d]pyrimidin-2-yl)cyclopropanecarboxamide

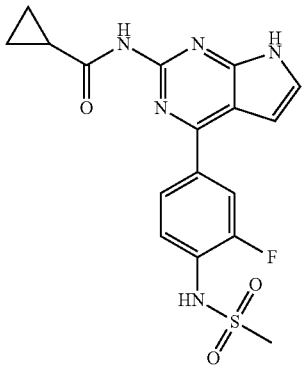 [SMILES: CS(=O)(=O)Nc1ccc(-c2nc(NC(=O)C3CC3)nc3[nH]ccc23)cc1F]

$^1$H NMR (400 MHz, DMSO-d$_6$) δ 12.10 (s, 1H), 10.62 (s, 1H), 8.06 (d, J=9.4 Hz, 2H), 7.62 (t, J=8.4 Hz, 1H), 7.52 (s, 1H), 6.88 (s, 1H), 3.13 (s, 3H), 2.17 (s, 1H), 0.82 (d, J=17.7 Hz, 4H).

MS(ESI+) m/z 390 (M+H)$^+$

Example 202: Synthesis of N-(4-(4-(ethylsulfonamido)-3-fluorophenyl)-7H-pyrrolo[2,3-d]pyrimidin-2-yl)cyclopropanecarboxamide

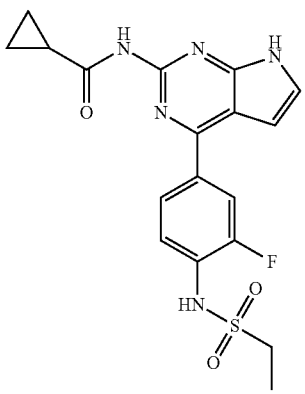 [SMILES: CCS(=O)(=O)Nc1ccc(-c2nc(NC(=O)C3CC3)nc3[nH]ccc23)cc1F]

$^1$H NMR (400 MHz, DMSO-d$_6$) δ 12.10 (s, 1H), 10.62 (s, 1H), 9.94 (s, 1H), 8.15-7.99 (m, 2H), 7.63 (t, J=8.3 Hz, 1H), 7.57-7.47 (m, 1H), 6.94-6.84 (m, 1H), 3.21 (q, J=7.3 Hz, 2H), 2.17 (s, 1H), 1.28 (t, J=7.1 Hz, 3H), 0.88-0.75 (m, 4H)

MS(ESI+) m/z 404 (M+H)$^+$

Example 203: Synthesis of N-(4-(3-fluoro-4-((3-fluoropropyl)sulfonamido)phenyl)-7H-pyrrolo[2,3-d]pyrimidin-2-yl)cyclopropanecarboxamide

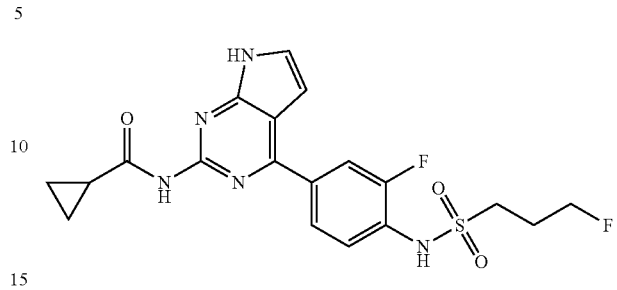

$^1$H NMR (400 MHz, DMSO-d$_6$) δ 12.10 (s, 1H), 10.62 (s, 1H), 10.08 (s, 1H), 8.06 (d, J=9.9 Hz, 2H), 7.63 (t, J=8.2 Hz, 1H), 7.56-7.48 (m, 1H), 6.95-6.85 (m, 1H), 4.55 (dt, J=6.0, 47.4 Hz, 2H), 2.14 (dd, J=8.0, 22.9 Hz, 3H), 0.84-0.78 (m, 4H).

MS(ESI+) m/z 436 (M+H)$^+$

Example 204: Synthesis of N-(4-(4-((3-cyanopropyl)sulfonamido)-3-fluorophenyl)-7H-pyrrolo[2,3-d]pyrimidin-2-yl)cyclopropanecarboxamide

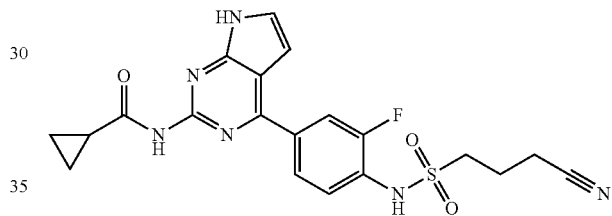

$^1$H NMR (400 MHz, DMSO-d$_6$) δ 12.10 (s, 1H), 10.63 (s, 1H), 10.12 (s, 1H), 8.06 (d, J=10.0 Hz, 2H), 7.62 (t, J=8.3 Hz, 1H), 7.58-7.46 (m, 1H), 6.95-6.78 (m, 1H), 2.69 (t, J=7.1 Hz, 2H), 2.17 (s, 1H), 2.07 (q, J=7.3 Hz, 2H), 0.88-0.80 (m, 4H).

MS(ESI+) m/z 443 (M+H)$^+$

Example 205: Synthesis of N-(4-(4-((3,4-difluorophenyl)sulfonamido)-3-fluorophenyl)-7H-pyrrolo[2,3-d]pyrimidin-2-yl)cyclopropanecarboxamide

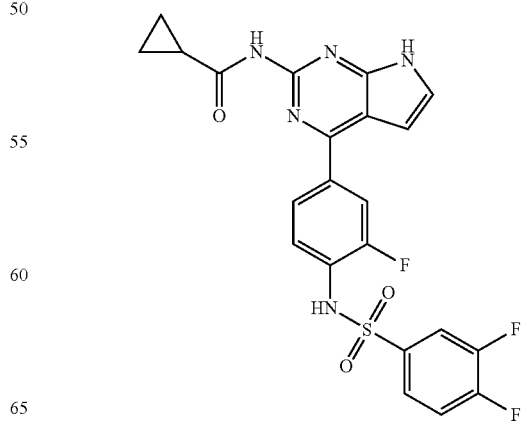

¹H NMR (400 MHz, DMSO-d₆) δ 12.11 (s, 1H), 10.67 (s, 1H), 10.62 (s, 1H), 8.06-7.93 (m, 2H), 7.91-7.83 (m, 1H), 7.76-7.61 (m, 2H), 7.57-7.44 (m, 2H), 6.91-6.78 (m, 1H), 2.14 (s, 1H), 0.90-0.74 (m, 4H).

MS(ESI+) m/z 488 (M+H)⁺

Example 206: Synthesis of (N-(4-(3-fluoro-4-(propylsulfonamido)phenyl)-7H-pyrrolo[2,3-d]pyrimidin-2-yl)cyclopropanecarboxamide)

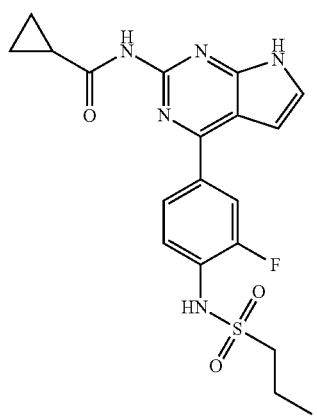 [SMILES: CCCS(=O)(=O)Nc1ccc(-c2nc(NC(=O)C3CC3)nc3[nH]ccc23)cc1F]

MS(ESI+) m/z 418 (M+H)⁺

Example 207: Synthesis of N-(7-(4-(ethylsulfonamido)phenyl)-3H-imidazo[4,5-b]pyridin-5-yl)cyclopropanecarboxamide

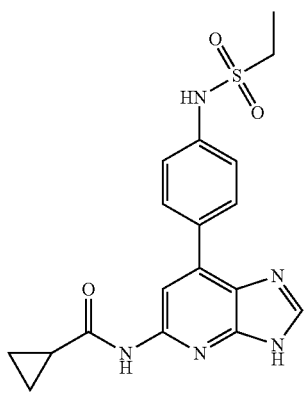 [SMILES: CCS(=O)(=O)Nc1ccc(-c2cc(NC(=O)C3CC3)nc3[nH]cnc23)cc1]

MS(ESI+) m/z 386 (M+H)⁺

Example 208: Synthesis of N-(6-(4-((3,4-difluorophenyl)sulfonamido)phenyl)-9H-purin-2-yl)cyclopropanecarboxamide

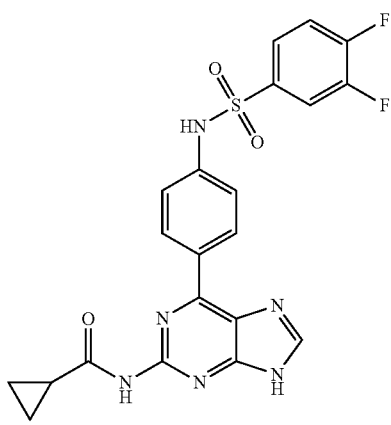 [SMILES: O=C(Nc1nc(-c2ccc(NS(=O)(=O)c3ccc(F)c(F)c3)cc2)c2nc[nH]c2n1)C1CC1]

¹H NMR (400 MHz, DMSO-d₆) δ 10.80 (s, 1H), 10.72 (s, 1H), 8.81-8.61 (m, 2H), 8.45 (s, 1H), 7.92 (ddd, J=9.7, 7.3, 2.2 Hz, 1H), 7.76-7.59 (m, 2H), 7.36-7.28 (m, 2H), 2.16 (s, 1H), 0.85-0.77 (m, 4H).

MS(ESI+) m/z 471 (M+H)⁺

Example 209: Synthesis of N-(6-(4-(ethylsulfonamido)phenyl)-9H-purin-2-yl)cyclopropanecarboxamide

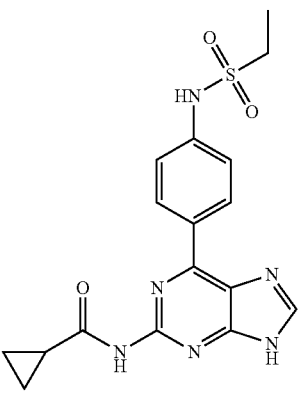 [SMILES: CCS(=O)(=O)Nc1ccc(-c2nc(NC(=O)C3CC3)nc3[nH]cnc23)cc1]

¹H NMR (400 MHz, DMSO-d₆) δ 10.73 (s, 1H), 10.18 (s, 1H), 8.77 (d, J=8.4 Hz, 2H), 8.46 (d, J=1.3 Hz, 1H), 7.46-7.34 (m, 2H), 3.26-3.18 (m, 2H), 2.26-2.13 (m, 1H), 1.22 (td, J=7.4, 1.3 Hz, 3H), 0.92-0.80 (m, 4H).

MS(ESI+) m/z 387 (M+H)⁺

Example 210: Synthesis of N-(6-(4-((3-cyanopropyl)sulfonamido)phenyl)-9H-purin-2-yl)cyclopropanecarboxamide

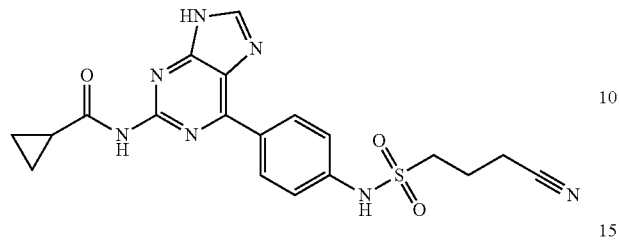

¹H NMR (400 MHz, DMSO-d₆) δ 10.77 (s, 1H), 10.32 (s, 1H), 8.83-8.75 (m, 2H), 8.48 (s, 1H), 7.45-7.36 (m, 2H), 3.59 (dq, J=12.1, 6.0 Hz, 2H), 3.35-3.25 (m, 2H), 2.19 (dt, J=7.8, 3.3 Hz, 1H), 2.00 (dq, J=9.5, 7.4 Hz, 2H), 1.03 (d, J=6.1 Hz, 6H), 0.91-0.79 (m, 4H).
MS(ESI+) m/z 426 (M+H)⁺

Example 211: Synthesis of N-(6-(4-((4,4,4-trifluorobutyl)sulfonamido)phenyl)-9H-purin-2-yl)cyclopropanecarboxamide

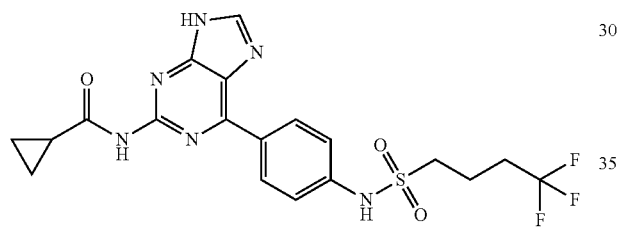

¹H NMR (400 MHz, DMSO-d₆) δ 10.74 (s, 1H), 10.31 (s, 1H), 8.78 (d, J=8.7 Hz, 2H), 8.47 (s, 1H), 7.43-7.35 (m, 2H), 3.34 (t, J=7.6 Hz, 2H), 2.49-2.34 (m, 2H), 2.19 (td, J=7.3, 3.7 Hz, 1H), 1.97-1.84 (m, 2H), 0.86-0.78 (m, 4H).
MS(ESI+) m/z 469 (M+H)⁺

Example 212: Synthesis of N-(4-(1-(propylsulfonyl)-2,5-dihydro-1H-pyrrol-3-yl)-1H-pyrrolo[2,3-b]pyridin-6-yl)cyclopropanecarboxamide

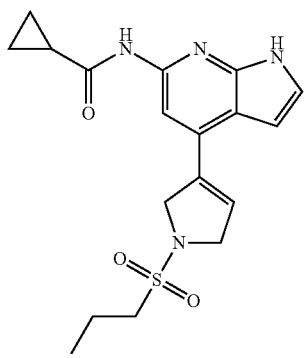 [SMILES: CCCS(=O)(=O)N1CC=C(c2cc(NC(=O)C3CC3)nc3[nH]ccc23)C1]

¹H NMR (400 MHz, DMSO-d₆) δ 11.57 (s, 1H), 10.61 (s, 1H), 7.82 (s, 1H), 7.43 (t, J=2.9 Hz, 1H), 6.70 (td, J=1.9, 3.6, 4.2 Hz, 2H), 4.58 (t, J=4.4 Hz, 2H), 4.40 (q, J=3.8 Hz, 2H), 3.26-3.15 (m, 2H), 2.03 (tt, J=4.5, 7.7 Hz, 1H), 1.80-1.65 (m, 2H), 1.00 (t, J=7.4 Hz, 3H), 0.83-0.76 (m, 4H).
MS(ESI+) m/z 375 (M+H)⁺

Example 213: Synthesis of N-(4-(1-(((1-cyanocyclopropyl)methyl)sulfonyl)-2,5-dihydro-1H-pyrrol-3-yl)-1H-pyrrolo[2,3-b]pyridin-6-yl)cyclopropanecarboxamide

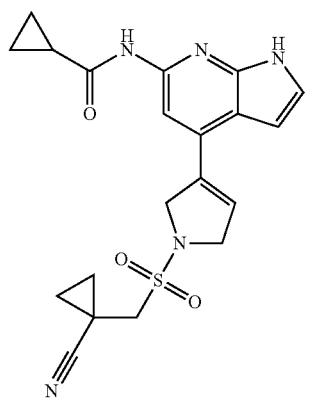 [SMILES: N#CC1(CS(=O)(=O)N2CC=C(c3cc(NC(=O)C4CC4)nc4[nH]ccc34)C2)CC1]

¹H NMR (400 MHz, DMSO-d₆) δ 11.58 (s, 1H), 10.62 (s, 1H), 7.83 (s, 1H), 7.52-7.35 (m, 1H), 6.75-6.65 (m, 2H), 4.64 (dd, J=3.1, 6.2 Hz, 2H), 4.46 (q, J=3.2, 3.7 Hz, 2H), 3.61 (s, 2H), 2.02 (td, J=4.0, 7.6 Hz, 1H), 1.40 (q, J=4.3, 4.7 Hz, 2H), 1.22 (q, J=4.9 Hz, 2H), 0.89-0.73 (m, 4H).
MS(ESI+) m/z 412 (M+H)⁺

Example 214: Synthesis of N-(4-(4-(morpholine-4-sulfonamido)phenyl)-1H-pyrrolo[2,3-b]pyridin-6-yl)cyclopropanecarboxamide

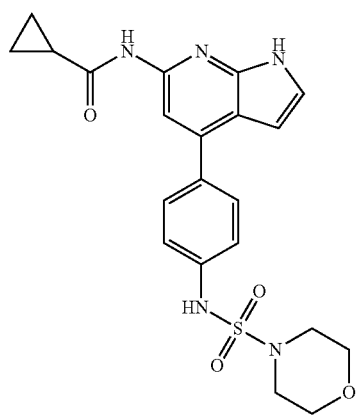 [SMILES: O=C(Nc1cc(-c2ccc(NS(=O)(=O)N3CCOCC3)cc2)c2cc[nH]c2n1)C1CC1]

A starting material, i.e., N-(4-(4-aminophenyl)-1-tosyl-1H-pyrrolo[2,3-b]pyridine-6-yl)cyclopropanecarboxamide (100 mg) was stirred in 1 mL of pyridine. 1.5 equivalent of morpholine-4-sulfonylchloride was inserted thereinto and stirred at 40° C. for 16 hours. Once the reaction was completed, d-HCl was added to the said mixture, then an extraction using dichloromethane was performed, and then an organic layer was accordingly separated. After concentrating the mixture, the resulting concentrate was dissolved in MeOH/THF (1:1) solution, and then 2N sodium hydroxide aqueous solution was added thereto and stirred at 30° C. for 12 hours. Once the reaction was completed, the said mixture was cooled down to room temperature, and saturated $NH_4C$ aqueous solution was added thereto while being stirred. A produced solid was filtered out, and finally a product, i.e., N-(4-(4-(morpholine-4-sulfonamido)phenyl)-1H-pyrrolo[2,3-b]pyridin-6-yl)cyclopropanecarboxamide was accordingly obtained.

$^1$H NMR (400 MHz, DMSO-$d_6$) δ 11.53 (s, 1H), 10.69 (s, 1H), 10.24 (s, 1H), 7.97 (d, J=5.7 Hz, 1H), 7.69 (d, J=7.6 Hz, 2H), 7.47 (d, J=8.2 Hz, 1H), 7.43-7.33 (m, 33H), 7.11 (d, J=7.8 Hz, 1H), 6.62-6.51 (m, 1H), 3.63-3.50 (m, 5H), 3.18-3.06 (m, 5H), 2.05 (d, J=8.9 Hz, 1H), 0.88-0.77 (m, 4H)

MS(ESI+) m/z 442 (M+H)$^+$

Examples 215 to 238

Hereinafter, in Examples 215 to 238, a corresponding compound was synthesized by means of the same method as shown in Example 214 or by means of an appropriate reactant under the consideration of the reaction formula 1 as well as a structure of the compound to be prepared.

Example 215: Synthesis of N-(4-(4-((N-ethyl-N-methylsulfamoyl)amino)phenyl)-1H-pyrrolo[2,3-b]pyridin-6-yl)cyclopropanecarboxamide

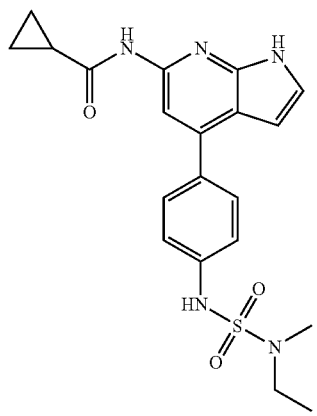 [SMILES: CCN(C)S(=O)(=O)Nc1ccc(-c2cc(NC(=O)C3CC3)nc3[nH]ccc23)cc1]

$^1$H NMR (400 MHz, DMSO-$d_6$) δ 11.50 (s, 1H), 10.59 (s, 1H), 10.07 (s, 1H), 7.99 (s, 1H), 7.71-7.60 (m, 2H), 7.43-7.35 (m, 1H), 7.31 (d, J=8.5 Hz, 2H), 6.58-6.48 (m, 1H), 3.18 (q, J=7.2 Hz, 2H), 2.74 (s, 3H), 2.04 (s, 1H), 1.04 (t, J=7.0 Hz, 3H), 0.88-0.74 (m, 4H).

MS(ESI+) m/z 414 (M+H)$^+$

Example 216: Synthesis of N-(4-(4-((N,N-diethylsulfamoyl)amino)phenyl)-1H-pyrrolo[2,3-b]pyridin-6-yl)cyclopropanecarboxamide

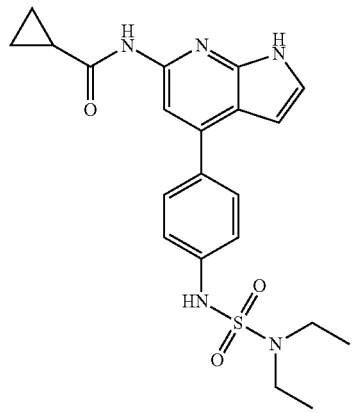 [SMILES: CCN(CC)S(=O)(=O)Nc1ccc(-c2cc(NC(=O)C3CC3)nc3[nH]ccc23)cc1]

$^1$H NMR (400 MHz, DMSO-$d_6$) δ 11.49 (s, 1H), 10.59 (s, 1H), 10.02 (s, 1H), 7.99 (s, 1H), 7.65 (d, J=8.0 Hz, 2H), 7.44-7.19 (m, 3H), 6.54 (d, J=10.6 Hz, 1H), 3.23 (t, J=6.9 Hz, 4H), 2.04 (s, 1H), 1.01 (t, J=7.2 Hz, 6H), 0.88-0.76 (m, 4H).

MS(ESI+) m/z 428 (M+H)$^+$

Example 217: Synthesis of N-(4-(4-((N-cyclopropyl-N-methylsulfamoyl)amino)phenyl)-1H-pyrrolo[2,3-b]pyridin-6-yl)cyclopropanecarboxamide

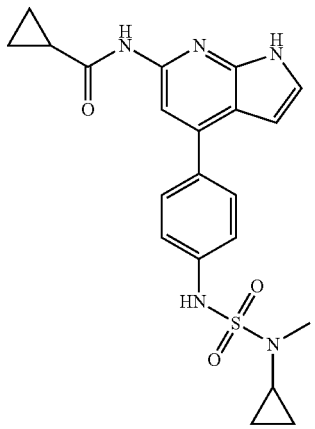 [SMILES: CN(C1CC1)S(=O)(=O)Nc1ccc(-c2cc(NC(=O)C3CC3)nc3[nH]ccc23)cc1]

$^1$H NMR (400 MHz, DMSO-$d_6$) δ 11.49 (s, 1H), 10.59 (s, 1H), 10.26 (s, 1H), 7.98 (s, 1H), 7.65 (d, J=8.1 Hz, 2H), 7.45-7.26 (m, 3H), 6.54 (s, 1H), 2.80 (t, J=5.5 Hz, 3H), 2.34 (s, 1H), 2.04 (s, 1H), 0.88-0.76 (m, 4H), 0.63 (d, J=22.6 Hz, 4H).

MS(ESI+) m/z 426 (M+H)$^+$

Example 218: Synthesis of N-(4-(4-(pyrrolidine-1-sulfonamido)phenyl)-1H-pyrrolo[2,3-b]pyridin-6-yl)cyclopropanecarboxamide

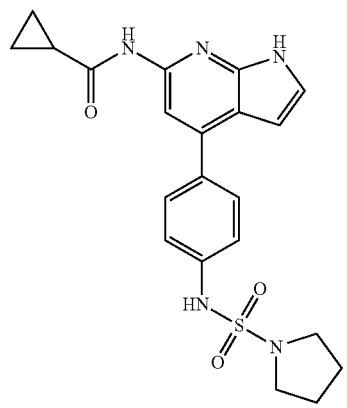 [SMILES: O=C(Nc1cc(-c2ccc(NS(=O)(=O)N3CCCC3)cc2)c2cc[nH]c2n1)C1CC1]

MS(ESI+) m/z 426 (M+H)$^+$

Example 219: Synthesis of N-(4-(4-(piperidine-1-sulfonamido)phenyl)-1H-pyrrolo[2,3-b]pyridin-6-yl)cyclopropanecarboxamide

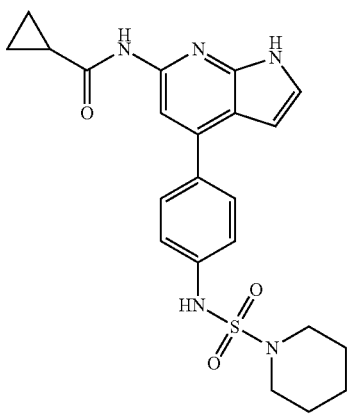

MS(ESI+) m/z 440 (M+H)$^+$

Example 220: Synthesis of N-(4-(4-((2,6-dimethyl-morpholine)-4-sulfonamido)phenyl)-1H-pyrrolo[2,3-b]pyridin-6-yl)cyclopropanecarboxamide

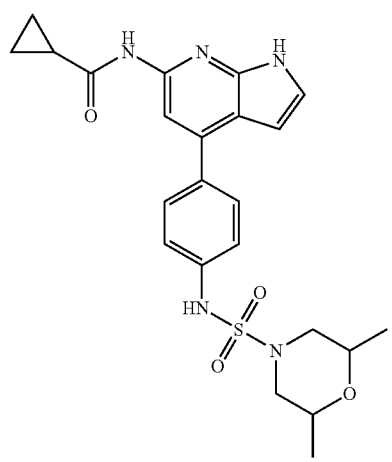 [SMILES: CC1CN(S(=O)(=O)Nc2ccc(-c3cc(NC(=O)C4CC4)nc4[nH]ccc34)cc2)CC(C)O1]

MS(ESI+) m/z 470 (M+H)$^+$

Example 221: Synthesis of N-(4-(4-((3-cyanoazetidine)-1-sulfonamido)phenyl)-1H-pyrrolo[2,3-b]pyridin-6-yl)cyclopropanecarboxamide

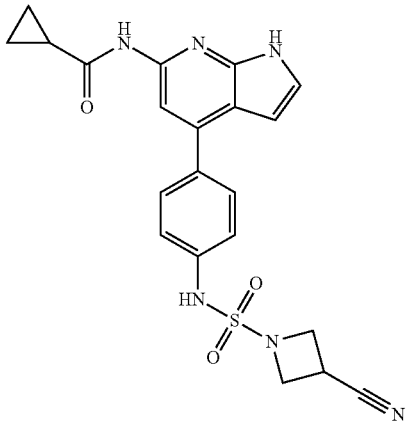 [SMILES: N#CC1CN(S(=O)(=O)Nc2ccc(-c3cc(NC(=O)C4CC4)nc4[nH]ccc34)cc2)C1]

MS(ESI+) m/z 437 (M+H)$^+$

Example 222: Synthesis of N-(4-(4-((N-isopropyl-N-methylsulfamoyl)amino)phenyl)-1H-pyrrolo[2,3-b]pyridin-6-yl)cyclopropanecarboxamide

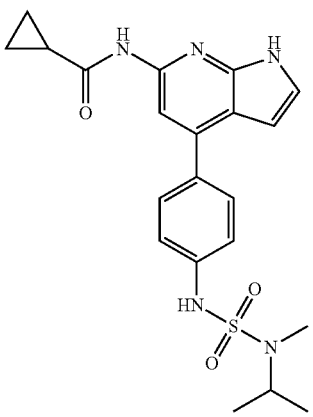

¹H NMR (400 MHz, DMSO-d₆) δ 11.49 (s, 1H), 10.58 (s, 1H), 10.06 (s, 1H), 7.98 (s, 1H), 7.65 (d, J=7.9 Hz, 2H), 7.38 (s, 1H), 7.26 (d, J=9.5 Hz, 2H), 6.52 (s, 1H), 4.03 (s, 1H), 2.65 (t, J=5.8 Hz, 3H), 2.04 (s, 1H), 1.03-0.95 (m, 6H), 0.81 (s, 4H).

MS(ESI+) m/z 428 (M+H)⁺

Example 223: Synthesis of N-(4-(4-((N-(2-methoxyethyl)-N-methylsulfamoyl)amino)phenyl)-1H-pyrrolo[2,3-b]pyridin-6-yl)cyclopropanecarboxamide

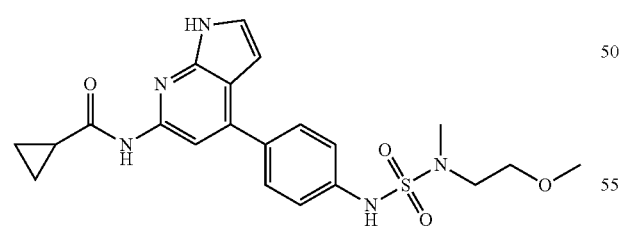

¹H NMR (400 MHz, DMSO-d₆) δ 11.50 (s, 1H), 10.59 (s, 1H), 10.07 (s, 1H), 7.99 (s, 1H), 7.66 (d, J=9.1 Hz, 2H), 7.35 (t, J=14.4 Hz, 3H), 6.53 (s, 1H), 3.41 (s, 2H), 3.19 (q, J=5.6, 6.3 Hz, 3H), 2.81 (t, J=5.9 Hz, 3H), 2.04 (s, 1H), 0.90-0.73 (m, 4H).

MS(ESI+) m/z 444 (M+H)⁺

Example 224: Synthesis of N-(4-(3-fluoro-4-(piperidine-1-sulfonamido)phenyl)-1H-pyrrolo[2,3-b]pyridin-6-yl)cyclopropanecarboxamide

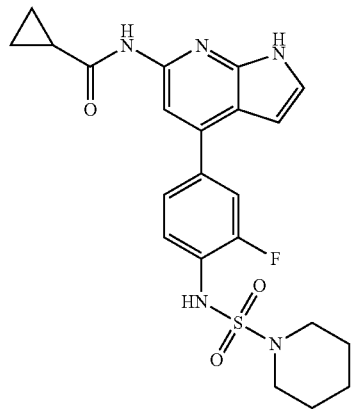 [SMILES: O=C(Nc1cc(-c2ccc(NS(=O)(=O)N3CCCCC3)c(F)c2)c2cc[nH]c2n1)C1CC1]

¹H NMR (400 MHz, DMSO-d₆) δ 11.60 (s, 1H), 10.68 (s, 1H), 9.85 (s, 1H), 8.02 (s, 1H), 7.61 (t, J=8.2 Hz, 1H), 7.54 (d, J=9.9 Hz, 2H), 7.43 (t, J=3.0 Hz, 1H), 6.58-6.54 (m, 1H), 3.12 (d, J=6.2 Hz, 4H), 2.04 (s, 1H), 1.47 (d, J=20.7 Hz, 6H), 0.85-0.78 (m, 4H).

MS(ESI+) m/z 458 (M+H)⁺

Example 225: Synthesis of N-(4-(3-fluoro-4-(pyrrolidine-1-sulfonamido)phenyl)-1H-pyrrolo[2,3-b]pyridin-6-yl)cyclopropanecarboxamide

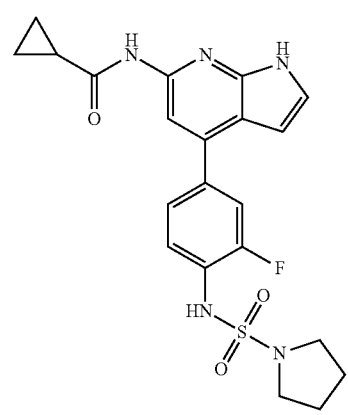 [SMILES: O=C(Nc1cc(-c2ccc(NS(=O)(=O)N3CCCC3)c(F)c2)c2cc[nH]c2n1)C1CC1]

¹H NMR (400 MHz, DMSO-d₆) δ 11.60 (s, 1H), 10.67 (s, 1H), 9.81 (s, 1H), 8.01 (s, 1H), 7.62 (t, J=8.3 Hz, 1H), 7.53 (d, J=8.4 Hz, 2H), 7.43 (t, J=3.0 Hz, 1H), 6.55 (dd, J=3.6, 1.9 Hz, 1H), 3.21 (d, J=6.0 Hz, 4H), 2.04 (s, 1H), 1.83-1.72 (m, 4H), 0.90-0.70 (m, 4H).

MS(ESI+) m/z 444 (M+H)⁺

Example 226: Synthesis of N-(4-(3-fluoro-4-(morpholine-4-sulfonamido)phenyl)-1H-pyrrolo[2,3-b]pyridin-6-yl)cyclopropanecarboxamide

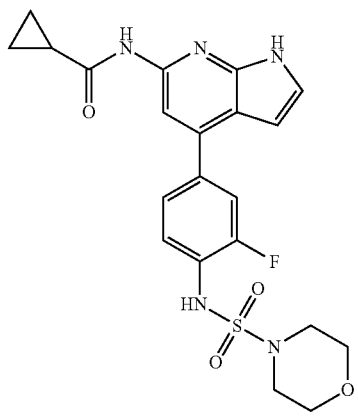 [SMILES: O=C(Nc1cc(-c2ccc(NS(=O)(=O)N3CCOCC3)c(F)c2)c2cc[nH]c2n1)C1CC1]

$^1$H NMR (400 MHz, DMSO-d$_6$) δ 11.61 (s, 1H), 10.69 (s, 1H), 10.02 (s, 1H), 8.03 (s, 1H), 7.63 (t, J=8.4 Hz, 1H), 7.60-7.52 (m, 2H), 7.44 (t, J=3.0 Hz, 1H), 6.56 (dd, J=3.6, 1.9 Hz, 1H), 3.60 (t, J=4.7 Hz, 4H), 3.10 (t, J=4.7 Hz, 4H), 2.04 (s, 1H), 0.90-0.68 (m, 4H).
MS(ESI+) m/z 460 (M+H)$^+$

Example 227: Synthesis of N-(4-(2-methyl-4-((N-(2,2,2-trifluoroethyl)sulfamoyl)amino)phenyl)-1H-pyrrolo[2,3-b]pyridin-6-yl)cyclopropanecarboxamide

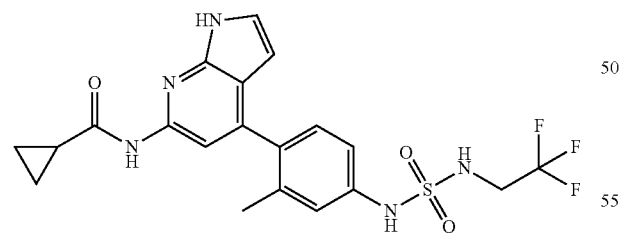

$^1$H NMR (400 MHz, DMSO-d$_6$) δ 11.59-11.42 (m, 1H), 10.63 (s, 1H), 7.76 (s, 1H), 7.38-7.26 (m, 1H), 7.21 (d, J=8.1 Hz, 1H), 7.15 (d, J=2.2 Hz, 1H), 7.09 (dd, J=2.4, 8.3 Hz, 1H), 6.07 (dd, J=1.9, 3.5 Hz, 1H), 3.70 (q, J=9.6 Hz, 2H), 2.14 (s, 3H), 2.04 (d, J=7.2 Hz, 1H), 0.82-0.75 (m, 4H).
MS(ESI+) m/z 468 (M+H)$^+$

Example 228: Synthesis of N-(4-(2-methyl-4-((N-methyl-N-(2,2,2-trifluoroethyl)sulfamoyl)amino)phenyl)-1H-pyrrolo[2,3-b]pyridin-6-yl)cyclopropanecarboxamide

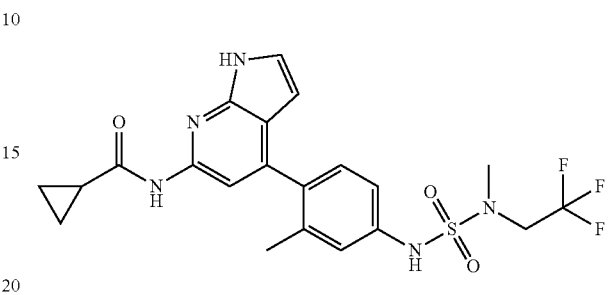

$^1$H NMR (400 MHz, DMSO-d$_6$) δ 11.50 (d, J=6.3 Hz, 1H), 10.64 (s, 1H), 7.77 (s, 1H), 7.34 (d, J=3.7 Hz, 1H), 7.23 (d, J=8.0 Hz, 1H), 7.17-7.07 (m, 2H), 6.09-6.04 (m, 1H), 4.06 (d, J=10.1 Hz, 2H), 2.92-2.85 (m, 3H), 2.14 (s, 3H), 2.04 (s, 1H), 0.82-0.75 (m, 4H).
MS(ESI+) m/z 482 (M+H)$^+$

Example 229: Synthesis of N-(4-(4-((1,1-dioxidothiomorpholine)-4-sulfonamido)phenyl)-1H-pyrrolo[2,3-b]pyridin-6-yl)cyclopropanecarboxamide

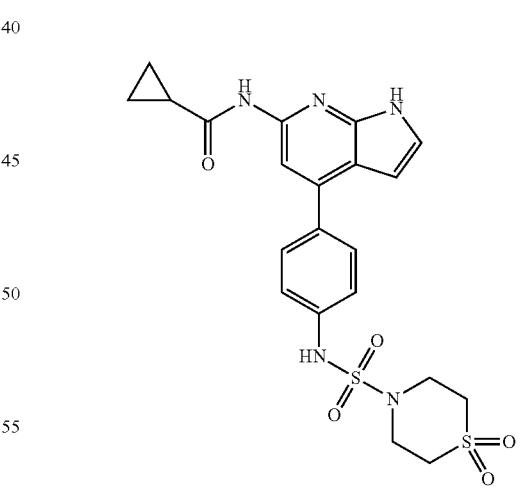

$^1$H NMR (400 MHz, DMSO-d$_6$) δ 11.52 (s, 1H), 10.61 (s, 1H), 10.39 (s, 1H), 8.01 (s, 1H), 7.71 (d, J=8.3 Hz, 2H), 7.38 (t, J=6.7 Hz, 3H), 6.58-6.50 (m, 1H), 3.66 (d, J=5.5 Hz, 4H), 3.16 (d, J=5.3 Hz, 4H), 2.04 (s, 1H), 0.85-0.76 (m, 4H).
MS(ESI+) m/z 490 (M+H)$^+$

Example 230: Synthesis of N-(4-(4-((4-(methyl-sulfonyl)piperazine)-1-sulfonamido)phenyl)-1H-pyrrolo[2,3-b]pyridin-6-yl)cyclopropanecarboxamide

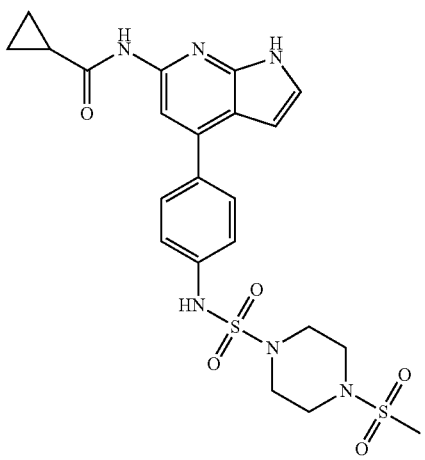 [SMILES: CS(=O)(=O)N1CCN(S(=O)(=O)Nc2ccc(-c3cc(NC(=O)C4CC4)nc4[nH]ccc34)cc2)CC1]

¹H NMR (400 MHz, DMSO-d$_6$) δ 11.51 (s, 1H), 10.61 (s, 1H), 10.30 (s, 1H), 8.00 (s, 1H), 7.69 (d, J=8.3 Hz, 2H), 7.42-7.34 (m, 3H), 6.54 (d, J=2.9 Hz, 1H), 3.26 (t, J=4.8 Hz, 4H), 3.13 (d, J=5.5 Hz, 4H), 2.85 (s, 3H), 2.04 (s, 1H), 0.85-0.77 (m, 4H).

MS(ESI+) m/z 519 (M+H)⁺

Example 231: Synthesis of N-(4-(4-(morpholine-4-sulfonamido)cyclohex-1-en-1-yl)-1H-pyrrolo[2,3-b]pyridin-6-yl)cyclopropanecarboxamide

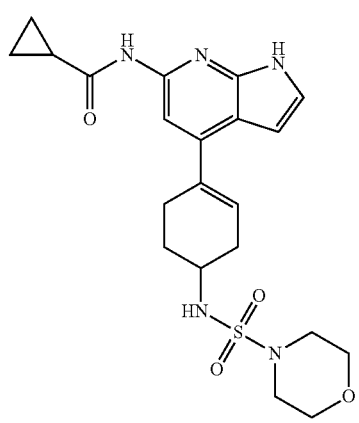 [SMILES: O=C(Nc1cc(C2=CCC(NS(=O)(=O)N3CCOCC3)CC2)c2cc[nH]c2n1)C1CC1]

¹H NMR (400 MHz, DMSO-d$_6$) δ 11.39 (s, 1H), 10.52 (s, 1H), 7.83 (d, J=3.1 Hz, 1H), 7.31 (s, 1H), 6.51 (s, 1H), 6.19 (d, J=4.1 Hz, 1H), 3.66 (d, J=4.7 Hz, 4H), 3.06-2.99 (m, 4H), 2.58 (d, J=22.0 Hz, 4H), 2.25 (d, J=14.2 Hz, 1H), 2.01 (d, J=12.6 Hz, 2H), 1.70 (s, 1H), 0.84-0.76 (m, 4H).

MS(ESI+) m/z 446 (M+H)⁺

Example 232: Synthesis of N-(4-(1-(N-(2,2,2-trifluoroethyl)sulfamoyl)-1,2,3,6-tetrahydropyridin-4-yl)-1H-pyrrolo[2,3-b]pyridin-6-yl)cyclopropanecarboxamide

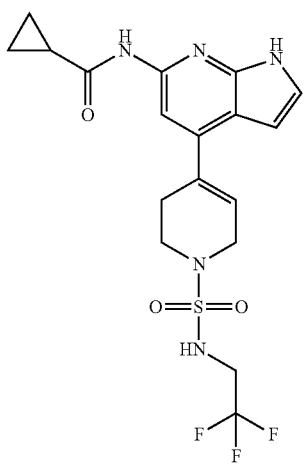 [SMILES: O=C(Nc1cc(C2=CCN(S(=O)(=O)NCC(F)(F)F)CC2)c2cc[nH]c2n1)C1CC1]

¹H NMR (400 MHz, DMSO-d$_6$) δ 11.45 (s, 1H), 10.55 (s, 1H), 8.10 (s, 1H), 7.87 (s, 1H), 7.41-7.29 (m, 1H), 6.57 (s, 1H), 6.36 (s, 1H), 3.89 (s, 2H), 3.79 (d, J=10.4 Hz, 2H), 2.64 (s, 2H), 2.07-1.97 (m, 1H), 0.79 (d, J=12.6 Hz, 4H).

MS(ESI+) m/z 444 (M+H)⁺

Example 233: Synthesis of N-(4-(1-(N-methyl-N-(2,2,2-trifluoroethyl)sulfamoyl)-1,2,3,6-tetrahydropyridin-4-yl)-1H-pyrrolo[2,3-b]pyridin-6-yl)cyclopropanecarboxamide

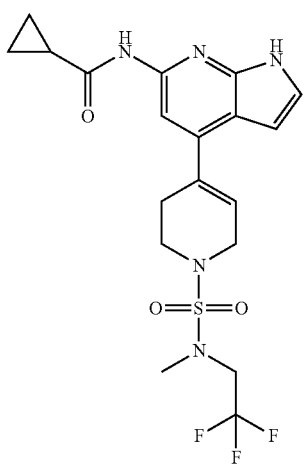 [SMILES: CN(CC(F)(F)F)S(=O)(=O)N1CC=C(c2cc(NC(=O)C3CC3)nc3[nH]ccc23)CC1]

¹H NMR (400 MHz, DMSO-d$_6$) δ 11.46 (s, 1H), 10.55 (s, 1H), 7.87 (d, J=3.8 Hz, 1H), 7.36 (s, 1H), 6.56 (s, 1H), 6.35 (s, 1H), 4.11 (d, J=10.7 Hz, 2H), 3.96 (s, 2H), 3.48 (s, 4H), 2.93 (d, J=3.8 Hz, 2H), 2.63 (s, 2H), 2.02 (s, 1H), 0.79 (d, J=12.0 Hz, 4H).

MS(ESI+) m/z 458 (M+H)⁺

Example 234: Synthesis of N-(4-(1-(morpholino-sulfonyl)-1,2,3,6-tetrahydropyridin-4-yl)-1H-pyrrolo[2,3-b]pyridin-6-yl)cyclopropanecarboxamide

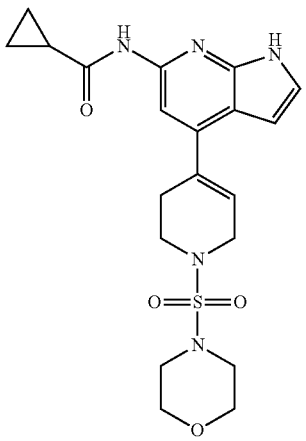 [SMILES: O=C(Nc1cc(C2=CCN(S(=O)(=O)N3CCOCC3)CC2)c2cc[nH]c2n1)C1CC1]

MS(ESI+) m/z 432 (M+H)+

Example 235: Synthesis of N-(4-(4-(morpholine-4-sulfonamido)phenyl)-7H-pyrrolo[2,3-d]pyrimidin-2-yl)cyclopropanecarboxamide

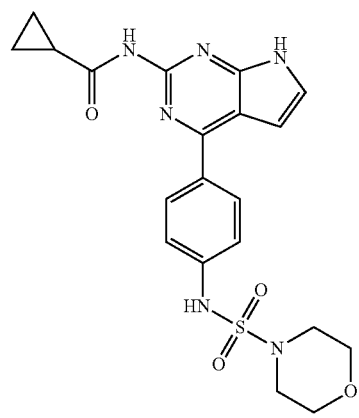 [SMILES: O=C(Nc1nc(-c2ccc(NS(=O)(=O)N3CCOCC3)cc2)c2cc[nH]c2n1)C1CC1]

MS(ESI+) m/z 443 (M+H)+

Example 236: Synthesis of N-(4-(4-((N,N-dimethylsulfamoyl)amino)phenyl)-7H-pyrrolo[2,3-d]pyrimidin-2-yl)cyclopropanecarboxamide

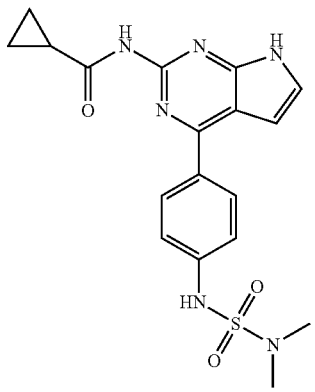 [SMILES: CN(C)S(=O)(=O)Nc1ccc(-c2nc(NC(=O)C3CC3)nc3[nH]ccc23)cc1]

MS(ESI+) m/z 401 (M+H)+

Example 237: Synthesis of N-(4-(4-((2,6-dimethylmorpholine)-4-sulfonamido)phenyl)-7H-pyrrolo[2,3-d]pyrimidin-2-yl)cyclopropanecarboxamide

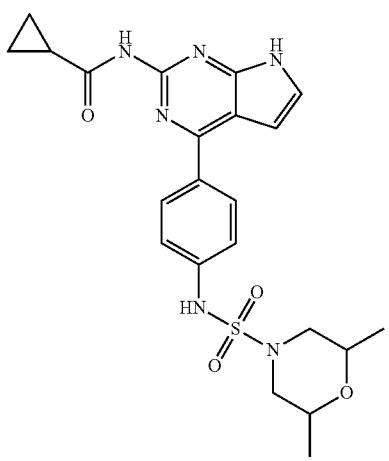 [SMILES: CC1CN(S(=O)(=O)Nc2ccc(-c3nc(NC(=O)C4CC4)nc4[nH]ccc34)cc2)CC(C)O1]

$^1$H NMR (400 MHz, DMSO-d$_6$) δ 12.01 (s, 1H), 10.56 (s, 1H), 10.30 (s, 1H), 8.19-8.13 (m, 2H), 7.51-7.45 (m, 2H), 7.38 (dd, J=2.1, 9.1 Hz, 2H), 6.84 (dd, J=1.8, 3.7 Hz, 1H), 3.53-3.45 (m, 4H), 2.41 (d, J=14.6 Hz, 2H), 2.19 (d, J=9.7 Hz, 1H), 1.06 (dd, J=2.9, 6.4 Hz, 6H), 0.89-0.75 (m, 4H).

MS(ESI+) m/z 471 (M+H)+

Example 238: Synthesis of N-(6-(4-(morpholine-4-sulfonamido)phenyl)-9H-purin-2-yl)cyclopropanecarboxamide

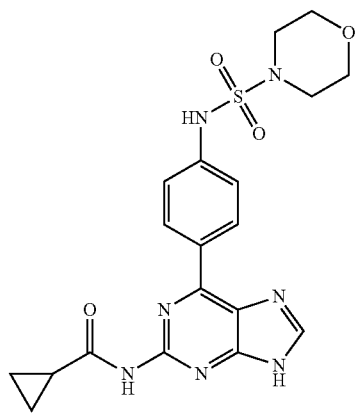 [SMILES: O=C(Nc1nc(-c2ccc(NS(=O)(=O)N3CCOCC3)cc2)c2nc[nH]c2n1)C1CC1]

¹H NMR (400 MHz, DMSO-d₆) δ 10.74 (s, 1H), 10.39 (s, 1H), 8.77 (d, J=8.5 Hz, 2H), 8.47 (s, 1H), 7.39 (d, J=8.4 Hz, 2H), 3.55 (t, J=4.8 Hz, 4H), 3.13 (t, J=4.7 Hz, 4H), 2.18 (dd, J=8.7, 4.3 Hz, 1H), 0.90-0.77 (m, 4H).
MS(ESI+) m/z 444 (M+H)⁺

Example 239: Synthesis of N-(4-(4-(2-cyanoacetamido)phenyl)-1H-pyrrolo[2,3-b]pyridine-6-yl)cyclopropanecarboxamide

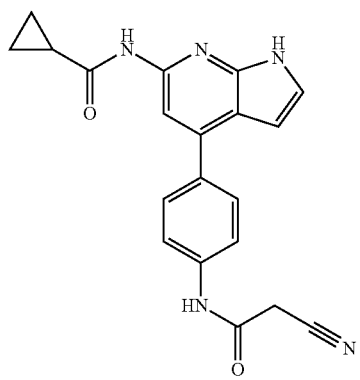 [SMILES: N#CCC(=O)Nc1ccc(-c2cc(NC(=O)C3CC3)nc3[nH]ccc23)cc1]

1.2 equivalent of 2-cyanoacetic acid was inserted into dichloromethane solution, and 1.6 equivalent of EDCI was added thereto. 1.4 equivalent of HOBt, 1.1 equivalent of DMAP and the synthesized N-(4-(4-aminophenyl)-1H-pyrrolo[2,3-b]pyridine-6-yl)cyclopropanecarboxamide (100 mg) were inserted into the mixture and stirred at room temperature. Once the reaction was completed, H₂O was added to the said mixture, then an extraction using dichloromethane was performed, and then an organic layer was accordingly separated. After concentrating the mixture, the resulting concentrate was separated via column chromatography, and finally a product. i.e., N-(4-(4-(4-(2-cyanoacetamino)phenyl)-1H-pyrrolo[2,3-b]pyridine-6-yl)cyclopropanecarboxamide was accordingly obtained.
¹H NMR (400 MHz, DMSO-d₆) δ 11.52 (s, 1H), 10.61 (s, 1H), 10.50 (s, 1H), 8.19 (d, J=6.7 Hz, 2H), 8.02 (s, 1H), 7.40 (s, 1H), 6.89 (d, J=6.8 Hz, 2H), 6.56 (s, 1H), 3.13 (s, 2H), 0.81 (d, J=6.6 Hz, 4H)
MS(ESI+) m/z 360 (M+H)⁺

Examples 240 to 430

Hereinafter, in Examples 240 to 430, a corresponding compound was synthesized by means of the same method as shown in Example 239 or by means of an appropriate reactant under the consideration of the reaction formula 1 as well as a structure of the compound to be prepared.

Example 240: Synthesis of N-(4-(4-(2-cyanoacetamido)-2-methylphenyl)-1H-pyrrolo[2,3-b]pyridin-6-yl)cyclopropanecarboxamide

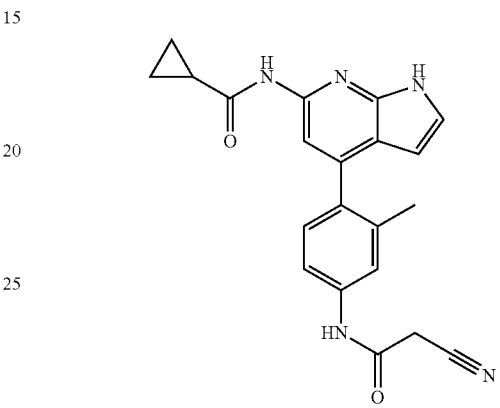

¹H NMR (400 MHz, DMSO-d₆) δ 11.48 (s, 1H), 10.62 (s, 1H), 10.41 (s, 1H), 7.78 (s, 1H), 7.54 (s, 1H), 7.49 (d, J=8.5 Hz, 1H), 7.33 (t, J=2.9 Hz, 1H), 7.25 (d, J=8.2 Hz, 1H), 6.07 (dd, J=3.4, 1.8 Hz, 1H), 3.93 (s, 2H), 2.15 (s, 3H), 2.03 (s, 1H), 0.84-0.75 (m, 4H).
MS(ESI+) m/z 374 (M+H)⁺

Example 241: Synthesis of N-(4-(4-(2-(1-cyanocyclopropyl)acetamido)phenyl)-1H-pyrrolo[2,3-b]pyridin-6-yl)cyclopropanecarboxamide

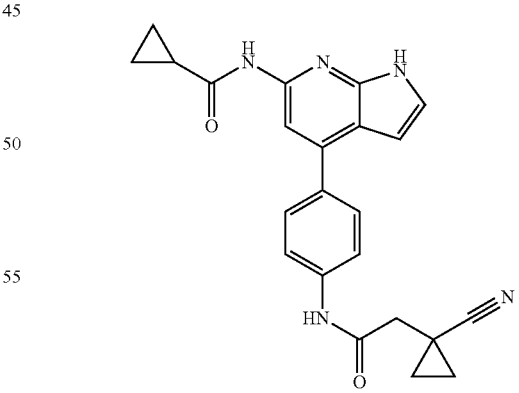

¹H NMR (400 MHz, DMSO-d₆) δ 11.51 (s, 1H), 10.60 (s, 1H), 10.19 (s, 1H), 8.10 (d, J=6.2 Hz, 1H), 7.78 (d, J=8.5 Hz, 2H), 7.69 (d, J=8.4 Hz, 2H), 7.40 (t, J=3.0 Hz, 1H), 6.56 (t, J=2.5 Hz, 1H), 2.05 (s, 1H), 1.28 (t, J=3.8 Hz, 2H), 1.06 (q, J=5.1 Hz, 2H), 0.88-0.79 (m, 4H).
MS(ESI+) m/z 400 (M+H)⁺

Example 242: Synthesis of N-(4-(4-propionamido-cyclohex-1-en-1-yl)-1H-pyrrolo[2,3-b]pyridin-6-yl) cyclopropanecarboxamide

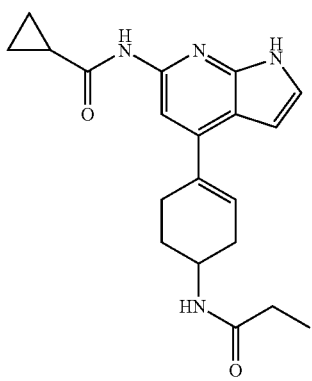 [SMILES: CCC(=O)NC1CC=C(c2cc(NC(=O)C3CC3)nc3[nH]ccc23)CC1]

$^1$H NMR (400 MHz, DMSO-d$_6$) δ 11.38 (s, 1H), 10.52 (s, 1H), 7.89-7.74 (m, 2H), 7.31 (dd, J=2.5, 3.5 Hz, 1H), 6.51 (dd, J=1.8, 3.5 Hz, 1H), 6.26-6.18 (m, 1H), 3.90 (s, 1H), 2.14 (d, J=13.0 Hz, 1H), 2.08 (t, J=7.6 Hz, 2H), 2.05-1.88 (m, 2H), 1.69-1.58 (m, 1H), 1.01 (t, J=7.6 Hz, 3H), 0.84-0.76 (m, 4H).

MS(ESI+) m/z 353 (M+H)$^+$

Example 243: Synthesis of N-(4-(6-(cyclopropan-ecarboxamido)-1H-pyrrolo[2,3-b]pyridin-4-yl)cyclo-hex-3-en-1-yl)benzamide

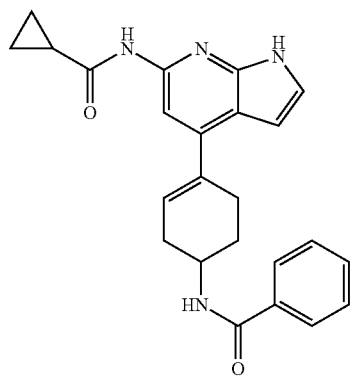 [SMILES: O=C(NC1CC=C(c2cc(NC(=O)C3CC3)nc3[nH]ccc23)CC1)c1ccccc1]

$^1$H NMR (400 MHz, DMSO-d$_6$) δ 11.40 (s, 1H), 10.53 (s, 1H), 8.40 (d, J=7.7 Hz, 1H), 7.88 (dt, J=1.6, 7.1 Hz, 3H), 7.56-7.43 (m, 3H), 7.32 (dd, J=2.4, 3.5 Hz, 1H), 6.54 (dd, J=1.8, 3.6 Hz, 1H), 6.32-6.22 (m, 1H), 4.15 (d, J=3.5 Hz, 1H), 2.71-2.54 (m, 4H), 2.41-2.29 (m, 1H), 2.04 (d, J=13.0 Hz, 2H), 1.81 (tq, J=5.6, 11.8 Hz, 1H), 0.85-0.74 (m, 4H).

MS(ESI+) m/z 401 (M+H)$^+$

Example 244: Synthesis of N-(4-(6-(cyclopropan-ecarboxamido)-1H-pyrrolo[2,3-b]pyridin-4-yl)cyclo-hex-3-en-1-yl)-2-methylcyclopropane-1-carboxam-ide

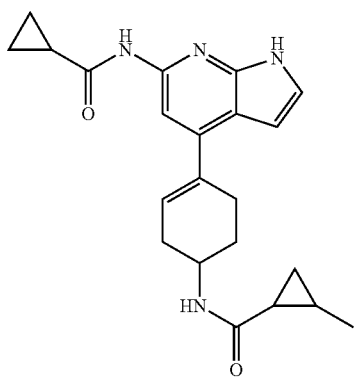 [SMILES: CC1CC1C(=O)NC1CC=C(c2cc(NC(=O)C3CC3)nc3[nH]ccc23)CC1]

MS(ESI+) m/z 379 (M+H)$^+$

Example 245: Synthesis of N-(4-(6-(cyclopropan-ecarboxamido)-1H-pyrrolo[2,3-b]pyridin-4-yl)cyclo-hex-3-en-1-yl)cyclopentanecarboxamide

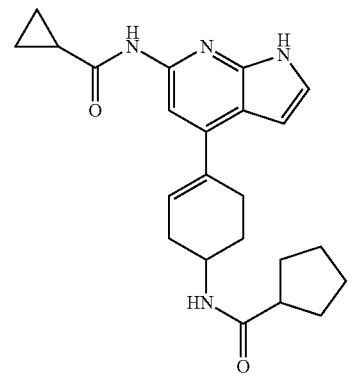 [SMILES: O=C(Nc1cc(C2=CCC(NC(=O)C3CCCC3)CC2)c2cc[nH]c2n1)C1CC1]

MS(ESI+) m/z 393 (M+H)$^+$

Example 246: Synthesis of N-(4-(6-(cyclopropanecarboxamido)-1H-pyrrolo[2,3-b]pyridin-4-yl)cyclohex-3-en-1-yl)cyclopropanecarboxamide

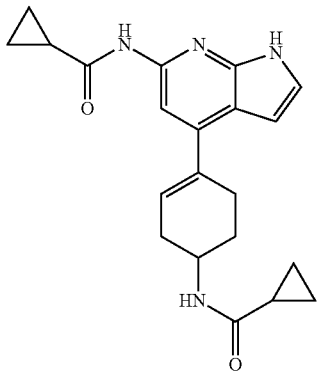 [SMILES: O=C(Nc1cc(C2=CCC(NC(=O)C3CC3)CC2)c2cc[nH]c2n1)C1CC1]

¹H NMR (400 MHz, DMSO-d₆) δ 11.38 (s, 1H), 10.51 (s, 1H), 8.13 (d, J=7.5 Hz, 1H), 7.84 (s, 1H), 7.31 (d, J=3.5 Hz, 1H), 6.52 (d, J=3.5 Hz, 1H), 6.24 (d, J=4.5 Hz, 1H), 3.92 (s, 1H), 2.60-2.54 (m, 2H), 2.20-2.09 (m, 1H), 2.00 (d, J=5.0 Hz, 1H), 1.94 (d, J=12.3 Hz, 1H), 1.70-1.54 (m, 2H), 0.82-0.74 (m, 4H), 0.71-0.59 (m, 4H).

MS(ESI+) m/z 365 (M+H)⁺

Example 247: Synthesis of N-(4-(4-(2-cyanoacetamido)cyclohex-1-en-1-yl)-1H-pyrrolo[2,3-b]pyridin-6-yl)cyclopropanecarboxamide

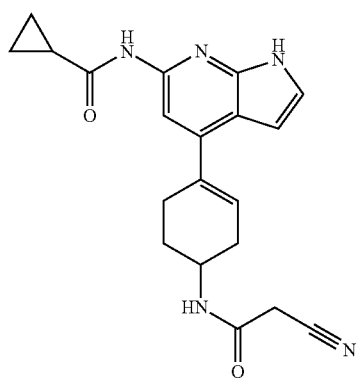 [SMILES: N#CCC(=O)NC1CC=C(c2cc(NC(=O)C3CC3)nc3[nH]ccc23)CC1]

¹H NMR (400 MHz, DMSO-d₆) δ 11.38 (s, 1H), 10.54 (s, 1H), 8.31 (d, J=7.3 Hz, 1H), 7.82 (s, 1H), 7.36-7.26 (m, 1H), 6.53 (dd, J=1.9, 3.6 Hz, 1H), 6.24 (s, 1H), 3.94 (s, 1H), 3.64 (s, 2H), 2.56 (d, J=6.3 Hz, 3H), 2.21-2.09 (m, 1H), 2.05-1.98 (m, 1H), 1.98-1.90 (m, 1H), 1.76-1.65 (m, 1H), 0.87-0.72 (m, 4H).

MS(ESI+) m/z 364 (M+H)⁺

Example 248: Synthesis of N-(4-(4-(4,4,4-trifluorobutanamido)cyclohex-1-en-1-yl)-1H-pyrrolo[2,3-b]pyridin-6-yl)cyclopropanecarboxamide

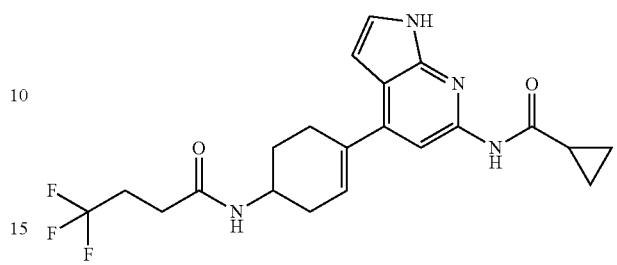

¹H NMR (400 MHz, DMSO-d₆) δ 11.37 (s, 1H), 10.49 (s, 1H), 8.06 (d, J=7.5 Hz, 1H), 7.85 (d, J=7.5 Hz, 1H), 7.31 (q, J=3.0, 3.6 Hz, 1H), 6.52 (dd, J=1.9, 3.6 Hz, 1H), 6.23 (d, J=4.4 Hz, 1H), 3.94 (d, J=10.0 Hz, 1H), 2.92 (d, J=22.6 Hz, 1H), 2.74-2.65 (m, 2H), 2.55 (s, 3H), 2.38 (dd, J=6.4, 8.7 Hz, 2H), 2.18-2.07 (m, 1H), 2.05-1.98 (m, 1H), 1.93 (dd, J=4.9, 12.4 Hz, 1H), 1.67 (q, J=9.7, 12.2 Hz, 1H), 1.25-1.19 (m, 4H), 0.86-0.74 (m, 4H).

MS(ESI+) m/z 421 (M+H)⁺

Example 249: Synthesis of N-(4-(1-(1,1-dioxidotetrahydro-2H-thiopyran-4-carbonyl)-1,2,3,6-tetrahydropyridin-4-yl)-1H-pyrrolo[2,3-b]pyridin-6-yl)cyclopropanecarboxamide

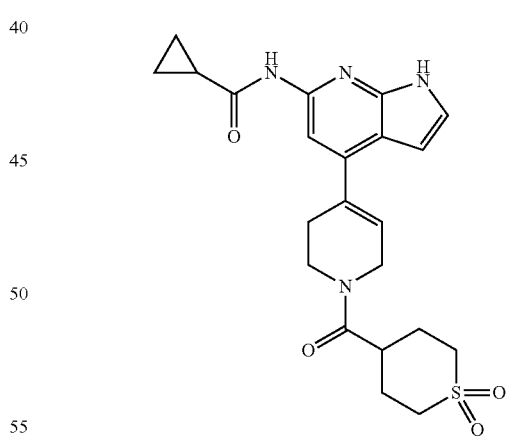

¹H NMR (400 MHz, DMSO-d₆) δ 11.44 (s, 1H), 10.54 (s, 1H), 7.87 (s, 1H), 7.35 (s, 1H), 6.57 (s, 1H), 6.34 (d, J=29.7 Hz, 1H), 4.38-3.97 (m, 3H), 3.75 (d, J=15.9 Hz, 2H), 3.11 (d, J=14.9 Hz, 5H), 2.64 (s, 2H), 2.02 (d, J=20.0 Hz, 6H), 1.26-1.12 (m, 2H), 0.85-0.76 (m, 4H).

MS(ESI+) m/z 443 (M+H)⁺

Example 250: Synthesis of N-(4-(1-(2-cyanoacetyl)-1,2,3,6-tetrahydropyridin-4-yl)-1H-pyrrolo[2,3-b]pyridin-6-yl)cyclopropanecarboxamide

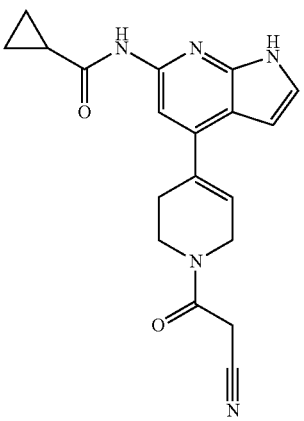 [SMILES: N#CCC(=O)N1CC=C(c2cc(NC(=O)C3CC3)nc3[nH]ccc23)CC1]

$^1$H NMR (400 MHz, Chloroform-d) δ 11.44 (s, 1H), 10.53 (s, 1H), 7.86 (s, 1H), 7.41-7.31 (m, 1H), 6.55 (s, 1H), 6.31 (d, J=25.9 Hz, 1H), 4.26-4.04 (m, 4H), 3.77-3.67 (m, 1H), 3.59 (t, J=5.3 Hz, 1H), 3.17 (s, 1H), 2.65 (s, 1H), 2.02 (s, 1H), 0.84-0.78 (m, 4H).

MS(ESI+) m/z 350 (M+H)$^+$

Example 251: Synthesis of N-(4-(1-(2-(1,1-dioxidothiomorpholino)acetyl)-1,2,3,6-tetrahydropyridin-4-yl)-1H-pyrrolo[2,3-b]pyridin-6-yl)cyclopropanecarboxamide

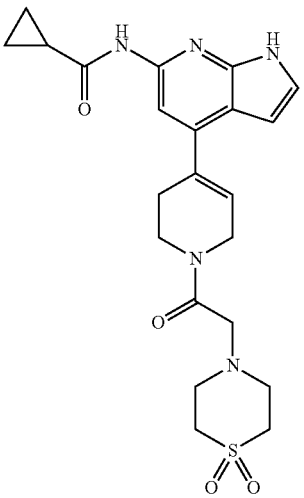 [SMILES: O=C(Nc1cc(C2=CCN(C(=O)CN3CCS(=O)(=O)CC3)CC2)c2cc[nH]c2n1)C1CC1]

$^1$H NMR (400 MHz, DMSO-d$_6$) δ 11.44 (s, 1H), 10.54 (s, 1H), 7.87 (s, 1H), 7.35 (t, J=3.1 Hz, 1H), 6.56 (s, 1H), 6.33 (d, J=24.9 Hz, 1H), 4.51-4.36 (m, 2H), 4.35-4.20 (m, 2H), 4.06-3.93 (m, 1H), 3.86-3.67 (m, 2H), 3.64-3.48 (m, 2H), 3.21 (d, J=14.0 Hz, 2H), 3.08 (d, J=12.0 Hz, 3H), 2.02 (s, 1H), 0.80 (d, J=8.0 Hz, 4H).

MS(ESI+) m/z 458 (M+H)$^+$

Example 252: Synthesis of N-(4-(1-(3-cyanopropanoyl)-1,2,3,6-tetrahydropyridin-4-yl)-1H-pyrrolo[2,3-b]pyridin-6-yl)cyclopropanecarboxamide

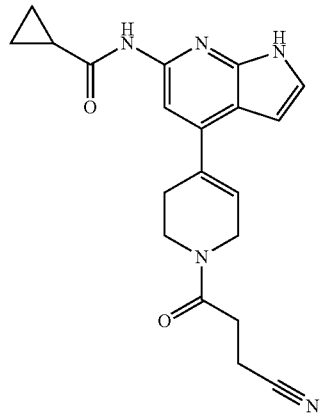 [SMILES: N#CCCC(=O)N1CC=C(c2cc(NC(=O)C3CC3)nc3[nH]ccc23)CC1]

$^1$H NMR (400 MHz, DMSO-d$_6$) δ 11.43 (s, 1H), 10.53 (s, 1H), 7.87 (s, 1H), 7.34 (t, J=3.0 Hz, 1H), 6.59-6.52 (m, 1H), 6.33 (d, J=21.2 Hz, 1H), 4.21 (s, 2H), 3.70 (dt, J=30.9, 5.5 Hz, 2H), 2.82 (dt, J=24.0, 6.8 Hz, 2H), 2.70-2.59 (m, 4H), 2.01 (d, J=6.2 Hz, 1H), 0.86-0.74 (m, 4H).

MS(ESI+) m/z 364 (M+H)$^+$

Example 253: Synthesis of N-(4-(1-(3,3,3-trifluoropropanoyl)-1,2,3,6-tetrahydropyridin-4-yl)-1H-pyrrolo[2,3-b]pyridin-6-yl)cyclopropanecarboxamide

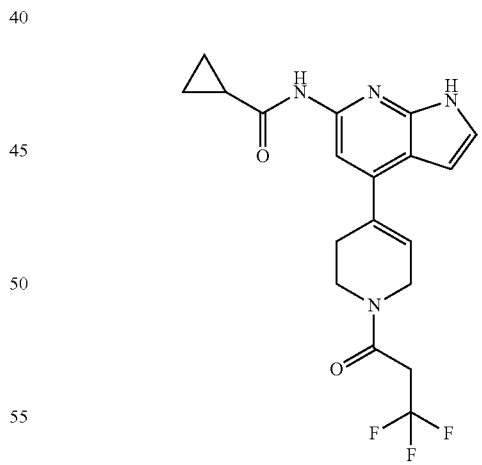

$^1$H NMR (400 MHz, DMSO-d$_6$) δ 11.43 (s, 1H), 10.53 (d, J=3.5 Hz, 1H), 7.86 (s, 1H), 7.34 (s, 1H), 6.55 (s, 1H), 6.31 (d, J=27.5 Hz, 1H), 4.19 (s, 2H), 3.64 (p, J=6.8, 6.0 Hz, 7H), 2.62 (s, 2H), 2.01 (s, 1H), 0.85-0.76 (m, 4H).

MS(ESI+) m/z 393 (M+H)$^+$

Example 254: Synthesis of N-(4-(1-(4,4,4-trifluorobutanoyl)-1,2,3,6-tetrahydropyridin-4-yl)-1H-pyrrolo[2,3-b]pyridin-6-yl)cyclopropanecarboxamide

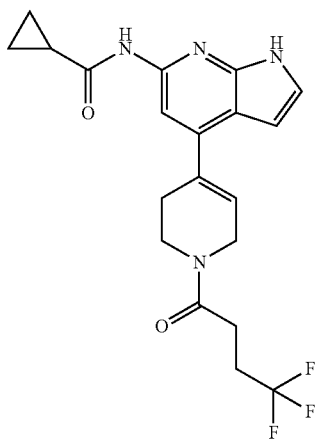 [SMILES: O=C(Nc1cc(C2=CCN(C(=O)CCC(F)(F)F)CC2)c2cc[nH]c2n1)C1CC1]

$^1$H NMR (400 MHz, DMSO-d$_6$) δ 11.43 (s, 1H), 10.52 (s, 1H), 7.85 (s, 1H), 7.34 (s, 1H), 6.55 (s, 1H), 6.34 (s, 1H), 4.19 (d, J=6.5 Hz, 2H), 3.75 (s, 2H), 3.24 (d, J=10.1 Hz, 4H), 2.65 (d, J=27.0 Hz, 2H), 2.00 (s, 1H), 0.78 (d, J=11.5 Hz, 4H).

MS(ESI+) m/z 407 (M+H)$^+$

Example 255: Synthesis of N-(4-(8-(3-cyanopropanoyl)-8-azabicyclo[3.2.1]oct-2-en-3-yl)-1H-pyrrolo[2,3-b]pyridin-6-yl)cyclopropanecarboxamide

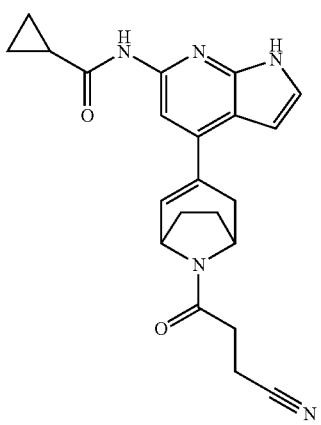 [SMILES: N#CCCC(=O)N1C2C=C(c3cc(NC(=O)C4CC4)nc4[nH]ccc34)CC1CC2]

MS(ESI+) m/z 390 (M+H)$^+$

Example 256: Synthesis of N-(4-(8-(cyclopropanecarbonyl)-8-azabicyclo[3.2.1]oct-2-en-3-yl)-1H-pyrrolo[2,3-b]pyridin-6-yl)cyclopropanecarboxamide

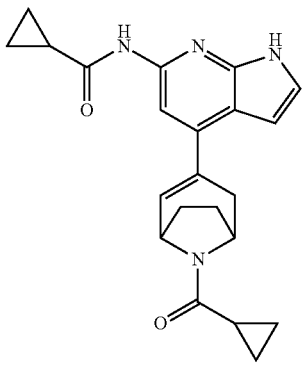 [SMILES: O=C(Nc1cc(C2=CC3CCC(C2)N3C(=O)C2CC2)c2cc[nH]c2n1)C1CC1]

MS(ESI+) m/z 377 (M+H)$^+$

Example 257: Synthesis of N-(4-(8-(2-cyanoacetyl)-8-azabicyclo[3.2.1]oct-2-en-3-yl)-1H-pyrrolo[2,3-b]pyridin-6-yl)cyclopropanecarboxamide

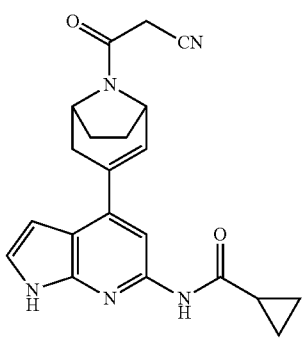 [SMILES: N#CCC(=O)N1C2C=C(c3cc(NC(=O)C4CC4)nc4[nH]ccc34)CC1CC2]

MS(ESI+) m/z 376 (M+H)$^+$

Example 258: Synthesis of N-(4-(8-(4,4,4-trifluorobutanoyl)-8-azabicyclo[3.2.1]oct-2-en-3-yl)-1H-pyrrolo[2,3-b]pyridin-6-yl)cyclopropanecarboxamide

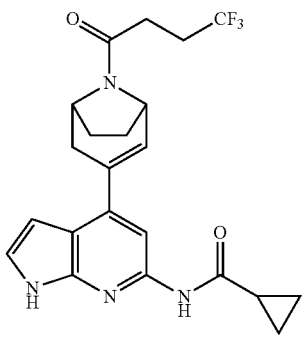 [SMILES: O=C(Nc1cc(C2=CC3CCC(C2)N3C(=O)CCC(F)(F)F)c2cc[nH]c2n1)C1CC1]

MS(ESI+) m/z 433 (M+H)$^+$

Example 259: Synthesis of N-(4-(1-(1-cyanocyclopropane-1-carbonyl)-1,2,3,6-tetrahydropyridin-4-yl)-1H-pyrrolo[2,3-b]pyridin-6-yl)cyclopropanecarboxamide

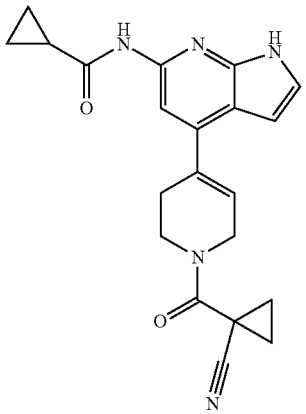 [SMILES: N#CC1(C(=O)N2CC=C(c3cc(NC(=O)C4CC4)nc4[nH]ccc34)CC2)CC1]

MS(ESI+) m/z 376 (M+H)+

Example 260: Synthesis of N-(4-(1-(3,3-difluorocyclobutane-1-carbonyl)-1,2,3,6-tetrahydropyridin-4-yl)-1H-pyrrolo[2,3-b]pyridin-6-yl)cyclopropanecarboxamide

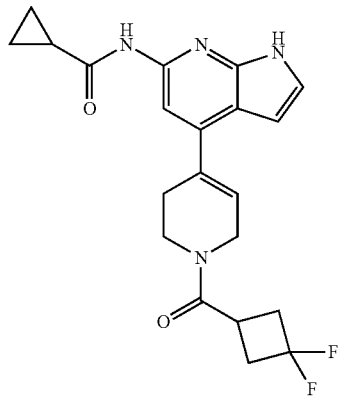 [SMILES: O=C(Nc1cc(C2=CCN(C(=O)C3CC(F)(F)C3)CC2)c2cc[nH]c2n1)C1CC1]

¹H NMR (400 MHz, DMSO-d₆) δ 11.53-11.35 (m, 1H), 10.53 (s, 1H), 7.86 (s, 1H), 7.34 (d, J=2.8 Hz, 1H), 6.63-6.48 (m, 1H), 6.38-6.24 (m, 1H), 4.19 (d, J=8.8 Hz, 2H), 3.68 (dt, J=5.6, 47.7 Hz, 2H), 2.81 (ddt, J=5.7, 11.0, 21.2 Hz, 4H), 2.59 (s, 2H), 2.00 (d, J=14.4 Hz, 1H), 0.85-0.73 (m, 4H)

MS(ESI+) m/z 401 (M+H)+

Example 261: Synthesis of N-(4-(8-(3,3,3-trifluoropropanoyl)-8-azabicyclo[3.2.1]oct-2-en-3-yl)-1H-pyrrolo[2,3-b]pyridin-6-yl)cyclopropanecarboxamide

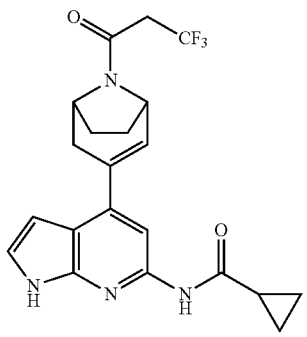 [SMILES: O=C(Nc1cc(C2=CC3CCC(C2)N3C(=O)CC(F)(F)F)c2cc[nH]c2n1)C1CC1]

MS(ESI+) m/z 419 (M+H)+

Example 262: Synthesis of N-(4-((1S,5R)-8-(2-cyanoacetyl)-8-azabicyclo[3.2.1]oct-2-en-3-yl)-1H-pyrrolo[2,3-b]pyridin-6-yl)cyclopropanecarboxamide

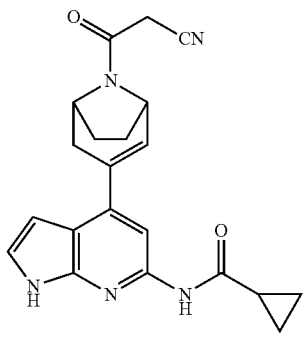 [SMILES: N#CCC(=O)N1C2C=C(c3cc(NC(=O)C4CC4)nc4[nH]ccc34)CC1CC2]

MS(ESI+) m/z 376 (M+H)+

Example 263: Synthesis of N-(4-(1-(2,2-difluorocyclopropane-1-carbonyl)-1,2,3,6-tetrahydropyridin-4-yl)-1H-pyrrolo[2,3-b]pyridin-6-yl)cyclopropanecarboxamide

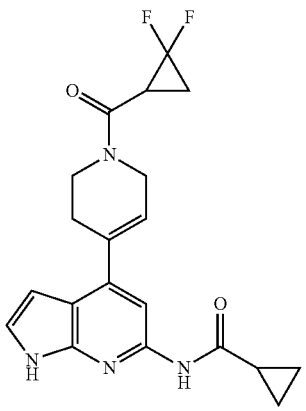 [SMILES: O=C(Nc1cc(C2=CCN(C(=O)C3CC3(F)F)CC2)c2cc[nH]c2n1)C1CC1]

¹H NMR (400 MHz, DMSO-d₆) δ 10.68 (s, 1H), 8.06 (d, J=2.3 Hz, 1H), 7.91 (d, J=4.2 Hz, 1H), 6.94 (dd, J=5.8, 4.1 Hz, 1H), 6.32 (s, 1H), 5.17 (q, J=10.6 Hz, 1H), 4.56-4.28 (m, 1H), 4.28-4.12 (m, 1H), 3.93 (s, 1H), 3.77 (t, J=5.8 Hz, 2H), 2.75 (s, 1H), 2.38-2.29 (m, 1H), 2.23 (d, J=11.8 Hz, 1H), 2.06-1.80 (m, 4H), 0.86 (d, J=5.7 Hz, 4H).

MS(ESI+) m/z 387 (M+H)⁺

Example 264: Synthesis of N-(4-(1-(cyclopropanecarbonyl)-1,2,3,6-tetrahydropyridin-4-yl)-1H-pyrrolo[2,3-b]pyridin-6-yl)cyclopropanecarboxamide

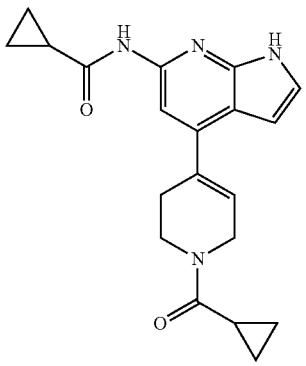 [SMILES: O=C(Nc1cc(C2=CCN(C(=O)C3CC3)CC2)c2cc[nH]c2n1)C1CC1]

¹H NMR (400 MHz, DMSO-d₆) δ 11.43 (s, 1H), 10.53 (s, 1H), 7.87 (s, 1H), 7.34 (dd, J=2.5, 3.5 Hz, 1H), 6.56 (dd, J=1.9, 3.6 Hz, 1H), 6.35 (s, 1H), 4.32 (d, J=110.2 Hz, 2H), 3.82 (d, J=78.9 Hz, 2H), 2.65 (d, J=9.9 Hz, 1H), 2.13-1.92 (m, 2H), 0.84-0.70 (m, 8H).

MS(ESI+) m/z 351 (M+H)⁺

Example 265: Synthesis of N-(4-(1-(4-cyanobutanoyl)-1,2,3,6-tetrahydropyridin-4-yl)-1H-pyrrolo[2,3-b]pyridin-6-yl)cyclopropanecarboxamide

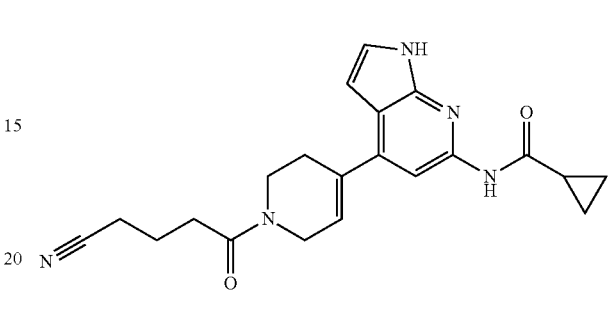

¹H NMR (400 MHz, DMSO-d₆) δ 11.43 (s, 1H), 10.53 (s, 1H), 7.86 (s, 1H), 7.37-7.30 (m, 1H), 6.56 (dd, J=1.9, 3.5 Hz, 1H), 6.33 (d, J=17.7 Hz, 1H), 4.20 (dd, J=3.2, 15.0 Hz, 2H), 3.70 (dt, J=5.6, 18.5 Hz, 2H), 2.64-2.52 (m, 6H), 2.01 (q, J=3.1, 3.7 Hz, 1H), 1.84 (p, J=7.4 Hz, 2H), 0.86-0.77 (m, 4H).

MS(ESI+) m/z 378 (M+H)⁺

Example 266: Synthesis of N-(4-(1-acryloyl-1,2,3,6-tetrahydropyridin-4-yl)-1H-pyrrolo[2,3-b]pyridin-6-yl)cyclopropanecarboxamide

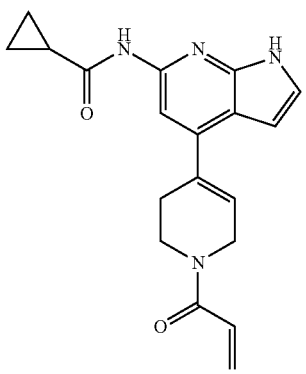 [SMILES: C=CC(=O)N1CC=C(c2cc(NC(=O)C3CC3)nc3[nH]ccc23)CC1]

¹H NMR (400 MHz, DMSO-d₆) δ 11.43 (s, 1H), 10.53 (s, 1H), 7.87 (s, 1H), 7.34 (t, J=3.0 Hz, 1H), 6.98-6.76 (m, 1H), 6.56 (s, 1H), 6.34 (d, J=24.5 Hz, 1H), 6.16 (d, J=16.6 Hz, 1H), 5.72 (d, J=10.2 Hz, 1H), 4.30 (d, J=40.6 Hz, 2H), 3.85-3.74 (m, 2H), 2.61 (s, 2H), 2.02 (s, 1H), 0.82-0.74 (m, 4H).

MS(ESI+) m/z 337 (M+H)⁺

Example 267: Synthesis of N-(4-(1-((1S,2S)-2-cyanocyclopropane-1-carbonyl)-1,2,3,6-tetrahydropyridin-4-yl)-1H-pyrrolo[2,3-b]pyridin-6-yl)cyclopropanecarboxamide

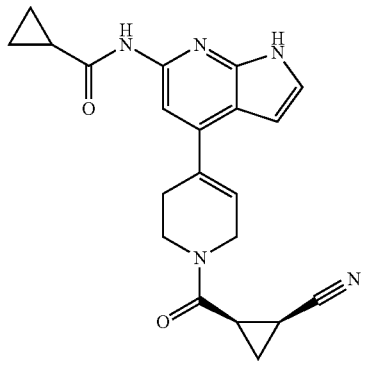 [SMILES: N#C[C@H]1C[C@H]1C(=O)N1CC=C(c2cc(NC(=O)C3CC3)nc3[nH]ccc23)CC1]

¹H NMR (400 MHz, DMSO-d₆) δ 11.44 (s, 1H), 10.54 (s, 1H), 7.88 (s, 1H), 7.35 (s, 1H), 6.57 (d, J=2.4 Hz, 1H), 6.35 (s, 1H), 4.50 (d, J=3.2 Hz, 1H), 4.19 (s, 1H), 4.00-3.87 (m, 1H), 3.83-3.64 (m, 1H), 3.03-2.80 (m, 1H), 2.10 (dt, J=5.2, 9.7 Hz, 1H), 2.02 (s, 1H), 1.45 (s, 1H), 1.35 (d, J=4.1 Hz, 1H), 0.86-0.73 (m, 4H).

MS(ESI+) m/z 376 (M+H)⁺

Example 268: Synthesis of N-(4-(1-(2-(1-cyanocyclopropyl)acetyl)-1,2,3,6-tetrahydropyridin-4-yl)-1H-pyrrolo[2,3-b]pyridin-6-yl)cyclopropanecarboxamide

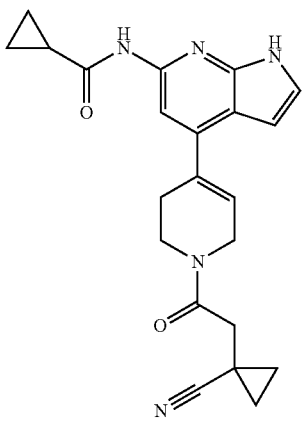 [SMILES: N#CC1(CC(=O)N2CC=C(c3cc(NC(=O)C4CC4)nc4[nH]ccc34)CC2)CC1]

¹H NMR (400 MHz, DMSO-d₆) δ 11.43 (s, 1H), 10.53 (s, 1H), 7.86 (s, 1H), 7.34 (t, J=3.0 Hz, 1H), 6.56 (d, J=4.1 Hz, 1H), 6.32 (d, J=37.2 Hz, 1H), 4.21 (s, 1H), 4.14 (s, 1H), 3.74 (t, J=5.6 Hz, 1H), 3.59 (t, J=4.9 Hz, 1H), 2.79 (s, 1H), 2.74 (s, 1H), 2.61 (s, 1H), 2.05-1.96 (m, 2H), 1.18 (s, 1H), 0.94 (dd, J=7.3, 4.8 Hz, 2H), 0.89-0.74 (m, 5H).

MS(ESI+) m/z 390 (M+H)⁺

Example 269: Synthesis of N-(4-(1-(2-cyanopropanoyl)-1,2,3,6-tetrahydropyridin-4-yl)-1H-pyrrolo[2,3-b]pyridin-6-yl)cyclopropanecarboxamide

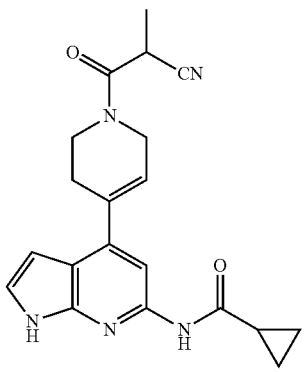 [SMILES: CC(C#N)C(=O)N1CC=C(c2cc(NC(=O)C3CC3)nc3[nH]ccc23)CC1]

MS(ESI+) m/z 364 (M+H)⁺

Example 270: Synthesis of N-(4-(1-(but-3-enoyl)-1,2,3,6-tetrahydropyridin-4-yl)-1H-pyrrolo[2,3-b]pyridin-6-yl)cyclopropanecarboxamide

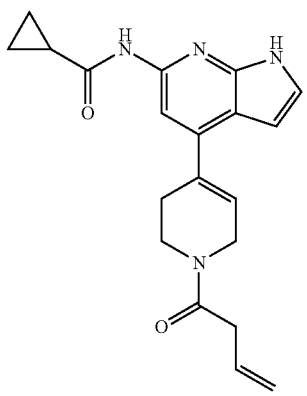 [SMILES: C=CCC(=O)N1CC=C(c2cc(NC(=O)C3CC3)nc3[nH]ccc23)CC1]

¹H NMR (400 MHz, DMSO-d₆) δ 11.44 (s, 1H), 10.57 (s, 1H), 7.84 (s, 1H), 7.35 (t, J=3.0 Hz, 1H), 6.56 (d, J=2.7 Hz, 1H), 6.34 (d, J=23.8 Hz, 1H), 6.02-5.85 (m, 1H), 5.15-5.08 (m, 2H), 4.25-4.14 (m, 2H), 3.24 (dd, J=18.3, 6.7 Hz, 2H), 3.02 (d, J=6.7 Hz, 1H), 2.69 (s, 2H), 2.06-1.95 (m, 2H), 0.86-0.78 (m, 4H).

MS(ESI+) m/z 351 (M+H)⁺

Example 271: Synthesis of N-(4-(1-(2-cyanobutanoyl)-1,2,3,6-tetrahydropyridin-4-yl)-1H-pyrrolo[2,3-b]pyridin-6-yl)cyclopropanecarboxamide

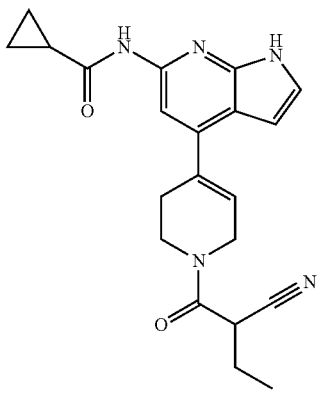 [SMILES: CCC(C#N)C(=O)N1CC=C(c2cc(NC(=O)C3CC3)nc3[nH]ccc23)CC1]

MS(ESI+) m/z 378 (M+H)+

Example 272: Synthesis of N-(4-(1-(2,2,2-trifluoroacetyl)-1,2,3,6-tetrahydropyridin-4-yl)-1H-pyrrolo[2,3-b]pyridin-6-yl)cyclopropanecarboxamide

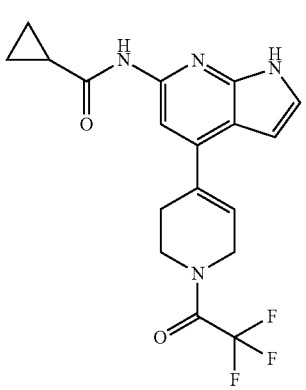 [SMILES: O=C(Nc1cc(C2=CCN(C(=O)C(F)(F)F)CC2)c2cc[nH]c2n1)C1CC1]

$^1$H NMR (400 MHz, DMSO-d$_6$) δ 11.46 (s, 1H), 10.56 (s, 1H), 7.88 (s, 1H), 7.36 (t, J=3.0 Hz, 1H), 6.57 (td, J=1.8, 3.5 Hz, 1H), 6.46-6.31 (m, 1H), 4.42-4.28 (m, 2H), 3.85 (dt, J=5.6, 10.9 Hz, 2H), 2.66 (d, J=15.5 Hz, 2H), 2.02 (ddd, J=3.4, 7.5, 14.4 Hz, 1H), 0.83-0.70 (m, 4H).

MS(ESI+) m/z 379 (M+H)+

Example 273: Synthesis of N-(4-(1-(2-methylcyclopropane-1-carbonyl)-1,2,3,6-tetrahydropyridin-4-yl)-1H-pyrrolo[2,3-b]pyridin-6-yl)cyclopropanecarboxamide

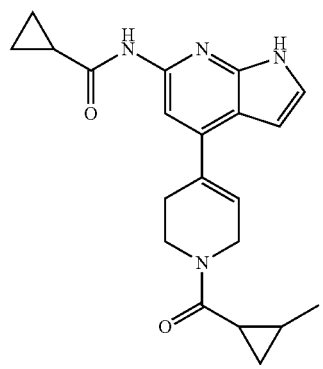 [SMILES: CC1CC1C(=O)N1CC=C(c2cc(NC(=O)C3CC3)nc3[nH]ccc23)CC1]

$^1$H NMR (400 MHz, DMSO-d$_6$) δ 11.45 (s, 1H), 10.56 (s, 1H), 7.88 (s, 1H), 7.40-7.26 (m, 1H), 6.56 (dd, J=1.9, 3.6 Hz, 1H), 6.35 (s, 1H), 4.44 (s, 1H), 4.16 (s, 1H), 3.90 (s, 1H), 3.70 (s, 1H), 2.65 (d, J=12.4 Hz, 1H), 2.02 (s, 1H), 1.77 (d, J=49.4 Hz, 1H), 1.26-1.09 (m, 5H), 0.95 (d, J=6.2 Hz, 1H), 0.83-0.76 (m, 4H).

MS(ESI+) m/z 365 (M+H)+

Example 274: Synthesis of N-(4-(1-(2-fluorocyclopropane-1-carbonyl)-1,2,3,6-tetrahydropyridin-4-yl)-1H-pyrrolo[2,3-b]pyridin-6-yl)cyclopropanecarboxamide

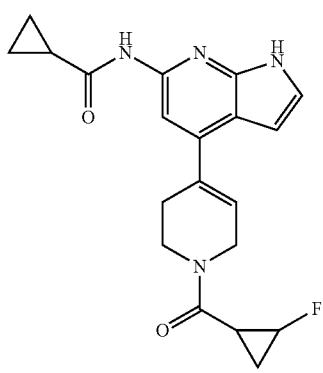 [SMILES: O=C(Nc1cc(C2=CCN(C(=O)C3CC3F)CC2)c2cc[nH]c2n1)C1CC1]

$^1$H NMR (400 MHz, DMSO-d$_6$) δ 11.43 (s, 1H), 10.54 (s, 1H), 7.86 (s, 1H), 7.33 (t, J=3.0 Hz, 1H), 6.55 (t, J=2.7 Hz, 1H), 6.33 (s, 1H), 4.74 (d, J=5.4 Hz, 1H), 4.46 (s, 1H), 4.15 (s, 1H), 3.92 (s, 1H), 3.78-3.58 (m, 1H), 2.71-2.61 (m, 2H), 2.00 (s, 1H), 1.43 (s, 1H), 1.18 (dt, J=7.0, 13.0 Hz, 1H), 0.84-0.73 (m, 4H).

MS(ESI+) m/z 369 (M+H)+

Example 275: Synthesis of 4-(1-(2-cyanoacetyl)-1,2,3,6-tetrahydropyridin-4-yl)-6-(cyclopropanecarboxamido)-1H-pyrrolo[2,3-b]pyridine 7-oxide

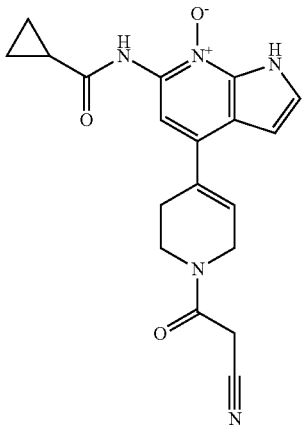 [SMILES: N#CCC(=O)N1CC=C(c2cc(NC(=O)C3CC3)[n+]([O-])c3[nH]ccc23)CC1]

MS(ESI+) m/z 366 (M+H)+

Example 276: Synthesis of N-(4-(1-(2-(3,4-difluorophenyl)acetyl)-1,2,3,6-tetrahydropyridin-4-yl)-1H-pyrrolo[2,3-b]pyridin-6-yl)cyclopropanecarboxamide

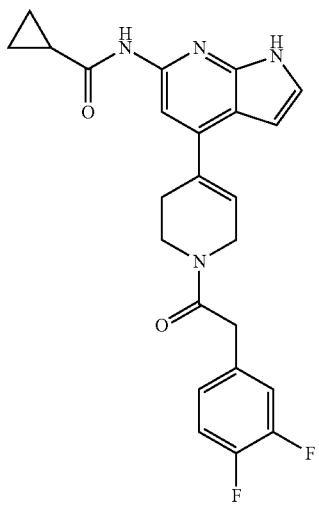 [SMILES: O=C(Nc1cc(C2=CCN(C(=O)Cc3ccc(F)c(F)c3)CC2)c2cc[nH]c2n1)C1CC1]

¹H NMR (400 MHz, Methanol-d₄) δ 11.45 (s, 1H), 10.56 (s, 1H), 7.87 (s, 1H), 7.42-7.30 (m, 3H), 7.10 (s, 1H), 6.53 (dd, J=1.8, 3.5 Hz, 1H), 6.33 (d, J=21.7 Hz, 1H), 4.30 (s, 1H), 4.20 (s, 1H), 3.82 (d, J=17.6 Hz, 2H), 3.75 (t, J=6.4 Hz, 2H), 2.68 (d, J=7.4 Hz, 2H), 2.02 (s, 1H), 0.87-0.76 (m, 4H).

MS(ESI+) m/z 437 (M+H)+

Example 277: Synthesis of N-(4-(1-isonicotinoyl-1,2,3,6-tetrahydropyridin-4-yl)-1H-pyrrolo[2,3-b]pyridin-6-yl)cyclopropanecarboxamide

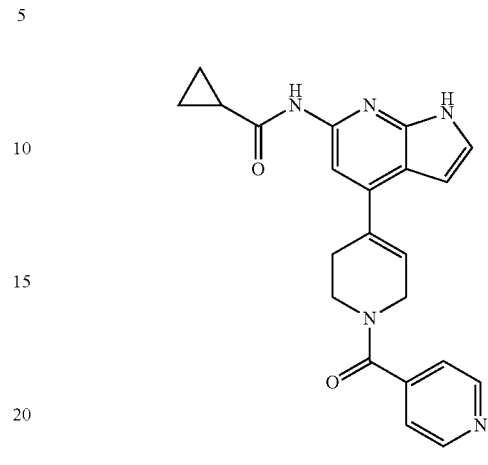

¹H NMR (400 MHz, Methanol-d₄) δ 11.46 (s, 1H), 10.56 (s, 1H), 8.70 (d, J=5.1 Hz, 2H), 7.88 (s, 1H), 7.53-7.43 (m, 2H), 7.35 (d, J=11.1 Hz, 1H), 6.64-6.51 (m, 1H), 6.32 (d, J=82.1 Hz, 1H), 4.36 (s, 1H), 4.08 (s, 1H), 3.91 (s, 1H), 3.51 (s, 1H), 2.63 (s, 2H), 2.02 (s, 1H), 0.85-0.74 (m, 4H).

MS(ESI+) m/z 388 (M+H)+

Example 278: Synthesis of N-(4-(1-(furan-3-carbonyl)-1,2,3,6-tetrahydropyridin-4-yl)-1H-pyrrolo[2,3-b]pyridin-6-yl)cyclopropanecarboxamide

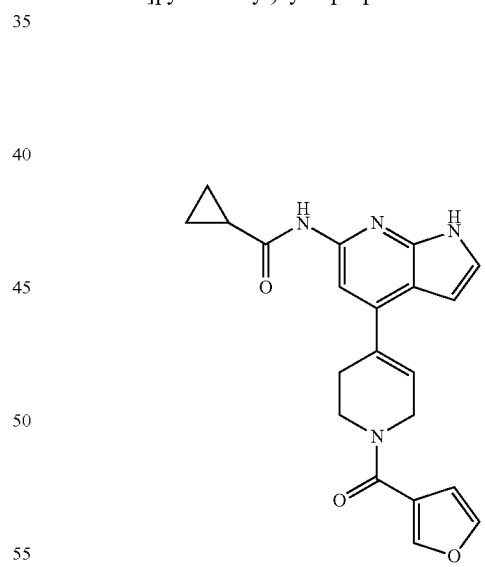

¹H NMR (400 MHz, Methanol-d₄) δ 11.45 (s, 1H), 10.56 (s, 1H), 8.15 (s, 1H), 7.89 (s, 1H), 7.80-7.72 (m, 1H), 7.43-7.27 (m, 1H), 6.76 (d, J=1.9 Hz, 1H), 6.59 (s, 1H), 6.36 (s, 1H), 4.32 (s, 2H), 3.81 (s, 2H), 2.68 (d, J=7.1 Hz, 2H), 2.01 (d, J=8.1 Hz, 1H), 0.83-0.75 (m, 4H)

MS(ESI+) m/z 377 (M+H)+

Example 279: Synthesis of N-(4-(1-(4-fluorobenzoyl)-1,2,3,6-tetrahydropyridin-4-yl)-1H-pyrrolo[2,3-b]pyridin-6-yl)cyclopropanecarboxamide

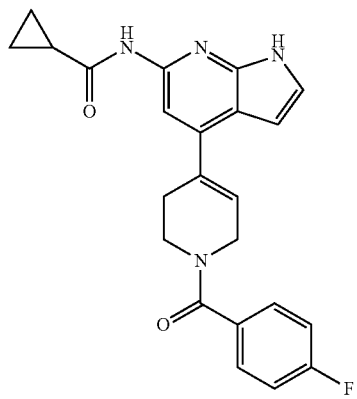 [SMILES: O=C(Nc1cc(C2=CCN(C(=O)c3ccc(F)cc3)CC2)c2cc[nH]c2n1)C1CC1]

¹H NMR (400 MHz, Methanol-d₄) δ 11.45 (s, 1H), 10.56 (s, 1H), 7.88 (s, 1H), 7.57 (dd, J=5.5, 8.5 Hz, 2H), 7.38-7.19 (m, 3H), 6.59 (s, 1H), 6.42 (s, 1H), 4.24 (d, J=60.2 Hz, 2H), 3.68-3.52 (m, 2H), 2.66 (d, J=24.6 Hz, 2H), 2.01 (s, 1H), 0.83-0.71 (m, 4H).

MS(ESI+) m/z 405 (M+H)⁺

Example 280: Synthesis of (N-(4-(1-(1-methylpyrrolidine-3-carbonyl)-1,2,3,6-tetrahydropyridin-4-yl)-1H-pyrrolo[2,3-b]pyridin-6-yl)cyclopropanecarboxamide)

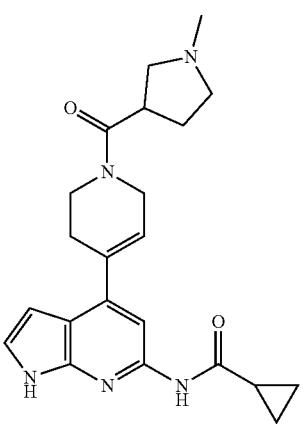 [SMILES: CN1CCC(C(=O)N2CC=C(c3cc(NC(=O)C4CC4)nc4[nH]ccc34)CC2)C1]

¹H NMR (400 MHz, Methanol-d₄) δ 11.45 (s, 1H), 10.55 (s, 1H), 7.86 (s, 1H), 7.35 (s, 1H), 6.56 (s, 1H), 6.34 (d, J=24.0 Hz, 1H), 4.22 (d, J=32.6 Hz, 2H), 3.71 (d, J=5.4 Hz, 2H), 2.67 (s, 2H), 2.36-2.21 (m, 4H), 2.00 (s, 3H), 0.88-0.71 (m, 4H).

MS(ESI+) m/z 394 (M+H)⁺

Example 281: Synthesis of (N-(4-(1-(dimethylglycyl)-1,2,3,6-tetrahydropyridin-4-yl)-1H-pyrrolo[2,3-b]pyridin-6-yl)cyclopropanecarboxamide)

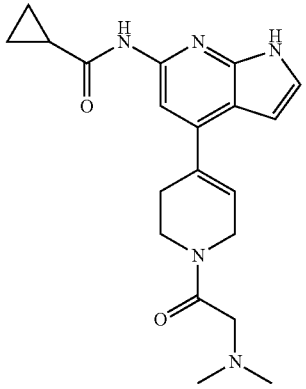 [SMILES: CN(C)CC(=O)N1CC=C(c2cc(NC(=O)C3CC3)nc3[nH]ccc23)CC1]

¹H NMR (400 MHz, Methanol-d₄) δ 11.47 (s, 1H), 10.57 (s, 1H), 7.88 (d, J=4.4 Hz, 1H), 7.36 (s, 1H), 6.56 (d, J=3.6 Hz, 1H), 6.40-6.28 (m, 1H), 4.20 (d, J=37.1 Hz, 4H), 3.78 (s, 1H), 3.60 (s, 1H), 2.77 (s, 6H), 2.62 (d, J=36.3 Hz, 3H), 2.05-1.97 (m, 1H), 0.79 (s, 4H).

MS(ESI+) m/z 368 (M+H)⁺

Example 282: Synthesis of N-(4-(1-(2-(trifluoromethyl)cyclopropane-1-carbonyl)-1,2,3,6-tetrahydropyridin-4-yl)-1H-pyrrolo[2,3-b]pyridin-6-yl)cyclopropanecarboxamide

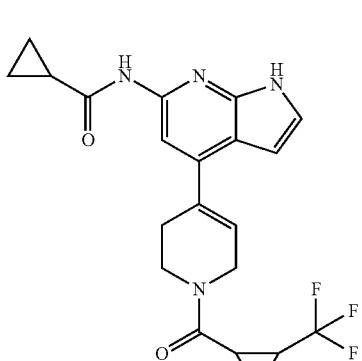

¹H NMR (400 MHz, Methanol-d₄) δ 11.45 (s, 1H), 10.55 (s, 1H), 7.87 (s, 1H), 7.35 (s, 1H), 6.56 (s, 1H), 6.34 (s, 1H), 4.47 (d, J=16.4 Hz, 1H), 4.20 (s, 1H), 3.92 (s, 1H), 3.64 (s, 2H), 2.67-2.61 (m, 2H), 2.26 (s, 1H), 2.01 (s, 1H), 0.78 (d, J=9.3 Hz, 4H).

MS(ESI+) m/z 419 (M+H)⁺

Example 283: Synthesis of N-(4-(1-(2-cyanoacetyl)-3-methyl-1,2,3,6-tetrahydropyridin-4-yl)-1H-pyrrolo[2,3-b]pyridin-6-yl)cyclopropanecarboxamide

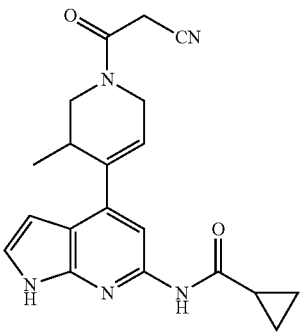 [SMILES: CC1CN(C(=O)CC#N)CC=C1c1cc(NC(=O)C2CC2)nc2[nH]ccc12]

$^1$H NMR (400 MHz, DMSO-d$_6$) δ 11.44 (s, 1H), 10.57 (s, 1H), 7.84 (d, J=10.2 Hz, 1H), 7.34 (d, J=3.1 Hz, 1H), 6.48 (dd, J=1.8, 3.7 Hz, 1H), 6.17-6.03 (m, 1H), 4.31-4.01 (m, 6H), 3.96-3.62 (m, 2H), 3.02 (m, J=36.6 Hz, 1H), 2.02 (s, 1H), 0.88 (s, 3H), 0.84-0.73 (m, 4H).

MS(ESI+) m/z 364 (M+H)$^+$

Example 284: Synthesis of N-(4-(1-(3-cyanopropanoyl)-3-methyl-1,2,3,6-tetrahydropyridin-4-yl)-1H-pyrrolo[2,3-b]pyridin-6-yl)cyclopropanecarboxamide

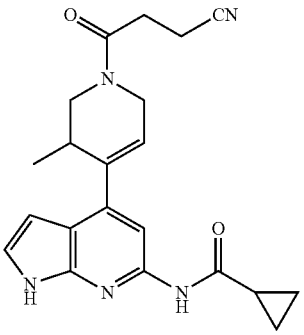 [SMILES: CC1CN(C(=O)CCC#N)CC=C1c1cc(NC(=O)C2CC2)nc2[nH]ccc12]

$^1$H NMR (400 MHz, DMSO-d$_6$) δ 11.44 (s, 1H), 10.56 (s, 1H), 7.85 (d, J=5.5 Hz, 1H), 7.34 (d, J=3.5 Hz, 1H), 6.49 (dt, J=2.0, 3.5 Hz, 1H), 6.11 (d, J=15.7 Hz, 1H), 4.31 (d, J=24.5 Hz, 1H), 4.14-3.90 (m, 2H), 3.57 (d, J=4.5 Hz, 2H), 3.00 (d, J=27.7 Hz, 2H), 2.85 (dd, J=7.7, 15.5 Hz, 4H), 2.02 (s, 1H), 0.88 (d, J=10.7 Hz, 3H), 0.82-0.76 (m, 4H).

MS(ESI+) m/z 378 (M+H)$^+$

Example 285: Synthesis of N-(4-(1-(4-cyanobutanoyl)-3-methyl-1,2,3,6-tetrahydropyridin-4-yl)-1H-pyrrolo[2,3-b]pyridin-6-yl)cyclopropanecarboxamide

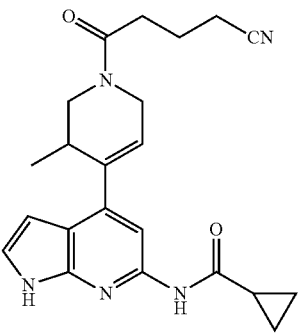 [SMILES: CC1CN(C(=O)CCCC#N)CC=C1c1cc(NC(=O)C2CC2)nc2[nH]ccc12]

$^1$H NMR (400 MHz, DMSO-d$_6$) δ 11.43 (s, 1H), 10.56 (s, 1H), 7.84 (d, J=5.1 Hz, 1H), 7.33 (s, 1H), 6.49 (s, 1H), 6.11 (d, J=10.4 Hz, 1H), 4.44-4.24 (m, 1H), 3.93 (d, J=17.1 Hz, 1H), 3.66-3.56 (m, 2H), 2.98 (d, J=26.6 Hz, 1H), 2.68 (s, 4H), 2.04 (d, J=19.1 Hz, 1H), 1.84 (p, J=6.3, 6.9 Hz, 2H), 0.93-0.84 (m, 3H), 0.83-0.71 (m, 4H).

MS(ESI+) m/z 392 (M+H)$^+$

Example 286: Synthesis of N-(4-(1-(1,2,5-oxadiazole-3-carbonyl)-1,2,3,6-tetrahydropyridin-4-yl)-1H-pyrrolo[2,3-b]pyridin-6-yl)cyclopropanecarboxamide

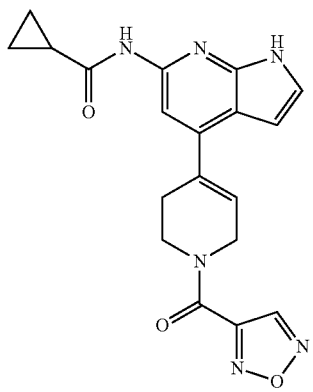 [SMILES: O=C(Nc1cc(C2=CCN(C(=O)c3cnon3)CC2)c2cc[nH]c2n1)C1CC1]

$^1$H NMR (400 MHz, DMSO-d$_6$) δ 11.47 (s, 1H), 10.57 (s, 1H), 9.32 (d, J=10.0 Hz, 1H), 7.89 (s, 1H), 7.36 (dt, J=6.3, 3.2 Hz, 1H), 6.57 (ddd, J=8.5, 3.6, 1.9 Hz, 1H), 6.36 (d, J=47.7 Hz, 1H), 4.42 (d, J=3.9 Hz, 2H), 3.96 (t, J=5.6 Hz, 1H), 3.84 (t, J=5.6 Hz, 1H), 2.68 (d, J=6.7 Hz, 2H), 2.04-1.99 (m, 1H), 0.82-0.75 (m, 4H).

MS(ESI+) m/z 379 (M+H)$^+$

Example 287: Synthesis of N-(4-(1-(isoxazole-4-carbonyl)-1,2,3,6-tetrahydropyridin-4-yl)-1H-pyrrolo[2,3-b]pyridin-6-yl)cyclopropanecarboxamide

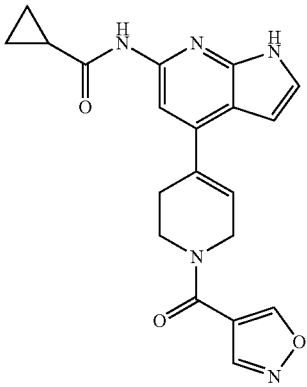 [SMILES: O=C(Nc1cc(C2=CCN(C(=O)c3cnoc3)CC2)c2cc[nH]c2n1)C1CC1]

$^1$H NMR (400 MHz, DMSO-d$_6$) δ 11.46 (s, 1H), 10.56 (s, 1H), 9.46 (s, 1H), 8.94 (s, 1H), 7.89 (s, 1H), 7.36 (s, 1H), 6.58 (d, J=18.3 Hz, 1H), 6.34 (d, J=47.3 Hz, 1H), 4.35 (d, J=34.0 Hz, 2H), 3.81 (d, J=39.9 Hz, 2H), 2.73 (s, 1H), 2.61 (s, 1H), 2.00 (d, J=13.2 Hz, 1H), 0.85-0.74 (m, 4H).

MS(ESI+) m/z 378 (M+H)$^+$

Example 288: Synthesis of N-(4-(1-(isoxazole-5-carbonyl)-1,2,3,6-tetrahydropyridin-4-yl)-1H-pyrrolo[2,3-b]pyridin-6-yl)cyclopropanecarboxamide

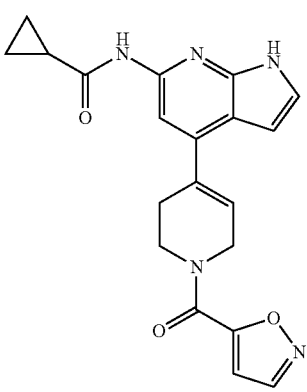 [SMILES: O=C(Nc1cc(C2=CCN(C(=O)c3ccno3)CC2)c2cc[nH]c2n1)C1CC1]

$^1$H NMR (400 MHz, DMSO-d$_6$) δ 11.46 (s, 1H), 10.56 (s, 1H), 8.79 (t, J=2.9 Hz, 1H), 7.89 (d, J=4.7 Hz, 1H), 7.36 (s, 1H), 7.07-7.00 (m, 1H), 6.58 (d, J=13.4 Hz, 1H), 6.35 (d, J=45.2 Hz, 1H), 4.36 (s, 2H), 3.91 (s, 1H), 3.75 (d, J=6.0 Hz, 1H), 2.70 (s, 1H), 2.64 (s, 1H), 2.00 (d, J=9.2 Hz, 1H), 0.85-0.76 (m, 4H).

MS(ESI+) m/z 378 (M+H)$^+$

Example 289: Synthesis of N-(4-(1-(2-cyanoacetyl)-1,2,3,6-tetrahydropyridin-4-yl)-5-methyl-1H-pyrrolo[2,3-b]pyridin-6-yl)cyclopropanecarboxamide

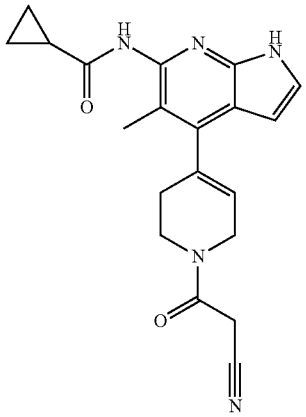 [SMILES: Cc1c(NC(=O)C2CC2)nc2[nH]ccc2c1C1=CCN(C(=O)CC#N)CC1]

$^1$H NMR (400 MHz, DMSO-d$_6$) δ 11.50 (s, 1H), 10.12 (s, 1H), 7.37 (t, J=2.9 Hz, 1H), 6.31 (s, 1H), 5.69 (d, J=7.0 Hz, 1H), 4.20-4.07 (m, 4H), 3.62 (t, J=5.8 Hz, 2H), 2.42 (s, 1H), 2.37-2.26 (m, 1H), 2.11 (s, 3H), 1.92-1.80 (m, 1H), 0.79 (d, J=6.0 Hz, 4H)

MS(ESI+) m/z 364 (M+H)$^+$

Example 290: Synthesis of N-(5-methyl-4-(1-(3,3,3-trifluoropropanoyl)-1,2,3,6-tetrahydropyridin-4-yl)-1H-pyrrolo[2,3-b]pyridin-6-yl)cyclopropanecarboxamide

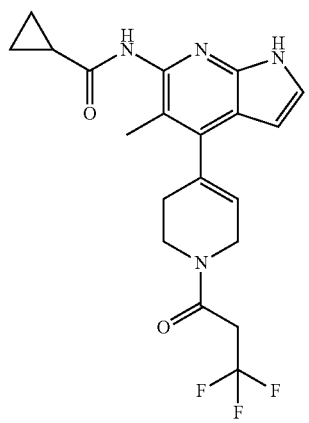 [SMILES: Cc1c(NC(=O)C2CC2)nc2[nH]ccc2c1C1=CCN(C(=O)CC(F)(F)F)CC1]

$^1$H NMR (400 MHz, DMSO-d$_6$) δ 11.45 (s, 1H), 10.04 (s, 1H), 7.35 (t, J=3.0 Hz, 1H), 6.26 (d, J=2.5 Hz, 1H), 5.68 (d, J=6.8 Hz, 1H), 4.26-4.12 (m, 2H), 3.84-3.66 (m, 4H), 2.41 (s, 1H), 2.30 (s, 1H), 2.09 (s, 3H), 1.83 (q, J=6.3 Hz, 1H), 0.76 (d, J=6.2 Hz, 4H).

MS(ESI+) m/z 407 (M+H)$^+$

Example 291: Synthesis of N-(4-(1-(thiazole-4-carbonyl)-1,2,3,6-tetrahydropyridin-4-yl)-1H-pyrrolo[2,3-b]pyridin-6-yl)cyclopropanecarboxamide

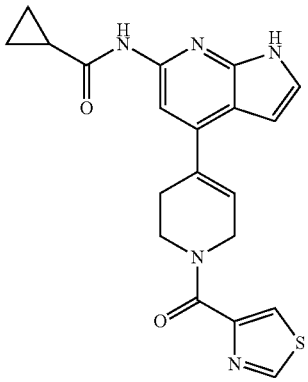 [SMILES: O=C(Nc1cc(C2=CCN(C(=O)c3cscn3)CC2)c2cc[nH]c2n1)C1CC1]

$^1$H NMR (400 MHz, DMSO-d$_6$) δ 11.45 (s, 1H), 10.56 (s, 1H), 9.22 (s, 1H), 8.24 (d, J=2.0 Hz, 1H), 7.89 (s, 1H), 7.35 (s, 1H), 6.57 (d, J=14.9 Hz, 1H), 6.37 (d, J=60.7 Hz, 1H), 4.40 (d, J=35.2 Hz, 2H), 3.88 (d, J=19.6 Hz, 2H), 2.65 (s, 2H), 2.01 (d, J=5.7 Hz, 1H), 1.24 (m, 2H), 0.80 (m, 2H).

MS(ESI+) m/z 394 (M+H)$^+$

Example 292: Synthesis of N-(4-(1-(isothiazole-4-carbonyl)-1,2,3,6-tetrahydropyridin-4-yl)-1H-pyrrolo[2,3-b]pyridin-6-yl)cyclopropanecarboxamide

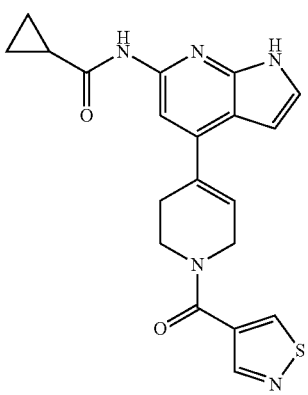 [SMILES: O=C(Nc1cc(C2=CCN(C(=O)c3cnsc3)CC2)c2cc[nH]c2n1)C1CC1]

$^1$H NMR (400 MHz, DMSO-d$_6$) δ 11.46 (s, 1H), 10.56 (s, 1H), 8.65 (d, J=1.8 Hz, 1H), 7.89 (s, 1H), 7.77 (s, 1H), 7.35 (s, 1H), 6.60 (s, 1H), 6.35 (d, J=53.1 Hz, 1H), 4.36 (d, J=3.1 Hz, 2H), 3.91 (s, 1H), 3.74 (s, 1H), 2.71-2.65 (m, 2H), 2.02 (dd, J=8.9, 4.0 Hz, 1H), 1.25 (m, 2H), 0.87-0.73 (m, 2H).

MS(ESI+) m/z 394 (M+H)$^+$

Example 293: Synthesis of N-(4-(1-(4-cyanobenzoyl)-1,2,3,6-tetrahydropyridin-4-yl)-1H-pyrrolo[2,3-b]pyridin-6-yl)cyclopropanecarboxamide

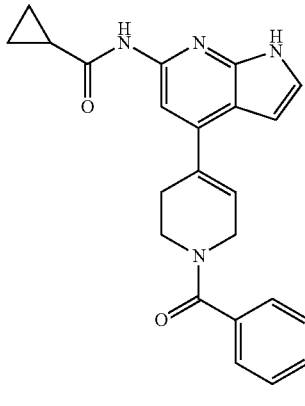

$^1$H NMR (400 MHz, DMSO-d$_6$) δ 11.45 (s, 1H), 10.56 (s, 1H), 7.96 (d, J=7.8 Hz, 2H), 7.88 (s, 1H), 7.69 (d, J=7.9 Hz, 2H), 7.36 (s, 1H), 6.57 (d, J=30.7 Hz, 1H), 6.32 (d, J=87.2 Hz, 1H), 4.35 (s, 1H), 3.99 (d, J=68.8 Hz, 2H), 3.50 (s, 1H), 2.62 (s, 2H), 2.04-1.96 (m, 1H), 0.80 (d, J=5.2 Hz, 4H).

MS(ESI+) m/z 412 (M+H)$^+$

Example 294: Synthesis of N-(4-(1-(2-cyanoacetyl)-3-ethyl-1,2,3,6-tetrahydropyridin-4-yl)-1H-pyrrolo[2,3-b]pyridin-6-yl)cyclopropanecarboxamide

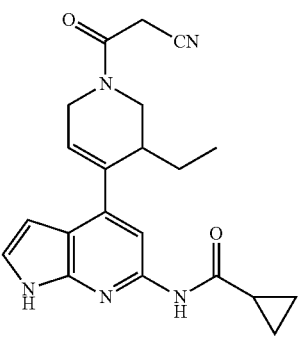 [SMILES: CCC1CN(C(=O)CC#N)CC=C1c1cc(NC(=O)C2CC2)nc2[nH]ccc12]

$^1$H NMR (400 MHz, DMSO-d$_6$) δ 11.44 (s, 1H), 10.56 (s, 1H), 7.83 (d, J=10.8 Hz, 1H), 7.34 (s, 1H), 6.48 (d, J=3.2 Hz, 1H), 6.10 (d, J=22.6 Hz, 1H), 4.34-4.19 (m, 2H), 4.04 (dd, J=9.2, 18.5 Hz, 2H), 3.62-3.57 (m, 1H), 2.76 (s, 1H), 2.00 (d, J=12.4 Hz, 1H), 1.28 (s, 2H), 1.03 (d, J=6.2 Hz, 3H), 0.87-0.73 (m, 7H).

MS(ESI+) m/z 378 (M+H)$^+$

Example 295: Synthesis of N-(4-(1-(3-cyanopropanoyl)-3-ethyl-1,2,3,6-tetrahydropyridin-4-yl)-1H-pyrrolo[2,3-b]pyridin-6-yl)cyclopropanecarboxamide

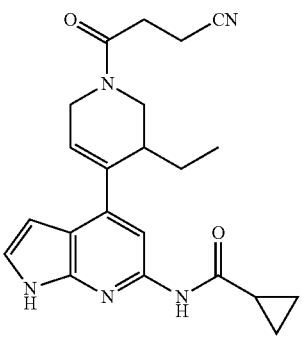 [SMILES: CCC1CN(C(=O)CCC#N)CC=C1c1cc(NC(=O)C2CC2)nc2[nH]ccc12]

$^1$H NMR (400 MHz, DMSO-d$_6$) δ 11.44 (s, 1H), 10.56 (s, 1H), 7.84 (d, J=5.5 Hz, 1H), 7.33 (s, 1H), 6.49 (d, J=2.9 Hz, 1H), 6.13 (d, J=23.5 Hz, 1H), 4.50-4.26 (m, 2H), 3.98 (dd, J=19.2, 50.3 Hz, 1H), 3.76-3.48 (m, 3H), 2.87 (s, 2H), 2.73 (d, J=6.4 Hz, 2H), 2.00 (d, J=12.8 Hz, 1H), 1.36-1.14 (m, 3H), 0.98-0.68 (m, 7H).

MS(ESI+) m/z 392 (M+H)$^+$

Example 296: Synthesis of N-(4-(1-(2-cyanoacetyl)-5-methyl-1,2,3,6-tetrahydropyridin-4-yl)-1H-pyrrolo[2,3-b]pyridin-6-yl)cyclopropanecarboxamide

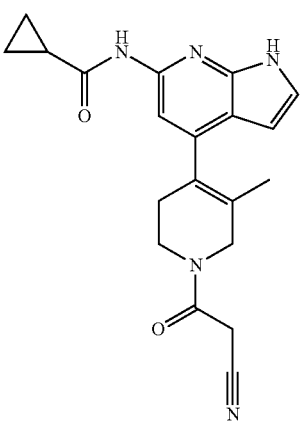 [SMILES: CC1=C(c2cc(NC(=O)C3CC3)nc3[nH]ccc23)CCN(C(=O)CC#N)C1]

$^1$H NMR (400 MHz, DMSO-d$_6$) δ 11.41 (s, 1H), 10.57 (s, 1H), 7.67 (s, 1H), 7.31 (t, J=3.0 Hz, 1H), 6.24 (tt, J=1.5, 3.3 Hz, 1H), 4.14 (dd, J=1.2, 3.5 Hz, 2H), 4.07-3.94 (m, 2H), 3.70 (t, J=5.7 Hz, 1H), 3.57 (t, J=5.7 Hz, 1H), 2.34 (s, 1H), 2.05-1.95 (m, 1H), 1.52 (s, 3H), 1.24 (d, J=8.3 Hz, 1H), 0.83-0.75 (m, 4H).

MS(ESI+) m/z 364 (M+H)$^+$

Example 297: Synthesis of N-(4-(1-(2-bromoacetyl)-1,2,3,6-tetrahydropyridin-4-yl)-1H-pyrrolo[2,3-b]pyridin-6-yl)cyclopropanecarboxamide

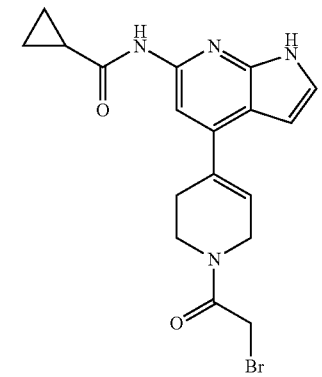 [SMILES: O=C(Nc1cc(C2=CCN(C(=O)CBr)CC2)c2cc[nH]c2n1)C1CC1]

MS(ESI+) m/z 404 (M+H)$^+$

Example 298: Synthesis of N-(4-(1-(2-chloroacetyl)-1,2,3,6-tetrahydropyridin-4-yl)-1H-pyrrolo[2,3-b]pyridin-6-yl)cyclopropanecarboxamide

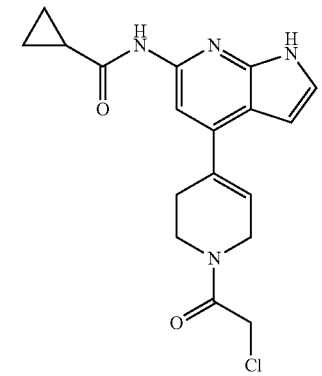 [SMILES: O=C(Nc1cc(C2=CCN(C(=O)CCl)CC2)c2cc[nH]c2n1)C1CC1]

MS(ESI+) m/z 359, 361 (M+H)$^+$

Example 299: Synthesis of N-(4-(1-(2-cyanoacetyl)-3,3-dimethyl-1,2,3,6-tetrahydropyridin-4-yl)-1H-pyrrolo[2,3-b]pyridin-6-yl)cyclopropanecarboxamide

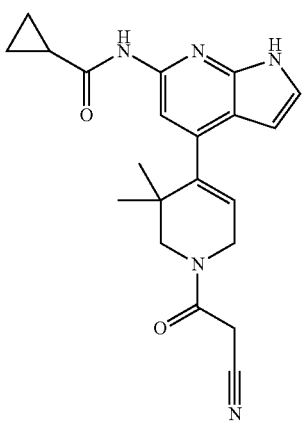 [SMILES: CC1(C)CN(C(=O)CC#N)CC=C1c1cc(NC(=O)C2CC2)nc2[nH]ccc12]

¹H NMR (400 MHz, DMSO-d₆) δ 11.38 (s, 1H), 10.56 (s, 1H), 7.73 (d, J=7.5 Hz, 1H), 7.28 (s, 1H), 6.30 (s, 1H), 5.67-5.54 (m, 1H), 4.19-4.06 (m, 4H), 3.48 (s, 2H), 2.01 (s, 1H), 1.01 (dd, J=3.7, 13.5 Hz, 6H), 0.80 (d, J=5.3 Hz, 4H).

MS(ESI+) m/z 378 (M+H)⁺

Example 300: Synthesis of N-(4-(1-(3-cyanopropanoyl)-3,3-dimethyl-1,2,3,6-tetrahydropyridin-4-yl)-1H-pyrrolo[2,3-b]pyridin-6-yl)cyclopropanecarboxamide

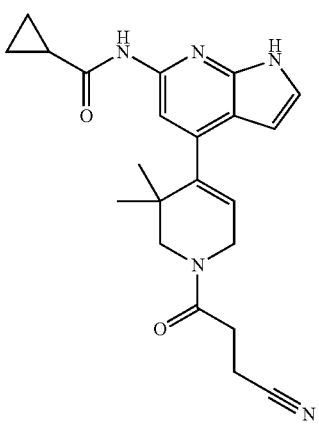 [SMILES: CC1(C)CN(C(=O)CCC#N)CC=C1c1cc(NC(=O)C2CC2)nc2[nH]ccc12]

¹H NMR (400 MHz, DMSO-d₆) δ 11.38 (s, 1H), 10.56 (s, 1H), 7.74 (d, J=8.2 Hz, 1H), 7.28 (s, 1H), 6.34-6.24 (m, 1H), 5.60 (d, J=10.1 Hz, 1H), 4.13 (dd, J=3.3, 14.9 Hz, 2H), 3.50-3.44 (m, 2H), 2.82 (d, J=3.8 Hz, 2H), 2.67 (d, J=4.4 Hz, 2H), 2.01 (s, 1H), 1.03 (s, 3H), 0.99 (s, 3H), 0.81-0.74 (m, 4H).

MS(ESI+) m/z 392 (M+H)⁺

Example 301: Synthesis of N-(4-(1-(2-cyanoacetyl)-1,2,3,6-tetrahydropyridin-4-yl)-1H-pyrrolo[2,3-b]pyridin-6-yl)furan-2-carboxamide

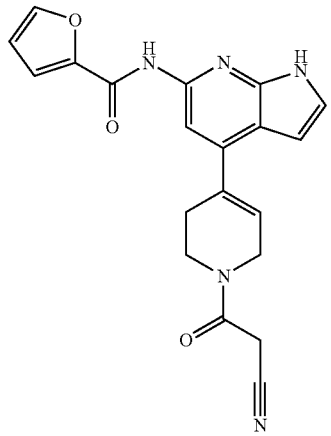 [SMILES: N#CCC(=O)N1CC=C(c2cc(NC(=O)c3ccco3)nc3[nH]ccc23)CC1]

MS(ESI+) m/z 376 (M+H)⁺

Example 302: Synthesis of N-(4-(5-(3-cyanopropanoyl)-5-azaspiro[2.5]oct-7-en-8-yl)-1H-pyrrolo[2,3-b]pyridin-6-yl)cyclopropanecarboxamide

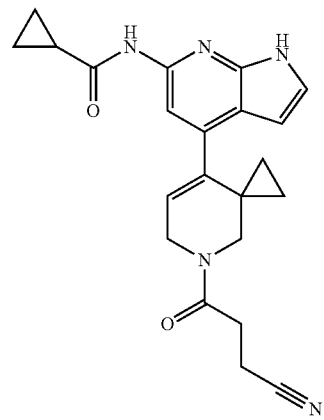 [SMILES: N#CCCC(=O)N1CC=C(c2cc(NC(=O)C3CC3)nc3[nH]ccc23)C2(CC2)C1]

¹H NMR (400 MHz, DMSO-d₆) δ 11.40 (s, 1H), 10.59-10.52 (m, 1H), 7.55 (d, J=8.5 Hz, 1H), 7.30 (q, J=3.0 Hz, 1H), 6.27 (ddd, J=10.1, 3.5, 1.9 Hz, 1H), 5.69 (dt, J=7.0, 3.3 Hz, 1H), 4.23 (dd, J=11.8, 3.2 Hz, 2H), 3.63 (dt, J=6.6, 3.3 Hz, 2H), 3.57 (d, J=19.1 Hz, 2H), 3.21-3.09 (m, 2H), 2.81 (dt, J=23.9, 6.8 Hz, 2H), 2.67 (t, J=6.3 Hz, 2H), 2.00 (d, J=7.2 Hz, 1H), 0.81-0.76 (m, 4H).

MS(ESI+) m/z 390 (M+H)⁺

Example 303: Synthesis of N-(4-(5-(2-cyanoacetyl)-5-azaspiro[2.5]oct-7-en-8-yl)-1H-pyrrolo[2,3-b]pyridin-6-yl)cyclopropanecarboxamide

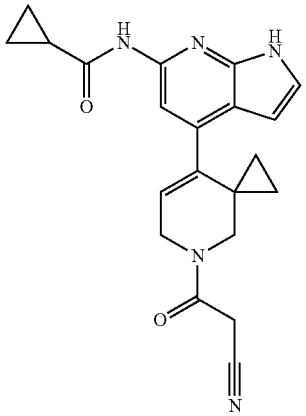 [SMILES: N#CCC(=O)N1CC=C(c2cc(NC(=O)C3CC3)nc3[nH]ccc23)C2(CC2)C1]

$^1$H NMR (400 MHz, DMSO-$d_6$) δ 11.44 (s, 1H), 10.53 (s, 1H), 7.86 (d, J=2.4 Hz, 1H), 7.35 (t, J=3.0 Hz, 1H), 6.55 (dd, J=3.5, 1.8 Hz, 1H), 6.31 (d, J=26.1 Hz, 1H), 4.21-4.17 (m, 1H), 4.13 (d, J=23.2 Hz, 3H), 3.72 (t, J=5.6 Hz, 1H), 3.59 (t, J=5.5 Hz, 1H), 2.64 (s, 2H), 2.55 (s, 1H), 2.01 (d, J=4.8 Hz, 1H), 0.83-0.77 (m, 4H).

MS(ESI+) m/z 376 (M+H)$^+$

Example 304: Synthesis of (S)—N-(4-(1-(2-cyanoacetyl)-3-methyl-1,2,3,6-tetrahydropyridin-4-yl)-1H-pyrrolo[2,3-b]pyridin-6-yl)cyclopropanecarboxamide

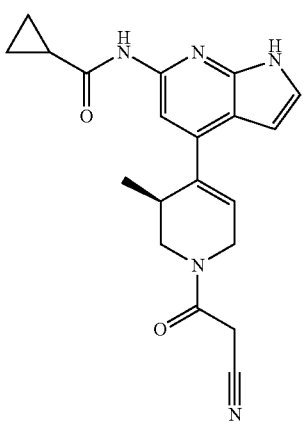 [SMILES: C[C@@H]1CN(C(=O)CC#N)CC=C1c1cc(NC(=O)C2CC2)nc2[nH]ccc12]

$^1$H NMR (400 MHz, DMSO-$d_6$) δ 11.44 (s, 1H), 10.57 (s, 1H), 7.84 (d, J=10.2 Hz, 1H), 7.34 (d, J=3.1 Hz, 1H), 6.48 (dd, J=1.8, 3.7 Hz, 1H), 6.17-6.03 (m, 1H), 4.31-4.01 (m, 6H), 3.96-3.62 (m, 2H), 3.02 (m J=36.6 Hz, 1H), 2.02 (s, 1H), 0.88 (s, 3H), 0.84-0.73 (m, 4H).

MS(ESI+) m/z 364 (M+H)$^+$

Example 305: Synthesis of ((R)—N-(4-(1-(2-cyanoacetyl)-3-methyl-1,2,3,6-tetrahydropyridin-4-yl)-1H-pyrrolo[2,3-b]pyridin-6-yl)cyclopropanecarboxamide)

$^1$H NMR (400 MHz, DMSO-$d_6$) δ 11.44 (s, 1H), 10.57 (s, 1H), 7.84 (d, J=10.2 Hz, 1H), 7.34 (d, J=3.1 Hz, 1H), 6.48 (dd, J=1.8, 3.7 Hz, 1H), 6.17-6.03 (m, 1H), 4.31-4.01 (m, 6H), 3.96-3.62 (m, 2H), 3.02 (m, J=36.6 Hz, 1H), 2.02 (s, 1H), 0.88 (s, 3H), 0.84-0.73 (m, 4H).

MS(ESI+) m/z 364 (M+H)$^+$

Example 306: Synthesis of (N-(4-(3-methyl-1-(2-methylthiazole-5-carbonyl)-1,2,3,6-tetrahydropyridin-4-yl)-1H-pyrrolo[2,3-b]pyridin-6-yl)cyclopropanecarboxamide)

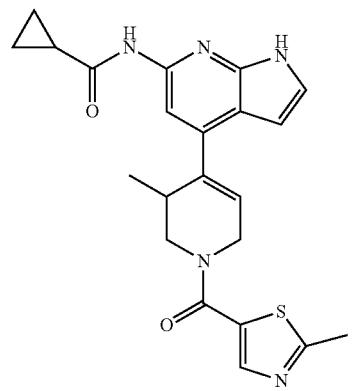 [SMILES: Cc1ncc(C(=O)N2CC=C(c3cc(NC(=O)C4CC4)nc4[nH]ccc34)C(C)C2)s1]

$^1$H NMR (400 MHz, DMSO-$d_6$) δ 11.43 (s, 1H), 10.55 (s, 1H), 8.03 (s, 1H), 7.85 (s, 1H), 7.33 (d, J=3.5 Hz, 1H), 6.51 (s, 1H), 6.12 (s, 1H), 4.51 (d, J=18.2 Hz, 1H), 4.25 (s, 1H), 3.83 (s, 2H), 3.07 (s, 1H), 2.70 (d, J=2.8 Hz, 3H), 2.01 (d, J=8.8 Hz, 1H), 0.90 (d, J=6.7 Hz, 3H), 0.86-0.74 (m, 4H).

MS(ESI+) m/z 422 (M+H)$^+$

Example 307: Synthesis of N-(4-(1-(2,4-dimethyl-thiazole-5-carbonyl)-3-methyl-1,2,3,6-tetrahydropyridin-4-yl)-1H-pyrrolo[2,3-b]pyridin-6-yl)cyclopropanecarboxamide

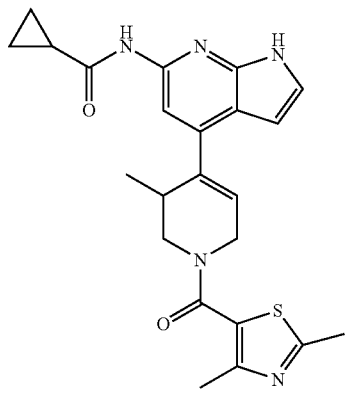 [SMILES: Cc1nc(C)c(C(=O)N2CC=C(c3cc(NC(=O)C4CC4)nc4[nH]ccc34)C(C)C2)s1]

¹H NMR (400 MHz, DMSO-d₆) δ 11.43 (s, 1H), 10.55 (s, 1H), 7.83 (s, 1H), 6.48 (s, 1H), 6.11 (s, 1H), 4.41 (s, 1H), 4.09 (d, J=18.6 Hz, 1H), 3.66 (s, 2H), 3.01 (s, 1H), 2.64 (d, J=3.3 Hz, 3H), 2.32 (d, J=3.4 Hz, 3H), 2.02 (s, 1H), 0.86 (d, J=6.5 Hz, 3H), 0.78 (d, J=9.6 Hz, 4H).

MS(ESI+) m/z 436 (M+H)⁺

Example 308: Synthesis of N-(4-(3-methyl-1-(4-methylthiazole-5-carbonyl)-1,2,3,6-tetrahydropyridin-4-yl)-1H-pyrrolo[2,3-b]pyridin-6-yl)cyclopropanecarboxamide

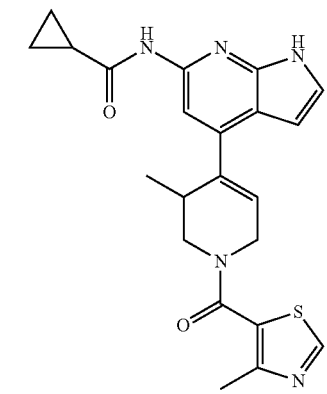

¹H NMR (400 MHz, DMSO-d₆) δ 11.43 (s, 1H), 10.55 (s, 1H), 9.12 (d, J=2.1 Hz, 1H), 7.84 (d, J=2.6 Hz, 1H), 7.33 (q, J=2.9 Hz, 1H), 6.48 (dt, J=4.2, 2.0 Hz, 1H), 6.12 (s, 1H), 4.51 (s, 1H), 4.09 (d, J=18.1 Hz, 1H), 3.74-3.59 (m, 1H), 3.01 (s, 1H), 2.41 (d, J=2.3 Hz, 3H), 2.02 (tt, J=8.8, 5.2 Hz, 1H), 0.94-0.83 (m, 3H), 0.82-0.74 (m, 4H).

MS(ESI+) m/z 422 (M+H)⁺

Example 309: Synthesis of N-(4-(1-(2-fluoroisonicotinoyl)-3-methyl-1,2,3,6-tetrahydropyridin-4-yl)-1H-pyrrolo[2,3-b]pyridin-6-yl)cyclopropanecarboxamide

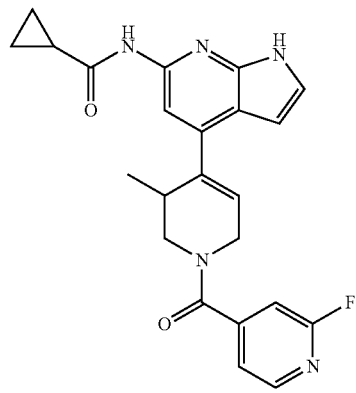 [SMILES: CC1CN(C(=O)c2ccnc(F)c2)CC=C1c1cc(NC(=O)C2CC2)nc2[nH]ccc12]

¹H NMR (400 MHz, DMSO-d₆) δ 11.43 (s, 1H), 10.55 (s, 1H), 8.37 (d, J=5.1 Hz, 1H), 7.83 (d, J=11.6 Hz, 1H), 7.44 (s, 1H), 7.33 (s, 2H), 6.50 (d, J=14.2 Hz, 1H), 6.08 (d, J=71.4 Hz, 1H), 4.54 (d, J=19.5 Hz, 1H), 4.11 (d, J=49.6 Hz, 2H), 3.60 (d, J=13.1 Hz, 1H), 2.02 (s, 1H), 0.95 (d, J=6.8 Hz, 1H), 0.84-0.73 (m, 6H).

MS(ESI+) m/z 420 (M+H)⁺

Example 310: Synthesis of N-(4-(1-(2-chloroisonicotinoyl)-3-methyl-1,2,3,6-tetrahydropyridin-4-yl)-1H-pyrrolo[2,3-b]pyridin-6-yl)cyclopropanecarboxamide

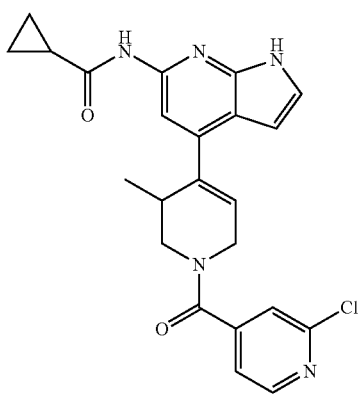 [SMILES: CC1CN(C(=O)c2ccnc(Cl)c2)CC=C1c1cc(NC(=O)C2CC2)nc2[nH]ccc12]

¹H NMR (400 MHz, DMSO-d₆) δ 11.43 (s, 1H), 10.55 (s, 1H), 8.54 (d, J=5.0 Hz, 1H), 7.83 (d, J=12.1 Hz, 1H), 7.65 (d, J=7.4 Hz, 1H), 7.51 (s, 1H), 7.32 (d, J=8.5 Hz, 1H), 6.50 (d, J=11.5 Hz, 1H), 6.08 (d, J=67.3 Hz, 1H), 4.58-4.10 (m, 1H), 4.05 (s, 1H), 3.60 (d, J=12.9 Hz, 1H), 3.02 (d, J=41.1 Hz, 1H), 2.01 (s, 1H), 0.94 (d, J=6.6 Hz, 1H), 0.86-0.74 (m, 6H).

MS(ESI+) m/z 436, 438 (M+H)⁺

Example 311: Synthesis of N-(4-(1-(3,4-difluorobenzoyl)-3-methyl-1,2,3,6-tetrahydropyridin-4-yl)-1H-pyrrolo[2,3-b]pyridin-6-yl)cyclopropanecarboxamide

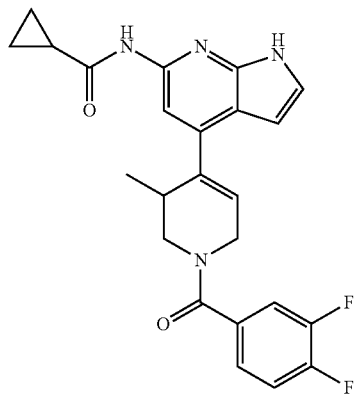 [SMILES: CC1CN(C(=O)c2ccc(F)c(F)c2)CC=C1c1cc(NC(=O)C2CC2)nc2[nH]ccc12]

¹H NMR (400 MHz, DMSO-d₆) δ 11.42 (s, 1H), 10.54 (s, 1H), 7.83 (s, 1H), 7.67-7.49 (m, 3H), 7.33 (s, 2H), 6.50 (s, 1H), 4.12 (s, 2H), 3.63 (d, J=12.5 Hz, 1H), 3.01 (s, 1H), 2.01 (s, 1H), 0.92 (s, 1H), 0.86-0.74 (m, 6H).

MS(ESI+) m/z 437 (M+H)⁺

Example 312: Synthesis of N-(4-(1-(3-fluoro-4-methoxybenzoyl)-3-methyl-1,2,3,6-tetrahydropyridin-4-yl)-1H-pyrrolo[2,3-b]pyridin-6-yl)cyclopropanecarboxamide

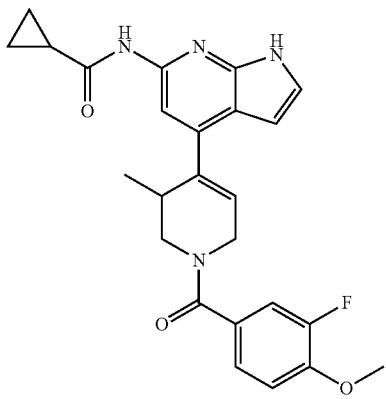 [SMILES: COc1ccc(C(=O)N2CC=C(c3cc(NC(=O)C4CC4)nc4[nH]ccc34)C(C)C2)cc1F]

¹H NMR (400 MHz, DMSO-d₆) δ 11.42 (s, 1H), 10.54 (s, 1H), 7.83 (s, 1H), 7.39-7.23 (m, 4H), 6.49 (s, 1H), 6.10 (s, 1H), 4.13 (d, J=18.7 Hz, 1H), 3.65 (d, J=11.9 Hz, 1H), 3.02 (s, 1H), 2.02 (s, 1H), 0.92-0.68 (m, 7H).

MS(ESI+) m/z 449 (M+H)⁺

Example 313: Synthesis of N-(4-(3-methyl-1-(1H-pyrrole-2-carbonyl)-1,2,3,6-tetrahydropyridin-4-yl)-1H-pyrrolo[2,3-b]pyridin-6-yl)cyclopropanecarboxamide

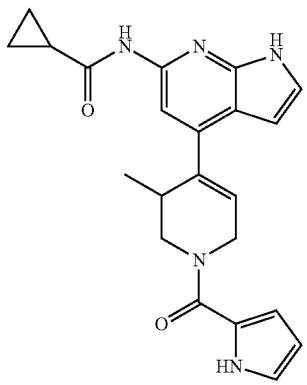 [SMILES: CC1CN(C(=O)c2ccc[nH]2)CC=C1c1cc(NC(=O)C2CC2)nc2[nH]ccc12]

¹H NMR (400 MHz, DMSO-d₆) δ 11.51 (s, 1H), 11.42 (s, 1H), 10.55 (s, 1H), 7.86 (s, 1H), 7.32 (s, 1H), 6.91 (s, 1H), 6.62 (s, 1H), 6.56-6.47 (m, 1H), 6.16 (s, 2H), 4.59 (d, J=19.0 Hz, 1H), 4.30 (d, J=19.2 Hz, 1H), 4.08-3.96 (m, 1H), 3.06 (s, 1H), 2.02 (s, 1H), 0.92 (d, J=6.7 Hz, 3H), 0.79 (s, 4H).

MS(ESI+) m/z 390 (M+H)⁺

Example 314: Synthesis of N-(4-(1-(3-fluoroisonicotinoyl)-3-methyl-1,2,3,6-tetrahydropyridin-4-yl)-1H-pyrrolo[2,3-b]pyridin-6-yl)cyclopropanecarboxamide

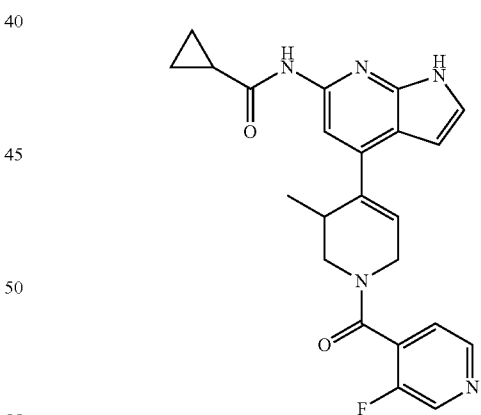

¹H NMR (400 MHz, DMSO-d₆) δ 11.43 (s, 1H), 10.55 (s, 1H), 8.74 (s, 1H), 8.62-8.47 (m, 1H), 7.84 (d, J=14.4 Hz, 1H), 7.57 (d, J=5.3 Hz, 1H), 7.34 (d, J=5.1 Hz, 1H), 6.49 (d, J=10.0 Hz, 1H), 6.09 (d, J=71.3 Hz, 1H), 4.17 (t, J=19.7 Hz, 1H), 3.99 (s, 1H), 3.60 (d, J=13.8 Hz, 1H), 3.01 (d, J=56.3 Hz, 1H), 2.02 (s, 1H), 0.95 (d, J=6.8 Hz, 1H), 0.79 (d, J=7.4 Hz, 6H).

MS(ESI+) m/z 420 (M+H)⁺

Example 315: Synthesis of N-(4-(1-(3-(2-(3,5-di-oxomorpholino)ethyl)benzoyl)-3-methyl-1,2,3,6-tetrahydropyridin-4-yl)-1H-pyrrolo[2,3-b]pyridin-6-yl)cyclopropanecarboxamide

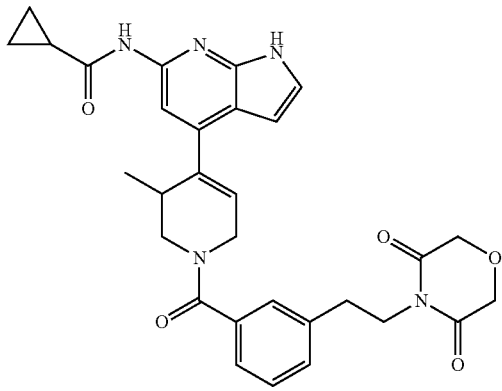 [SMILES: CC1CN(C(=O)c2cccc(CCN3C(=O)COCC3=O)c2)CC=C1c1cc(NC(=O)C2CC2)nc2[nH]ccc12]

$^1$H NMR (400 MHz, DMSO-d$_6$) δ 11.42 (s, 1H), 10.54 (s, 1H), 7.81 (d, J=17.3 Hz, 1H), 7.40 (t, J=7.7 Hz, 1H), 7.30 (d, J=9.5 Hz, 4H), 6.50 (s, 1H), 6.09 (d, J=71.6 Hz, 1H), 4.05 (d, J=28.5 Hz, 2H), 3.91 (t, J=7.4 Hz, 3H), 3.62 (dd, J=13.1, 4.2 Hz, 1H), 3.38 (q, J=7.0 Hz, 2H), 2.98 (s, 1H), 2.84 (t, J=7.4 Hz, 2H), 2.01 (d, J=5.1 Hz, 1H), 1.09 (t, J=7.0 Hz, 2H), 0.93 (s, 1H), 0.89-0.69 (m, 7H).

MS(ESI+) m/z 542 (M+H)$^+$

Example 316: Synthesis of N-(4-(3-methyl-1-(3-(phenylamino)benzoyl)-1,2,3,6-tetrahydropyridin-4-yl)-1H-pyrrolo[2,3-b]pyridin-6-yl)cyclopropanecarboxamide

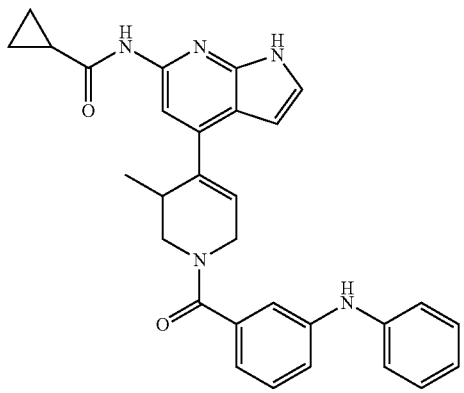 [SMILES: CC1CN(C(=O)c2cccc(Nc3ccccc3)c2)CC=C1c1cc(NC(=O)C2CC2)nc2[nH]ccc12]

$^1$H NMR (400 MHz, DMSO-d$_6$) δ 11.42 (s, 1H), 10.55 (s, 1H), 9.20 (s, 1H), 8.18 (d, J=4.9 Hz, 1H), 7.84 (s, 1H), 7.58 (ddd, J=8.7, 7.1, 2.0 Hz, 1H), 7.37-7.29 (m, 2H), 6.94 (d, J=7.6 Hz, 1H), 6.84 (d, J=8.3 Hz, 1H), 6.76 (dd, J=7.0, 4.9 Hz, 1H), 6.49 (s, 1H), 4.46 (s, 1H), 4.27-4.05 (m, 2H), 3.67 (s, 1H), 3.04 (s, 1H), 2.02 (s, 1H), 0.88-0.69 (m, 7H)

MS(ESI+) m/z 492 (M+H)$^+$

Example 317: Synthesis of (N-(4-(1-(6-(2,4-difluorophenyl)-2-oxo-1,2-dihydropyridine-3-carbonyl)-3-methyl-1,2,3,6-tetrahydropyridin-4-yl)-1H-pyrrolo[2,3-b]pyridin-6-yl)cyclopropanecarboxamide)

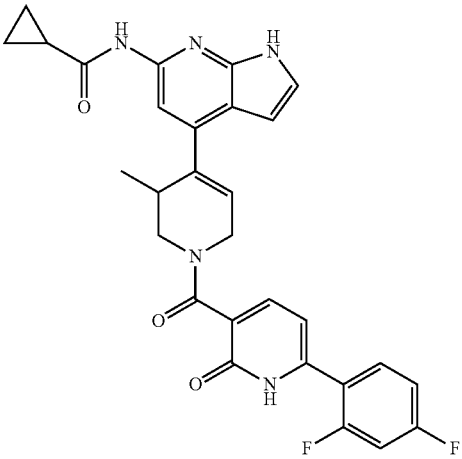 [SMILES: CC1CN(C(=O)c2ccc(-c3ccc(F)cc3F)[nH]c2=O)CC=C1c1cc(NC(=O)C2CC2)nc2[nH]ccc12]

$^1$H NMR (400 MHz, DMSO-d$_6$) δ 11.42 (s, 1H), 8.37 (d, J=7.5 Hz, 1H), 7.84-7.75 (m, 2H), 7.52-7.41 (m, 2H), 7.36-7.20 (m, 3H), 6.88 (dd, J=7.6, 1.5 Hz, 1H), 4.20-4.05 (m, 1H), 4.01 (p, J=6.6 Hz, 1H), 3.49 (dt, J=14.8, 6.9 Hz, 1H), 3.15 (q, J=9.1 Hz, 1H), 2.07-1.99 (m, 1H), 1.94 (q, J=12.1, 10.2 Hz, 1H), 1.25-1.17 (m, 3H), 0.81 (td, J=14.7, 12.6, 5.0 Hz, 4H).

MS(ESI+) m/z 530 (M+H)$^+$

Example 318: Synthesis of methyl 1-(4-(6-(cyclopropanecarboxamido)-1H-pyrrolo[2,3-b]pyridin-4-yl)-3-methyl-1,2,3,6-tetrahydropyridine-1-carbonyl)cyclobutane-1-carboxylate

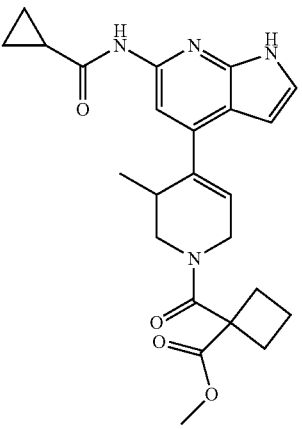 [SMILES: COC(=O)C1(C(=O)N2CC=C(c3cc(NC(=O)C4CC4)nc4[nH]ccc34)C(C)C2)CCC1]

$^1$H NMR (400 MHz, DMSO-d$_6$) δ 11.43 (s, 1H), 10.54 (s, 1H), 7.82 (d, J=3.4 Hz, 1H), 7.39-7.26 (m, 1H), 6.45 (d, J=15.8 Hz, 1H), 6.06 (d, J=43.3 Hz, 1H), 4.32-4.00 (m, 2H), 2.93 (s, 1H), 2.07-1.90 (m, 3H), 1.82 (s, 1H), 1.31-1.19 (m, 1H), 0.98-0.69 (m, 10H).

MS(ESI+) m/z 437 (M+H)$^+$

Example 319: Synthesis of methyl 1-(4-(6-(cyclopropanecarboxamido)-1H-pyrrolo[2,3-b]pyridin-4-yl)-3-methyl-1,2,3,6-tetrahydropyridine-1-carbonyl)cyclopropane-1-carboxylate

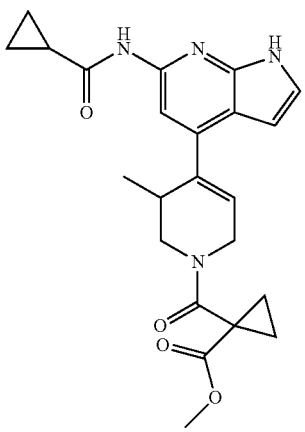 [SMILES: COC(=O)C1(C(=O)N2CC=C(c3cc(NC(=O)C4CC4)nc4[nH]ccc34)C(C)C2)CC1]

$^1$H NMR (400 MHz, DMSO-d$_6$) δ 11.42 (s, 1H), 10.55 (s, 1H), 7.84 (d, J=7.6 Hz, 1H), 7.41-7.26 (m, 1H), 6.48 (s, 1H), 6.11 (d, J=6.0 Hz, 1H), 4.28 (t, J=20.9 Hz, 2H), 4.06 (d, J=15.8 Hz, 2H), 3.68 (d, J=8.6 Hz, 5H), 2.99 (d, J=27.0 Hz, 1H), 2.02 (s, 1H), 1.40 (q, J=11.2, 7.4 Hz, 4H), 1.32-1.21 (m, 2H), 0.88 (t, J=7.4 Hz, 4H), 0.84-0.74 (m, 4H).

MS(ESI+) m/z 423 (M+H)$^+$

Example 320: Synthesis of methyl 3-(4-(6-(cyclopropanecarboxamido)-1H-pyrrolo[2,3-b]pyridin-4-yl)-3-methyl-3,6-dihydropyridin-1(2H)-yl)-2-methyl-3-oxopropanoate

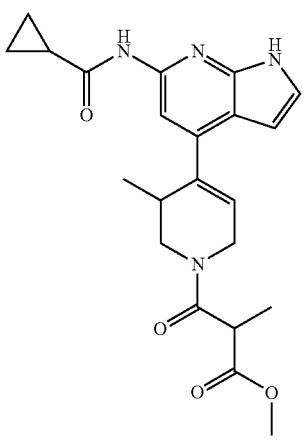 [SMILES: COC(=O)C(C)C(=O)N1CC=C(c2cc(NC(=O)C3CC3)nc3[nH]ccc23)C(C)C1]

$^1$H NMR (400 MHz, DMSO-d$_6$) δ 11.43 (s, 1H), 10.55 (s, 1H), 7.85 (s, 1H), 7.34 (s, 1H), 6.48 (d, J=8.4 Hz, 1H), 6.12 (d, J=16.1 Hz, 1H), 4.21-3.97 (m, 6H), 3.68 (d, J=19.0 Hz, 1H), 3.00 (s, 1H), 2.03 (s, 1H), 1.26 (dd, J=7.6, 4.2 Hz, 4H), 0.87-0.74 (m, 7H).

MS(ESI+) m/z 411 (M+H)$^+$

Example 321: Synthesis of N-(4-(1-(6-(tert-butyl)-2-oxo-1,2-dihydropyridine-3-carbonyl)-3-methyl-1,2,3,6-tetrahydropyridin-4-yl)-1H-pyrrolo[2,3-b]pyridin-6-yl)cyclopropanecarboxamide

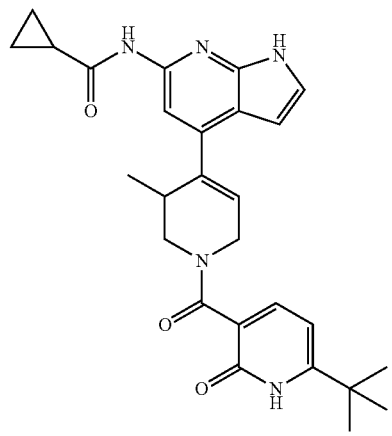 [SMILES: CC1CN(C(=O)c2ccc(C(C)(C)C)[nH]c2=O)CC=C1c1cc(NC(=O)C2CC2)nc2[nH]ccc12]

$^1$H NMR (400 MHz, DMSO-d$_6$) δ 11.62 (s, 1H), 11.41 (s, 1H), 10.54 (s, 1H), 7.83 (d, J=12.1 Hz, 1H), 7.48 (t, J=6.5 Hz, 1H), 7.36-7.25 (m, 1H), 6.48 (s, 1H), 6.09 (d, J=37.7 Hz, 2H), 4.26 (dd, J=94.3, 20.9 Hz, 1H), 4.05 (s, 1H), 3.60-3.41 (m, 1H), 3.26 (dd, J=13.0, 5.2 Hz, 1H), 3.04 (d, J=24.5 Hz, 1H), 2.00 (d, J=13.7 Hz, 1H), 1.28 (s, 9H), 0.84-0.72 (m, 7H).

MS(ESI+) m/z 474 (M+H)$^+$

Example 322: Synthesis of N-(4-(1-(6-(4-fluorophenyl)-2-oxo-1,2-dihydropyridine-3-carbonyl)-3-methyl-1,2,3,6-tetrahydropyridin-4-yl)-1H-pyrrolo[2,3-b]pyridin-6-yl)cyclopropanecarboxamide

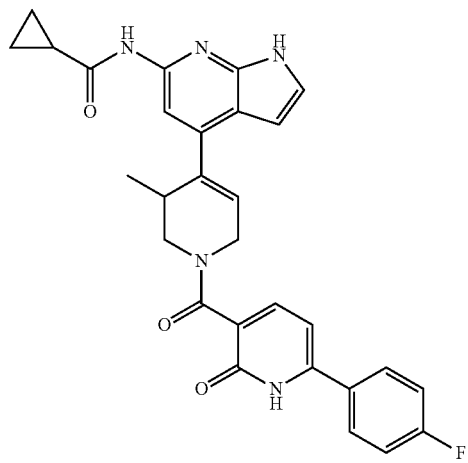 [SMILES: CC1CN(C(=O)c2ccc(-c3ccc(F)cc3)[nH]c2=O)CC=C1c1cc(NC(=O)C2CC2)nc2[nH]ccc12]

$^1$H NMR (400 MHz, DMSO-d$_6$) δ 12.21 (s, 1H), 11.42 (s, 1H), 10.54 (s, 1H), 8.00-7.80 (m, 3H), 7.64 (d, J=7.4 Hz, 1H), 7.35 (t, J=8.6 Hz, 3H), 6.49 (t, J=2.0 Hz, 1H), 6.10 (d, J=44.8 Hz, 1H), 4.26-4.03 (m, 2H), 3.69-3.44 (m, 2H), 3.05 (s, 1H), 2.02 (s, 1H), 0.91-0.70 (m, 7H).

MS(ESI+) m/z 512 (M+H)$^+$

Example 323: Synthesis of N-(4-(1-(3-fluoro-4-((2-morpholinoethyl)amino)benzoyl)-3-methyl-1,2,3,6-tetrahydropyridin-4-yl)-1H-pyrrolo[2,3-b]pyridin-6-yl)cyclopropanecarboxamide

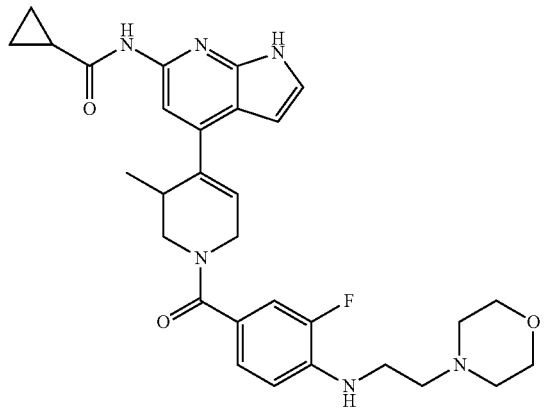 [SMILES: CC1CN(C(=O)c2ccc(NCCN3CCOCC3)c(F)c2)CC=C1c1cc(NC(=O)C2CC2)nc2[nH]ccc12]

¹H NMR (400 MHz, DMSO-d₆) δ 11.42 (s, 1H), 10.54 (s, 1H), 7.43-7.28 (m, 1H), 7.25-7.12 (m, 2H), 6.78 (t, J=8.6 Hz, 1H), 6.56-6.44 (m, 1H), 6.10 (s, 1H), 5.64 (s, 1H), 4.42-4.07 (m, 2H), 3.69 (s, 2H), 3.64-3.52 (m, 4H), 3.26 (t, J=6.2 Hz, 2H), 3.03 (s, 1H), 2.43 (s, 2H), 2.11-1.94 (m, 1H), 0.85 (d, J=6.8 Hz, 4H), 0.83-0.74 (m, 4H).

MS(ESI+) m/z 547 (M+H)⁺

Example 324: Synthesis of N-(4-(1-(5-bromonicotinoyl)-3-methyl-1,2,3,6-tetrahydropyridin-4-yl)-1H-pyrrolo[2,3-b]pyridin-6-yl)cyclopropanecarboxamide

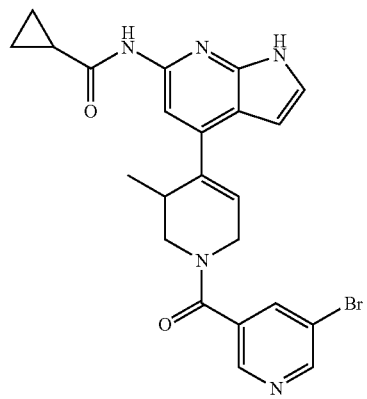 [SMILES: CC1CN(C(=O)c2cncc(Br)c2)CC=C1c1cc(NC(=O)C2CC2)nc2[nH]ccc12]

¹H NMR (400 MHz, DMSO-d₆) δ 11.43 (s, 1H), 10.55 (s, 1H), 8.82 (d, J=2.4 Hz, 1H), 8.68 (d, J=4.6 Hz, 1H), 8.22 (d, J=8.6 Hz, 1H), 7.84 (d, J=8.6 Hz, 1H), 7.33 (s, 1H), 6.50 (d, J=12.8 Hz, 1H), 6.09 (d, J=63.9 Hz, 1H), 4.16 (d, J=15.0 Hz, 2H), 3.64 (s, 1H), 3.36 (d, J=7.5 Hz, 1H), 3.04 (d, J=25.2 Hz, 1H), 2.00 (d, J=14.1 Hz, 1H), 0.89-0.71 (m, 7H).

MS(ESI+) m/z 480, 482 (M+H)⁺

Example 325: Synthesis of N-(4-(1-(2,3-dihydrobenzo[b][1,4]dioxine-6-carbonyl)-3-methyl-1,2,3,6-tetrahydropyridin-4-yl)-1H-pyrrolo[2,3-b]pyridin-6-yl)cyclopropanecarboxamide

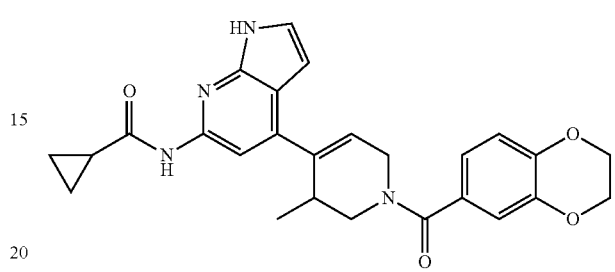

¹H NMR (400 MHz, DMSO-d₆) δ 11.42 (s, 1H), 10.54 (s, 1H), 7.82 (s, 1H), 7.35-7.25 (m, 1H), 7.00-6.88 (m, 3H), 6.49 (s, 1H), 6.10 (s, 1H), 4.27 (s, 4H), 4.17-4.04 (m, 1H), 3.72-3.57 (m, 1H), 3.00 (s, 1H), 2.01 (td, J=7.8, 7.4, 3.7 Hz, 1H), 0.85 (s, 3H), 0.84-0.76 (m, 4H).

MS(ESI+) m/z 459 (M+H)⁺

Example 326: Synthesis of N-(4-(1-(benzo[d][1,3]dioxole-5-carbonyl)-3-methyl-1,2,3,6-tetrahydropyridin-4-yl)-1H-pyrrolo[2,3-b]pyridin-6-yl)cyclopropanecarboxamide

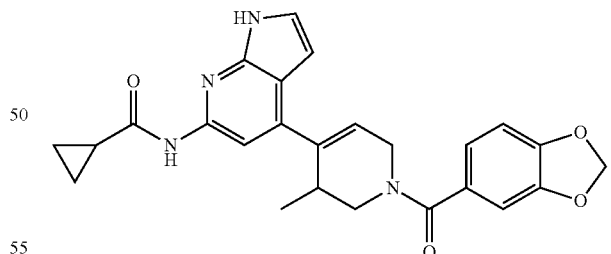

¹H NMR (400 MHz, DMSO-d₆) δ 11.41 (s, 1H), 10.54 (s, 1H), 7.82 (s, 1H), 7.32 (t, J=3.0 Hz, 1H), 7.04 (s, 1H), 6.98 (d, J=2.4 Hz, 2H), 6.49 (d, J=3.4 Hz, 1H), 6.09 (s, 3H), 4.18-4.02 (m, 1H), 3.69-3.57 (m, 1H), 3.01 (s, 1H), 2.01 (td, J=7.4, 3.6 Hz, 1H), 0.84 (s, 3H), 0.81-0.75 (m, 4H).

MS(ESI+) m/z 445 (M+H)⁺

Example 327: Synthesis of N-(4-(1-(1H-indole-6-carbonyl)-3-methyl-1,2,3,6-tetrahydropyridin-4-yl)-1H-pyrrolo[2,3-b]pyridin-6-yl)cyclopropanecarboxamide

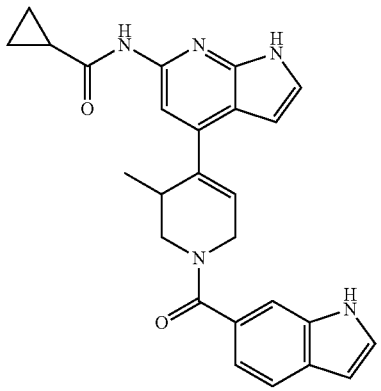 [SMILES: CC1CN(C(=O)c2ccc3cc[nH]c3c2)CC=C1c1cc(NC(=O)C2CC2)nc2[nH]ccc12]

$^1$H NMR (400 MHz, DMSO-d$_6$) δ 11.42 (d, J=2.8 Hz, 1H), 11.31 (s, 1H), 10.55 (s, 1H), 7.88-7.82 (m, 1H), 7.61 (d, J=8.1 Hz, 1H), 7.51 (d, J=1.4 Hz, 1H), 7.47 (t, J=2.7 Hz, 1H), 7.32 (t, J=3.0 Hz, 1H), 7.10 (dd, J=8.1, 1.5 Hz, 1H), 6.49 (t, J=2.5 Hz, 2H), 6.12 (s, 1H), 4.22-4.11 (m, 1H), 3.75-3.65 (m, 1H), 3.03 (s, 1H), 2.02 (td, J=8.6, 7.9, 4.2 Hz, 1H), 0.88 (s, 3H), 0.83-0.74 (m, 4H).

MS(ESI+) m/z 440 (M+H)$^+$

Example 328: Synthesis of N-(4-(3-methyl-1-(1H-pyrrolo[2,3-b]pyridine-4-carbonyl)-1,2,3,6-tetrahydropyridin-4-yl)-1H-pyrrolo[2,3-b]pyridin-6-yl)cyclopropanecarboxamide

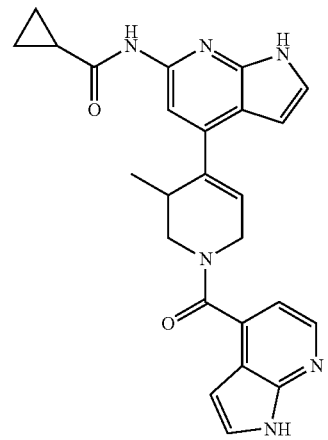 [SMILES: CC1CN(C(=O)c2ccnc3[nH]ccc23)CC=C1c1cc(NC(=O)C2CC2)nc2[nH]ccc12]

$^1$H NMR (400 MHz, DMSO-d$_6$) δ 11.42 (s, 1H), 10.54 (s, 1H), 7.83 (s, 1H), 7.32 (t, J=3.0 Hz, 1H), 7.10-6.96 (m, 3H), 6.49 (s, 1H), 6.11 (s, 1H), 4.13 (d, J=18.8 Hz, 1H), 3.80 (d, J=4.3 Hz, 6H), 3.66 (dd, J=12.9, 4.2 Hz, 1H), 3.02 (s, 1H), 2.02 (dq, J=8.6, 4.2, 3.3 Hz, 1H), 0.95-0.84 (m, 3H), 0.84-0.70 (m, 4H).

MS(ESI+) m/z 441 (M+H)$^+$

Example 329: Synthesis of N-(4-(1-(3,4-dimethoxybenzoyl)-3-methyl-1,2,3,6-tetrahydropyridin-4-yl)-1H-pyrrolo[2,3-b]pyridin-6-yl)cyclopropanecarboxamide

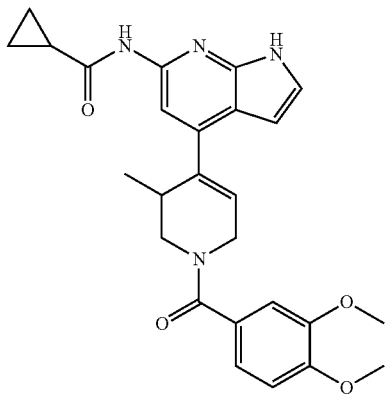 [SMILES: COc1ccc(C(=O)N2CC=C(c3cc(NC(=O)C4CC4)nc4[nH]ccc34)C(C)C2)cc1OC]

$^1$H NMR (400 MHz, DMSO-d$_6$) δ 11.42 (s, 1H), 10.54 (s, 1H), 7.83 (s, 1H), 7.39 (t, J=7.9 Hz, 1H), 7.32 (s, 1H), 7.07-6.96 (m, 3H), 6.49 (s, 1H), 4.17-3.99 (m, 2H), 3.80 (s, 3H), 3.62 (dd, J=13.0, 4.1 Hz, 1H), 2.98 (s, 1H), 2.06-1.98 (m, 1H), 0.92 (s, 1H), 0.86-0.72 (m, 6H).

MS(ESI+) m/z 461 (M+H)$^+$

Example 330: Synthesis of N-(4-(1-(3-methoxybenzoyl)-3-methyl-1,2,3,6-tetrahydropyridin-4-yl)-1H-pyrrolo[2,3-b]pyridin-6-yl)cyclopropanecarboxamide

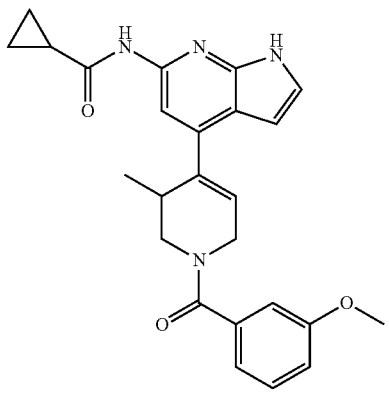 [SMILES: COc1cccc(C(=O)N2CC=C(c3cc(NC(=O)C4CC4)nc4[nH]ccc34)C(C)C2)c1]

$^1$H NMR (400 MHz, DMSO-d$_6$) δ 11.42 (s, 1H), 10.54 (s, 1H), 7.83 (s, 1H), 7.39 (t, J=7.9 Hz, 1H), 7.32 (s, 1H), 7.06-7.01 (m, 2H), 6.99 (d, J=4.8 Hz, 1H), 6.49 (s, 1H), 4.19-4.00 (m, 2H), 3.80 (s, 3H), 3.62 (dd, J=13.0, 4.1 Hz, 1H), 2.98 (s, 1H), 2.02 (td, J=7.7, 3.9 Hz, 1H), 0.92 (s, 1H), 0.86-0.74 (m, 6H).

MS(ESI+) m/z 431 (M+H)$^+$

Example 331: Synthesis of N-(4-(3-methyl-1-(4-nitrobenzoyl)-1,2,3,6-tetrahydropyridin-4-yl)-1H-pyrrolo[2,3-b]pyridin-6-yl)cyclopropanecarboxamide

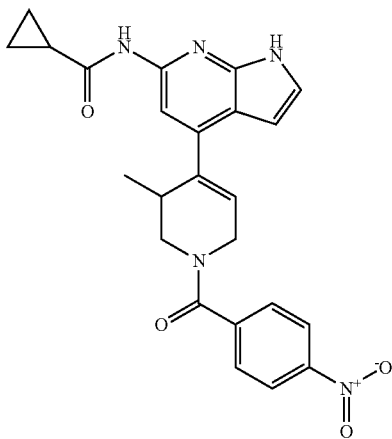

$^1$H NMR (400 MHz, DMSO-d$_6$) δ 11.43 (s, 1H), 10.55 (s, 1H), 8.32 (dd, J=8.5, 6.1 Hz, 3H), 7.84 (d, J=9.3 Hz, 1H), 7.75 (d, J=8.1 Hz, 2H), 7.32 (d, J=9.2 Hz, 1H), 6.50 (d, J=17.8 Hz, 1H), 6.09 (d, J=79.2 Hz, 1H), 4.37 (dd, J=155.6, 19.8 Hz, 1H), 4.13-3.94 (m, 2H), 3.62 (d, J=11.6 Hz, 1H), 3.04 (d, J=44.3 Hz, 1H), 2.02 (dq, J=8.0, 3.9, 2.8 Hz, 1H), 0.95 (d, J=6.8 Hz, 1H), 0.83-0.74 (m, 6H).

MS(ESI+) m/z 446 (M+H)$^+$

Example 332: Synthesis of N-(4-(1-(3-acetylbenzoyl)-3-methyl-1,2,3,6-tetrahydropyridin-4-yl)-1H-pyrrolo[2,3-b]pyridin-6-yl)cyclopropanecarboxamide

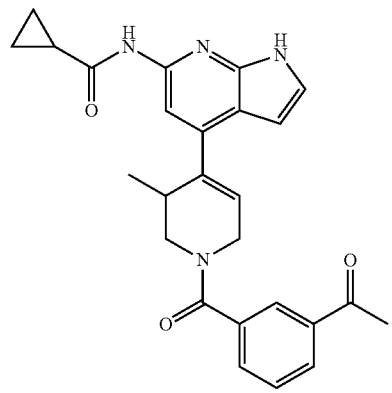 [SMILES: CC(=O)c1cccc(C(=O)N2CC=C(c3cc(NC(=O)C4CC4)nc4[nH]ccc34)C(C)C2)c1]

$^1$H NMR (400 MHz, DMSO-d$_6$) δ 11.42 (s, 1H), 10.55 (s, 1H), 8.08-8.03 (m, 1H), 8.01 (s, 1H), 7.84 (s, 1H), 7.74 (d, J=7.5 Hz, 1H), 7.64 (t, J=7.8 Hz, 1H), 7.32 (s, 1H), 6.50 (s, 1H), 6.10 (d, J=74.1 Hz, 1H), 4.65-4.15 (m, 1H), 4.08 (d, J=33.0 Hz, 1H), 3.64 (d, J=13.1 Hz, 1H), 3.03 (d, J=33.6 Hz, 1H), 2.63 (d, J=1.4 Hz, 3H), 2.02 (dd, J=8.6, 4.2 Hz, 1H), 0.95 (s, 1H), 0.85-0.73 (m, 6H).

MS(ESI+) m/z 443 (M+H)$^+$

Example 333: Synthesis of N-(4-(1-(4-chlorobenzoyl)-3-methyl-1,2,3,6-tetrahydropyridin-4-yl)-1H-pyrrolo[2,3-b]pyridin-6-yl)cyclopropanecarboxamide

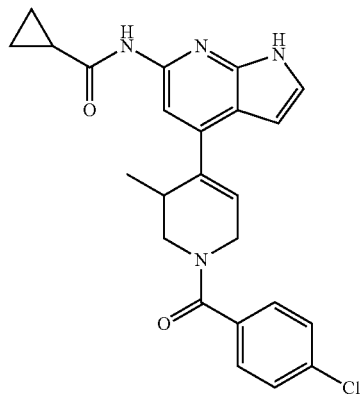 [SMILES: CC1CN(C(=O)c2ccc(Cl)cc2)CC=C1c1cc(NC(=O)C2CC2)nc2[nH]ccc12]

$^1$H NMR (400 MHz, DMSO-d$_6$) δ 11.42 (s, 1H), 10.54 (s, 1H), 7.83 (s, 1H), 7.53 (t, J=9.6 Hz, 4H), 7.32 (s, 1H), 6.50 (s, 1H), 6.09 (d, J=63.6 Hz, 1H), 4.52 (d, J=19.2 Hz, 1H), 4.10 (s, 1H), 3.63 (dd, J=13.0, 4.2 Hz, 1H), 3.00 (s, 1H), 2.06-1.97 (m, 1H), 0.92 (s, 1H), 0.82-0.75 (m, 6H).

MS(ESI+) m/z 435, 437 (M+H)$^+$

Example 334: Synthesis of N-(4-(1-(3-bromobenzoyl)-3-methyl-1,2,3,6-tetrahydropyridin-4-yl)-1H-pyrrolo[2,3-b]pyridin-6-yl)cyclopropanecarboxamide

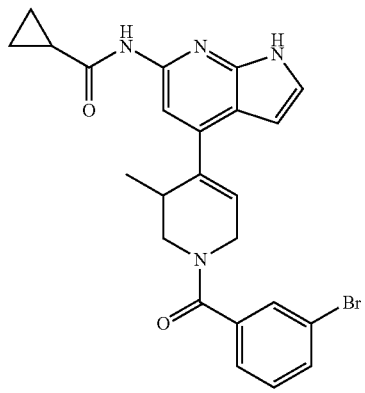 [SMILES: CC1CN(C(=O)c2cccc(Br)c2)CC=C1c1cc(NC(=O)C2CC2)nc2[nH]ccc12]

$^1$H NMR (400 MHz, DMSO-d$_6$) δ 11.42 (s, 1H), 10.54 (s, 1H), 7.83 (s, 1H), 7.68 (d, J=11.0 Hz, 2H), 7.45 (d, J=8.0 Hz, 2H), 7.32 (s, 1H), 6.50 (s, 1H), 6.09 (d, J=61.5 Hz, 1H), 4.55 (d, J=19.7 Hz, 1H), 4.09 (s, 1H), 3.68-3.55 (m, 1H), 3.01 (d, J=23.9 Hz, 1H), 2.02 (s, 1H), 0.93 (s, 1H), 0.84-0.74 (m, 6H).

MS(ESI+) m/z 479, 481 (M+H)$^+$

Example 335: Synthesis of N-(4-(1-(6-chloronicotinoyl)-3-methyl-1,2,3,6-tetrahydropyridin-4-yl)-1H-pyrrolo[2,3-b]pyridin-6-yl)cyclopropanecarboxamide

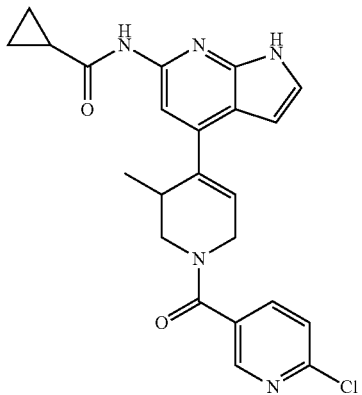 [SMILES: CC1CN(C(=O)c2ccc(Cl)nc2)CC=C1c1cc(NC(=O)C2CC2)nc2[nH]ccc12]

$^{1}$H NMR (400 MHz, DMSO-d$_{6}$) δ 11.42 (s, 1H), 10.55 (s, 1H), 8.59-8.51 (m, 1H), 7.99 (d, J=8.0 Hz, 1H), 7.83 (s, 1H), 7.64 (d, J=8.2 Hz, 1H), 7.32 (s, 1H), 6.50 (d, J=13.3 Hz, 1H), 6.08 (d, J=69.0 Hz, 1H), 4.57-4.17 (m, 1H), 4.14 (s, 1H), 3.65 (d, J=12.5 Hz, 1H), 3.02 (s, 1H), 2.02 (dq, J=8.1, 3.9, 2.8 Hz, 1H), 0.93 (s, 1H), 0.85-0.75 (m, 6H).

MS(ESI+) m/z 436, 438 (M+H)$^{+}$

Example 336: Synthesis of N-(4-(1-isonicotinoyl-3-methyl-1,2,3,6-tetrahydropyridin-4-yl)-1H-pyrrolo[2,3-b]pyridin-6-yl)cyclopropanecarboxamide

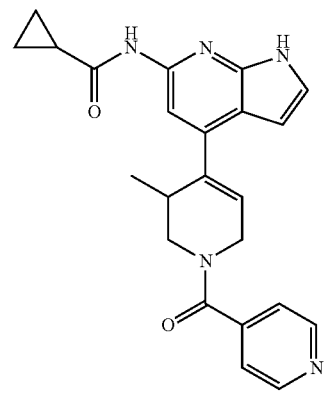 [SMILES: CC1CN(C(=O)c2ccncc2)CC=C1c1cc(NC(=O)C2CC2)nc2[nH]ccc12]

$^{1}$H NMR (400 MHz, DMSO-d$_{6}$) δ 11.43 (s, 1H), 10.55 (s, 1H), 8.74-8.64 (m, 2H), 7.83 (d, J=10.7 Hz, 1H), 7.48-7.44 (m, 2H), 7.32 (dt, J=10.4, 2.9 Hz, 1H), 6.56-6.44 (m, 1H), 6.22-5.96 (m, 1H), 4.35 (dd, J=166.5, 19.8 Hz, 1H), 4.06 (d, J=9.2 Hz, 1H), 3.60 (dd, J=13.4, 5.2 Hz, 1H), 3.02 (d, J=39.5 Hz, 1H), 2.01 (td, J=7.8, 7.4, 3.7 Hz, 1H), 0.94 (d, J=6.8 Hz, 1H), 0.84-0.74 (m, 6H).

MS(ESI+) m/z 402 (M+H)$^{+}$

Example 337: Synthesis of N-(4-(1-(6-bromopicolinoyl)-3-methyl-1,2,3,6-tetrahydropyridin-4-yl)-1H-pyrrolo[2,3-b]pyridin-6-yl)cyclopropanecarboxamide

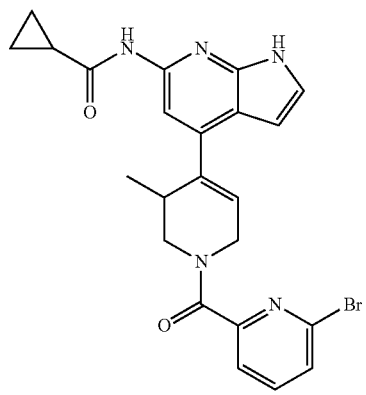 [SMILES: CC1CN(C(=O)c2cccc(Br)n2)CC=C1c1cc(NC(=O)C2CC2)nc2[nH]ccc12]

$^{1}$H NMR (400 MHz, DMSO-d$_{6}$) δ 11.43 (s, 1H), 10.55 (s, 1H), 7.94-7.89 (m, 1H), 7.85 (d, J=6.6 Hz, 1H), 7.78 (dd, J=8.1, 1.0 Hz, 1H), 7.69 (dd, J=7.5, 3.8 Hz, 1H), 7.32 (dt, J=10.3, 2.9 Hz, 1H), 6.49 (ddd, J=8.0, 3.5, 1.9 Hz, 1H), 6.11 (dt, J=60.3, 3.4 Hz, 1H), 4.61-4.17 (m, 1H), 4.16-4.11 (m, 1H), 3.63 (dd, J=13.1, 3.5 Hz, 1H), 3.52 (dd, J=13.3, 4.1 Hz, 1H), 3.04 (d, J=32.1 Hz, 1H), 2.05-1.99 (m, 1H), 0.90 (dd, J=35.3, 6.8 Hz, 3H), 0.83-0.72 (m, 4H).

MS(ESI+) m/z 480, 482 (M+H)$^{+}$

Example 338: Synthesis of N-(4-(1-(3-bromobutanoyl)-3-methyl-1,2,3,6-tetrahydropyridin-4-yl)-1H-pyrrolo[2,3-b]pyridin-6-yl)cyclopropanecarboxamide

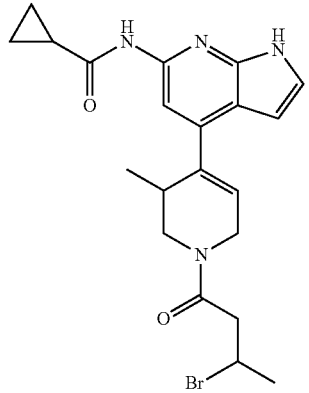 [SMILES: CC(Br)CC(=O)N1CC=C(c2cc(NC(=O)C3CC3)nc3[nH]ccc23)C(C)C1]

$^{1}$H NMR (400 MHz, DMSO-d$_{6}$) δ 11.42 (s, 1H), 10.55 (s, 1H), 7.83 (s, 1H), 7.32 (t, J=2.9 Hz, 1H), 6.49 (s, 1H), 6.11 (s, 1H), 5.25 (s, 1H), 5.05 (s, 1H), 2.97 (s, 1H), 2.02 (s, 1H), 1.91 (s, 3H), 0.90-0.84 (m, 4H), 0.83-0.74 (m, 6H).

MS(ESI+) m/z 445, 447 (M+H)$^{+}$

Example 339: Synthesis of (E)-N-(4-(1-(5-bromopent-2-enoyl)-3-methyl-1,2,3,6-tetrahydropyridin-4-yl)-1H-pyrrolo[2,3-b]pyridin-6-yl)cyclopropanecarboxamide

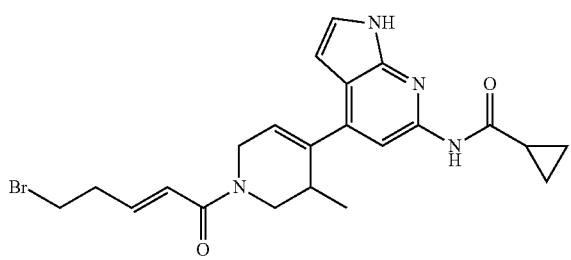 [SMILES: CC1CN(C(=O)/C=C/CCBr)CC=C1c1cc(NC(=O)C2CC2)nc2[nH]ccc12]

MS(ESI+) m/z 457, 459 (M+H)+

Example 340: Synthesis of N-(4-(1-(2-cyclopentylacetyl)-3-methyl-1,2,3,6-tetrahydropyridin-4-yl)-1H-pyrrolo[2,3-b]pyridin-6-yl)cyclopropanecarboxamide

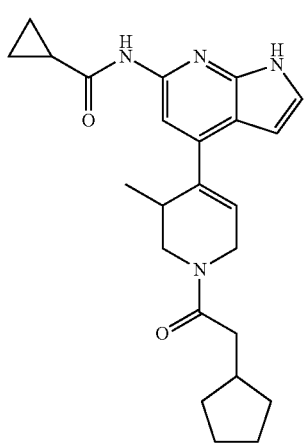 [SMILES: CC1CN(C(=O)CC2CCCC2)CC=C1c1cc(NC(=O)C2CC2)nc2[nH]ccc12]

$^1$H NMR (400 MHz, DMSO-$d_6$) δ 11.41 (s, 1H), 10.53 (s, 1H), 7.83 (d, J=3.8 Hz, 1H), 7.32 (s, 1H), 6.48 (dd, J=3.5, 1.8 Hz, 1H), 6.10 (d, J=12.7 Hz, 1H), 4.36 (t, J=17.9 Hz, 1H), 3.96-3.87 (m, 1H), 2.96 (d, J=19.7 Hz, 1H), 2.02 (d, J=5.6 Hz, 1H), 1.78 (d, J=7.5 Hz, 2H), 1.59 (s, 2H), 1.50 (d, J=7.3 Hz, 2H), 1.15 (s, 2H), 0.89 (d, J=6.8 Hz, 2H), 0.84-0.77 (m, 7H)

MS(ESI+) m/z 407 (M+H)+

Example 341: Synthesis of N-(4-(1-(2-(4-methoxyphenyl)acetyl)-3-methyl-1,2,3,6-tetrahydropyridin-4-yl)-1H-pyrrolo[2,3-b]pyridin-6-yl)cyclopropanecarboxamide

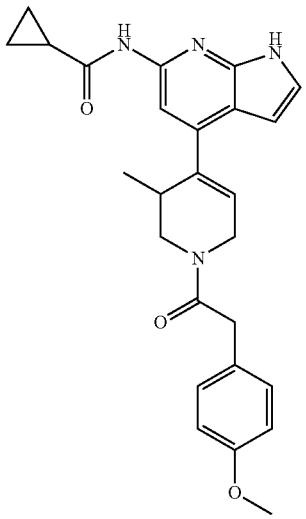 [SMILES: COc1ccc(CC(=O)N2CC=C(c3cc(NC(=O)C4CC4)nc4[nH]ccc34)C(C)C2)cc1]

MS(ESI+) m/z 445 (M+H)+

Example 342: Synthesis of N-(4-(3-methyl-1-(3-methylthiophene-2-carbonyl)-1,2,3,6-tetrahydropyridin-4-yl)-1H-pyrrolo[2,3-b]pyridin-6-yl)cyclopropanecarboxamide

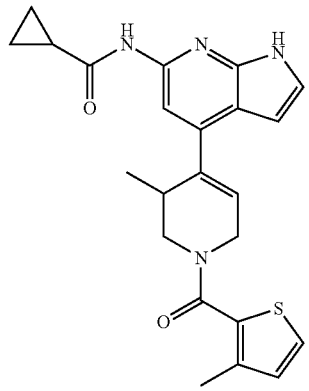 [SMILES: Cc1ccsc1C(=O)N1CC=C(c2cc(NC(=O)C3CC3)nc3[nH]ccc23)C(C)C1]

$^1$H NMR (400 MHz, DMSO-$d_6$) δ 11.42 (s, 1H), 10.54 (s, 1H), 7.83 (s, 1H), 7.59 (d, J=5.0 Hz, 1H), 7.32 (d, J=2.9 Hz, 1H), 6.96 (s, 1H), 6.47 (dd, J=3.5, 1.8 Hz, 1H), 6.12 (s, 1H), 4.08 (d, J=18.8 Hz, 2H), 2.01 (s, 1H), 0.86 (d, J=6.9 Hz, 6H), 0.81-0.78 (m, 4H).

MS(ESI+) m/z 421 (M+H)+

Example 343: Synthesis of N-(4-(3-methyl-1-(pyrazine-2-carbonyl)-1,2,3,6-tetrahydropyridin-4-yl)-1H-pyrrolo[2,3-b]pyridin-6-yl)cyclopropanecarboxamide

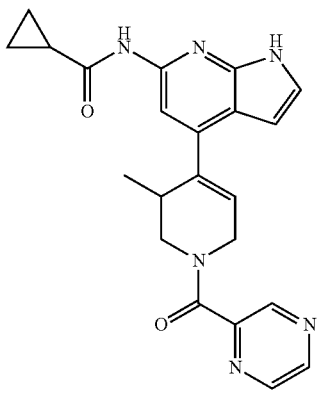 [SMILES: CC1CN(C(=O)c2cnccn2)CC=C1c1cc(NC(=O)C2CC2)nc2[nH]ccc12]

¹H NMR (400 MHz, DMSO-d₆) δ 11.42 (s, 1H), 10.54 (s, 1H), 8.90 (dd, J=6.0, 1.6 Hz, 1H), 8.77 (d, J=2.5 Hz, 1H), 8.74-8.70 (m, 1H), 7.83 (d, J=10.3 Hz, 1H), 7.32 (dt, J=8.9, 3.0 Hz, 1H), 6.49 (ddd, J=9.7, 3.5, 1.8 Hz, 1H), 6.21-5.96 (m, 1H), 4.31-4.11 (m, 2H), 2.01 (s, 1H), 0.95 (d, J=6.8 Hz, 2H), 0.82-0.74 (m, 7H).

MS(ESI+) m/z 403 (M+H)⁺

Example 344: Synthesis of N-(4-(3-methyl-1-(5-methylpyrazine-2-carbonyl)-1,2,3,6-tetrahydropyridin-4-yl)-1H-pyrrolo[2,3-b]pyridin-6-yl)cyclopropanecarboxamide

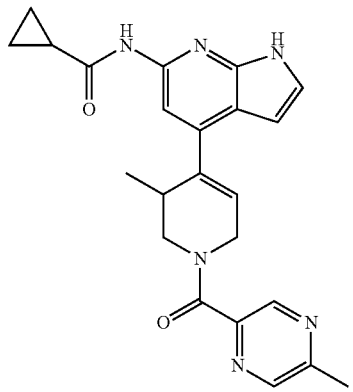 [SMILES: Cc1cnc(C(=O)N2CC=C(c3cc(NC(=O)C4CC4)nc4[nH]ccc34)C(C)C2)cn1]

¹H NMR (400 MHz, DMSO-d₆) δ 11.42 (s, 1H), 10.54 (s, 1H), 8.76 (d, J=7.1 Hz, 1H), 8.61 (s, 1H), 7.83 (d, J=9.7 Hz, 1H), 7.36-7.29 (m, 1H), 6.48 (d, J=9.3 Hz, 1H), 6.10 (d, J=72.7 Hz, 1H), 4.23-4.10 (m, 2H), 2.01 (s, 1H), 1.23 (s, 3H), 0.81-0.77 (m, 7H).

MS(ESI+) m/z 417 (M+H)⁺

Example 345: Synthesis of N-(4-(3-methyl-1-(2-(thiophen-2-yl)acetyl)-1,2,3,6-tetrahydropyridin-4-yl)-1H-pyrrolo[2,3-b]pyridin-6-yl)cyclopropanecarboxamide

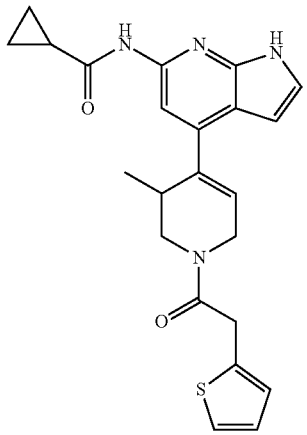 [SMILES: CC1CN(C(=O)Cc2cccs2)CC=C1c1cc(NC(=O)C2CC2)nc2[nH]ccc12]

¹H NMR (400 MHz, DMSO-d₆) δ 11.41 (s, 1H), 10.53 (s, 1H), 7.82 (d, J=7.2 Hz, 1H), 7.35 (dd, J=26.6, 4.3 Hz, 3H), 7.00-6.93 (m, 3H), 6.45 (s, 1H), 6.09 (d, J=15.0 Hz, 1H), 4.52-4.16 (m, 2H), 4.04 (dd, J=17.1, 3.4 Hz, 2H), 2.95 (d, J=8.0 Hz, 1H), 2.01 (s, 1H), 0.84 (d, J=6.9 Hz, 3H), 0.81-0.77 (m, 4H).

MS(ESI+) m/z 421 (M+H)⁺

Example 346: Synthesis of N-(4-(1-(2-(3-fluorophenyl)acetyl)-3-methyl-1,2,3,6-tetrahydropyridin-4-yl)-1H-pyrrolo[2,3-b]pyridin-6-yl)cyclopropanecarboxamide

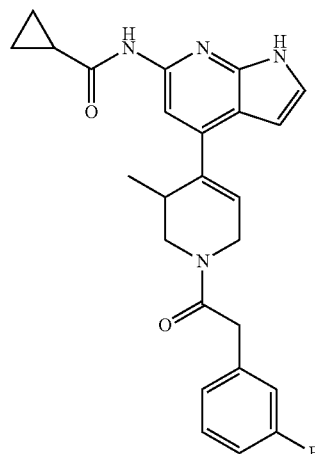

¹H NMR (400 MHz, DMSO-d₆) δ 11.41 (s, 1H), 10.53 (s, 1H), 7.82 (d, J=5.9 Hz, 1H), 7.36 (dd, J=6.4, 2.8 Hz, 1H), 7.33-7.31 (m, 1H), 7.13 (d, J=9.0 Hz, 1H), 7.10-7.03 (m, 2H), 6.44 (p, J=2.1 Hz, 1H), 6.09 (dd, J=18.3, 3.5 Hz, 1H), 4.37 (dd, J=28.8, 18.3 Hz, 1H), 4.12 (dd, J=11.4, 6.1 Hz, 1H), 3.85 (d, J=13.5 Hz, 2H), 3.71 (s, 2H), 2.04-1.98 (m, 1H), 0.83 (dd, J=6.9, 2.0 Hz, 3H), 0.80-0.74 (m, 4H).

MS(ESI+) m/z 433 (M+H)⁺

Example 347: Synthesis of N-(4-(1-(2-(3-bromophenyl)acetyl)-3-methyl-1,2,3,6-tetrahydropyridin-4-yl)-1H-pyrrolo[2,3-b]pyridin-6-yl)cyclopropanecarboxamide

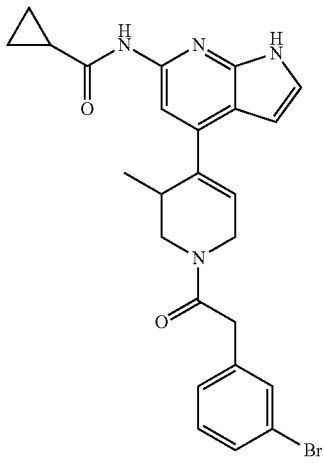 [SMILES: CC1CN(C(=O)Cc2cccc(Br)c2)CC=C1c1cc(NC(=O)C2CC2)nc2[nH]ccc12]

¹H NMR (400 MHz, DMSO-d₆) δ 11.42 (s, 1H), 10.54 (s, 1H), 8.12 (d, J=6.2 Hz, 1H), 7.83 (d, J=6.5 Hz, 1H), 7.49 (d, J=15.6 Hz, 1H), 7.44 (dt, J=6.6, 3.1 Hz, 1H), 7.28 (s, 1H), 6.74-6.68 (m, 1H), 6.47-6.41 (m, 1H), 6.09 (dt, J=15.0, 3.4 Hz, 1H), 4.08 (d, J=50.7 Hz, 2H), 3.84 (d, J=15.6 Hz, 2H), 3.71 (s, 2H), 2.96 (s, 1H), 2.01 (t, J=4.9 Hz, 1H), 0.84 (d, J=6.8 Hz, 3H), 0.81-0.76 (m, 4H).

MS(ESI+) m/z 494 (M+H)⁺

Example 348: Synthesis of N-(4-(1-(2-chloroacetyl)-3-methyl-1,2,3,6-tetrahydropyridin-4-yl)-1H-pyrrolo[2,3-b]pyridin-6-yl)cyclopropanecarboxamide

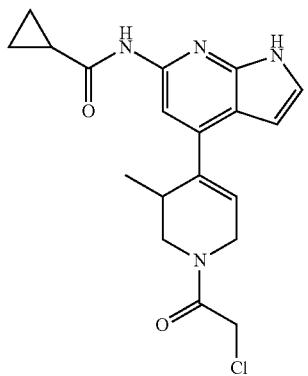 [SMILES: CC1CN(C(=O)CCl)CC=C1c1cc(NC(=O)C2CC2)nc2[nH]ccc12]

¹H NMR (400 MHz, DMSO-d₆) δ 11.42 (s, 1H), 10.54 (s, 1H), 7.83 (d, J=7.2 Hz, 1H), 7.32 (t, J=3.0 Hz, 1H), 6.48 (d, J=3.1 Hz, 1H), 6.10 (d, J=13.3 Hz, 1H), 4.52-4.41 (m, 2H), 4.37-4.04 (m, 2H), 2.97 (s, 1H), 2.00 (q, J=7.3, 6.1 Hz, 1H), 0.88 (dd, J=17.0, 6.9 Hz, 3H), 0.79 (dd, J=9.1, 6.0 Hz, 4H).

MS(ESI+) m/z 373, 375 (M+H)⁺

Example 349: Synthesis of N-(4-(1-(2-chloronicotinoyl)-3-methyl-1,2,3,6-tetrahydropyridin-4-yl)-1H-pyrrolo[2,3-b]pyridin-6-yl)cyclopropanecarboxamide

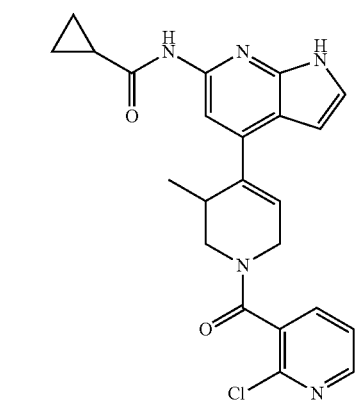 [SMILES: CC1CN(C(=O)c2cccnc2Cl)CC=C1c1cc(NC(=O)C2CC2)nc2[nH]ccc12]

MS(ESI+) m/z 436, 438 (M+H)⁺

Example 350: Synthesis of N-(4-(1-(4-hydroxybenzoyl)-3-methyl-1,2,3,6-tetrahydropyridin-4-yl)-1H-pyrrolo[2,3-b]pyridin-6-yl)cyclopropanecarboxamide

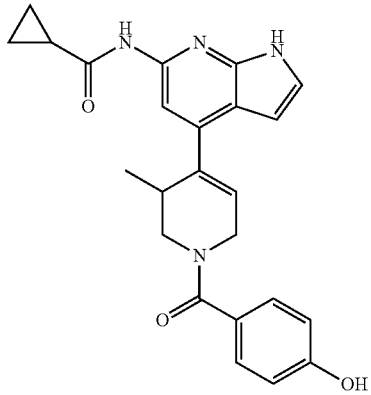 [SMILES: CC1CN(C(=O)c2ccc(O)cc2)CC=C1c1cc(NC(=O)C2CC2)nc2[nH]ccc12]

MS(ESI+) m/z 417 (M+H)⁺

Example 351: Synthesis of N-(4-(1-(3,5-dichloro-2-hydroxybenzoyl)-3-methyl-1,2,3,6-tetrahydropyridin-4-yl)-1H-pyrrolo[2,3-b]pyridin-6-yl)cyclopropanecarboxamide

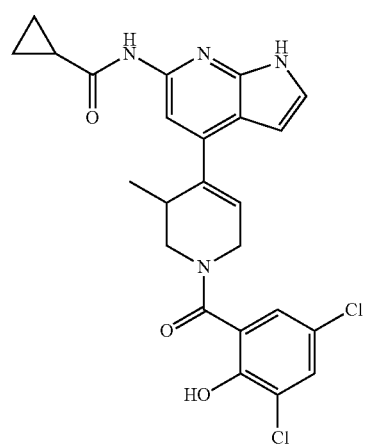 [SMILES: CC1CN(C(=O)c2cc(Cl)cc(Cl)c2O)CC=C1c1cc(NC(=O)C2CC2)nc2[nH]ccc12]

MS(ESI+) m/z 486 (M+H)+

Example 352: Synthesis of N-(4-(1-(benzofuran-2-carbonyl)-3-methyl-1,2,3,6-tetrahydropyridin-4-yl)-1H-pyrrolo[2,3-b]pyridin-6-yl)cyclopropanecarboxamide

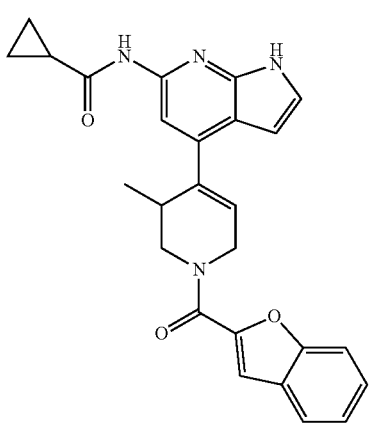 [SMILES: CC1CN(C(=O)c2cc3ccccc3o2)CC=C1c1cc(NC(=O)C2CC2)nc2[nH]ccc12]

MS(ESI+) m/z 441 (M+H)+

Example 353: Synthesis of N-(4-(1-(3,4-dichlorobenzoyl)-3-methyl-1,2,3,6-tetrahydropyridin-4-yl)-1H-pyrrolo[2,3-b]pyridin-6-yl)cyclopropanecarboxamide

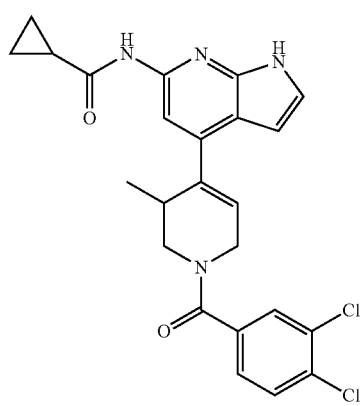 [SMILES: CC1CN(C(=O)c2ccc(Cl)c(Cl)c2)CC=C1c1cc(NC(=O)C2CC2)nc2[nH]ccc12]

MS(ESI+) m/z 469, 471, 473 (M+H)+

Example 354: Synthesis of N-(4-(3-methyl-1-(4-(methylsulfonyl)benzoyl)-1,2,3,6-tetrahydropyridin-4-yl)-1H-pyrrolo[2,3-b]pyridin-6-yl)cyclopropanecarboxamide

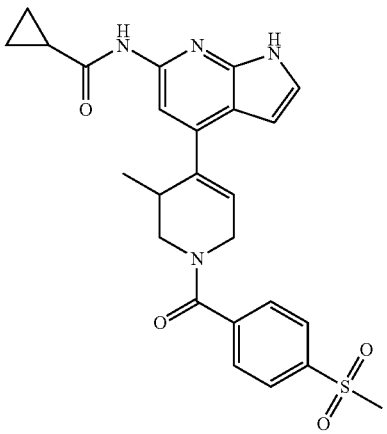 [SMILES: CC1CN(C(=O)c2ccc(S(C)(=O)=O)cc2)CC=C1c1cc(NC(=O)C2CC2)nc2[nH]ccc12]

MS(ESI+) m/z 479 (M+H)+

Example 355: Synthesis of N-(4-(1-(2-chloro-4-fluorobenzoyl)-3-methyl-1,2,3,6-tetrahydropyridin-4-yl)-1H-pyrrolo[2,3-b]pyridin-6-yl)cyclopropanecarboxamide

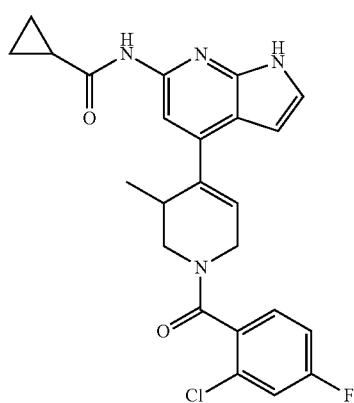 [SMILES: CC1CN(C(=O)c2ccc(F)cc2Cl)CC=C1c1cc(NC(=O)C2CC2)nc2[nH]ccc12]

MS(ESI+) m/z 453, 455 (M+H)+

Example 356: Synthesis of N-(4-(1-(2,4-dimethoxybenzoyl)-3-methyl-1,2,3,6-tetrahydropyridin-4-yl)-1H-pyrrolo[2,3-b]pyridin-6-yl)cyclopropanecarboxamide

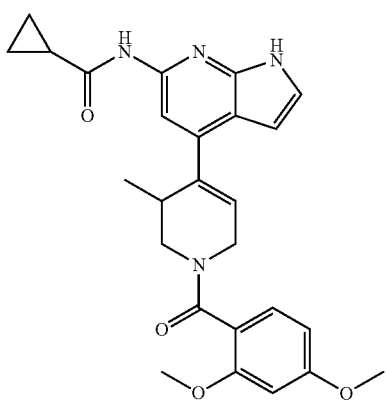 [SMILES: COc1ccc(C(=O)N2CC=C(c3cc(NC(=O)C4CC4)nc4[nH]ccc34)C(C)C2)c(OC)c1]

MS(ESI+) m/z 461 (M+H)+

Example 357: Synthesis of N-(4-(3-methyl-1-(2-(methylthio)benzoyl)-1,2,3,6-tetrahydropyridin-4-yl)-1H-pyrrolo[2,3-b]pyridin-6-yl)cyclopropanecarboxamide

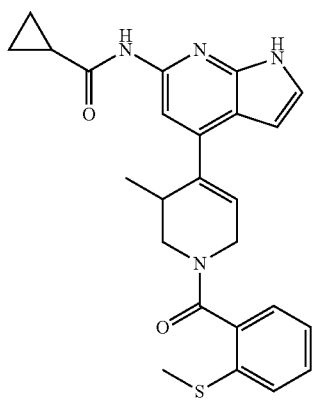 [SMILES: CSc1ccccc1C(=O)N1CC=C(c2cc(NC(=O)C3CC3)nc3[nH]ccc23)C(C)C1]

MS(ESI+) m/z 447 (M+H)+

Example 358: Synthesis of N-(4-(1-(3,5-difluorobenzoyl)-3-methyl-1,2,3,6-tetrahydropyridin-4-yl)-1H-pyrrolo[2,3-b]pyridin-6-yl)cyclopropanecarboxamide

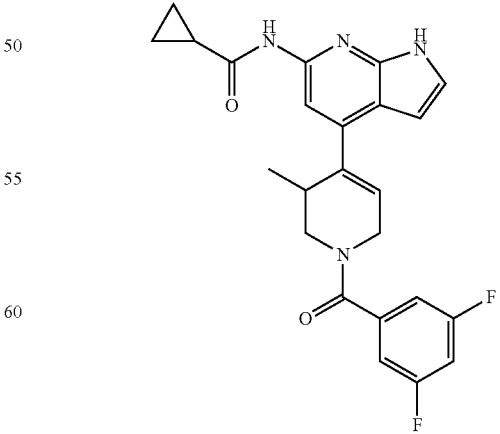

MS(ESI+) m/z 437 (M+H)+

Example 359: Synthesis of N-(4-(1-(2-cyano-3-(4-fluorophenyl)propanoyl)-3-methyl-1,2,3,6-tetrahydropyridin-4-yl)-1H-pyrrolo[2,3-b]pyridin-6-yl)cyclopropanecarboxamide

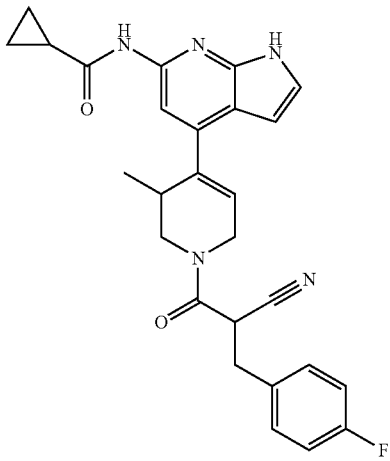 [SMILES: CC1CN(C(=O)C(C#N)Cc2ccc(F)cc2)CC=C1c1cc(NC(=O)C2CC2)nc2[nH]ccc12]

MS(ESI+) m/z 472 (M+H)+

Example 360: Synthesis of N-(4-(1-(2-cyano-3-phenylpropanoyl)-3-methyl-1,2,3,6-tetrahydropyridin-4-yl)-1H-pyrrolo[2,3-b]pyridin-6-yl)cyclopropanecarboxamide

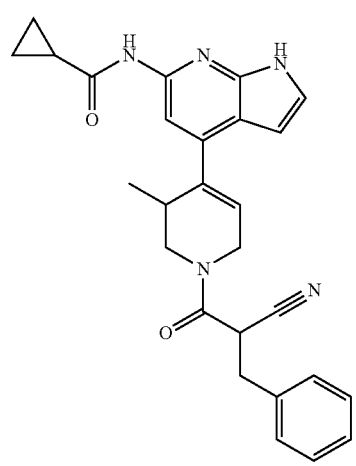 [SMILES: CC1CN(C(=O)C(C#N)Cc2ccccc2)CC=C1c1cc(NC(=O)C2CC2)nc2[nH]ccc12]

MS(ESI+) m/z 454 (M+H)+

Example 361: Synthesis of N-(4-(1-(1-cyanocyclopentane-1-carbonyl)-3-methyl-1,2,3,6-tetrahydropyridin-4-yl)-1H-pyrrolo[2,3-b]pyridin-6-yl)cyclopropanecarboxamide

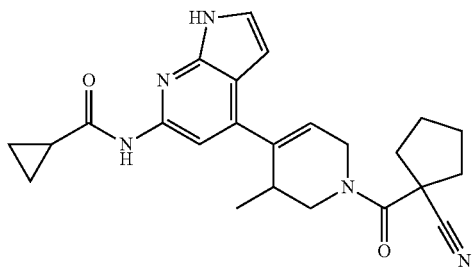 [SMILES: CC1CN(C(=O)C2(C#N)CCCC2)CC=C1c1cc(NC(=O)C2CC2)nc2[nH]ccc12]

MS(ESI+) m/z 418 (M+H)+

Example 362: Synthesis of N-(4-(3-methyl-1-(3-morpholino-3-oxopropanoyl)-1,2,3,6-tetrahydropyridin-4-yl)-1H-pyrrolo[2,3-b]pyridin-6-yl)cyclopropanecarboxamide

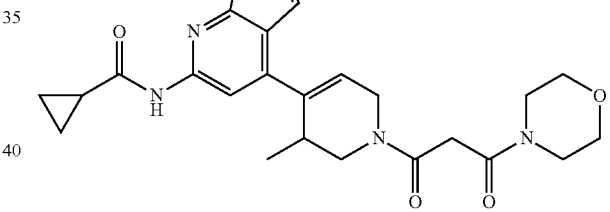

MS(ESI+) m/z 452 (M+H)+

Example 363: Synthesis of N-(4-(1-(2-cyanoacetyl)-2-methyl-1,2,3,6-tetrahydropyridin-4-yl)-1H-pyrrolo[2,3-b]pyridin-6-yl)cyclopropanecarboxamide

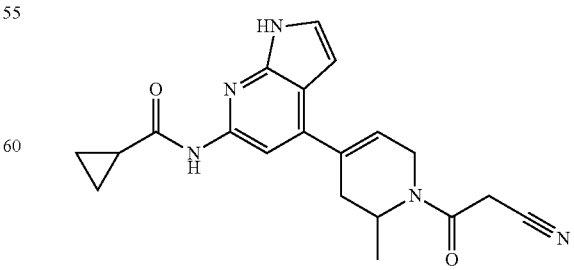

MS(ESI+) m/z 364 (M+H)+

Example 365: Synthesis of N-(4-(3-methyl-1-(2-phenylacetyl)-1,2,3,6-tetrahydropyridin-4-yl)-1H-pyrrolo[2,3-b]pyridin-6-yl)cyclopropanecarboxamide

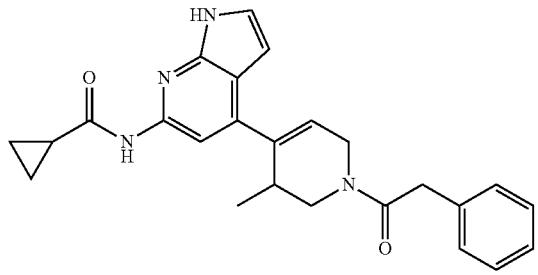 [SMILES: CC1CN(C(=O)Cc2ccccc2)CC=C1c1cc(NC(=O)C2CC2)nc2[nH]ccc12]

$^1$H NMR (400 MHz, DMSO-d$_6$) δ 11.40 (s, 1H), 10.53 (s, 1H), 7.82 (d, J=8.0 Hz, 1H), 7.33-7.23 (m, 6H), 6.41 (d, J=3.8 Hz, 1H), 6.07 (d, J=23.4 Hz, 1H), 4.37 (dd, J=29.9, 18.8 Hz, 1H), 4.13-4.01 (m, 1H), 3.81 (dd, J=11.9, 4.6 Hz, 2H), 2.88 (s, 1H), 2.08 (d, J=1.5 Hz, 2H), 2.01 (d, J=1.5 Hz, 1H), 0.86-0.77 (m, 7H).

MS(ESI+) m/z 415 (M+H)$^+$

Example 366: Synthesis of N-(4-(9-(2-fluoroisonicotinoyl)-9-azabicyclo[3.3.1]non-2-en-3-yl)-1H-pyrrolo[2,3-b]pyridin-6-yl)cyclopropanecarboxamide

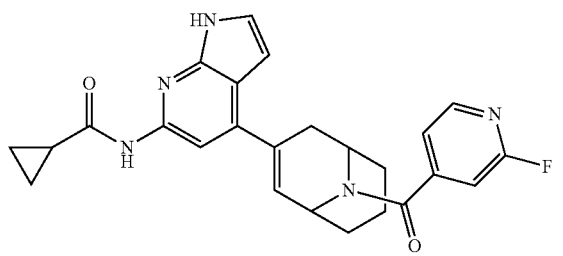 [SMILES: O=C(Nc1cc(C2=CC3CCCC(C2)N3C(=O)c2ccnc(F)c2)c2cc[nH]c2n1)C1CC1]

$^1$H NMR (400 MHz, DMSO-d$_6$) δ 11.45 (s, 1H), 10.55 (d, J=3.3 Hz, 1H), 8.35 (t, J=5.6 Hz, 1H), 7.90 (d, J=3.2 Hz, 1H), 7.47-7.38 (m, 1H), 7.37-7.25 (m, 2H), 6.53 (ddd, J=33.6, 3.5, 1.8 Hz, 1H), 6.30 (dd, J=68.3, 5.4 Hz, 1H), 5.34-4.94 (m, 1H), 4.31-3.88 (m, 1H), 2.96 (dd, J=17.4, 8.2 Hz, 1H), 2.37 (d, J=17.9 Hz, 1H), 2.02 (s, 1H), 1.86-1.54 (m, 6H), 0.89-0.71 (m, 4H).

MS(ESI+) m/z 446 (M+H)$^+$

Example 367: Synthesis of N-(4-(9-(2-chloroisonicotinoyl)-9-azabicyclo[3.3.1]non-2-en-3-yl)-1H-pyrrolo[2,3-b]pyridin-6-yl)cyclopropanecarboxamide

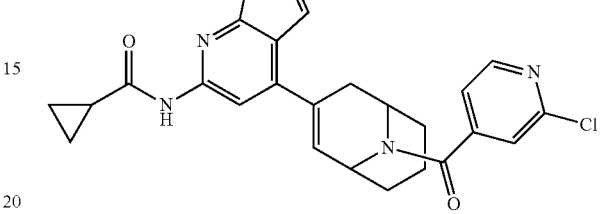

$^1$H NMR (400 MHz, DMSO-d$_6$) δ 11.46 (s, 1H), 10.66-10.23 (m, 1H), 8.52 (dd, J=7.0, 5.0 Hz, 1H), 7.90 (d, J=3.4 Hz, 1H), 7.62 (d, J=24.1 Hz, 1H), 7.54-7.42 (m, 1H), 7.35 (dt, J=6.7, 2.9 Hz, 1H), 6.53 (ddd, J=31.9, 3.6, 1.9 Hz, 1H), 6.31 (dd, J=63.6, 5.4 Hz, 1H), 5.36-4.91 (m, 1H), 4.33-3.82 (m, 1H), 2.97 (dt, J=17.0, 7.9 Hz, 1H), 2.37 (d, J=18.0 Hz, 1H), 2.01 (d, J=8.1 Hz, 1H), 1.89-1.55 (m, 6H), 0.86-0.72 (m, 4H).

MS(ESI+) m/z 462, 464 (M+H)$^+$

Example 368: Synthesis of N-(4-(9-(6-chloronicotinoyl)-9-azabicyclo[3.3.1]non-2-en-3-yl)-1H-pyrrolo[2,3-b]pyridin-6-yl)cyclopropanecarboxamide $^1$H NMR (400 MHz, DMSO-d$_6$) δ 11.45 (s, 1H), 10.55 (s, 1H), 8.53 (dd, J=12.8, 2.3 Hz, 1H), 7.97 (ddd, J=16.5, 8.3, 2.4 Hz, 1H), 7.90 (s, 1H), 7.62 (t, J=8.2 Hz, 1H), 7.35 (dt, J=8.3, 2.8 Hz, 1H), 6.61-6.47 (m, 1H), 6.31 (dd, J=63.7, 5.4 Hz, 1H), 5.35-4.89 (m, 1H), 4.23 (d, J=141.9 Hz, 1H), 2.99 (dd, J=18.2, 7.2 Hz, 1H), 2.38 (d, J=17.9 Hz, 1H), 2.08-1.97 (m, 1H), 1.87-1.57 (m, 6H), 0.85-0.71 (m, 4H).

MS(ESI+) m/z 462, 464 (M+H)$^+$

Example 369: Synthesis of N-(4-(9-(3-fluoroisonicotinoyl)-9-azabicyclo[3.3.1]non-2-en-3-yl)-1H-pyrrolo[2,3-b]pyridin-6-yl)cyclopropanecarboxamide

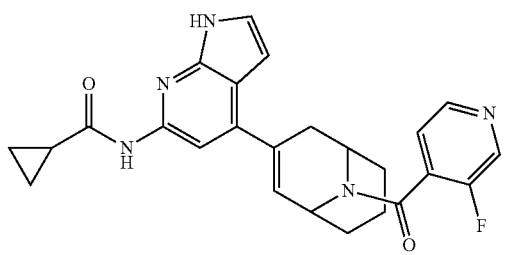 [SMILES: O=C(Nc1cc(C2=CC3CCCC(C2)N3C(=O)c2ccncc2F)c2cc[nH]c2n1)C1CC1]

$^1$H NMR (400 MHz, DMSO-d$_6$) δ 11.47 (s, 1H), 10.56 (s, 1H), 8.72 (d, J=2.5 Hz, 1H), 8.54 (dt, J=4.4, 2.1 Hz, 1H), 7.90 (d, J=7.1 Hz, 1H), 7.58 (t, J=5.3 Hz, 1H), 7.36 (dt, J=8.5, 3.0 Hz, 1H), 6.51 (ddd, J=30.4, 3.6, 1.9 Hz, 1H), 6.31 (dd, J=71.8, 5.5 Hz, 1H), 5.20 (d, J=113.1 Hz, 1H), 4.04 (d, J=127.2 Hz, 1H), 2.92 (td, J=21.1, 18.1, 6.8 Hz, 1H), 2.39 (d, J=17.9 Hz, 1H), 2.02 (d, J=7.6 Hz, 1H), 1.86 (d, J=10.6 Hz, 2H), 1.74 (d, J=34.5 Hz, 3H), 1.62 (d, J=12.4 Hz, 1H), 0.86-0.72 (m, 4H).

MS(ESI+) m/z 446 (M+H)$^+$

Example 370: Synthesis of N-(4-(9-(4-nitrobenzoyl)-9-azabicyclo[3.3.1]non-2-en-3-yl)-1H-pyrrolo[2,3-b]pyridin-6-yl)cyclopropanecarboxamide

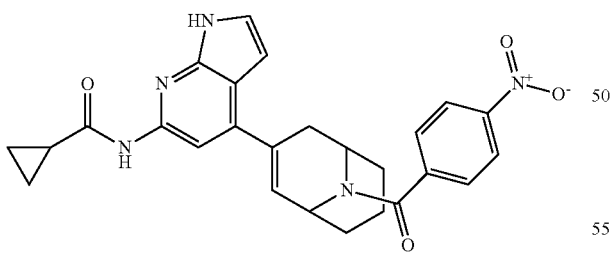

$^1$H NMR (400 MHz, DMSO-d$_6$) δ 11.46 (s, 1H), 10.56 (s, 1H), 8.31 (dd, J=8.4, 5.7 Hz, 2H), 7.91 (d, J=2.6 Hz, 1H), 7.73 (dd, J=14.0, 8.4 Hz, 2H), 7.36 (dt, J=10.5, 3.0 Hz, 1H), 6.61-6.47 (m, 1H), 6.31 (dd, J=82.6, 5.4 Hz, 1H), 5.16 (d, J=118.0 Hz, 1H), 4.13 (d, J=138.3 Hz, 1H), 2.97 (ddd, J=25.3, 18.1, 7.3 Hz, 1H), 2.38 (d, J=17.9 Hz, 1H), 2.01 (d, J=14.0 Hz, 1H), 1.81 (d, J=30.8 Hz, 3H), 1.64 (d, J=22.4 Hz, 3H), 0.83-0.74 (m, 4H).

MS(ESI+) m/z 472 (M+H)$^+$

Example 371: Synthesis of N-(4-(9-(3-bromobenzoyl)-9-azabicyclo[3.3.1]non-2-en-3-yl)-1H-pyrrolo[2,3-b]pyridin-6-yl)cyclopropanecarboxamide

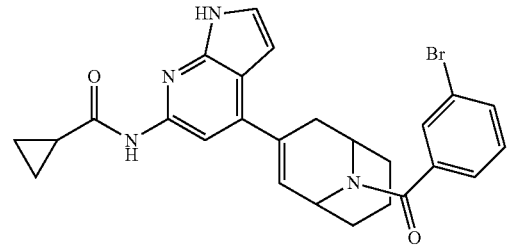 [SMILES: O=C(Nc1cc(C2=CC3CCCC(C2)N3C(=O)c2cccc(Br)c2)c2cc[nH]c2n1)C1CC1]

$^1$H NMR (400 MHz, DMSO-d$_6$) δ 11.45 (s, 1H), 10.55 (s, 1H), 7.90 (s, 1H), 7.68 (d, J=7.1 Hz, 1H), 7.63 (d, J=15.3 Hz, 1H), 7.50-7.39 (m, 2H), 7.36 (dd, J=7.1, 3.9 Hz, 1H), 6.59-6.46 (m, 1H), 6.32 (dd, J=60.3, 5.3 Hz, 1H), 5.12 (d, J=114.0 Hz, 1H), 4.20 (d, J=137.6 Hz, 1H), 3.03-2.84 (m, 1H), 2.45-2.33 (m, 1H), 2.02 (s, 1H), 1.83 (s, 3H), 1.71 (d, J=24.0 Hz, 2H), 1.61 (d, J=9.5 Hz, 1H), 0.85-0.73 (m, 4H).

MS(ESI+) m/z 506 (M+H)$^+$

Example 372: Synthesis of N-(4-(1-(2,6-dichloroisonicotinoyl)-3-methyl-1,2,3,6-tetrahydropyridin-4-yl)-1H-pyrrolo[2,3-b]pyridin-6-yl)cyclopropanecarboxamide

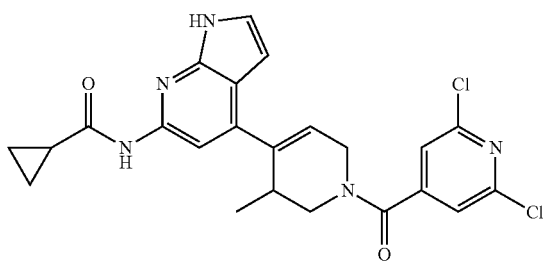

$^1$H NMR (400 MHz, DMSO-d$_6$) δ 11.42 (s, 1H), 10.54 (s, 1H), 7.83 (d, J=13.7 Hz, 1H), 7.72 (d, J=6.8 Hz, 2H), 7.36-7.29 (m, 1H), 6.49 (d, J=9.7 Hz, 1H), 6.07 (d, J=65.0 Hz, 1H), 4.50 (d, J=19.2 Hz, 1H), 4.17-4.01 (m, 3H), 2.01 (s, 1H), 1.23 (s, 3H), 0.80 (d, J=7.3 Hz, 4H).

MS(ESI+) m/z 471 (M+H)$^+$

Example 373: Synthesis of N-(4-(1-(2,5-dichloroisonicotinoyl)-3-methyl-1,2,3,6-tetrahydropyridin-4-yl)-1H-pyrrolo[2,3-b]pyridin-6-yl)cyclopropanecarboxamide

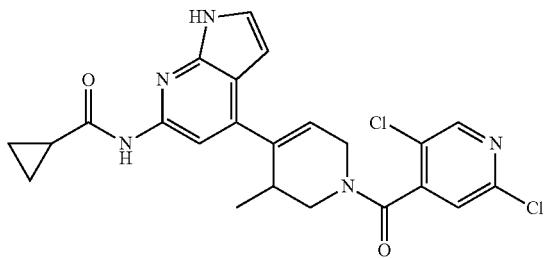 [SMILES: CC1CN(C(=O)c2cc(Cl)ncc2Cl)CC=C1c1cc(NC(=O)C2CC2)nc2[nH]ccc12]

¹H NMR (400 MHz, DMSO-d₆) δ 11.43 (s, 1H), 10.54 (s, 1H), 8.65 (s, 1H), 7.86 (d, J=5.7 Hz, 1H), 7.81-7.75 (m, 1H), 7.35-7.28 (m, 1H), 6.48 (d, J=19.5 Hz, 1H), 6.08 (d, J=63.9 Hz, 1H), 4.62-4.09 (m, 1H), 3.92 (d, J=32.5 Hz, 1H), 2.02 (d, J=7.1 Hz, 1H), 0.97 (s, 2H), 0.83-0.74 (m, 7H).

MS(ESI+) m/z 471 (M+H)⁺

Example 374: Synthesis of N-(4-(1-(3,5-dichloroisonicotinoyl)-3-methyl-1,2,3,6-tetrahydropyridin-4-yl)-1H-pyrrolo[2,3-b]pyridin-6-yl)cyclopropanecarboxamide

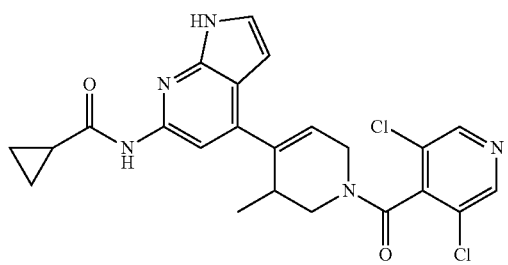 [SMILES: CC1CN(C(=O)c2c(Cl)cncc2Cl)CC=C1c1cc(NC(=O)C2CC2)nc2[nH]ccc12]

¹H NMR (400 MHz, DMSO-d₆) δ 11.43 (s, 1H), 10.55 (s, 1H), 8.78 (d, J=4.8 Hz, 2H), 7.83 (d, J=15.9 Hz, 1H), 7.33 (s, 1H), 6.46 (d, J=11.8 Hz, 1H), 6.09 (d, J=71.5 Hz, 1H), 4.30-4.19 (m, 1H), 2.01 (s, 2H), 0.99 (d, J=6.9 Hz, 2H), 0.87-0.71 (m, 7H).

MS(ESI+) m/z 470, 472, 474 (M+H)⁺

Example 375: Synthesis of N-(4-(1-(2-chloro-6-methylisonicotinoyl)-3-methyl-1,2,3,6-tetrahydropyridin-4-yl)-1H-pyrrolo[2,3-b]pyridin-6-yl)cyclopropanecarboxamide

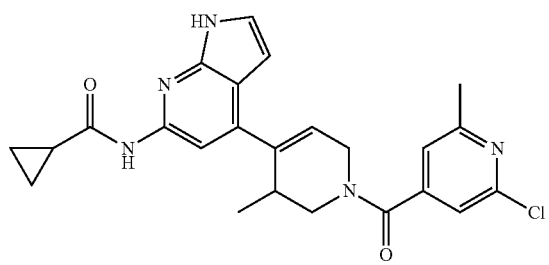 [SMILES: Cc1cc(C(=O)N2CC=C(c3cc(NC(=O)C4CC4)nc4[nH]ccc34)C(C)C2)cc(Cl)n1]

¹H NMR (400 MHz, DMSO-d₆) δ 11.42 (s, 1H), 10.54 (s, 1H), 7.83 (d, J=12.0 Hz, 1H), 7.41 (d, J=8.0 Hz, 1H), 7.35 (d, J=10.1 Hz, 1H), 7.31 (t, J=3.6 Hz, 1H), 6.50 (dd, J=10.5, 2.8 Hz, 1H), 6.08 (d, J=65.0 Hz, 1H), 4.32 (dd, J=170.8, 19.5 Hz, 1H), 4.05 (s, 1H), 3.59 (d, J=10.5 Hz, 1H), 2.96 (s, 1H), 2.03-1.97 (m, 1H), 0.94 (d, J=6.8 Hz, 2H), 0.85-0.70 (m, 7H).

MS(ESI+) m/z 450, 452 (M+H)⁺

Example 376: Synthesis of N-(4-(1-(3-chloroisonicotinoyl)-3-methyl-1,2,3,6-tetrahydropyridin-4-yl)-1H-pyrrolo[2,3-b]pyridin-6-yl)cyclopropanecarboxamide

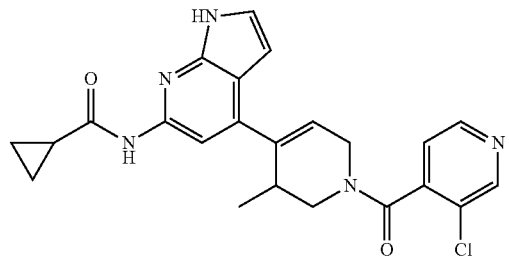 [SMILES: CC1CN(C(=O)c2ccncc2Cl)CC=C1c1cc(NC(=O)C2CC2)nc2[nH]ccc12]

¹H NMR (400 MHz, DMSO-d₆) δ 11.43 (s, 1H), 10.54 (s, 1H), 8.77 (s, 1H), 8.64 (d, J=5.1 Hz, 1H), 7.83 (d, J=16.8 Hz, 1H), 7.53 (d, J=4.7 Hz, 1H), 7.35-7.30 (m, 1H), 6.47 (d, J=13.2 Hz, 1H), 6.09 (d, J=68.6 Hz, 1H), 4.37 (d, J=21.7 Hz, 1H), 3.91 (s, 1H), 2.01 (s, 1H), 0.98 (s, 2H), 0.88-0.74 (m, 7H).

MS(ESI+) m/z 436, 438 (M+H)⁺

Example 377: Synthesis of N-(4-(1-(3-hydroxyisonicotinoyl)-3-methyl-1,2,3,6-tetrahydropyridin-4-yl)-1H-pyrrolo[2,3-b]pyridin-6-yl)cyclopropanecarboxamide

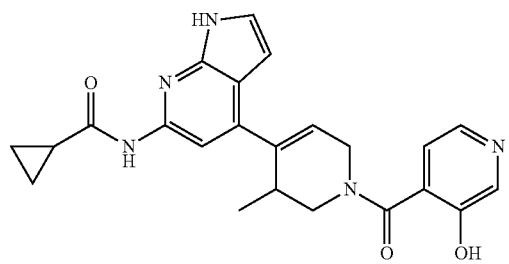 [SMILES: CC1CN(C(=O)c2ccncc2O)CC=C1c1cc(NC(=O)C2CC2)nc2[nH]ccc12]

¹H NMR (400 MHz, DMSO-d₆) δ 11.42 (d, J=5.8 Hz, 1H), 8.26 (s, 1H), 8.11 (d, J=4.8 Hz, 1H), 7.80 (s, 1H), 7.21 (t, J=3.6 Hz, 1H), 6.48 (s, 1H), 6.03 (d, J=21.4 Hz, 1H), 5.81 (d, J=7.7 Hz, 1H), 4.53 (d, J=19.6 Hz, 1H), 3.93 (s, 1H), 2.96 (s, 2H), 2.01 (s, 1H), 1.00-0.90 (m, 3H), 0.76 (d, J=6.4 Hz, 4H).

MS(ESI+) m/z 418 (M+H)⁺

Example 378: Synthesis of N-(4-(1-(2,3-difluorobenzoyl)-3-methyl-1,2,3,6-tetrahydropyridin-4-yl)-1H-pyrrolo[2,3-b]pyridin-6-yl)cyclopropanecarboxamide

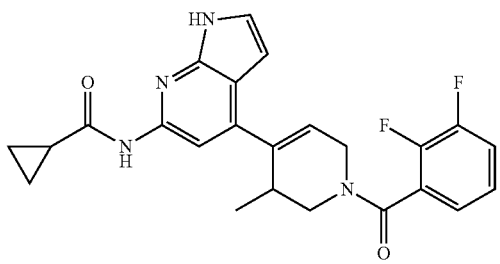 [SMILES: CC1CN(C(=O)c2cccc(F)c2F)CC=C1c1cc(NC(=O)C2CC2)nc2[nH]ccc12]

¹H NMR (400 MHz, DMSO-d₆) δ 11.43 (s, 1H), 10.55 (s, 1H), 8.20-8.09 (m, 1H), 7.83 (d, J=14.1 Hz, 1H), 7.52 (d, J=4.4 Hz, 1H), 7.33 (q, J=5.2, 4.0 Hz, 1H), 6.48 (d, J=8.4 Hz, 1H), 6.07 (d, J=75.5 Hz, 1H), 4.63-4.19 (m, 1H), 4.15 (s, 1H), 4.04 (d, J=7.8 Hz, 1H), 2.93 (s, 1H), 2.01 (s, 1H), 0.95-0.77 (m, 7H).
MS(ESI+) m/z 437 (M+H)⁺

Example 379: Synthesis of N-(4-(3-methyl-1-(2-methylisonicotinoyl)-1,2,3,6-tetrahydropyridin-4-yl)-1H-pyrrolo[2,3-b]pyridin-6-yl)cyclopropanecarboxamide

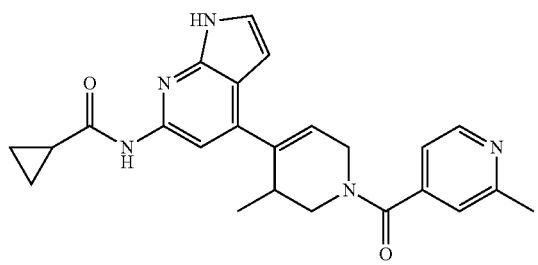 [SMILES: Cc1cc(C(=O)N2CC=C(c3cc(NC(=O)C4CC4)nc4[nH]ccc34)C(C)C2)ccn1]

¹H NMR (400 MHz, DMSO-d₆) δ 11.42 (s, 1H), 10.54 (s, 1H), 8.55 (d, J=5.0 Hz, 1H), 7.83 (d, J=10.1 Hz, 1H), 7.31 (d, J=8.6 Hz, 2H), 7.24 (s, 1H), 6.49 (d, J=14.8 Hz, 1H), 6.08 (d, J=70.1 Hz, 1H), 4.33 (dd, J=173.7, 19.7 Hz, 1H), 4.04 (s, 1H), 2.52 (s, 3H), 2.01 (s, 1H), 0.94-0.77 (m, 7H).
MS(ESI+) m/z 416 (M+H)⁺

Example 380: Synthesis of N-(4-(1-(6-methoxynicotinoyl)-3-methyl-1,2,3,6-tetrahydropyridin-4-yl)-1H-pyrrolo[2,3-b]pyridin-6-yl)cyclopropanecarboxamide

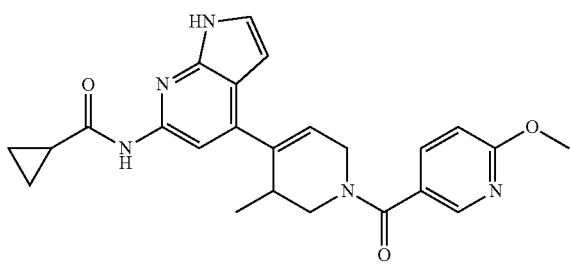 [SMILES: COc1ccc(C(=O)N2CC=C(c3cc(NC(=O)C4CC4)nc4[nH]ccc34)C(C)C2)cn1]

¹H NMR (400 MHz, DMSO-d₆) δ 11.42 (s, 1H), 10.54 (s, 1H), 8.32-8.24 (m, 1H), 7.82 (d, J=11.3 Hz, 1H), 7.32 (d, J=8.5 Hz, 1H), 7.03 (d, J=5.2 Hz, 1H), 6.86 (s, 1H), 6.49 (d, J=13.4 Hz, 1H), 6.08 (d, J=67.4 Hz, 1H), 4.58-4.08 (m, 1H), 4.04 (s, 1H), 3.89 (s, 3H), 3.59 (d, J=13.6 Hz, 2H), 2.95 (s, 1H), 2.01 (s, 1H), 0.94-0.77 (m, 7H).
MS(ESI+) m/z 432 (M+H)⁺

Example 381: Synthesis of N-(4-(1-(2-aminoisonicotinoyl)-3-methyl-1,2,3,6-tetrahydropyridin-4-yl)-1H-pyrrolo[2,3-b]pyridin-6-yl)cyclopropanecarboxamide

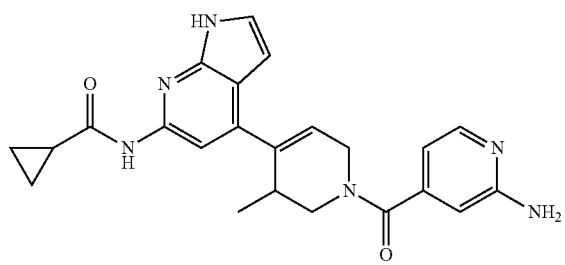 [SMILES: CC1CN(C(=O)c2ccnc(N)c2)CC=C1c1cc(NC(=O)C2CC2)nc2[nH]ccc12]

MS(ESI+) m/z 417 (M+H)⁺

Example 382: Synthesis of N-(4-(1-(2-bromoisonicotinoyl)-3-methyl-1,2,3,6-tetrahydropyridin-4-yl)-1H-pyrrolo[2,3-b]pyridin-6-yl)cyclopropanecarboxamide

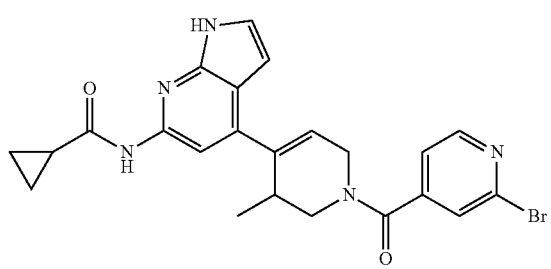 [SMILES: CC1CN(C(=O)c2ccnc(Br)c2)CC=C1c1cc(NC(=O)C2CC2)nc2[nH]ccc12]

¹H NMR (400 MHz, DMSO-d₆) δ 11.42 (s, 1H), 10.54 (s, 1H), 8.51 (d, J=5.0 Hz, 1H), 7.83 (d, J=12.2 Hz, 1H), 7.76 (d, J=8.0 Hz, 1H), 7.59-7.48 (m, 1H), 7.33 (dd, J=7.4, 4.4 Hz, 1H), 6.55-6.41 (m, 1H), 6.08 (d, J=65.3 Hz, 1H), 4.33 (dd, J=166.6, 19.5 Hz, 1H), 4.05 (d, J=3.5 Hz, 1H), 3.59 (dd, J=13.2, 4.2 Hz, 1H), 3.02 (d, J=40.4 Hz, 1H), 2.00 (dt, J=7.9, 4.7 Hz, 1H), 0.95-0.77 (m, 7H).
MS(ESI+) m/z 481 (M+H)⁺

Example 383: Synthesis of N-(4-(1-(2-hydroxyisonicotinoyl)-3-methyl-1,2,3,6-tetrahydropyridin-4-yl)-1H-pyrrolo[2,3-b]pyridin-6-yl)cyclopropanecarboxamide

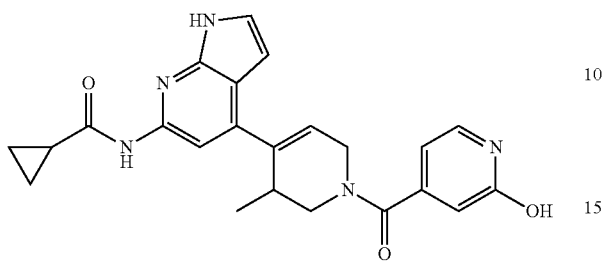

MS(ESI+) m/z 418 (M+H)⁺

Example 384: Synthesis of N-(4-(3-methyl-1-(2-(trifluoromethyl)isonicotinoyl)-1,2,3,6-tetrahydropyridin-4-yl)-1H-pyrrolo[2,3-b]pyridin-6-yl)cyclopropanecarboxamide

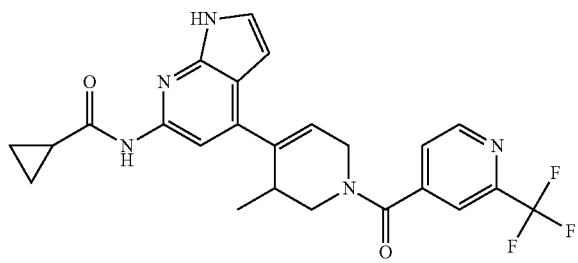 [SMILES: CC1CN(C(=O)c2ccnc(C(F)(F)F)c2)CC=C1c1cc(NC(=O)C2CC2)nc2[nH]ccc12]

$^1$H NMR (400 MHz, DMSO-d$_6$) δ 11.42 (s, 1H), 10.54 (s, 1H), 8.90 (d, J=4.9 Hz, 1H), 8.03-7.77 (m, 3H), 7.37-7.26 (m, 1H), 6.50 (d, J=12.5 Hz, 1H), 6.08 (d, J=73.2 Hz, 1H), 4.62-4.13 (m, 1H), 4.07 (s, 1H), 2.98 (s, 1H), 2.07-1.96 (m, 1H), 0.97-0.77 (m, 7H).

MS(ESI+) m/z 470 (M+H)⁺

Example 385: Synthesis of N-(4-(1-(2-fluoroisonicotinoyl)-2,2-dimethyl-1,2,3,6-tetrahydropyridin-4-yl)-1H-pyrrolo[2,3-b]pyridin-6-yl)cyclopropanecarboxamide

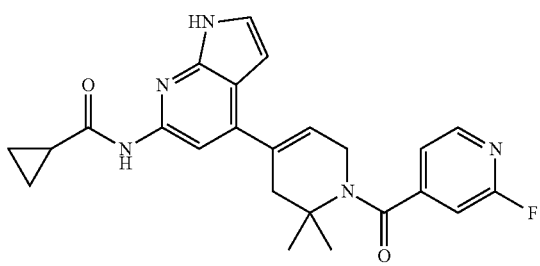 [SMILES: CC1(C)CC(c2cc(NC(=O)C3CC3)nc3[nH]ccc23)=CCN1C(=O)c1ccnc(F)c1]

$^1$H NMR (400 MHz, DMSO-d$_6$) δ 11.46 (s, 1H), 10.56 (s, 1H), 8.34 (d, J=5.1 Hz, 1H), 7.90 (s, 1H), 7.43-7.33 (m, 2H), 7.27 (d, J=2.2 Hz, 1H), 6.54 (dd, J=3.6, 1.9 Hz, 1H), 6.45 (t, J=4.6 Hz, 1H), 3.95 (d, J=4.5 Hz, 2H), 2.72 (s, 2H), 2.03 (hept, J=4.7 Hz, 1H), 1.58 (s, 6H), 0.87-0.71 (m, 4H).

MS(ESI+) m/z 434 (M+H)⁺

Example 386: Synthesis of N-(4-(1-(2-chloroisonicotinoyl)-2,2-dimethyl-1,2,3,6-tetrahydropyridin-4-yl)-1H-pyrrolo[2,3-b]pyridin-6-yl)cyclopropanecarboxamide

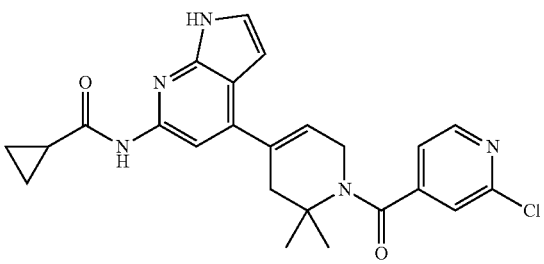 [SMILES: CC1(C)CC(c2cc(NC(=O)C3CC3)nc3[nH]ccc23)=CCN1C(=O)c1ccnc(Cl)c1]

$^1$H NMR (400 MHz, DMSO-d$_6$) δ 11.46 (s, 1H), 10.56 (s, 1H), 8.57-8.44 (m, 1H), 7.90 (s, 1H), 7.59 (s, 1H), 7.45 (s, 1H), 7.35 (s, 1H), 6.49 (d, J=35.6 Hz, 2H), 3.95 (s, 2H), 2.72 (s, 2H), 2.03 (s, 1H), 1.57 (d, J=5.9 Hz, 6H), 0.83 (d, J=20.3 Hz, 4H).

MS(ESI+) m/z 450, 452 (M+H)⁺

Example 387: Synthesis of N-(4-(1-(2-cyanoacetyl)-2,2-dimethyl-1,2,3,6-tetrahydropyridin-4-yl)-1H-pyrrolo[2,3-b]pyridin-6-yl)cyclopropanecarboxamide

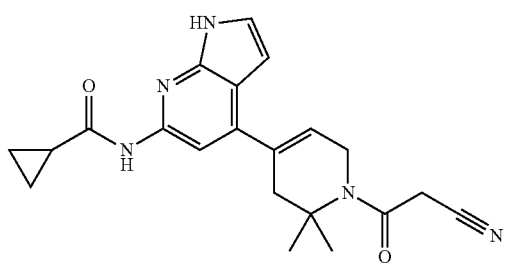 [SMILES: CC1(C)CC(c2cc(NC(=O)C3CC3)nc3[nH]ccc23)=CCN1C(=O)CC#N]

$^1$H NMR (400 MHz, DMSO-d$_6$) δ 11.48 (s, 1H), 10.56 (s, 1H), 7.89 (s, 1H), 7.36 (t, J=3.0 Hz, 1H), 6.54 (dd, J=3.5, 1.8 Hz, 1H), 6.46 (t, J=4.6 Hz, 1H), 4.09 (s, 2H), 4.02 (d, J=4.6 Hz, 2H), 2.64 (s, 2H), 2.05-1.98 (m, 1H), 1.47 (s, 6H), 0.85-0.71 (m, 4H).

MS(ESI+) m/z 378 (M+H)⁺

Example 388: Synthesis of (R)—N-(4-(1-(2-cyano-acetyl)-6-methyl-1,2,3,6-tetrahydropyridin-4-yl)-1H-pyrrolo[2,3-b]pyridin-6-yl)cyclopropanecarboxamide

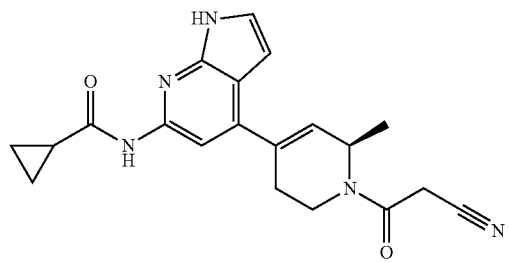 [SMILES: C[C@@H]1C=C(c2cc(NC(=O)C3CC3)nc3[nH]ccc23)CCN1C(=O)CC#N]

$^1$H NMR (400 MHz, DMSO-d$_6$) δ 11.44 (s, 1H), 10.53 (s, 1H), 7.85 (d, J=3.4 Hz, 1H), 7.35 (t, J=3.0 Hz, 1H), 6.60-6.38 (m, 1H), 6.24 (dd, J=24.2, 3.9 Hz, 1H), 4.99-4.41 (m, 1H), 4.59-3.69 (ddd, J=13.8, 5.2 Hz, 1H), 4.14 (m, 1H), 3.04-2.75 (m, 1H), 2.46-2.31 (m, 1H), 2.08-1.93 (m, 1H), 1.31 (dd, J=42.5, 6.8 Hz, 3H), 0.80 (m, 4H).

MS(ESI+) m/z 364 (M+H)$^+$

Example 389: Synthesis of (R)—N-(4-(1-(2-cyano-acetyl)-2-methyl-1,2,3,6-tetrahydropyridin-4-yl)-1H-pyrrolo[2,3-b]pyridin-6-yl)cyclopropanecarboxamide

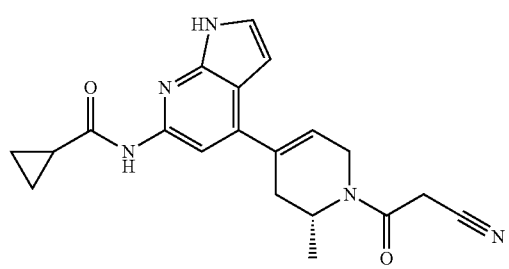

$^1$H NMR (400 MHz, DMSO-d$_6$) δ 11.44 (s, 1H), 10.54 (s, 1H), 7.85 (s, 1H), 7.35 (t, J=3.0 Hz, 1H), 6.53 (d, J=3.0 Hz, 1H), 6.28 (d, J=23.9 Hz, 1H), 5.02-4.88 (m, 1H), 4.66 (d, J=20.0 Hz, 1H), 4.28-3.95 (m, 4H), 3.66 (d, J=20.5 Hz, 1H), 3.01 (d, J=17.1 Hz, 1H), 2.37-2.26 (m, 1H), 2.08-1.93 (m, 1H), 1.31-1.18 (m, 3H), 0.82 (m, 4H).

MS(ESI+) m/z 364 (M+H)$^+$

Example 390: Synthesis of (S)—N-(4-(1-(2-cyano-acetyl)-6-methyl-1,2,3,6-tetrahydropyridin-4-yl)-1H-pyrrolo[2,3-b]pyridin-6-yl)cyclopropanecarboxamide)

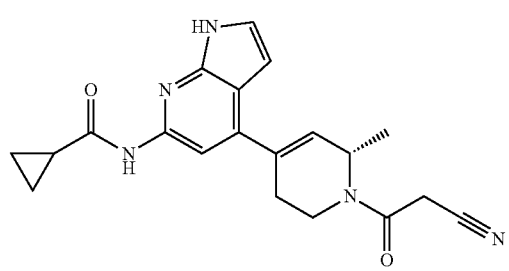 [SMILES: C[C@H]1C=C(c2cc(NC(=O)C3CC3)nc3[nH]ccc23)CCN1C(=O)CC#N]

$^1$H NMR (400 MHz, DMSO-d$_6$) δ 11.44 (s, 1H), 10.53 (s, 1H), 7.85 (d, J=3.7 Hz, 1H), 7.35 (t, J=3.0 Hz, 1H), 6.53 (dd, J=3.4, 1.7 Hz, 1H), 6.33-6.13 (m, 1H), 4.99-4.40 (m, 1H), 4.56-3.71 (dd, J=13.7, 5.2 Hz, 1H), 4.34-3.97 (m, 2H), 3.39-3.23 (m, 1H), 2.87 (dt, J=46.3, 13.5 Hz, 1H), 2.48-2.31 (m, 1H), 2.1-1.95 (m, 1H), 1.31 (dd, J=42.6, 6.7 Hz, 3H), 0.80 (dt, J=11.5, 5.5 Hz, 4H).

MS(ESI+) m/z 364 (M+H)$^+$

Example 391: Synthesis of (S)—N-(4-(1-(2-cyano-acetyl)-2-methyl-1,2,3,6-tetrahydropyridin-4-yl)-1H-pyrrolo[2,3-b]pyridin-6-yl)cyclopropanecarboxamide

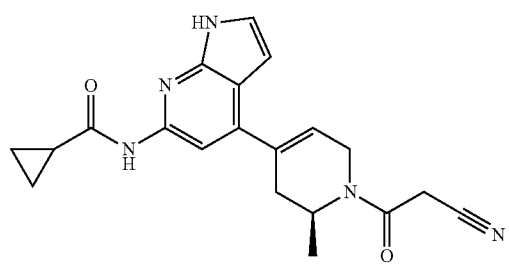 [SMILES: C[C@H]1CC(c2cc(NC(=O)C3CC3)nc3[nH]ccc23)=CCN1C(=O)CC#N]

$^1$H NMR (400 MHz, DMSO-d$_6$) δ 11.44 (s, 1H), 10.54 (s, 1H), 7.85 (s, 1H), 7.35 (t, J=3.0 Hz, 1H), 6.53 (d, J=3.0 Hz, 1H), 6.28 (d, J=23.9 Hz, 1H), 5.02-4.88 (m, 1H), 4.66 (d, J=20.0 Hz, 1H), 4.28-3.95 (m, 4H), 3.66 (d, J=20.5 Hz, 1H), 3.01 (d, J=17.1 Hz, 1H), 2.37-2.26 (m, 1H), 2.08-1.93 (m, 1H), 1.31-1.18 (m, 3H), 0.82 (m, 4H).

MS(ESI+) m/z 364 (M+H)$^+$

Example 392: Synthesis of N-(4-(1-(2-cyanoisonicotinoyl)-3-methyl-1,2,3,6-tetrahydropyridin-4-yl)-1H-pyrrolo[2,3-b]pyridin-6-yl)cyclopropanecarboxamide

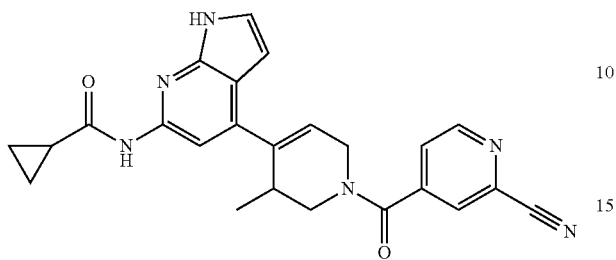

¹H NMR (400 MHz, DMSO-d₆) δ 11.45 (s, 1H), 10.59 (d, J=3.2 Hz, 1H), 8.87 (d, J=5.4 Hz, 1H), 8.20 (d, J=9.9 Hz, 1H), 7.83 (q, J=4.9 Hz, 2H), 7.33 (d, J=9.6 Hz, 1H), 6.50 (d, J=15.1 Hz, 1H), 6.07 (d, J=75.8 Hz, 1H), 4.59-4.15 (m, 1H), 4.06 (s, 1H), 3.58 (s, 1H), 3.26 (s, 1H), 3.03 (d, J=43.5 Hz, 1H), 2.00 (s, 1H), 0.95-0.76 (m, 7H).
MS(ESI+) m/z 427 (M+H)⁺

Example 393: Synthesis of N-(4-(1-(2-cyanoacetyl)-2-(trifluoromethyl)-1,2,3,6-tetrahydropyridin-4-yl)-1H-pyrrolo[2,3-b]pyridin-6-yl)cyclopropanecarboxamide

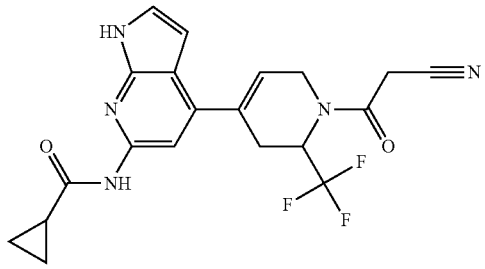 [SMILES: N#CCC(=O)N1CC=C(c2cc(NC(=O)C3CC3)nc3[nH]ccc23)CC1C(F)(F)F]

MS(ESI+) m/z 418 (M+H)⁺

Example 394: Synthesis of N-(4-(9-(2-cyanoacetyl)-9-azabicyclo[3.3.1]non-2-en-3-yl)-1H-pyrrolo[2,3-b]pyridin-6-yl)cyclopropanecarboxamide

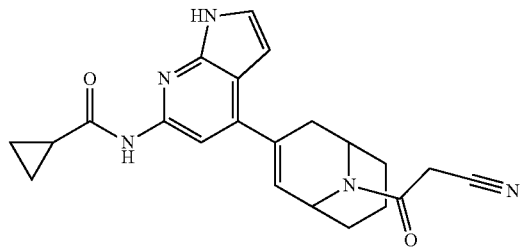 [SMILES: N#CCC(=O)N1C2C=C(c3cc(NC(=O)C4CC4)nc4[nH]ccc34)CC1CCC2]

¹H NMR (400 MHz, DMSO-d₆) δ 11.45 (s, 1H), 10.55 (s, 1H), 7.89 (s, 1H), 7.35 (d, J=3.2 Hz, 1H), 6.55 (d, J=11.5 Hz, 1H), 6.29 (d, J=13.7 Hz, 1H), 5.17 (s, 1H), 4.71 (d, J=141.5 Hz, 1H), 4.22-4.11 (m, 2H), 3.18-3.07 (m, 1H), 2.91-2.64 (m, 1H), 2.38 (d, J=18.0 Hz, 2H), 2.02 (s, 1H), 1.80 (d, J=8.8 Hz, 2H), 1.62 (d, J=31.9 Hz, 2H), 0.79 (d, J=11.9 Hz, 4H).
MS(ESI+) m/z 390 (M+H)⁺

Example 395: Synthesis of (S)—N-(4-(1-(2-fluoroisonicotinoyl)-3-methyl-1,2,3,6-tetrahydropyridin-4-yl)-1H-pyrrolo[2,3-b]pyridin-6-yl)cyclopropanecarboxamide

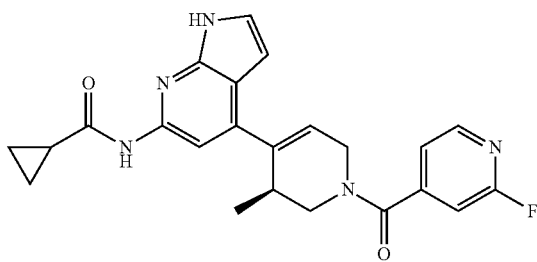 [SMILES: C[C@@H]1CN(C(=O)c2ccnc(F)c2)CC=C1c1cc(NC(=O)C2CC2)nc2[nH]ccc12]

MS(ESI+) m/z 420 (M+H)⁺

Example 396: Synthesis of ((S)—N-(4-(1-(2,3-difluoroisonicotinoyl)-3-methyl-1,2,3,6-tetrahydropyridin-4-yl)-1H-pyrrolo[2,3-b]pyridin-6-yl)cyclopropanecarboxamide)

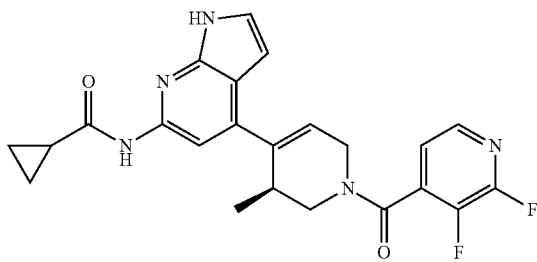 [SMILES: C[C@@H]1CN(C(=O)c2ccnc(F)c2F)CC=C1c1cc(NC(=O)C2CC2)nc2[nH]ccc12]

¹H NMR (400 MHz, DMSO-d₆) δ 11.44 (s, 1H), 10.55 (s, 1H), 8.21-8.13 (m, 1H), 7.84 (d, J=14.3 Hz, 1H), 7.58-7.49 (m, 1H), 7.33 (dt, J=5.5, 2.8 Hz, 1H), 6.48 (d, J=8.5 Hz, 1H), 6.08 (dd, J=75.5, 3.0 Hz, 1H), 4.63-4.22 (m, 1H), 4.18 (d, J=18.5 Hz, 1H), 4.12-3.92 (m, 1H), 3.61 (dd, J=30.9, 12.6 Hz, 1H), 3.01 (d, J=64.9 Hz, 1H), 2.02 (s, 1H), 0.97-0.91 (m, 1H), 0.84-0.73 (m, 6H).
MS(ESI+) m/z 438 (M+H)⁺

Example 397: Synthesis of (S)—N-(4-(1-(3-bromobenzoyl)-3-methyl-1,2,3,6-tetrahydropyridin-4-yl)-1H-pyrrolo[2,3-b]pyridin-6-yl)cyclopropanecarboxamide

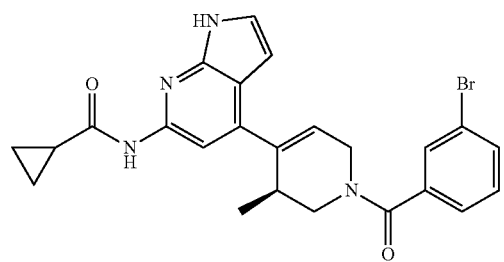 [SMILES: C[C@@H]1CN(C(=O)c2cccc(Br)c2)CC=C1c1cc(NC(=O)C2CC2)nc2[nH]ccc12]

¹H NMR (400 MHz, DMSO-d₆) δ 11.42 (s, 1H), 10.54 (s, 1H), 7.83 (s, 1H), 7.67 (t, J=8.0 Hz, 2H), 7.45 (d, J=8.6 Hz, 2H), 7.32 (s, 1H), 6.50 (s, 1H), 6.21-5.96 (m, 1H), 4.59-4.12 (m, 1H), 4.09 (s, 1H), 3.61 (d, J=12.3 Hz, 1H), 3.02 (d, J=28.7 Hz, 1H), 2.01 (d, J=7.7 Hz, 1H), 0.94-0.75 (m, 7H).

MS(ESI+) m/z 479, 481 (M+H)⁺

Example 398: Synthesis of (S)—N-(4-(3-methyl-1-(4-nitrobenzoyl)-1,2,3,6-tetrahydropyridin-4-yl)-1H-pyrrolo[2,3-b]pyridin-6-yl)cyclopropanecarboxamide

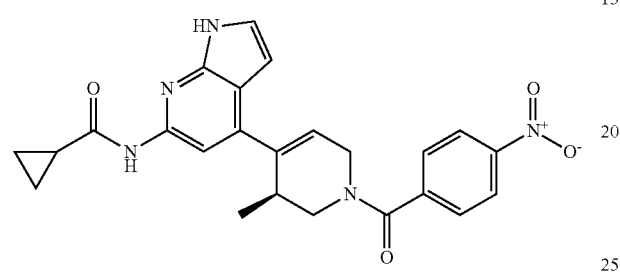

¹H NMR (400 MHz, DMSO-d₆) δ 11.43 (s, 1H), 10.55 (s, 1H), 8.33 (d, J=8.0 Hz, 2H), 7.84 (d, J=9.4 Hz, 1H), 7.75 (d, J=8.1 Hz, 2H), 7.33 (s, 1H), 6.50 (d, J=17.6 Hz, 1H), 6.09 (d, J=79.5 Hz, 1H), 4.37 (dd, J=155.9, 19.7 Hz, 1H), 4.08 (d, J=23.1 Hz, 1H), 3.61 (d, J=13.3 Hz, 1H), 3.13-2.93 (m, 1H), 2.02 (s, 1H), 0.98-0.90 (m, 1H), 0.79 (t, J=8.0 Hz, 6H).

MS(ESI+) m/z 446 (M+H)⁺

Example 399: Synthesis of (S)—N-(4-(1-(2-chloroisonicotinoyl)-3-methyl-1,2,3,6-tetrahydropyridin-4-yl)-1H-pyrrolo[2,3-b]pyridin-6-yl)cyclopropanecarboxamide

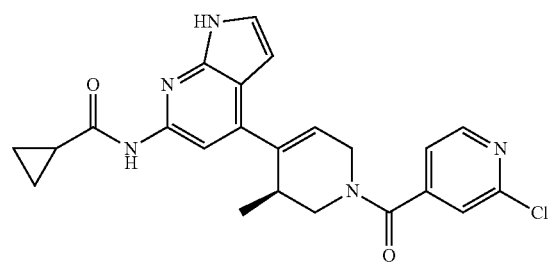 [SMILES: C[C@@H]1CN(C(=O)c2ccnc(Cl)c2)CC=C1c1cc(NC(=O)C2CC2)nc2[nH]ccc12]

¹H NMR (400 MHz, DMSO-d₆) δ 11.43 (s, 1H), 10.55 (s, 1H), 8.61-8.46 (m, 1H), 7.84 (d, J=12.1 Hz, 1H), 7.65 (d, J=7.5 Hz, 1H), 7.50 (d, J=5.6 Hz, 1H), 7.38-7.26 (m, 1H), 6.53-6.42 (m, 1H), 6.23-5.97 (m, 1H), 4.34 (dd, J=164.5, 20.3 Hz, 1H), 4.05 (s, 1H), 3.63-3.53 (m, 1H), 3.12-2.93 (m, 1H), 2.01 (d, J=7.4 Hz, 1H), 0.94 (d, J=6.8 Hz, 1H), 0.84-0.74 (m, 6H).

MS(ESI+) m/z 436, 438 (M+H)⁺

Example 400: Synthesis of (S)—N-(4-(1-(6-chloronicotinoyl)-3-methyl-1,2,3,6-tetrahydropyridin-4-yl)-1H-pyrrolo[2,3-b]pyridin-6-yl)cyclopropanecarboxamide

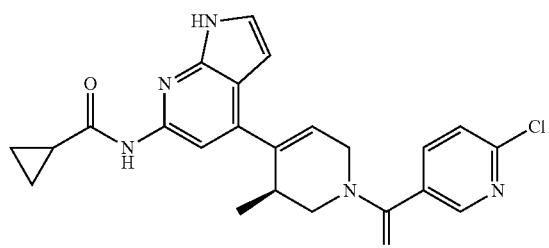

¹H NMR (400 MHz, DMSO-d₆) δ 11.43 (s, 1H), 10.55 (s, 1H), 8.55 (s, 1H), 7.99 (d, J=7.8 Hz, 1H), 7.84 (s, 1H), 7.64 (d, J=8.2 Hz, 1H), 7.33 (d, J=5.2 Hz, 1H), 6.50 (d, J=13.3 Hz, 1H), 6.09 (d, J=69.3 Hz, 1H), 4.57-4.18 (m, 1H), 4.14 (s, 1H), 3.65 (d, J=12.1 Hz, 1H), 3.05 (d, J=23.3 Hz, 1H), 2.01 (d, J=7.4 Hz, 1H), 0.94 (s, 1H), 0.83-0.74 (m, 6H).

MS(ESI+) m/z 436, 438 (M+H)⁺

Example 401: Synthesis of (S)—N-(4-(1-(2-chloroacetyl)-3-methyl-1,2,3,6-tetrahydropyridin-4-yl)-1H-pyrrolo[2,3-b]pyridin-6-yl)cyclopropanecarboxamide

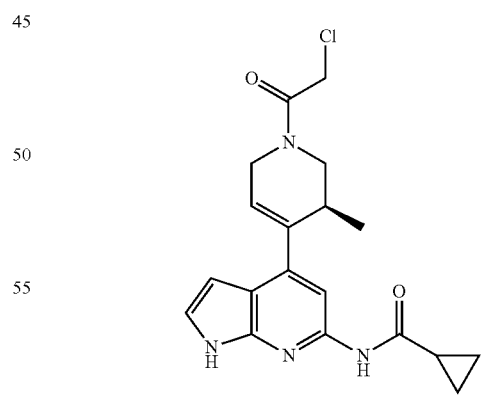

¹H NMR (400 MHz, DMSO-d₆) δ 11.43 (s, 1H), 10.55 (s, 1H), 7.84 (d, J=6.9 Hz, 1H), 7.33 (s, 1H), 6.48 (s, 1H), 6.10 (d, J=14.2 Hz, 1H), 4.54-4.40 (m, 2H), 4.37-3.97 (m, 2H), 3.77-3.36 (m, 2H), 3.02 (d, J=32.0 Hz, 1H), 2.01 (d, J=7.2 Hz, 1H), 0.92-0.84 (m, 3H), 0.83-0.69 (m, 4H).

MS(ESI+) m/z 373, 375 (M+H)⁺

Example 402: Synthesis of (S)—N-(4-(1-(3-fluoroisonicotinoyl)-3-methyl-1,2,3,6-tetrahydropyridin-4-yl)-1H-pyrrolo[2,3-b]pyridin-6-yl)cyclopropanecarboxamide

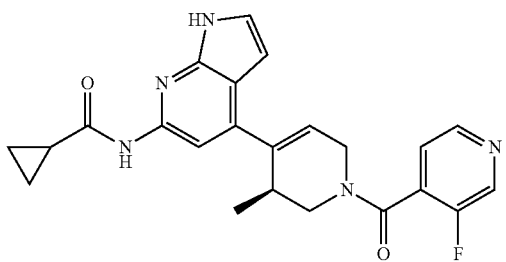 [SMILES: C[C@@H]1CN(C(=O)c2ccncc2F)CC=C1c1cc(NC(=O)C2CC2)nc2[nH]ccc12]

¹H NMR (400 MHz, DMSO-d₆) δ 11.43 (s, 1H), 10.55 (s, 1H), 8.74 (s, 1H), 8.64-8.50 (m, 1H), 7.84 (d, J=14.3 Hz, 1H), 7.58 (d, J=4.9 Hz, 1H), 7.33 (dd, J=7.1, 3.4 Hz, 1H), 6.49 (d, J=10.2 Hz, 1H), 6.09 (d, J=71.2 Hz, 1H), 4.70-4.08 (m, 2H), 3.99 (s, 1H), 3.59 (t, J=14.5 Hz, 1H), 3.12-2.90 (m, 1H), 2.02 (s, 1H), 0.95 (d, J=6.9 Hz, 1H), 0.79 (q, J=6.6 Hz, 6H).

MS(ESI+) m/z 420 (M+H)⁺

Example 403: Synthesis of (S)—N-(4-(1-(2-cyano-3-(thiophen-2-yl)acryloyl)-3-methyl-1,2,3,6-tetrahydropyridin-4-yl)-1H-pyrrolo[2,3-b]pyridin-6-yl)cyclopropanecarboxamide

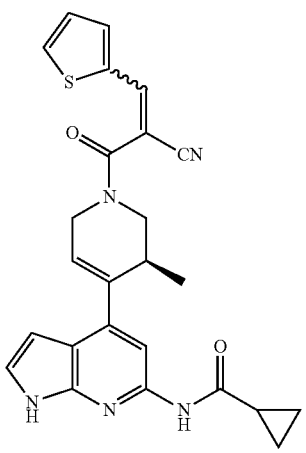 [SMILES: C[C@@H]1CN(C(=O)C(C#N)=Cc2cccs2)CC=C1c1cc(NC(=O)C2CC2)nc2[nH]ccc12]

¹H NMR (400 MHz, DMSO-d₆) δ 11.43 (s, 1H), 10.55 (s, 1H), 8.20-8.03 (m, 1H), 7.95 (s, 1H), 7.86 (q, J=3.1 Hz, 1H), 7.57 (d, J=6.6 Hz, 1H), 7.37-7.27 (m, 2H), 6.50 (s, 1H), 6.15 (d, J=13.1 Hz, 1H), 4.45 (d, J=18.5 Hz, 1H), 4.39-3.46 (m, 3H), 3.10 (s, 1H), 2.09-1.97 (m, 1H), 0.96-0.87 (m, 3H), 0.83-0.74 (m, 4H).

MS(ESI+) m/z 458 (M+H)⁺

Example 404: Synthesis of (S)—N-(4-(1-(2-(cyanomethyl)-3-phenylacryloyl)-3-methyl-1,2,3,6-tetrahydropyridin-4-yl)-1H-pyrrolo[2,3-b]pyridin-6-yl)cyclopropanecarboxamide

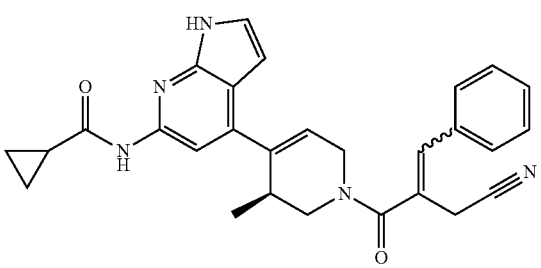 [SMILES: C[C@@H]1CN(C(=O)C(=Cc2ccccc2)CC#N)CC=C1c1cc(NC(=O)C2CC2)nc2[nH]ccc12]

¹H NMR (400 MHz, DMSO-d₆) δ 11.44 (s, 1H), 10.56 (s, 1H), 7.99-7.91 (m, 2H), 7.87 (d, J=8.8 Hz, 1H), 7.58 (d, J=4.2 Hz, 2H), 7.50 (s, 1H), 7.34 (s, 1H), 6.51 (s, 1H), 6.13 (s, 1H), 4.47 (s, 1H), 4.37-4.07 (m, 1H), 3.97 (d, J=22.1 Hz, 1H), 3.80-3.45 (m, 1H), 3.10 (s, 1H), 2.01 (d, J=8.0 Hz, 1H), 0.92 (d, J=7.1 Hz, 3H), 0.79 (t, J=8.3 Hz, 4H).

MS(ESI+) m/z 466 (M+H)⁺

Example 405: Synthesis of (S)—N-(4-(3-methyl-1-(1-methyl-2-oxo-1,2-dihydropyridine-3-carbonyl)-1,2,3,6-tetrahydropyridin-4-yl)-1H-pyrrolo[2,3-b]pyridin-6-yl)cyclopropanecarboxamide

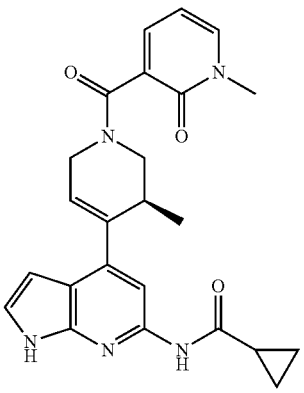 [SMILES: C[C@@H]1CN(C(=O)c2cccn(C)c2=O)CC=C1c1cc(NC(=O)C2CC2)nc2[nH]ccc12]

¹H NMR (400 MHz, DMSO-d₆) δ 11.41 (s, 1H), 10.54 (s, 1H), 7.82 (d, J=12.8 Hz, 2H), 7.51 (d, J=6.6 Hz, 1H), 7.32 (d, J=6.5 Hz, 1H), 6.48 (s, 1H), 6.29 (d, J=7.0 Hz, 1H), 6.08 (d, J=54.1 Hz, 1H), 4.27 (dd, J=137.1, 19.1 Hz, 2H), 4.00 (s, 1H), 3.56 (s, 1H), 3.49 (s, 3H), 2.98 (s, 1H), 2.02 (s, 1H), 0.94 (d, J=6.9 Hz, 1H), 0.85-0.72 (m, 6H).

MS(ESI+) m/z 432 (M+H)⁺

Example 406: Synthesis of (S)—N-(4-(1-(2-(1-cyanocyclohexyl)acetyl)-3-methyl-1,2,3,6-tetrahydropyridin-4-yl)-1H-pyrrolo[2,3-b]pyridin-6-yl)cyclopropanecarboxamide

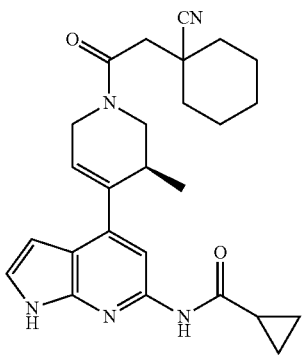 [SMILES: C[C@@H]1CN(C(=O)CC2(C#N)CCCCC2)CC=C1c1cc(NC(=O)C2CC2)nc2[nH]ccc12]

¹H NMR (400 MHz, DMSO-d₆) δ 11.42 (s, 1H), 10.54 (s, 1H), 7.84 (d, J=7.1 Hz, 1H), 7.33 (s, 1H), 6.49 (s, 1H), 6.09 (d, J=20.9 Hz, 1H), 4.43-4.27 (m, 1H), 4.13-3.93 (m, 1H), 3.72-3.51 (m, 1H), 3.38 (d, J=12.6 Hz, 1H), 2.99 (d, J=23.7 Hz, 1H), 2.84 (d, J=9.4 Hz, 1H), 2.69 (d, J=8.1 Hz, 1H), 2.09 (d, J=13.0 Hz, 2H), 2.01 (d, J=7.2 Hz, 1H), 1.67 (d, J=11.6 Hz, 3H), 1.54-1.33 (m, 4H), 1.18 (dd, J=20.2, 9.7 Hz, 1H), 0.87 (dd, J=17.1, 6.8 Hz, 3H), 0.83-0.71 (m, 4H).

MS(ESI+) m/z 446 (M+H)⁺

Example 407: Synthesis of (S)—N-(4-(1-(4-cyanotetrahydro-2H-pyran-4-carbonyl)-3-methyl-1,2,3,6-tetrahydropyridin-4-yl)-1H-pyrrolo[2,3-b]pyridin-6-yl)cyclopropanecarboxamide

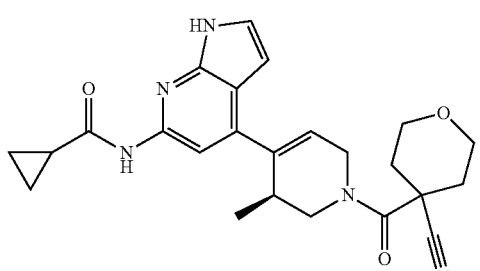

¹H NMR (400 MHz, DMSO-d₆) δ 11.42 (s, 1H), 10.54 (s, 1H), 7.84 (d, J=6.7 Hz, 1H), 7.32 (t, J=3.0 Hz, 1H), 6.48 (dt, J=4.7, 2.3 Hz, 1H), 6.09 (dt, J=28.1, 3.4 Hz, 1H), 4.28 (dd, J=52.8, 18.4 Hz, 1H), 4.07-3.96 (m, 1H), 3.94-3.57 (m, 1H), 3.43 (ddd, J=12.4, 7.9, 4.5 Hz, 1H), 3.00 (s, 1H), 2.90-2.62 (m, 2H), 2.01 (td, J=7.4, 3.7 Hz, 1H), 1.34-1.14 (m, 3H), 1.01-0.89 (m, 2H), 0.87 (dd, J=6.9, 5.1 Hz, 3H), 0.84-0.73 (m, 4H).

MS(ESI+) m/z 434 (M+H)⁺

Example 408: Synthesis of (S)—N-(4-(1-(2-cyano-3-methylbut-2-enoyl)-3-methyl-1,2,3,6-tetrahydropyridin-4-yl)-1H-pyrrolo[2,3-b]pyridin-6-yl)cyclopropanecarboxamide

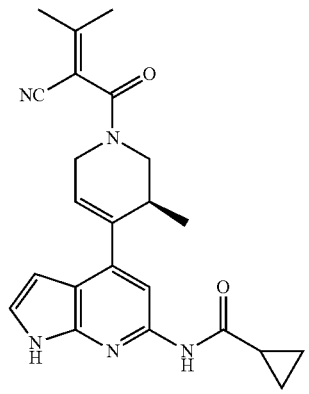 [SMILES: CC(C)=C(C#N)C(=O)N1CC=C(c2cc(NC(=O)C3CC3)nc3[nH]ccc23)[C@H](C)C1]

¹H NMR (400 MHz, DMSO-d₆) δ 11.44 (s, 1H), 10.56 (s, 1H), 7.84 (s, 1H), 7.33 (s, 1H), 6.48 (s, 1H), 6.11 (d, J=21.5 Hz, 1H), 4.58-4.23 (m, 1H), 4.07 (t, J=22.3 Hz, 2H), 3.77-3.55 (m, 1H), 3.54-3.44 (m, 1H), 3.03 (s, 1H), 2.14 (s, 3H), 2.02 (s, 1H), 1.93 (d, J=7.1 Hz, 3H), 0.88 (d, J=6.7 Hz, 3H), 0.79 (dd, J=13.1, 5.2 Hz, 4H).

MS(ESI+) m/z 404 (M+H)⁺

Example 409: Synthesis of N-(4-(1-(2-cyanoacetyl)-2,6-diethyl-1,2,3,6-tetrahydropyridin-4-yl)-1H-pyrrolo[2,3-b]pyridin-6-yl)cyclopropanecarboxamide

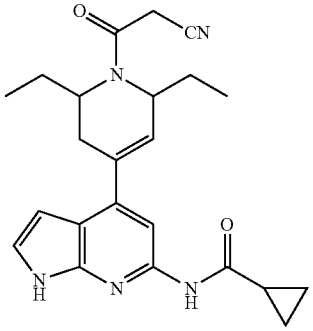 [SMILES: CCC1C=C(c2cc(NC(=O)C3CC3)nc3[nH]ccc23)CC(CC)N1C(=O)CC#N]

¹H NMR (400 MHz, DMSO-d₆) δ 11.46 (s, 1H), 10.55 (s, 1H), 7.85 (s, 1H), 7.44-7.34 (m, 1H), 6.46 (dd, J=3.8, 1.8 Hz, 1H), 6.30 (t, J=3.0 Hz, 1H), 4.70-4.55 (m, 1H), 4.29-4.01 (m, 2H), 3.90 (d, J=6.7 Hz, 1H), 2.01 (d, J=5.2 Hz, 1H), 1.65 (dddd, J=51.1, 21.4, 14.7, 7.4 Hz, 4H), 1.23 (s, 2H), 1.08-0.97 (m, 3H), 0.88 (dt, J=13.5, 7.3 Hz, 3H), 0.83-0.71 (m, 4H).

MS(ESI+) m/z 406 (M+H)⁺

Example 410: Synthesis of N-(4-(1-(2-cyanoacetyl)-2-isopropyl-1,2,3,6-tetrahydropyridin-4-yl)-1H-pyrrolo[2,3-b]pyridin-6-yl)cyclopropanecarboxamide

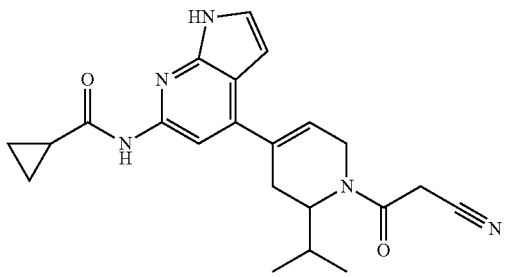 [SMILES: CC(C)C1CC(c2cc(NC(=O)C3CC3)nc3[nH]ccc23)=CCN1C(=O)CC#N]

$^1$H NMR (400 MHz, DMSO-d$_6$) δ 11.45 (s, 1H), 10.54 (s, 1H), 7.87 (s, 1H), 7.35 (s, 1H), 6.58-6.40 (m, 1H), 6.37-6.19 (m, 1H), 4.29-4.08 (m, 2H), 4.08-3.89 (m, 1H), 3.84-3.54 (m, 1H), 3.01-2.81 (m, 1H), 2.37 (s, 1H), 2.01 (s, 2H), 1.23 (s, 2H), 1.06 (d, J=6.6 Hz, 2H), 0.92 (t, J=5.7 Hz, 2H), 0.87 (dd, J=13.0, 6.5 Hz, 2H), 0.83-0.75 (m, 4H).
MS(ESI+) m/z 392 (M+H)$^+$

Example 411: Synthesis of N-(4-(1-(2-cyanoacetyl)-6-propyl-1,2,3,6-tetrahydropyridin-4-yl)-1H-pyrrolo[2,3-b]pyridin-6-yl)cyclopropanecarboxamide

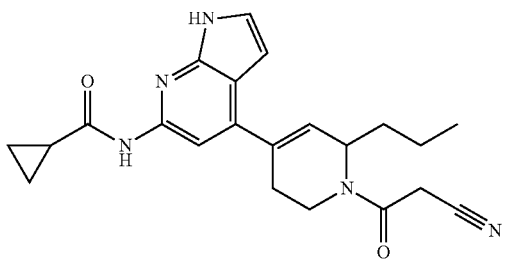 [SMILES: CCCC1C=C(c2cc(NC(=O)C3CC3)nc3[nH]ccc23)CCN1C(=O)CC#N]

MS(ESI+) m/z 392 (M+H)$^+$

Example 412: Synthesis of N-(4-(6-(tert-butyl)-1-(2-cyanoacetyl)-1,2,3,6-tetrahydropyridin-4-yl)-1H-pyrrolo[2,3-b]pyridin-6-yl)cyclopropanecarboxamide

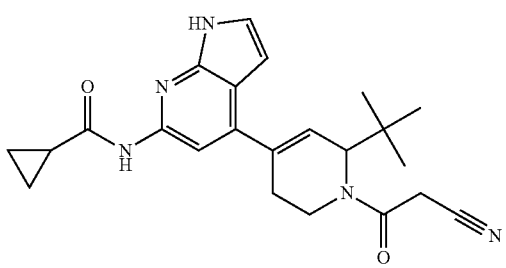 [SMILES: CC(C)(C)C1C=C(c2cc(NC(=O)C3CC3)nc3[nH]ccc23)CCN1C(=O)CC#N]

MS(ESI+) m/z 406 (M+H)$^+$

Example 413: Synthesis of N-(4-(1-(2-cyanoacetyl)-2-ethyl-1,2,3,6-tetrahydropyridin-4-yl)-1H-pyrrolo[2,3-b]pyridin-6-yl)cyclopropanecarboxamide

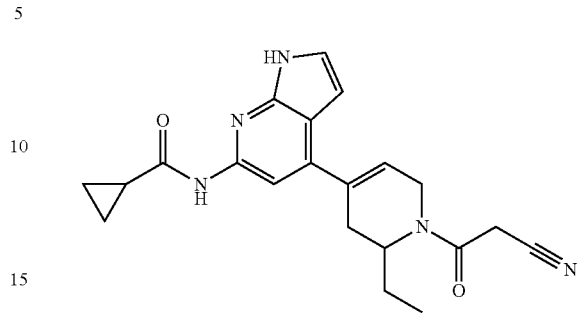

$^1$H NMR (400 MHz, DMSO-d$_6$) δ 11.44 (s, 1H), 10.54 (s, 1H), 7.85 (s, 1H), 7.35 (t, J=2.9 Hz, 1H), 6.52 (s, 1H), 6.25 (d, J=28.2 Hz, 1H), 4.81-4.65 (m, 1H), 4.20-4.08 (m, 2H), 4.00-3.90 (m, 1H), 3.01 (d, J=17.1 Hz, 1H), 2.08-1.91 (m, 1H), 1.74-1.46 (m, 2H), 1.23 (s, 2H), 0.86 (dd, J=12.2, 7.3 Hz, 3H), 0.86-0.69 (m, 4H).
MS(ESI+) m/z 378 (M+H)$^+$

Example 414: Synthesis of N-(4-(5-(2-cyanoacetyl)-5-azaspiro[3.5]non-7-en-8-yl)-1H-pyrrolo[2,3-b]pyridin-6-yl)cyclopropanecarboxamide

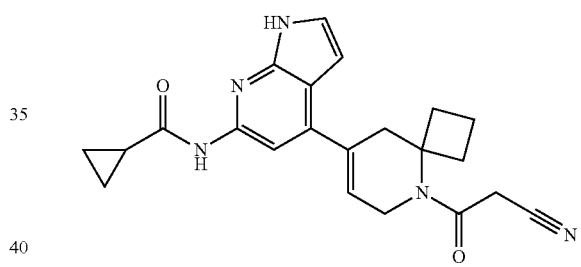

$^1$H NMR (400 MHz, DMSO-d$_6$) δ 11.44 (s, 1H), 10.54 (s, 1H), 7.86 (s, 1H), 7.37-7.15 (m, 1H), 6.55 (s, 1H), 6.28 (s, 1H), 4.03 (s, 4H), 2.36 (s, 2H), 2.12-1.97 (m, 3H), 1.79 (dt, J=28.8, 10.1 Hz, 2H), 0.83-0.74 (m, 4H).
MS(ESI+) m/z 390 (M+H)$^+$

Example 415: Synthesis of (S)—N-(4-(1-(2-(1-cyanocyclopropyl)acetyl)-3-methyl-1,2,3,6-tetrahydropyridin-4-yl)-1H-pyrrolo[2,3-b]pyridin-6-yl)cyclopropanecarboxamide

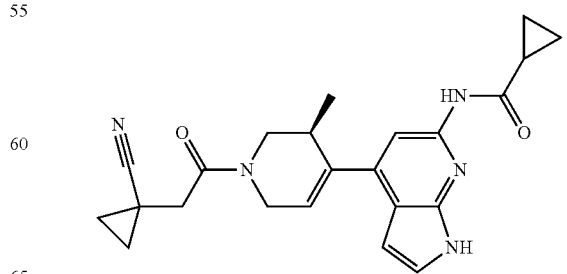

MS(ESI+) m/z 404 (M+H)$^+$

Example 416: Synthesis of (R)—N-(4-(1-(2-cyano-acetyl)-6-ethyl-1,2,3,6-tetrahydropyridin-4-yl)-1H-pyrrolo[2,3-b]pyridin-6-yl)cyclopropanecarboxamide

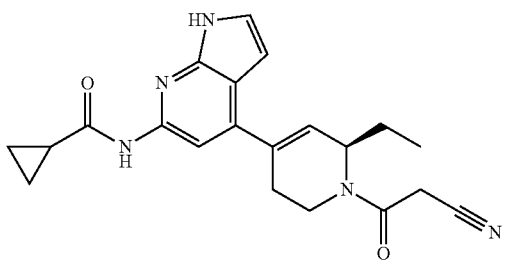 [SMILES: CC[C@@H]1C=C(c2cc(NC(=O)C3CC3)nc3[nH]ccc23)CCN1C(=O)CC#N]

MS(ESI+) m/z 378 (M+H)+

Example 417: Synthesis of (R)—N-(4-(1-(2-cyano-acetyl)-2-ethyl-1,2,3,6-tetrahydropyridin-4-yl)-1H-pyrrolo[2,3-b]pyridin-6-yl)cyclopropanecarboxamide

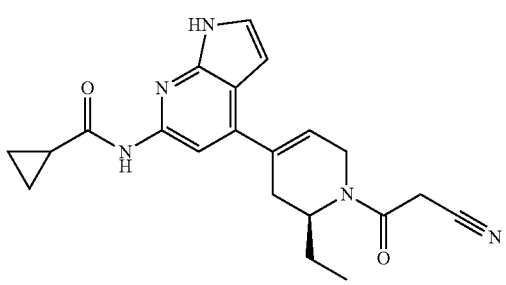 [SMILES: CC[C@H]1CC(c2cc(NC(=O)C3CC3)nc3[nH]ccc23)=CCN1C(=O)CC#N]

MS(ESI+) m/z 378 (M+H)+

Example 418: Synthesis of N-(4-(1-(3-cyanopropanoyl)-1,4,5,6-tetrahydropyridin-3-yl)-1H-pyrrolo[2,3-b]pyridin-6-yl)cyclopropanecarboxamide

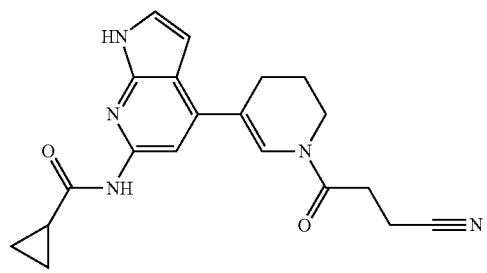 [SMILES: N#CCCC(=O)N1C=C(c2cc(NC(=O)C3CC3)nc3[nH]ccc23)CCC1]

MS(ESI+) m/z 364 (M+H)+

Example 419: Synthesis of N-(4-(1-(2-cyanoacetyl)-1,4,5,6-tetrahydropyridin-3-yl)-1H-pyrrolo[2,3-b]pyridin-6-yl)cyclopropanecarboxamide

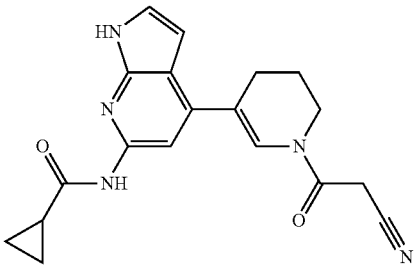 [SMILES: N#CCC(=O)N1C=C(c2cc(NC(=O)C3CC3)nc3[nH]ccc23)CCC1]

MS(ESI+) m/z 350 (M+H)+

Example 420: Synthesis of N-(4-(1-(2-cyanoacetyl)-1,2,5,6-tetrahydropyridin-3-yl)-1H-pyrrolo[2,3-b]pyridin-6-yl)cyclopropanecarboxamide

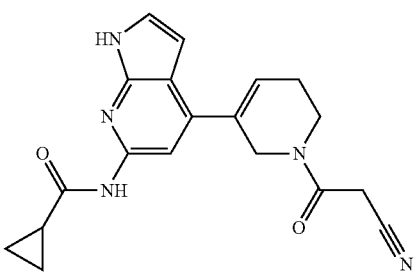 [SMILES: N#CCC(=O)N1CCC=C(c2cc(NC(=O)C3CC3)nc3[nH]ccc23)C1]

$^1$H NMR (400 MHz, DMSO-$d_6$) δ 11.47 (s, 1H), 10.55 (d, J=5.3 Hz, 1H), 7.84 (d, J=7.8 Hz, 1H), 7.36 (q, J=2.7 Hz, 1H), 6.60-6.50 (m, 1H), 6.48-6.33 (m, 1H), 4.35 (dd, J=40.1, 2.7 Hz, 2H), 4.15 (d, J=5.6 Hz, 2H), 3.61 (dt, J=43.3, 5.8 Hz, 2H), 2.46-2.28 (m, 2H), 2.02 (d, J=6.0 Hz, 1H), 0.90-0.71 (m, 4H).
MS(ESI+) m/z 350 (M+H)+

Example 421: Synthesis of N-(4-(1-(3-cyanopropanoyl)-1,2,5,6-tetrahydropyridin-3-yl)-1H-pyrrolo[2,3-b]pyridin-6-yl)cyclopropanecarboxamide

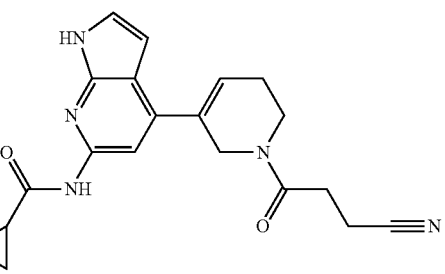

$^1$H NMR (400 MHz, DMSO-$d_6$) δ 11.46 (s, 1H), 10.55 (s, 1H), 7.86 (d, J=4.1 Hz, 1H), 7.35 (t, J=3.0 Hz, 1H), 6.58-6.51 (m, 1H), 6.48-6.39 (m, 1H), 4.46-4.29 (m, 2H), 3.65 (dt, J=24.4, 5.8 Hz, 2H), 2.82 (dt, J=14.1, 6.8 Hz, 2H), 2.64 (dt, J=14.0, 6.7 Hz, 2H), 2.38 (d, J=39.9 Hz, 2H), 2.01 (d, J=7.9 Hz, 1H), 0.85-0.76 (m, 4H).
MS(ESI+) m/z 364 (M+H)⁺

Example 422: Synthesis of N-(4-(1-(2-cyanoacetyl)-2,5,6,7-tetrahydro-1H-azepin-4-yl)-1H-pyrrolo[2,3-b]pyridin-6-yl)cyclopropanecarboxamide

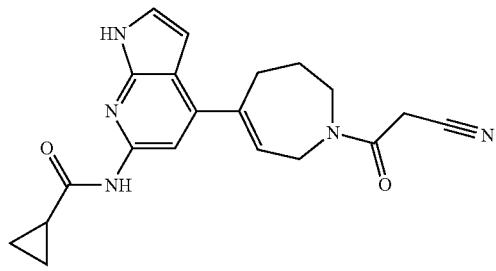 [SMILES: N#CCC(=O)N1CC=C(c2cc(NC(=O)C3CC3)nc3[nH]ccc23)CCC1]

¹H NMR (400 MHz, DMSO-d₆) δ 11.40 (d, J=7.3 Hz, 1H), 10.57-10.47 (m, 1H), 7.79 (d, J=8.5 Hz, 1H), 7.32 (q, J=3.0 Hz, 1H), 6.40 (ddd, J=1.9, 3.6, 8.7 Hz, 1H), 6.24 (dt, J=5.4, 32.4 Hz, 1H), 4.15 (dd, J=5.4, 11.3 Hz, 2H), 4.08 (d, J=20.8 Hz, 2H), 3.67 (dt, J=5.9, 41.9 Hz, 2H), 2.71 (dt, J=5.7, 16.7 Hz, 2H), 2.01 (t, J=5.9 Hz, 1H), 1.96 (s, 1H), 1.91 (d, J=12.1 Hz, 1H), 0.84-0.75 (m, 4H).
MS(ESI+) m/z 364 (M+H)⁺

Example 423: Synthesis of N-(4-(1-(2-fluoroisonicotinoyl)-2,5,6,7-tetrahydro-1H-azepin-4-yl)-1H-pyrrolo[2,3-b]pyridin-6-yl)cyclopropanecarboxamide

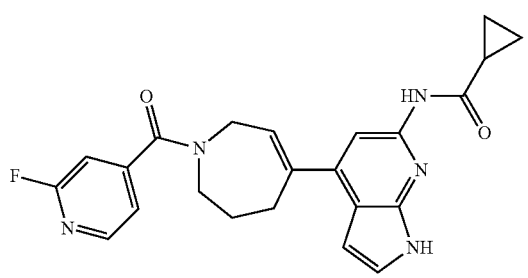 [SMILES: O=C(Nc1cc(C2=CCN(C(=O)c3ccnc(F)c3)CCC2)c2cc[nH]c2n1)C1CC1]

MS(ESI+) m/z 420 (M+H)⁺

Example 424: Synthesis of N-(4-(1-(2,3-difluoroisonicotinoyl)-2,5,6,7-tetrahydro-1H-azepin-4-yl)-1H-pyrrolo[2,3-b]pyridin-6-yl)cyclopropanecarboxamide

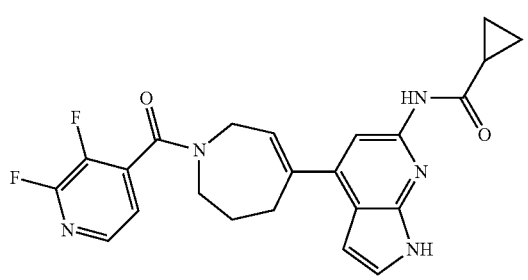 [SMILES: O=C(Nc1cc(C2=CCN(C(=O)c3ccnc(F)c3F)CCC2)c2cc[nH]c2n1)C1CC1]

MS(ESI+) m/z 438 (M+H)⁺

Example 425: Synthesis of N-(4-(1-(2-cyanoacetyl)-1,2,3,6-tetrahydropyridin-4-yl)-7H-pyrrolo[2,3-d]pyrimidin-2-yl)cyclopropanecarboxamide

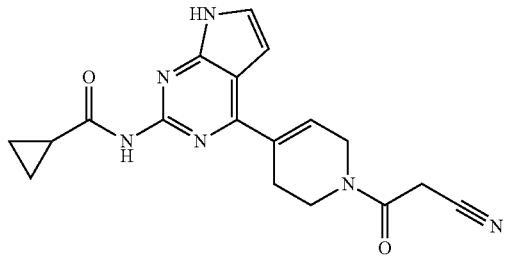 [SMILES: N#CCC(=O)N1CC=C(c2nc(NC(=O)C3CC3)nc3[nH]ccc23)CC1]

¹H NMR (400 MHz, DMSO-d₆) δ 11.95 (s, 1H), 10.44 (d, J=5.0 Hz, 1H), 7.42 (s, 1H), 6.89 (d, J=11.4 Hz, 1H), 6.70 (s, 1H), 4.24 (d, J=16.4 Hz, 2H), 4.14 (d, J=17.7 Hz, 2H), 3.65 (dt, J=5.8, 50.5 Hz, 2H), 2.85-2.62 (m, 2H), 2.17 (s, 1H), 0.81-0.77 (m, 4H).
MS(ESI+) m/z 351 (M+H)⁺

Example 426: Synthesis of N-(4-(1-(2-cyanoacetyl)-2,5-dihydro-1H-pyrrol-3-yl)-1H-pyrrolo[2,3-b]pyridin-6-yl)cyclopropanecarboxamide

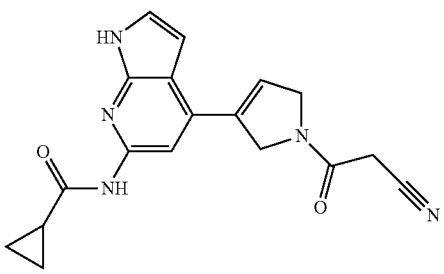 [SMILES: N#CCC(=O)N1CC=C(c2cc(NC(=O)C3CC3)nc3[nH]ccc23)C1]

¹H NMR (400 MHz, DMSO-d₆) δ 11.57 (s, 1H), 10.61 (s, 1H), 7.85 (d, J=3.2 Hz, 1H), 7.43 (s, 1H), 6.74 (d, J=20.3 Hz, 2H), 4.75 (s, 1H), 4.55 (d, J=16.5 Hz, 2H), 4.38 (s, 1H), 4.15 (d, J=3.5 Hz, 1H), 4.04 (d, J=3.2 Hz, 1H), 2.03 (s, 1H), 0.81 (s, 4H).
MS(ESI+) m/z 336 (M+H)⁺

Example 427: Synthesis of N-(4-(1-(3-cyanopropanoyl)-2,5-dihydro-1H-pyrrol-3-yl)-1H-pyrrolo[2,3-b]pyridin-6-yl)cyclopropanecarboxamide

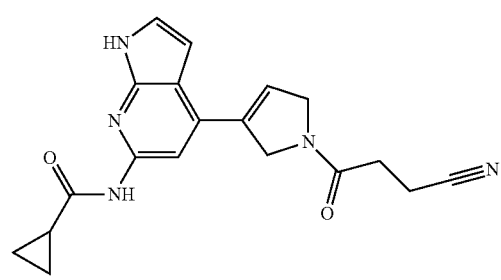 [SMILES: N#CCCC(=O)N1CC=C(c2cc(NC(=O)C3CC3)nc3[nH]ccc23)C1]

¹H NMR (400 MHz, DMSO-d₆) δ 11.56 (s, 1H), 10.60 (s, 1H), 7.86 (d, J=5.1 Hz, 1H), 7.43 (d, J=2.3 Hz, 1H), 6.79-6.69 (m, 2H), 4.77 (s, 1H), 4.56 (s, 2H), 4.40-4.31 (m, 1H), 2.96 (s, 1H), 2.83 (t, J=6.9 Hz, 1H), 2.77-2.72 (m, 1H), 2.68 (q, J=6.6 Hz, 2H), 2.02 (dd, J=4.8, 9.6 Hz, 1H), 0.81 (dt, J=4.0, 18.4 Hz, 4H).

MS(ESI+) m/z 350 (M+H)⁺

Example 428: Synthesis of N-(4-(1-(3,3,3-trifluoropropanoyl)-2,5-dihydro-1H-pyrrol-3-yl)-1H-pyrrolo[2,3-b]pyridin-6-yl)cyclopropanecarboxamide

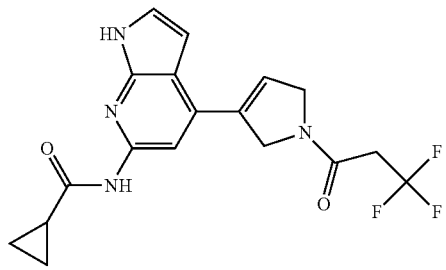 [SMILES: O=C(Nc1cc(C2=CCN(C(=O)CC(F)(F)F)C2)c2cc[nH]c2n1)C1CC1]

¹H NMR (400 MHz, DMSO-d₆) δ 11.56 (s, 1H), 10.60 (d, J=2.7 Hz, 1H), 7.86 (d, J=2.8 Hz, 1H), 7.43 (d, J=3.1 Hz, 1H), 6.81-6.63 (m, 2H), 4.80 (d, J=4.2 Hz, 1H), 4.58 (s, 2H), 4.38 (d, J=4.0 Hz, 1H), 3.72 (dq, J=11.0, 41.9 Hz, 2H), 2.02 (q, J=3.0, 4.8 Hz, 1H), 0.87-0.74 (m, 4H).

MS(ESI+) m/z 379 (M+H)⁺

Example 429: Synthesis of N-(4-(1-(4,4,4-trifluorobutanoyl)-2,5-dihydro-1H-pyrrol-3-yl)-1H-pyrrolo[2,3-b]pyridin-6-yl)cyclopropanecarboxamide

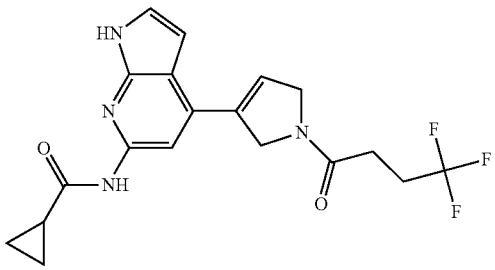 [SMILES: O=C(Nc1cc(C2=CCN(C(=O)CCC(F)(F)F)C2)c2cc[nH]c2n1)C1CC1]

¹H NMR (400 MHz, DMSO-d₆) δ 11.59 (s, 1H), 10.62 (s, 1H), 7.87 (s, 1H), 7.43 (s, 1H), 6.74 (t, J=11.6 Hz, 2H), 4.80 (s, 1H), 4.57 (d, J=10.9 Hz, 2H), 4.37 (s, 1H), 2.74-2.61 (m, 2H), 2.04-1.98 (m, 1H), 1.15 (s, 2H), 0.82 (dd, J=6.5, 21.7 Hz, 4H).

MS(ESI+) m/z 393 (M+H)⁺

Example 430: Synthesis of N-(4-(1-(1-cyanocyclopropane-1-carbonyl)-2,5-dihydro-1H-pyrrol-3-yl)-1H-pyrrolo[2,3-b]pyridin-6-yl)cyclopropanecarboxamide

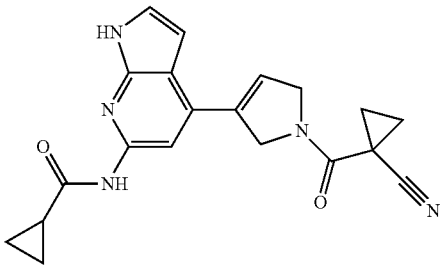 [SMILES: N#CC1(C(=O)N2CC=C(c3cc(NC(=O)C4CC4)nc4[nH]ccc34)C2)CC1]

MS(ESI+) m/z 362 (M+H)⁺

Example 431: Synthesis of N-(4-(4-(3-ethylureido)phenyl)-1H-pyrrolo[2,3-b]pyridin-6-yl)cyclopropanecarboxamide

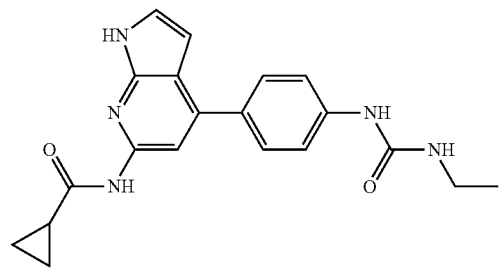 [SMILES: CCNC(=O)Nc1ccc(-c2cc(NC(=O)C3CC3)nc3[nH]ccc23)cc1]

N-(4-(4-aminophenyl)-1-tosyl-1H-pyrrolo[2,3-b]pyridine-6-yl)cyclopropanecarboxamide (100 mg) was stirred with pyridine. 4 equivalent of ethyl isocyanate was inserted into the mixture and stirred at room temperature for 12 hours. Once the reaction was completed, d-HCl was added to the said mixture, then an extraction using dichloromethane was performed, and then an organic layer was separated. After concentrating the mixture, the resulting concentrate was dissolved in MeOH/THF (1:1) solution, and then 2N sodium hydroxide aqueous solution was added thereto and stirred at 30-40° C. for 4 hours. Once the reaction was completed, the said mixture was cooled down to room temperature, and saturated ammonium chloride aqueous solution was added thereto while being stirred. A produced solid was filtered out, and finally a product, i.e., N-(4-(4-(3-ethylureido)phenyl)-1H-pyrrolo[2,3-b]pyridin-6-yl)cyclopropanecarboxamide was accordingly obtained.

¹H NMR (400 MHz, DMSO-d₆) δ 11.46 (s, 1H), 10.56 (s, 1H), 8.68 (s, 1H), 7.98 (s, 1H), 7.58 (q, J=8.2, 8.7 Hz, 4H), 7.37 (s, 1H), 6.55 (s, 1H), 6.22 (s, 1H), 5.75 (s, 1H), 3.14 (d, J=6.4 Hz, 2H), 2.04 (s, 1H), 1.07 (t, J=6.7 Hz, 3H), 0.88-0.75 (m, 4H).

MS(ESI+) m/z 364 (M+H)⁺

Examples 432 to 453

Hereinafter, in Examples 432 to 453, a corresponding compound was synthesized by means of the same method as shown in Example 431 or by means of an appropriate reactant under the consideration of the reaction formula 1 as well as a structure of the compound to be prepared.

Example 432: Synthesis of N-(4-(6-(cyclopropanecarboxamido)-1H-pyrrolo[2,3-b]pyridin-4-yl)phenyl)morpholine-4-carboxamide

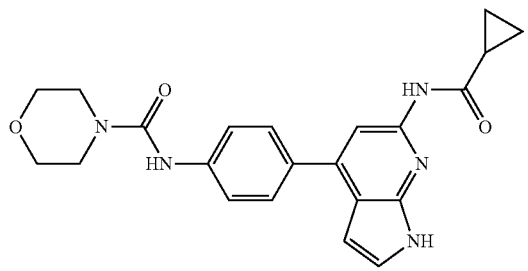 [SMILES: O=C(Nc1cc(-c2ccc(NC(=O)N3CCOCC3)cc2)c2cc[nH]c2n1)C1CC1]

$^1$H NMR (400 MHz, DMSO-d$_6$) δ 11.47 (s, 1H), 10.57 (s, 1H), 8.73 (s, 1H), 8.00 (s, 1H), 7.73-7.56 (m, 4H), 7.37 (d, J=3.5 Hz, 1H), 6.56 (d, J=3.2 Hz, 1H), 3.63 (s, 4H), 3.46 (s, 4H), 2.04 (s, 1H), 0.87-0.78 (m, 4H).

MS(ESI+) m/z 406 (M+H)$^+$

Example 433: Synthesis of N-(4-(4-(3-butylureido)phenyl)-1H-pyrrolo[2,3-b]pyridin-6-yl)cyclopropanecarboxamide

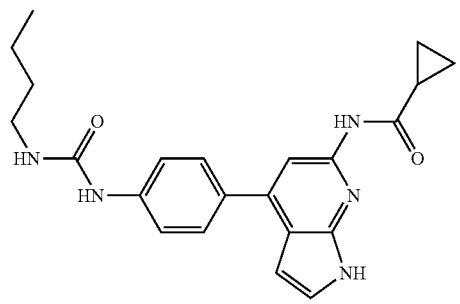 [SMILES: CCCCNC(=O)Nc1ccc(-c2cc(NC(=O)C3CC3)nc3[nH]ccc23)cc1]

$^1$H NMR (400 MHz, DMSO-d$_6$) δ 11.46 (s, 1H), 10.56 (s, 1H), 8.63 (s, 1H), 7.98 (s, 1H), 7.70-7.51 (m, 5H), 7.46-7.36 (m, 1H), 6.55 (s, 1H), 6.21 (d, J=5.7 Hz, 1H), 3.19-3.07 (m, 2H), 2.05 (s, 1H), 1.37 (ddd, J=7.0, 14.2, 40.2 Hz, 5H), 0.90 (t, J=7.2 Hz, 4H), 0.88-0.73 (m, 4H).

MS(ESI+) m/z 392 (M+H)$^+$

Example 434: Synthesis of N-(4-(4-(3-(4-fluorophenyl)ureido)phenyl)-1H-pyrrolo[2,3-b]pyridin-6-yl)cyclopropanecarboxamide

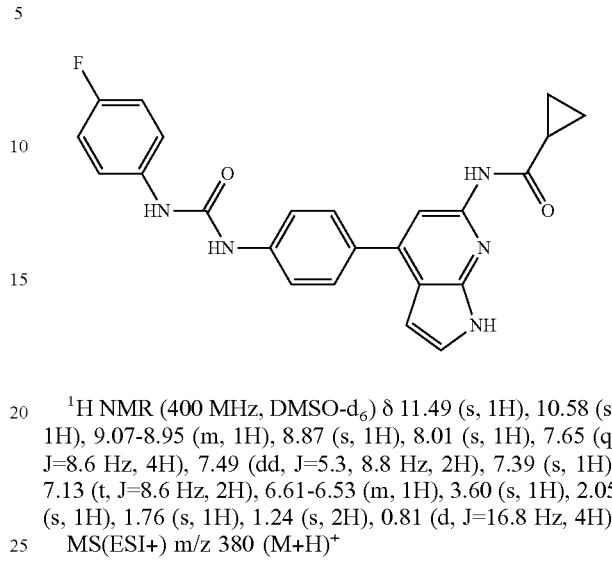

$^1$H NMR (400 MHz, DMSO-d$_6$) δ 11.49 (s, 1H), 10.58 (s, 1H), 9.07-8.95 (m, 1H), 8.87 (s, 1H), 8.01 (s, 1H), 7.65 (q, J=8.6 Hz, 4H), 7.49 (dd, J=5.3, 8.8 Hz, 2H), 7.39 (s, 1H), 7.13 (t, J=8.6 Hz, 2H), 6.61-6.53 (m, 1H), 3.60 (s, 1H), 2.05 (s, 1H), 1.76 (s, 1H), 1.24 (s, 2H), 0.81 (d, J=16.8 Hz, 4H).

MS(ESI+) m/z 380 (M+H)$^+$

Example 435: Synthesis of N-(4-(4-(3-(2,2,2-trifluoroethyl)ureido)phenyl)-1H-pyrrolo[2,3-b]pyridin-6-yl)cyclopropanecarboxamide

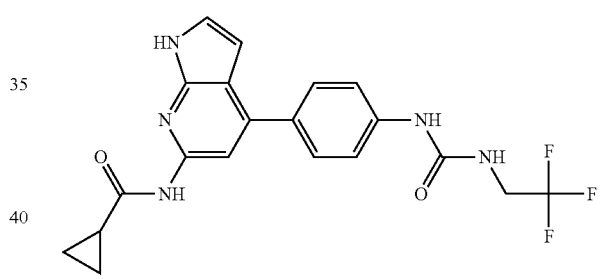

$^1$H NMR (400 MHz, DMSO-d$_6$) δ 11.49 (s, 1H), 10.59 (s, 1H), 9.07 (s, 1H), 7.99 (s, 1H), 7.61 (q, J=8.5 Hz, 4H), 7.38 (d, J=3.1 Hz, 1H), 6.92 (s, 1H), 6.59-6.47 (m, 1H), 3.95 (dd, J=6.5, 14.9 Hz, 2H), 2.03 (s, 1H), 0.81 (s, 4H).

MS(ESI+) m/z 418 (M+H)$^+$

Example 436: Synthesis of N-(4-(2-methyl-4-(3-(2,2,2-trifluoroethyl)ureido)phenyl)-1H-pyrrolo[2,3-b]pyridin-6-yl)cyclopropanecarboxamide

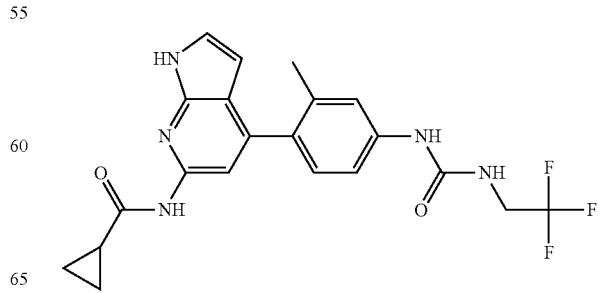

¹H NMR (400 MHz, DMSO-d₆) δ 11.45 (s, 1H), 10.61 (s, 1H), 8.92 (s, 1H), 7.76 (s, 1H), 7.41 (s, 1H), 7.33 (dd, J=5.7, 8.6 Hz, 2H), 7.17 (d, J=8.3 Hz, 1H), 6.89 (s, 1H), 6.12-5.99 (m, 1H), 3.97-3.89 (m, 2H), 2.13 (s, 4H), 2.03 (s, 1H), 0.79 (s, 4H).

MS(ESI+) m/z 432 (M+H)⁺

Example 437: Synthesis of N-(4-(4-(3-cyclopropylureido)phenyl)-7H-pyrrolo[2,3-d]pyrimidin-2-yl)cyclopropanecarboxamide

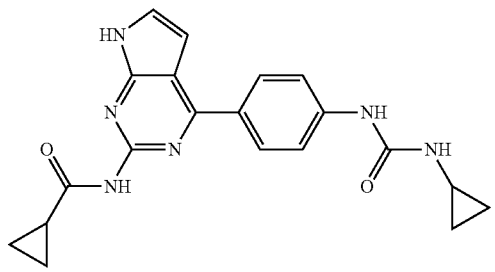 [SMILES: O=C(Nc1ccc(-c2nc(NC(=O)C3CC3)nc3[nH]ccc23)cc1)NC1CC1]

MS(ESI+) m/z 377 (M+H)⁺

Example 438: Synthesis of N-(4-(4-(3-ethylureido)phenyl)-7H-pyrrolo[2,3-d]pyrimidin-2-yl)cyclopropanecarboxamide

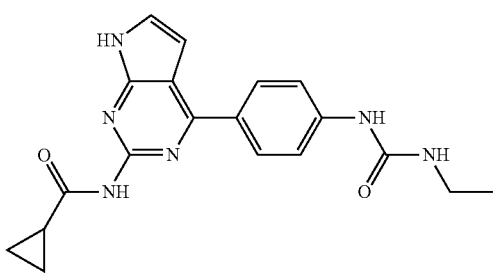

MS(ESI+) m/z 365 (M+H)⁺

Example 439: Synthesis of N-(4-(4-(3-butylureido)phenyl)-7H-pyrrolo[2,3-d]pyrimidin-2-yl)cyclopropanecarboxamide

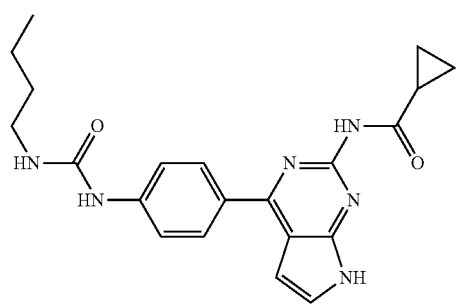 [SMILES: CCCCNC(=O)Nc1ccc(-c2nc(NC(=O)C3CC3)nc3[nH]ccc23)cc1]

MS(ESI+) m/z 393 (M+H)⁺

Example 440: Synthesis of N-(4-(4-(3-(3,4-difluorophenyl)ureido)phenyl)-7H-pyrrolo[2,3-d]pyrimidin-2-yl)cyclopropanecarboxamide

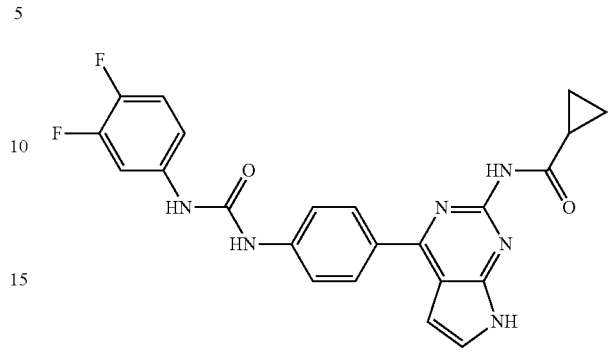

MS(ESI+) m/z 449 (M+H)⁺

Example 441: Synthesis of N-(4-(4-(3-(4-fluorophenyl)ureido)phenyl)-7H-pyrrolo[2,3-d]pyrimidin-2-yl)cyclopropanecarboxamide

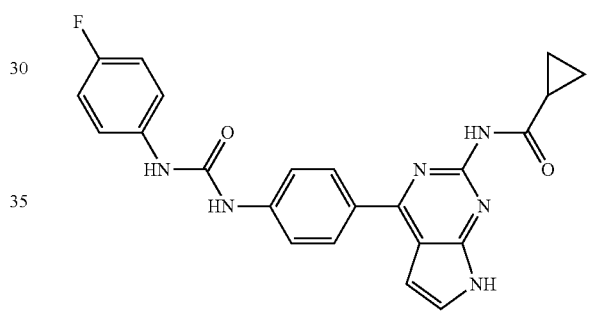

MS(ESI+) m/z 431 (M+H)⁺

Example 442: Synthesis of N-(4-(4-(3-(2,2,2-trifluoroethyl)ureido)cyclohex-1-en-1-yl)-1H-pyrrolo[2,3-b]pyridin-6-yl)cyclopropanecarboxamide

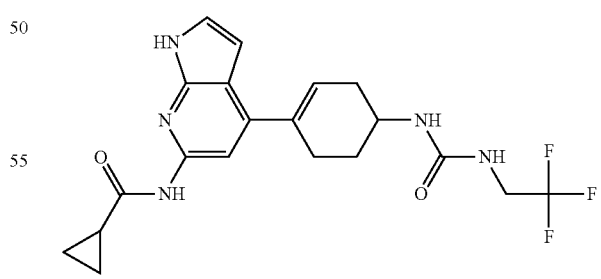

¹H NMR (400 MHz, DMSO-d₆) δ 11.37 (s, 1H), 10.50 (s, 1H), 7.86 (d, J=3.9 Hz, 1H), 7.37-7.27 (m, 1H), 6.51 (dd, J=1.9, 3.6 Hz, 1H), 6.44 (t, J=6.5 Hz, 1H), 6.33-6.19 (m, 2H), 3.83 (dq, J=6.7, 9.8, 16.0 Hz, 3H), 2.15-1.88 (m, 3H), 1.68 (d, J=9.0 Hz, 1H), 0.86-0.75 (m, 4H).

MS(ESI+) m/z 422 (M+H)⁺

Example 443: Synthesis of 4-(6-(cyclopropanecarboxamido)-1H-pyrrolo[2,3-b]pyridin-4-yl)-N-(2,2,2-trifluoroethyl)-3,6-dihydropyridine-1 (2H)-carboxamide

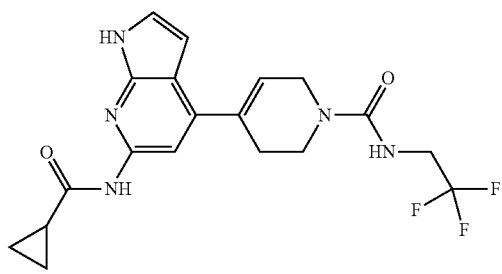 [SMILES: O=C(Nc1cc(C2=CCN(C(=O)NCC(F)(F)F)CC2)c2cc[nH]c2n1)C1CC1]

$^1$H NMR (400 MHz, DMSO-d$_6$) δ 11.45 (s, 1H), 10.55 (s, 1H), 7.86 (s, 1H), 7.42-7.32 (m, 1H), 7.22 (t, J=5.8 Hz, 1H), 6.54 (dd, J=1.9, 3.7 Hz, 1H), 6.33 (s, 1H), 4.10 (s, 2H), 3.93-3.81 (m, 3H), 3.61 (t, J=5.3 Hz, 2H), 2.02 (s, 1H), 0.82-0.75 (m, 4H).

MS(ESI+) m/z 408 (M+H)$^+$

Example 444: Synthesis of N-butyl-4-(6-(cyclopropanecarboxamido)-1H-pyrrolo[2,3-b]pyridin-4-yl)-3,6-dihydropyridine-1 (2H)-carboxamide

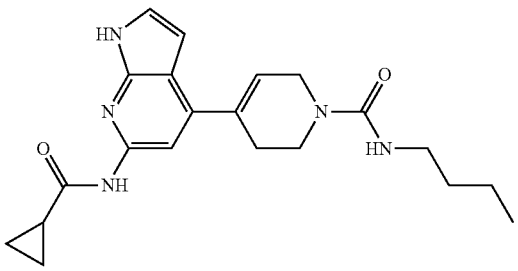 [SMILES: CCCCNC(=O)N1CC=C(c2cc(NC(=O)C3CC3)nc3[nH]ccc23)CC1]

MS(ESI+) m/z 382 (M+H)$^+$

Example 445: Synthesis of N-(4-(1-(1,1-dioxidothiomorpholine-4-carbonyl)-1,2,3,6-tetrahydropyridin-4-yl)-1H-pyrrolo[2,3-b]pyridin-6-yl)cyclopropanecarboxamide

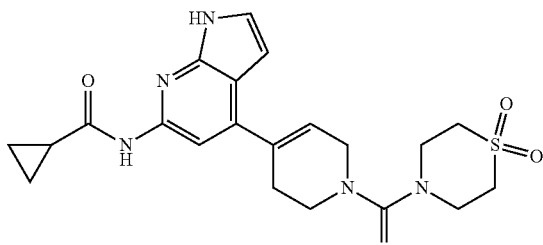

$^1$H NMR (400 MHz, DMSO-d$_6$) δ 11.43 (s, 1H), 10.53 (s, 1H), 7.87 (s, 1H), 7.34 (s, 1H), 6.56 (s, 1H), 6.34 (s, 1H), 4.03 (d, J=8.9 Hz, 2H), 3.63 (d, J=18.8 Hz, 6H), 3.45 (s, 3H), 3.22-3.14 (m, 4H), 2.00 (s, 1H), 1.20 (d, J=25.7 Hz, 2H), 1.04 (d, J=6.1 Hz, 2H), 0.80 (s, 4H).

MS(ESI+) m/z 444 (M+H)$^+$

Example 446: Synthesis of N-(4-(1-(morpholine-4-carbonyl)-1,2,3,6-tetrahydropyridin-4-yl)-1H-pyrrolo[2,3-b]pyridin-6-yl)cyclopropanecarboxamide

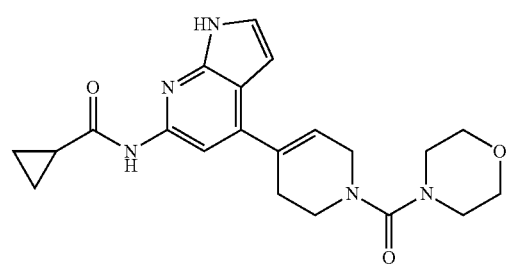 [SMILES: O=C(Nc1cc(C2=CCN(C(=O)N3CCOCC3)CC2)c2cc[nH]c2n1)C1CC1]

$^1$H NMR (400 MHz, DMSO-d$_6$) δ 11.42 (s, 1H), 10.53 (s, 1H), 7.86 (s, 1H), 7.34 (s, 1H), 6.56 (s, 1H), 6.34 (s, 1H), 3.96 (s, 2H), 3.60 (s, 6H), 3.17 (d, J=5.2 Hz, 4H), 2.02 (s, 1H), 1.04 (d, J=5.6 Hz, 2H), 0.80 (s, 4H).

MS(ESI+) m/z 396 (M+H)$^+$

Example 447: Synthesis of N-(cyanomethyl)-4-(6-(cyclopropanecarboxamido)-1H-pyrrolo[2,3-b]pyridin-4-yl)-3,6-dihydropyridine-1 (2H)-carboxamide

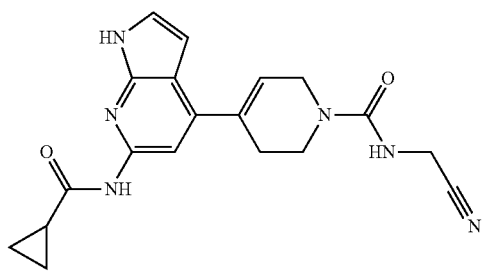 [SMILES: N#CCNC(=O)N1CC=C(c2cc(NC(=O)C3CC3)nc3[nH]ccc23)CC1]

$^1$H NMR (400 MHz, DMSO-d$_6$) δ 11.43 (s, 1H), 10.53 (s, 1H), 7.85 (s, 1H), 7.34 (s, 1H), 6.54 (s, 1H), 6.31 (s, 1H), 4.12 (s, 2H), 4.03 (d, J=6.8 Hz, 1H), 3.65 (s, 3H), 3.63 (s, 2H), 2.00 (d, J=12.2 Hz, 2H), 0.78 (d, J=13.1 Hz, 4H).

MS(ESI+) m/z 365 (M+H)$^+$

Example 448: Synthesis of 3-(6-(cyclopropanecarboxamido)-1H-pyrrolo[2,3-b]pyridin-4-yl)-N-(2,2,2-trifluoroethyl)-8-azabicyclo[3.2.1]oct-2-ene-8-carboxamide

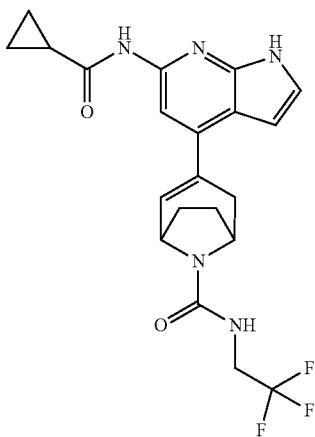 [SMILES: O=C(Nc1cc(C2=CC3CCC(C2)N3C(=O)NCC(F)(F)F)c2cc[nH]c2n1)C1CC1]

MS(ESI+) m/z 434 (M+H)+

Example 449: Synthesis of N-butyl-3-(6-(cyclopropanecarboxamido)-1H-pyrrolo[2,3-b]pyridin-4-yl)-8-azabicyclo[3.2.1]oct-2-ene-8-carboxamide

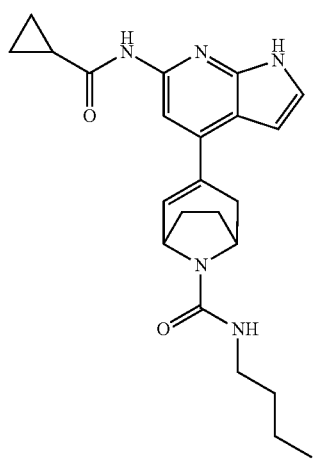 [SMILES: CCCCNC(=O)N1C2C=C(c3cc(NC(=O)C4CC4)nc4[nH]ccc34)CC1CC2]

MS(ESI+) m/z 408 (M+H)+

Example 450: Synthesis of 4-(6-(cyclopropanecarboxamido)-1H-pyrrolo[2,3-b]pyridin-4-yl)-N-(1-cyclopropyl-2,2,2-trifluoroethyl)-3,6-dihydropyridine-1 (2H)-carboxamide

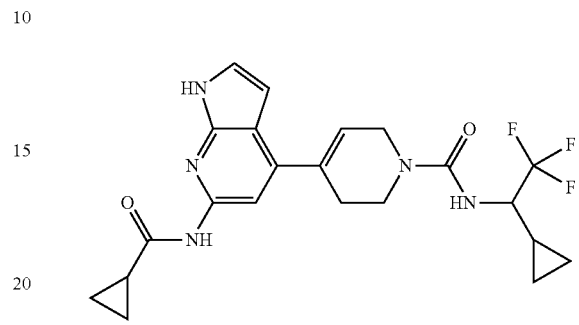

$^1$H NMR (400 MHz, DMSO-d$_6$) δ 10.81 (s, 1H), 10.05 (dd, J=3.0, 8.9 Hz, 1H), 7.84 (d, J=4.0 Hz, 1H), 7.81 (d, J=4.8 Hz, 1H), 6.89 (d, J=4.1 Hz, 1H), 6.36 (d, J=4.6 Hz, 1H), 4.43 (d, J=3.2 Hz, 1H), 4.32 (s, 1H), 4.08 (p, J=8.7 Hz, 1H), 3.93 (t, J=5.5 Hz, 1H), 3.80 (t, J=5.7 Hz, 1H), 2.68 (s, 2H), 1.94 (q, J=6.2 Hz, 1H), 1.55 (dd, J=6.6, 12.0 Hz, 1H), 1.16-1.10 (m, 1H), 0.92-0.86 (m, 4H), 0.72 (dd, J=5.6, 22.3 Hz, 2H), 0.64 (d, J=25.9 Hz, 1H), 0.46-0.35 (m, 1H).

MS(ESI+) m/z 448 (M+H)+

Example 451: Synthesis of N-(4-(1-(1H-imidazole-1-carbonyl)-1,2,3,6-tetrahydropyridin-4-yl)-1H-pyrrolo[2,3-b]pyridin-6-yl)cyclopropanecarboxamide

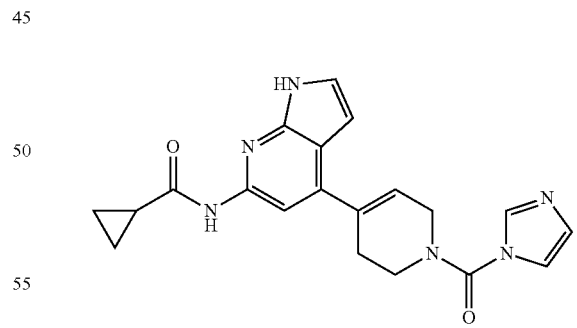

$^1$H NMR (400 MHz, Methanol-d$_4$) δ 11.46 (s, 1H), 10.57 (s, 1H), 8.13 (s, 1H), 7.90 (s, 1H), 7.58 (d, J=1.4 Hz, 1H), 7.36 (t, J=3.0 Hz, 1H), 7.06 (s, 1H), 6.60 (d, J=2.8 Hz, 1H), 6.34 (s, 1H), 4.29 (d, J=3.6 Hz, 2H), 3.71 (d, J=6.3 Hz, 2H), 2.72 (s, 2H), 1.99 (s, 1H), 0.85-0.69 (m, 4H).

MS(ESI+) m/z 377 (M+H)+

Example 452: Synthesis of N-(4-(1-(1H-imidazole-1-carbonyl)-3-methyl-1,2,3,6-tetrahydropyridin-4-yl)-1H-pyrrolo[2,3-b]pyridin-6-yl)cyclopropanecarboxamide

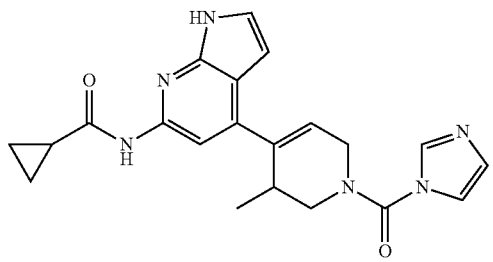 [SMILES: CC1CN(C(=O)n2ccnc2)CC=C1c1cc(NC(=O)C2CC2)nc2[nH]ccc12]

$^1$H NMR (400 MHz, DMSO-d$_6$) δ 11.45 (s, 1H), 10.57 (s, 1H), 8.13 (s, 1H), 7.85 (s, 1H), 7.58 (d, J=1.8 Hz, 1H), 7.38-7.30 (m, 1H), 7.07 (s, 1H), 6.59-6.50 (m, 1H), 6.10 (s, 1H), 4.37-4.22 (m, 2H), 3.70 (s, 2H), 3.14 (s, 1H), 2.00 (d, J=15.8 Hz, 1H), 0.90 (d, J=7.0 Hz, 3H), 0.85-0.72 (m, 4H).

MS(ESI+) m/z 391 (M+H)$^+$

Example 453: Synthesis of 4-(6-(cyclopropanecarboxamido)-1H-pyrrolo[2,3-b]pyridin-4-yl)-3-methyl-N-(2,2,2-trifluoroethyl)-3,6-dihydropyridine-1 (2H)-carboxamide

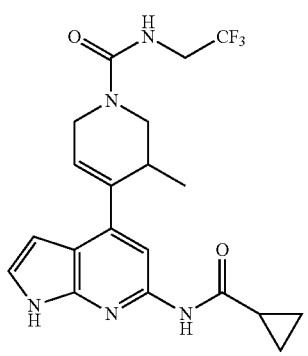 [SMILES: CC1CN(C(=O)NCC(F)(F)F)CC=C1c1cc(NC(=O)C2CC2)nc2[nH]ccc12]

$^1$H NMR (400 MHz, DMSO-d$_6$) δ 11.43 (s, 1H), 10.56 (s, 1H), 7.83 (s, 1H), 7.39-7.30 (m, 1H), 7.25-7.16 (m, 1H), 6.46 (dd, J=2.0, 3.6 Hz, 1H), 6.10 (d, J=3.5 Hz, 1H), 4.23 (d, J=18.2 Hz, 1H), 3.99-3.84 (m, 3H), 3.62-3.49 (m, 2H), 2.94 (s, 1H), 2.03 (d, J=8.3 Hz, 1H), 0.86 (d, J=6.9 Hz, 3H), 0.82-0.73 (m, 4H).

MS(ESI+) m/z 422 (M+H)$^+$

Example 454: Synthesis of tert-butyl 4-(6-(cyclopropanecarboxamido)-1H-pyrrolo[2,3-b]pyridin-4-yl)-3,6-dihydropyridine-1 (2H)-carboxylate

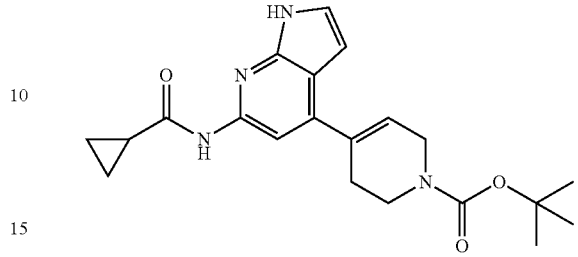

[Step 1]

4.0 g (8.3 mmol) of N-(4-(4,4,5,5-tetramethyl-1,3,2-dioxaborolan-2-yl)-1-tosyl-1H-pyrrolo[2,3-b]pyridine-6-yl)cyclopropanecarboxamide prepared from the reaction formula 3 above was dissolved in DMF/H$_2$O=2:1 solution, and then 3.3 g (10.0 mmol) of tert-butyl-4-(((trifluoromethyl)sulfonyl)oxy)-3,6-dehydropyridine-1 (2H)-carboxylate, 0.9 g (0.8 mmol) of Pd(PPh$_3$)$_4$ and 0.57 mL of 2M K$_2$CO$_3$ aqueous solution were inserted thereinto and stirred at 100-110° C. for 2 hours. Once the reaction was completed, the said mixture was cooled down at room temperature, then water was added thereto, and then an extraction using ethyl acetate was performed. After that, a solution extracted therefrom was dried by means of magnesium sulfate anhydrous, and concentrated under reduced pressure, from which a residue was accordingly obtained. The residue was separated via NH-silica gel column chromatography (n-hexane/ethyl acetate=5:1), and finally tert-butyl 4-(6-(cyclopropanecarboxamido)-1-tosyl-1H-pyrrolo[2,3-b]pyridine-4-yl)-3,6-dehydropyridine-1-(2H)-carboxylate was accordingly obtained.

MS(ESI+) m/z 537 (M+H)$^+$

[Step 2]

The synthesized material was dissolved in MeOH/THF (1:1) solution, and then 2N sodium hydroxide aqueous solution was added thereto and stirred at 30-40° C. for 4 hours. Once the reaction was completed, the said mixture was cooled down to room temperature, and then saturated ammonium chloride aqueous solution was added thereto while being stirred. A produced solid was filtered out, and finally a product, i.e., tert-butyl 4-(6-(cyclopropanecarboxamido)-1H-pyrrolo[2,3-b]pyridin-4-yl)-3,6-dehydropyridine-1 (2H)-carboxylate was accordingly obtained.

$^1$H NMR (400 MHz, DMSO-d$_6$) 11.42 (s, 1H), 10.53 (s, 1H), 7.86 (s, 1H), 7.43-7.26 (m, 1H), 6.61-6.45 (m, 1H), 6.31 (s, 1H), 4.07 (s, 2H), 3.67-3.46 (m, 2H), 2.59-2.52 (m, 2H), 2.02 (td, J=3.7, 7.8 Hz, 1H), 1.44 (s, 9H), 0.80 (dt, J=5.9, 12.2 Hz, 4H).

MS(ESI+) m/z 383 (M+H)$^+$

Examples 455 to 461

Hereinafter, in Examples 455 to 461, a corresponding compound was synthesized by means of the same method as shown in Example 454 or by means of an appropriate reactant under the consideration of the reaction formula 1 as well as a structure of the compound to be prepared.

Example 455: Synthesis of cyanomethyl 4-(6-(cyclopropanecarboxamido)-1H-pyrrolo[2,3-b]pyridin-4-yl)-3,6-dihydropyridine-1 (2H)-carboxylate

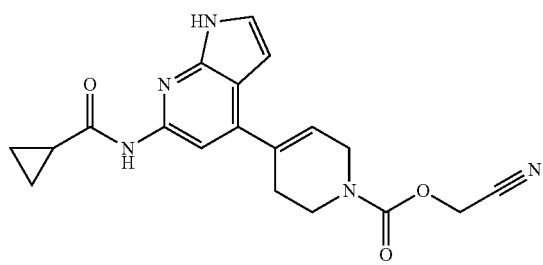

$^1$H NMR (400 MHz, DMSO-d$_6$) δ 11.45 (s, 1H), 10.56 (s, 1H), 7.87 (s, 1H), 7.41-7.30 (m, 1H), 6.56 (dd, J=1.9, 3.6 Hz, 1H), 6.32 (d, J=14.8 Hz, 1H), 4.98 (s, 2H), 4.16 (s, 2H), 3.67 (q, J=5.6, 7.9 Hz, 2H), 2.58 (s, 3H), 2.02 (s, 1H), 0.85-0.73 (m, 4H).
MS(ESI+) m/z 366 (M+H)$^+$

Example 456: Synthesis of tert-butyl 4-(6-(cyclopropanecarboxamido)-1H-pyrrolo[2,3-b]pyridin-4-yl)-3-methyl-3,6-dihydropyridine-1 (2H)-carboxylate

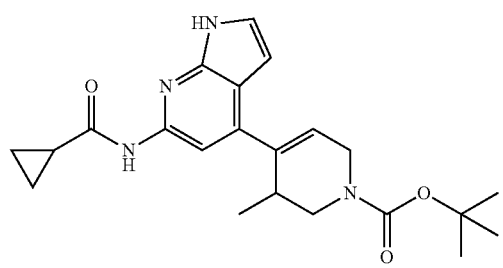 [SMILES: CC1CN(C(=O)OC(C)(C)C)CC=C1c1cc(NC(=O)C2CC2)nc2[nH]ccc12]

$^1$H NMR (400 MHz, DMSO-d$_6$) δ 11.43 (s, 1H), 10.56 (s, 1H), 7.83 (s, 1H), 7.32 (t, J=3.1 Hz, 1H), 6.48 (d, J=3.0 Hz, 1H), 6.08 (s, 1H), 4.25 (s, 1H), 3.88 (s, 1H), 3.68-3.37 (m, 2H), 2.92 (s, 1H), 2.01 (s, 1H), 0.86 (d, J=6.7 Hz, 3H), 0.81-0.71 (m, 4H).
MS(ESI+) m/z 397 (M+H)$^+$

Example 457: Synthesis of tert-butyl 4-(6-(cyclopropanecarboxamido)-5-methyl-1H-pyrrolo[2,3-b]pyridin-4-yl)-3,6-dihydropyridine-1 (2H)-carboxylate

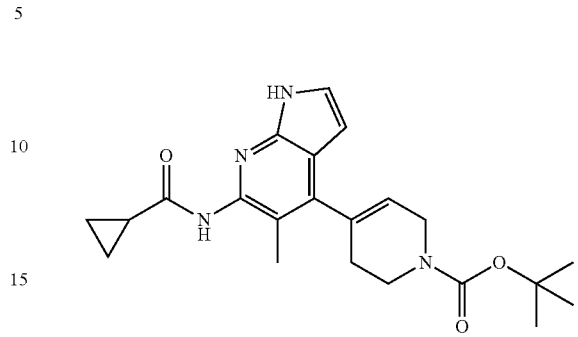

$^1$H NMR (400 MHz, DMSO-d$_6$) δ 11.43 (s, 1H), 10.03 (s, 1H), 7.34 (t, J=2.9 Hz, 1H), 6.23 (dd, J=3.5, 1.9 Hz, 1H), 5.66 (s, 1H), 4.03 (s, 2H), 3.61 (d, J=5.7 Hz, 2H), 2.30 (s, 2H), 2.08 (s, 3H), 1.45 (s, 9H), 0.76 (d, J=6.2 Hz, 4H).
MS(ESI+) m/z 397 (M+H)$^+$

Example 458: Synthesis of tert-butyl 4-(6-(cyclopropanecarboxamido)-1H-pyrrolo[2,3-b]pyridin-4-yl)-3-ethyl-3,6-dihydropyridine-1 (2H)-carboxylate

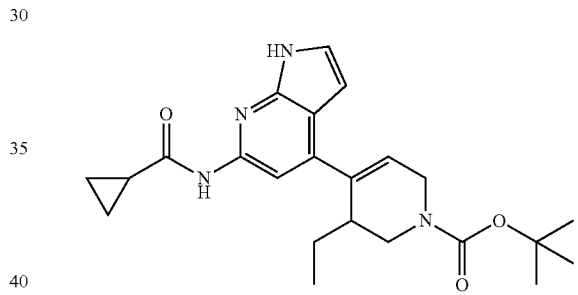

$^1$H NMR (400 MHz, DMSO-d$_6$) δ 11.43 (s, 1H), 10.55 (s, 1H), 7.83 (s, 1H), 7.42-7.25 (m, 1H), 6.58-6.48 (m, 1H), 6.11 (s, 1H), 4.33 (dd, J=19.3, 44.4 Hz, 1H), 4.10-3.67 (m, 2H), 3.21 (dd, J=3.7, 13.1 Hz, 1H), 2.67 (d, J=1.7 Hz, 1H), 2.02 (s, 1H), 1.44 (s, 9H), 1.22 (d, J=15.5 Hz, 3H), 0.87-0.73 (m, 7H).
MS(ESI+) m/z 411 (M+H)$^+$

Example 459: Synthesis of tert-butyl 5-(6-(cyclopropanecarboxamido)-1H-pyrrolo[2,3-b]pyridin-4-yl)-3,4-dihydropyridine-1 (2H)-carboxylate

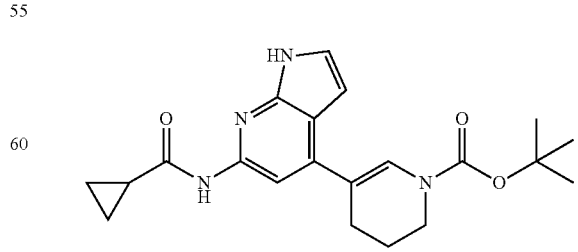

$^1$H NMR (400 MHz, DMSO-d$_6$) δ 11.38 (s, 1H), 10.46 (s, 1H), 7.85 (s, 1H), 7.68 (s, 1H), 7.33 (s, 1H), 6.48 (dd, J=3.5, 1.9 Hz, 1H), 3.59 (s, 2H), 2.46 (s, 2H), 2.01 (q, J=6.3 Hz, 1H), 1.93 (t, J=6.0 Hz, 2H), 0.85-0.71 (m, 4H).

MS(ESI+) m/z 383 (M+H)+

Example 460: Synthesis of tert-butyl 5-(6-(cyclopropanecarboxamido)-1H-pyrrolo[2,3-b]pyridin-4-yl)-3,6-dihydropyridine-1 (2H)-carboxylate

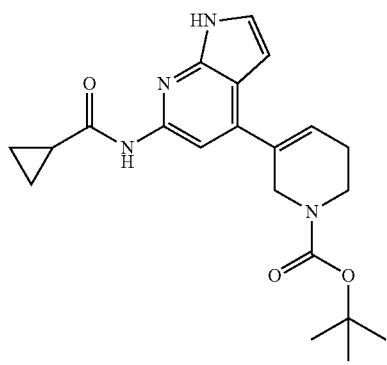 [SMILES: CC(C)(C)OC(=O)N1CCC=C(c2cc(NC(=O)C3CC3)nc3[nH]ccc23)C1]

$^1$H NMR (400 MHz, DMSO-d$_6$) δ 11.46 (s, 1H), 10.55 (s, 1H), 7.84 (s, 1H), 7.35 (t, J=3.0 Hz, 1H), 6.52 (s, 1H), 6.39 (s, 1H), 4.26 (s, 2H), 3.53 (t, J=5.8 Hz, 2H), 2.34 (td, J=6.9, 6.3, 2.8 Hz, 2H), 2.02 (tt, J=7.5, 4.5 Hz, 1H), 1.43 (s, 9H), 0.80 (ddt, J=10.9, 5.4, 3.0 Hz, 4H).

MS(ESI+) m/z 383 (M+H)+

Example 461: Synthesis of tert-butyl 3-(6-(cyclopropanecarboxamido)-1H-pyrrolo[2,3-b]pyridin-4-yl)-2,5-dihydro-1H-pyrrole-1-carboxylate

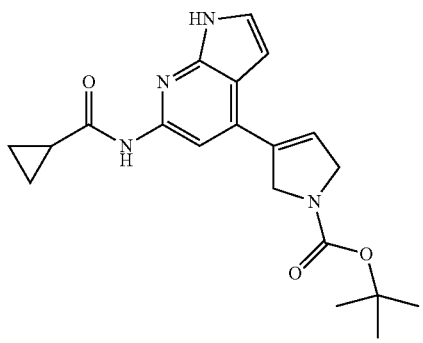 [SMILES: CC(C)(C)OC(=O)N1CC=C(c2cc(NC(=O)C3CC3)nc3[nH]ccc23)C1]

MS(ESI+) m/z 369 (M+H)+

Example 462: Synthesis of N-(4-(4-(3-ethylthioureido)phenyl)-1H-pyrrolo[2,3-b]pyridin-6-yl)cyclopropanecarboxamide

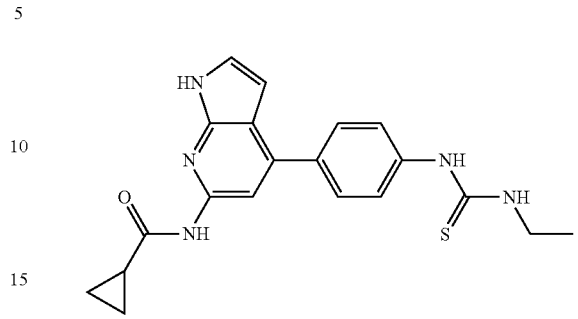

N-(4-(4-aminophenyl)-1-tosyl-1H-pyrrolo[2,3-b]pyridine-6-yl)cyclopropanecarboxamide (100 mg) was stirred with pyridine. 4 equivalent of ethyl isothiocyanate was inserted into the mixture and stirred at 50-60° C. for 16 hours. Once the reaction was completed, the said mixture was concentrated and dissolved in MeOH/THF (1:1) solution. After that, 2N sodium hydroxide aqueous solution was added thereto and stirred at 30-40° C. for 4 hours. Once the reaction was completed, the said mixture was cooled down to room temperature, and then saturated ammonium chloride aqueous solution was added thereto while being stirred. A produced solid was filtered out, and finally a product, i.e., N-(4-(4-(3-ethylthioureido)phenyl)-H-pyrrolo[2,3-b]pyridin-6-yl)cyclopropanecarboxamide was accordingly obtained.

$^1$H NMR (400 MHz, DMSO-d$_6$) 11.52 (s, 1H), 10.60 (s, 1H), 9.71 (s, 1H), 7.99 (d, J=23.1 Hz, 2H), 7.63 (dd, J=8.6, 31.6 Hz, 44H), 7.40 (s, 1H), 6.55 (d, J=3.5 Hz, 1H), 2.05 (s, 1H), 1.25-1.13 (m, 3H), 0.82 (d, J=7.6 Hz, 4H).

MS(ESI+) m/z 380 (M+H)+

Examples 463 to 469

Hereinafter, in Examples 463 to 469, a corresponding compound was synthesized by means of the same method as shown in Example 462 or by means of an appropriate reactant under the consideration of the reaction formula 1 as well as a structure of the compound to be prepared.

Example 463: Synthesis of N-(4-(4-(3-butylthioureido)phenyl)-1H-pyrrolo[2,3-b]pyridin-6-yl)cyclopropanecarboxamide

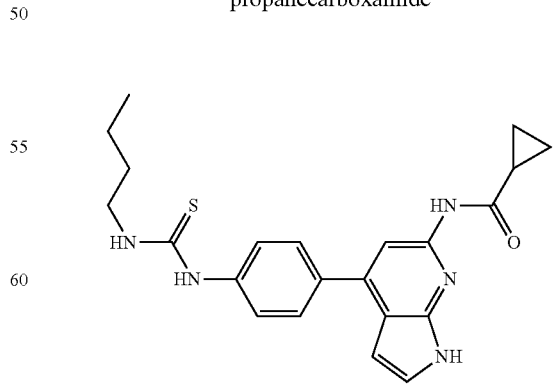

$^1$H NMR (400 MHz, DMSO-d$_6$) δ 11.54 (s, 1H), 10.69 (s, 1H), 9.78 (s, 1H), 7.99 (s, 2H), 7.65 (q, J=8.5 Hz, 3H), 7.41

(d, J=3.1 Hz, 1H), 6.57 (d, J=3.3 Hz, 1H), 3.49 (s, 2H), 2.06 (d, J=13.5 Hz, 1H), 1.60-1.49 (m, 2H), 1.34 (q, J=7.4 Hz, 2H), 1.24 (s, 1H), 0.92 (t, J=7.2 Hz, 3H), 0.83 (d, J=6.8 Hz, 4H).

MS(ESI+) m/z 408 (M+H)$^+$

Example 464: Synthesis of N-(4-(4-(3-cyclohexyl-thioureido)phenyl)-7H-pyrrolo[2,3-d]pyrimidin-2-yl)cyclopropanecarboxamide

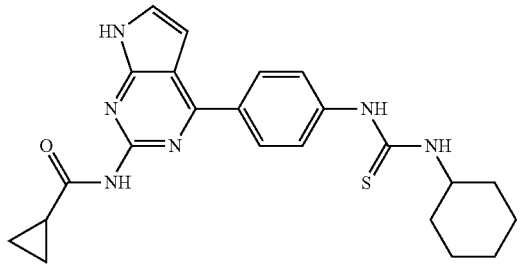 [SMILES: O=C(Nc1nc(-c2ccc(NC(=S)NC3CCCCC3)cc2)c2cc[nH]c2n1)C1CC1]

MS(ESI+) m/z 435 (M+H)$^+$

Example 465: Synthesis of N-(4-(4-(3-butylthioureido)phenyl)-7H-pyrrolo[2,3-d]pyrimidin-2-yl)cyclopropanecarboxamide

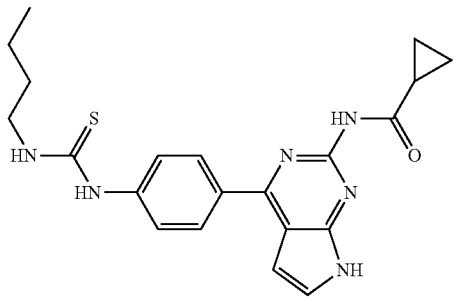

MS(ESI+) m/z 409 (M+H)$^+$

Example 466: Synthesis of N-(4-(4-(3-ethylthioureido)phenyl)-7H-pyrrolo[2,3-d]pyrimidin-2-yl)cyclopropanecarboxamide

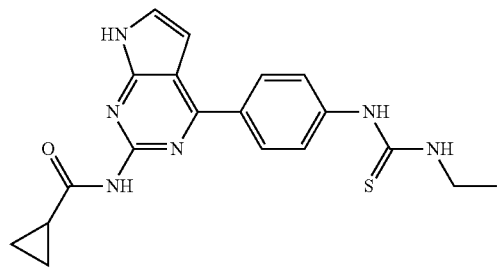 [SMILES: CCNC(=S)Nc1ccc(-c2nc(NC(=O)C3CC3)nc3[nH]ccc23)cc1]

MS(ESI+) m/z 381 (M+H)$^+$

Example 467: Synthesis of N-(4-(4-(3-propylthioureido)phenyl)-7H-pyrrolo[2,3-d]pyrimidin-2-yl)cyclopropanecarboxamide

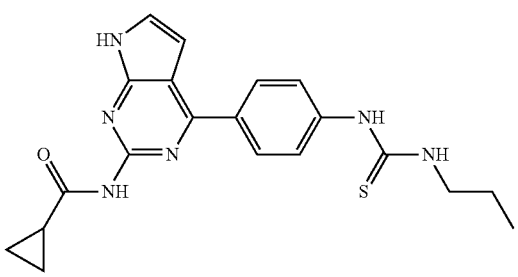 [SMILES: CCCNC(=S)Nc1ccc(-c2nc(NC(=O)C3CC3)nc3[nH]ccc23)cc1]

MS(ESI+) m/z 395 (M+H)$^+$

Example 468: Synthesis of N-(4-(1-(ethylcarbamothioyl)-1,2,3,6-tetrahydropyridin-4-yl)-1H-pyrrolo[2,3-b]pyridin-6-yl)cyclopropanecarboxamide

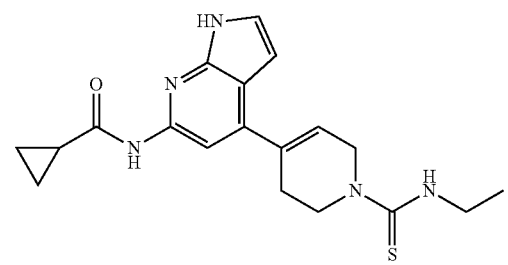 [SMILES: CCNC(=S)N1CC=C(c2cc(NC(=O)C3CC3)nc3[nH]ccc23)CC1]

MS(ESI+) m/z 370 (M+H)$^+$

Example 469: Synthesis of N-(4-(8-(ethylcarbamothioyl)-8-azabicyclo[3.2.1]oct-2-en-3-yl)-1H-pyrrolo[2,3-b]pyridin-6-yl)cyclopropanecarboxamide

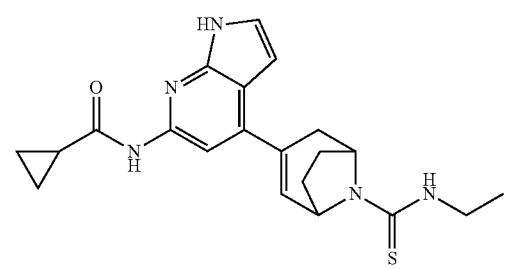 [SMILES: CCNC(=S)N1C2C=C(c3cc(NC(=O)C4CC4)nc4[nH]ccc34)CC1CC2]

MS(ESI+) m/z 396 (M+H)$^+$

Example 470: Preparation of N-(4-(4-((cyclopropylmethyl)amino)phenyl)-1H-pyrrolo[2,3-b]pyridin-6-yl)cyclopropanecarboxamide

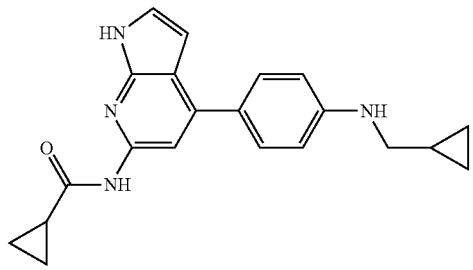 [SMILES: O=C(Nc1cc(-c2ccc(NCC3CC3)cc2)c2cc[nH]c2n1)C1CC1]

N-(4-(4-aminophenyl)-1-tosyl-1H-pyrrolo[2,3-b]pyridine-6-yl)cyclopropanecarboxamide (100 mg) was dissolved in dichloroethane, and then 3 equivalent of cyclopropanecarbaldehyde and 3 equivalent of acetic acid were inserted thereinto and stirred at room temperature for 30 minutes. 3 equivalent of sodium triacetoxyborohydride was inserted into the reaction mixture and stirred at 40° C. for 16 hours. Once the reaction was completed, the said mixture was concentrated and dissolved in MeOH/THF (1:1) solution. After that, 2N sodium hydroxide aqueous solution was added thereto and stirred at 30-40° C. for 4 hours. Once the reaction was completed, the said mixture was cooled down at room temperature, and an extraction using dichloromethane was performed. A solution extracted therefrom was dried by means of magnesium sulfate anhydrous and concentrated under reduced pressure, from which a residue was accordingly obtained. After that, a prep. TLC (DCM:MeOH=30:1) method was applied to the residue, and finally a target compound, i.e., N-(4-(4-((cyclopropylmethyl)amino)phenyl)-1H-pyrrolo[2,3-b]pyridin-6-yl)cyclopropanecarboxamide was accordingly obtained.

MS(ESI+) m/z 347 (M+H)+

Examples 471 to 489

Hereinafter, in Examples 471 to 489, a corresponding compound was synthesized by means of the same method as shown in Example 470 or by means of an appropriate reactant under the consideration of the reaction formula 1 as well as a structure of the compound to be prepared.

Example 471: Synthesis of N-(4-(4-((cyclohexylmethyl)amino)phenyl)-1H-pyrrolo[2,3-b]pyridin-6-yl)cyclopropanecarboxamide

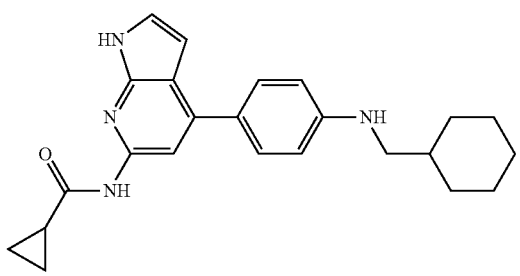 [SMILES: O=C(Nc1cc(-c2ccc(NCC3CCCCC3)cc2)c2cc[nH]c2n1)C1CC1]

$^1$H NMR (400 MHz, DMSO-d$_6$) δ 11.37 (s, 1H), 10.50 (s, 1H), 7.92 (s, 1H), 7.48 (d, J=8.6 Hz, 2H), 7.32 (dd, J=2.4, 3.5 Hz, 1H), 6.69 (d, J=8.5 Hz, 2H), 6.54 (dd, J=1.9, 3.5 Hz, 1H), 6.02 (t, J=5.7 Hz, 1H), 3.64-3.55 (m, 2H), 2.91 (t, J=6.2 Hz, 2H), 2.03 (s, 1H), 1.82-1.52 (m, 7H), 1.25-1.12 (m, 3H), 0.95 (q, J=12.0, 12.5 Hz, 2H), 0.86-0.72 (m, 4H).

MS(ESI+) m/z 389 (M+H)+

Example 472: Synthesis of N-(4-(4-(benzylamino)phenyl)-1H-pyrrolo[2,3-b]pyridin-6-yl)cyclopropanecarboxamide

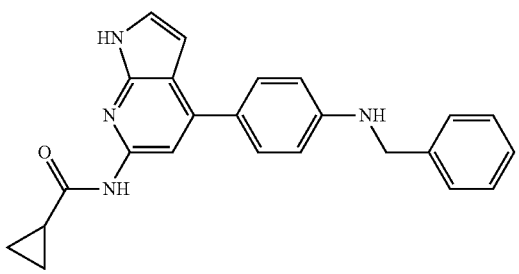 [SMILES: O=C(Nc1cc(-c2ccc(NCc3ccccc3)cc2)c2cc[nH]c2n1)C1CC1]

$^1$H NMR (400 MHz, DMSO-d$_6$) δ 11.38 (s, 1H), 10.50 (s, 1H), 7.91 (s, 1H), 7.46 (d, J=8.6 Hz, 2H), 7.42-7.28 (m, 5H), 7.24 (t, J=7.3 Hz, 1H), 6.73 (d, J=8.6 Hz, 2H), 6.63 (t, J=6.0 Hz, 1H), 6.52 (dd, J=1.8, 3.5 Hz, 1H), 4.34 (d, J=6.0 Hz, 2H), 2.02 (s, 1H), 0.83-0.72 (m, 4H).

MS(ESI+) m/z 383 (M+H)+

Example 473: Synthesis of N-(4-(4-((4-fluorobenzyl)amino)phenyl)-7H-pyrrolo[2,3-d]pyrimidin-2-yl)cyclopropanecarboxamide

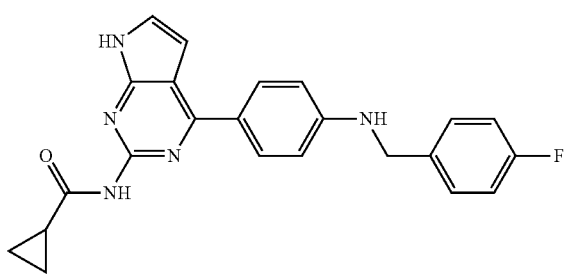 [SMILES: O=C(Nc1nc(-c2ccc(NCc3ccc(F)cc3)cc2)c2cc[nH]c2n1)C1CC1]

MS(ESI+) m/z 402 (M+H)+

Example 474: Synthesis of N-(4-(4-((3-fluorobenzyl)amino)phenyl)-7H-pyrrolo[2,3-d]pyrimidin-2-yl)cyclopropanecarboxamide

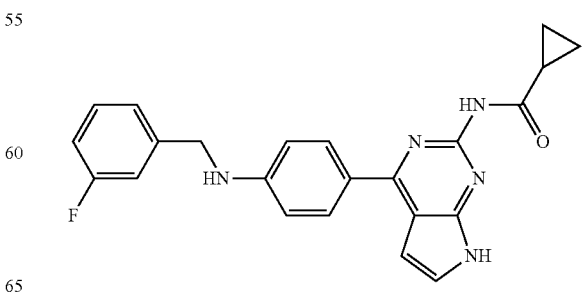

MS(ESI+) m/z 402 (M+H)+

Example 475: Synthesis of N-(4-(4-((4-chlorobenzyl)amino)phenyl)-7H-pyrrolo[2,3-d]pyrimidin-2-yl)cyclopropanecarboxamide

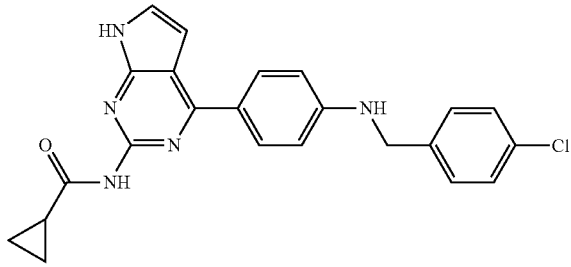 [SMILES: O=C(Nc1nc(-c2ccc(NCc3ccc(Cl)cc3)cc2)c2cc[nH]c2n1)C1CC1]

MS(ESI+) m/z 418, 420 (M+H)+

Example 476: Synthesis of N-(4-(4-((3-hydroxypropyl)amino)phenyl)-7H-pyrrolo[2,3-d]pyrimidin-2-yl)cyclopropanecarboxamide

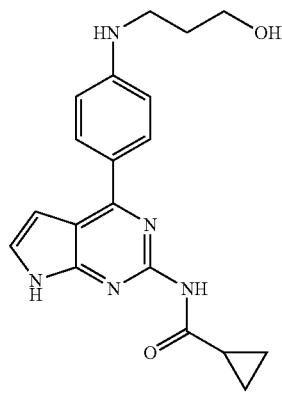 [SMILES: O=C(Nc1nc(-c2ccc(NCCCO)cc2)c2cc[nH]c2n1)C1CC1]

MS(ESI+) m/z 352 (M+H)+

Example 477: Synthesis of N-(4-(1-(2-cyanoethyl)-1H-pyrazol-4-yl)-1H-pyrrolo[2,3-b]pyridin-6-yl)cyclopropanecarboxamide

¹H NMR (400 MHz, DMSO-d$_6$) δ 11.44 (s, 1H), 10.53 (s, 1H), 8.50 (s, 1H), 8.06 (d, J=9.1 Hz, 2H), 7.48-7.35 (m, 1H), 7.00 (s, 1H), 6.72 (d, J=4.1 Hz, 1H), 4.57-4.45 (m, 2H), 3.22-3.11 (m, 2H), 2.05 (s, 1H), 0.82 (d, J=12.2 Hz, 4H).
MS(ESI+) m/z 321 (M+H)+

Example 478: Synthesis of N-(4-(1-(cyclopropylmethyl)-1H-pyrazol-4-yl)-1H-pyrrolo[2,3-b]pyridin-6-yl)cyclopropanecarboxamide

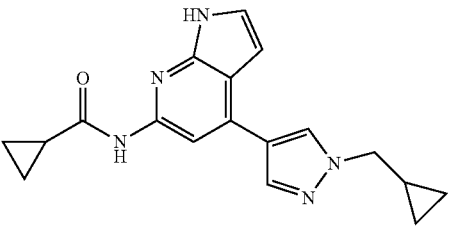 [SMILES: O=C(Nc1cc(-c2cnn(CC3CC3)c2)c2cc[nH]c2n1)C1CC1]

¹H NMR (400 MHz, DMSO-d$_6$) δ 11.42 (d, J=12.3 Hz, 1H), 10.51 (s, 1H), 8.39 (s, 1H), 8.01 (d, J=32.6 Hz, 2H), 7.48-7.31 (m, 1H), 6.72 (s, 1H), 4.06 (d, J=7.7 Hz, 2H), 2.04 (s, 1H), 1.33 (s, 1H), 0.89-0.74 (m, 4H), 0.62-0.38 (m, 4H).
MS(ESI+) m/z 322 (M+H)+

Example 479: Synthesis of N-(4-(1-benzyl-1H-pyrazol-4-yl)-1H-pyrrolo[2,3-b]pyridin-6-yl)cyclopropanecarboxamide

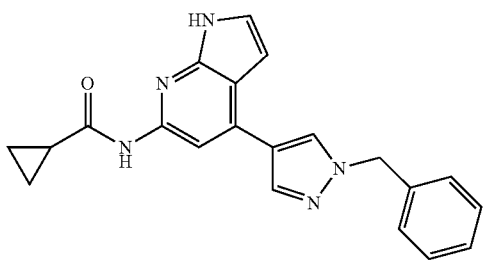 [SMILES: O=C(Nc1cc(-c2cnn(Cc3ccccc3)c2)c2cc[nH]c2n1)C1CC1]

¹H NMR (400 MHz, DMSO-d$_6$) δ 11.41 (s, 1H), 10.50 (s, 1H), 8.54 (s, 1H), 8.09-7.91 (m, 3H), 7.35 (d, J=13.5 Hz, 8H), 7.23 (s, 1H), 6.71 (s, 1H), 5.42 (d, J=4.1 Hz, 2H), 2.03 (s, 1H), 0.82 (s, 4H).
MS(ESI+) m/z 358 (M+H)+

Example 480: Synthesis of N-(4-(1-(2-cyanoethyl)-3,5-dimethyl-1H-pyrazol-4-yl)-1H-pyrrolo[2,3-b]pyridin-6-yl)cyclopropanecarboxamide

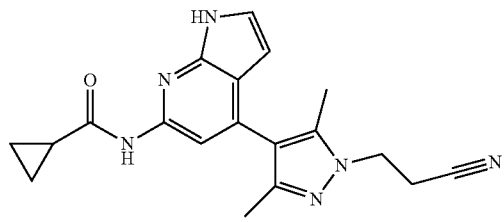 [SMILES: Cc1nn(CCC#N)c(C)c1-c1cc(NC(=O)C2CC2)nc2[nH]ccc12]

¹H NMR (400 MHz, DMSO-d$_6$) δ 11.42 (s, 1H), 10.55 (s, 1H), 7.72 (s, 1H), 7.32 (s, 1H), 6.14 (s, 1H), 4.33 (d, J=5.9 Hz, 2H), 3.06 (d, J=5.9 Hz, 2H), 2.27-2.17 (m, 3H), 2.10 (s, 3H), 2.02 (s, 1H), 0.78 (d, J=12.9 Hz, 4H).
MS(ESI+) m/z 349 (M+H)+

Example 481: Synthesis of N-(4-(1-benzyl-1H-1,2,3-triazol-4-yl)-1H-pyrrolo[2,3-b]pyridin-6-yl)cyclopropanecarboxamide

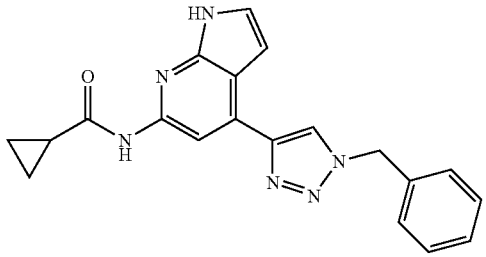 [SMILES: O=C(Nc1cc(-c2cn(Cc3ccccc3)nn2)c2cc[nH]c2n1)C1CC1]

¹H NMR (400 MHz, DMSO-d₆) δ 11.51 (s, 1H), 10.58 (s, 1H), 8.93 (s, 1H), 8.40 (s, 1H), 7.51-7.30 (m, 6H), 6.88 (dd, J=3.5, 1.9 Hz, 1H), 5.69 (s, 2H) 2.10-1.95 (m, 1H), 0.96-0.72 (m, 4H).
MS(ESI+) m/z 421 (M+H)⁺

Example 482: Synthesis of N-(4-(1-((6-cyanopyridin-3-yl)methyl)-1H-pyrazol-4-yl)-7H-pyrrolo[2,3-d]pyrimidin-2-yl)cyclopropanecarboxamide

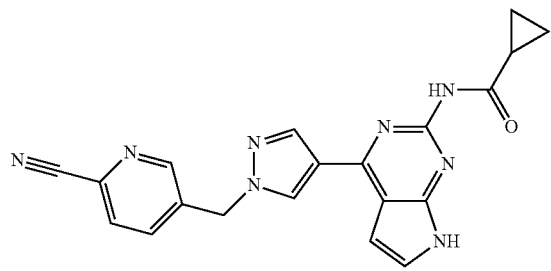 [SMILES: N#Cc1ccc(Cn2cc(-c3nc(NC(=O)C4CC4)nc4[nH]ccc34)cn2)cn1]

¹H NMR (400 MHz, DMSO-d₆) δ 11.92 (s, 1H), 10.42 (s, 1H), 9.16 (s, 1H), 8.78 (s, 1H), 8.71 (d, J=2.1 Hz, 1H), 8.29 (d, J=3.3 Hz, 1H), 7.88-7.76 (m, 2H), 7.43 (d, J=3.8 Hz, 1H), 6.87 (d, J=3.8 Hz, 1H), 5.60 (d, J=6.2 Hz, 2H), 2.20 (s, 1H), 0.80 (ddt, J=3.0, 4.9, 10.7 Hz, 4H).
MS(ESI+) m/z 385 (M+H)⁺

Example 483: Synthesis of N-(4-(1-(2-cyanoethyl)-1H-pyrrol-3-yl)-1H-pyrrolo[2,3-b]pyridin-6-yl)cyclopropanecarboxamide

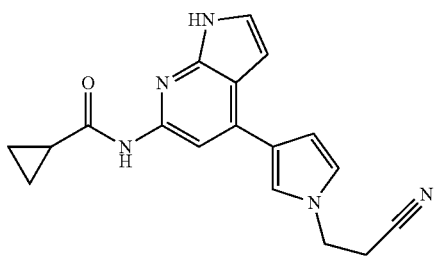 [SMILES: N#CCCn1ccc(-c2cc(NC(=O)C3CC3)nc3[nH]ccc23)c1]

¹H NMR (400 MHz, DMSO-d₆) δ 11.30 (s, 1H), 10.44 (s, 1H), 8.01 (s, 1H), 7.56 (d, J=2.1 Hz, 1H), 7.31 (d, J=2.5 Hz, 1H), 6.98 (t, J=2.5 Hz, 1H), 6.71 (d, J=3.2 Hz, 1H), 6.54 (d, J=2.5 Hz, 1H), 4.27 (t, J=6.5 Hz, 2H), 3.09 (t, J=6.4 Hz, 2H), 2.03 (s, 1H), 0.83-0.76 (m, 4H).
MS(ESI+) m/z 320 (M+H)⁺

Example 484: Synthesis of N-(4-(1-(2-morpholinoethyl)-2,5-dihydro-1H-pyrrol-3-yl)-1H-pyrrolo[2,3-b]pyridin-6-yl)cyclopropanecarboxamide

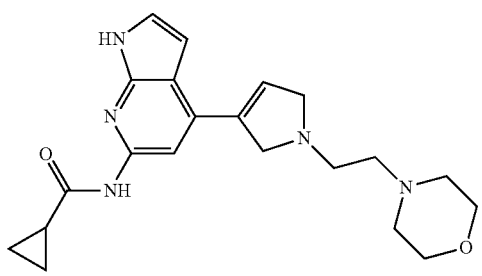 [SMILES: O=C(Nc1cc(C2=CCN(CCN3CCOCC3)C2)c2cc[nH]c2n1)C1CC1]

¹H NMR (400 MHz, DMSO-d₆) δ 11.56 (s, 1H), 10.61 (s, 1H), 7.83 (d, J=8.0 Hz, 1H), 7.42 (d, J=3.1 Hz, 1H), 6.81-6.64 (m, 2H), 4.55 (d, J=10.5 Hz, 2H), 4.37 (s, 2H), 4.19 (t, J=6.7 Hz, 2H), 3.57 (d, J=4.7 Hz, 4H), 2.59 (d, J=6.2 Hz, 2H), 2.45 (d, J=4.6 Hz, 2H), 2.03 (s, 1H), 0.84-0.74 (m, 4H).
MS(ESI+) m/z 382 (M+H)⁺

Example 485: Synthesis of N-(4-(1-(2-cyanoethyl)-2,5-dihydro-1H-pyrrol-3-yl)-1H-pyrrolo[2,3-b]pyridin-6-yl)cyclopropanecarboxamide

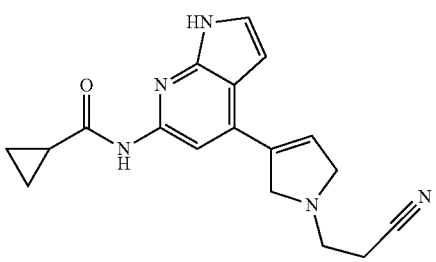 [SMILES: N#CCCN1CC=C(c2cc(NC(=O)C3CC3)nc3[nH]ccc23)C1]

¹H NMR (400 MHz, DMSO-d₆) δ 11.48 (s, 1H), 10.55 (s, 1H), 7.80 (s, 1H), 7.38 (t, J=3.0 Hz, 1H), 6.67-6.57 (m, 2H), 3.93 (q, J=3.7 Hz, 2H), 3.73 (td, J=2.1, 4.5 Hz, 2H), 2.94 (t, J=6.7 Hz, 2H), 2.73 (t, J=6.7 Hz, 2H), 2.02 (tt, J=4.5, 7.7 Hz, 1H), 0.80 (ddd, J=2.8, 5.3, 11.3 Hz, 4H).
MS(ESI+) m/z 322 (M+H)⁺

Example 486: Synthesis of N-(4-(1-(2-cyanoethyl)-1,2,3,6-tetrahydropyridin-4-yl)-1H-pyrrolo[2,3-b]pyridin-6-yl)cyclopropanecarboxamide

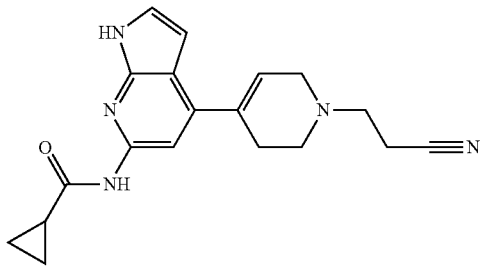 [SMILES: N#CCCN1CC=C(c2cc(NC(=O)C3CC3)nc3[nH]ccc23)CC1]

$^1$H NMR (400 MHz, DMSO-$d_6$) δ 11.40 (s, 1H), 10.50 (s, 1H), 7.86 (s, 1H), 7.33 (d, J=2.7 Hz, 1H), 6.54 (d, J=3.5 Hz, 1H), 6.32 (s, 1H), 3.23 (t, J=3.1 Hz, 2H), 2.73 (dd, J=4.5, 7.5 Hz, 5H), 2.02 (s, 1H), 0.82-0.75 (m, 4H).
MS(ESI+) m/z 336 (M+H)$^+$

Example 487: Synthesis of N-(4-(1-((3-methyloxetan-3-yl)methyl)-1,2,3,6-tetrahydropyridin-4-yl)-1H-pyrrolo[2,3-b]pyridin-6-yl)cyclopropanecarboxamide

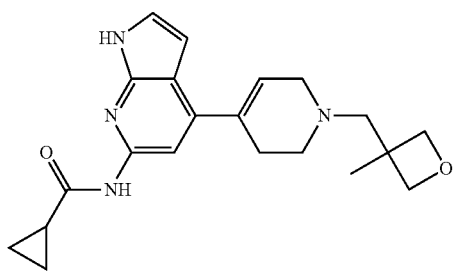 [SMILES: CC1(CN2CC=C(c3cc(NC(=O)C4CC4)nc4[nH]ccc34)CC2)COC1]

MS(ESI+) m/z 367 (M+H)$^+$

Example 488: Synthesis of N-(4-(1-(isothiazol-5-ylmethyl)-1,2,3,6-tetrahydropyridin-4-yl)-1H-pyrrolo[2,3-b]pyridin-6-yl)cyclopropanecarboxamide

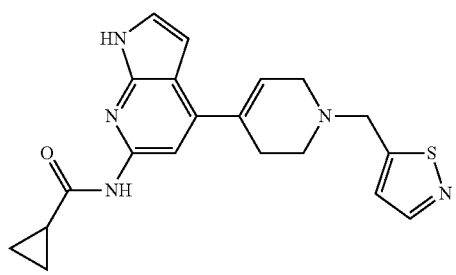 [SMILES: O=C(Nc1cc(C2=CCN(Cc3ccns3)CC2)c2cc[nH]c2n1)C1CC1]

$^1$H NMR (400 MHz, DMSO-$d_6$) δ 11.41 (s, 1H), 10.53 (s, 1H), 8.50 (d, J=1.6 Hz, 1H), 7.86 (s, 1H), 7.33 (d, J=2.1 Hz, 2H), 6.55 (d, J=2.7 Hz, 1H), 6.33 (s, 1H), 3.29 (d, J=3.4 Hz, 2H), 2.77 (t, J=5.6 Hz, 2H), 2.56 (s, 2H), 2.01 (d, J=4.1 Hz, 1H), 0.88-0.72 (m, 4H).
MS(ESI+) m/z 380 (M+H)$^+$

Example 489: Synthesis of N-(4-(1-((2,2-difluorocyclopropyl)methyl)-1,2,3,6-tetrahydropyridin-4-yl)-1H-pyrrolo[2,3-b]pyridin-6-yl)cyclopropanecarboxamide

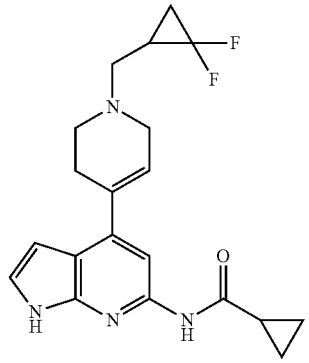 [SMILES: O=C(Nc1cc(C2=CCN(CC3CC3(F)F)CC2)c2cc[nH]c2n1)C1CC1]

$^1$H NMR (400 MHz, DMSO-$d_6$) δ 11.41 (s, 1H), 10.52 (s, 1H), 7.85 (s, 1H), 7.35-7.29 ((m, 1H), 6.54 (dd, J=3.5, 1.8 Hz, 1H), 6.33 (d, J=3.4 Hz, 1H), 3.25-3.19 (m, 2H), 2.72 (dp, J=16.1, 5.4 Hz, 3H), 2.50 (m, 3H), 2.01 (s, 1H), 1.90 (tt, J=13.8, 6.9 Hz, 1H), 1.62 (qt, J=12.1, 5.9 Hz, 1H), 1.19 (dd, J=7.9, 3.8 Hz, 1H), 0.87-0.72 (m, 4H)
MS(ESI+) m/z 373 (M+H)$^+$

Example 490: Synthesis of N-(4-(1-(3-cyanocyclobutyl)-1,2,3,6-tetrahydropyridin-4-yl)-1H-pyrrolo[2,3-b]pyridin-6-yl)cyclopropanecarboxamide

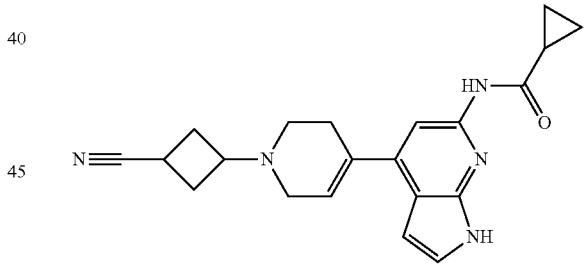

1.0 g (3.37 mmol) of the synthesized N-(4-(4-aminocyclohex-1-en-1-yl)-1H-pyrrolo[2,3-b]pyridin-6-yl)cyclopropanecarboxamide and 3-oxocyclobutane-1-carbonitrile were dissolved in THF solution, and then NaBH(OAc)$_3$ and DIPEA were inserted thereinto and stirred at room temperature for a day. Once the reaction was completed, water was added thereto and an extraction using dichloromethane was performed. A solution extracted therefrom was dried by means of magnesium sulfate anhydrous and concentrated under reduced pressure, from which a residue was accordingly obtained. The residue was separated via silica gel column chromatography, and finally N-(4-(1-(3-cyanocyclobutyl)-1,2,3,6-tetrahydropyridin-4-yl)-1H-pyrrolo[2,3-b]pyridin-6-yl)cyclopropanecarboxamide was accordingly obtained.

MS(ESI+) m/z 362 (M+H)$^+$

Examples 441 to 518

Hereinafter, in Examples 491 to 518, a corresponding compound was synthesized by means of the same method as shown in Example 490 or by means of an appropriate reactant under the consideration of the reaction formula 1 as well as a structure of the compound to be prepared.

Example 491: Synthesis of N-(4-(4-((1-(3,5-difluorobenzoyl)piperidin-4-yl)amino)cyclohex-1-en-1-yl)-1H-pyrrolo[2,3-b]pyridin-6-yl)cyclopropanecarboxamide

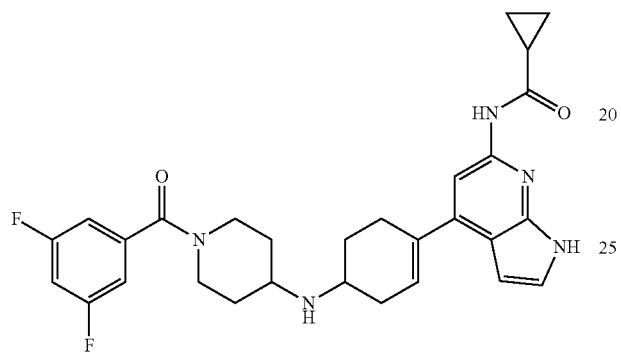

$^1$H NMR (400 MHz, DMSO-$d_6$) δ 11.35 (s, 1H), 10.48 (s, 1H), 7.82 (s, 1H), 7.38-7.20 (m, 2H), 7.17-7.10 (m, 2H), 6.48 (dd, J=3.5, 1.8 Hz, 1H), 6.23 (s, 1H), 4.28 (s, 1H), 3.47 (s, 1H), 2.98 (s, 3H), 2.00 (s, 3H), 1.81 (s, 1H), 1.48 (s, 2H), 1.25 (d, J=9.2 Hz, 5H), 0.82-0.74 (m, 4H).

MS(ESI+) m/z 520 (M+H)$^+$

Example 492: Synthesis of N-(4-(4-((1-(cyclohexanecarbonyl)piperidin-4-yl)amino)cyclohex-1-en-1-yl)-1H-pyrrolo[2,3-b]pyridin-6-yl)cyclopropanecarboxamide

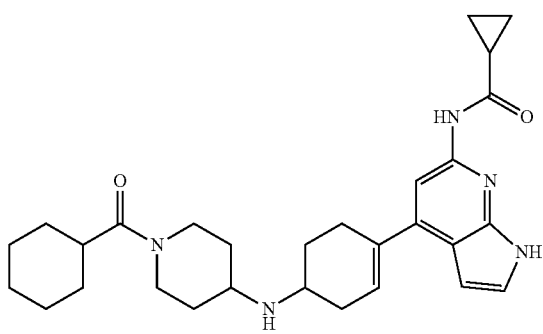 [SMILES: O=C(Nc1cc(C2=CCC(NC3CCN(C(=O)C4CCCCC4)CC3)CC2)c2cc[nH]c2n1)C1CC1]

$^1$H NMR (400 MHz, DMSO-$d_6$) δ 11.35 (s, 1H), 10.48 (s, 1H), 7.82 (s, 1H), 7.30 (t, J=3.0 Hz, 1H), 6.49 (dd, J=3.6, 1.9 Hz, 1H), 6.22 (s, 1H), 4.26 (d, J=13.7 Hz, 1H), 3.88 (d, J=13.5 Hz, 1H), 3.56 (t, J=7.0 Hz, 1H), 3.14 (dd, J=7.5, 5.6 Hz, 1H), 2.19 (d, J=6.7 Hz, 1H), 2.01 (s, 4H), 1.70 (d, J=11.1 Hz, 4H), 1.61 (t, J=6.9 Hz, 6H), 1.30 (s, 6H), 1.18 (d, J=9.8 Hz, 2H), 1.07 (t, J=7.2 Hz, 2H), 0.82-0.77 (m, 4H).

MS(ESI+) m/z 490 (M+H)$^+$

Example 493: Synthesis of N-(4-(4-((1-(2-fluoroisonicotinoyl)piperidin-4-yl)amino)cyclohex-1-en-1-yl)-1H-pyrrolo[2,3-b]pyridin-6-yl)cyclopropanecarboxamide

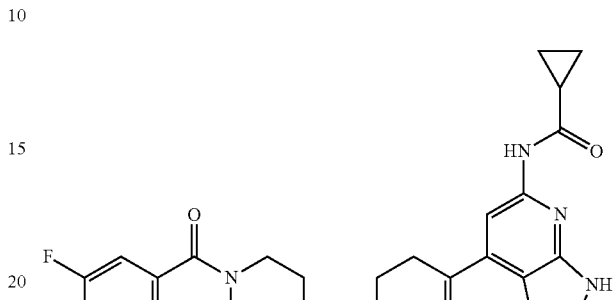

$^1$H NMR (400 MHz, DMSO-$d_6$) δ 11.36 (s, 1H), 10.48 (s, 1H), 8.33 (d, J=5.0 Hz, 1H), 7.82 (s, 1H), 7.32 (dt, J=18.3, 3.9 Hz, 2H), 7.23 (s, 1H), 6.49 (dd, J=3.6, 1.9 Hz, 1H), 6.22 (s, 1H), 4.32 (d, J=12.7 Hz, 1H), 3.43 (d, J=13.8 Hz, 1H), 3.04 (dt, J=39.7, 12.3 Hz, 4H), 1.98 (d, J=22.7 Hz, 4H), 0.84-0.75 (m, 4H).

MS(ESI+) m/z 503 (M+H)$^+$

Example 494: Synthesis of N-(4-(4-((1-(4-nitrobenzoyl)piperidin-4-yl)amino)cyclohex-1-en-1-yl)-1H-pyrrolo[2,3-b]pyridin-6-yl)cyclopropanecarboxamide

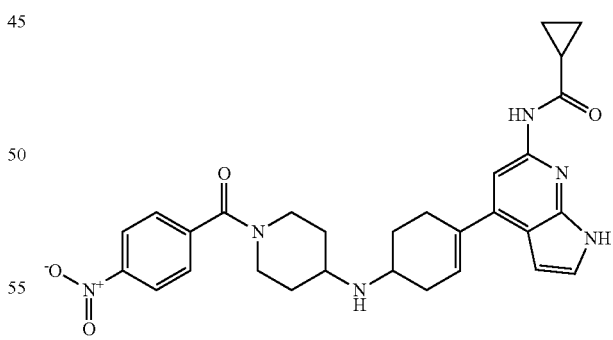

$^1$H NMR (400 MHz, DMSO-$d_6$) δ 11.35 (d, J=3.2 Hz, 1H), 10.48 (s, 1H), 8.32-8.25 (m, 2H), 7.82 (s, 1H), 7.71-7.59 (m, 2H), 7.29 (t, J=3.1 Hz, 1H), 6.48 (dd, J=3.5, 1.9 Hz, 1H), 6.22 (s, 1H), 4.32 (d, J=12.4 Hz, 1H), 3.43 (d, J=13.3 Hz, 1H), 3.03 (d, J=52.9 Hz, 4H), 2.00 (d, J=7.2 Hz, 4H), 1.78 (s, 1H), 1.47 (s, 2H), 1.25 (d, J=17.8 Hz, 4H), 0.85-0.73 (m, 4H).

MS(ESI+) m/z 529 (M+H)$^+$

Example 495: Synthesis of N-(4-(4-((1-(3,5-difluorobenzoyl)azetidin-3-yl)amino)cyclohex-1-en-1-yl)-1H-pyrrolo[2,3-b]pyridin-6-yl)cyclopropanecarboxamide

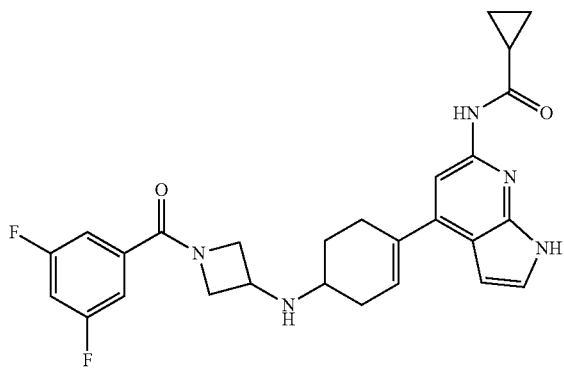 [SMILES: O=C(Nc1cc(C2=CCC(NC3CN(C(=O)c4cc(F)cc(F)c4)C3)CC2)c2cc[nH]c2n1)C1CC1]

¹H NMR (400 MHz, DMSO-d₆) δ 11.35 (s, 1H), 10.47 (s, 1H), 7.43 (tt, J=9.5, 2.5 Hz, 1H), 7.30 (dq, J=5.8, 2.1 Hz, 3H), 7.19-7.12 (m, 1H), 6.48 (t, J=2.7 Hz, 1H), 6.21 (d, J=4.1 Hz, 1H), 4.47 (d, J=8.4 Hz, 1H), 4.22 (d, J=10.5 Hz, 1H), 4.03 (s, 1H), 3.78 (dd, J=7.0, 3.8 Hz, 2H), 3.63 (t, J=7.0 Hz, 1H), 3.01 (qd, J=7.2, 5.3 Hz, 1H), 1.91 (d, J=6.9 Hz, 1H), 0.83-0.72 (m, 4H).

MS(ESI+) m/z 492 (M+H)⁺

Example 496: Synthesis of N-(4-(4-((1-(2-fluoroisonicotinoyl)azetidin-3-yl)amino)cyclohex-1-en-1-yl)-1H-pyrrolo[2,3-b]pyridin-6-yl)cyclopropanecarboxamide

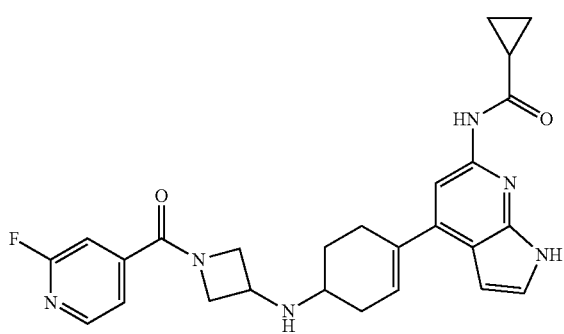 [SMILES: O=C(Nc1cc(C2=CCC(NC3CN(C(=O)c4ccnc(F)c4)C3)CC2)c2cc[nH]c2n1)C1CC1]

¹H NMR (400 MHz, DMSO-d₆) δ 11.35 (s, 1H), 10.48 (s, 1H), 8.34 (dd, J=22.8, 5.1 Hz, 1H), 7.82 (s, 1H), 7.52 (dt, J=5.1, 1.6 Hz, 1H), 7.33 (t, J=1.7 Hz, 1H), 7.29 (t, J=3.1 Hz, 1H), 6.47 (dt, J=3.7, 2.0 Hz, 1H), 6.21 (s, 1H), 4.46 (td, J=7.6, 6.5, 3.9 Hz, 1H), 4.24 (d, J=10.7 Hz, 1H), 4.04-4.01 (m, 1H), 3.79 (dt, J=7.7, 4.2 Hz, 2H), 3.00 (ddd, J=8.6, 6.9, 5.3 Hz, 1H), 2.80 (s, 1H), 2.18 (t, J=3.4 Hz, 1H), 2.03-1.99 (m, 2H), 1.91 (d, J=5.9 Hz, 1H), 0.82-0.74 (m, 4H).

MS(ESI+) m/z 475 (M+H)⁺

Example 497: Synthesis of N-(4-(4-((1-(2-methoxyisonicotinoyl)azetidin-3-yl)amino)cyclohex-1-en-1-yl)-1H-pyrrolo[2,3-b]pyridin-6-yl)cyclopropanecarboxamide

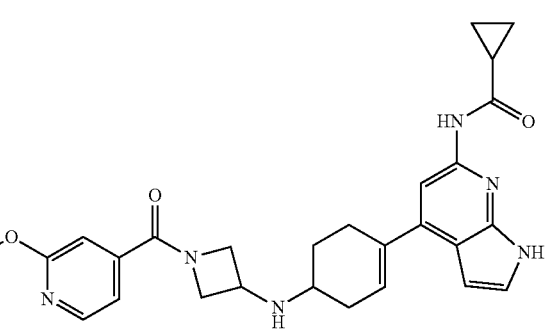

¹H NMR (400 MHz, DMSO-d₆) δ 11.35 (s, 1H), 10.48 (s, 1H), 8.27 (d, J=5.3 Hz, 1H), 7.81 (s, 1H), 7.33-7.26 (m, 1H), 7.12 (dd, J=5.2, 1.4 Hz, 1H), 6.92 (t, J=1.0 Hz, 1H), 6.53-6.43 (m, 1H), 6.21 (s, 1H), 4.43 (s, 1H), 4.23 (s, 1H), 3.99 (s, 1H), 3.78 (s, 2H), 2.81 (s, 1H), 2.00 (d, J=5.4 Hz, 2H), 1.91 (s, 1H), 1.48 (s, 2H), 0.81-0.74 (m, 4H).

MS(ESI+) m/z 487 (M+H)⁺

Example 498: Synthesis of 4-((4-(6-(cyclopropanecarboxamido)-1H-pyrrolo[2,3-b]pyridin-4-yl)-2-fluorophenyl)amino)-N-phenylpiperidine-1-carboxamide

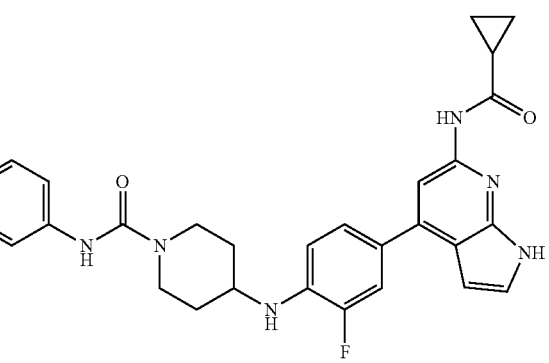

¹H NMR (400 MHz, DMSO-d₆) δ 11.45 (s, 1H), 10.54 (s, 1H), 8.52 (s, 1H), 7.95 (s, 1H), 7.51-7.45 (m, 2H), 7.42-7.33 (m, 3H), 7.25-7.19 (m, 2H), 7.00 (t, J=8.8 Hz, 1H), 6.94-6.87 (m, 1H), 6.56 (dd, J=3.5, 1.9 Hz, 1H), 5.61 (d, J=7.9 Hz, 1H), 4.15 (d, J=13.3 Hz, 2H), 3.61 (s, 1H), 2.96 (t, J=12.5 Hz, 2H), 2.04 (s, 1H), 1.94 (t, J=14.5 Hz, 2H), 1.52-1.42 (m, 3H), 1.23 (s, 6H), 0.82 (dd, J=8.8, 5.0 Hz, 4H).

MS(ESI+) m/z 513 (M+H)⁺

Example 499: Synthesis of N-(4-(4-((1-(3,5-difluorobenzoyl)piperidin-4-yl)amino)-3-fluorophenyl)-1H-pyrrolo[2,3-b]pyridin-6-yl)cyclopropanecarboxamide MS(ESI+) m/z 534 (M+H)+

Example 500: Synthesis of N-(4-(3-fluoro-4-((1-(2-fluoroisonicotinoyl)piperidin-4-yl)amino)phenyl)-1H-pyrrolo[2,3-b]pyridin-6-yl)cyclopropanecarboxamide

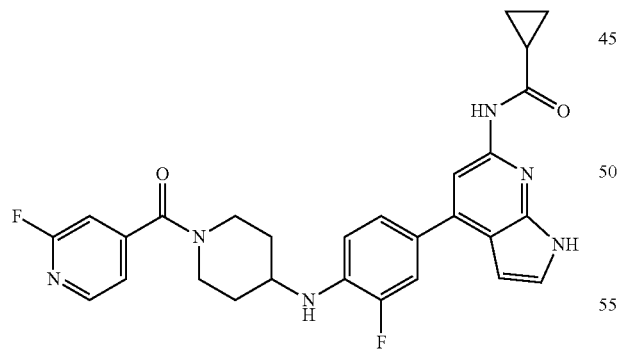

1H NMR (400 MHz, DMSO-d6) δ 11.45 (s, 1H), 10.55 (s, 1H), 8.35 (d, J=5.0 Hz, 1H), 7.94 (s, 1H), 7.42-7.28 (m, 3H), 7.24 (s, 1H), 6.99 (s, 1H), 6.58-6.48 (m, 1H), 5.55 (d, J=9.0 Hz, 1H), 5.32 (s, 1H), 2.01 (t, J=7.5 Hz, 4H), 1.91 (s, 1H), 1.56-1.39 (m, 4H), 1.23 (s, 9H), 0.83 (d, J=14.1 Hz, 4H).

MS(ESI+) m/z 517 (M+H)+

Example 501: Synthesis of 4-((4-(6-(cyclopropanecarboxamido)-1H-pyrrolo[2,3-b]pyridin-4-yl)-2-fluorophenyl)amino)-N-(2,4-difluorophenyl)piperidine-1-carboxamide

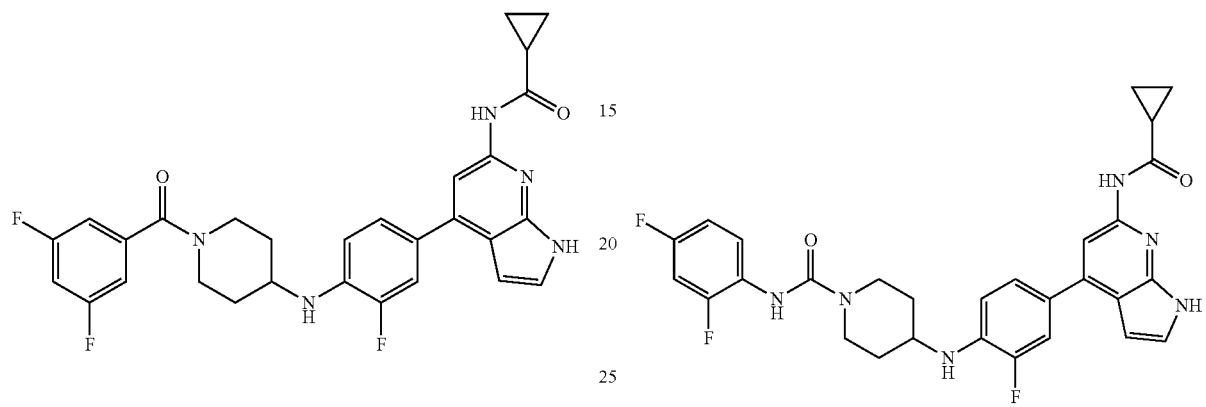

1H NMR (400 MHz, DMSO-d6) δ 11.48 (s, 1H), 10.58 (s, 1H), 8.34 (s, 1H), 7.95 (s, 1H), 7.42-7.33 (m, 5H), 7.31-7.17 (m, 3H), 7.00 (q, J=8.5 Hz, 2H), 6.59-6.50 (m, 1H), 5.68-5.60 (m, 1H), 4.86-4.73 (m, 1H), 4.10 (d, J=13.3 Hz, 2H), 3.60 (s, 2H), 2.96 (t, J=12.6 Hz, 2H), 2.18 (t, J=7.4 Hz, 1H), 0.86-0.78 (m, 6H).

MS(ESI+) m/z 549 (M+H)+

Example 502: Synthesis of N-(4-(4-(((2S)-1-(3,5-difluorobenzoyl)-2-methylpiperidin-4-yl)amino)phenyl)-1H-pyrrolo[2,3-b]pyridin-6-yl)cyclopropanecarboxamide

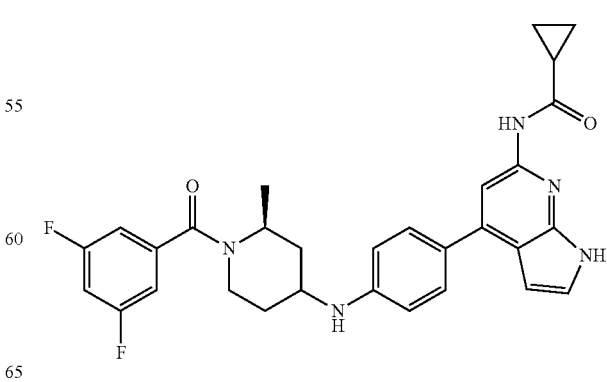

MS(ESI+) m/z 530 (M+H)+

Example 503: Synthesis of N-(4-(4-(((2S)-1-(2-fluoroisonicotinoyl)-2-methylpiperidin-4-yl)amino)phenyl)-1H-pyrrolo[2,3-b]pyridin-6-yl)cyclopropanecarboxamide Example 505: Synthesis of 4-((4-(6-(cyclopropanecarboxamido)-1H-pyrrolo[2,3-b]pyridin-4-yl)-2-fluorophenyl)amino)-N-(2,2,2-trifluoroethyl)piperidine-1-carboxamide

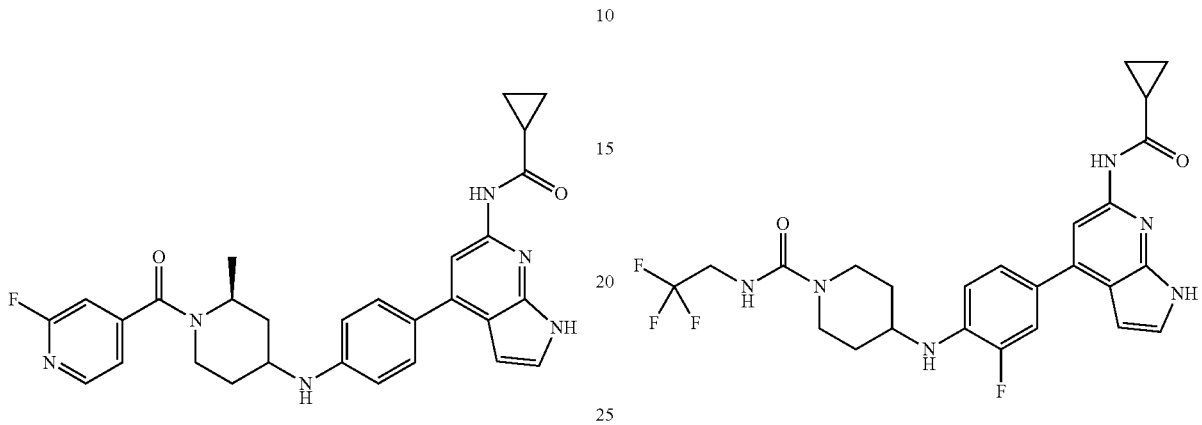

MS(ESI+) m/z 513 (M+H)+

Example 504: Synthesis of (2S)-4-((4-(6-(cyclopropanecarboxamido)-1H-pyrrolo[2,3-b]pyridin-4-yl)phenyl)amino)-2-methyl-N-(2,2,2-trifluoroethyl)piperidine-1-carboxamide $^1$H NMR (400 MHz, DMSO-$d_6$) δ 11.47 (s, 1H), 10.58 (s, 1H), 7.95 (s, 1H), 7.40-7.34 (m, 3H), 7.17 (t, J=6 Hz, 1H), 6.99 (t, J=8.8 Hz, 1H), 6.55 (m, 1H), 5.63 (d, J=8.4 Hz, 1H), 4.02 (d, J=13.6 Hz, 2H), 3.87 (m, 2H), 3.57 (m, 1H), 2.90 (t, J=12.4 Hz, 2H), 2.03 (m, 1H), 1.91 (d, J=10.8 Hz, 2H), 1.42 (m, 2H), 0.84 (m, 4H).

MS(ESI+) m/z 519 (M+H)+

Example 506: Synthesis of (2S)-4-((4-(6-(cyclopropanecarboxamido)-1H-pyrrolo[2,3-b]pyridin-4-yl)phenyl)amino)-N-(2,4-difluorophenyl)-2-methylpiperidine-1-carboxamide

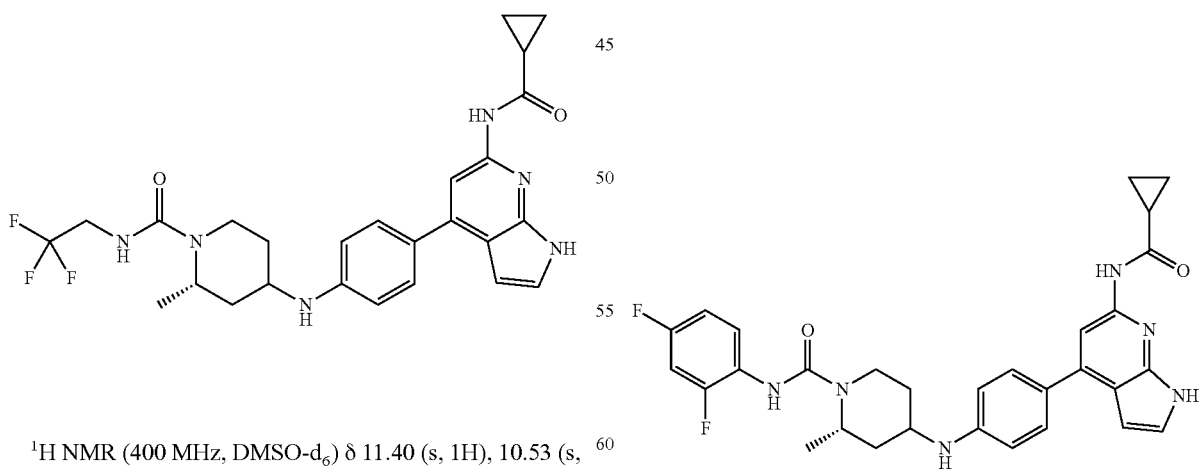

$^1$H NMR (400 MHz, DMSO-$d_6$) δ 11.40 (s, 1H), 10.53 (s, 1H), 7.94 (s, 1H), 7.54-7.47 (m, 2H), 7.33 (dd, J=3.5, 2.5 Hz, 1H), 6.75 (dd, J=8.9, 3.1 Hz, 2H), 6.55 (td, J=3.4, 1.9 Hz, 1H), 3.93-3.77 (m, 3H), 3.59 (d, J=2.8 Hz, 1H), 2.05-2.00 (m, 1H), 1.95-1.80 (m, 2H), 1.66 (dd, J=30.6, 12.3 Hz, 2H), 1.23 (s, 2H), 1.17 (d, J=6.7 Hz, 2H), 0.83-0.77 (m, 4H).

MS(ESI+) m/z 515 (M+H)+

MS(ESI+) m/z 545 (M+H)+

Example 507: Synthesis of N-(4-(4-((1-isonicotinoylpiperidin-4-yl)amino)phenyl)-1H-pyrrolo[2,3-b]pyridin-6-yl)cyclopropanecarboxamide

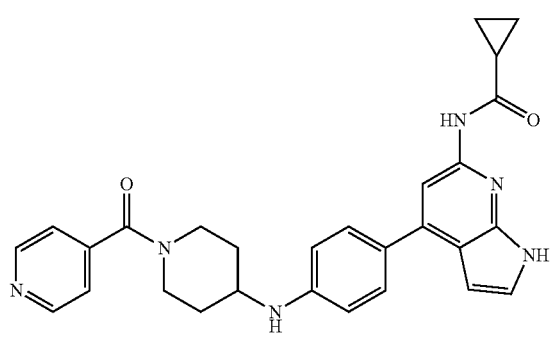 [SMILES: O=C(Nc1cc(-c2ccc(NC3CCN(C(=O)c4ccncc4)CC3)cc2)c2cc[nH]c2n1)C1CC1]

MS(ESI+) m/z 481 (M+H)+

Example 508: Synthesis of N-(4-(4-((1-(3,5-difluorobenzoyl)piperidin-4-yl)amino)phenyl)-1H-pyrrolo[2,3-b]pyridin-6-yl)cyclopropanecarboxamide

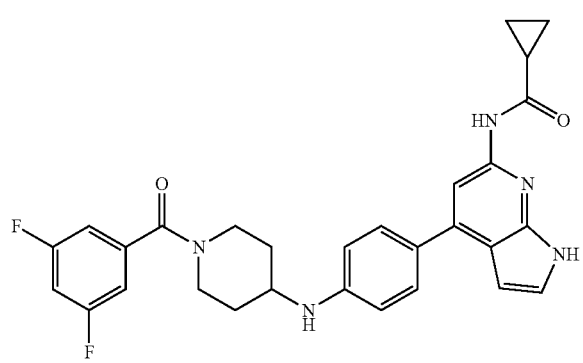 [SMILES: O=C(Nc1cc(-c2ccc(NC3CCN(C(=O)c4cc(F)cc(F)c4)CC3)cc2)c2cc[nH]c2n1)C1CC1]

$^1$H NMR (400 MHz, DMSO-d$_6$) δ 11.40 (s, 1H), 10.52 (s, 1H), 7.94 (d, J=7.9 Hz, 1H), 7.56-7.30 (m, 4H), 7.17 (dt, J=5.8, 2.2 Hz, 2H), 6.82-6.70 (m, 2H), 6.53 (dd, J=3.5, 1.9 Hz, 1H), 5.94 (d, J=7.7 Hz, 1H), 4.32 (d, J=13.3 Hz, 1H), 3.69-3.49 (m, 3H), 3.16 (d, J=46.7 Hz, 3H), 2.03 (s, 2H), 1.91 (s, 1H), 0.82-0.73 (m, 4H).

MS(ESI+) m/z 516 (M+H)+

Example 509: Synthesis of N-(4-(4-((1-(2-fluoroisonicotinoyl)piperidin-4-yl)amino)phenyl)-1H-pyrrolo[2,3-b]pyridin-6-yl)cyclopropanecarboxamide

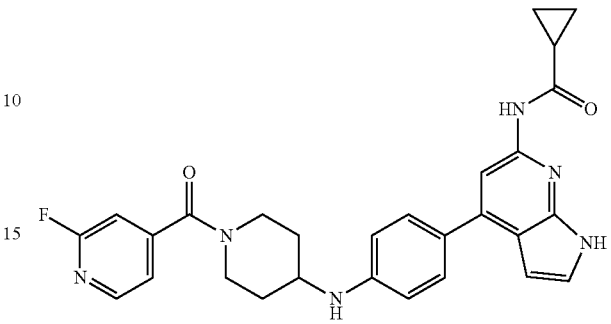

$^1$H NMR (400 MHz, DMSO-d$_6$) δ 11.40 (s, 1H), 10.52 (s, 1H), 8.35 (d, J=5.0 Hz, 1H), 7.93 (s, 1H), 7.53-7.45 (m, 2H), 7.37 (dt, J=4.9, 1.8 Hz, 1H), 7.33 (dd, J=3.5, 2.5 Hz, 1H), 7.26 (t, J=1.5 Hz, 1H), 6.80-6.73 (m, 2H), 6.53 (dd, J=3.5, 1.9 Hz, 1H), 5.96 (d, J=7.8 Hz, 1H), 4.33 (d, J=13.2 Hz, 1H), 3.63 (s, 1H), 3.47 (d, J=13.9 Hz, 1H), 3.22 (t, J=12.0 Hz, 1H), 3.13 (t, J=11.5 Hz, 1H), 2.06 (d, J=15.0 Hz, 2H), 1.93 (s, 1H), 1.50-1.31 (m, 2H), 0.79 (m, 4H).

MS(ESI+) m/z 499 (M+H)+

Example 510: Synthesis of N-(4-(4-((1-(3,5-difluorobenzoyl)azetidin-3-yl)amino)phenyl)-1H-pyrrolo[2,3-b]pyridin-6-yl)cyclopropanecarboxamide

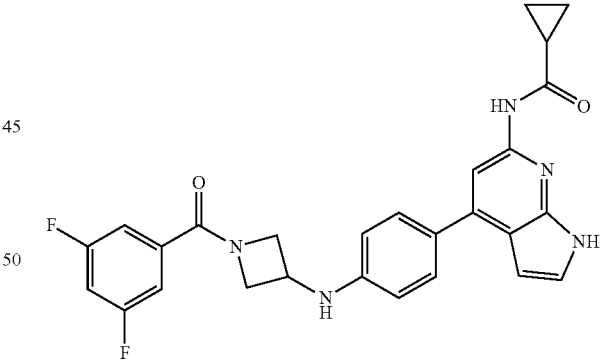

$^1$H NMR (400 MHz, DMSO-d$_6$) δ 11.42 (s, 1H), 10.54 (s, 1H), 7.94 (s, 1H), 7.57-7.49 (m, 4H), 7.46 (tt, J=9.2, 2.4 Hz, 2H), 7.34 (dt, J=6.2, 2.1 Hz, 3H), 6.68 (dd, J=11.8, 7.5 Hz, 3H), 6.53 (dd, J=3.5, 1.9 Hz, 1H), 4.72 (t, J=7.9 Hz, 1H), 4.46 (t, J=8.8 Hz, 1H), 4.37-4.27 (m, 1H), 4.13 (dd, J=8.6, 4.9 Hz, 1H), 3.93 (dd, J=10.4, 5.0 Hz, 1H), 2.03 (s, 1H), 0.82-0.75 (m, 4H).

MS(ESI+) m/z 488 (M+H)+

Example 511: Synthesis of 4-((4-(6-(cyclopropanecarboxamido)-1H-pyrrolo[2,3-b]pyridin-4-yl)phenyl)amino)-N-(2,4-difluorophenyl)piperidine-1-carboxamide

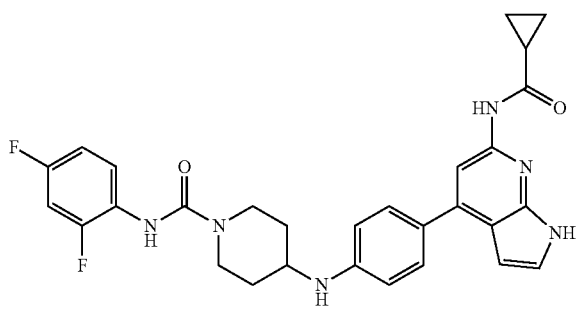 [SMILES: O=C(Nc1cc(-c2ccc(NC3CCN(C(=O)Nc4ccc(F)cc4F)CC3)cc2)c2cc[nH]c2n1)C1CC1]

¹H NMR (400 MHz, DMSO-d₆) δ 11.40 (s, 1H), 10.53 (s, 1H), 8.94 (d, J=2.2 Hz, 1H), 8.34 (s, 1H), 8.10 (td, J=9.2, 6.1 Hz, 1H), 7.94 (d, J=4.3 Hz, 1H), 7.50 (d, J=8.6 Hz, 2H), 7.35-7.30 (m, 1H), 7.24 (ddd, J=10.7, 9.1, 2.9 Hz, 1H), 7.08-6.93 (m, 1H), 6.76 (d, J=8.7 Hz, 2H), 6.55 (dd, J=3.5, 1.9 Hz, 1H), 5.96 (d, J=8.1 Hz, 1H), 4.03 (d, J=13.4 Hz, 2H), 3.55 (d, J=9.8 Hz, 1H), 3.03 (t, J=11.7 Hz, 2H), 2.11-1.92 (m, 3H), 1.41-1.31 (m, 2H), 0.85-0.71 (m, 4H).

MS(ESI+) m/z 531 (M+H)⁺

Example 512: Synthesis of 4-((4-(6-(cyclopropanecarboxamido)-1H-pyrrolo[2,3-b]pyridin-4-yl)phenyl)amino)-N-(2,2,2-trifluoroethyl)piperidine-1-carboxamide

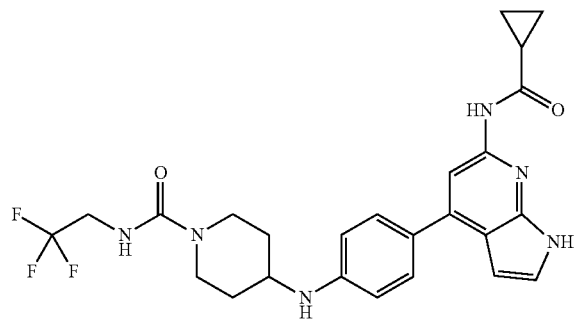 [SMILES: O=C(Nc1cc(-c2ccc(NC3CCN(C(=O)NCC(F)(F)F)CC3)cc2)c2cc[nH]c2n1)C1CC1]

¹H NMR (400 MHz, DMSO-d₆) δ 11.39 (s, 1H), 10.52 (s, 1H), 7.93 (s, 1H), 7.49 (d, J=8.6 Hz, 2H), 7.33 (dd, J=3.5, 2.5 Hz, 1H), 7.16 (t, J=6.2 Hz, 1H), 6.74 (d, J=8.5 Hz, 2H), 6.54 (dd, J=3.5, 1.9 Hz, 1H), 5.92 (d, J=8.1 Hz, 1H), 3.93 (d, J=13.4 Hz, 2H), 3.84 (dtd, J=16.1, 9.7, 6.5 Hz, 3H), 3.51 (s, 1H), 2.94 (t, J=12.4 Hz, 2H), 2.05 (d, J=17.6 Hz, 1H), 1.92 (d, J=12.2 Hz, 2H), 0.84-0.76 (m, 4H).

MS(ESI+) m/z 501 (M+H)⁺

Example 513: Synthesis of 3-((4-(6-(cyclopropanecarboxamido)-1H-pyrrolo[2,3-b]pyridin-4-yl)phenyl)amino)-N-(2,4-difluorophenyl)azetidine-1-carboxamide ¹H NMR (400 MHz, DMSO-d₆) δ 11.42 (s, 1H), 10.54 (s, 1H), 8.27 (s, 1H), 7.95 (s, 1H), 7.53 (dq, J=8.9, 3.1 Hz, 3H), 7.34 (dd, J=3.5, 2.5 Hz, 1H), 7.26 (ddd, J=10.8, 9.0, 2.9 Hz, 1H), 7.07-6.97 (m, 1H), 6.69 (d, J=8.8 Hz, 3H), 6.54 (dd, J=3.5, 1.9 Hz, 1H), 4.32 (m, 3H), 3.79 (dd, J=8.2, 4.1 Hz, 2H), 2.03 (s, 1H), 0.84-0.76 (m, 4H).

MS(ESI+) m/z 503 (M+H)⁺

Example 514: Synthesis of 3-((4-(6-(cyclopropanecarboxamido)-1H-pyrrolo[2,3-b]pyridin-4-yl)phenyl)amino)-N-(2,2,2-trifluoroethyl)azetidine-1-carboxamide

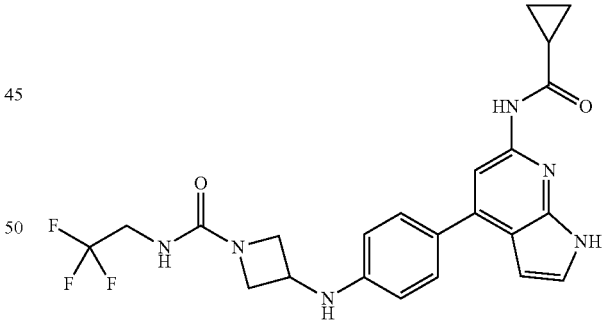

¹H NMR (400 MHz, DMSO-d₆) δ 11.42 (s, 1H), 10.54 (s, 1H), 7.95 (d, J=2.9 Hz, 2H), 7.52 (d, J=8.6 Hz, 2H), 7.34 (dd, J=3.5, 2.5 Hz, 1H), 7.08 (t, J=6.3 Hz, 1H), 6.67 (d, J=8.7 Hz, 2H), 6.53 (dd, J=3.5, 1.9 Hz, 1H), 4.26-4.22 (m, 2H), 3.86-3.72 (m, 3H), 3.71-3.65 (m, 2H), 2.03 (s, 1H), 0.87-076 (m, 4H).

MS(ESI+) m/z 473 (M+H)⁺

Example 515: Synthesis of N-(4-(4-((1-(2-cyano-acetyl)azetidin-3-yl)amino)phenyl)-1H-pyrrolo[2,3-b]pyridin-6-yl)cyclopropanecarboxamide

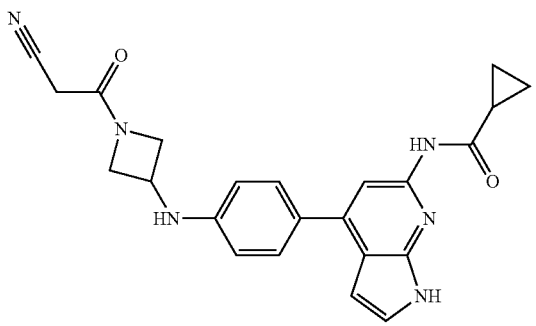 [SMILES: N#CCC(=O)N1CC(Nc2ccc(-c3cc(NC(=O)C4CC4)nc4[nH]ccc34)cc2)C1]

MS(ESI+) m/z 415 (M+H)+

Example 516: Synthesis of N-(4-(4-((1-(2-cyano-acetyl)piperidin-4-yl)amino)phenyl)-1H-pyrrolo[2,3-b]pyridin-6-yl)cyclopropanecarboxamide

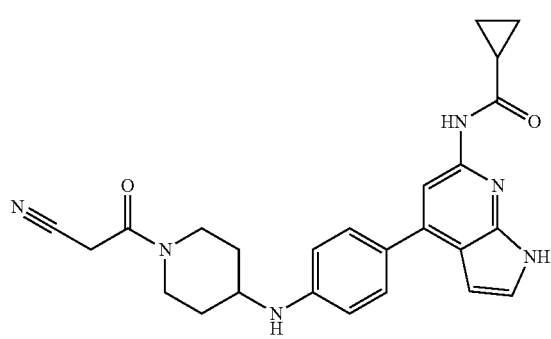 [SMILES: N#CCC(=O)N1CCC(Nc2ccc(-c3cc(NC(=O)C4CC4)nc4[nH]ccc34)cc2)CC1]

MS(ESI+) m/z 443 (M+H)+

Example 517: Synthesis of N-(4-(4-((1-(3,3,3-trifluoropropanoyl)azetidin-3-yl)amino)phenyl)-1H-pyrrolo[2,3-b]pyridin-6-yl)cyclopropanecarboxamide

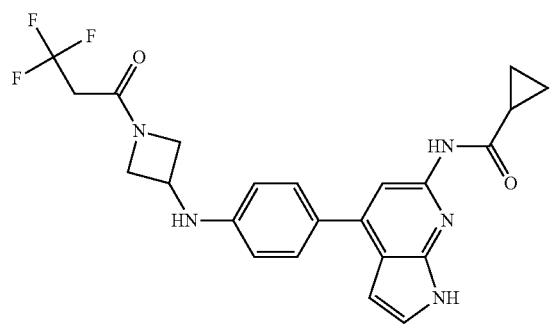 [SMILES: O=C(Nc1cc(-c2ccc(NC3CN(C(=O)CC(F)(F)F)C3)cc2)c2cc[nH]c2n1)C1CC1]

$^1$H NMR (400 MHz, DMSO-$d_6$) δ 11.42 (s, 1H), 10.54 (s, 1H), 7.95 (s, 1H), 7.53 (d, J=8.4 Hz, 2H), 7.34 (t, J=3.0 Hz, 1H), 6.67 (d, J=8.3 Hz, 3H), 6.53 (dd, J=3.5, 1.9 Hz, 1H), 4.55 (t, J=7.7 Hz, 1H), 4.29 (d, J=6.2 Hz, 2H), 4.03-3.90 (m, 1H), 3.75 (d, J=5.3 Hz, 1H), 3.40 (m, 2H), 2.03 (s, 1H), 0.84-0.76 (m, 4H).

MS(ESI+) m/z 458 (M+H)+

Example 518: Synthesis of N-(4-(4-((1-(3,3,3-trifluoropropanoyl)piperidin-4-yl)amino)phenyl)-1H-pyrrolo[2,3-b]pyridin-6-yl)cyclopropanecarboxamide

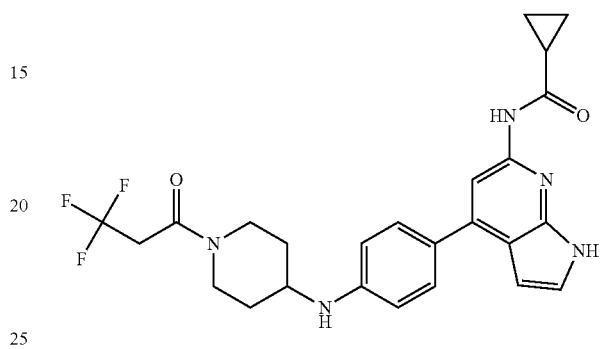

$^1$H NMR (400 MHz, DMSO-$d_6$) δ 11.39 (s, 1H), 10.52 (s, 1H), 7.94 (s, 1H), 7.50 (d, J=8.6 Hz, 2H), 7.33 (dd, J=3.5, 2.5 Hz, 1H), 6.76 (d, J=8.6 Hz, 2H), 6.54 (dd, J=3.5, 1.9 Hz, 1H), 5.95 (d, J=8.0 Hz, 1H), 4.25 (d, J=13.2 Hz, 1H), 3.82 (d, J=13.8 Hz, 1H), 3.76-3.53 (m, 3H), 3.21 (t, J=11.9 Hz, 1H), 2.90 (t, J=11.3 Hz, 1H), 2.05-1.90 (m, 3H), 1.44-1.22 (m, 2H), 0.85-0.76 (m, 4H).

MS(ESI+) m/z 486 (M+H)+

Example 519: Synthesis of N-(4-(4-(2-cyanoacetyl)phenyl)-1H-pyrrolo[2,3-b]pyridin-6-yl)cyclopropanecarboxamide

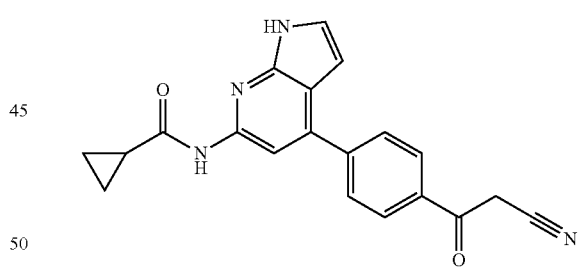

1.0 g (2.1 mmol) of N-(4-(4,4,5,5-tetramethyl-1,3,2-dioxaborolan-2-yl)-1-tosyl-1H-pyrrolo[2,3-b]pyridine-6-yl) cyclopropanecarboxamide prepared from the reaction formula 3 above was dissolved in DMF/H$_2$O=2:1 solution, and then 0.6 g (2.5 mmol) of 3-(4-bromophenyl)-3-oxopropanenitrile, 0.2 g (0.2 mmol) of Pd(PPh$_3$)$_4$ and 0.15 mL of 2M K$_2$CO$_3$ aqueous solution were inserted thereinto and stirred at 100-110° C. for 2 hours. Once the reaction was completed, the said mixture was cooled down at room temperature, then water was added thereto, and then an extraction using ethyl acetate was performed. After that, a solution extracted therefrom was dried by means of magnesium sulfate anhydrous and concentrated under reduced pressure, from which a residue was accordingly obtained. The residue was separated via NH-silica gel column chromatography (n-hexane/ ethyl acetate=5:1), and N-(4-(4-(2-cyanoacetyl)phenyl)-1-tosyl-1H-pyrrolo[2,3-b]pyridine-6-yl)cyclopropanecarboxamide was synthesized. A synthesized material was dissolved in MeOH/THF (1:1) solution, and then 2N sodium hydroxide aqueous solution was added thereto and stirred at 30-40° C. for 4 hours. Once the reaction was completed, the said mixture was cooled down to room temperature, and saturated ammonium chloride aqueous solution was added thereto while being stirred. A produced solid was filtered out, and finally a product, i.e., N-(4-(4-(2-cyanoacetyl)phenyl)-1H-pyrrolo[2,3-b]pyridin-6-yl)cyclopropanecarboxamide was accordingly obtained.

MS(ESI+) m/z 345 (M+H)$^+$

Examples 520 to 598

Hereinafter, in Examples 520 to 598, a corresponding compound was synthesized by means of the same method as shown in Example 519 or by means of an appropriate reactant under the consideration of the reaction formula 1 as well as a structure of the compound to be prepared.

Example 520: Synthesis of N-(4-(4-(1,1-dioxidothiomorpholine-4-carbonyl)phenyl)-1H-pyrrolo[2,3-b]pyridin-6-yl)cyclopropanecarboxamide

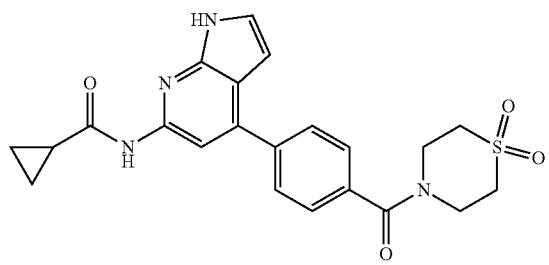 [SMILES: O=C(Nc1cc(-c2ccc(C(=O)N3CCS(=O)(=O)CC3)cc2)c2cc[nH]c2n1)C1CC1]

MS(ESI+) m/z 439 (M+H)$^+$

Example 521: Synthesis of N-(4-(4-(thiomorpholine-4-carbonyl)phenyl)-1H-pyrrolo[2,3-b]pyridin-6-yl)cyclopropanecarboxamide

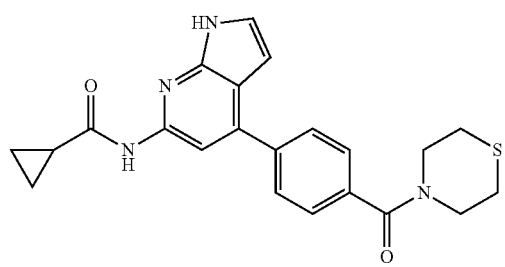 [SMILES: O=C(Nc1cc(-c2ccc(C(=O)N3CCSCC3)cc2)c2cc[nH]c2n1)C1CC1]

$^1$H NMR (400 MHz, DMSO-d$_6$) δ 11.59 (s, 1H), 10.66 (s, 1H), 8.17-8.01 (m, 1H), 7.78 (d, J=7.7 Hz, 2H), 7.57 (d, J=7.7 Hz, 2H), 7.43 (s, 1H), 6.56 (s, 1H), 3.76 (d, J=100.0 Hz, 6H), 2.76-2.61 (m, 6H), 2.07 (d, J=13.0 Hz, 1H), 0.80 (d, J=12.3 Hz, 4H).

MS(ESI+) m/z 407 (M+H)$^+$

Example 522: Synthesis of N-(4-(2-methyl-4-(morpholine-4-carbonyl)phenyl)-1H-pyrrolo[2,3-b]pyridin-6-yl)cyclopropanecarboxamide

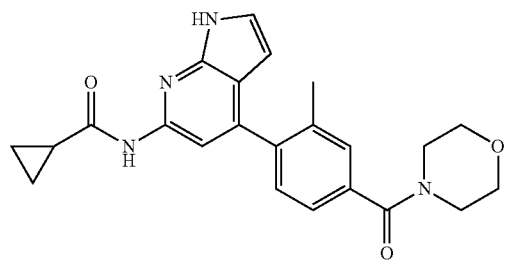 [SMILES: Cc1cc(C(=O)N2CCOCC2)ccc1-c1cc(NC(=O)C2CC2)nc2[nH]ccc12]

MS(ESI+) m/z 405 (M+H)$^+$

Example 523: Synthesis of N-(cyanomethyl)-4-(6-(cyclopropanecarboxamido)-1H-pyrrolo[2,3-b]pyridin-4-yl)benzamide

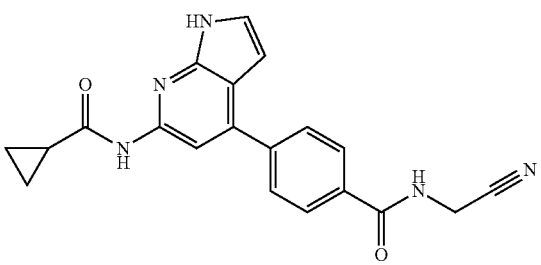 [SMILES: N#CCNC(=O)c1ccc(-c2cc(NC(=O)C3CC3)nc3[nH]ccc23)cc1]

$^1$H NMR (400 MHz, DMSO-d$_6$) δ 11.61 (s, 1H), 10.67 (s, 1H), 9.32 (s, 1H), 8.09 (s, 1H), 8.04 (d, J=8.0 Hz, 2H), 7.84 (d, J=8.0 Hz, 2H), 7.44 (d, J=3.3 Hz, 1H), 6.55 (d, J=3.4 Hz, 1H), 4.35 (d, J=5.2 Hz, 2H), 2.07 (d, J=12.0 Hz, 1H), 0.87-0.75 (m, 4H).

MS(ESI+) m/z 360 (M+H)$^+$

Example 524: Synthesis of 4-(6-(cyclopropanecarboxamido)-1H-pyrrolo[2,3-b]pyridin-4-yl)-N-(2,2,2-trifluoroethyl)benzamide

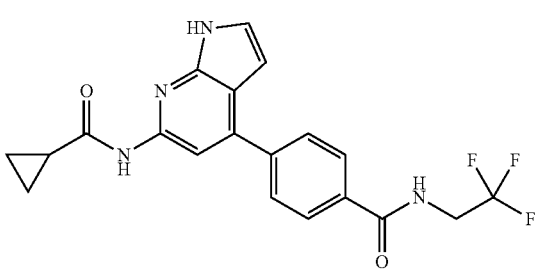 [SMILES: O=C(NCC(F)(F)F)c1ccc(-c2cc(NC(=O)C3CC3)nc3[nH]ccc23)cc1]

$^1$H NMR (400 MHz, DMSO-d$_6$) δ 11.52 (s, 1H), 10.60 (s, 1H), 8.02 (s, 1H), 7.65 (d, J=8.0 Hz, 2H), 7.42 (dd, J=5.4, 17.0 Hz, 3H), 6.53 (s, 1H), 3.54-3.47 (m, 2H), 2.02 (dd, J=7.9, 15.2 Hz, 1H), 0.84-0.77 (m, 4H).

MS(ESI+) m/z 403 (M+H)$^+$

Example 525: Synthesis of 4-(6-(cyclopropanecarboxamido)-1H-pyrrolo[2,3-b]pyridin-4-yl)-3-methyl-N-(2,2,2-trifluoroethyl)benzamide

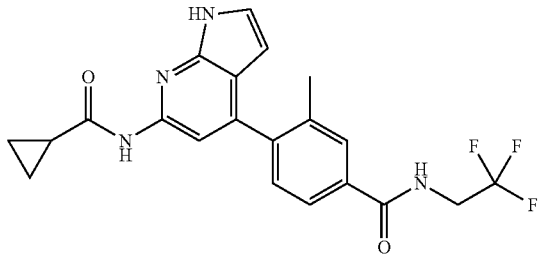 [SMILES: Cc1cc(C(=O)NCC(F)(F)F)ccc1-c1cc(NC(=O)C2CC2)nc2[nH]ccc12]

MS(ESI+) m/z 417 (M+H)+

Example 526: Synthesis of N-(cyanomethyl)-4-(6-(cyclopropanecarboxamido)-1H-pyrrolo[2,3-b]pyridin-4-yl)-3-methylbenzamide

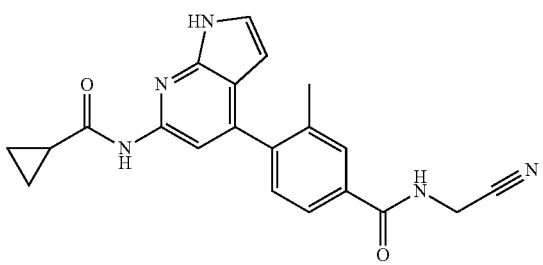 [SMILES: Cc1cc(C(=O)NCC#N)ccc1-c1cc(NC(=O)C2CC2)nc2[nH]ccc12]

MS(ESI+) m/z 374 (M+H)+

Example 527: Synthesis of N-(cyanomethyl)-4-(6-(cyclopropanecarboxamido)-1H-pyrrolo[2,3-b]pyridin-4-yl)-N,3-dimethylbenzamide

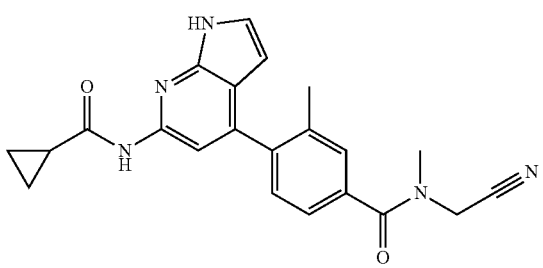 [SMILES: Cc1cc(C(=O)N(C)CC#N)ccc1-c1cc(NC(=O)C2CC2)nc2[nH]ccc12]

MS(ESI+) m/z 388 (M+H)+

Example 528: Synthesis of N-(cyanomethyl)-4-(6-(cyclopropanecarboxamido)-1H-pyrrolo[2,3-b]pyridin-4-yl)-2-fluorobenzamide

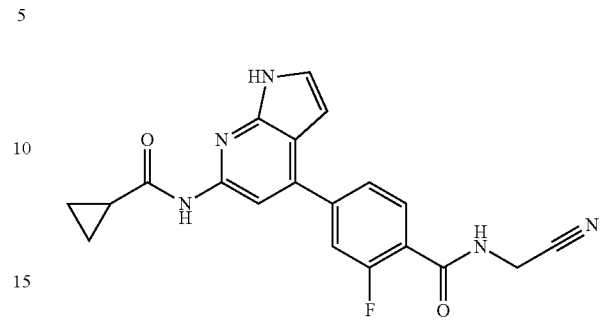

MS(ESI+) m/z 378 (M+H)+

Example 529: Synthesis of N-(cyanomethyl)-4-(6-(cyclopropanecarboxamido)-1H-pyrrolo[2,3-b]pyridin-4-yl)-2,6-difluorobenzamide

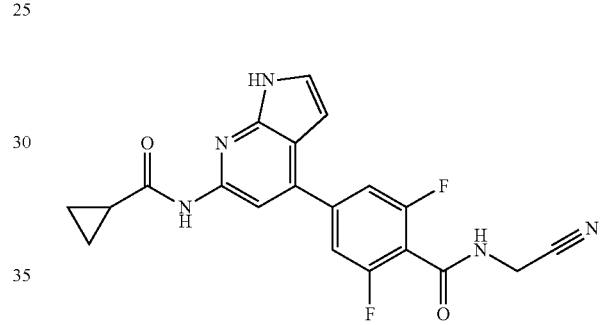

MS(ESI+) m/z 396 (M+H)+

Example 530: Synthesis of N-(cyanomethyl)-4-(6-(cyclopropanecarboxamido)-1H-pyrrolo[2,3-b]pyridin-4-yl)cyclohex-3-ene-1-carboxamide

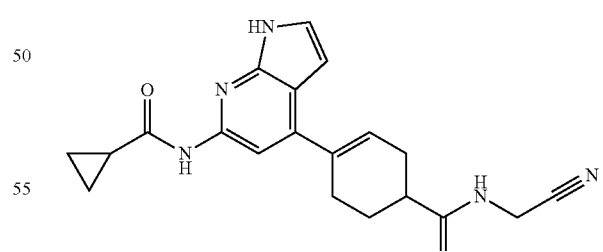

$^1$H NMR (400 MHz, DMSO-$d_6$) δ 11.37 (s, 1H), 10.49 (s, 1H), 8.62 (t, J=5.6 Hz, 1H), 7.83 (s, 1H), 7.31 (dd, J=3.5, 2.5 Hz, 1H), 6.50 (dd, J=3.6, 1.8 Hz, 1H), 6.31 (s, 1H), 4.16 (d, J=5.6 Hz, 2H), 2.40 (s, 2H), 2.00 (d, J=12.1 Hz, 2H), 1.72 (ddt, J=17.9, 12.1, 6.3 Hz, 1H), 0.79 (ddt, J=13.1, 5.1, 3.0 Hz, 4H).

MS(ESI+) m/z 364 (M+H)+

Example 531: Synthesis of 4-(6-(cyclopropanecarboxamido)-1H-pyrrolo[2,3-b]pyridin-4-yl)-N-(2,2,2-trifluoroethyl)cyclohex-3-ene-1-carboxamide

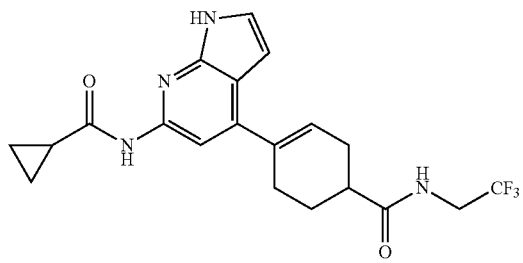 [SMILES: O=C(NCC(F)(F)F)C1CC=C(c2cc(NC(=O)C3CC3)nc3[nH]ccc23)CC1]

$^1$H NMR (400 MHz, DMSO-d$_6$) δ 11.37 (s, 1H), 10.49 (s, 1H), 8.55 (t, J=6.4 Hz, 1H), 7.83 (s, 1H), 7.31 (dd, J=3.5, 2.4 Hz, 1H), 6.49 (dd, J=3.6, 1.9 Hz, 1H), 6.32 (d, J=4.0 Hz, 1H), 3.94 (ddt, J=11.6, 9.1, 4.9 Hz, 2H), 2.62-2.54 (m, 2H), 2.39 (d, J=6.7 Hz, 2H), 2.05-1.95 (m, 3H), 1.73 (ddt, J=17.9, 12.1, 6.3 Hz, 1H), 0.87-0.72 (m, 4H).
MS(ESI+) m/z 407 (M+H)$^+$

Example 532: Synthesis of N-(2-cyanoethyl)-4-(6-(cyclopropanecarboxamido)-1H-pyrrolo[2,3-b]pyridin-4-yl)cyclohex-3-ene-1-carboxamide

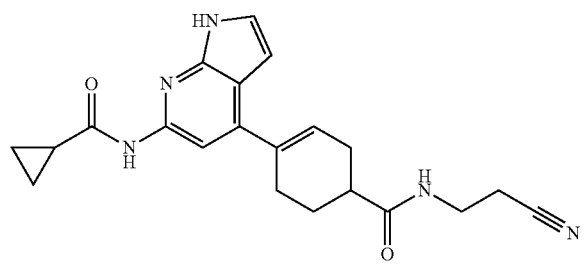 [SMILES: N#CCCNC(=O)C1CC=C(c2cc(NC(=O)C3CC3)nc3[nH]ccc23)CC1]

$^1$H NMR (400 MHz, DMSO-d$_6$) δ 11.37 (s, 1H), 10.49 (s, 1H), 8.27 (t, J=5.8 Hz, 1H), 7.83 (s, 1H), 7.38-7.27 (m, 1H), 6.50 (dd, J=3.6, 1.9 Hz, 1H), 6.31 (s, 1H), 2.67 (t, J=6.5 Hz, 2H), 2.56-2.43 (m, 3H) 2.38 (d, J=6.0 Hz, 2H), 2.06-1.93 (m, 3H), 1.79-1.67 (m, 1H), 0.85 (t, J=6.4 Hz, 1H), 0.79 (ddt, J=10.1, 5.0, 2.6 Hz, 4H).
MS(ESI+) m/z 378 (M+H)$^+$

Example 533: Synthesis of N-(4-(4-((N-methylsulfamoyl)methyl)phenyl)-1H-pyrrolo[2,3-b]pyridin-6-yl)cyclopropanecarboxamide

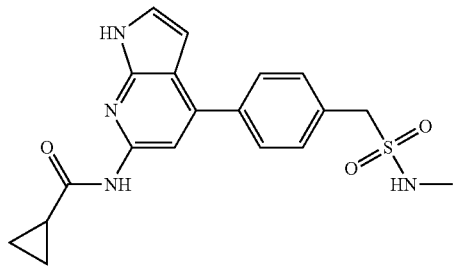 [SMILES: CNS(=O)(=O)Cc1ccc(-c2cc(NC(=O)C3CC3)nc3[nH]ccc23)cc1]

$^1$H NMR (400 MHz, DMSO-d$_6$) δ 11.57 (s, 1H), 10.66 (s, 1H), 8.05 (d, J=4.7 Hz, 1H), 7.73 (d, J=7.9 Hz, 2H), 7.54 (d, J=7.9 Hz, 2H), 7.42 (t, J=3.1 Hz, 1H), 7.04-6.94 (m, 1H), 6.54 (dd, J=3.7, 1.8 Hz, 1H), 4.42 (s, 2H), 2.62 (d, J=4.7 Hz, 3H), 2.07-2.00 (m, 1H), 0.85-0.72 (m, 4H).
MS(ESI+) m/z 385 (M+H)$^+$

Example 534: Synthesis of N-(4-(4-((morpholinosulfonyl)methyl)phenyl)-1H-pyrrolo[2,3-b]pyridin-6-yl)cyclopropanecarboxamide

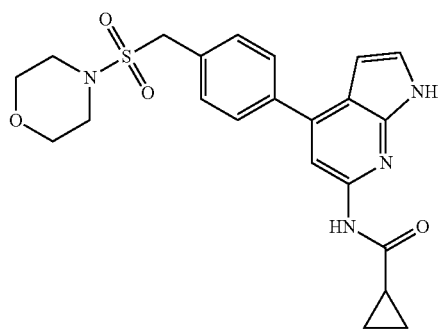 [SMILES: O=C(Nc1cc(-c2ccc(CS(=O)(=O)N3CCOCC3)cc2)c2cc[nH]c2n1)C1CC1]

$^1$H NMR (400 MHz, DMSO-d$_6$) δ 11.58 (s, 1H), 10.66 (s, 1H), 8.06 (s, 1H), 7.75 (d, J=7.8 Hz, 2H), 7.59 (d, J=7.8 Hz, 2H), 7.43 (s, 1H), 6.54 (s, 1H), 4.54 (s, 2H), 3.61 (s, 4H), 3.15 (d, J=5.8 Hz, 4H), 2.05 (s, 1H), 0.86-0.75 (m, 4H).
MS(ESI+) m/z 441 (M+H)$^+$

Example 535: Synthesis of N-(4-(4-(2-(1,1-dioxidothiomorpholino)-2-oxoethyl)phenyl)-1H-pyrrolo[2,3-b]pyridin-6-yl)cyclopropanecarboxamide

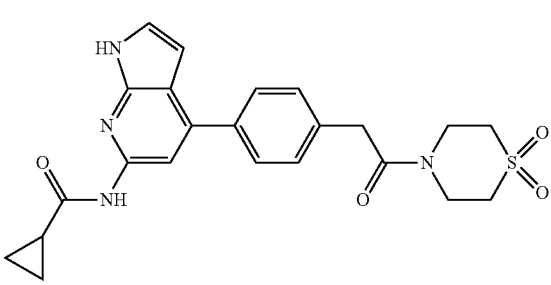 [SMILES: O=C(Nc1cc(-c2ccc(CC(=O)N3CCS(=O)(=O)CC3)cc2)c2cc[nH]c2n1)C1CC1]

$^1$H NMR (400 MHz, DMSO-d$_6$) δ 11.53 (s, 1H), 10.62 (s, 1H), 8.03 (s, 1H), 7.67 (d, J=7.8 Hz, 2H), 7.56 (s, 1H), 7.41 (d, J=6.9 Hz, 2H), 6.54 (s, 1H), 3.94-3.88 (m, 4H), 3.16 (d, J=21.7 Hz, 4H), 2.05 (s, 1H), 0.89-0.76 (m, 4H).
MS(ESI+) m/z 453 (M+H)$^+$

Example 536: Synthesis of N-(4-(4-(2-morpholino-2-oxoethyl)phenyl)-1H-pyrrolo[2,3-b]pyridin-6-yl)cyclopropanecarboxamide

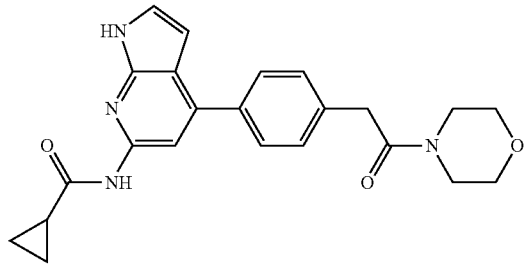 [SMILES: O=C(Nc1cc(-c2ccc(CC(=O)N3CCOCC3)cc2)c2cc[nH]c2n1)C1CC1]

¹H NMR (400 MHz, DMSO-d$_6$) δ 11.53 (s, 1H), 10.62 (s, 1H), 8.03 (s, 1H), 7.67 (d, J=7.7 Hz, 2H), 7.39 (d, J=7.5 Hz, 2H), 6.54 (s, 1H), 3.81 (s, 2H), 3.53 (s, 6H), 3.48 (s, 2H), 2.05 (s, 1H), 0.88-0.77 (m, 4H).
MS(ESI+) m/z 405 (M+H)$^+$

Example 537: Synthesis of N-(4-(4-(2-oxo-2-((2,2,2-trifluoroethyl)amino)ethyl)phenyl)-1H-pyrrolo[2,3-b]pyridin-6-yl)cyclopropanecarboxamide

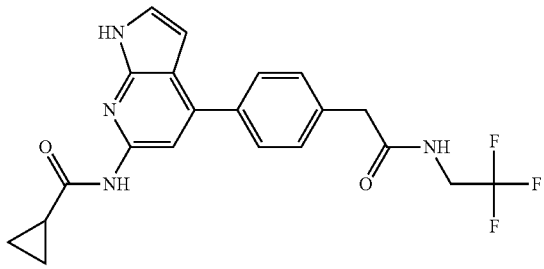 [SMILES: O=C(Cc1ccc(-c2cc(NC(=O)C3CC3)nc3[nH]ccc23)cc1)NCC(F)(F)F]

¹H NMR (400 MHz, DMSO-d$_6$) δ 11.55 (s, 1H), 10.63 (s, 1H), 8.83 (s, 1H), 8.02 (s, 1H), 7.66 (d, J=7.7 Hz, 2H), 7.59-7.54 (m, 1H), 7.42 (t, J=7.1 Hz, 2H), 6.53 (s, 1H), 4.00-3.91 (m, 2H), 3.61 (s, 2H), 2.05 (s, 1H), 0.87-0.76 (m, 4H).
MS(ESI+) m/z 417 (M+H)$^+$

Example 538: Synthesis of N-(4-(4-(2-((1,1-dioxidotetrahydrothiophen-3-yl)amino)-2-oxoethyl)phenyl)-1H-pyrrolo[2,3-b]pyridin-6-yl)cyclopropanecarboxamide

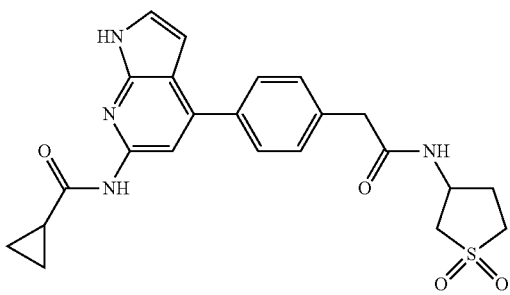 [SMILES: O=C(Cc1ccc(-c2cc(NC(=O)C3CC3)nc3[nH]ccc23)cc1)NC1CCS(=O)(=O)C1]

MS(ESI+) m/z 453 (M+H)$^+$

Example 539: Synthesis of N-(4-(4-(2-(methylamino)-2-oxoethyl)phenyl)-1H-pyrrolo[2,3-b]pyridin-6-yl)cyclopropanecarboxamide

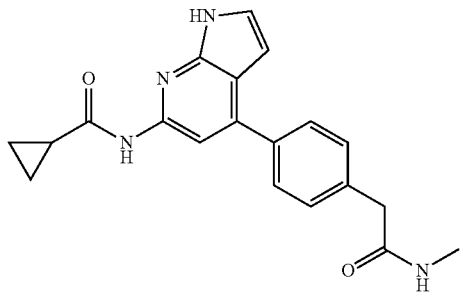 [SMILES: CNC(=O)Cc1ccc(-c2cc(NC(=O)C3CC3)nc3[nH]ccc23)cc1]

¹H NMR (400 MHz, DMSO-d$_6$) δ 11.54 (s, 1H), 10.63 (s, 1H), 8.03 (d, J=8.0 Hz, 2H), 7.69-7.60 (m, 2H), 7.47-7.36 (m, 3H), 6.53 (dd, J=3.5, 1.9 Hz, 1H), 3.47 (s, 3H), 2.60 (d, J=4.6 Hz, 2H), 2.08-1.98 (m, 1H), 0.83-0.73 (m, 4H).
MS(ESI+) m/z 349 (M+H)$^+$

Example 540: Synthesis of N-(4-(4-(2-(dimethylamino)-2-oxoethyl)phenyl)-1H-pyrrolo[2,3-b]pyridin-6-yl)cyclopropanecarboxamide

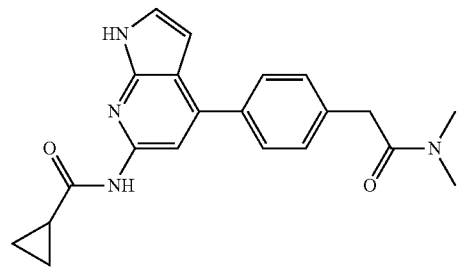 [SMILES: CN(C)C(=O)Cc1ccc(-c2cc(NC(=O)C3CC3)nc3[nH]ccc23)cc1]

¹H NMR (400 MHz, DMSO-d$_6$) δ 11.54 (s, 1H), 10.63 (s, 1H), 8.02 (s, 1H), 7.71-7.62 (m, 2H), 7.43-7.35 (m, 3H), 6.54 (dd, J=3.5, 1.8 Hz, 1H), 3.77 (s, 2H), 3.04 (s, 3H), 2.85 (s, 3H), 2.03 (d, J=8.1 Hz, 1H), 0.83-0.76 (m, 4H).
MS(ESI+) m/z 363 (M+H)$^+$

Example 541: Synthesis of N-(4-(4-(2-(ethylamino)-2-oxoethyl)phenyl)-1H-pyrrolo[2,3-b]pyridin-6-yl)cyclopropanecarboxamide

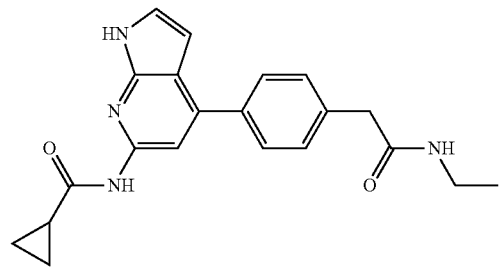 [SMILES: CCNC(=O)Cc1ccc(-c2cc(NC(=O)C3CC3)nc3[nH]ccc23)cc1]

¹H NMR (400 MHz, DMSO-d₆) δ 11.54 (s, 1H), 10.63 (s, 1H), 8.11 (t, J=5.2 Hz, 1H), 8.02 (s, 1H), 7.72-7.59 (m, 2H), 7.49-7.31 (m, 4H), 6.53 (dd, J=3.5, 1.9 Hz, 1H), 3.45 (s, 2H), 3.08 (qd, J=7.2, 5.4 Hz, 2H), 2.09-1.98 (m, 1H), 1.03 (t, J=7.2 Hz, 3H), 0.85-0.72 (m, 4H).
MS(ESI+) m/z 363 (M+H)⁺

Example 542: Synthesis of N-(4-(4-(2-(4-(methylsulfonyl)piperazin-1-yl)-2-oxoethyl)phenyl)-1H-pyrrolo[2,3-b]pyridin-6-yl)cyclopropanecarboxamide

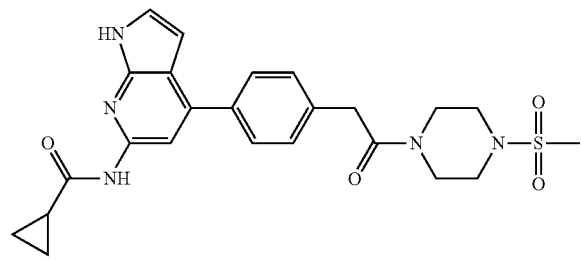 [SMILES: CS(=O)(=O)N1CCN(C(=O)Cc2ccc(-c3cc(NC(=O)C4CC4)nc4[nH]ccc34)cc2)CC1]

¹H NMR (400 MHz, DMSO-d₆) δ 11.55 (s, 1H), 10.64 (s, 1H), 8.03 (s, 1H), 7.67 (d, J=8.1 Hz, 2H), 7.46-7.36 (m, 3H), 6.54 (dd, J=3.5, 1.9 Hz, 1H), 3.84 (s, 2H), 3.66 (s, 4H), 3.09 (d, J=5.3 Hz, 4H), 2.88 (s, 3H), 2.09-1.99 (m, 1H), 0.84-0.73 (m, 4H).
MS(ESI+) m/z 482 (M+H)⁺

Example 543: Synthesis of N-(4-(4-(2-(4-acetylpiperazin-1-yl)-2-oxoethyl)phenyl)-1H-pyrrolo[2,3-b]pyridin-6-yl)cyclopropanecarboxamide

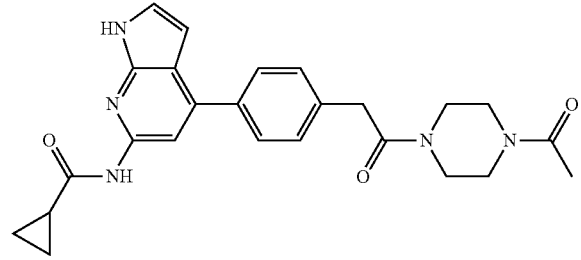 [SMILES: CC(=O)N1CCN(C(=O)Cc2ccc(-c3cc(NC(=O)C4CC4)nc4[nH]ccc34)cc2)CC1]

MS(ESI+) m/z 446 (M+H)⁺

Example 544: Synthesis of N-(4-(4-(2-(isoxazol-3-ylamino)-2-oxoethyl)phenyl)-1H-pyrrolo[2,3-b]pyridin-6-yl)cyclopropanecarboxamide

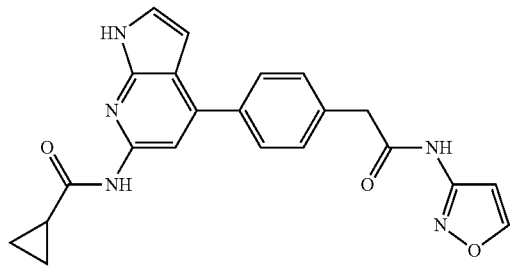 [SMILES: O=C(Cc1ccc(-c2cc(NC(=O)C3CC3)nc3[nH]ccc23)cc1)Nc1ccon1]

¹H NMR (400 MHz, Chloroform-d) δ 8.23 (d, J=1.7 Hz, 1H), 8.01 (s, 1H), 7.70 (d, J=7.8 Hz, 2H), 7.42 (d, J=7.8 Hz, 2H), 7.20 (d, J=3.5 Hz, 1H), 7.01 (s, 1H), 6.58 (s, 1H), 3.75 (s, 2H), 2.19-2.10 (m, 1H), 1.97 (d, J=12.6 Hz, 1H), 0.83-0.80 (m, 4H).
MS(ESI+) m/z 402 (M+H)⁺

Example 545: Synthesis of N-(4-(4-(2-(1,1-dioxidothiomorpholino)-2-oxoethyl)-2-methylphenyl)-1H-pyrrolo[2,3-b]pyridin-6-yl)cyclopropanecarboxamide

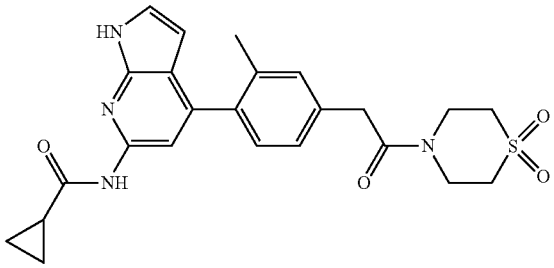 [SMILES: Cc1cc(CC(=O)N2CCS(=O)(=O)CC2)ccc1-c1cc(NC(=O)C2CC2)nc2[nH]ccc12]

MS(ESI+) m/z 467 (M+H)⁺

Example 546: Synthesis of N-(4-(4-(2-(azetidin-1-yl)-2-oxoethyl)phenyl)-1H-pyrrolo[2,3-b]pyridin-6-yl)cyclopropanecarboxamide

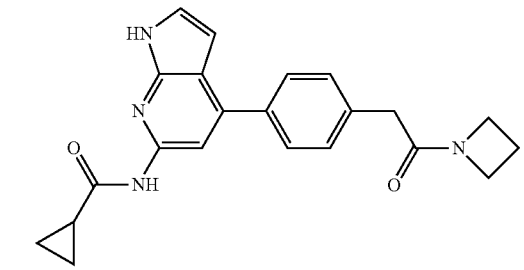 [SMILES: O=C(Nc1cc(-c2ccc(CC(=O)N3CCC3)cc2)c2cc[nH]c2n1)C1CC1]

¹H NMR (400 MHz, DMSO-d₆) δ 11.54 (s, 1H), 10.63 (s, 1H), 8.02 (s, 1H), 7.71-7.62 (m, 2H), 7.42-7.36 (m, 3H), 6.54 (dd, J=3.5, 1.7 Hz, 1H), 4.21 (t, J=7.7 Hz, 2H), 3.84 (dt, J=16.3, 8.0 Hz, 2H), 3.48 (s, 6H), 2.19 (p, J=7.7 Hz, 1H), 2.01 (dd, J=14.7, 7.3 Hz, 3H), 0.85-0.71 (m, 4H).
MS(ESI+) m/z 375 (M+H)⁺

Example 547: Synthesis of N-(4-(4-(2-oxo-2-(pyrrolidin-1-yl)ethyl)phenyl)-1H-pyrrolo[2,3-b]pyridin-6-yl)cyclopropanecarboxamide

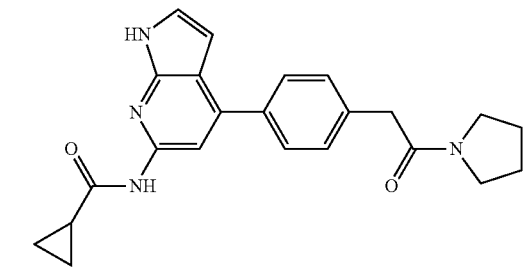 [SMILES: O=C(Nc1cc(-c2ccc(CC(=O)N3CCCC3)cc2)c2cc[nH]c2n1)C1CC1]

¹H NMR (400 MHz, DMSO-d₆) δ 11.54 (s, 1H), 10.63 (s, 1H), 8.02 (s, 1H), 7.70-7.62 (m, 2H), 7.43-7.37 (m, 3H), 6.54 (dd, J=3.5, 1.9 Hz, 1H), 3.70 (s, 2H), 3.51 (t, J=6.8 Hz, 2H), 3.31 (t, J=6.8 Hz, 2H), 2.07-1.97 (m, 1H), 1.89 (p, J=6.8 Hz, 2H), 1.77 (p, J=6.8 Hz, 2H), 0.84-0.74 (m, 4H).
MS(ESI+) m/z 389 (M+H)⁺

Example 548: Synthesis of N-(4-(4-(2-(4-cyanopiperidin-1-yl)-2-oxoethyl)phenyl)-1H-pyrrolo[2,3-b]pyridin-6-yl)cyclopropanecarboxamide

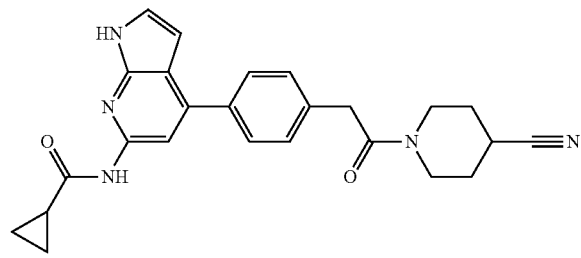 [SMILES: N#CC1CCN(C(=O)Cc2ccc(-c3cc(NC(=O)C4CC4)nc4[nH]ccc34)cc2)CC1]

¹H NMR (400 MHz, DMSO-d₆) δ 11.54 (s, 1H), 10.63 (s, 1H), 8.02 (s, 1H), 7.71-7.63 (m, 2H), 7.44-7.36 (m, 3H), 6.53 (dd, J=3.5, 1.9 Hz, 1H), 3.89-3.78 (m, 3H), 3.08 (s, 1H), 2.07-1.94 (m, 2H), 1.90-1.77 (m, 2H), 1.60 (ddt, J=12.8, 8.9, 4.7 Hz, 2H), 0.83-0.75 (m, 4H).
MS(ESI+) m/z 428 (M+H)⁺

Example 549: Synthesis of N-(4-(4-(2-oxo-2-(4-oxopiperidin-1-yl)ethyl)phenyl)-1H-pyrrolo[2,3-b]pyridin-6-yl)cyclopropanecarboxamide

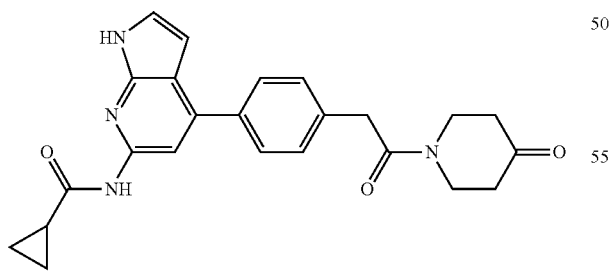

¹H NMR (400 MHz, DMSO-d₆) δ 11.54 (s, 1H), 10.63 (s, 1H), 8.02 (s, 1H), 7.67 (d, J=7.9 Hz, 2H), 7.46-7.37 (m, 3H), 6.54 (dd, J=3.6, 1.9 Hz, 1H), 3.90 (s, 2H), 3.86-3.73 (m, 4H), 2.36 (q, J=5.5, 4.8 Hz, 2H), 2.06-1.96 (m, 2H), 1.15 (d, J=6.6 Hz, 2H), 0.80 (m, 4H).
MS(ESI+) m/z 417 (M+H)⁺

Example 550: Synthesis of N-(4-(4-(2-(4-methylpiperazin-1-yl)-2-oxoethyl)phenyl)-1H-pyrrolo[2,3-b]pyridin-6-yl)cyclopropanecarboxamide

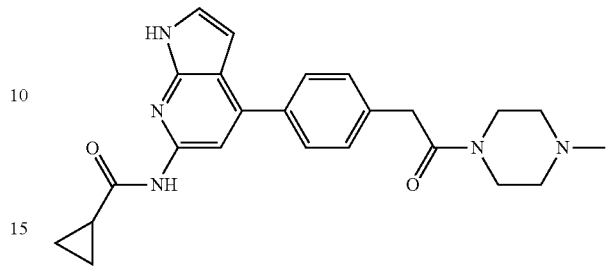

¹H NMR (400 MHz, DMSO-d₆) δ 11.54 (s, 1H), 10.63 (s, 1H), 8.03 (s, 1H), 7.71-7.63 (m, 2H), 7.42-7.36 (m, 3H), 6.53 (dd, J=3.5, 1.8 Hz, 1H), 3.79 (s, 2H), 3.55-3.44 (m, 4H), 2.24 (q, J=4.6 Hz, 4H), 2.15 (s, 3H), 2.08-1.98 (m, 1H), 0.80 (m, 4H).
MS(ESI+) m/z 418 (M+H)⁺

Example 551: Synthesis of N-(4-(4-(2-(4-ethylpiperazin-1-yl)-2-oxoethyl)phenyl)-1H-pyrrolo[2,3-b]pyridin-6-yl)cyclopropanecarboxamide

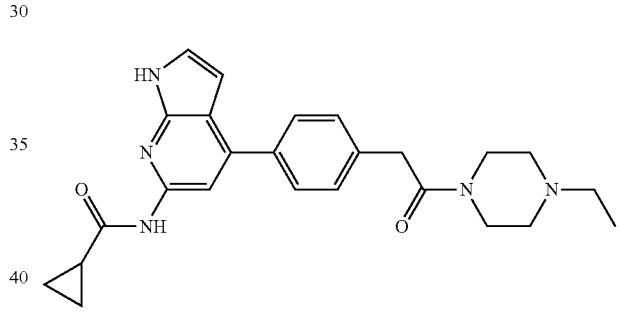

¹H NMR (400 MHz, DMSO-d₆) δ 11.54 (s, 1H), 10.63 (s, 1H), 8.03 (s, 1H), 7.70-7.63 (m, 2H), 7.43-7.37 (m, 3H), 6.56-6.50 (m, 1H), 3.79 (s, 2H), 3.55-3.44 (m, 4H), 2.29 (td, J=8.4, 7.8, 5.2 Hz, 6H), 2.04-1.96 (m, 1H), 0.98 (t, J=6.8 Hz, 3H), 0.83-0.71 (m, 4H).
MS(ESI+) m/z 432 (M+H)⁺

Example 552: Synthesis of N-(4-(4-(2-(4-isopropylpiperazin-1-yl)-2-oxoethyl)phenyl)-1H-pyrrolo[2,3-b]pyridin-6-yl)cyclopropanecarboxamide

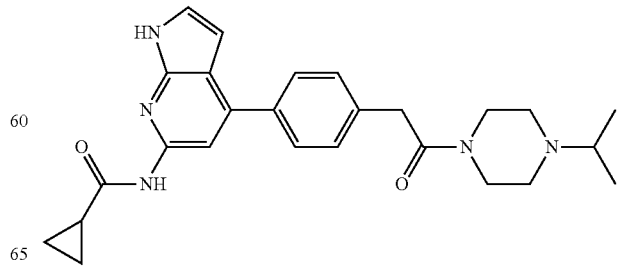

¹H NMR (400 MHz, DMSO-d₆) δ 11.54 (s, 1H), 10.63 (s, 1H), 8.02 (s, 1H), 7.70-7.62 (m, 2H), 7.49-7.44 (m, 1H), 7.42-7.35 (m, 3H), 7.11 (d, J=7.8 Hz, 1H), 6.53 (dd, J=3.5, 1.9 Hz, 1H), 3.79 (s, 2H), 3.55-3.43 (m, 4H), 2.63 (d, J=6.5 Hz, 1H), 2.37 (d, J=9.1 Hz, 4H), 2.05-1.95 (m, 1H), 0.94 (d, J=6.5 Hz, 6H), 0.81 (qd, J=9.0, 7.8, 4.5 Hz, 4H).

MS(ESI+) m/z 446 (M+H)⁺

Example 553: Synthesis of N-(4-(4-(2-((2-cyanoethyl)amino)-2-oxoethyl)phenyl)-1H-pyrrolo[2,3-b]pyridin-6-yl)cyclopropanecarboxamide

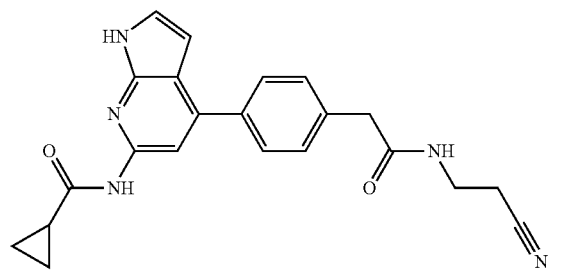 [SMILES: N#CCCNC(=O)Cc1ccc(-c2cc(NC(=O)C3CC3)nc3[nH]ccc23)cc1]

¹H NMR (400 MHz, DMSO-d₆) δ 11.53 (s, 1H), 10.63 (s, 1H), 8.02 (s, 1H), 7.65 (d, J=8.1 Hz, 2H), 7.49-7.36 (m, 3H), 6.53 (dd, J=3.5, 1.8 Hz, 1H), 3.53 (s, 2H), 3.31 (m, 2H), 2.66 (m, 2H), 2.07-1.96 (m, 1H), 0.82 (m, 4H).

MS(ESI+) m/z 388 (M+H)⁺

Example 554: Synthesis of tert-butyl 4-(2-(4-(6-(cyclopropanecarboxamido)-1H-pyrrolo[2,3-b]pyridin-4-yl)phenyl)acetyl)piperazine-1-carboxylate

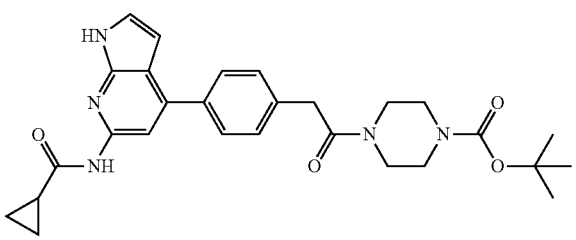 [SMILES: CC(C)(C)OC(=O)N1CCN(C(=O)Cc2ccc(-c3cc(NC(=O)C4CC4)nc4[nH]ccc34)cc2)CC1]

¹H NMR (400 MHz, DMSO-d₆) δ 11.54 (d, J=2.6 Hz, 1H), 10.63 (s, 1H), 8.03 (s, 1H), 7.72-7.63 (m, 2H), 7.44-7.35 (m, 3H), 6.54 (dd, J=3.6, 1.9 Hz, 1H), 3.82 (s, 2H), 3.58-3.43 (m, 4H), 3.32-3.24 (m, 4H), 2.07-1.94 (m, 1H), 1.40 (s, 9H), 0.87-0.74 (m, 4H).

MS(ESI+) m/z 504 (M+H)⁺

Example 555: Synthesis of tert-butyl 3-(2-(4-(6-(cyclopropanecarboxamido)-1H-pyrrolo[2,3-b]pyridin-4-yl)phenyl)acetamido)piperidine-1-carboxylate

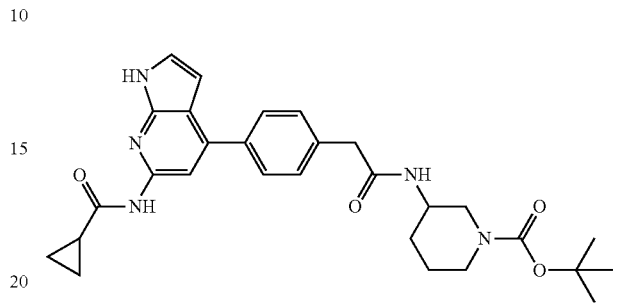

¹H NMR (400 MHz, DMSO-d₆) δ 11.53 (s, 1H), 10.63 (s, 1H), 8.11 (d, J=7.5 Hz, 1H), 8.02 (s, 1H), 7.65 (d, J=8.1 Hz, 2H), 7.46-7.37 (m, 3H), 6.53 (dd, J=3.4, 1.8 Hz, 1H), 3.64-3.53 (m, 2H), 3.50 (s, 3H), 2.00 (dt, J=14.5, 6.7 Hz, 2H), 1.85-1.76 (m, 1H), 1.73-1.61 (m, 1H), 1.37 (s, 13H), 1.23 (s, 5H), 0.88-0.72 (m, 6H).

MS(ESI+) m/z 518 (M+H)⁺

Example 556: Synthesis of N-(4-(4-(2-((1-methyl-1H-pyrazol-3-yl)amino)-2-oxoethyl)phenyl)-1H-pyrrolo[2,3-b]pyridin-6-yl)cyclopropanecarboxamide

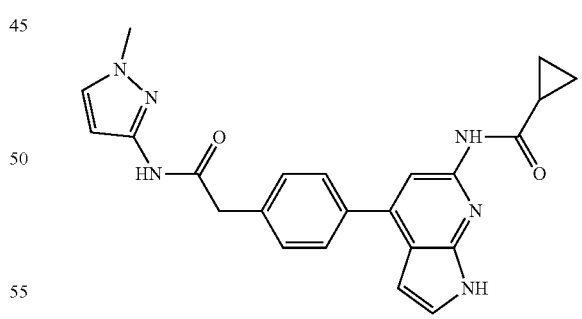

¹H NMR (400 MHz, DMSO-d₆) δ 11.53 (s, 1H), 10.68 (s, 1H), 10.63 (s, 1H), 8.02 (s, 1H), 7.67 (d, J=8.1 Hz, 2H), 7.53 (d, J=2.2 Hz, 1H), 7.48 (d, J=8.0 Hz, 2H), 7.40 (dd, J=3.5, 2.4 Hz, 1H), 6.54 (dd, J=3.5, 1.9 Hz, 1H), 6.42 (d, J=2.2 Hz, 1H), 3.73 (s, 3H), 3.68 (s, 2H), 2.02 (m, 1H), 0.84-0.73 (m, 4H).

MS(ESI+) m/z 415 (M+H)⁺

Example 557: Synthesis of N-(4-(4-(2-oxo-2-(piperidin-1-yl)ethyl)phenyl)-1H-pyrrolo[2,3-b]pyridin-6-yl)cyclopropanecarboxamide

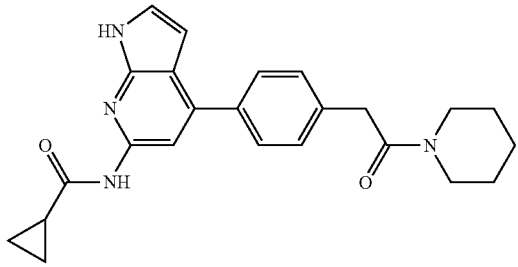 [SMILES: O=C(Nc1cc(-c2ccc(CC(=O)N3CCCCC3)cc2)c2cc[nH]c2n1)C1CC1]

¹H NMR (400 MHz, DMSO-d₆) δ 11.52 (s, 1H), 10.60 (d, J=3.9 Hz, 1H), 8.03 (d, J=3.2 Hz, 1H), 7.67 (d, J=6.8 Hz, 2H), 7.40 (s, 3H), 6.53 (s, 1H), 3.78 (s, 2H), 3.60 (s, 2H), 3.46 (s, 2H), 2.04 (s, 1H), 1.75 (d, J=4.4 Hz, 2H), 1.55 (s, 2H), 1.41 (s, 2H), 0.82-0.75 (m, 4H).
MS(ESI+) m/z 403 (M+H)⁺

Example 558: Synthesis of N-(4-(4-(2-oxo-2-(piperazin-1-yl)ethyl)phenyl)-1H-pyrrolo[2,3-b]pyridin-6-yl)cyclopropanecarboxamide

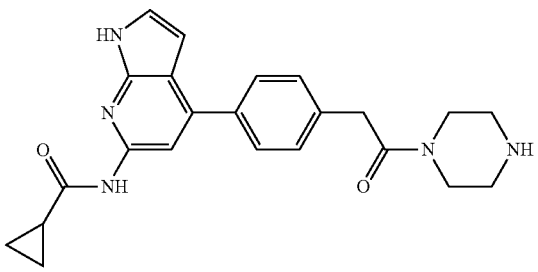 [SMILES: O=C(Nc1cc(-c2ccc(CC(=O)N3CCNCC3)cc2)c2cc[nH]c2n1)C1CC1]

¹H NMR (400 MHz, CDCl₃) δ 8.05 (s, 1H), 7.69 (dd, J=8.2, 3.9 Hz, 2H), 7.36-7.29 (m, 2H), 7.20 (q, J=3.1 Hz, 1H), 6.57 (q, J=3.1 Hz, 1H), 5.34-5.24 (m, 2H), 3.84-3.73 (m, 2H), 3.63 (d, J=5.2 Hz, 2H), 3.45 (d, J=5.3 Hz, 2H), 2.81 (s, 2H), 2.67 (d, J=5.3 Hz, 2H), 1.65 (s, 1H), 1.07 (q, J=3.9 Hz, 2H), 0.85 (m, 2H).
MS(ESI+) m/z 404 (M+H)⁺

Example 559: Synthesis of N-(4-(4-(2-(1,1-dioxidothiomorpholino)-2-oxoethyl)-3-fluorophenyl)-1H-pyrrolo[2,3-b]pyridin-6-yl)cyclopropanecarboxamide

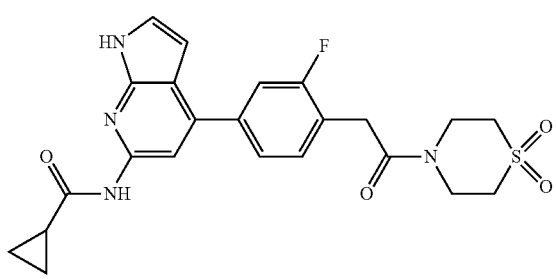 [SMILES: O=C(Nc1cc(-c2ccc(CC(=O)N3CCS(=O)(=O)CC3)c(F)c2)c2cc[nH]c2n1)C1CC1]

MS(ESI+) m/z 471 (M+H)⁺

Example 560: Synthesis of N-(4-(4-(2-oxo-2-thiomorpholinoethyl)phenyl)-1H-pyrrolo[2,3-b]pyridin-6-yl)cyclopropanecarboxamide

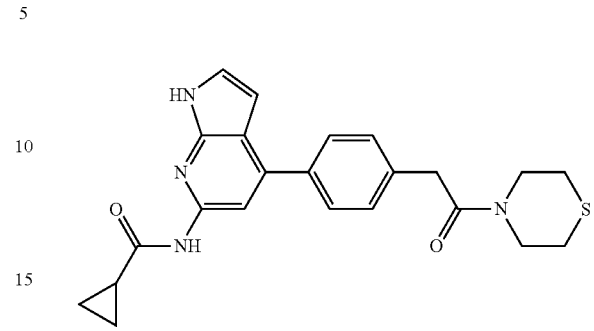

MS(ESI+) m/z 421 (M+H)⁺

Example 561: Synthesis of N-(4-(4-(2-(4,4-difluoropiperidin-1-yl)-2-oxoethyl)phenyl)-1H-pyrrolo[2,3-b]pyridin-6-yl)cyclopropanecarboxamide

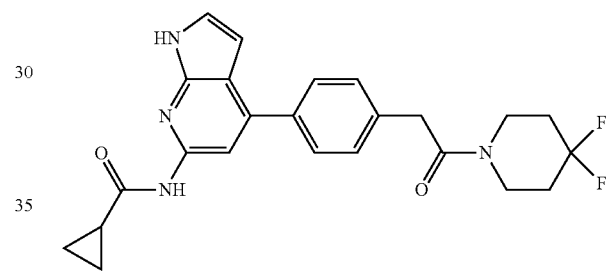

MS(ESI+) m/z 439 (M+H)⁺

Example 562: Synthesis of N-(4-(4-(2-oxo-2-(4-(trifluoromethylsulfonyl)piperazin-1-yl)ethyl)phenyl)-1H-pyrrolo[2,3-b]pyridin-6-yl)cyclopropanecarboxamide

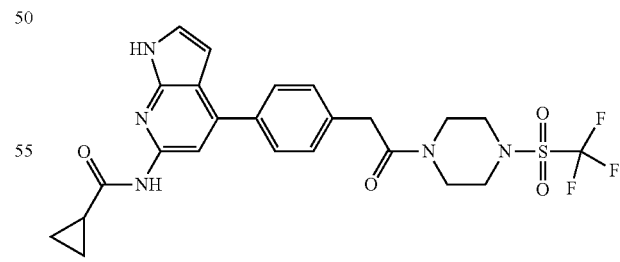

¹H NMR (400 MHz, DMSO-d₆) δ 11.51 (s, 1H), 10.60 (s, 1H), 8.01 (s, 1H), 7.65 (d, J=8.0 Hz, 2H), 7.43-7.31 (m, 3H), 6.52 (dd, J=3.5, 1.9 Hz, 1H), 4.33 (d, J=4.3 Hz, 1H), 3.77 (s, 2H), 2.60 (dd, J=12.1, 5.3 Hz, 8H), 2.00 (m, 1H), 0.84-0.76 (m, 4H).
MS(ESI+) m/z 537 (M+H)⁺

Example 563: Synthesis of N-(4-(4-(2-(4-(ethyl-sulfonyl)piperazin-1-yl)-2-oxoethyl)phenyl)-1H-pyrrolo[2,3-b]pyridin-6-yl)cyclopropanecarboxamide

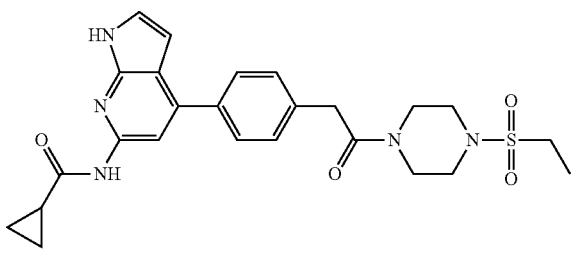 [SMILES: CCS(=O)(=O)N1CCN(C(=O)Cc2ccc(-c3cc(NC(=O)C4CC4)nc4[nH]ccc34)cc2)CC1]

¹H NMR (400 MHz, DMSO-d₆) δ 11.52 (s, 1H), 10.61 (s, 1H), 8.03 (s, 1H), 7.67 (d, J=8.0 Hz, 2H), 7.40 (d, J=7.6 Hz, 3H), 6.53 (d, J=3.4 Hz, 1H), 3.84 (s, 2H), 3.64-3.57 (m, 2H), 3.20-3.10 (m, 4H), 3.11-2.99 (m, 4H), 2.07-1.95 (m, 1H), 1.24-1.14 (m, 3H), 0.82 (dd, J=16.1, 11.1 Hz, 4H).
MS(ESI+) m/z 497 (M+H)⁺

Example 564: Synthesis of N-(4-(4-(2-oxo-2-(4-(propylsulfonyl)piperazin-1-yl)ethyl)phenyl)-1H-pyrrolo[2,3-b]pyridin-6-yl)cyclopropanecarboxamide

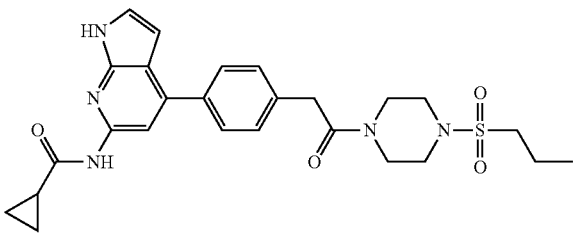 [SMILES: CCCS(=O)(=O)N1CCN(C(=O)Cc2ccc(-c3cc(NC(=O)C4CC4)nc4[nH]ccc34)cc2)CC1]

¹H NMR (400 MHz, DMSO-d₆) δ 11.53 (s, 1H), 10.61 (s, 1H), 8.03 (s, 1H), 7.67 (d, J=8.0 Hz, 2H), 7.40 (dd, J=6.2, 2.1 Hz, 3H), 6.54 (dd, J=3.5, 1.9 Hz, 1H), 3.84 (s, 2H), 3.68-3.54 (m, 4H), 3.14 (m, 4H), 3.08-2.99 (m, 2H), 2.04-1.97 (m, 1H), 1.75-1.60 (m, 2H), 0.95 (t, J=7.4 Hz, 3H), 0.85-0.74 (m, 4H).
MS(ESI+) m/z 511 (M+H)⁺

Example 565: Synthesis of ethyl 4-(2-(4-(6-(cyclopropanecarboxamido)-1H-pyrrolo[2,3-b]pyridin-4-yl)phenyl)acetyl)piperazine-1-carboxylate

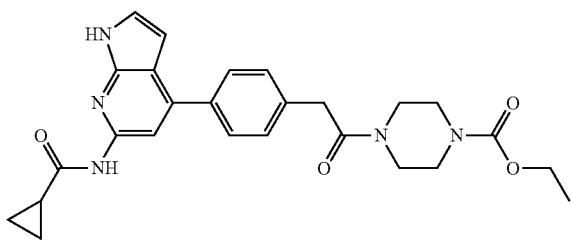 [SMILES: CCOC(=O)N1CCN(C(=O)Cc2ccc(-c3cc(NC(=O)C4CC4)nc4[nH]ccc34)cc2)CC1]

¹H NMR (400 MHz, DMSO-d₆) δ 11.52 (s, 1H), 10.61 (s, 1H), 8.03 (s, 1H), 7.66 (d, J=7.8 Hz, 2H), 7.45-7.35 (m, 3H), 6.54 (dd, J=3.5, 1.8 Hz, 1H), 4.05 (q, J=7.0 Hz, 2H), 3.83 (s, 2H), 3.58-3.44 (m, 4H), 2.07-1.96 (m, 1H), 1.18 (t, J=6.9 Hz, 3H), 0.85-0.75 (m, 4H).
MS(ESI+) m/z 477 (M+H)⁺

Example 566: Synthesis of (N-(4-(4-(2-oxo-2-(4-(N-(2,2,2-trifluoroethyl)sulfamoyl)piperazin-1-yl)ethyl)phenyl)-1H-pyrrolo[2,3-b]pyridin-6-yl)cyclopropanecarboxamide)

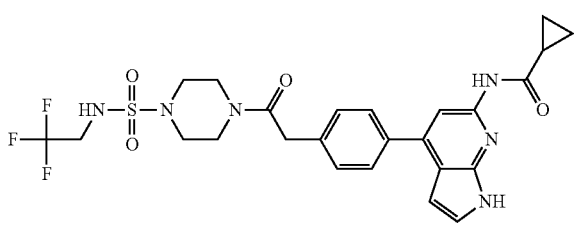 [SMILES: O=C(Nc1cc(-c2ccc(CC(=O)N3CCN(S(=O)(=O)NCC(F)(F)F)CC3)cc2)c2cc[nH]c2n1)C1CC1]

MS(ESI+) m/z 565 (M+H)⁺

Example 567: Synthesis of N-(4-(4-(2-(3-cyanopyrrolidin-1-yl)-2-oxoethyl)phenyl)-1H-pyrrolo[2,3-b]pyridin-6-yl)cyclopropanecarboxamide

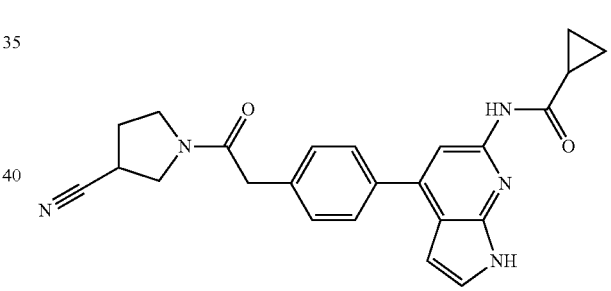

MS(ESI+) m/z 414 (M+H)⁺

Example 568: Synthesis of N-(4-(4-(2-(3-cyanoazetidin-1-yl)-2-oxoethyl)phenyl)-1H-pyrrolo[2,3-b]pyridin-6-yl)cyclopropanecarboxamide

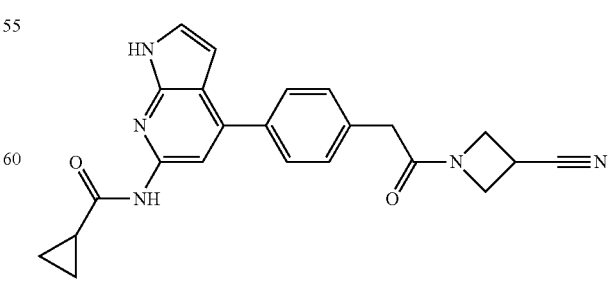

MS(ESI+) m/z 400 (M+H)⁺

Example 569: Synthesis of N-(4-(4-(2-(3,3-difluoropyrrolidin-1-yl)-2-oxoethyl)phenyl)-1H-pyrrolo[2,3-b]pyridin-6-yl)cyclopropanecarboxamide

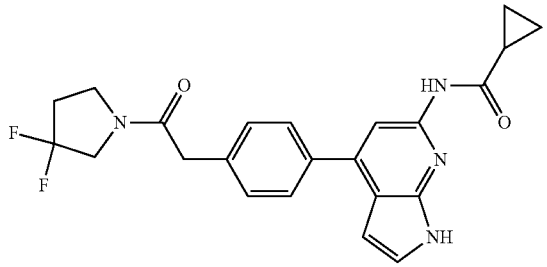 [SMILES: O=C(Nc1cc(-c2ccc(CC(=O)N3CCC(F)(F)C3)cc2)c2cc[nH]c2n1)C1CC1]

¹H NMR (400 MHz, DMSO-d₆) δ 11.52 (d, J=4.0 Hz, 1H), 10.60 (d, J=3.6 Hz, 1H), 8.02 (d, J=3.4 Hz, 1H), 7.66 (d, J=6.0 Hz, 2H), 7.40 (s, 3H), 6.54 (s, 1H), 4.11-3.98 (m, 1H), 3.78 (dd, J=25.2, 10.0 Hz, 5H), 3.55 (s, 2H), 2.03 (s, 1H), 0.82-0.75 (s, 4H).
MS(ESI+) m/z 425 (M+H)⁺

Example 570: Synthesis of N-(4-(4-(2-oxo-2-(4-(trifluoromethyl)piperidin-1-yl)ethyl)phenyl)-1H-pyrrolo[2,3-b]pyridin-6-yl)cyclopropanecarboxamide

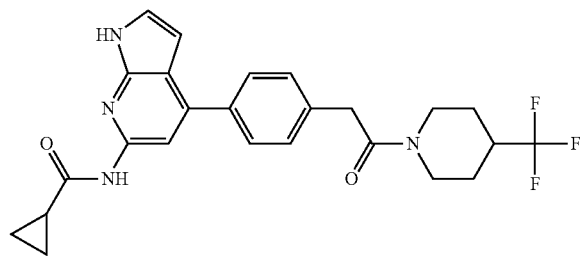 [SMILES: O=C(Nc1cc(-c2ccc(CC(=O)N3CCC(C(F)(F)F)CC3)cc2)c2cc[nH]c2n1)C1CC1]

¹H NMR (400 MHz, DMSO-d₆) δ 11.52 (s, 1H), 10.61 (d, J=2.9 Hz, 1H), 8.02 (d, J=2.8 Hz, 1H), 7.66 (t, J=6.1 Hz, 2H), 7.40 (d, J=4.1 Hz, 3H), 6.52 (s, 1H), 4.56-4.47 (m, 1H), 4.09 (d, J=13.9 Hz, 1H), 3.85-3.79 (m, 2H), 3.06 (t, J=13.5 Hz, 1H), 2.58 (d, J=12.3 Hz, 2H), 2.03 (s, 1H), 1.87-1.73 (m, 2H), 1.25 (d, J=13.1 Hz, 2H), 0.82-0.75 (m, 4H).
MS(ESI+) m/z 471 (M+H)⁺

Example 571: Synthesis of N-(4-(4-(2-(1,1-dioxidothiomorpholino)-1,1-difluoro-2-oxoethyl)phenyl)-1H-pyrrolo[2,3-b]pyridin-6-yl)cyclopropanecarboxamide

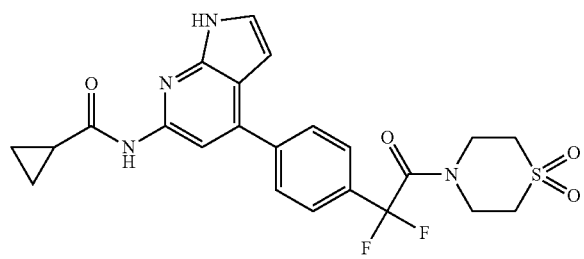 [SMILES: O=C(Nc1cc(-c2ccc(C(F)(F)C(=O)N3CCS(=O)(=O)CC3)cc2)c2cc[nH]c2n1)C1CC1]

MS(ESI+) m/z 489 (M+H)⁺

Example 572: Synthesis of N-(4-(4-(1,1-difluoro-2-morpholino-2-oxoethyl)phenyl)-1H-pyrrolo[2,3-b]pyridin-6-yl)cyclopropanecarboxamide

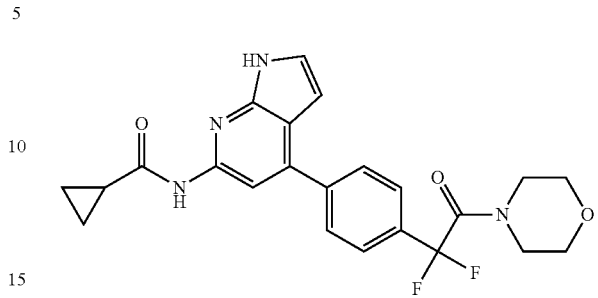

MS(ESI+) m/z 441 (M+H)⁺

Example 573: Synthesis of N-(4-(4-(2-((cyanomethyl)(methyl)amino)-2-oxoethyl)phenyl)-1H-pyrrolo[2,3-b]pyridin-6-yl)cyclopropanecarboxamide

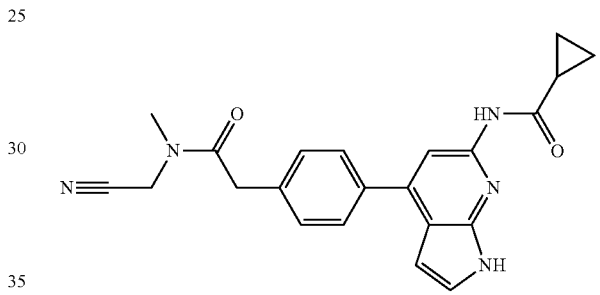

¹H NMR (400 MHz, DMSO-d₆) δ 11.54 (s, 1H), 10.67 (s, 1H), 8.00 (s, 1H), 7.68 (d, J=8.1 Hz, 2H), 7.43-7.37 (m, 3H), 6.55 (dd, J=3.6, 1.9 Hz, 1H), 4.43 (s, 2H), 3.88 (s, 3H), 3.15 (s, 3H), 2.06-2.02 (m, 1H), 0.85-0.80 (m, 4H).
MS(ESI+) m/z 388 (M+H)⁺

Example 574: Synthesis of N-(4-(4-(2-(1-oxidothiomorpholino)-2-oxoethyl)phenyl)-1H-pyrrolo[2,3-b]pyridin-6-yl)cyclopropanecarboxamide

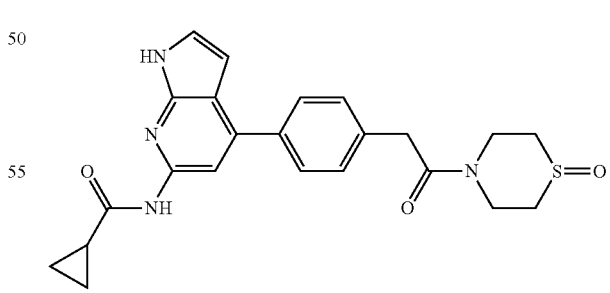

¹H NMR (400 MHz, DMSO-d₆) δ 11.53 (s, 1H), 10.65 (s, 1H), 8.02 (s, 1H), 7.68 (d, J=7.9 Hz, 2H), 7.44-7.38 (m, 3H), 6.55 (dd, J=3.5, 1.9 Hz, 1H), 3.87 (d, J=11.3 Hz, 2H), 3.62 (dd, J=6.6, 3.9 Hz, 4H), 3.13 (tt, J=7.4, 3.7 Hz, 4H), 2.04 (d, J=6.5 Hz, 1H), 0.85-0.79 (m, 4H).
MS(ESI+) m/z 437 (M+H)⁺

Example 575: Synthesis of N-(4-(4-(2-(4-cyanopiperidin-1-yl)-1,1-difluoro-2-oxoethyl)phenyl)-1H-pyrrolo[2,3-b]pyridin-6-yl)cyclopropanecarboxamide

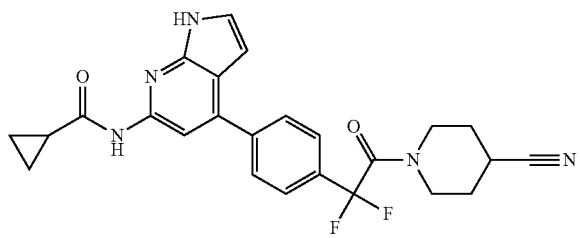 [SMILES: N#CC1CCN(C(=O)C(F)(F)c2ccc(-c3cc(NC(=O)C4CC4)nc4[nH]ccc34)cc2)CC1]

MS(ESI+) m/z 464 (M+H)+

Example 576: Synthesis of N-(4-(4-(2-(3-cyanomorpholino)-2-oxoethyl)phenyl)-1H-pyrrolo[2,3-b]pyridin-6-yl)cyclopropanecarboxamide

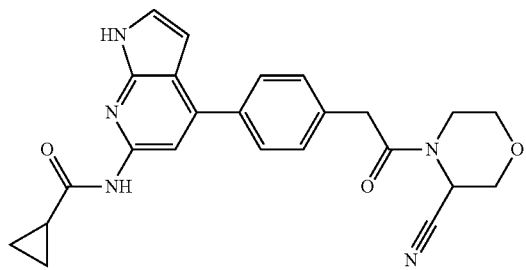 [SMILES: N#CC1COCCN1C(=O)Cc1ccc(-c2cc(NC(=O)C3CC3)nc3[nH]ccc23)cc1]

$^1$H NMR (400 MHz, DMSO-$d_6$) δ 11.53 (s, 1H), 10.62 (s, 1H), 8.04 (s, 1H), 7.71-7.66 (m, 2H), 7.45-7.36 (m, 3H), 6.54 (dd, J=3.5, 1.8 Hz, 1H), 4.03 (d, J=12.3 Hz, 2H), 3.94-3.90 (m, 2H), 3.62-3.56 (m, 1H), 3.46 (s, 1H), 2.04 (d, J=9.1 Hz, 1H), 1.28-1.23 (m, 4H), 0.86-0.79 (m, 4H).

MS(ESI+) m/z 430 (M+H)+

Example 577: Synthesis of N-(4-(4-(1-(1,1-dioxidothiomorpholine-4-carbonyl)cyclopropyl)phenyl)-1H-pyrrolo[2,3-b]pyridin-6-yl)cyclopropanecarboxamide

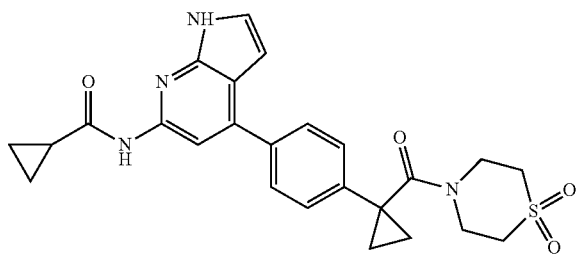 [SMILES: O=C(Nc1cc(-c2ccc(C3(C(=O)N4CCS(=O)(=O)CC4)CC3)cc2)c2cc[nH]c2n1)C1CC1]

$^1$H NMR (400 MHz, DMSO-$d_6$) δ 11.54 (s, 1H), 10.62 (s, 1H), 8.03 (s, 1H), 7.70 (dd, J=7.6, 5.9 Hz, 3H), 7.42-7.40 (m, 1H), 7.34 (d, J=8.3 Hz, 2H), 6.53 (dd, J=3.5, 1.9 Hz, 1H), 3.39 (s, 2H), 2.92 (s, 2H), 2.04-2.00 (m, 1H), 1.51-1.47 (m, 2H), 1.26 (dd, J=9.2, 4.0 Hz, 4H), 0.84-0.77 (m, 4H).

MS(ESI+) m/z 479 (M+H)+

Example 578: Synthesis of N-(4-(1-(2-(1,1-dioxidothiomorpholino)-2-oxoethyl)-1,2,3,6-tetrahydropyridin-4-yl)-1H-pyrrolo[2,3-b]pyridin-6-yl)cyclopropanecarboxamide

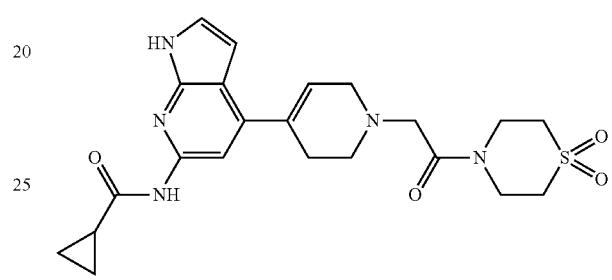

$^1$H NMR (400 MHz, Chloroform-d) δ 11.40 (s, 1H), 10.51 (s, 1H), 7.86 (s, 1H), 7.37-7.28 (m, 1H), 6.60-6.52 (m, 1H), 6.33 (s, 1H), 3.99 (s, 2H), 3.89 (s, 2H), 3.39 (s, 2H), 3.19 (d, J=37.2 Hz, 5H), 2.74 (t, J=5.6 Hz, 2H), 2.00 (d, J=11.4 Hz, 1H), 0.88-0.75 (m, 4H).

MS(ESI+) m/z 458 (M+H)+

Example 579: Synthesis of N-(4-(6-(cyclopropanecarboxamido)-1H-pyrrolo[2,3-b]pyridin-4-yl)benzyl)morpholine-4-carboxamide

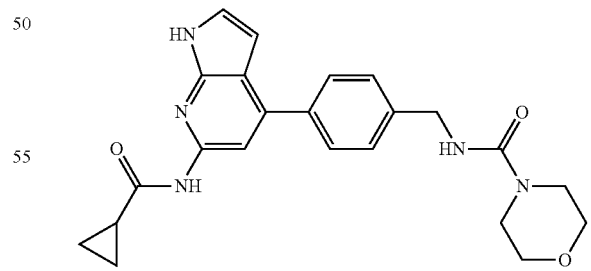

$^1$H NMR (400 MHz, DMSO-$d_6$) δ 11.53 (s, 1H), 10.62 (s, 1H), 8.01 (s, 1H), 7.66 (d, J=8.3 Hz, 2H), 7.42 (d, J=8.4 Hz, 3H), 7.21 (s, 1H), 6.53 (s, 1H), 4.32 (s, 2H), 2.42-2.83 (m, 4H), 1.98-2.12 (m, 1H), 1.21-1.41 (m, 4H), 0.72-0.95 (m, 4H).

MS(ESI+) m/z 420 (M+H)+

Example 580: Synthesis of N-(4-(6-(cyclopropanecarboxamido)-1H-pyrrolo[2,3-b]pyridin-4-yl)benzyl)thiomorpholine-4-carboxamide 1,1-dioxide

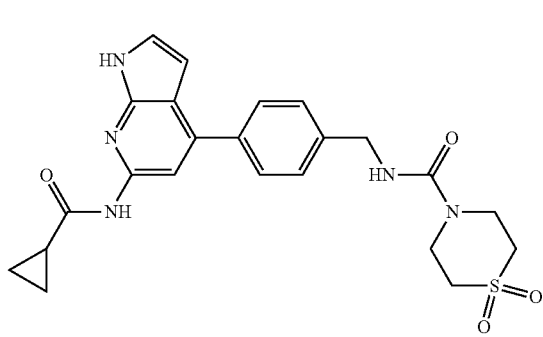 [SMILES: O=C(Nc1cc(-c2ccc(CNC(=O)N3CCS(=O)(=O)CC3)cc2)c2cc[nH]c2n1)C1CC1]

$^1$H NMR (400 MHz, DMSO-d$_6$) δ 11.54 (s, 1H), 10.63 (s, 1H), 8.02 (s, 1H), 7.67 (d, J=8.0 Hz, 2H), 7.51 (d, J=5.1 Hz, 1H), 7.44 (d, J=7.9 Hz, 2H), 7.42-7.38 (m, 1H), 6.58-6.49 (m, 1H), 4.34 (d, J=5.8 Hz, 2H), 3.82 (d, J=5.5 Hz, 4H), 3.16-3.06 (m, 4H), 2.04 (s, 1H), 0.80 (dd, J=4.0, 12.0 Hz, 4H).

MS(ESI+) m/z 468 (M+H)$^+$

Example 581: Synthesis of N-(4-(4-((3-(2,2,2-trifluoroethyl)ureido)methyl)phenyl)-1H-pyrrolo[2,3-b]pyridin-6-yl)cyclopropanecarboxamide

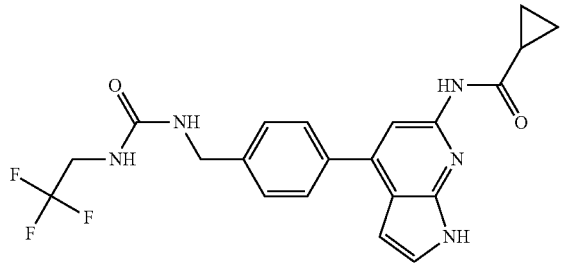 [SMILES: O=C(NCc1ccc(-c2cc(NC(=O)C3CC3)nc3[nH]ccc23)cc1)NCC(F)(F)F]

$^1$H NMR (400 MHz, DMSO-d$_6$) δ 11.54 (s, 1H), 10.63 (s, 1H), 8.02 (s, 1H), 7.67 (d, J=7.8 Hz, 2H), 7.45-7.34 (m, 3H), 6.75 (t, J=6.0 Hz, 1H), 6.66 (t, J=6.6 Hz, 1H), 6.55-6.47 (m, 1H), 4.32 (d, J=6.0 Hz, 2H), 3.93-3.78 (m, 2H), 2.04 (s, 1H), 0.81 (dt, J=5.3, 10.2 Hz, 4H).

MS(ESI+) m/z 432 (M+H)$^+$

Example 582: Synthesis of N-(4-(4-(((3,4-difluorophenyl)sulfonamido)methyl)phenyl)-1H-pyrrolo[2,3-b]pyridin-6-yl)cyclopropanecarboxamide

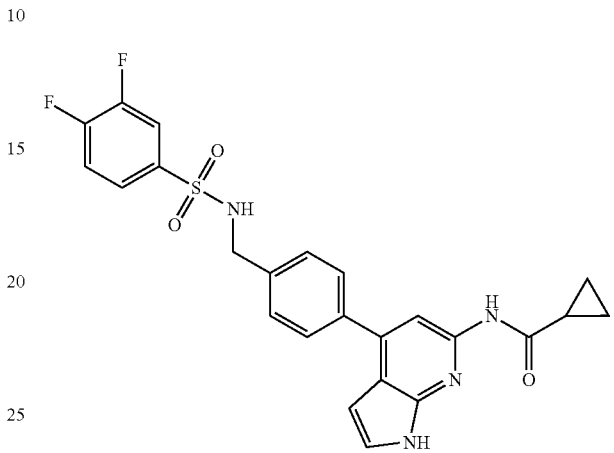

$^1$H NMR (400 MHz, DMSO-d$_6$) δ 11.53 (s, 1H), 10.61 (s, 1H), 8.24 (br s, 1H), 7.99 (s, 1H), 7.79 (d, J=2.3 Hz, 1H), 7.69-7.58 (m, 4H), 7.44-7.33 (m, 3H), 6.52-6.43 (m, 1H), 4.13 (s, 2H), 2.04 (d, J=5.7 Hz, 1H), 0.88-0.74 (m, 4H).

MS(ESI+) m/z 483 (M+H)$^+$

Example 583: Synthesis of N-(4-(4-(propylsulfonamidomethyl)phenyl)-1H-pyrrolo[2,3-b]pyridin-6-yl)cyclopropanecarboxamide

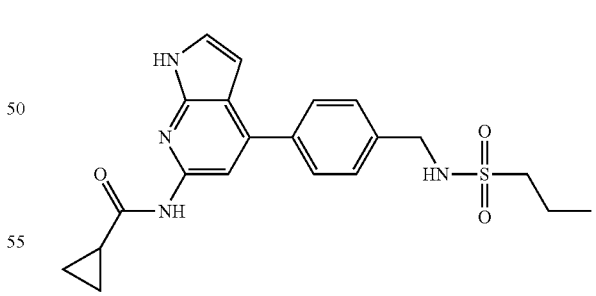

$^1$H NMR (400 MHz, DMSO-d$_6$) δ 11.56 (s, 1H), 10.64 (s, 1H), 8.05 (d, J=15.8 Hz, 1H), 7.79-7.65 (m, 3H), 7.52 (d, J=8.1 Hz, 2H), 7.41 (s, 1H), 6.52 (s, 1H), 4.22 (d, J=4.7 Hz, 2H), 3.02-2.91 (m, 2H), 2.05 (s, 1H), 1.72-1.59 (m, 2H), 0.92 (t, J=7.4 Hz, 3H), 0.81 (d, J=6.7 Hz, 4H).

MS(ESI+) m/z 413 (M+H)$^+$

Example 584: Synthesis of N-(4-(4-((1,1-dioxidothiomorpholino)methyl)phenyl)-1H-pyrrolo[2,3-b]pyridin-6-yl)cyclopropanecarboxamide

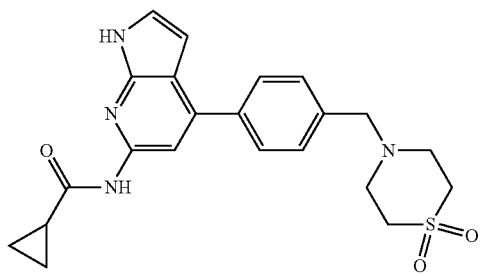 [SMILES: O=C(Nc1cc(-c2ccc(CN3CCS(=O)(=O)CC3)cc2)c2cc[nH]c2n1)C1CC1]

¹H NMR (400 MHz, DMSO-d₆) δ 11.53 (s, 1H), 10.62 (s, 1H), 8.03 (s, 1H), 7.70 (d, J=7.9 Hz, 2H), 7.51 (d, J=7.9 Hz, 2H), 7.40 (t, J=3.0 Hz, 1H), 6.63-6.39 (m, 1H), 3.75 (s, 2H), 3.13 (t, J=5.1 Hz, 5H), 3.01-2.82 (m, 4H), 2.05 (t, J=11.7 Hz, 1H), 0.81 (dt, J=5.7, 10.4 Hz, 4H).
MS(ESI+) m/z 425 (M+H)⁺

Example 585: Synthesis of N-(4-(4-((4-oxopiperidin-1-yl)methyl)phenyl)-1H-pyrrolo[2,3-b]pyridin-6-yl)cyclopropanecarboxamide

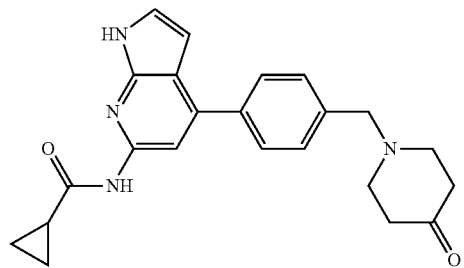 [SMILES: O=C1CCN(Cc2ccc(-c3cc(NC(=O)C4CC4)nc4[nH]ccc34)cc2)CC1]

¹H NMR (400 MHz, DMSO-d₆) δ 11.53 (s, 1H), 10.62 (s, 1H), 8.04 (s, 1H), 7.78-7.66 (m, 2H), 7.53 (d, J=7.9 Hz, 2H), 7.40 (t, J=3.0 Hz, 1H), 6.55 (dd, J=1.8, 3.5 Hz, 1H), 3.70 (s, 2H), 2.74 (t, J=6.0 Hz, 4H), 2.38 (t, J=6.0 Hz, 4H), 2.04 (d, J=8.8 Hz, 1H), 0.91-0.75 (m, 4H).
MS(ESI+) m/z 389 (M+H)⁺

Example 586: Synthesis of N-(4-(4-((3-cyanoazetidin-1-yl)methyl)phenyl)-1H-pyrrolo[2,3-b]pyridin-6-yl)cyclopropanecarboxamide

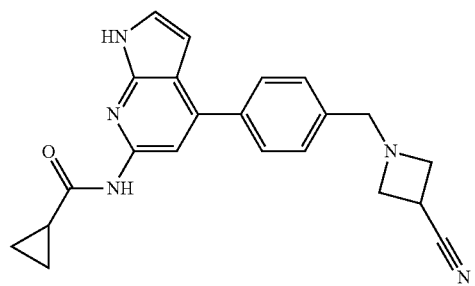 [SMILES: N#CC1CN(Cc2ccc(-c3cc(NC(=O)C4CC4)nc4[nH]ccc34)cc2)C1]

¹H NMR (400 MHz, DMSO-d₆) δ 11.53 (s, 1H), 10.61 (s, 1H), 8.02 (s, 1H), 7.75-7.64 (m, 2H), 7.48-7.41 (m, 2H), 7.40 (dd, J=2.4, 3.5 Hz, 1H), 6.53 (dd, J=1.8, 3.5 Hz, 1H), 3.66 (s, 2H), 3.55-3.45 (m, 4H), 2.04 (d, J=7.0 Hz, 1H), 0.81 (ddd, J=2.6, 6.4, 11.7 Hz, 4H).
MS(ESI+) m/z 372 (M+H)⁺

Example 587: Synthesis of N-(4-(4-((4-(methylsulfonyl)piperazin-1-yl)methyl)phenyl)-1H-pyrrolo[2,3-b]pyridin-6-yl)cyclopropanecarboxamide

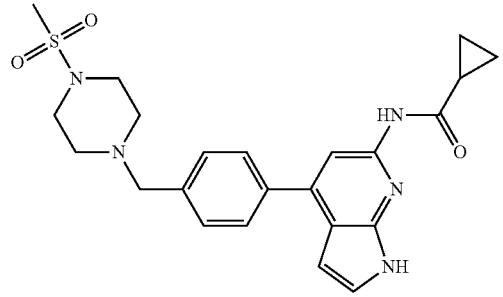 [SMILES: CS(=O)(=O)N1CCN(Cc2ccc(-c3cc(NC(=O)C4CC4)nc4[nH]ccc34)cc2)CC1]

MS(ESI+) m/z 454 (M+H)⁺

Example 588: Synthesis of N-(4-(4-((1,1-dioxidothiomorpholino)methyl)phenyl)-1H-pyrrolo[2,3-b]pyridin-6-yl)-2-methylcyclopropane-1-carboxamide

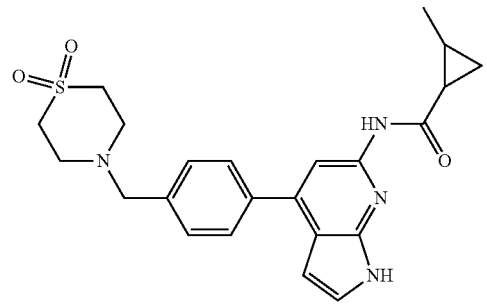 [SMILES: CC1CC1C(=O)Nc1cc(-c2ccc(CN3CCS(=O)(=O)CC3)cc2)c2cc[nH]c2n1]

MS(ESI+) m/z 439 (M+H)⁺

Example 589: Synthesis of N-(4-(4-(1-(1,1-dioxidothiomorpholino)ethyl)phenyl)-1H-pyrrolo[2,3-b]pyridin-6-yl)cyclopropanecarboxamide

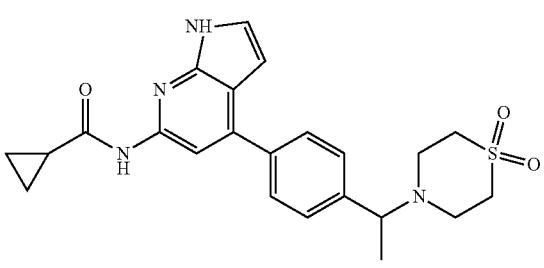 [SMILES: CC(c1ccc(-c2cc(NC(=O)C3CC3)nc3[nH]ccc23)cc1)N1CCS(=O)(=O)CC1]

¹H NMR (400 MHz, DMSO-d₆) δ 11.53 (s, 1H), 10.62 (s, 1H), 8.03 (s, 1H), 7.70 (d, J=8.0 Hz, 2H), 7.54 (d, J=7.9 Hz,

2H), 7.45-7.36 (m, 1H), 6.55 (s, 1H), 3.99 (s, 1H), 3.10 (s, 4H), 2.93 (s, 4H), 2.05 (s, 1H), 1.40 (d, J=6.7 Hz, 3H), 0.83-0.77 (m, 4H).

MS(ESI+) m/z 439 (M+H)+

Example 590: Synthesis of N-(4-(3,5-difluoro-4-(morpholinomethyl)phenyl)-1H-pyrrolo[2,3-b]pyridin-6-yl)cyclopropanecarboxamide

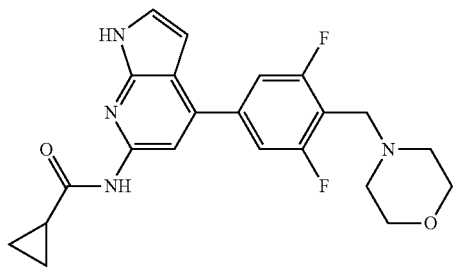 [SMILES: O=C(Nc1cc(-c2cc(F)c(CN3CCOCC3)c(F)c2)c2cc[nH]c2n1)C1CC1]

¹H NMR (400 MHz, DMSO-d₆) δ 11.68 (s, 1H), 10.72 (s, 1H), 8.05 (s, 1H), 7.47 (d, J=2.8 Hz, 1H), 7.44-7.35 (m, 2H), 6.63-6.55 (m, 1H), 3.63 (s, 2H), 3.56 (t, J=4.5 Hz, 4H), 2.45-2.42 (m, 2H), 2.04 (s, 1H), 0.86-0.78 (m, 4H).

MS(ESI+) m/z 413 (M+H)+

Example 591: Synthesis of N-(4-(4-(2-(1,1-dioxidothiomorpholino)ethyl)phenyl)-1H-pyrrolo[2,3-b]pyridin-6-yl)cyclopropanecarboxamide

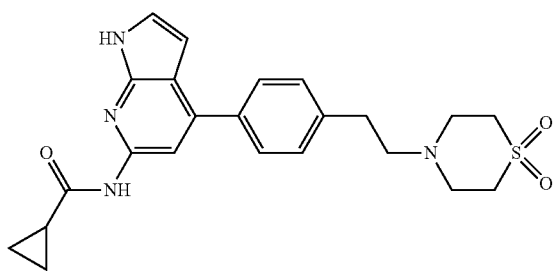 [SMILES: O=C(Nc1cc(-c2ccc(CCN3CCS(=O)(=O)CC3)cc2)c2cc[nH]c2n1)C1CC1]

¹H NMR (400 MHz, DMSO-d₆) δ 11.51 (s, 1H), 10.60 (s, 1H), 8.01 (s, 1H), 7.71-7.59 (m, 2H), 7.50-7.34 (m, 3H), 6.52 (dd, J=3.5, 1.7 Hz, 1H), 3.10 (d, J=5.6 Hz, 4H), 3.05-2.93 (m, 4H), 2.86-2.73 (m, 4H), 2.03 (m, 1H), 0.90-0.74 (m, 4H).

MS(ESI+) m/z 439 (M+H)+

Example 592: Synthesis of N-(6-(4-((1,1-dioxidothiomorpholino)methyl)phenyl)-9H-purin-2-yl)cyclopropanecarboxamide

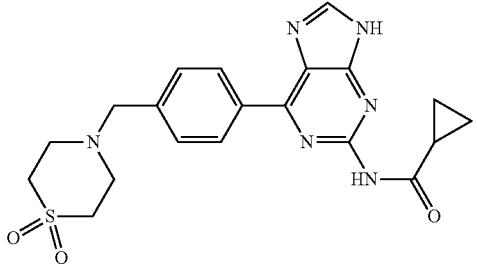 [SMILES: O=C(Nc1nc(-c2ccc(CN3CCS(=O)(=O)CC3)cc2)c2nc[nH]c2n1)C1CC1]

¹H NMR (400 MHz, DMSO-d₆) δ 10.79 (s, 1H), 8.88-8.79 (m, 2H), 8.51 (s, 1H), 7.69-7.58 (m, 2H), 3.62-3.55 (m, 2H), 3.29 (d, J=21.0 Hz, 8H), 2.18 (dd, J=8.6, 3.7 Hz, 1H), 0.84 (ddt, J=10.7, 4.9, 2.9 Hz, 4H).

MS(ESI+) m/z 427 (M+H)+

Example 593: Synthesis of N-(7-(4-((5-methyl-2H-tetrazol-2-yl)methyl)phenyl)-3H-imidazo[4,5-b]pyridin-5-yl)cyclopropanecarboxamide

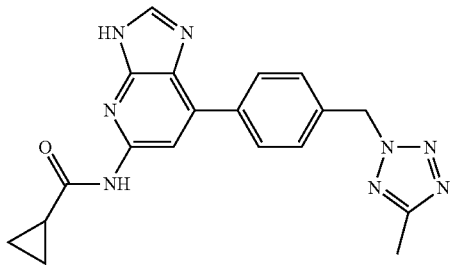 [SMILES: Cc1nnn(Cc2ccc(-c3cc(NC(=O)C4CC4)nc4[nH]cnc34)cc2)n1]

MS(ESI+) m/z 375 (M+H)+

Example 594: Synthesis of N-(7-(4-((5-methyl-1H-tetrazol-1-yl)methyl)phenyl)-3H-imidazo[4,5-b]pyridin-5-yl)cyclopropanecarboxamide

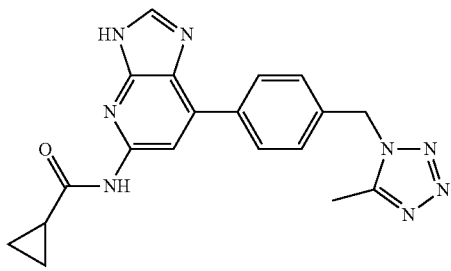 [SMILES: Cc1nnnn1Cc1ccc(-c2cc(NC(=O)C3CC3)nc3[nH]cnc23)cc1]

MS(ESI+) m/z 375 (M+H)+

Example 595: Synthesis of N-(4-(4-(((1,1-dioxido-tetrahydrothiophen-3-yl)amino)methyl)phenyl)-1H-pyrrolo[2,3-b]pyridin-6-yl)cyclopropanecarboxamide

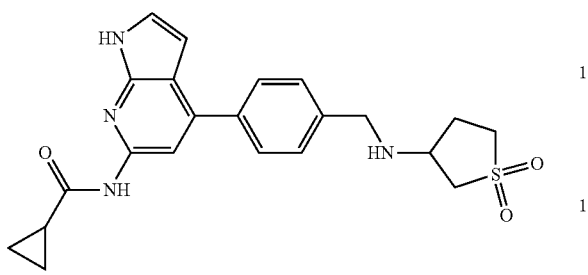

¹H NMR (400 MHz, DMSO-d₆) δ 11.52 (s, 1H), 10.61 (s, 1H), 8.02 (s, 1H), 7.74-7.65 (m, 2H), 7.51 (d, J=7.9 Hz, 2H), 7.45-7.38 (m, 1H), 6.58-6.46 (m, 1H), 3.80 (s, 2H), 3.48 (s, 1H), 3.28-3.19 (m, 1H), 3.05 (dt, J=7.6, 12.6 Hz, 1H), 2.94 (dd, J=6.5, 13.1 Hz, 1H), 2.70 (d, J=23.9 Hz, 2H), 2.30-2.23 (m, 1H), 2.04 (dd, J=7.2, 13.5 Hz, 2H), 0.88-0.78 (m, 4H)
MS(ESI+) m/z 425 (M+H)⁺

Example 596: Synthesis of N-(4-(4-(((1,1-dioxido-tetrahydro-2H-thiopyran-4-yl)amino)methyl)phenyl)-1H-pyrrolo[2,3-b]pyridin-6-yl)cyclopropanecarboxamide

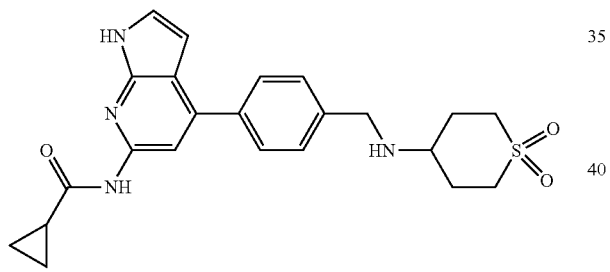

¹H NMR (400 MHz, DMSO-d₆) δ 11.52 (s, 1H), 10.61 (s, 1H), 8.02 (s, 1H), 7.76-7.35 (m, 9H), 6.65-6.47 (m, 1H), 3.78 (s, 1H), 3.09 (d, J=53.8 Hz, 4H), 2.01 (d, J=52.3 Hz, 5H), 0.89-0.75 (m, 4H).
MS(ESI+) m/z 439 (M+H)⁺

Example 597: Synthesis of N-(6-(4-(((4-fluorophenyl)amino)methyl)phenyl)-9H-purin-2-yl)cyclopropanecarboxamide

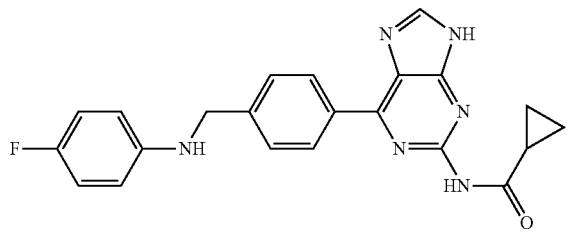 [SMILES: O=C(Nc1nc(-c2ccc(CNc3ccc(F)cc3)cc2)c2nc[nH]c2n1)C1CC1]

¹H NMR (400 MHz, DMSO-d₆) δ 10.67 (s, 1H), 8.76 (d, J=7.9 Hz, 2H), 8.42 (s, 1H), 7.55 (d, J=8.1 Hz, 2H), 6.89 (t, J=8.7 Hz, 2H), 6.58 (dd, J=8.8, 4.5 Hz, 2H), 6.24 (t, J=6.1 Hz, 1H), 4.33 (d, J=6.1 Hz, 2H), 2.20 (s, 1H), 0.91-0.79 (m, 4H).
MS(ESI+) m/z 403 (M+H)⁺

Example 598: Synthesis of N-(6-(4-(((3-fluorophenyl)amino)methyl)phenyl)-9H-purin-2-yl)cyclopropanecarboxamide

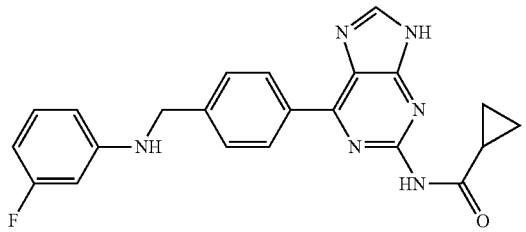 [SMILES: O=C(Nc1nc(-c2ccc(CNc3cccc(F)c3)cc2)c2nc[nH]c2n1)C1CC1]

¹H NMR (400 MHz, DMSO-d₆) δ 10.73 (s, 1H), 8.72 (d, J=37.7 Hz, 2H), 8.46 (s, 1H), 7.56 (d, J=8.0 Hz, 2H), 7.05 (q, J=7.8 Hz, 2H), 6.65 (q, J=9.8, 8.1 Hz, 1H), 6.44 (d, J=8.5 Hz, 1H), 6.41-6.26 (m, 2H), 4.37 (d, J=6.1 Hz, 2H), 2.19 (s, 1H), 0.86-0.69 (m, 4H).
MS(ESI+) m/z 403 (M+H)⁺

Example 599: Synthesis of (N-(4-(1-(1-((trifluoromethyl)sulfonyl)azetidin-3-yl)-1H-pyrazol-4-yl)-1H-pyrrolo[2,3-b]pyridin-6-yl)cyclopropanecarboxamide

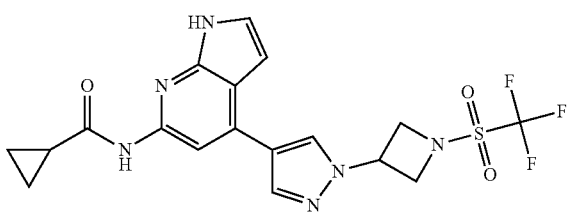 [SMILES: O=C(Nc1cc(-c2cnn(C3CN(S(=O)(=O)C(F)(F)F)C3)c2)c2cc[nH]c2n1)C1CC1]

Step 1) Synthesis of tert-butyl 3-(4-(6-(cyclopropanecarboxamido)-1-tosyl-1H-pyrrolo[2,3-b]pyridin-4-yl)-1H-pyrazol-1-yl)azetidin-1-carboxylate

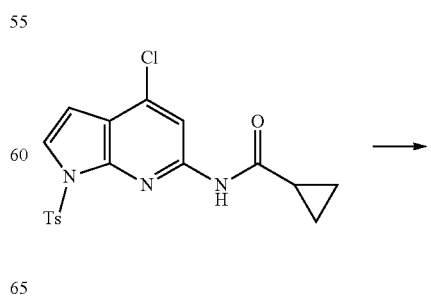

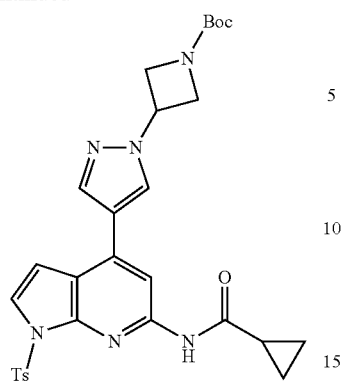

2.5 g (6.44 mmol) of the synthesized N-(4-chloro-1-tosyl-H-pyrrolo[2,3-b]pyridine-6-yl)cyclopropanecarboxamide was dissolved in DMF/H₂O=2:1 solution (50 mL), and then 2.5 g (7.1 mmol) of tert-butyl 3-(4-(4,4,5,5-tetramethyl-1,3,2-dioxaborolan-2-yl)-1H-pyrazol-1-yl)azetidin-1-carboxylate, 0.8 g (0.97 mmol) of Pd(dppf)Cl₂ and 1.6 g (7.7 mmol) of K₃PO₄ were inserted thereinto and stirred at 80-90° C. for 2 hours. Once the reaction was completed, the said mixture was cooled down at room temperature, and water and dilute hydrochloric acid were added thereto. After that, an extraction using ethyl acetate was performed at pH 4-5. Then, a solution extracted therefrom was dried by means of magnesium sulfate anhydrous and concentrated under reduced pressure, from which a residue was accordingly obtained. The residue was separated via silica gel column chromatography (n-hexane/ethyl acetate=1:1), and finally a mixture was accordingly obtained, wherein tert-butyl 3-(4-(6-(cyclopropanecarboxamido)-1-tosyl-1H-pyrrolo[2,3-b]pyridine-4-yl)-1H-pyrazol-1-yl)azetidin-1-carboxylate is a main product.

MS(ESI+) m/z 577 (M+H)⁺

Step 2) Synthesis of N-(4-(1-(azetidin-3-yl)-1H-pyrazol-4-yl)-1-tosyl-1H-pyrrolo[2,3-b]pyridine-6-yl)cyclopropanecarboxamide

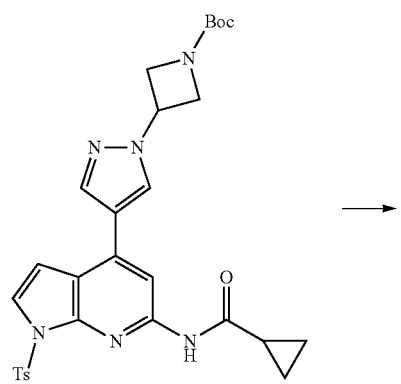

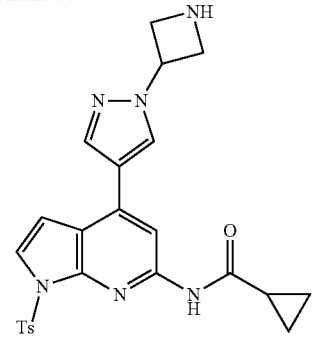

5 g of the said compound, i.e., tert-butyl 3-(4-(6-(cyclopropanecarboxamido)-1-tosyl-1H-pyrrolo[2,3-b]pyridine-4-yl)-1H-pyrazol-1-yl)azetidin-1-carboxylate was dissolved in dichloromethane (50 mL), and then TFA (5 mL) was inserted thereinto and stirred at room temperature for 2 hours. For the said compound, following steps were performed without a separate separation process:

MS(ESI+) m/z 477 (M+H)⁺

Step 3) Synthesis of N-(1-tosyl-4-(1-(1-((trifluoromethyl)sulfonyl)azetidin-3-yl)-1H-pyrazol-4-yl)-1H-pyrrolo[2,3-b]pyridin-6-yl)cyclopropanecarboxamide

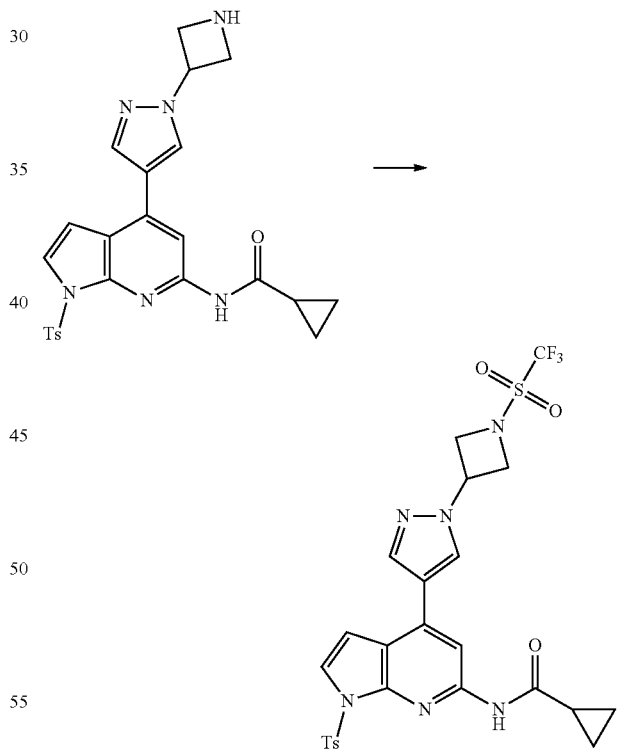

The synthesized N-(4-(1-(azetidin-3-yl)-1H-pyrazol-4-yl)-1-tosyl-1H-pyrrolo[2,3-b]pyridine-6-yl)cyclopropanecarboxamide (2 g) was dissolved in dichloromethane (20 mL), and then Et₃N (2 equivalent, 1.17 mL) was inserted thereinto and stirred. Trifluoromethanesulfonyl chloride (1.5 equivalent, 1.06 g) was inserted thereinto at 0° C. and stirred at room temperature for 2 hours, and finally 1.6 g of a compound, i.e., N-(1-tosyl-4-(1-(1-((trifluoromethyl)sulfonyl)azetidin-3-yl)-1H-pyrazol-4-yl)-1H-pyrrolo[2,3-b]pyridin-6-yl)cyclopropanecarboxamide (41%, a rolled throughput yield for step 3) was accordingly obtained.

MS(ESI+) m/z 609 (M+H)+

Step 4) Synthesis of N-(4-(1-(1-(((trifluoromethyl)sulfonyl)azetidin-3-yl)-1H-pyrazol-4-yl)-1H-pyrrolo[2,3-b]pyridin-6-yl)cyclopropanecarboxamide

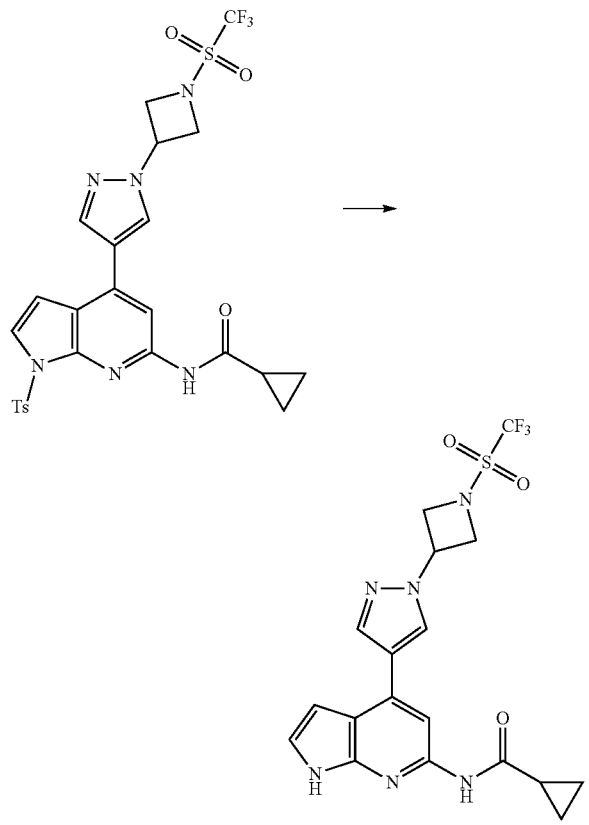

The synthesized N-(1-tosyl-4-(1-(1-(((trifluoromethyl)sulfonyl)azetidin-3-yl)-1H-pyrazol-4-yl)-1H-pyrrolo[2,3-b]pyridin-6-yl)cyclopropanecarboxamide was dissolved in 50 mL of MeOH/THF (2:1), and then 10 mL of 2N sodium hydroxide aqueous solution was added thereto and stirred at 30-40° C. for 4 hours. Once the reaction was completed, the said mixture was cooled down at room temperature, then dilute hydrochloric acid aqueous solution was added thereto, and then an extraction using dichloromethane was performed at pH-neutral. Then, a solution extracted therefrom was dried by means of magnesium sulfate anhydrous and concentrated under reduced pressure, from which a residue was accordingly obtained. After that, a prep. TLC (DCM:MeOH=30:1) method was applied to the residue. Finally a target compound of Example 599, i.e., N-(4-(1-(1-(((trifluoromethyl)sulfonyl)azetidin-3-yl)-1H-pyrazol-4-yl)-1H-pyrrolo[2,3-b]pyridin-6-yl)cyclopropanecarboxamide was accordingly obtained.

$^1$H NMR (400 MHz, DMSO-$d_6$) δ 11.45 (s, 1H), 10.53 (s, 1H), 8.55 (d, J=9.1 Hz, 1H), 8.20 (s, 1H), 8.07 (s, 1H), 7.47-7.35 (m, 1H), 6.82-6.70 (m, 1H), 5.68-5.55 (m, 1H), 4.71 (dt, J=7.2, 15.1 Hz, 4H), 2.06 (d, J=18.0 Hz, 1H), 0.88-0.76 (m, 4H).

MS(ESI+) m/z 455 (M+H)+

Examples 600 to 611

Hereinafter, in Examples 600 to 611, a corresponding compound was synthesized by means of the same method as shown in Example 599 or by means of an appropriate reactant under the consideration of the reaction formula 1 as well as a structure of the compound to be prepared.

Example 600: Synthesis of N-(4-(1-(azetidin-3-yl)-1H-pyrazol-4-yl)-1H-pyrrolo[2,3-b]pyridin-6-yl)cyclopropanecarboxamide

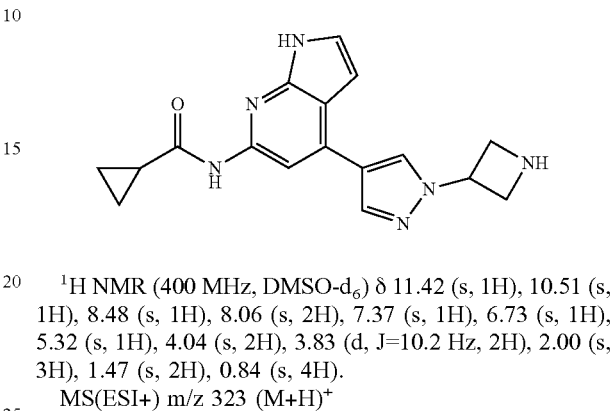

$^1$H NMR (400 MHz, DMSO-$d_6$) δ 11.42 (s, 1H), 10.51 (s, 1H), 8.48 (s, 1H), 8.06 (s, 2H), 7.37 (s, 1H), 6.73 (s, 1H), 5.32 (s, 1H), 4.04 (s, 2H), 3.83 (d, J=10.2 Hz, 2H), 2.00 (s, 3H), 1.47 (s, 2H), 0.84 (s, 4H).

MS(ESI+) m/z 323 (M+H)+

Example 601: Synthesis of N-(4-(1-(1-(ethylsulfonyl)azetidin-3-yl)-1H-pyrazol-4-yl)-1H-pyrrolo[2,3-b]pyridin-6-yl)cyclopropanecarboxamide

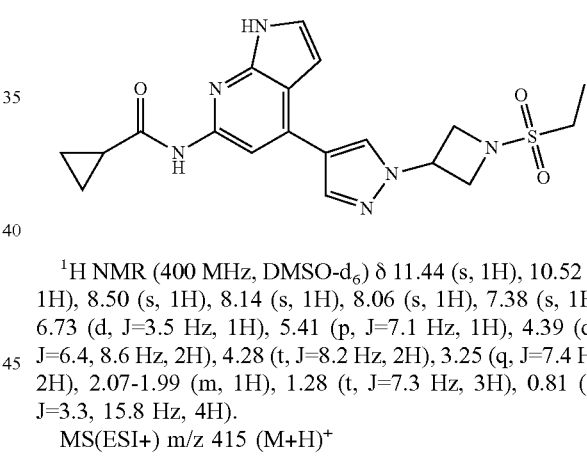

$^1$H NMR (400 MHz, DMSO-$d_6$) δ 11.44 (s, 1H), 10.52 (s, 1H), 8.50 (s, 1H), 8.14 (s, 1H), 8.06 (s, 1H), 7.38 (s, 1H), 6.73 (d, J=3.5 Hz, 1H), 5.41 (p, J=7.1 Hz, 1H), 4.39 (dd, J=6.4, 8.6 Hz, 2H), 4.28 (t, J=8.2 Hz, 2H), 3.25 (q, J=7.4 Hz, 2H), 2.07-1.99 (m, 1H), 1.28 (t, J=7.3 Hz, 3H), 0.81 (dt, J=3.3, 15.8 Hz, 4H).

MS(ESI+) m/z 415 (M+H)+

Example 602: Synthesis of N-(4-(1-(1-(butylsulfonyl)azetidin-3-yl)-1H-pyrazol-4-yl)-1H-pyrrolo[2,3-b]pyridin-6-yl)cyclopropanecarboxamide

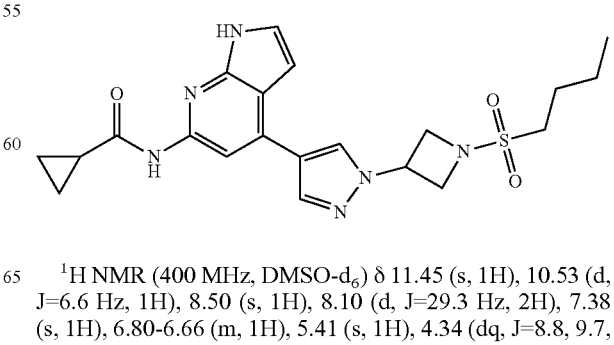

$^1$H NMR (400 MHz, DMSO-$d_6$) δ 11.45 (s, 1H), 10.53 (d, J=6.6 Hz, 1H), 8.50 (s, 1H), 8.10 (d, J=29.3 Hz, 2H), 7.38 (s, 1H), 6.80-6.66 (m, 1H), 5.41 (s, 1H), 4.34 (dq, J=8.8, 9.7, 40.3 Hz, 4H), 3.27-3.19 (m, 2H), 2.04 (s, 1H), 1.71 (d, J=10.7 Hz, 2H), 1.52-1.39 (m, 2H), 1.03-0.89 (m, 4H), 0.82 (s, 4H).
MS(ESI+) m/z 443 (M+H)+

Example 603: Synthesis of N-(4-(1-(1-(methylsulfonyl)azetidin-3-yl)-1H-pyrazol-4-yl)-1H-pyrrolo[2,3-b]pyridin-6-yl)cyclopropanecarboxamide

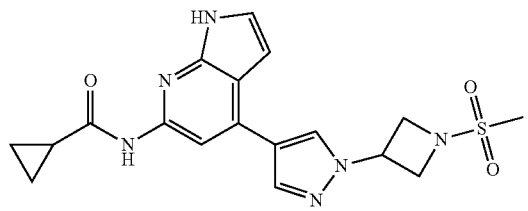 [SMILES: CS(=O)(=O)N1CC(n2cc(-c3cc(NC(=O)C4CC4)nc4[nH]ccc34)cn2)C1]

$^1$H NMR (400 MHz, DMSO-d$_6$) δ 11.44 (s, 1H), 10.53 (s, 1H), 8.52 (s, 1H), 8.10 (d, J=31.4 Hz, 2H), 7.38 (s, 1H), 6.74 (s, 1H), 5.50-5.31 (m, 1H), 4.33 (dd, J=8.8, 16.6 Hz, 4H), 3.15 (p, J=6.0 Hz, 3H), 2.03 (s, 1H), 0.83 (d, J=6.3 Hz, 4H).
MS(ESI+) m/z 401 (M+H)+

Example 604: Synthesis of N-(4-(1-(1-(phenylsulfonyl)azetidin-3-yl)-1H-pyrazol-4-yl)-1H-pyrrolo[2,3-b]pyridin-6-yl)cyclopropanecarboxamide

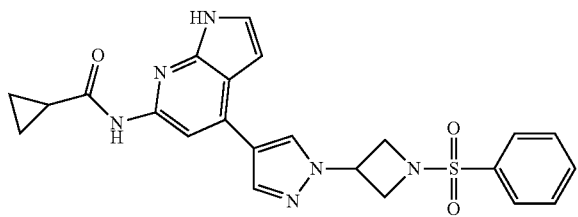 [SMILES: O=C(Nc1cc(-c2cnn(C3CN(S(=O)(=O)c4ccccc4)C3)c2)c2cc[nH]c2n1)C1CC1]

$^1$H NMR (400 MHz, DMSO-d$_6$) δ 11.42 (s, 1H), 10.51 (s, 1H), 8.21 (s, 1H), 8.03-7.86 (m, 4H), 7.76 (q, J=8.2, 14.4 Hz, 3H), 7.36 (s, 1H), 6.62 (s, 1H), 5.24 (s, 1H), 4.18 (dt, J=9.0, 38.6 Hz, 4H), 2.03 (s, 1H), 0.88-0.73 (m, 4H).
MS(ESI+) m/z 463 (M+H)+

Example 605: Synthesis of N-(4-(1-(1-((3,4-difluorophenyl)sulfonyl)azetidin-3-yl)-1H-pyrazol-4-yl)-1H-pyrrolo[2,3-b]pyridin-6-yl)cyclopropanecarboxamide

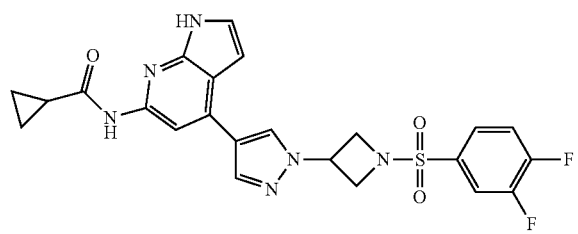 [SMILES: O=C(Nc1cc(-c2cnn(C3CN(S(=O)(=O)c4ccc(F)c(F)c4)C3)c2)c2cc[nH]c2n1)C1CC1]

$^1$H NMR (400 MHz, DMSO-d$_6$) δ 11.43 (s, 1H), 10.51 (s, 1H), 8.31 (s, 1H), 7.98 (d, J=21.8 Hz, 2H), 7.75 (d, J=12.9 Hz, 2H), 7.48 (s, 1H), 7.36 (s, 1H), 6.64 (s, 1H), 5.23 (s, 1H), 4.19 (d, J=24.7 Hz, 4H), 3.96 (s, 3H), 2.02 (s, 1H), 0.80 (d, J=15.3 Hz, 4H).
MS(ESI+) m/z 499 (M+H)+

Example 606: Synthesis of N-(4-(1-(1-(cyclohexylsulfonyl)azetidin-3-yl)-1H-pyrazol-4-yl)-1H-pyrrolo[2,3-b]pyridin-6-yl)cyclopropanecarboxamide

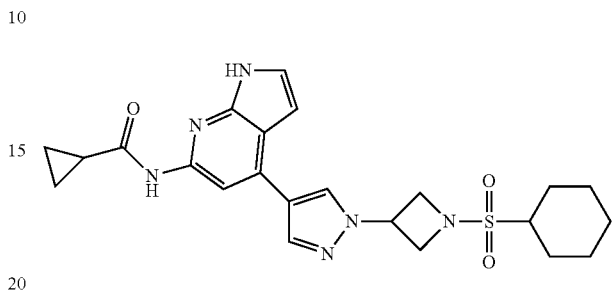

$^1$H NMR (400 MHz, DMSO-d$_6$) δ 11.44 (s, 1H), 10.52 (s, 1H), 8.49 (s, 1H), 8.11 (d, J=31.0 Hz, 2H), 7.44-7.30 (m, 1H), 6.73 (s, 1H), 5.40 (d, J=9.8 Hz, 1H), 4.44-4.15 (m, 4H), 3.11 (s, 1H), 2.08 (d, J=12.9 Hz, 3H), 1.80 (d, J=11.5 Hz, 2H), 1.64 (s, 1H), 1.27 (dd, J=35.0, 51.6 Hz, 7H), 0.81 (d, J=16.2 Hz, 4H).
MS(ESI+) m/z 469 (M+H)+

Example 607: Synthesis of N-(4-(1-(1-(methylsulfonyl)piperidin-4-yl)-1H-pyrazol-4-yl)-1H-pyrrolo[2,3-b]pyridin-6-yl)cyclopropanecarboxamide

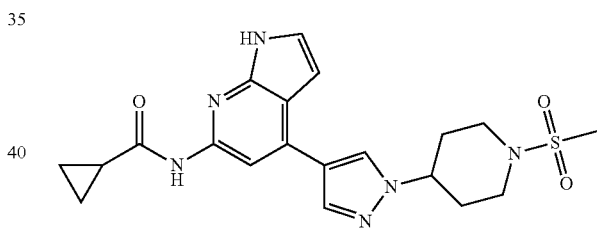

$^1$H NMR (400 MHz, DMSO-d$_6$) δ 11.40 (s, 1H), 10.50 (s, 1H), 8.43 (s, 1H), 8.02 (d, J=16.4 Hz, 2H), 7.36 (s, 1H), 6.75 (s, 1H), 4.44 (s, 1H), 3.70 (d, J=11.9 Hz, 2H), 2.95 (d, J=6.9 Hz, 5H), 2.27-1.98 (m, 6H), 0.86-0.75 (m, 4H).
MS(ESI+) m/z 429 (M+H)+

Example 608: Synthesis of N-(4-(1-(1-(ethylsulfonyl)piperidin-4-yl)-1H-pyrazol-4-yl)-1H-pyrrolo[2,3-b]pyridin-6-yl)cyclopropanecarboxamide

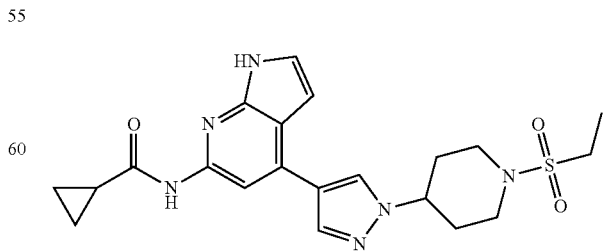

$^1$H NMR (400 MHz, DMSO-d$_6$) δ 11.40 (s, 1H), 10.49 (s, 1H), 8.42 (s, 1H), 8.02 (d, J=16.8 Hz, 2H), 7.42-7.32 (m,

1H), 6.75 (d, J=3.2 Hz, 1H), 4.44 (d, J=12.9 Hz, 1H), 3.74 (d, J=12.2 Hz, 2H), 3.07 (ddd, J=8.6, 13.4, 31.8 Hz, 4H), 2.20-1.96 (m, 5H), 1.24 (t, J=7.3 Hz, 3H), 0.80 (d, J=17.7 Hz, 4H).

MS(ESI+) m/z 443 (M+H)+

Example 609: Synthesis of N-(4-(1-(1-((trifluoromethyl)sulfonyl)piperidin-4-yl)-1H-pyrazol-4-yl)-1H-pyrrolo[2,3-b]pyridin-6-yl)cyclopropanecarboxamide

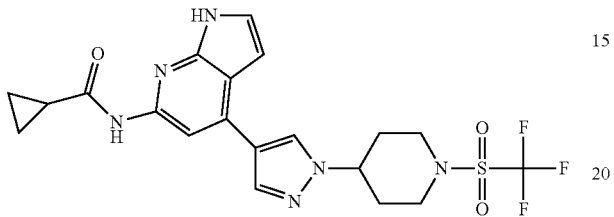

¹H NMR (400 MHz, DMSO-d₆) δ 11.41 (s, 1H), 10.50 (s, 1H), 8.41 (d, J=34.0 Hz, 1H), 8.03 (d, J=12.2 Hz, 2H), 7.36 (s, 1H), 6.75 (s, 1H), 3.94 (d, J=13.2 Hz, 2H), 2.90 (d, J=12.4 Hz, 1H), 2.26-1.99 (m, 6H), 0.86-0.76 (m, 4H).

MS(ESI+) m/z 483 (M+H)+

Example 610: Synthesis of N-(4-(1-(1-(2-cyanoacetyl)azetidin-3-yl)-1H-pyrazol-4-yl)-1H-pyrrolo[2,3-b]pyridin-6-yl)cyclopropanecarboxamide

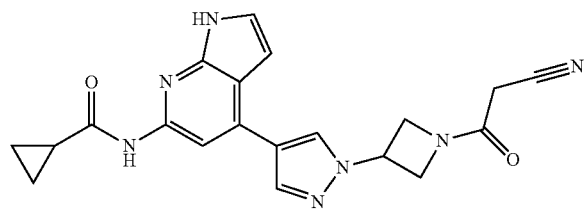 [SMILES: N#CCC(=O)N1CC(n2cc(-c3cc(NC(=O)C4CC4)nc4[nH]ccc34)cn2)C1]

¹H NMR (400 MHz, DMSO-d₆) δ 11.43 (s, 1H), 10.52 (s, 1H), 8.56 (s, 1H), 8.12 (s, 1H), 8.07 (s, 1H), 7.38 (t, J=3.0 Hz, 1H), 6.77-6.71 (m, 1H), 5.41 (t, J=6.7 Hz, 1H), 4.64 (t, J=8.6 Hz, 1H), 4.56-4.49 (m, 1H), 4.41 (t, J=9.3 Hz, 1H), 4.28 (dd, J=10.2, 5.4 Hz, 1H), 3.84 (d, J=3.5 Hz, 2H), 2.04-1.96 (m, 1H), 0.84-0.77 (m, 4H).

MS(ESI+) m/z 390 (M+H)+

Example 611: Synthesis of N-(4-(1-(1-(cyanomethyl)piperidin-4-yl)-1H-pyrazol-4-yl)-1H-pyrrolo[2,3-b]pyridin-6-yl)cyclopropanecarboxamide

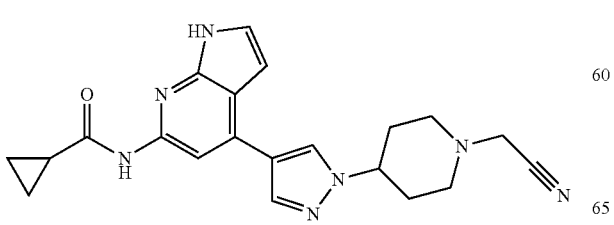

¹H NMR (400 MHz, DMSO-d₆) δ 11.39 (s, 1H), 10.49 (s, 1H), 8.39 (s, 1H), 8.01 (d, J=19.9 Hz, 3H), 7.39-7.30 (m, 1H), 6.73 (s, 1H), 4.44-4.18 (m, 2H), 2.93 (d, J=11.1 Hz, 4H), 2.37 (s, 3H), 2.09 (d, J=8.3 Hz, 7H), 0.80 (d, J=18.3 Hz, 7H).

MS(ESI+) m/z 390 (M+H)+

Example 612: Synthesis of N-(4-(1-(3-(cyanomethyl)oxetan-3-yl)-1,2,3,6-tetrahydropyridin-4-yl)-1H-pyrrolo[2,3-b]pyridine-6-yl) cyclopropanecarboxamide

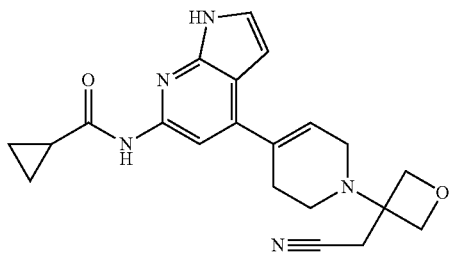 [SMILES: N#CCC1(N2CC=C(c3cc(NC(=O)C4CC4)nc4[nH]ccc34)CC2)COC1]

1.0 g (3.5 mmol) of the above synthesized N-(4-(1,2,3,6-tetrahydropyridine-4-yl)-1H-pyrrolo[2,3-b]pyridine-6-yl) cyclopropanecarboxamide was dissolved in acetonitrile, and then 0.4 g (3.9 mmol) of 2-(oxetan-3-ylidene)acetonitrile and 1.6 g (10.5 mmol) of DBU were inserted thereinto and stirred at 30-40° C. for 16 hours. Once the reaction was completed, the said mixture was cooled down at room temperature, then water was added thereto, and then an extraction using ethyl acetate was performed. After that, a solution extracted therefrom was dried by means of magnesium sulfate anhydrous and concentrated under reduced pressure, from which a residue was accordingly obtained. The residue was separated via silica gel column chromatography (DCM/MeOH=30:1), and finally N-(4-(1-(3-(cyanomethyl)oxetan-3-yl)-1,2,3,6-tetrahydropyridin-4-yl)-1H-pyrrolo[2,3-b]pyridine-6-yl) cyclopropanecarboxamide was accordingly obtained.

MS(ESI+) m/z 378 (M+H)+

Examples 613 to 628

Hereinafter, in Examples 613 to 628, a corresponding compound was synthesized by means of the same method as shown in Example 612 or by means of an appropriate reactant under the consideration of the reaction formula 1 as well as a structure of the compound to be prepared.

Example 613: Synthesis of N-(4-(1-(3-(cyanomethyl)oxetan-3-yl)-3-methyl-1,2,3,6-tetrahydropyridin-4-yl)-1H-pyrrolo[2,3-b]pyridin-6-yl)cyclopropanecarboxamide

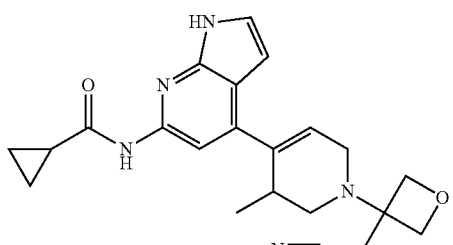

¹H NMR (400 MHz, DMSO-d₆) δ 11.40 (s, 1H), 10.54 (s, 1H), 7.81 (s, 1H), 7.35-7.26 (m, 1H), 6.46 (d, J=3.8 Hz, 1H), 6.09 (s, 1H), 4.64 (d, J=6.6 Hz, 1H), 4.53 (d, J=6.6 Hz, 1H), 4.43 (t, J=7.0 Hz, 2H), 3.27 (d, J=18.0 Hz, 1H), 3.15 (d, J=17.0 Hz, 1H), 3.08 (d, J=3.8 Hz, 2H), 2.96 (s, 1H), 2.76-2.65 (m, 2H), 2.40 (dd, J=4.6, 11.2 Hz, 1H), 2.02 (s, 1H), 0.91 (d, J=6.9 Hz, 3H), 0.81-0.76 (m, 4H).

MS(ESI+) m/z 392 (M+H)⁺

Example 614: Synthesis of tert-butyl 3-(cyanomethyl)-3-(4-(6-(cyclopropanecarboxamido)-1H-pyrrolo[2,3-b]pyridin-4-yl)-3,6-dihydropyridin-1 (2H)-yl)azetidine-1-carboxylate

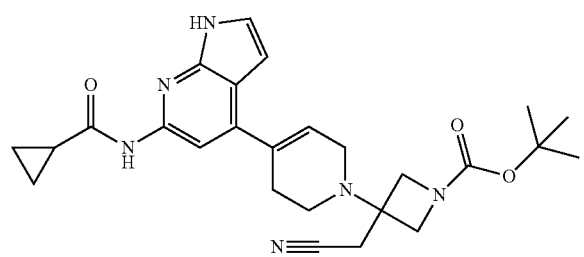 [SMILES: CC(C)(C)OC(=O)N1CC(CC#N)(N2CC=C(c3cc(NC(=O)C4CC4)nc4[nH]ccc34)CC2)C1]

¹H NMR (400 MHz, DMSO-d₆) δ 11.42 (s, 1H), 10.53 (s, 1H), 7.85 (s, 1H), 7.33 (t, J=3.0 Hz, 1H), 6.53 (dd, J=3.6, 1.8 Hz, 1H), 6.31 (d, J=3.9 Hz, 1H), 3.83 (d, J=35.4 Hz, 4H), 3.29-3.21 (m, 2H), 3.03 (s, 2H), 2.72-2.62 (m, 2H), 2.55 (s, 2H), 2.08-1.96 (m, 1H), 1.39 (s, 9H), 0.82-0.75 (m, 4H).

MS(ESI+) m/z 477 (M+H)⁺

Example 615: Synthesis of N-(4-(1-(3-(cyanomethyl)azetidin-3-yl)-1,2,3,6-tetrahydropyridin-4-yl)-1H-pyrrolo[2,3-b]pyridin-6-yl)cyclopropanecarboxamide

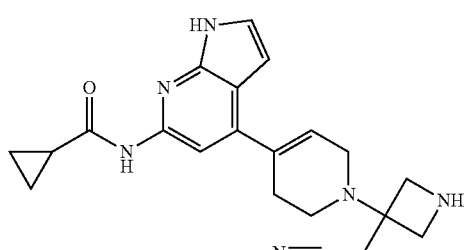

¹H NMR (400 MHz, DMSO-d₆) δ 11.44 (s, 1H), 10.55 (s, 1H), 7.86 (s, 1H), 7.34 (t, J=3.1 Hz, 1H), 6.53 (d, J=2.6 Hz, 1H), 6.35 (s, 1H), 3.89 (d, J=10.4 Hz, 2H), 3.76 (d, J=10.4 Hz, 2H), 3.09 (s, 2H), 2.75 (t, J=5.4 Hz, 2H), 2.58 (s, 2H), 2.02 (s, 1H), 0.87-0.73 (m, 4H).

MS(ESI+) m/z 377 (M+H)⁺

Example 616: Synthesis of N-(4-(1-(3-(cyanomethyl)-1-(ethylsulfonyl)azetidin-3-yl)-1,2,3,6-tetrahydropyridin-4-yl)-1H-pyrrolo[2,3-b]pyridin-6-yl)cyclopropanecarboxamide

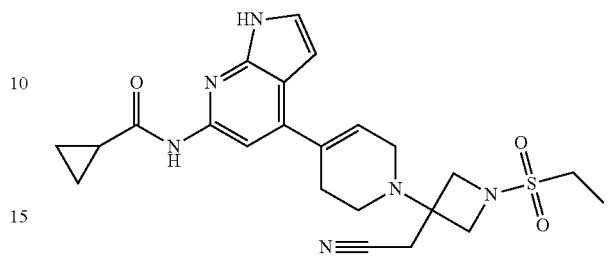

¹H NMR (400 MHz, DMSO-d₆) δ 11.42 (s, 1H), 10.53 (s, 1H), 7.86 (s, 1H), 7.33 (t, J=3.0 Hz, 1H), 6.54 (t, J=2.7 Hz, 1H), 6.33 (d, J=3.4 Hz, 1H), 4.00 (d, J=8.2 Hz, 2H), 3.75 (d, J=8.2 Hz, 2H), 3.28 (d, J=3.3 Hz, 2H), 3.17 (q, J=7.3 Hz, 2H), 3.11 (s, 2H), 2.70 (t, J=5.4 Hz, 2H), 2.55 (s, 2H), 2.06-1.96 (m, 1H), 1.25 (t, J=7.3 Hz, 3H), 0.82-0.75 (m, 4H).

MS(ESI+) m/z 469 (M+H)⁺

Example 617: Synthesis of N-(4-(1-(3-(cyanomethyl)-1-(isopropylsulfonyl)azetidin-3-yl)-1,2,3,6-tetrahydropyridin-4-yl)-1H-pyrrolo[2,3-b]pyridin-6-yl)cyclopropanecarboxamide

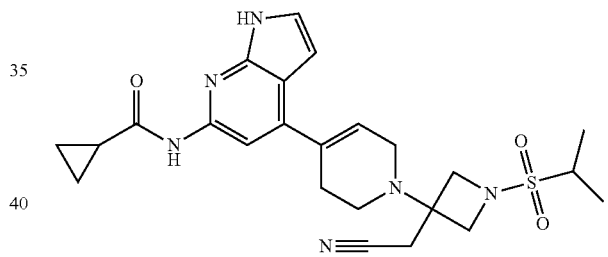

¹H NMR (400 MHz, DMSO-d₆) δ 11.42 (s, 1H), 10.53 (s, 1H), 7.85 (s, 1H), 7.36-7.29 (m, 1H), 6.54 (dd, J=3.5, 1.9 Hz, 1H), 6.32 (s, 1H), 4.01 (d, J=7.9 Hz, 2H), 3.72 (d, J=7.9 Hz, 2H), 3.24 (s, 2H), 3.10 (s, 2H), 2.67 (d, J=6.0 Hz, 2H), 2.02 (s, 1H), 1.26 (d, J=6.8 Hz, 6H), 1.17 (s, 1H), 0.80 (q, J=3.4 Hz, 4H).

MS(ESI+) m/z 483 (M+H)⁺

Example 618: Synthesis of N-(4-(1-(3-(cyanomethyl)-1-((3-cyanopropyl)sulfonyl)azetidin-3-yl)-1,2,3,6-tetrahydropyridin-4-yl)-1H-pyrrolo[2,3-b]pyridin-6-yl)cyclopropanecarboxamide

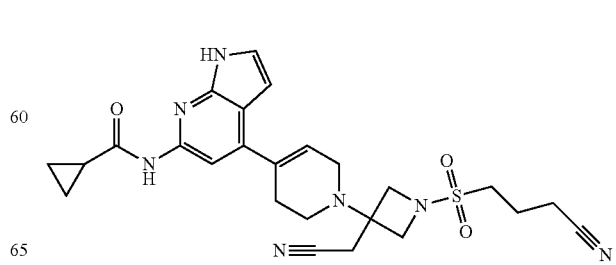

¹H NMR (400 MHz, DMSO-d₆) δ 11.43 (s, 1H), 10.53 (s, 1H), 7.86 (s, 1H), 7.34 (t, J=2.9 Hz, 1H), 6.54 (dt, J=5.0, 2.5 Hz, 1H), 6.32 (s, 1H), 4.00 (s, 1H), 3.78 (d, J=8.2 Hz, 1H), 3.29 (d, J=6.3 Hz, 2H), 3.14 (d, J=12.4 Hz, 2H), 2.71 (d, J=7.1 Hz, 2H), 2.66 (t, J=7.3 Hz, 2H), 2.56 (s, 2H), 2.02 (d, J=7.5 Hz, 2H), 0.82-0.74 (m, 4H).

MS(ESI+) m/z 508 (M+H)⁺

Example 619: Synthesis of N-(4-(1-(3-(cyanomethyl)-1-((trifluoromethyl)sulfonyl)azetidin-3-yl)-1,2,3,6-tetrahydropyridin-4-yl)-1H-pyrrolo[2,3-b]pyridin-6-yl)cyclopropanecarboxamide

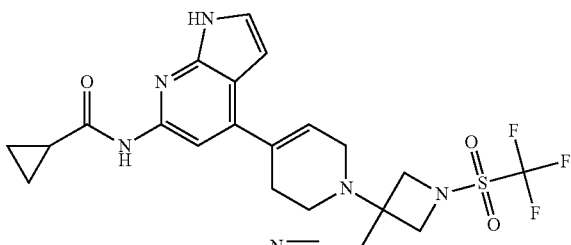

¹H NMR (400 MHz, DMSO-d₆) δ 11.43 (s, 1H), 10.54 (s, 1H), 7.86 (s, 1H), 7.34 (t, J=3.0 Hz, 1H), 6.54 (dd, J=3.6, 1.9 Hz, 1H), 6.32 (d, J=3.8 Hz, 1H), 4.35-4.18 (m, 4H), 3.29 (d, J=3.4 Hz, 2H), 3.15 (s, 2H), 2.71 (t, J=5.5 Hz, 2H), 2.57 (s, 2H), 2.01 (d, J=7.5 Hz, 1H), 0.83-0.77 (m, 4H).

MS(ESI+) m/z 509 (M+H)⁺

Example 620: Synthesis of N-(4-(1-(3-(cyanomethyl)-1-(piperidin-4-yl)azetidin-3-yl)-1,2,3,6-tetrahydropyridin-4-yl)-1H-pyrrolo[2,3-b]pyridin-6-yl)cyclopropanecarboxamide

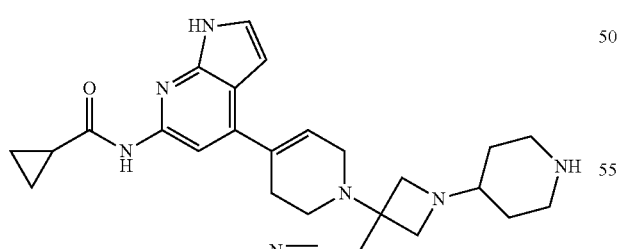

¹H NMR (400 MHz, DMSO-d₆) δ 11.57 (s, 1H), 11.00 (s, 1H), 9.45 (s, 1H), 8.77 (s, 1H), 7.80 (s, 1H), 7.39 (s, 1H), 6.59 (s, 1H), 6.39 (s, 1H), 4.15 (d, J=10.7 Hz, 2H), 3.70-3.58 (m, 2H), 3.56 (s, 1H), 3.54-3.46 (m, 2H), 3.46-3.33 (m, 2H), 2.97 (s, 2H), 2.84 (dd, J=22.8, 10.4 Hz, 2H), 2.67 (s, 2H), 2.18-1.93 (m, 3H), 1.88-1.68 (m, 2H), 0.83 (m, 4H).

MS(ESI+) m/z 460 (M+H)⁺

Example 621: Synthesis of N-(4-(1-(3-(cyanomethyl)-1-(1-(4-(trifluoromethyl)thiazole-2-carbonyl)piperidin-4-yl)azetidin-3-yl)-1,2,3,6-tetrahydropyridin-4-yl)-1H-pyrrolo[2,3-b]pyridin-6-yl)cyclopropanecarboxamide

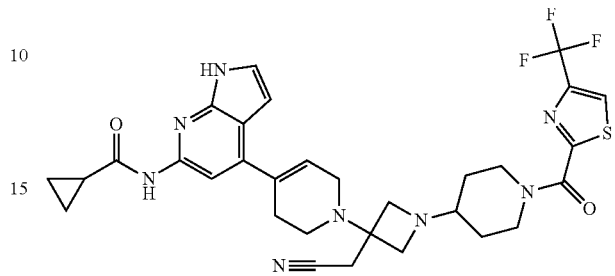

¹H NMR (400 MHz, DMSO-d₆) δ 11.41 (s, 1H), 10.52 (s, 1H), 8.77 (s, 1H), 7.85 (s, 1H), 7.38-7.30 (m, 1H), 6.53 (s, 1H), 6.33 (s, 1H), 4.47-4.44 (m, 1H), 3.98-3.97 (m, 1H), 3.83-3.78 (m, 1H), 3.31-3.21 (m, 4H), 3.15-3.02 (m, 4H), 2.72 (m, 2H), 2.03-1.96 (m, 1H), 1.78-1.69 (m, 2H), 1.38-1.26 (m, 2H) 0.79 (dd, J=9.4, 6.2 Hz, 4H).

MS(ESI+) m/z 639 (M+H)⁺

Example 622: Synthesis of N-(4-(1-(1-(1-(2-cyanoacetyl)piperidin-4-yl)-3-(cyanomethyl)azetidin-3-yl)-1,2,3,6-tetrahydropyridin-4-yl)-1H-pyrrolo[2,3-b]pyridin-6-yl)cyclopropanecarboxamide

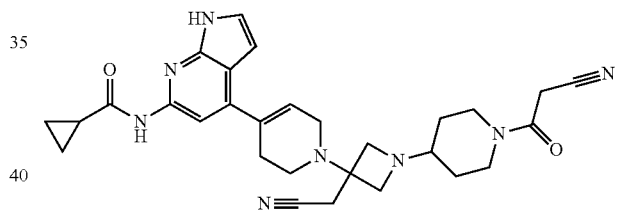

¹H NMR (400 MHz, DMSO-d₆) δ 11.42 (s, 1H), 10.53 (s, 1H), 7.84 (s, 1H), 7.33 (d, J=3.3 Hz, 1H), 6.53 (s, 1H), 6.32 (s, 1H), 4.02 (s, 2H), 3.90-3.18 (m, 1H), 3.52 (m, 1H), 3.30-3.18 (m, 4H), 3.16-2.93 (m, 5H), 2.80-2.63 (m, 2H), 2.43-2.25 (m, 2H), 2.07-1.93 (m, 1H), 1.71-1.53 (m, 2H), 1.19-1.05 (m, 2H), 0.85-0.77 (m, 4H).

MS(ESI+) m/z 527 (M+H)⁺

Example 623: Synthesis of N-(4-(1-(3-(cyanomethyl)-1-((4-fluorophenyl)sulfonyl)azetidin-3-yl)-1,2,3,6-tetrahydropyridin-4-yl)-1H-pyrrolo[2,3-b]pyridin-6-yl)cyclopropanecarboxamide

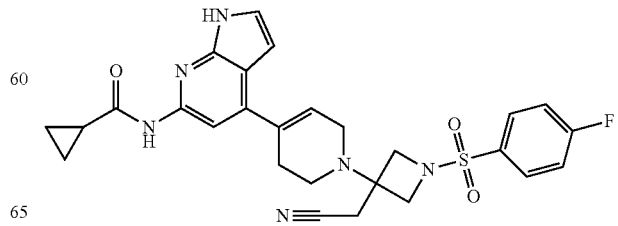

¹H NMR (400 MHz, DMSO-d₆) δ 11.41 (s, 1H), 10.52 (s, 1H), 7.98-7.91 (m, 2H), 7.81 (s, 1H), 7.50-7.42 (m, 2H), 7.33 (dd, J=3.5, 2.4 Hz, 1H), 6.48 (dd, J=3.5, 1.9 Hz, 1H), 6.18 (d, J=3.2 Hz, 1H), 3.76 (s, 4H), 3.07 (d, J=3.5 Hz, 2H), 2.96 (s, 2H), 2.33 (s, 2H), 2.01 (d, J=4.9 Hz, 1H), 0.79 (dt, J=11.0, 3.5 Hz, 4H).

MS(ESI+) m/z 535 (M+H)⁺

Example 624: Synthesis of 3-(cyanomethyl)-3-(4-(6-(cyclopropanecarboxamido)-1H-pyrrolo[2,3-b]pyridin-4-yl)-3,6-dihydropyridin-1(2H)-yl)-N-(2,2,2-trifluoroethyl)azetidine-1-carboxamide

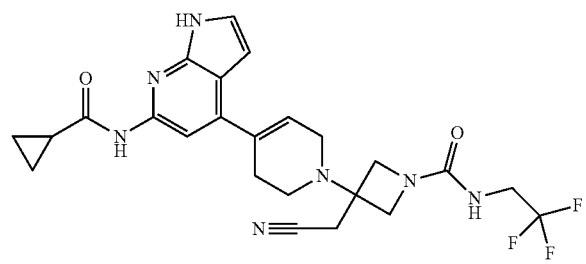 [SMILES: N#CCC1(N2CC=C(c3cc(NC(=O)C4CC4)nc4[nH]ccc34)CC2)CN(C(=O)NCC(F)(F)F)C1]

¹H NMR (400 MHz, DMSO-d₆) δ 11.42 (d, J=2.6 Hz, 1H), 10.53 (s, 1H), 7.85 (s, 1H), 7.33 (dd, J=3.5, 2.5 Hz, 1H), 6.53 (dd, J=3.6, 1.9 Hz, 1H), 6.34 (d, J=3.3 Hz, 1H), 4.25 (d, J=9.2 Hz, 1H), 4.12 (d, J=9.1 Hz, 1H), 3.93 (d, J=10.3 Hz, 1H), 3.83 (d, J=10.2 Hz, 1H), 3.41 (dd, J=11.3, 3.4 Hz, 2H), 3.10 (s, 2H), 2.75-2.66 (m, 2H), 2.55 (d, J=7.1 Hz, 2H), 2.01 (q, J=8.5, 6.4 Hz, 1H), 0.79 (ddd, J=11.3, 6.3, 2.6 Hz, 4H).

MS(ESI+) m/z 502 (M+H)⁺

Example 625: Synthesis of N-(4-(1-(3-(cyanomethyl)-1-(3,3,3-trifluoropropanoyl)azetidin-3-yl)-1,2,3,6-tetrahydropyridin-4-yl)-1H-pyrrolo[2,3-b]pyridin-6-yl)cyclopropanecarboxamide

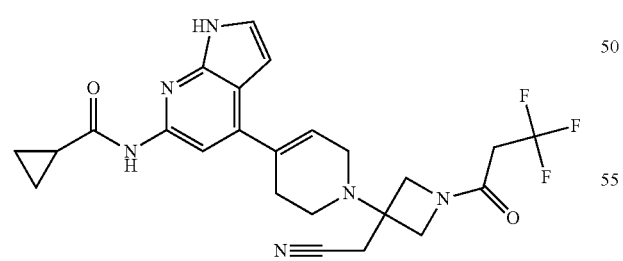

¹H NMR (400 MHz, DMSO-d₆) δ 11.44-11.35 (m, 1H), 10.53 (s, 1H), 7.85 (s, 1H), 7.36-7.27 (m, 1H), 7.17 (t, J=6.3 Hz, 1H), 6.55 (dd, J=3.9, 2.1 Hz, 1H), 6.33 (d, J=3.6 Hz, 1H), 3.88 (d, J=8.7 Hz, 2H), 3.83-3.72 (m, 4H), 3.08 (s, 2H), 2.69 (d, J=5.7 Hz, 2H), 2.56 (s, 2H), 2.02-1.97 (m, 1H), 0.81-0.75 (m, 4H).

MS(ESI+) m/z 487 (M+H)⁺

Example 626: Synthesis of N-(4-(1-(3-(cyanomethyl)-1-(ethylsulfonyl)azetidin-3-yl)-3-methyl-1,2,3,6-tetrahydropyridin-4-yl)-1H-pyrrolo[2,3-b]pyridin-6-yl)cyclopropanecarboxamide

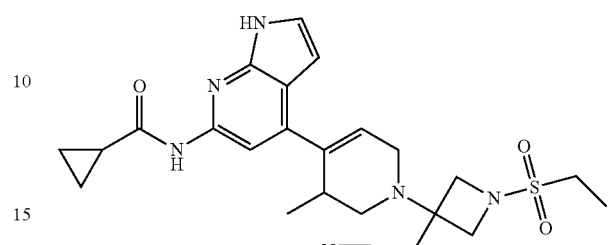

¹H NMR (400 MHz, Chloroform-d) δ 11.40 (s, 1H), 10.54 (s, 1H), 7.80 (s, 1H), 7.36-7.25 (m, 1H), 6.45 (dd, J=1.9, 3.5 Hz, 1H), 6.07 (s, 1H), 4.01 (dd, J=8.3, 13.4 Hz, 1H), 3.90 (d, J=8.3 Hz, 1H), 3.73 (dd, J=8.1, 11.7 Hz, 2H), 3.23-3.07 (m, 4H), 2.95 (s, 1H), 2.77-2.65 (m, 1H), 2.07 (s, 3H), 1.99 (d, J=6.5 Hz, 1H), 1.25-1.21 (m, 3H), 0.82-0.73 (m, 4H).

MS(ESI+) m/z 483 (M+H)⁺

Example 627: Synthesis of (S)—N-(4-(1-(3-(cyanomethyl)-1-(ethylsulfonyl)azetidin-3-yl)-3-methyl-1,2,3,6-tetrahydropyridin-4-yl)-1H-pyrrolo[2,3-b]pyridin-6-yl)cyclopropanecarboxamide

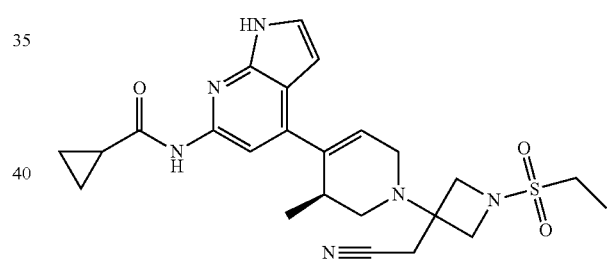

MS(ESI+) m/z 483 (M+H)⁺

Example 628: Synthesis of (S)—N-(4-(1-(3-(cyanomethyl)-1-((trifluoromethyl)sulfonyl)azetidin-3-yl)-3-methyl-1,2,3,6-tetrahydropyridin-4-yl)-1H-pyrrolo[2,3-b]pyridin-6-yl)cyclopropanecarboxamide

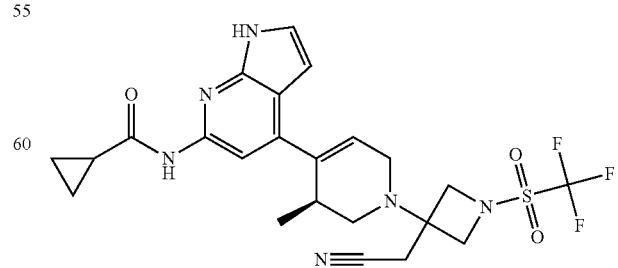

MS(ESI+) m/z 523 (M+H)⁺

Examples 629 to 644

Hereinafter, in Examples 629 to 644, a corresponding compound was synthesized by means of the same method as shown in Example 1 or by means of an appropriate reactant under the consideration of the reaction formula 1 as well as a structure of the compound to be prepared.

Example 629: Synthesis of 4-(6-(cyclopropanecarboxamido)-1H-pyrrolo[2,3-b]pyridin-4-yl)phenyl ethanesulfonate

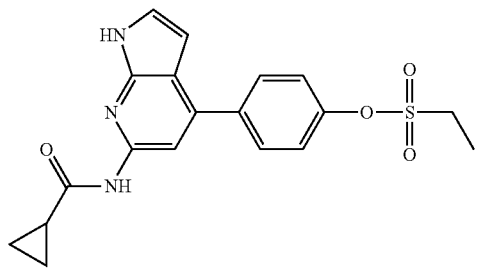 [SMILES: CCS(=O)(=O)Oc1ccc(-c2cc(NC(=O)C3CC3)nc3[nH]ccc23)cc1]

MS(ESI+) m/z 386 (M+H)+

Example 630: Synthesis of 4-(6-(cyclopropanecarboxamido)-1H-pyrrolo[2,3-b]pyridin-4-yl)phenyl 4-fluorobenzenesulfonate

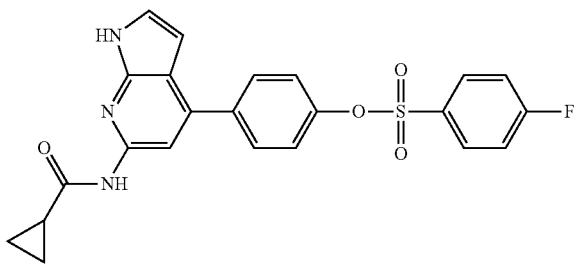 [SMILES: O=C(Nc1cc(-c2ccc(OS(=O)(=O)c3ccc(F)cc3)cc2)c2cc[nH]c2n1)C1CC1]

MS(ESI+) m/z 452 (M+H)+

Example 631: Synthesis of 4-(6-(cyclopropanecarboxamido)-1H-pyrrolo[2,3-b]pyridin-4-yl)phenyl propane-1-sulfonate

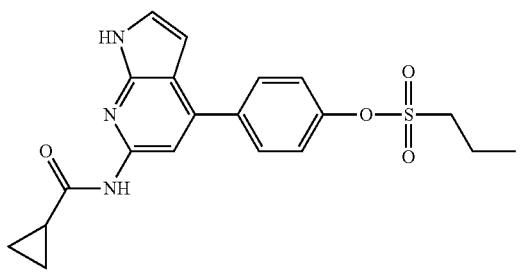 [SMILES: CCCS(=O)(=O)Oc1ccc(-c2cc(NC(=O)C3CC3)nc3[nH]ccc23)cc1]

$^1$H NMR (400 MHz, DMSO-d$_6$) δ 11.59 (s, 1H), 10.66 (s, 1H), 8.05 (s, 1H), 7.82 (d, J=8.1 Hz, 2H), 7.50 (d, J=8.1 Hz, 2H), 7.44 (s, 1H), 6.55 (s, 1H), 3.58 (t, J=7.6 Hz, 2H), 2.05 (s, 1H), 1.89 (q, J=8.0, 7.6 Hz, 2H), 1.06 (t, J=7.5 Hz, 3H), 0.89-0.74 (m, 4H).

MS(ESI+) m/z 400 (M+H)+

Example 632: Synthesis of 4-(6-(cyclopropanecarboxamido)-1H-pyrrolo[2,3-b]pyridin-4-yl)phenyl butane-1-sulfonate

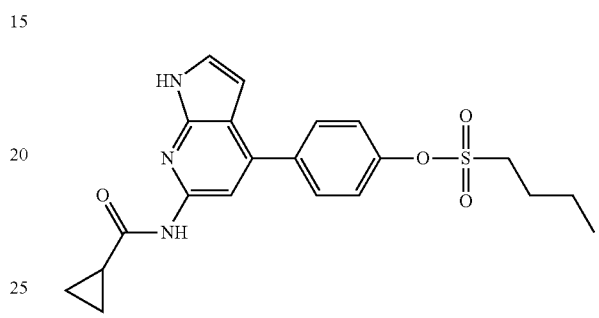

$^1$H NMR (400 MHz, DMSO-d$_6$) δ 11.59 (s, 1H), 10.66 (s, 1H), 8.04 (s, 1H), 7.91-7.74 (m, 2H), 7.50 (d, J=8.3 Hz, 2H), 7.44 (t, J=3.2 Hz, 1H), 6.54 (s, 1H), 3.67-3.53 (m, 2H), 2.05 (s, 1H), 1.84 (s, 2H), 1.48 (q, J=7.6 Hz, 2H), 0.93 (t, J=7.3 Hz, 3H), 0.86-0.72 (m, 4H).

MS(ESI+) m/z 414 (M+H)+

Example 633: Synthesis of 4-(6-(cyclopropanecarboxamido)-1H-pyrrolo[2,3-b]pyridin-4-yl)phenyl propane-2-sulfonate

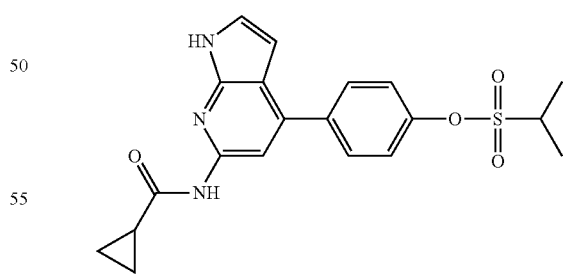

$^1$H NMR (400 MHz, DMSO-d$_6$) δ 11.59 (s, 1H), 10.66 (s, 1H), 8.04 (s, 1H), 7.82 (d, J=8.1 Hz, 2H), 7.49 (d, J=8.1 Hz, 2H), 7.44 (s, 1H), 6.60-6.50 (m, 1H), 3.87-3.73 (m, 1H), 2.05 (s, 1H), 1.47 (d, J=6.5 Hz, 6H), 0.89-0.72 (m, 4H).

MS(ESI+) m/z 400 (M+H)+

Example 634: Synthesis of 4-(6-(cyclopropanecarboxamido)-1H-pyrrolo[2,3-b]pyridin-4-yl)phenyl cyclohexanesulfonate

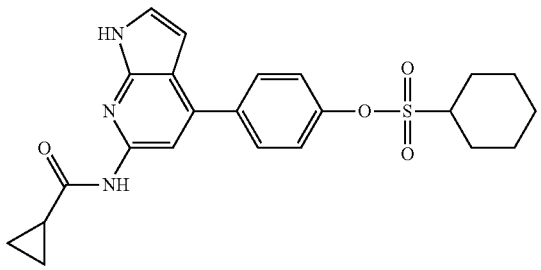 [SMILES: O=C(Nc1cc(-c2ccc(OS(=O)(=O)C3CCCCC3)cc2)c2cc[nH]c2n1)C1CC1]

¹H NMR (400 MHz, DMSO-d₆) δ 11.59 (s, 1H), 10.66 (s, 1H), 8.04 (s, 1H), 7.81 (d, J=8.3 Hz, 2H), 7.48 (d, J=8.3 Hz, 2H), 7.44 (s, 1H), 6.54 (s, 1H), 3.61 (s, 1H), 2.24 (d, J=12.1 Hz, 2H), 2.05 (s, 1H), 1.84 (d, J=12.8 Hz, 2H), 1.70-1.53 (m, 3H), 1.40 (d, J=13.4 Hz, 2H), 1.24 (t, J=12.9 Hz, 1H), 0.87-0.74 (m, 4H).

MS(ESI+) m/z 440 (M+H)⁺

Example 635: Synthesis of 4-(6-(cyclopropanecarboxamido)-1H-pyrrolo[2,3-b]pyridin-4-yl)phenyl 3-fluoropropane-1-sulfonate

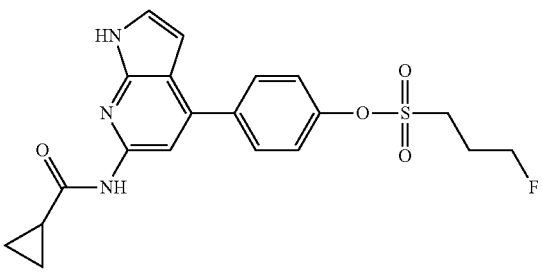 [SMILES: O=C(Nc1cc(-c2ccc(OS(=O)(=O)CCCF)cc2)c2cc[nH]c2n1)C1CC1]

¹H NMR (400 MHz, DMSO-d₆) δ 11.60 (s, 1H), 10.66 (s, 1H), 8.05 (s, 1H), 7.86-7.76 (m, 2H), 7.52 (d, J=8.2 Hz, 2H), 7.44 (d, J=3.4 Hz, 1H), 6.54 (s, 1H), 4.61 (dt, J=47.2, 6.0 Hz, 2H), 3.70 (t, J=7.7 Hz, 2H), 2.27 (d, J=25.7 Hz, 3H), 2.05 (s, 1H), 0.87-0.75 (m, 4H).

MS(ESI+) m/z 418 (M+H)⁺

Example 636: Synthesis of 4-(6-(cyclopropanecarboxamido)-1H-pyrrolo[2,3-b]pyridin-4-yl)phenyl prop-2-ene-1-sulfonate

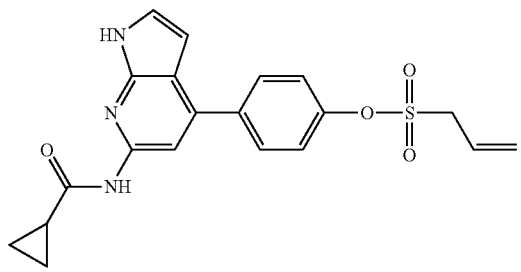 [SMILES: C=CCS(=O)(=O)Oc1ccc(-c2cc(NC(=O)C3CC3)nc3[nH]ccc23)cc1]

¹H NMR (400 MHz, DMSO-d₆) δ 11.60 (s, 1H), 10.66 (s, 1H), 8.05 (s, 1H), 7.82 (d, J=8.3 Hz, 2H), 7.57-7.47 (m, 2H), 7.45-7.38 (m, 1H), 6.60-6.45 (m, 1H), 5.95 (ddt, J=17.2, 10.3, 6.9 Hz, 1H), 5.58 (dd, J=31.7, 13.6 Hz, 2H), 4.44 (d, J=7.2 Hz, 2H), 2.04 (d, J=8.2 Hz, 1H), 0.82 (dt, J=10.0, 5.6 Hz, 4H).

MS(ESI+) m/z 398 (M+H)⁺

Example 637: Synthesis of 4-(6-(cyclopropanecarboxamido)-1H-pyrrolo[2,3-b]pyridin-4-yl)phenyl cyclohexylmethanesulfonate

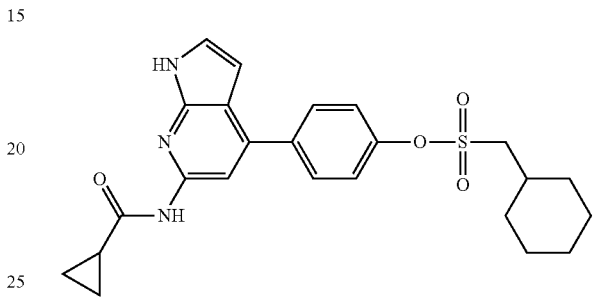

¹H NMR (400 MHz, DMSO-d₆) δ 11.59 (s, 1H), 10.66 (s, 1H), 8.04 (s, 1H), 7.82 (d, J=8.2 Hz, 2H), 7.50 (d, J=8.2 Hz, 2H), 7.44 (s, 1H), 6.54 (s, 1H), 3.51 (d, J=6.5 Hz, 2H), 2.04 (s, 2H), 1.92 (d, J=12.8 Hz, 2H), 1.69 (d, J=11.0 Hz, 2H), 1.63 (s, 1H), 1.26 (t, J=12.6 Hz, 2H), 1.20-1.07 (m, 3H), 0.80 (d, J=11.1 Hz, 4H).

MS(ESI+) m/z 454 (M+H)⁺

Example 638: Synthesis of 4-(6-(cyclopropanecarboxamido)-1H-pyrrolo[2,3-b]pyridin-4-yl)phenyl (tetrahydrofuran-3-yl)methanesulfonate

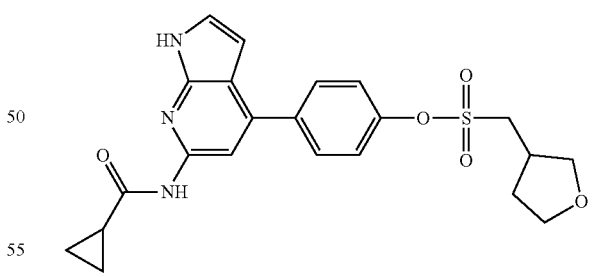

¹H NMR (400 MHz, DMSO-d₆) δ 11.59 (s, 1H), 10.66 (s, 1H), 8.04 (s, 1H), 7.82 (d, J=7.9 Hz, 2H), 7.52 (d, J=8.2 Hz, 2H), 7.44 (s, 1H), 6.54 (s, 1H), 3.92 (t, J=7.8 Hz, 1H), 3.77 (d, J=7.1 Hz, 3H), 3.68 (d, J=8.0 Hz, 1H), 2.17 (s, 1H), 2.05 (s, 1H), 1.76 (d, J=11.5 Hz, 1H), 1.15-1.03 (m, 1H), 0.82 (s, 4H).

MS(ESI+) m/z 442 (M+H)⁺

Example 639: Synthesis of 4-(6-(cyclopropanecarboxamido)-1H-pyrrolo[2,3-b]pyridin-4-yl)phenyl 3-cyanopropane-1-sulfonate

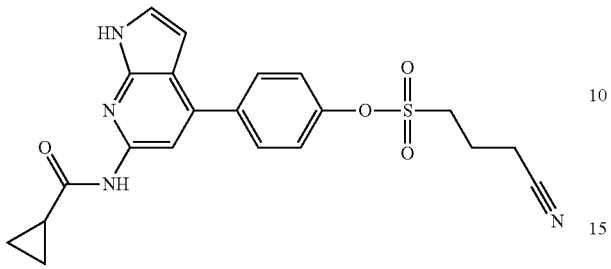

¹H NMR (400 MHz, DMSO-d₆) δ 11.60 (s, 1H), 10.66 (s, 1H), 8.05 (s, 1H), 7.83 (d, J=8.2 Hz, 2H), 7.54 (d, J=8.3 Hz, 2H), 7.44 (d, J=3.7 Hz, 1H), 6.54 (s, 1H), 3.69 (t, J=7.5 Hz, 2H), 2.73 (t, J=7.3 Hz, 2H), 2.21 (q, J=7.7 Hz, 2H), 2.05 (s, 1H), 0.85-0.76 (m, 4H).
MS(ESI+) m/z 425 (M+H)⁺

Example 640: Synthesis of 4-(1-(3-cyanopropyl)-6-(cyclopropanecarboxamido)-1H-pyrrolo[2,3-b]pyridin-4-yl)phenyl 3-cyanopropane-1-sulfonate

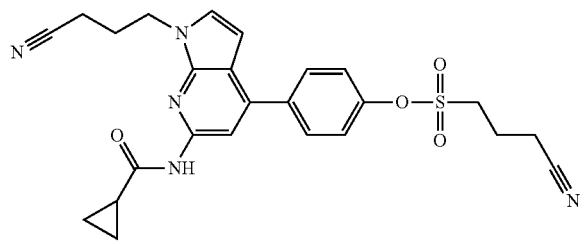 [SMILES: N#CCCCn1ccc2c(-c3ccc(OS(=O)(=O)CCCC#N)cc3)cc(NC(=O)C3CC3)nc21]

¹H NMR (400 MHz, DMSO-d₆) δ 10.94 (s, 1H), 8.28 (s, 1H), 7.82 (d, J=8.3 Hz, 2H), 7.69 (d, J=4.1 Hz, 1H), 7.57 (d, J=8.2 Hz, 2H), 6.86 (s, 1H), 4.12 (d, J=9.1 Hz, 2H), 3.71 (d, J=8.0 Hz, 2H), 2.72 (d, J=7.3 Hz, 2H), 2.63 (d, J=5.1 Hz, 2H), 2.20 (s, 2H), 1.92 (s, 1H), 1.83 (t, J=7.2 Hz, 2H), 0.85 (d, J=6.5 Hz, 4H).
MS(ESI+) m/z 492 (M+H)⁺

Example 641: Synthesis of N-(4-(4-((4-fluorobenzyl)oxy)phenyl)-1H-pyrrolo[2,3-b]pyridin-6-yl)cyclopropanecarboxamide

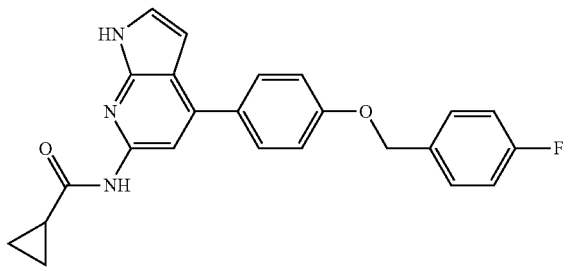 [SMILES: O=C(Nc1cc(-c2ccc(OCc3ccc(F)cc3)cc2)c2cc[nH]c2n1)C1CC1]

¹H NMR (400 MHz, Methanol-d₄) δ 11.49 (s, 1H), 10.58 (s, 1H), 7.99 (s, 1H), 7.75-7.63 (m, 2H), 7.55 (dd, J=5.6, 8.4 Hz, 2H), 7.38 (t, J=2.9 Hz, 1H), 7.29-7.13 (m, 5H), 6.52 (dd, J=1.7, 3.5 Hz, 1H), 2.13-1.87 (m, 2H), 0.82 (td, J=6.2, 12.0, 14.1 Hz, 5H).
MS(ESI+) m/z 402 (M+H)⁺

Example 642: Synthesis of N-(4-(4-(2-morpholinoethoxy)phenyl)-1H-pyrrolo[2,3-b]pyridin-6-yl)cyclopropanecarboxamide

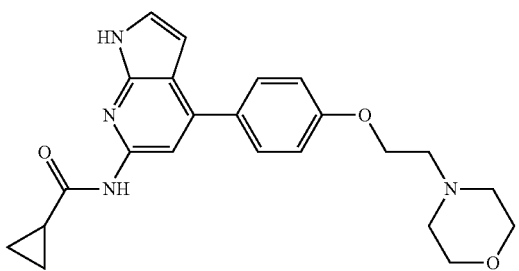 [SMILES: O=C(Nc1cc(-c2ccc(OCCN3CCOCC3)cc2)c2cc[nH]c2n1)C1CC1]

¹H NMR (400 MHz, DMSO-d₆) δ 11.48 (s, 1H), 10.58 (s, 1H), 7.99 (s, 1H), 7.69-7.61 (m, 2H), 7.38 (dd, J=2.5, 3.5 Hz, 1H), 7.17-7.07 (m, 2H), 6.52 (dd, J=1.9, 3.5 Hz, 1H), 4.17 (t, J=5.7 Hz, 2H), 3.66-3.53 (m, 4H), 2.73 (t, J=5.7 Hz, 2H), 2.09-1.99 (m, 1H), 1.24 (d, J=3.6 Hz, 3H), 0.85-0.73 (m, 4H).
MS(ESI+) m/z 407 (M+H)⁺

Example 643: Synthesis of N-(4-(4-butoxyphenyl)-1H-pyrrolo[2,3-b]pyridin-6-yl)cyclopropanecarboxamide

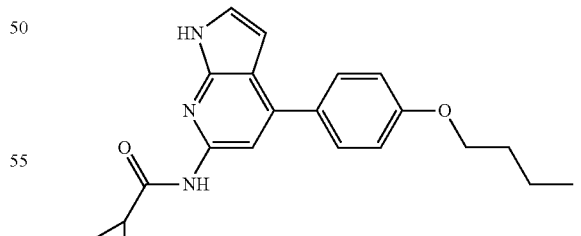

¹H NMR (400 MHz, DMSO-d₆) δ 11.48 (s, 1H), 10.57 (s, 1H), 7.99 (s, 1H), 7.70-7.60 (m, 2H), 7.38 (d, J=3.5 Hz, 1H), 7.13-7.05 (m, 2H), 6.53 (d, J=3.5 Hz, 1H), 4.05 (t, J=6.4 Hz, 2H), 2.04 (s, 1H), 1.78-1.67 (m, 2H), 1.47 (h, J=7.3 Hz, 2H), 0.96 (t, J=7.4 Hz, 3H), 0.87-0.75 (m, 4H).
MS(ESI+) m/z 350 (M+H)⁺

Example 644: Synthesis of N-(6-(4-((6-cyanopyridin-3-yl)methoxy)phenyl)-9H-purin-2-yl)cyclopropanecarboxamide

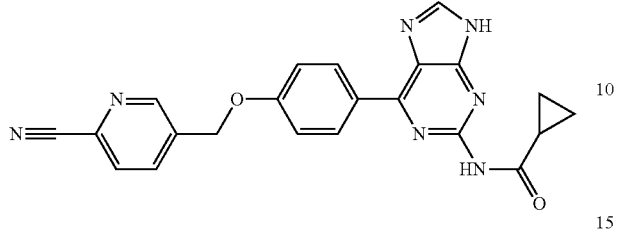

$^1$H NMR (400 MHz, DMSO-d$_6$) δ 10.73 (s, 1H), 8.90 (d, J=2.0 Hz, 1H), 8.84 (d, J=8.8 Hz, 2H), 8.45 (s, 1H), 8.18 (dd, J=8.1, 2.1 Hz, 1H), 8.10 (d, J=7.9 Hz, 1H), 7.27 (d, J=9.0 Hz, 2H), 5.38 (s, 2H), 2.20-2.13 (m, 1H), 0.84 (tt, J=8.0, 3.1 Hz, 4H).

MS(ESI+) m/z 412 (M+H)$^+$

Example 645: Synthesis of N-(4-(4-(ethylsulfonamido)cyclohexyl)-1H-pyrrolo[2,3-b]pyridin-6-yl)cyclopropanecarboxamide

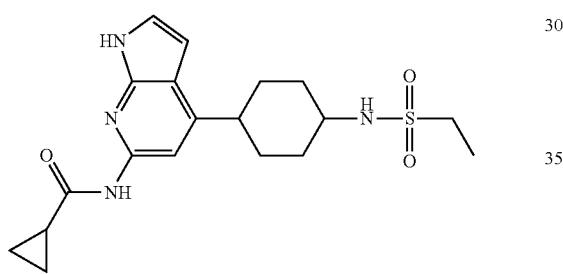

1.0 g of the above synthesized N-(4-(4-aminocyclohex-1-en-1-yl)-1-tosyl-1H-pyrrolo[2,3-b]pyridine-6-yl)cyclopropanecarboxamide was dissolved in 20 mL of MeOH, and then 0.1 g of Pd/C was inserted thereinto and stirred under hydrogen gas at room temperature for 16 hours. Once the reaction was completed, the said mixture was filtered through celite and washed by means of MeOH. The remaining solution was concentrated, and finally a product, i.e., N-(4-(4-aminocyclohexyl)-1-tosyl-1H-pyrrolo[2,3-b]pyridine-6-yl)cyclopropanecarboxamide was accordingly obtained.

Then, the obtained N-(4-(4-aminocyclohexyl)-1-tosyl-1H-pyrrolo[2,3-b]pyridine-6-yl)cyclopropanecarboxamide as a starting material was processed through the same method as in Example 1, and a final product, i.e., N-(4-(4-(ethylsulfonamido)cyclohexyl)-1H-pyrrolo[2,3-b]pyridin-6-yl)cyclopropanecarboxamide was accordingly obtained.

MS(ESI+) m/z 391 (M+H)$^+$

Examples 646 to 659

Hereinafter, in Examples 646 to 659, a corresponding compound was synthesized by means of the same method as shown in Example 645 or by means of an appropriate reactant under the consideration of the reaction formula 1 as well as a structure of the compound to be prepared.

Example 646: Synthesis of N-(4-(8-(ethylsulfonyl)-8-azabicyclo[3.2.1]octan-3-yl)-1H-pyrrolo[2,3-b]pyridin-6-yl)cyclopropanecarboxamide

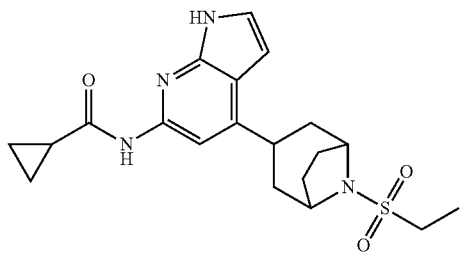 [SMILES: CCS(=O)(=O)N1C2CCC1CC(c1cc(NC(=O)C3CC3)nc3[nH]ccc13)C2]

MS(ESI+) m/z 403 (M+H)$^+$

Example 647: Synthesis of N-(4-(8-(cyclopropylsulfonyl)-8-azabicyclo[3.2.1]octan-3-yl)-1H-pyrrolo[2,3-b]pyridin-6-yl)cyclopropanecarboxamide

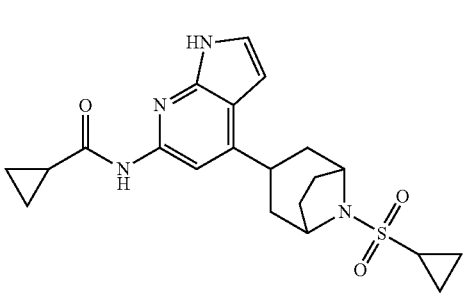 [SMILES: O=C(Nc1cc(C2CC3CCC(C2)N3S(=O)(=O)C2CC2)c2cc[nH]c2n1)C1CC1]

MS(ESI+) m/z 415 (M+H)$^+$

Example 648: Synthesis of N-(4-(8-((3-fluoropropyl)sulfonyl)-8-azabicyclo[3.2.1]octan-3-yl)-1H-pyrrolo[2,3-b]pyridin-6-yl)cyclopropanecarboxamide

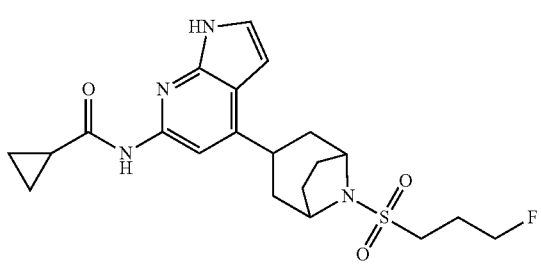 [SMILES: O=C(Nc1cc(C2CC3CCC(C2)N3S(=O)(=O)CCCF)c2cc[nH]c2n1)C1CC1]

MS(ESI+) m/z 435 (M+H)$^+$

Example 649: Synthesis of N-(4-(8-((3,4-difluorophenyl)sulfonyl)-8-azabicyclo[3.2.1]octan-3-yl)-1H-pyrrolo[2,3-b]pyridin-6-yl)cyclopropanecarboxamide

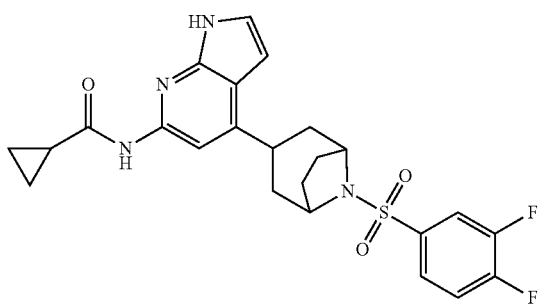 [SMILES: O=C(Nc1cc(C2CC3CCC(C2)N3S(=O)(=O)c2ccc(F)c(F)c2)c2cc[nH]c2n1)C1CC1]

MS(ESI+) m/z 487 (M+H)+

Example 650: Synthesis of N-(4-(8-(cyclopropanecarbonyl)-8-azabicyclo[3.2.1]octan-3-yl)-1H-pyrrolo[2,3-b]pyridin-6-yl)cyclopropanecarboxamide

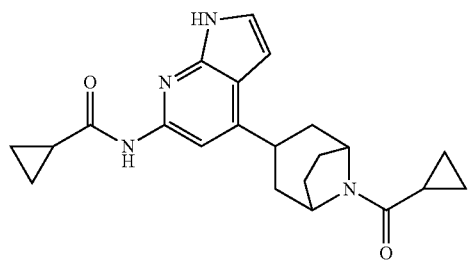 [SMILES: O=C(Nc1cc(C2CC3CCC(C2)N3C(=O)C2CC2)c2cc[nH]c2n1)C1CC1]

MS(ESI+) m/z 379 (M+H)+

Example 651: Synthesis of N-(4-(8-pentanoyl-8-azabicyclo[3.2.1]octan-3-yl)-1H-pyrrolo[2,3-b]pyridin-6-yl)cyclopropanecarboxamide

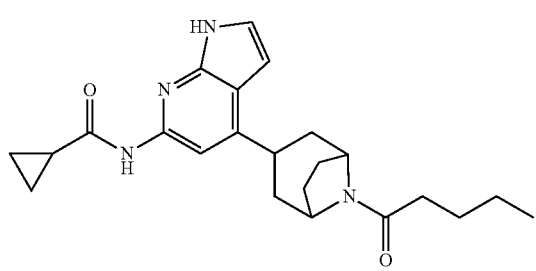 [SMILES: CCCCC(=O)N1C2CCC1CC(c1cc(NC(=O)C3CC3)nc3[nH]ccc13)C2]

MS(ESI+) m/z 395 (M+H)+

Example 652: Synthesis of N-(4-(1-(2-cyanoacetyl)piperidin-4-yl)-1H-pyrrolo[2,3-b]pyridin-6-yl)cyclopropanecarboxamide $^1$H NMR (400 MHz, DMSO-$d_6$) δ 11.34 (s, 1H), 10.49 (s, 1H), 7.79 (s, 1H), 7.32-7.26 (m, 1H), 6.52 (dd, J=3.5, 1.8 Hz, 1H), 4.54-4.46 (m, 1H), 4.10 (q, J=18.8 Hz, 2H), 3.78 (d, J=13.8 Hz, 1H), 3.28-3.14 (m, 3H), 2.78 (t, J=12.6 Hz, 1H), 2.05-1.96 (m, 1H), 1.82 (dtt, J=22.0, 13.6, 7.6 Hz, 3H), 1.60-1.47 (m, 1H), 0.78 (m, 4H).

MS(ESI+) m/z 352 (M+H)+

Example 653: Synthesis of N-butyl-4-(6-(cyclopropanecarboxamido)-1H-pyrrolo[2,3-b]pyridin-4-yl)piperidine-1-carboxamide MS(ESI+) m/z 384 (M+H)+

Example 654: Synthesis of 4-(6-(cyclopropanecarboxamido)-1H-pyrrolo[2,3-b]pyridin-4-yl)-N-(2,2,2-trifluoroethyl)piperidine-1-carboxamide

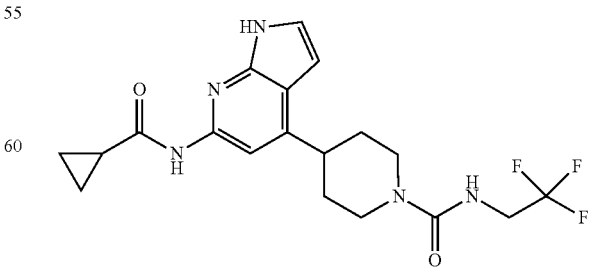

MS(ESI+) m/z 410 (M+H)+

Example 655: Synthesis of tert-butyl 4-(6-(cyclopropanecarboxamido)-1H-pyrrolo[2,3-b]pyridin-4-yl)-3-hydroxypiperidine-1-carboxylate

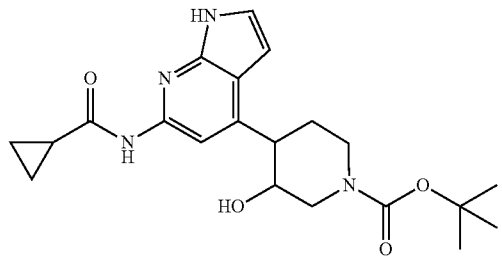 [SMILES: CC(C)(C)OC(=O)N1CCC(c2cc(NC(=O)C3CC3)nc3[nH]ccc23)C(O)C1]

MS(ESI+) m/z 401 (M+H)+

Example 656: Synthesis of tert-butyl 4-(6-(cyclopropanecarboxamido)-1H-pyrrolo[2,3-b]pyridin-4-yl)-3-fluoropiperidine-1-carboxylate

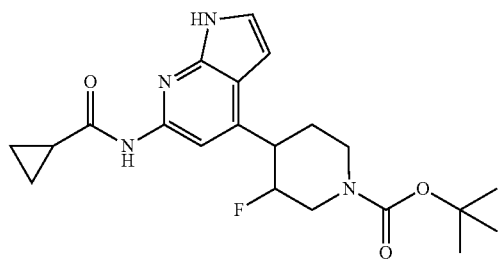 [SMILES: CC(C)(C)OC(=O)N1CCC(c2cc(NC(=O)C3CC3)nc3[nH]ccc23)C(F)C1]

MS(ESI+) m/z 403 (M+H)+

Example 657: Synthesis of N-(4-(8-(ethylcarbamothioyl)-8-azabicyclo[3.2.1]octan-3-yl)-1H-pyrrolo[2,3-b]pyridin-6-yl)cyclopropanecarboxamide

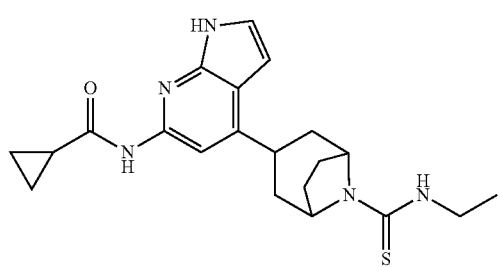 [SMILES: CCNC(=S)N1C2CCC1CC(c1cc(NC(=O)C3CC3)nc3[nH]ccc13)C2]

MS(ESI+) m/z 398 (M+H)+

Example 658: Synthesis of N-(4-(1-(ethylcarbamothioyl)piperidin-4-yl)-1H-pyrrolo[2,3-b]pyridin-6-yl)cyclopropanecarboxamide

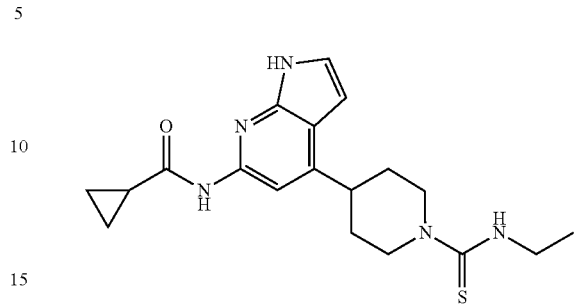

MS(ESI+) m/z 372 (M+H)+

Example 659: Synthesis of N-(4-(1-(butylcarbamothioyl)piperidin-4-yl)-1H-pyrrolo[2,3-b]pyridin-6-yl)cyclopropanecarboxamide

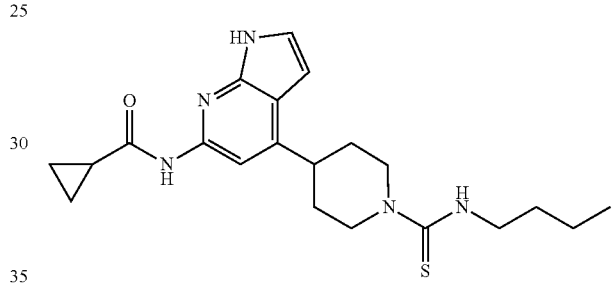

$^1$H NMR (400 MHz, DMSO-d$_6$) δ 11.36 (s, 1H), 10.51 (s, 1H), 7.78 (s, 1H), 7.66 (t, J=5.4 Hz, 1H), 7.29 (t, J=2.7 Hz, 1H), 6.48 (dd, J=1.8, 3.5 Hz, 1H), 4.89-4.75 (m, 2H), 3.51 (q, J=6.6 Hz, 2H), 3.23 (t, J=11.8 Hz, 1H), 3.09 (t, J=12.9 Hz, 2H), 1.99 (d, J=7.8 Hz, 1H), 1.83 (d, J=12.9 Hz, 2H), 1.69-1.48 (m, 4H), 1.29 (h, J=7.4 Hz, 2H), 0.90 (t, J=7.3 Hz, 3H), 0.83-0.72 (m, 4H).
MS(ESI+) m/z 400 (M+H)+

Example 660: Synthesis of N-(4-(4-(methylsulfonyl)piperazin-1-yl)-1H-pyrrolo[2,3-b]pyridin-6-yl)cyclopropanecarboxamide

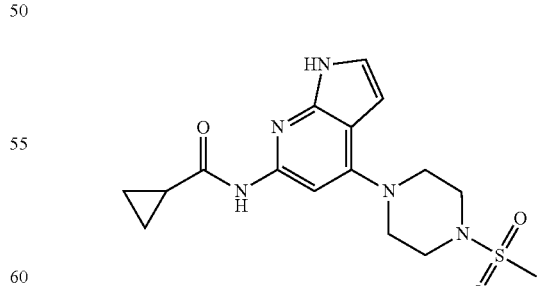

1.0 g (2.6 mmol) of the above synthesized N-(4-chloro-1-tosyl-H-pyrrolo[2,3-b]pyridine-6-yl)cyclopropanecarboxamide was dissolved in BuOH, and then 0.6 g (3.9 mmol) of 1-(methylsulfonyl)piperazine and 1 g (5.2 mmol) of DIPEA were inserted thereinto and stirred at 120-130° C. for 3 hours. Once the reaction was completed, the said mixture was cooled down at room temperature, then water was added thereto, and then an extraction using ethyl acetate was performed. After that, a solution extracted therefrom was dried by means of magnesium sulfate anhydrous and concentrated under reduced pressure, from which a residue was accordingly obtained. The residue was separated via silica gel column chromatography (DCM/MeOH=30:1) and concentrated. The synthesized material was dissolved in MeOH/THF (1:1) solution, and then 2N sodium hydroxide aqueous solution was added thereto and stirred at 30-40° C. for 4 hours. Once the reaction was completed, the said mixture was cooled down to room temperature, and saturated ammonium chloride aqueous solution was added thereto while being stirred. A produced solid was filtered out, and finally a product, i.e., N-(4-(4-(methylsulfonyl)piperazin-1-yl)-1H-pyrrolo[2,3-b]pyridin-6-yl)cyclopropanecarboxamide was accordingly obtained.

MS(ESI+) m/z 364 (M+H)+

Examples 661 to 704

Hereinafter, in Examples 661 to 704, a corresponding compound was synthesized by means of the same method as shown in Example 661 or by means of an appropriate reactant under the consideration of the reaction formula 1 as well as a structure of the compound to be prepared.

Example 661: Synthesis of N-(4-(8-(methylsulfonyl)-3,8-diazabicyclo[3.2.1]octan-3-yl)-1H-pyrrolo[2,3-b]pyridin-6-yl)cyclopropanecarboxamide

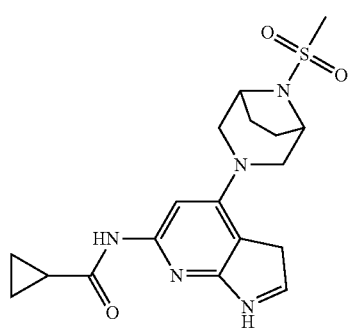 [SMILES: CS(=O)(=O)N1C2CCC1CN(c1cc(NC(=O)C3CC3)nc3c1CC=N3)C2]

¹H NMR (400 MHz, DMSO-d₆) δ 11.15 (s, 1H), 10.32 (s, 1H), 7.35 (s, 1H), 7.11 (t, J=3.0 Hz, 1H), 6.46 (dd, J=3.7, 2.0 Hz, 1H), 4.30 (d, J=4.0 Hz, 2H), 3.80 (d, J=10.3 Hz, 2H), 3.08 (d, J=11.9 Hz, 2H), 3.04 (s, 3H), 1.99 (s, 3H), 1.86 (d, J=7.4 Hz, 2H), 0.82-0.71 (m, 4H).
MS(ESI+) m/z 390 (M+H)+

Example 662: Synthesis of N-(4-(4-(((1-cyanocyclopropyl)methyl)sulfonyl)piperazin-1-yl)-1H-pyrrolo[2,3-b]pyridin-6-yl)cyclopropanecarboxamide

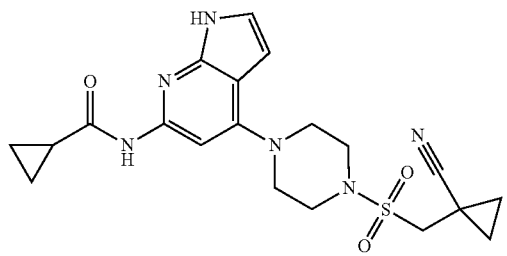 [SMILES: N#CC1(CS(=O)(=O)N2CCN(c3cc(NC(=O)C4CC4)nc4[nH]ccc34)CC2)CC1]

MS(ESI+) m/z 429 (M+H)+

Example 663: Synthesis of N-(4-(4-((3-fluoropropyl)sulfonyl)piperazin-1-yl)-1H-pyrrolo[2,3-b]pyridin-6-yl)cyclopropanecarboxamide

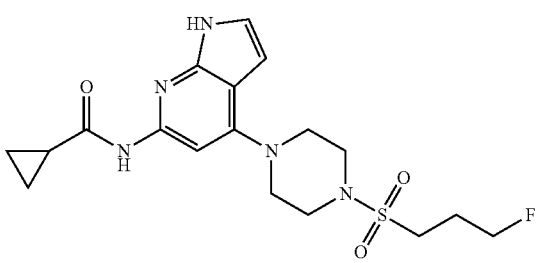 [SMILES: O=C(Nc1cc(N2CCN(S(=O)(=O)CCCF)CC2)c2cc[nH]c2n1)C1CC1]

¹H NMR (400 MHz, DMSO-d₆) δ 11.21 (s, 1H), 10.39 (s, 1H), 7.43 (s, 1H), 7.16 (s, 1H), 6.43 (s, 1H), 4.61 (t, J=6.0 Hz, 1H), 4.49 (t, J=6.0 Hz, 1H), 3.60 (s, 1H), 3.40 (d, J=6.3 Hz, 5H), 3.24-3.17 (m, 2H), 2.15-1.98 (m, 3H), 1.76 (s, 1H), 0.78 (dd, J=6.1, 11.2 Hz, 4H).
MS(ESI+) m/z 410 (M+H)+

Example 664: Synthesis of N-(4-(8-((3-cyanopropyl)sulfonyl)-3,8-diazabicyclo[3.2.1]octan-3-yl)-1H-pyrrolo[2,3-b]pyridin-6-yl)cyclopropanecarboxamide

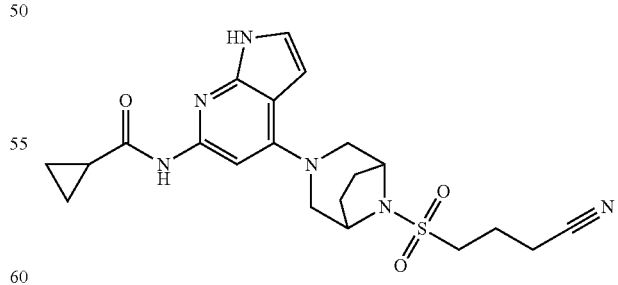

¹H NMR (400 MHz, DMSO-d₆) δ 11.14 (s, 1H), 10.31 (s, 1H), 7.36 (s, 1H), 7.17-7.05 (m, 1H), 6.46 (dd, J=1.9, 3.6 Hz, 1H), 4.31 (s, 2H), 3.80 (d, J=11.6 Hz, 2H), 3.27 (d, J=7.7 Hz, 2H), 3.11 (d, J=11.5 Hz, 2H), 2.72-2.64 (m, 2H), 2.04 (q, J=7.4 Hz, 3H), 1.89 (s, 2H), 0.84-0.72 (m, 4H).
MS(ESI+) m/z 443 (M+H)+

Example 665: Synthesis of N-(4-(8-(((1-(cyanomethyl)cyclopropyl)methyl)sulfonyl)-3,8-diazabicyclo[3.2.1]octan-3-yl)-1H-pyrrolo[2,3-b]pyridin-6-yl)cyclopropanecarboxamide

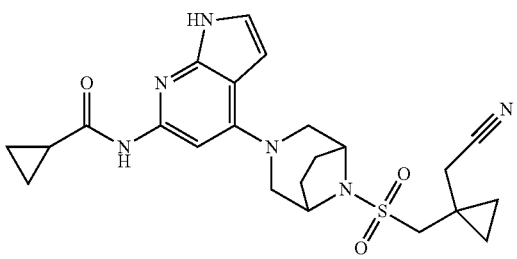 [SMILES: N#CCC1(CS(=O)(=O)N2C3CCC2CN(c2cc(NC(=O)C4CC4)nc4[nH]ccc24)C3)CC1]

$^1$H NMR (400 MHz, DMSO-d$_6$) δ 11.15 (s, 1H), 10.31 (s, 1H), 7.35 (s, 1H), 7.11 (dd, J=2.5, 3.6 Hz, 1H), 6.46 (dd, J=2.0, 3.6 Hz, 1H), 4.33 (s, 2H), 3.84-3.69 (m, 2H), 3.12 (d, J=11.8 Hz, 2H), 2.83 (s, 2H), 2.00 (s, 1H), 1.89 (d, J=3.7 Hz, 2H), 0.88-0.81 (m, 2H), 0.76 (ddt, J=3.0, 5.1, 12.9 Hz, 4H), 0.71-0.65 (m, 2H).

MS(ESI+) m/z 469 (M+H)$^+$

Example 666: Synthesis of N-(4-(8-((4,4,4-trifluorobutyl)sulfonyl)-3,8-diazabicyclo[3.2.1]octan-3-yl)-1H-pyrrolo[2,3-b]pyridin-6-yl)cyclopropanecarboxamide

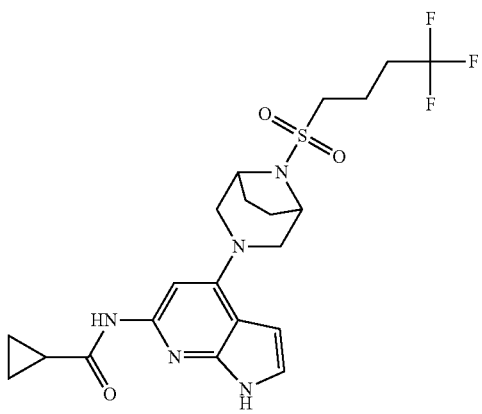 [SMILES: O=C(Nc1cc(N2CC3CCC(C2)N3S(=O)(=O)CCCC(F)(F)F)c2cc[nH]c2n1)C1CC1]

$^1$H NMR (400 MHz, DMSO-d$_6$) δ 11.15 (s, 1H), 10.31 (s, 1H), 7.35 (s, 1H), 7.11 (dd, J=2.5, 3.6 Hz, 1H), 6.46 (dd, J=2.0, 3.6 Hz, 1H), 4.33 (s, 2H), 3.84-3.69 (m, 2H), 3.12 (d, J=11.8 Hz, 2H), 2.83 (s, 2H), 2.00 (s, 1H), 1.89 (d, J=3.7 Hz, 2H), 0.88-0.81 (m, 2H), 0.76 (ddt, J=3.0, 5.1, 12.9 Hz, 4H), 0.71-0.65 (m, 2H).

MS(ESI+) m/z 486 (M+H)$^+$

Example 667: Synthesis of N-(4-(8-(((1-cyanocyclopropyl)methyl)sulfonyl)-3,8-diazabicyclo[3.2.1]octan-3-yl)-1H-pyrrolo[2,3-b]pyridin-6-yl)cyclopropanecarboxamide

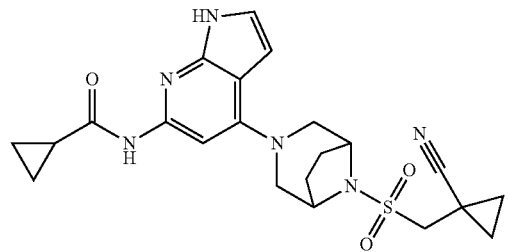 [SMILES: N#CC1(CS(=O)(=O)N2C3CCC2CN(c2cc(NC(=O)C4CC4)nc4[nH]ccc24)C3)CC1]

$^1$H NMR (400 MHz, DMSO-d$_6$) δ 11.14 (s, 1H), 10.30 (s, 1H), 7.35 (s, 1H), 7.11 (dd, J=2.4, 3.6 Hz, 1H), 6.45 (dd, J=1.9, 3.6 Hz, 1H), 4.68 (s, 1H), 4.40-4.28 (m, 1H), 3.85-3.75 (m, 1H), 3.65 (d, J=11.2 Hz, 1H), 3.04 (dd, J=11.3, 42.2 Hz, 2H), 2.83-2.57 (m, 2H), 1.98 (d, J=7.0 Hz, 1H), 1.97-1.81 (m, 4H), 1.24-1.17 (m, 2H), 1.02-0.90 (m, 2H), 0.82-0.70 (m, 4H).

MS(ESI+) m/z 455 (M+H)$^+$

Example 668: Synthesis of N-(4-(4-(propylsulfonyl)piperazin-1-yl)-7H-pyrrolo[2,3-d]pyrimidin-2-yl)cyclopropanecarboxamide

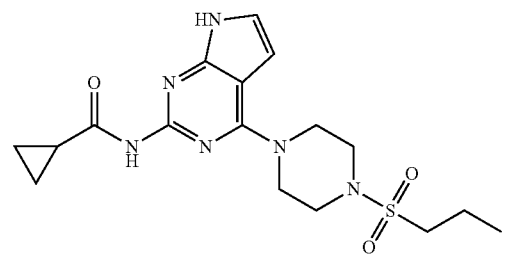 [SMILES: CCCS(=O)(=O)N1CCN(c2nc(NC(=O)C3CC3)nc3[nH]ccc23)CC1]

$^1$H NMR (400 MHz, DMSO-d$_6$) δ 11.57 (s, 1H), 10.05 (s, 1H), 7.09 (d, J=3.6 Hz, 1H), 6.57 (d, J=3.6 Hz, 1H), 4.02-3.90 (m, 4H), 3.28 (s, 4H), 3.08-3.01 (m, 2H), 2.18 (s, 1H), 1.70 (q, J=7.5 Hz, 2H), 0.98 (t, J=7.4 Hz, 3H), 0.81-0.72 (m, 4H).

MS(ESI+) m/z 393 (M+H)$^+$

Example 669: Synthesis of N-(4-(8-(ethylsulfonyl)-3,8-diazabicyclo[3.2.1]octan-3-yl)-7H-pyrrolo[2,3-d]pyrimidin-2-yl)cyclopropanecarboxamide

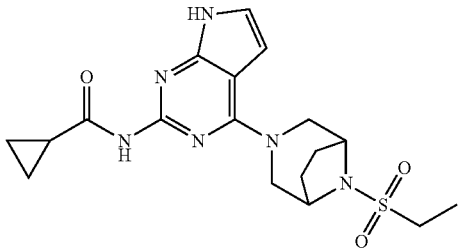 [SMILES: CCS(=O)(=O)N1C2CCC1CN(c1nc(NC(=O)C3CC3)nc3[nH]ccc13)C2]

MS(ESI+) m/z 405 (M+H)$^+$

Example 670: Synthesis of (S)—N-(4-(3-(propylsulfonamido)pyrrolidin-1-yl)-7H-pyrrolo[2,3-d]pyrimidin-2-yl)cyclopropanecarboxamide

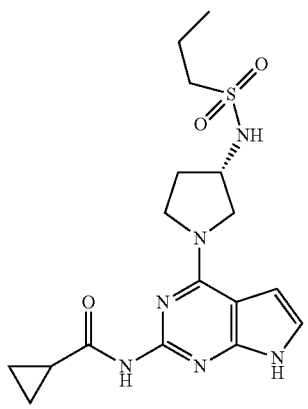 [SMILES: CCCS(=O)(=O)N[C@H]1CCN(c2nc(NC(=O)C3CC3)nc3[nH]ccc23)C1]

$^1$H NMR (400 MHz, DMSO-d$_6$) δ 11.44 (s, 1H), 9.87 (s, 1H), 7.49 (d, J=6.4 Hz, 1H), 7.06-6.95 (m, 1H), 6.48 (s, 1H), 4.07-3.57 (m, 7H), 3.06 (dd, J=6.4, 9.1 Hz, 2H), 2.23 (s, 1H), 1.97 (s, 1H), 1.68 (q, J=7.6 Hz, 2H), 1.17 (s, 2H), 0.98 (t, J=7.4 Hz, 3H).

MS(ESI+) m/z 393 (M+H)$^+$

Example 671: Synthesis of (S)—N-(4-(3-(allylsulfonamido)pyrrolidin-1-yl)-7H-pyrrolo[2,3-d]pyrimidin-2-yl)cyclopropanecarboxamide

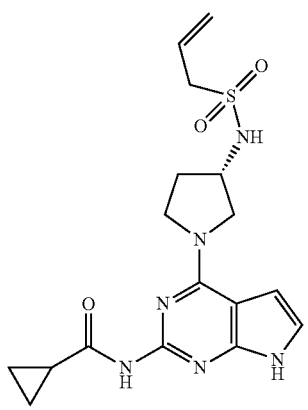 [SMILES: C=CCS(=O)(=O)N[C@H]1CCN(c2nc(NC(=O)C3CC3)nc3[nH]ccc23)C1]

$^1$H NMR (400 MHz, DMSO-d$_6$) δ 11.45 (s, 1H), 9.89 (s, 1H), 7.62 (s, 1H), 7.05-6.97 (m, 1H), 6.53-6.42 (m, 1H), 5.89-5.74 (m, 4H), 5.40 (t, J=13.6 Hz, 3H), 3.94-3.85 (m, 7H), 2.23 (s, 1H), 1.94 (d, J=28.2 Hz, 1H), 0.80-0.73 (m, 4H).

MS(ESI+) m/z 391 (M+H)$^+$

Example 672: Synthesis of (S)—N-(4-(3-(N-methylethylsulfonamido)pyrrolidin-1-yl)-1H-pyrrolo[2,3-b]pyridin-6-yl)cyclopropanecarboxamide

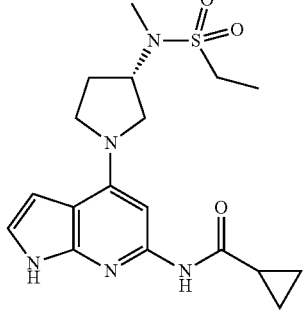

$^1$H NMR (400 MHz, DMSO-d$_6$) δ 10.97 (s, 1H), 10.17 (s, 1H), 7.09-6.94 (m, 2H), 6.54 (dd, J=3.6, 1.9 Hz, 1H), 4.52 (p, J=8.0 Hz, 1H), 3.73 (t, J=8.9 Hz, 2H), 3.56 (q, J=8.2 Hz, 2H), 3.22-3.09 (m, 2H), 2.82 (s, 3H), 2.18 (q, J=8.2, 7.7 Hz, 2H), 1.99 (s, 1H), 1.22 (t, J=7.3 Hz, 3H), 0.84-0.63 (m, 4H).
MS(ESI+) m/z 392 (M+H)$^+$

Example 673: Synthesis of N-(4-(4-(morpholinosulfonyl)piperazin-1-yl)-1H-pyrrolo[2,3-b]pyridin-6-yl)cyclopropanecarboxamide

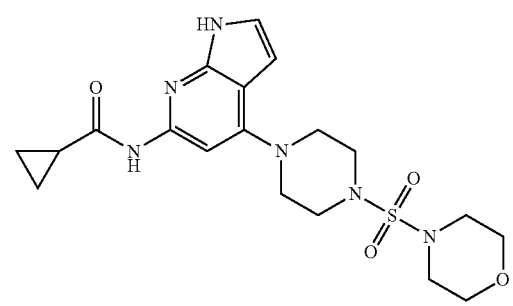 [SMILES: O=C(Nc1cc(N2CCN(S(=O)(=O)N3CCOCC3)CC2)c2cc[nH]c2n1)C1CC1]

$^1$H NMR (400 MHz, DMSO-d$_6$) δ 11.21 (s, 1H), 10.39 (s, 1H), 7.43 (s, 1H), 7.20-7.06 (m, 1H), 6.43 (dd, J=1.9, 3.6 Hz, 1H), 3.63 (t, J=4.6 Hz, 4H), 3.16 (d, J=5.1 Hz, 8H), 2.00 (s, 1H), 0.83-075 (m, 4H).
MS(ESI+) m/z 435 (M+H)$^+$

Example 674: Synthesis of N-(4-(4-(N,N-dimethylsulfamoyl)piperazin-1-yl)-1H-pyrrolo[2,3-b]pyridin-6-yl)cyclopropanecarboxamide

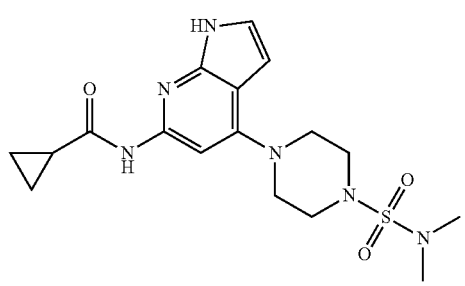 [SMILES: CN(C)S(=O)(=O)N1CCN(c2cc(NC(=O)C3CC3)nc3[nH]ccc23)CC1]

¹H NMR (400 MHz, DMSO-d₆) δ 11.21 (s, 1H), 10.39 (s, 1H), 7.43 (s, 1H), 7.15 (t, J=3.0 Hz, 1H), 6.43 (dd, J=1.9, 3.6 Hz, 1H), 3.17 (d, J=5.2 Hz, 8H), 2.81 (s, 6H), 2.00 (s, 1H), 0.85-0.70 (m, 4H).

MS(ESI+) m/z 393 (M+H)⁺

Example 675: Synthesis of N-(4-(4-(2-cyanoacetamido)piperidin-1-yl)-1H-pyrrolo[2,3-b]pyridin-6-yl)cyclopropanecarboxamide

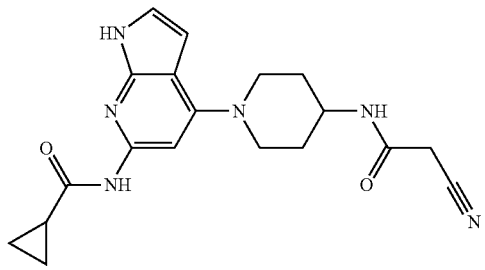 [SMILES: N#CCC(=O)NC1CCN(c2cc(NC(=O)C3CC3)nc3[nH]ccc23)CC1]

MS(ESI+) m/z 367 (M+H)⁺

Example 676: Synthesis of N-(4-(4-(2-cyanoacetyl)piperazin-1-yl)-1H-pyrrolo[2,3-b]pyridin-6-yl)cyclopropanecarboxamide

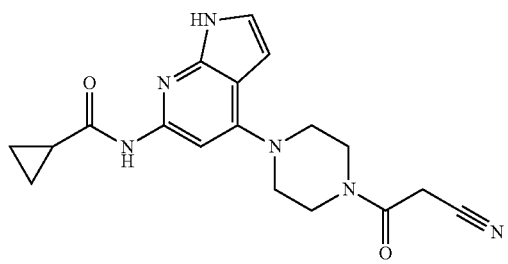 [SMILES: N#CCC(=O)N1CCN(c2cc(NC(=O)C3CC3)nc3[nH]ccc23)CC1]

¹H NMR (400 MHz, DMSO-d₆) δ 11.18 (s, 1H), 10.35 (s, 1H), 7.40 (s, 1H), 7.14 (t, J 3.0 Hz, 1H), 6.44 (dd, J=1.9, 3.6 Hz, 1H), 4.10 (s, 2H), 3.66 (s, 2H), 3.56 (s, 2H), 3.38 (s, 4H), 2.08 (s, 3H), 2.00 (s, 1H), 0.82-0.73 (m, 4H).

MS(ESI+) m/z 353 (M+H)⁺

Example 677: Synthesis of N-(4-(8-(2-cyanoacetyl)-3,8-diazabicyclo[3.2.1]octan-3-yl)-1H-pyrrolo[2,3-b]pyridin-6-yl)cyclopropanecarboxamide

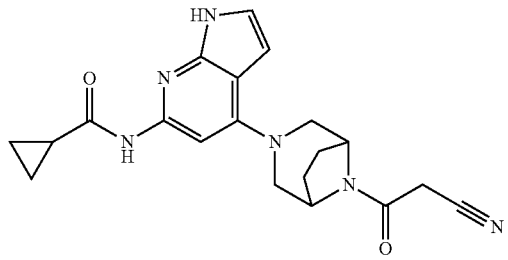 [SMILES: N#CCC(=O)N1C2CCC1CN(c1cc(NC(=O)C3CC3)nc3[nH]ccc13)C2]

¹H NMR (400 MHz, DMSO-d₆) δ 11.16 (s, 1H), 10.33 (s, 1H), 7.36 (s, 1H), 7.15-7.09 (m, 1H), 6.45 (dd, J=3.8, 2.0 Hz, 1H), 4.64 (s, 1H), 4.33 (d, J=6.5 Hz, 1H), 4.09 (d, J=4.5 Hz, 2H), 3.81 (d, J=11.4 Hz, 1H), 3.65 (d, J=11.6 Hz, 1H), 3.16 (d, J=11.8 Hz, 1H), 2.98 (d, J=11.4 Hz, 1H), 2.00 (q, J=7.2 Hz, 2H), 1.90 (d, J=5.5 Hz, 1H), 1.87 (s, 2H), 0.82-0.72 (m, 4H).

MS(ESI+) m/z 379 (M+H)⁺

Example 678: Synthesis of N-(4-(3-(2-cyanoacetyl)-3,8-diazabicyclo[3.2.1]octan-8-yl)-1H-pyrrolo[2,3-b]pyridin-6-yl)cyclopropanecarboxamide

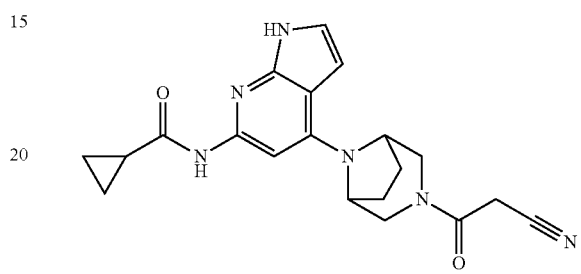

¹H NMR (400 MHz, DMSO-d₆) δ 11.16 (s, 1H), 10.33 (s, 1H), 7.39 (s, 1H), 7.17-7.09 (m, 1H), 6.50 (dd, J=1.9, 3.6 Hz, 1H), 4.61-4.46 (m, 2H), 4.18 (d, J=18.9 Hz, 1H), 4.10-3.98 (m, 2H), 3.87 (d, J=18.9 Hz, 1H), 1.97-1.84 (m, 3H), 1.27-1.14 (m, 4H), 0.77 (ddt, J=3.1, 5.2, 10.9 Hz, 4H).

MS(ESI+) m/z 379 (M+H)⁺

Example 679: Synthesis of N-(4-((1S,4S)-5-(2-cyanoacetyl)-2,5-diazabicyclo[2.2.1]heptan-2-yl)-1H-pyrrolo[2,3-b]pyridin-6-yl)cyclopropanecarboxamide

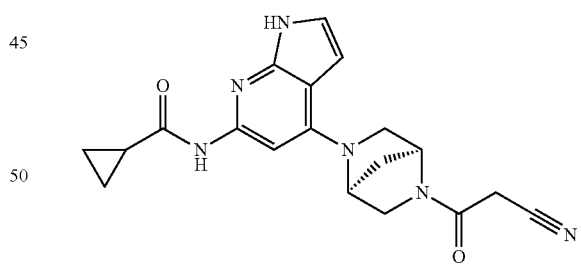

¹H NMR (400 MHz, DMSO-d₆) δ 11.01 (d, J=8.5 Hz, 1H), 10.19 (s, 1H), 7.09 (s, 1H), 7.02 (ddd, J=6.6, 3.6, 2.4 Hz, 1H), 6.43 (ddd, J=13.9, 3.5, 1.9 Hz, 1H), 4.84-4.61 (m, 2H), 4.09-4.05 (m, 1H), 4.04-3.97 (m, 1H), 3.90-3.72 (m, 3H), 3.56 (d, J=28.4 Hz, 1H), 3.43 (d, J=6.6 Hz, 1H), 3.17 (d, J=5.1 Hz, 1H), 2.12-2.07 (m, 1H), 1.24 (s, 1H), 0.80-0.77 (m, 2H), 0.74 (dd, J=7.6, 3.5 Hz, 2H).

MS(ESI+) m/z 365 (M+H)⁺

Example 680: Synthesis of N-(4-((1S,4S)-5-(3-cyanopropanoyl)-2,5-diazabicyclo[2.2.1]heptan-2-yl)-1H-pyrrolo[2,3-b]pyridin-6-yl)cyclopropanecarboxamide

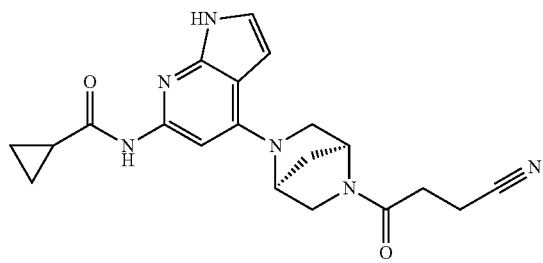 [SMILES: N#CCCC(=O)N1C[C@@H]2C[C@H]1CN2c1cc(NC(=O)C2CC2)nc2[nH]ccc12]

¹H NMR (400 MHz, DMSO-d₆) δ 11.00 (s, 1H), 10.19 (s, 1H), 7.09 (s, 1H), 7.02 (td, J=3.9, 2.4 Hz, 1H), 6.44 (ddd, J=6.3, 3.7, 2.0 Hz, 1H), 4.86-4.65 (m, 2H), 3.87 (d, J=9.2 Hz, 1H), 3.68-3.48 (m, 2H), 3.43 (s, 1H), 2.89-2.65 (m, 2H), 2.57 (dd, J=16.5, 9.4 Hz, 2H), 2.07 (s, 1H), 0.79-0.71 (m, 4H).
MS(ESI+) m/z 379 (M+H)⁺

Example 681: Synthesis of N-(4-((1R,4R)-5-(2-cyanoacetyl)-2,5-diazabicyclo[2.2.1]heptan-2-yl)-1H-pyrrolo[2,3-b]pyridin-6-yl)cyclopropanecarboxamide

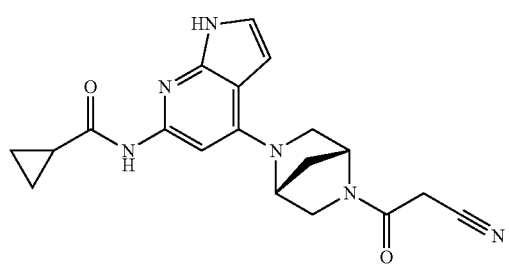 [SMILES: N#CCC(=O)N1C[C@H]2C[C@@H]1CN2c1cc(NC(=O)C2CC2)nc2[nH]ccc12]

¹H NMR (400 MHz, DMSO-d₆) δ 11.03 (d, J=8.7 Hz, 1H), 10.22 (s, 1H), 7.09 (s, 1H), 7.03 (dt, J=6.7, 3.1 Hz, 1H), 6.43 (d, J=14.4 Hz, 1H), 4.83-4.60 (m, 2H), 4.08 (q, J=18.8 Hz, 2H), 3.90-3.72 (m, 2H), 3.61-3.49 (m, 1H), 3.43 (d, J=6.4 Hz, 1H), 2.04 (dt, J=45.1, 6.5 Hz, 2H), 1.89 (d, J=9.3 Hz, 1H), 0.81-0.69 (m, 4H).
MS(ESI+) m/z 365 (M+H)⁺

Example 682: Synthesis of N-(4-((1R,4R)-5-(3-cyanopropanoyl)-2,5-diazabicyclo[2.2.1]heptan-2-yl)-1H-pyrrolo[2,3-b]pyridin-6-yl)cyclopropanecarboxamide

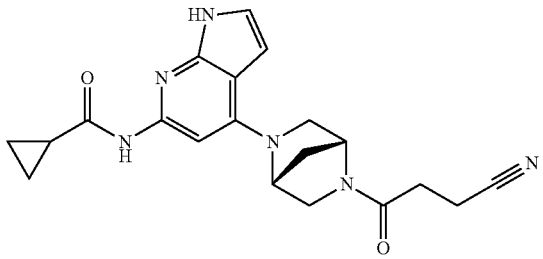 [SMILES: N#CCCC(=O)N1C[C@H]2C[C@@H]1CN2c1cc(NC(=O)C2CC2)nc2[nH]ccc12]

¹H NMR (400 MHz, DMSO-d₆) δ 11.02 (s, 1H), 10.22 (s, 1H), 7.09 (s, 1H), 7.02 (q, J=3.7 Hz, 1H), 6.43 (s, 1H), 4.84-4.66 (m, 2H), 3.87 (d, J=9.0 Hz, 1H), 3.66-3.47 (m, 2H), 3.16 (d, J=5.2 Hz, 2H), 2.11-1.93 (m, 4H), 1.89 (d, J=10.0 Hz, 1H), 0.75 (ddd, J=13.6, 6.3, 3.9 Hz, 4H).
MS(ESI+) m/z 379 (M+H)⁺

Example 683: Synthesis of N-(4-(4-(2-(1-cyanocyclopropyl)acetyl)piperazin-1-yl)-1H-pyrrolo[2,3-b]pyridin-6-yl)cyclopropanecarboxamide

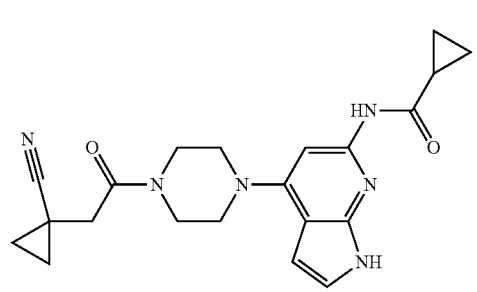 [SMILES: N#CC1(CC(=O)N2CCN(c3cc(NC(=O)C4CC4)nc4[nH]ccc34)CC2)CC1]

¹H NMR (400 MHz, DMSO-d₆) δ 11.19 (s, 1H), 10.37 (s, 1H), 7.40 (s, 1H), 7.22-7.10 (m, 1H), 6.50-6.40 (m, 1H), 3.68 (s, 2H), 3.56 (s, 2H), 2.73 (d, J=6.0 Hz, 4H), 2.00 (s, 1H), 0.95-0.90 (m, 2H), 0.82-0.73 (m, 4H).
MS(ESI+) m/z 393 (M+H)⁺

Example 684: Synthesis of N-(4-(4-(3-cyanopropanoyl)piperazin-1-yl)-1H-pyrrolo[2,3-b]pyridin-6-yl)cyclopropanecarboxamide

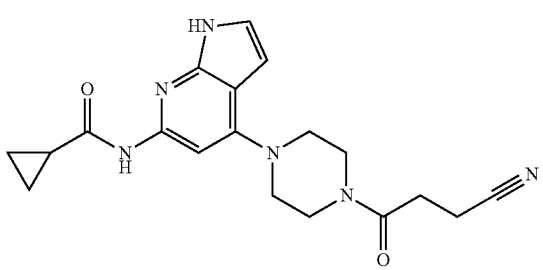 [SMILES: N#CCCC(=O)N1CCN(c2cc(NC(=O)C3CC3)nc3[nH]ccc23)CC1]

¹H NMR (400 MHz, DMSO-d₆) δ 11.19 (s, 1H), 10.37 (s, 1H), 7.40 (s, 1H), 7.20-7.06 (m, 1H), 6.56-6.38 (m, 1H), 3.65 (d, J=17.9 Hz, 4H), 2.92-2.66 (m, 4H), 2.66-2.53 (m, 4H), 2.00 (s, 1H), 0.81-0.71 (m, 4H).

MS(ESI+) m/z 367 (M+H)+

Example 685: Synthesis of N-(4-(6-(2-cyanoacetyl)-3,6-diazabicyclo[3.1.1]heptan-3-yl)-1H-pyrrolo[2,3-b]pyridin-6-yl)cyclopropanecarboxamide

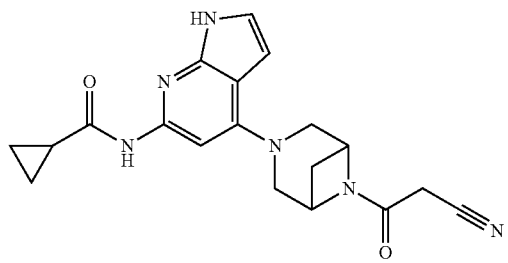 [SMILES: N#CCC(=O)N1C2CC1CN(c1cc(NC(=O)C3CC3)nc3[nH]ccc13)C2]

MS(ESI+) m/z 365 (M+H)+

Example 686: Synthesis of N-(4-(8-(3-cyanobenzoyl)-3,8-diazabicyclo[3.2.1]octan-3-yl)-1H-pyrrolo[2,3-b]pyridin-6-yl)cyclopropanecarboxamide

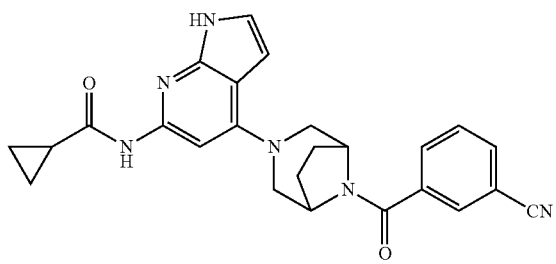 [SMILES: N#Cc1cccc(C(=O)N2C3CCC2CN(c2cc(NC(=O)C4CC4)nc4[nH]ccc24)C3)c1]

MS(ESI+) m/z 441 (M+H)+

Example 687: Synthesis of N-(4-(4-(2-cyanoacetyl)piperazin-1-yl)-7H-pyrrolo[2,3-d]pyrimidin-2-yl)cyclopropanecarboxamide

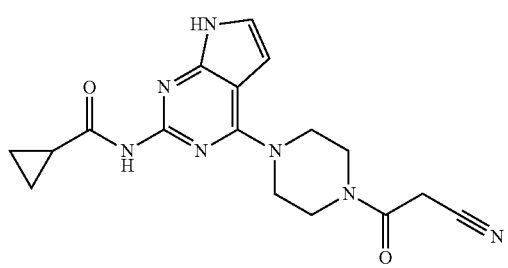 [SMILES: N#CCC(=O)N1CCN(c2nc(NC(=O)C3CC3)nc3[nH]ccc23)CC1]

$^1$H NMR (400 MHz, DMSO-$d_6$) δ 11.55 (s, 1H), 10.03 (s, 1H), 7.07 (t, J=2.9 Hz, 1H), 6.56 (d, J=2.8 Hz, 1H), 4.10 (s, 2H), 3.91 (dt, J=5.1, 19.7 Hz, 3H), 3.57 (dt, J=5.5, 41.4 Hz, 4H), 2.20 (d, J=10.8 Hz, 1H), 0.76 (dt, J=3.8, 11.0 Hz, 4H).

MS(ESI+) m/z 354 (M+H)+

Example 688: Synthesis of (N-(4-(8-(2-cyanoacetyl)-3,8-diazabicyclo[3.2.1]octan-3-yl)-7H-pyrrolo[2,3-d]pyrimidin-2-yl)cyclopropanecarboxamide)

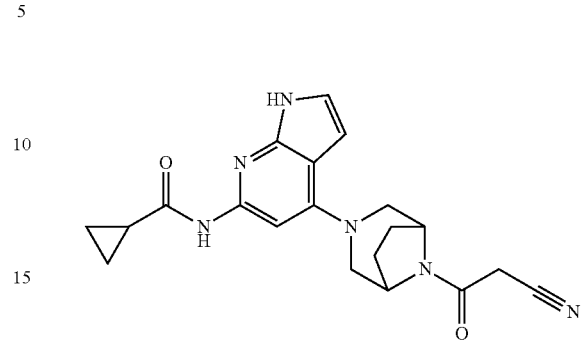

MS(ESI+) m/z 380 (M+H)+

Example 689: Synthesis of N-(4-(8-(2-(1-cyanocyclopropyl)acetyl)-3,8-diazabicyclo[3.2.1]octan-3-yl)-7H-pyrrolo[2,3-d]pyrimidin-2-yl)cyclopropanecarboxamide

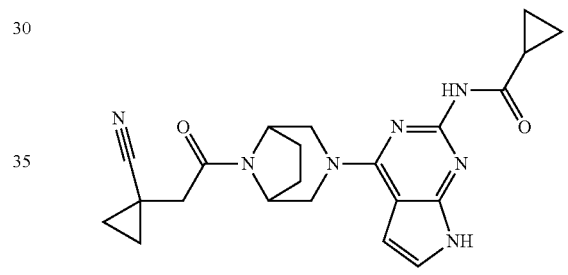

MS(ESI+) m/z 420 (M+H)+

Example 690: Synthesis of 4-(6-(cyclopropanecarboxamido)-1H-pyrrolo[2,3-b]pyridin-4-yl)-N-(2,2,2-trifluoroethyl)piperazine-1-carboxamide

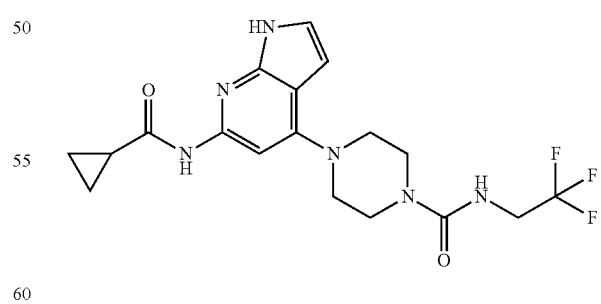

$^1$H NMR (400 MHz, DMSO-$d_6$) δ 11.18 (s, 1H), 10.36 (s, 1H), 7.40 (s, 1H), 7.25 (t, J=6.1 Hz, 1H), 7.14 (d, J=3.5 Hz, 1H), 6.88 (s, 1H), 6.44 (s, 1H), 3.85 (dt, J=5.9, 10.8 Hz, 4H), 3.59 (d, J=6.6 Hz, 2H), 3.54 (s, 4H), 2.00 (s, 1H), 0.81-0.74 (m, 4H).

MS(ESI+) m/z 411 (M+H)+

Example 691: Synthesis of 3-(6-(cyclopropanecarboxamido)-1H-pyrrolo[2,3-b]pyridin-4-yl)-N-(2,2,2-trifluoroethyl)-3,8-diazabicyclo[3.2.1]octane-8-carboxamide

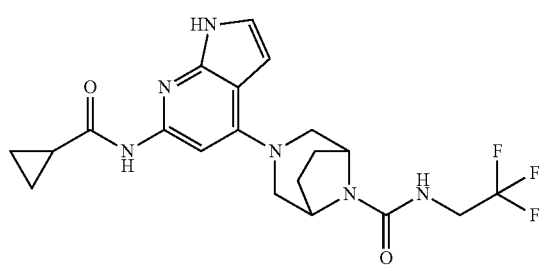 [SMILES: O=C(Nc1cc(N2CC3CCC(C2)N3C(=O)NCC(F)(F)F)c2cc[nH]c2n1)C1CC1]

$^1$H NMR (400 MHz, DMSO-d$_6$) δ 11.13 (s, 1H), 10.30 (s, 1H), 7.33 (d, J=6.9 Hz, 2H), 7.10 (dd, J=2.5, 3.6 Hz, 1H), 6.45 (dd, J=1.9, 3.6 Hz, 1H), 4.42 (s, 2H), 3.93-3.78 (m, 2H), 3.70-3.61 (m, 2H), 3.03 (d, J=11.3 Hz, 2H), 1.99 (s, 1H), 1.86 (s, 4H), 0.83-0.71 (m, 4H).
MS(ESI+) m/z 437 (M+H)$^+$

Example 692: Synthesis of tert-butyl 4-(6-(cyclopropanecarboxamido)-1H-pyrrolo[2,3-b]pyridine-4-yl)piperazin-1-carboxylate

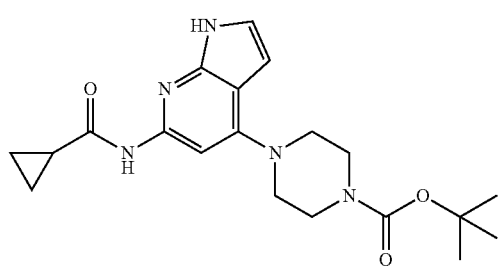 [SMILES: CC(C)(C)OC(=O)N1CCN(c2cc(NC(=O)C3CC3)nc3[nH]ccc23)CC1]

MS(ESI+) m/z 386 (M+H)$^+$

Example 693: Synthesis of tert-butyl 3-(6-(cyclopropanecarboxamido)-1H-pyrrolo[2,3-b]pyridin-4-yl)-3,8-diazabicyclo[3.2.1]octane-8-carboxylate

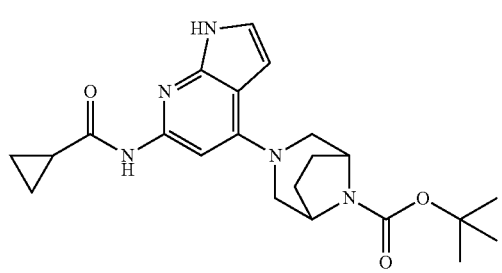 [SMILES: CC(C)(C)OC(=O)N1C2CCC1CN(c1cc(NC(=O)C3CC3)nc3[nH]ccc13)C2]

$^1$H NMR (400 MHz, DMSO-d$_6$) δ 11.14 (s, 1H), 10.31 (s, 1H), 7.34 (s, 1H), 7.11 (d, J=3.0 Hz, 1H), 6.46 (d, J=3.1 Hz, 1H), 4.26 (d, J=5.3 Hz, 2H), 3.71 (d, J=11.5 Hz, 2H), 3.00 (d, J=12.0 Hz, 2H), 1.99 (s, 1H), 1.85 (s, 4H), 1.42 (s, 9H), 0.89-0.67 (m, 4H).
MS(ESI+) m/z 412 (M+H)$^+$

Example 694: Synthesis of tert-butyl 8-(6-(cyclopropanecarboxamido)-1H-pyrrolo[2,3-b]pyridin-4-yl)-3,8-diazabicyclo[3.2.1]octane-3-carboxylate

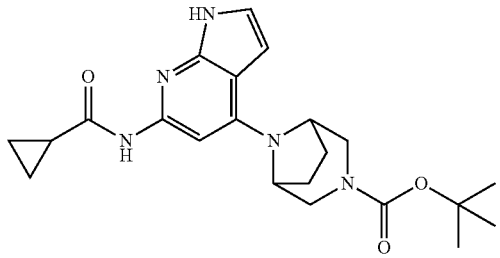 [SMILES: CC(C)(C)OC(=O)N1CC2CCC(C1)N2c1cc(NC(=O)C2CC2)nc2[nH]ccc12]

$^1$H NMR (400 MHz, DMSO-d$_6$) δ 11.12 (s, 1H), 10.30 (s, 1H), 7.36 (s, 1H), 7.09 (dd, J=2.5, 3.6 Hz, 1H), 6.49 (dd, J=2.0, 3.7 Hz, 1H), 4.49 (s, 2H), 3.68 (t, J=16.9 Hz, 3H), 3.42 (d, J=10.5 Hz, 1H), 3.20-3.12 (m, 1H), 3.02 (d, J=12.4 Hz, 1H), 2.03-1.92 (m, 3H), 1.39 (s, 9H), 0.80-0.72 (m, 4H).
MS(ESI+) m/z 412 (M+H)$^+$

Example 695: Synthesis of tert-butyl 3-(2-(cyclopropanecarboxamido)-7H-pyrrolo[2,3-d]pyrimidin-4-yl)-3,8-diazabicyclo[3.2.1]octane-8-carboxylate

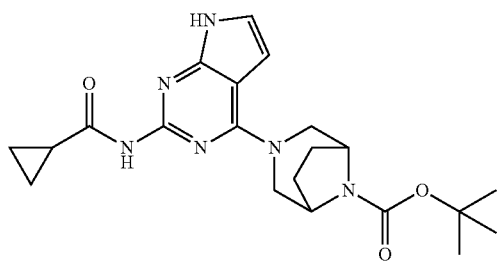 [SMILES: CC(C)(C)OC(=O)N1C2CCC1CN(c1nc(NC(=O)C3CC3)nc3[nH]ccc13)C2]

MS(ESI+) m/z 413 (M+H)$^+$

Example 696: Synthesis of tert-butyl (S)-(1-(2-(cyclopropanecarboxamido)-7H-pyrrolo[2,3-d]pyrimidin-4-yl)pyrrolidin-3-yl)carbamate

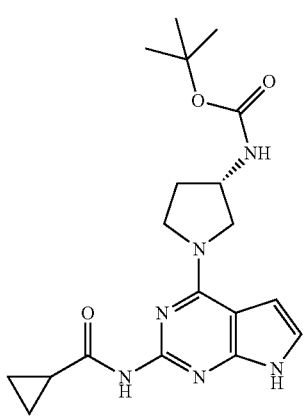 [SMILES: CC(C)(C)OC(=O)N[C@H]1CCN(c2nc(NC(=O)C3CC3)nc3[nH]ccc23)C1]

MS(ESI+) m/z 387 (M+H)$^+$

Example 697: Synthesis of tert-butyl (S)-(1-(6-(cyclopropanecarboxamido)-1H-pyrrolo[2,3-b]pyridin-4-yl)pyrrolidin-3-yl)carbamate

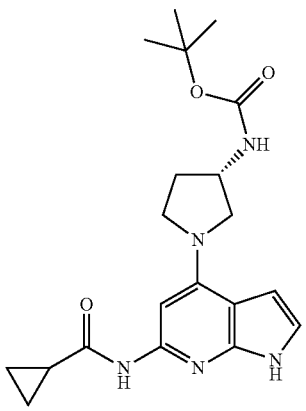 [SMILES: CC(C)(C)OC(=O)N[C@H]1CCN(c2cc(NC(=O)C3CC3)nc3[nH]ccc23)C1]

MS(ESI+) m/z 386 (M+H)$^+$

Example 698: Synthesis of N-(4-(4-(isothiazol-5-ylmethyl)piperazin-1-yl)-1H-pyrrolo[2,3-b]pyridin-6-yl)cyclopropanecarboxamide

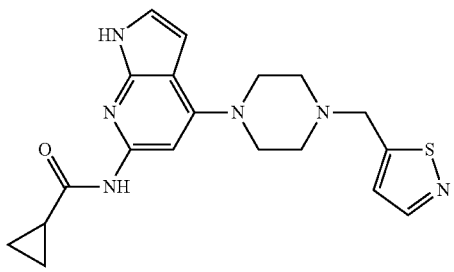 [SMILES: O=C(Nc1cc(N2CCN(Cc3ccns3)CC2)c2cc[nH]c2n1)C1CC1]

$^1$H NMR (400 MHz, DMSO-d$_6$) δ 11.15 (s, 1H), 10.34 (s, 1H), 8.49 (d, J=1.7 Hz, 1H), 7.39 (s, 1H), 7.31 (d, J=1.6 Hz, 1H), 7.11 (t, J=3.0 Hz, 1H), 6.39 (dd, J=1.9, 3.6 Hz, 1H), 4.11 (t, J=5.2 Hz, 1H), 3.96 (s, 2H), 3.17 (d, J=5.2 Hz, 3H), 2.66 (t, J=4.7 Hz, 4H), 2.00 (s, 1H), 0.82-0.74 (m, 4H).
MS(ESI+) m/z 383 (M+H)$^+$

Example 699: Synthesis of (S)—N-(4-(4-((2,2-difluorocyclopropyl)methyl)piperazin-1-yl)-1H-pyrrolo[2,3-b]pyridin-6-yl)cyclopropanecarboxamide

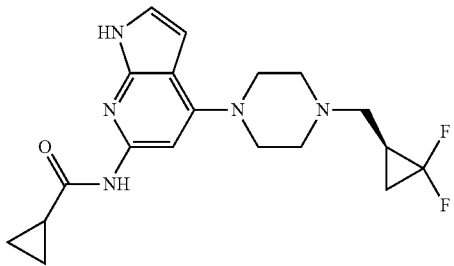 [SMILES: O=C(Nc1cc(N2CCN(C[C@@H]3CC3(F)F)CC2)c2cc[nH]c2n1)C1CC1]

$^1$H NMR (400 MHz, DMSO-d$_6$) δ 11.41 (s, 1H), 10.57 (s, 1H), 7.67 (s, 1H), 7.31 (t, J=3.0 Hz, 1H), 6.24 (tt, J=1.5, 3.3 Hz, 1H), 4.14 (dd, J=1.2, 3.5 Hz, 2H), 4.07-3.94 (m, 2H), 3.70 (t, J=5.7 Hz, 1H), 3.57 (t, J=5.7 Hz, 1H), 2.34 (s, 1H), 2.05-1.95 (m, 1H), 1.52 (s, 3H), 1.24 (d, J=8.3 Hz, 1H), 0.83-0.75 (m, 4H).
MS(ESI+) m/z 376 (M+H)$^+$

Example 700: Synthesis of N-(4-(4-(3-(cyanomethyl)-1-(ethylsulfonyl)azetidin-3-yl)piperazin-1-yl)-1H-pyrrolo[2,3-b]pyridin-6-yl)cyclopropanecarboxamide

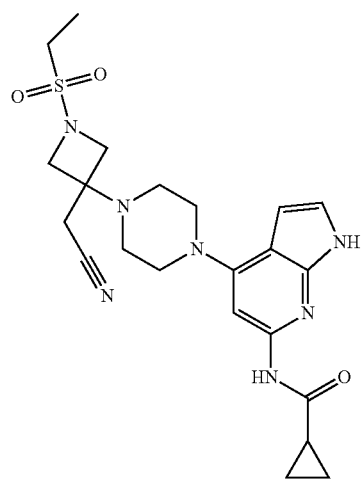 [SMILES: CCS(=O)(=O)N1CC(CC#N)(N2CCN(c3cc(NC(=O)C4CC4)nc4[nH]ccc34)CC2)C1]

MS(ESI+) m/z 472 (M+H)$^+$

Example 701: Synthesis of N-(4-(8-(3-(cyanomethyl)-1-(ethylsulfonyl)azetidin-3-yl)-3,8-diazabicyclo[3.2.1]octan-3-yl)-1H-pyrrolo[2,3-b]pyridin-6-yl)cyclopropanecarboxamide

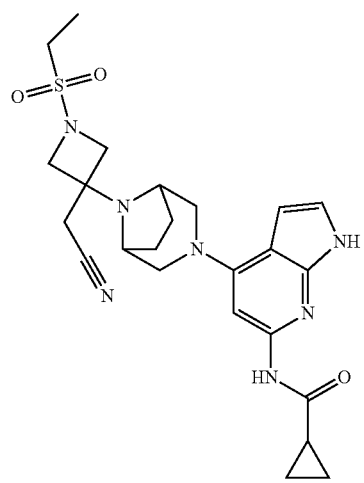 [SMILES: CCS(=O)(=O)N1CC(CC#N)(N2C3CCC2CN(c2cc(NC(=O)C4CC4)nc4[nH]ccc24)C3)C1]

$^1$H NMR (400 MHz, DMSO-d$_6$) δ 10.29 (s, 1H), 9.46 (s, 1H), 7.49-7.37 (m, 2H), 6.71-6.60 (m, 1H), 4.54 (d, J=9.2 Hz, 2H), 4.24 (d, J=9.1 Hz, 2H), 4.14 (s, 2H), 3.87-3.74 (m, 2H), 3.19 (q, J=7.3 Hz, 2H), 2.37 (q, J=7.4 Hz, 2H), 1.99 (s, 5H), 1.25-1.21 (m, 3H), 1.05 (t, J=7.4 Hz, 3H), 0.82-0.74 (m, 4H).
MS(ESI+) m/z 498 (M+H)$^+$

Example 702: Synthesis of N-(4-(4-(2-(1,1-dioxido-thiomorpholino)-2-oxoethyl)piperazin-1-yl)-1H-pyrrolo[2,3-b]pyridin-6-yl)cyclopropanecarboxamide

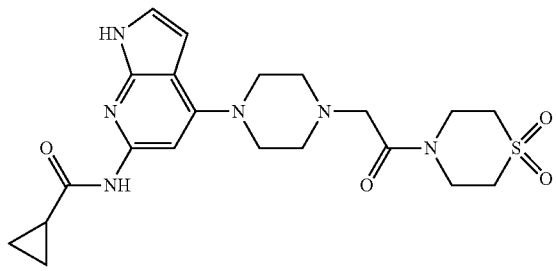 [SMILES: O=C(Nc1cc(N2CCN(CC(=O)N3CCS(=O)(=O)CC3)CC2)c2cc[nH]c2n1)C1CC1]

MS(ESI+) m/z 461 (M+H)+

Example 703: Synthesis of N-(4-(8-(2-((R)-2-cyanopyrrolidin-1-yl)-2-oxoethyl)-3,8-diazabicyclo[3.2.1]octan-3-yl)-1H-pyrrolo[2,3-b]pyridin-6-yl)cyclopropanecarboxamide

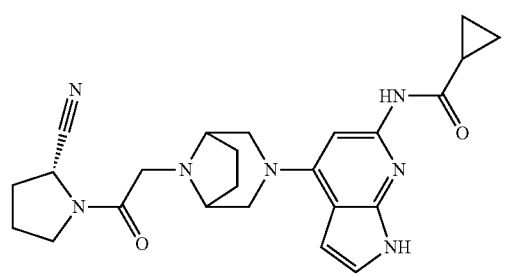 [SMILES: N#C[C@H]1CCCN1C(=O)CN1C2CCC1CN(c1cc(NC(=O)C3CC3)nc3[nH]ccc13)C2]

$^1$H NMR (400 MHz, DMSO-d$_6$) δ 11.49 (s, 1H), 9.96 (s, 1H), 7.01 (t, J=2.9 Hz, 1H), 6.53 (d, J=3.3 Hz, 1H), 4.31 (dt, J=8.5, 4.3 Hz, 2H), 3.74 (dt, J=9.8, 6.3 Hz, 1H), 3.63 (s, 2H), 3.56 (s, 1H), 3.28-3.14 (m, 4H), 2.24-2.11 (m, 2H), 1.94-1.83 (m, 4H), 1.54 (d, J=8.7 Hz, 2H), 0.75 (qd, J=8.5, 4.8 Hz, 4H).
MS(ESI+) m/z 448 (M+H)+

Example 704: Synthesis of N-(4-(8-(2-(1,1-dioxido-thiomorpholino)-2-oxoethyl)-3,8-diazabicyclo[3.2.1]octan-3-yl)-7H-pyrrolo[2,3-d]pyrimidin-2-yl)cyclopropanecarboxamide

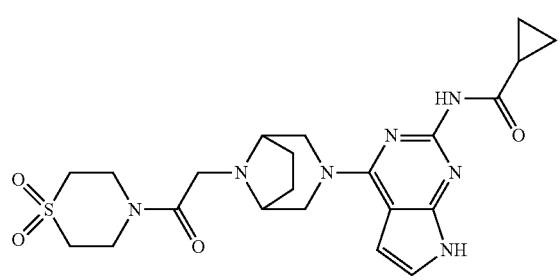 [SMILES: O=C(Nc1nc(N2CC3CCC(C2)N3CC(=O)N2CCS(=O)(=O)CC2)c2cc[nH]c2n1)C1CC1]

MS(ESI+) m/z 488 (M+H)+

Example 705: Synthesis of (S)-3-(4-(6-amino-1H-pyrrolo[2,3-b]pyridin-4-yl)-3-methyl-3,6-dihydropyridin-1 (2H)-yl)-3-oxopropanenitrile

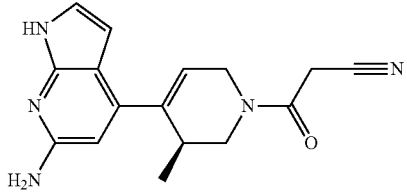 [SMILES: C[C@@H]1CN(C(=O)CC#N)CC=C1c1cc(N)nc2[nH]ccc12]

MS(ESI+) m/z 296 (M+H)+

Example 706: Synthesis of N-(4-(4-(ethylsulfonamido)-3-fluorophenyl)-1H-pyrrolo[2,3-b]pyridin-6-yl)cyclopentanecarboxamide

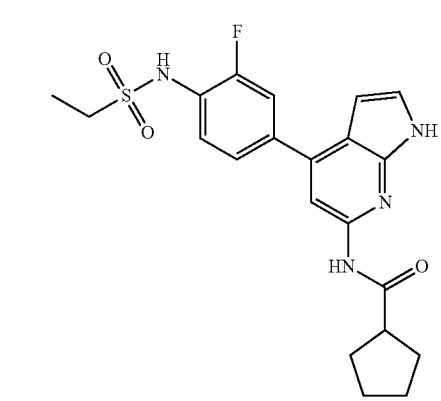 [SMILES: CCS(=O)(=O)Nc1ccc(-c2cc(NC(=O)C3CCCC3)nc3[nH]ccc23)cc1F]

$^1$H NMR (400 MHz, DMSO-d$_6$) δ 11.57 (s, 1H), 10.29 (s, 1H), 9.83 (s, 1H), 8.04 (s, 1H), 7.58 (d, J=9.0 Hz, 3H), 7.43 (s, 1H), 6.56 (s, 1H), 3.18 (q, J=7.5 Hz, 2H), 2.97 (s, 1H), 1.85 (s, 2H), 1.69 (s, 4H), 1.55 (s, 2H), 1.29 (t, J=7.7 Hz, 4H).
MS(ESI+) m/z 417 (M+H)+

Example 707: Synthesis of N-(4-(4-(ethylsulfonamido)-3-fluorophenyl)-1H-pyrrolo[2,3-b]pyridin-6-yl)cyclohexanecarboxamide

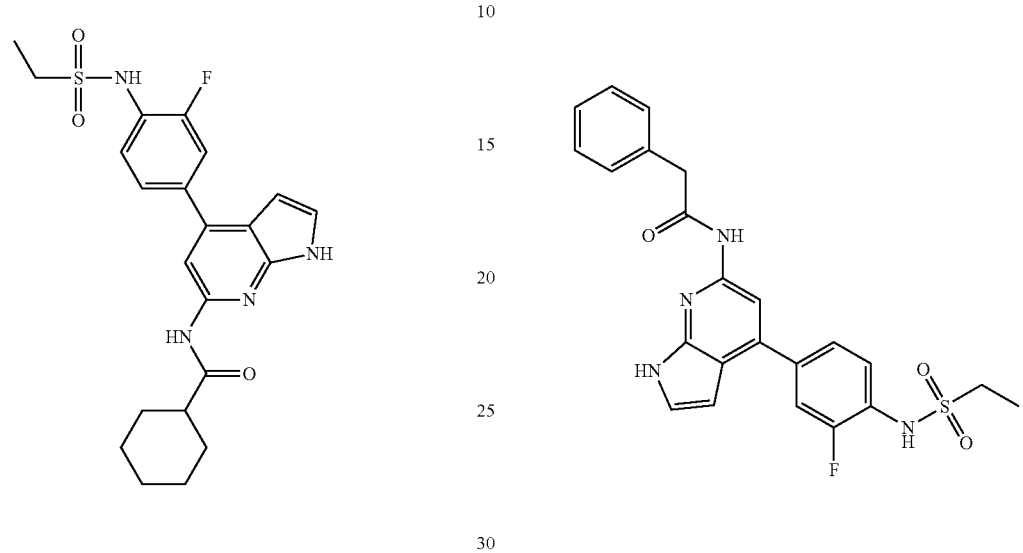

¹H NMR (400 MHz, DMSO-d₆) δ 11.56 (s, 1H), 10.21 (s, 1H), 8.22 (s, 1H), 8.03 (s, 1H), 7.56 (s, 3H), 7.42 (s, 2H), 6.55 (s, 1H), 3.17 (q, 2H), 2.36 (s, 1H), 1.76 (d, J=23.4 Hz, 4H), 1.68-1.56 (m, 2H), 1.41 (d, J=11.7 Hz, 4H), 1.29 (t, J=7.1 Hz, 4H).

MS(ESI+) m/z 421 (M+H)⁺

Example 708: Synthesis of N-(4-(4-(ethylsulfonamido)-3-fluorophenyl)-1H-pyrrolo[2,3-b]pyridin-6-yl)propionamide

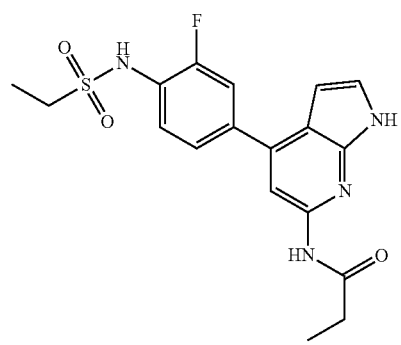 [SMILES: CCC(=O)Nc1cc(-c2ccc(NS(=O)(=O)CC)c(F)c2)c2cc[nH]c2n1]

¹H NMR (400 MHz, DMSO-d₆) δ 11.38 (s, 1H), 10.14 (s, 1H), 7.94 (s, 1H), 7.47-7.36 (m, 1H), 7.33 (s, 1H), 7.26 (t, J=9.0 Hz, 2H), 6.56 (s, 1H), 2.79 (q, J=8.0 Hz, 2H), 2.41 (q, J=7.7 Hz, 2H), 1.17 (t, 3H), 1.09 (t, J=7.2 Hz, 3H).

MS(ESI+) m/z 433 (M+H)⁺

Example 709: Synthesis of N-(4-(4-(ethylsulfonamido)-3-fluorophenyl)-1H-pyrrolo[2,3-b]pyridin-6-yl)-2-phenylacetamide ¹H NMR (400 MHz, DMSO-d₆) δ 11.71-11.50 (s, 1H), 10.58 (s, 1H), 9.81 (s, 1H), 8.00 (s, 1H), 7.56 (d, J=10.0 Hz, 3H), 7.45 (s, 1H), 7.41-7.27 (m, 5H), 7.25 (d, J 7.4 Hz, 1H), 6.56 (s, 1H), 3.74 (s, 2H), 3.23-3.04 (q, 2H), 1.35-1.25 (t, 3H).

MS(ESI+) m/z 494 (M+H)⁺

Example 710: Synthesis of N-(4-(4-(ethylsulfonamido)-3-fluorophenyl)-1H-pyrrolo[2,3-b]pyridin-6-yl)acetamide

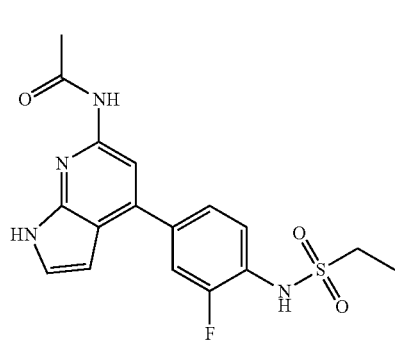 [SMILES: CCS(=O)(=O)Nc1ccc(-c2cc(NC(C)=O)nc3[nH]ccc23)cc1F]

¹H NMR (400 MHz, DMSO-d₆) δ 11.58 (s, 1H), 10.34 (s, 1H), 9.79 (s, 1H), 7.99 (s, 1H), 7.65-7.48 (m, 3H), 7.46-7.36 (m, 1H), 6.55 (d, J=3.2 Hz, 1H), 3.14 (q, 2H), 2.11 (s, 3H), 1.29 (t, 3H).

MS(ESI+) m/z 377 (M+H)⁺

Example 711: Synthesis of N-(4-(4-(ethylsulfonamido)-3-fluorophenyl)-1H-pyrrolo[2,3-b]pyridin-6-yl)isobutyramide

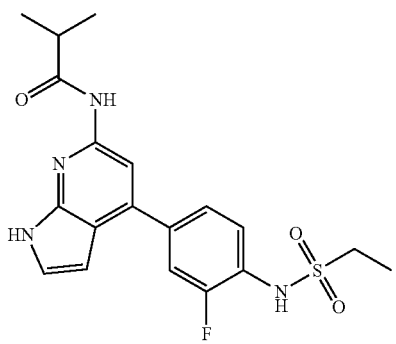 [SMILES: CCS(=O)(=O)Nc1ccc(-c2cc(NC(=O)C(C)C)nc3[nH]ccc23)cc1F]

¹H NMR (400 MHz, DMSO-d₆) δ 11.57 (s, 1H), 10.28 (s, 1H), 9.83 (s, 1H), 8.04 (s, 1H), 7.58 (d, J=8.1 Hz, 3H), 7.49-7.38 (m, 1H), 6.63-6.50 (m, 1H), 3.18 (q, J=7.2 Hz, 2H), 2.85-2.71 (m, 1H), 1.29 (t, J=7.0 Hz, 3H), 1.10 (d, J=6.7 Hz, 6H).

MS(ESI+) m/z 405 (M+H)⁺

Example 712: Synthesis of N-(4-(4-(ethylsulfonamido)-3-fluorophenyl)-1H-pyrrolo[2,3-b]pyridin-6-yl)butyramide

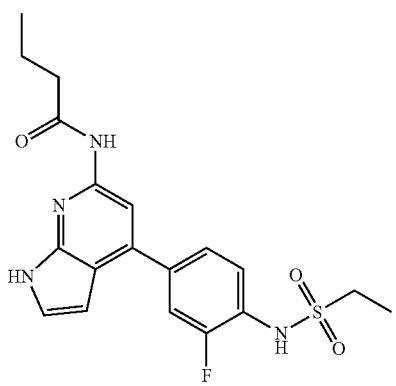 [SMILES: CCCC(=O)Nc1cc(-c2ccc(NS(=O)(=O)CC)c(F)c2)c2cc[nH]c2n1]

¹H NMR (400 MHz, DMSO-d₆) δ 11.60 (s, 1H), 10.29 (s, 1H), 8.02 (s, 1H), 7.70-7.51 (m, 3H), 7.45-7.37 (m, 1H), 6.56 (d, J=3.4 Hz, 1H), 2.37 (q, J=6.9 Hz, 2H), 1.62 (q, J=7.5 Hz, 2H), 1.34-1.26 (m, 5H), 0.92 (t, J=7.3 Hz, 3H).

MS(ESI+) m/z 405 (M+H)⁺

Example 713: Synthesis of N-(4-(6-((cyclopropylmethyl)amino)-1H-pyrrolo[2,3-b]pyridin-4-yl)-2-fluorophenyl)ethanesulfonamide

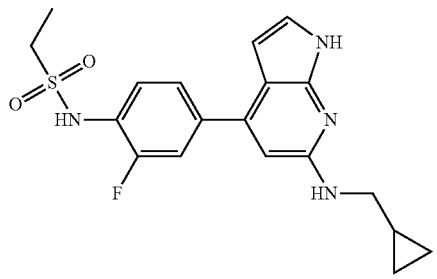 [SMILES: CCS(=O)(=O)Nc1ccc(-c2cc(NCC3CC3)nc3[nH]ccc23)cc1F]

MS(ESI+) m/z 389 (M+H)⁺

Example 714: Synthesis of (Z)—N-(4-(4-(ethylsulfonamido)phenyl)-1H-pyrrolo[2,3-b]pyridin-6-yl)-N'-methylcyclopropanecarboximidamide

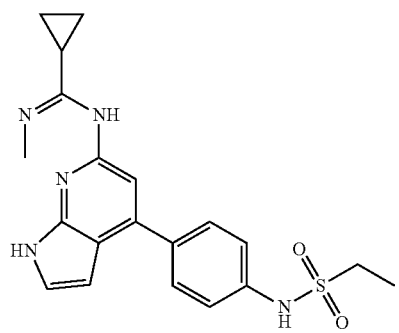 [SMILES: CCS(=O)(=O)Nc1ccc(-c2cc(N/C(=N\C)C3CC3)nc3[nH]ccc23)cc1]

MS(ESI+) m/z 398 (M+H)⁺

Example 715: Synthesis of N-(4-(4-(ethylsulfonamido)phenyl)-1H-pyrrolo[2,3-b]pyridin-6-yl)cyclopropanecarbothioamide

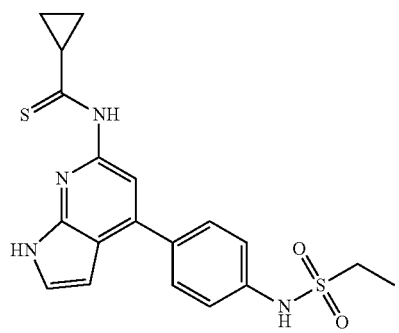 [SMILES: CCS(=O)(=O)Nc1ccc(-c2cc(NC(=S)C3CC3)nc3[nH]ccc23)cc1]

MS(ESI+) m/z 401 (M+H)⁺

Example 716: Synthesis of N-(4-(4-(ethylsulfonamido)-3-fluorophenyl)-1H-pyrrolo[2,3-b]pyridin-6-yl)cyclopropanesulfonamide

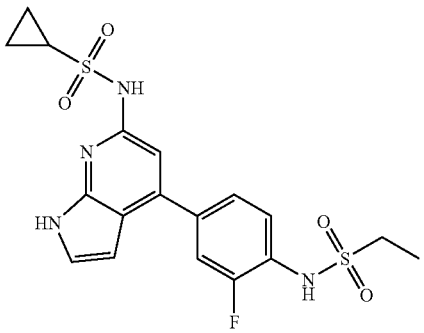 [SMILES: CCS(=O)(=O)Nc1ccc(-c2cc(NS(=O)(=O)C3CC3)nc3[nH]ccc23)cc1F]

$^1$H NMR (400 MHz, Chloroform-d) δ 10.37 (s, 1H), 7.77 (t, J=8.3 Hz, 1H), 7.65-7.47 (m, 3H), 7.44-7.31 (m, 1H), 6.79 (s, 1H), 6.70-6.57 (m, 1H), 3.23 (q, J=7.3 Hz, 2H), 2.65 (tt, J=8.3, 4.7 Hz, 1H), 1.45 (t, J=7.4 Hz, 3H), 0.99 (dt, J=7.8, 3.7 Hz, 4H).
MS(ESI+) m/z 439 (M+H)$^+$

Example 717: Synthesis of 1-cyclopropyl-3-(4-(4-((1,1-dioxidothiomorpholino)methyl)phenyl)-1H-pyrrolo[2,3-b]pyridin-6-yl)urea

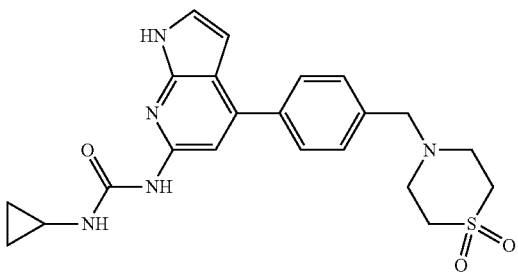 [SMILES: O=C(Nc1cc(-c2ccc(CN3CCS(=O)(=O)CC3)cc2)c2cc[nH]c2n1)NC1CC1]

MS(ESI+) m/z 440 (M+H)$^+$

Example 718: Synthesis of N-(4-(2-(dimethylamino)-7H-pyrrolo[2,3-d]pyrimidin-4-yl)phenyl)-3,4-difluorobenzenesulfonamide

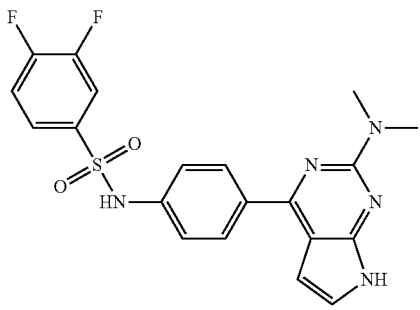 [SMILES: CN(C)c1nc(-c2ccc(NS(=O)(=O)c3ccc(F)c(F)c3)cc2)c2cc[nH]c2n1]

$^1$H NMR (400 MHz, Methanol-d$_4$) δ 8.09-8.02 (m, 2H), 7.77 (ddd, J=2.3, 7.3, 9.7 Hz, 1H), 7.66 (ddt, J=1.8, 3.9, 8.6 Hz, 1H), 7.42 (ddd, J=7.6, 8.7, 10.1 Hz, 1H), 7.32-7.25 (m, 2H), 7.02 (d, J=3.6 Hz, 1H), 6.56 (d, J=3.7 Hz, 1H), 3.23 (s, 6H).
MS(ESI+) m/z 430 (M+H)$^+$

Example 719: Synthesis of N-(2-fluoro-4-(2-(phenylamino)-7H-pyrrolo[2,3-d]pyrimidin-4-yl)phenyl)ethanesulfonamide

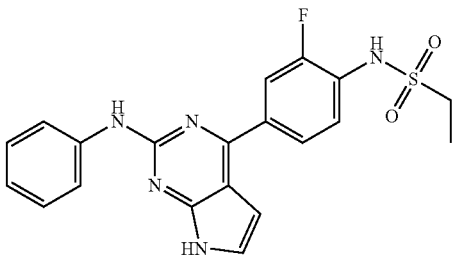 [SMILES: CCS(=O)(=O)Nc1ccc(-c2nc(Nc3ccccc3)nc3[nH]ccc23)cc1F]

$^1$H NMR (400 MHz, DMSO-d$_6$) δ 11.69 (s, 1H), 9.93 (s, 1H), 9.30 (s, 1H), 8.04-7.95 (m, 2H), 7.93-7.84 (m, 2H), 7.62 (t, J=8.5 Hz, 1H), 7.29 (ddd, J=1.8, 5.4, 8.5 Hz, 3H), 6.90 (dd, J=6.8, 8.0 Hz, 1H), 6.75 (dd, J=1.8, 3.7 Hz, 1H), 3.18 (q, J=7.3 Hz, 2H), 1.28 (t, J=7.3 Hz, 3H).
MS(ESI+) m/z 412 (M+H)$^+$

Example 720: Synthesis of N-(4-(2-(phenylamino)-7H-pyrrolo[2,3-d]pyrimidin-4-yl)phenyl)ethanesulfonamide

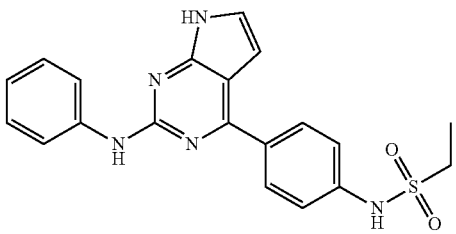 [SMILES: CCS(=O)(=O)Nc1ccc(-c2nc(Nc3ccccc3)nc3[nH]ccc23)cc1]

MS(ESI+) m/z 394 (M+H)$^+$

Example 721: Synthesis of 3-oxo-3-(3-(2-(phenylamino)-7H-pyrrolo[2,3-d]pyrimidin-4-yl)-3,8-diazabicyclo[3.2.1]octan-8-yl)propanenitrile

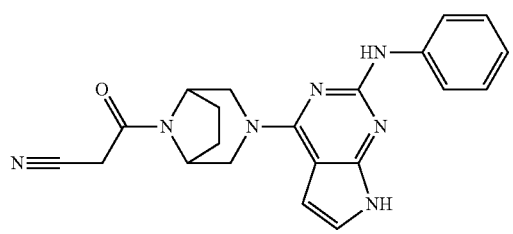 [SMILES: N#CCC(=O)N1C2CCC1CN(c1nc(Nc3ccccc3)nc3[nH]ccc13)C2]

MS(ESI+) m/z 388 (M+H)$^+$

Test Example 1: Analysis of JAK1 Activity Inhibition Ability of Compound of Formula 1 (ADP-Glo™ Kinase Assay)

A JAK inhibition ability of a compound according to the present invention was identified as follows.

A control material and a test material were prepared for each concentration, in such a way that they were diluted by means of DMSO. At the same time, ATP (250 uM) and JAK substrate (JAK1, IRS-itide 40 ng/mL) were prepared, in such a way that they were diluted by means of kinase buffer (40 mM Tris-HCl pH 7.5, 20 mM $MgCl_2$, 0.5 mg/mL BSA, 50 uM DTT).

A test drug for each concentration, substrate, ATP and JAK enzyme were mixed in an eppendorf tube, and reacted in a 30° C. incubator for 40 minutes.

ADP-Glo™ reagent contained in ADP-Glo™ Kinase Enzyme System (Promega, USA, V9571) was added into each eppendorf tube, and reacted in a 30° C. incubator for 40 minutes. A kinase detection reagent contained in ADP-Go™ Kinase Enzyme System was inserted into the eppendorf tube, then an integration time was set to 1 second by using Wallac Victor 2™, then luminescence was measured, and then JAKs phosphorylation inhibition ability of the test material was analyzed. The concentration of the compound, which causes 50% of the JAK enzyme activity inhibition in comparison With the control group, was determined as IC50 (nM) of an inhibitor, wherein the results thereof are shown in a following table 1.

TABLE 1

| Example | IC50 |
|---|---|
| 1 | + + + |
| 2 | + + + |
| 3 | + + + |
| 4 | + + + |
| 5 | + + + |
| 6 | + + + |
| 7 | + + + |
| 8 | + + |
| 9 | + + + |
| 10 | + + + |
| 11 | + + + |
| 12 | + + + |
| 13 | + + + |
| 14 | + + + |
| 15 | + + |
| 16 | + + |
| 17 | + + |
| 18 | + + |
| 19 | + + + |
| 20 | + + |
| 21 | + + |
| 22 | + + |
| 23 | + + + |
| 24 | + + + |
| 25 | + + + |
| 26 | + + |
| 27 | + + |
| 28 | + + |
| 29 | + + + |
| 30 | + + + |
| 31 | + + |
| 32 | + + |
| 33 | + + |
| 34 | + + + |
| 35 | + + + |
| 36 | + + + |
| 37 | + + |
| 38 | + + |
| 39 | + + |
| 40 | + + |
| 41 | + + + |
| 42 | + + + |
| 43 | + + + |
| 44 | + + + |
| 45 | + + + |
| 46 | + + + |
| 47 | + + + |
| 48 | + + + |
| 49 | + + |
| 50 | + + |
| 51 | + + |
| 52 | + + + |
| 53 | + + |
| 54 | + + + |
| 55 | + + + |
| 56 | + + + |
| 57 | + + + |
| 58 | + + + |
| 59 | + |
| 60 | + |
| 61 | + |
| 62 | + |
| 63 | + + |
| 64 | + + + |
| 65 | + + + |
| 66 | + + + |
| 67 | + + + |
| 68 | + + + |
| 69 | + + + |
| 70 | + + |
| 71 | + + + |
| 72 | + + + |
| 73 | + + + |
| 74 | + |
| 75 | + + + |
| 76 | + + + |
| 77 | + + + |
| 78 | + + + |
| 79 | + + + |
| 80 | + + + |
| 81 | + + |
| 82 | + + |
| 83 | + + + |
| 84 | + + + |
| 85 | + + + |
| 86 | + + + |
| 87 | + + |
| 88 | + + + |
| 89 | + + + |
| 90 | + + |
| 91 | + + |
| 92 | + + |
| 93 | + + |
| 94 | + + |
| 95 | + + |
| 96 | + + |
| 97 | + + |
| 98 | + + |
| 99 | + + + |
| 100 | + + |
| 101 | + + |
| 102 | + + + |
| 103 | + + + |
| 104 | + + |
| 105 | + + + |
| 106 | + + + |
| 107 | + + |
| 108 | + + + |
| 109 | + + + |
| 110 | + + + |
| 111 | + + + |
| 112 | + + |
| 113 | + + + |
| 114 | + + + |
| 115 | + + + |
| 116 | + + |
| 117 | + + + |
| 118 | + + |
| 119 | + + |
| 120 | + + |
| 121 | + + |
| 122 | + + |
| 123 | + + + |
| 124 | + + + |
| 125 | + + + |
| 126 | + + + |

TABLE 1-continued

| Example | IC50 |
|---|---|
| 127 | + + |
| 128 | + + + |
| 129 | + |
| 130 | + |
| 131 | + + |
| 132 | + + |
| 133 | + + + |
| 134 | + + |
| 135 | + + |
| 136 | + + |
| 137 | + + + |
| 138 | + |
| 139 | + |
| 140 | + |
| 141 | + |
| 142 | + |
| 143 | + |
| 144 | + + |
| 145 | + + |
| 146 | + |
| 147 | + |
| 148 | + + |
| 149 | + |
| 150 | + |
| 151 | + + |
| 152 | + + |
| 153 | + + |
| 154 | + + |
| 155 | + + + |
| 156 | + + + |
| 157 | + + + |
| 158 | + + + |
| 159 | + + + |
| 160 | + + + |
| 161 | + + + |
| 162 | + + + |
| 163 | + + + |
| 164 | + + + |
| 165 | + + + |
| 166 | + + |
| 167 | + + |
| 168 | + + |
| 169 | + |
| 170 | + + |
| 171 | + + |
| 172 | + + |
| 173 | + + |
| 174 | + + |
| 175 | + + |
| 176 | + + |
| 177 | + + |
| 178 | + + |
| 179 | + |
| 180 | + + |
| 181 | + + + |
| 182 | + + |
| 183 | + + + |
| 184 | + + |
| 185 | + + + |
| 186 | + + |
| 187 | + + |
| 188 | + + + |
| 189 | + + |
| 190 | + + + |
| 191 | + + + |
| 192 | + + + |
| 193 | + |
| 194 | + + + |
| 195 | + + |
| 196 | + + |
| 197 | + |
| 198 | + |
| 199 | + |
| 200 | + |
| 201 | + |
| 202 | + + |
| 203 | + + + |
| 204 | + + |

TABLE 1-continued

| Example | IC50 |
|---|---|
| 205 | + + |
| 206 | + + |
| 207 | + |
| 208 | + |
| 209 | + |
| 210 | + |
| 211 | + |
| 212 | + |
| 213 | + |
| 214 | + + + |
| 215 | + + + |
| 216 | + + |
| 217 | + + + |
| 218 | + + + |
| 219 | + + + |
| 220 | + + |
| 221 | + + |
| 222 | + + |
| 223 | + + |
| 224 | + + + |
| 225 | + + + |
| 226 | + + + |
| 227 | + + |
| 228 | + + + |
| 229 | + + + |
| 230 | + + + |
| 231 | + + + |
| 232 | + + |
| 233 | + + |
| 234 | + + |
| 235 | + + |
| 236 | + + |
| 237 | + |
| 238 | + |
| 239 | + + |
| 240 | + |
| 241 | + + |
| 242 | + |
| 243 | + + |
| 244 | + |
| 245 | + + |
| 246 | + + |
| 247 | + + |
| 248 | + |
| 249 | + + |
| 250 | + + + |
| 251 | + + |
| 252 | + + + |
| 253 | + + |
| 254 | + + |
| 255 | + + + |
| 256 | + + + |
| 257 | + + + |
| 258 | + + + |
| 259 | + |
| 260 | + + |
| 261 | + + |
| 262 | + + |
| 263 | + + + |
| 264 | + + |
| 265 | + + + |
| 266 | + + |
| 267 | + + + |
| 268 | + + |
| 269 | + + + |
| 270 | + |
| 271 | + + |
| 272 | + + |
| 273 | + + |
| 274 | + + + |
| 275 | + + + |
| 276 | + + |
| 277 | + |
| 278 | + + |
| 279 | + + |
| 280 | + |
| 281 | + |
| 282 | + + |

TABLE 1-continued

| Example | IC50 |
|---|---|
| 283 | + + + |
| 284 | + + + |
| 285 | + + |
| 286 | + + |
| 287 | + + |
| 288 | + + |
| 289 | + |
| 290 | + |
| 291 | + |
| 292 | + + + |
| 293 | + + |
| 294 | + + + |
| 295 | + + + |
| 296 | + + |
| 297 | + |
| 298 | + + |
| 299 | + + |
| 300 | + + |
| 301 | + |
| 302 | + + |
| 303 | + + + |
| 304 | + + + |
| 305 | + + |
| 306 | + + |
| 307 | + |
| 308 | + + |
| 309 | + + + |
| 310 | + + + |
| 311 | + + |
| 312 | + + |
| 313 | + + |
| 314 | + + |
| 315 | + |
| 316 | + |
| 317 | + |
| 318 | + |
| 319 | + |
| 320 | + |
| 321 | + |
| 322 | + |
| 323 | + |
| 324 | + + |
| 325 | + + |
| 326 | + + |
| 327 | + + |
| 328 | + + |
| 329 | + + |
| 330 | + + |
| 331 | + + |
| 332 | + |
| 333 | + + |
| 334 | + + |
| 335 | + + |
| 336 | + + |
| 337 | + + |
| 338 | + + |
| 339 | + + |
| 340 | + + |
| 341 | + |
| 342 | + + |
| 343 | + + |
| 344 | + |
| 345 | + + |
| 346 | + + |
| 347 | + + |
| 348 | + + |
| 349 | + + |
| 350 | + + |
| 351 | + |
| 352 | + + |
| 353 | + + |
| 354 | + + |
| 355 | + + |
| 356 | + |
| 357 | + + |
| 358 | + + |
| 359 | + + |
| 360 | + + |

TABLE 1-continued

| Example | IC50 |
|---|---|
| 361 | + + |
| 362 | + + |
| 363 | + + + |
| 365 | + + |
| 366 | + + + |
| 367 | + + |
| 368 | + + + |
| 369 | + + |
| 370 | + + |
| 371 | + + |
| 372 | + + |
| 373 | + |
| 374 | + + |
| 375 | + + |
| 376 | + + |
| 377 | + |
| 378 | + + + |
| 379 | + + |
| 380 | + + |
| 381 | + |
| 382 | + + |
| 383 | + |
| 384 | + + |
| 385 | + + + |
| 386 | + + |
| 387 | + + |
| 388 | + + + |
| 389 | + + + |
| 390 | + + + |
| 391 | + + |
| 392 | + + |
| 393 | + + + |
| 394 | + + + |
| 395 | + + + |
| 396 | + + + |
| 397 | + + + |
| 398 | + + + |
| 399 | + + + |
| 400 | + + + |
| 401 | + + |
| 402 | + + + |
| 403 | + + |
| 404 | + + |
| 405 | + |
| 406 | + + + |
| 407 | + + |
| 408 | + + |
| 409 | + + + |
| 410 | + + + |
| 411 | + + |
| 412 | + + + |
| 413 | + + + |
| 414 | + + + |
| 415 | + + + |
| 416 | + + + |
| 417 | + + + |
| 418 | + |
| 419 | + |
| 420 | + + |
| 421 | + + |
| 422 | + + + |
| 423 | + + + |
| 424 | + + + |
| 425 | + + |
| 426 | + |
| 427 | + |
| 428 | + |
| 429 | + |
| 430 | + |
| 431 | + + |
| 432 | + + |
| 433 | + + |
| 434 | + |
| 435 | + + |
| 436 | + + |
| 437 | + |
| 438 | + |
| 439 | + + |

TABLE 1-continued

| Example | IC50 |
|---|---|
| 440 | + + |
| 441 | + + |
| 442 | + + + |
| 443 | + + + |
| 444 | + + |
| 445 | + + |
| 446 | + |
| 447 | + + |
| 448 | + + + |
| 449 | + + |
| 450 | + |
| 451 | + + |
| 452 | + + + |
| 453 | + + + |
| 454 | + + |
| 455 | + + + |
| 456 | + |
| 457 | + |
| 458 | + |
| 459 | + |
| 460 | + |
| 461 | + |
| 462 | + + |
| 463 | + |
| 464 | + |
| 465 | + + |
| 466 | + + |
| 467 | + + |
| 468 | + + |
| 469 | + + + |
| 470 | + + |
| 471 | + |
| 472 | + |
| 473 | + + + |
| 474 | + + + |
| 475 | + + + |
| 476 | + |
| 477 | + + + |
| 478 | + + + |
| 479 | + + |
| 480 | + + |
| 481 | + + |
| 482 | + |
| 483 | + + + |
| 484 | + |
| 485 | + + |
| 486 | + + |
| 487 | + |
| 488 | + + + |
| 489 | + + |
| 490 | + + |
| 491 | + |
| 492 | + |
| 493 | + + |
| 494 | + |
| 495 | + + |
| 496 | + |
| 497 | + + |
| 498 | + + |
| 499 | + |
| 500 | + |
| 501 | + + |
| 502 | + |
| 503 | + |
| 504 | + |
| 505 | + + |
| 506 | + + |
| 507 | + |
| 508 | + |
| 509 | + |
| 510 | + |
| 511 | + + |
| 512 | + + |
| 513 | + |
| 514 | + |
| 515 | + + |
| 516 | + + |
| 517 | + + |

TABLE 1-continued

| Example | IC50 |
|---|---|
| 518 | + |
| 519 | + |
| 520 | + |
| 521 | + + |
| 522 | + + |
| 523 | + + + |
| 524 | + + + |
| 525 | + + |
| 526 | + + |
| 527 | + |
| 528 | + + |
| 529 | + + |
| 530 | + + |
| 531 | + + |
| 532 | + + |
| 533 | + + |
| 534 | + |
| 535 | + + |
| 536 | + + |
| 537 | + + |
| 538 | + + |
| 539 | + + |
| 540 | + + |
| 541 | + + |
| 542 | + + + |
| 543 | + |
| 544 | + + |
| 545 | + + |
| 546 | + + |
| 547 | + + |
| 548 | + + |
| 549 | + + |
| 550 | + + |
| 551 | + |
| 552 | + |
| 553 | + + |
| 554 | + + |
| 555 | + |
| 556 | + + |
| 557 | + + |
| 558 | + |
| 559 | + + |
| 560 | + + |
| 561 | + + |
| 562 | + |
| 563 | + + |
| 564 | + + |
| 565 | + + |
| 566 | + |
| 567 | + + |
| 568 | + + |
| 569 | + + + |
| 570 | + + |
| 571 | + + |
| 572 | + + |
| 573 | + + |
| 574 | + + |
| 575 | + + |
| 576 | + + |
| 577 | + + |
| 578 | + + |
| 579 | + |
| 580 | + + |
| 581 | + + |
| 582 | + + + |
| 583 | + + |
| 584 | + + + |
| 585 | + + + |
| 586 | + + |
| 587 | + + + |
| 588 | + + + |
| 589 | + + + |
| 590 | + + + |
| 591 | + + |
| 592 | + |
| 593 | + |
| 594 | + |
| 595 | + + |

TABLE 1-continued

| Example | IC50 |
|---|---|
| 596 | + + |
| 597 | + |
| 598 | + |
| 599 | + + + |
| 600 | + + |
| 601 | + + |
| 602 | + |
| 603 | + + |
| 604 | + + |
| 605 | + + |
| 606 | + |
| 607 | + + |
| 608 | + + |
| 609 | + + |
| 610 | + + |
| 611 | + + |
| 612 | + |
| 613 | + + |
| 614 | + |
| 615 | + + |
| 616 | + + + |
| 617 | + + + |
| 618 | + + + |
| 619 | + + + |
| 620 | + |
| 621 | + + |
| 622 | + + |
| 623 | + + |
| 624 | + + |
| 625 | + + |
| 626 | + + + |
| 627 | + + + |
| 628 | + + + |
| 629 | + + |
| 630 | + |
| 631 | + + |
| 632 | + + |
| 633 | + + |
| 634 | + |
| 635 | + + |
| 636 | + + + |
| 637 | + |
| 638 | + + |
| 639 | + + |
| 640 | + |
| 641 | + |
| 642 | + + |
| 643 | + |
| 644 | + |
| 645 | + + |
| 646 | + |
| 647 | + |
| 648 | + |
| 649 | + |
| 650 | + |
| 651 | + |
| 652 | + + |
| 653 | + |
| 654 | + |
| 655 | + |
| 656 | + |
| 657 | + + |
| 658 | + |
| 659 | + |
| 660 | + |
| 661 | + + |
| 662 | + |
| 663 | + |
| 664 | + + |
| 665 | + + |
| 666 | + |
| 667 | + + + |
| 668 | + |
| 669 | + + |
| 670 | + |
| 671 | + |
| 672 | + |
| 673 | + |

TABLE 1-continued

| Example | IC50 |
|---|---|
| 674 | + |
| 675 | + |
| 676 | + |
| 677 | + + + |
| 678 | + + |
| 679 | + |
| 680 | + |
| 681 | + |
| 682 | + |
| 683 | + + |
| 684 | + |
| 685 | + |
| 686 | + + + |
| 687 | + |
| 688 | + + |
| 689 | + + |
| 690 | + |
| 691 | + + + |
| 692 | + |
| 693 | + + |
| 694 | + |
| 695 | + + |
| 696 | + |
| 697 | + |
| 698 | + + |
| 699 | + + |
| 700 | + |
| 701 | + |
| 702 | + |
| 703 | + |
| 704 | + |
| 705 | + |
| 706 | + |
| 707 | + |
| 708 | + |
| 709 | + |
| 710 | + + |
| 711 | + |
| 712 | + |
| 713 | + |
| 714 | + |
| 715 | + + |
| 716 | + |
| 717 | + + |
| 718 | + |
| 719 | + + |
| 720 | + + |
| 721 | + + |

+ + +: <20 nM,
+ +: 20~200 nM,
+: >200 nM

The invention claimed is:
1. A compound represented by formula 1, a stereoisomer thereof or a pharmaceutically acceptable salt thereof:

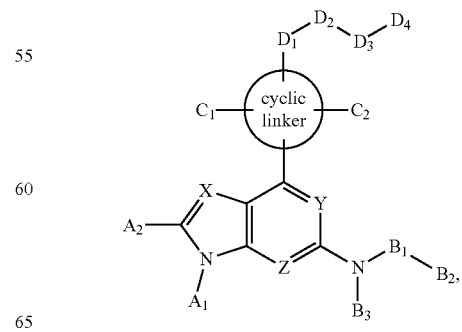

[Formula 1]

wherein

X is C-A₃ or N;

Y is C-A₄;

Z is N or N—O;

A₁ to A₄ are each independently H, C1-C6 alkyl, C1-C6 alkoxy, C1-C6 hydroxyalkyl, C1-C6 haloalkyl, C1-C6 cyanoalkyl, C(=O)—OH, C(=O)—O—C1-C6 alkyl, S(=O)₂—C1-C6 alkyl, aryl or heteroaryl;

B₁ is —C(=O)—, —C(=S)—, —C(=NR₁)—, —C(=O)—NR₁— or —S(=O)₂—;

B₂ is H, C3-C7 cycloalkyl, 5-6 membered heterocycloalkyl, C1-C6 alkyl-aryl or C1-C6 alkyl-heteroaryl, wherein at least one H of C3-C7 cycloalkyl, 5-6 membered heterocycloalkyl, C1-C6 alkyl-aryl or C1-C6 alkyl-heteroaryl may be substituted with C1-C6 alkyl, hydroxy or halogen;

B₃ is H or C1-C6 alkyl;

Cyclic linker is C3-C7 cycloalkyl, C3-C7 cycloalkenyl, 5-6 membered heterocycloalkyl, 5-6 membered heterocycloalkenyl, aryl or heteroaryl;

C₁ and C₂ are each independently H, C1-C6 alkyl, C1-C6 alkoxy, C1-C6 hydroxyalkyl, C1-C6 cyanoalkyl, C1-C6 haloalkyl, hydroxy, cyano, halogen, C(=O)—OH, C(=O)—O—C1-C6 alkyl, S(=O)₂—C1-C6 alkyl, aryl or heteroaryl, or C₁ and C₂ may be linked to each other through at least one carbon atom to make a bicyclic ring or spiro ring;

D₁ is —(CH₂)ₘ—, —(CH₂)ₘ—NR₁—, —O—

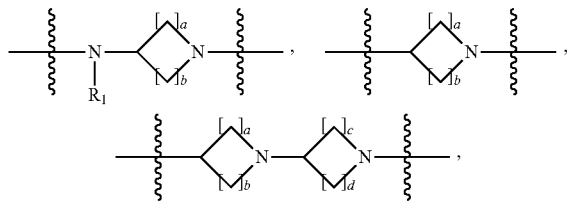

or null, wherein at least one H of —(CH₂)ₘ— or —(CH₂)ₘ—NR₁— may be substituted with C1-C6 alkyl, halogen or cyano, or may be linked to each other along with at least one carbon atom to form a ring; and at least one H of

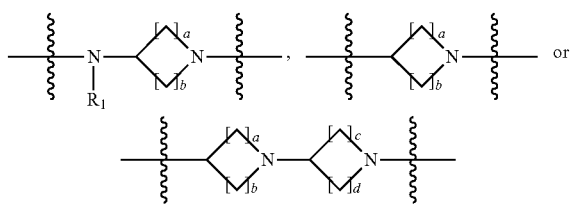

may be substituted with C1-C6 alkyl, C1-C6 hydroxyalkyl, C1-C6 haloalkyl or C1-C6 cyanoalkyl;

D₂ is —C(=O)—, —C(=O)—CH₂—C(=O)—, —C(=S)—, —S(=O)₂— or null, wherein at least one H of —C(=O)—CH₂—C(=O)— may be substituted with C1-C6 alkyl or halogen;

D₃ is —(CH₂)ₘ—, —(CH₂)ₘ—NR₁—, —O—,

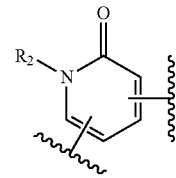

or null, wherein at least one H of —(CH₂)ₘ— or —(CH₂)ₘ—NR₁— may be substituted with C1-C6 alkyl, halogen or cyano, or may be linked to each other along with at least one carbon atom to form a ring;

D₄ is H, C1-C6 alkyl, C2-C6 alkenyl, C1-C6 alkoxyalkyl, C1-C6 hydroxyalkyl, C1-C6haloalkyl, C1-C6 cyanoalkyl, S(=O)₂—C1-C6 alkyl, C3-C7 cycloalkyl,

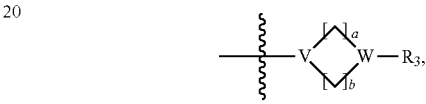

aryl or heteroaryl, wherein at least one H of C1-C6 alkyl, C2-C6 alkenyl, C1-C6 alkoxyalkyl, C1-C6 hydroxyalkyl, C1-C6 haloalkyl or C1-C6 cyanoalkyl may be substituted with C3-C7 cycloalkyl;

at least one H of C3-C7 cycloalkyl or

may be substituted with C1-C6 alkyl, C1-C6 haloalkyl, C1-C6 cyanoalkyl, cyano, halogen, —C(=O)—R₄ or —C(=O)—O—R₄; and at least one H of aryl or heteroaryl may be substituted with C1-C6 alkyl, C1-C6 alkoxy, C1-C6 haloalkyl, C1-C6 hydroxyalkyl, C1-C6 cyanoalkyl, C1-C6 thioalkyl, hydroxy, cyano, nitro, halogen, —C(=O)—R₄, —C(=O)—NR₁—R₄, —S(=O)₂—R₄, —S(=O)₂—NR₁—R₄, —NR₁—R₅,

aryl or heteroaryl, wherein, at this time, at least one H of

may be substituted with C1-C6 alkyl or (=O));

R₁ and R₂ are each independently H or C1-C6 alkyl;

R₃ is H, C1-C6 alkyl, —C(=O)—R₄, —C(=O)—O—R₄, —S(=O)₂—R₄ or —S(=O)₂—NR₁—R₄, wherein in case W is —O—, —C(=O)— or —S(=O)₂—, R₃ is null;

$R_4$ is H, C1-C6 alkyl or C1-C6 haloalkyl;
$R_5$ is H, C1-C6 alkyl,

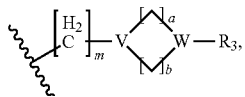

aryl or heteroaryl, wherein at least one H of

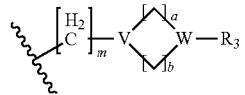

may be substituted with C1-C6 alkyl or (=O); and at least one H of aryl or heteroaryl may be substituted with C1-C6 alkyl or halogen;

V is —CH— or —N—;
W is —CH—, —N—, —O—, —S—, —C(=O)—, —S(=O)— or —S(=O)$_2$—, wherein in case V is —CH—, W is not —CH—;
a to d are each independently 1, 2 or 3; and
m is 1, 2 or 3.

2. The compound, the stereoisomer thereof or the pharmaceutically acceptable salt thereof according to claim 1, wherein:

X is C—$A_3$ or N;
Y is C—$A_4$;
Z is N or N—O;
$A_1$ to $A_4$ are each independently H, C1-C6 alkyl or C1-C6 cyanoalkyl;
$B_1$ is —C(=O)—, —C(=S)—, —C(=NR$_1$)—, —C(=O)—NR$_1$— or —S(=O)$_2$;
$B_2$ is H, C3-C7 cycloalkyl or C1-C6 alkyl-aryl, wherein at least one H of C3-C7 cycloalkyl or C1-C6 alkyl-aryl may be substituted with C1-C6 alkyl;
$B_3$ is H or C1-C6 alkyl;
Cyclic linker is C3-C7 cycloalkyl, C3-C7 cycloalkenyl, 5-6 membered heterocycloalkyl, 5-6 membered heterocycloalkenyl, aryl or heteroaryl;
$C_1$ and $C_2$ are each independently H, C1-C6 alkyl, C1-C6 haloalkyl, hydroxy, cyano, halogen, C(=O)—OH, C(=O)—O—C1-C6 alkyl or aryl,
or $C_1$ and $C_2$ may be linked to each other through at least one carbon atom to make a bicyclic ring or spiro ring;
$D_1$ is —(CH$_2$)$_m$—, —(CH$_2$)$_m$—NR$_1$—, —O—,

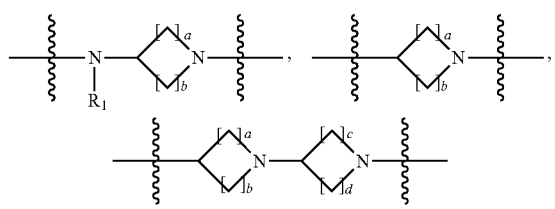

or null, wherein at least one H of —(CH$_2$)$_m$— or —(CH$_2$)$_m$—NR$_1$— may be substituted with C1-C6 alkyl or halogen, or may be linked to each other along with at least one carbon atom to form a ring; and at least one H of

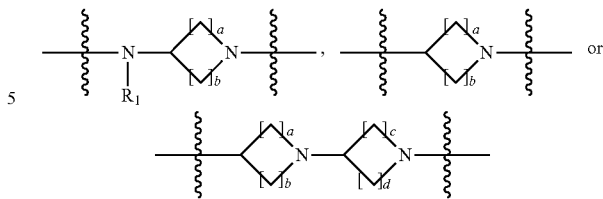

may be substituted with C1-C6 alkyl or C1-C6 cyanoalkyl;
$D_2$ is —C(=O)—, —C(=O)—CH$_2$—C(=O)—, —C(=S)—, —S(=O)$_2$— or null, wherein at least one H of —C(=O)—CH$_2$—C(=O)— may be substituted with C1-C6 alkyl;
$D_3$ is —(CH$_2$)$_m$—, —(CH$_2$)$_m$—NR$_1$—, —NR$_1$—O—,

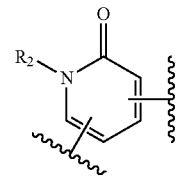

or null, wherein at least one H of —(CH$_2$)$_m$— or —(CH$_2$)$_m$—NR$_1$— may be substituted with cyano;
$D_4$ is H, C1-C6 alkyl, C2-C6 alkenyl, C1-C6 alkoxyalkyl, C1-C6 hydroxyalkyl, C1-C6haloalkyl, C1-C6 cyanoalkyl, S(=O)$_2$—C1-C6 alkyl, C3-C7 cycloalkyl,

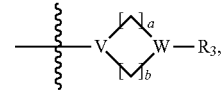

aryl or heteroaryl,
wherein at least one H of C1-C6 alkyl, C2-C6 alkenyl, C1-C6 alkoxyalkyl, C1-C6 hydroxyalkyl, C1-C6 haloalkyl or C1-C6 cyanoalkyl may be substituted with C3-C7 cycloalkyl;
at least one H of C3-C7 cycloalkyl or

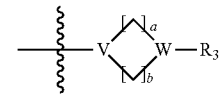

may be substituted with C1-C6 alkyl, C1-C6 haloalkyl, C1-C6 cyanoalkyl, cyano, halogen or —C(=O)—O—R$_4$; and
at least one H of aryl or heteroaryl may be substituted with C1-C6 alkyl, C1-C6 alkoxy, C1-C6 haloalkyl, C1-C6 thioalkyl, hydroxy, cyano, nitro, halogen, —C(=O)—R$_4$, —C(=O)—NR$_1$—R$_4$, —S(=O)$_2$—R$_4$, —S(=O)$_2$—NR$_1$—R$_4$, —NR$_1$—R$_5$ or

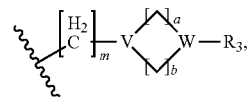

wherein at least one H of

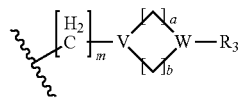

may be substituted with (=O));
R₁ and R₂ are each independently H or C1-C6 alkyl;
R₃ is H, C1-C6 alkyl, —C(=O)—R₄, —C(=O)—O—R₄, —S(=O)₂—R₄ or —S(=O)₂—NR₁—R₄, wherein in case W is —O—, —C(=O)— or —S(=O)₂—, R₃ is null;
R₄ is H, C1-C6 alkyl or C1-C6 haloalkyl;
R₅ is H,

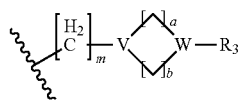

or aryl, wherein at least one H of

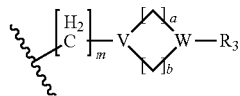

may be substituted with (=O); and at least one H of aryl may be substituted with C1-C6 alkyl or halogen;
V is —CH— or —N—;
W is —CH, —N—, —O—, —S—, —C(=O)—, —S(=O)— or —S(=O)₂—, wherein in case V is —CH—, W is not —CH—;
a to d are each independently 1, 2 or 3; and
m is 1 or 2.

3. The compound, the stereoisomer thereof or the pharmaceutically acceptable salt thereof according to claim 2, wherein:
X is C—A₃;
Y is C—A₄;
Z is N or N—O;
A₁ to A₄ are each independently H, C1-C6 alkyl or C1-C6 cyanoalkyl;
B₁ is —C(=O)—, —C(=S)—, —C(=NR₁)—, —C(=O)—NR₁— or —S(=O)₂;
B₂ is H, C3-C7 cycloalkyl or C1-C6 alkyl-aryl, wherein at least one H of C3-C7 cycloalkyl or C1-C6 alkyl-aryl may be substituted with C1-C6 alkyl;
B₃ is H;
Cyclic linker is C3-C7 cycloalkyl, C3-C7 cycloalkenyl, 5-6 membered heterocycloalkyl, 5-6 membered heterocycloalkenyl, aryl or heteroaryl;
C₁ and C₂ are each independently H, C1-C6 alkyl, C1-C6 haloalkyl, hydroxy, cyano, halogen, C(=O)—OH, C(=O)—O—C1-C6 alkyl or aryl,
or C₁ and C₂ may be linked to each other through at least one carbon atom to make a bicyclic ring or spiro ring;

D₁ is —(CH₂)ₘ—, —(CH₂)ₘ—NR₁—, —O—,

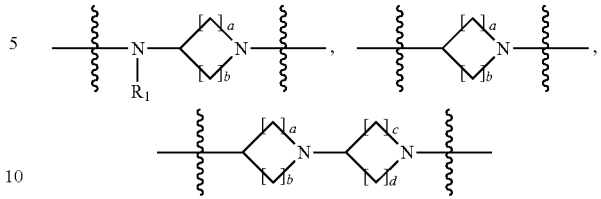

or null, wherein at least one H of —(CH₂)ₘ— or —(CH₂)ₘ—NR₁— may be substituted with C1-C6 alkyl or halogen, or may be linked to each other along with at least one carbon atom to form a ring; and at least one H of

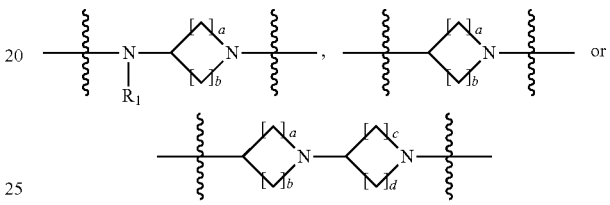

may be substituted with C1-C6 alkyl or C1-C6 cyanoalkyl;
D₂ is —C(=O)—, —C(=O)—CH₂—C(=O)—, —C(=S)—, —S(=O)₂— or null, wherein at least one H of —C(=O)—CH₂—C(=O)— may be substituted with C1-C6 alkyl;
D₃ is —(CH₂)ₘ—, —(CH₂)ₘ—NR₁—, —NR₁—, —O—,

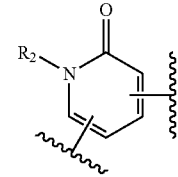

or null, wherein at least one H of —(CH₂)ₘ— or —(CH₂)ₘ—NR₁— may be substituted with cyano;
D₄ is H, C1-C6 alkyl, C2-C6 alkenyl, C1-C6 alkoxyalkyl, C1-C6 haloalkyl, C1-C6 cyanoalkyl, S(=O)₂—C1-C6 alkyl, C3-C7 cycloalkyl,

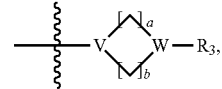

aryl or heteroaryl,
wherein at least one H of C1-C6 alkyl, C2-C6 alkenyl, C1-C6 alkoxyalkyl, C1-C6 haloalkyl or C1-C6 cyanoalkyl may be substituted with C3-C7 cycloalkyl;
at least one H of C3-C7 cycloalkyl or

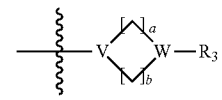

may be substituted with C1-C6 alkyl, C1-C6 haloalkyl, C1-C6 cyanoalkyl, cyano, halogen or —C(=O)—O—R$_4$; and at least one H of aryl or heteroaryl may be substituted with C1-C6 alkyl, C1-C6 alkoxy, C1-C6 haloalkyl, C1-C6 thioalkyl, hydroxy, cyano, nitro, halogen, —C(=O)—R$_4$, —C(=O)—NR$_1$—R$_4$, —S(=O)$_2$—R$_4$, —S(=O)$_2$—NR$_1$—R$_4$, —NR$_1$—R$_5$ or

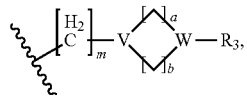

wherein at least one H of

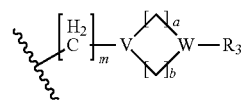

may be substituted with (=O));

R$_1$ and R$_2$ are each independently H or C1-C6 alkyl;

R$_3$ is H, C1-C6 alkyl, —C(=O)—R$_4$, —C(=O)—O—R$_4$, —S(=O)$_2$—R$_4$ or —S(=O)$_2$—NR$_1$—R$_4$, wherein in case W is —O—, —C(=O)— or —S(=O)$_2$—, R$_3$ is null;

R$_4$ is H, C1-C6 alkyl or C1-C6 haloalkyl;

R$_5$ is H,

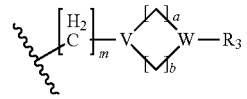

or aryl, wherein at least one H of

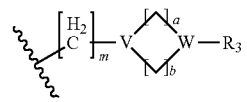

may be substituted with (=O); and at least one H of aryl may be substituted with C1-C6 alkyl or halogen;

V is —CH— or —N—;

W is —CH—, —N—, —O—, —S—, —C(=O)—, —S(=O)— or —S(=O)$_2$—, wherein in case V is —CH—, W is not —CH—;

a to d are each independently 1, 2 or 3; and m is 1 or 2.

4. A compound represented by formula 1, a stereoisomer thereof or a pharmaceutically acceptable salt thereof:

[Formula 1]

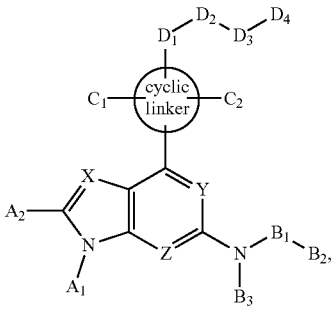

wherein
X is C—A$_3$;
Y is N;
Z is N;
A$_1$ to A$_3$ are each independently H or C1-C6 alkyl;
B$_1$ is —C(=O)—;
B$_2$ is C3-C7 cycloalkyl, wherein at least one H of C3-C7 cycloalkyl may be substituted with C1-C6 alkyl;
B$_3$ is H or C1-C6 alkyl;
Cyclic linker is 5-6 membered heterocycloalkyl, 5-6 membered heterocycloalkenyl, aryl or heteroaryl;
C$_1$ and C$_2$ are each independently H, C1-C6 alkyl or halogen,
or C$_1$ and C$_2$ may be linked to each other through at least one carbon atom to make a bicyclic ring;
D$_1$ is —(CH$_2$)$_m$—, or null;
D$_2$ is —C(=O)—, —C(=S)—, —S(=O)$_2$— or null;
D$_3$ is —(CH$_2$)$_m$—, —O— or null;
D$_4$ is C1-C6 alkyl, C2-C6 alkenyl, C1-C6 hydroxyalkyl, C1-C6 haloalkyl, C1-C6 cyanoalkyl, C3-C7 cycloalkyl,

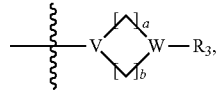

aryl or heteroaryl,
wherein at least one H of C3-C7 cycloalkyl or

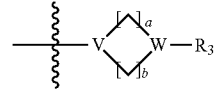

may be substituted with C1-C6 alkyl or cyano; and
at least one H of aryl or heteroaryl may be substituted with C1-C6 alkyl, cyano, halogen or —C(=O)—NR$_1$—R$_4$;
R$_1$ is H or C1-C6 alkyl;
R$_3$ is null;
R$_4$ is H;
V is —CH— or —N—;
W is —O— or —S(=O)$_2$—;
a and b are each independently 1, 2 or 3; and
m is 1 or 2.

5. The compound, the stereoisomer thereof or the pharmaceutically acceptable salt thereof according to claim 2, wherein
X is N;
Y is C—A$_4$;
Z is N;

A₁, A₂ and A₄ are each independently H or C1-C6 alkyl;
B₁ is —C(=O)—;
B₂ is C3-C7 cycloalkyl, wherein at least one H of C3-C7 cycloalkyl may be substituted with C1-C6 alkyl;
B₃ is H;
Cyclic linker is aryl;
C₁ and C₂ are each independently H, C1-C6 alkyl or halogen;
D₁ is —(CH₂)$_m$— or —NR₁—;
D₂ is —S(=O)₂— or null;
D₃ is null;
D₄ is C1-C6 alkyl, C1-C6 haloalkyl or heteroaryl, wherein at least one H of C1-C6 alkyl or C1-C6 haloalkyl may be substituted with C3-C7 cycloalkyl; and
at least one H of heteroaryl may be substituted with C1-C6 alkyl;
R₁ is H; and
m is 1 or 2.

6. A compound, the stereoisomer thereof or the pharmaceutically acceptable salt thereof, wherein it is one selected from the group consisting of the following compounds:

1) N-(4-(4-(ethylsulfonamido)-3-fluorophenyl)-1H-pyrrolo[2,3-b]pyridin-6-yl)cyclopropanecarboxamide
2) N-(4-(4-((3,4-difluorophenyl)sulfonamido)phenyl)-1H-pyrrolo[2,3-b]pyridin-6-yl)cyclopropanecarboxamide
3) N-(4-(4-((3-fluoropropyl)sulfonamido)phenyl)-1H-pyrrolo[2,3-b]pyridin-6-yl)cyclopropanecarboxamide
4) N-(4-(4-(ethylsulfonamido)phenyl)-1H-pyrrolo[2,3-b]pyridin-6-yl)cyclopropanecarboxamide
5) N-(4-(4-(propylsulfonamido)phenyl)-1H-pyrrolo[2,3-b]pyridin-6-yl)cyclopropanecarboxamide
6) N-(4-(4-(butylsulfonamido)phenyl)-1H-pyrrolo[2,3-b]pyridin-6-yl)cyclopropanecarboxamide
7) N-(4-(4-(cyclohexanesulfonamido)phenyl)-1H-pyrrolo[2,3-b]pyridin-6-yl)cyclopropanecarboxamide
8) N-(4-(4-((2-fluoroethyl)sulfonamido)phenyl)-1H-pyrrolo[2,3-b]pyridin-6-yl)cyclopropanecarboxamide
9) N-(4-(4-((1,1-dioxidotetrahydro-2H-thiopyran)-4-sulfonamido)phenyl)-1H-pyrrolo[2,3-b]pyridin-6-yl)cyclopropanecarboxamide
10) N-(4-(4-((1,1-dioxidotetrahydrothiophene)-3-sulfonamido)phenyl)-1H-pyrrolo[2,3-b]pyridin-6-yl)cyclopropanecarboxamide
11) N-(4-(4-((1,1-dioxidothietane)-3-sulfonamido)phenyl)-1H-pyrrolo[2,3-b]pyridin-6-yl)cyclopropanecarboxamide
12) N-(4-(4-((6-chloropyridine)-3-sulfonamido)phenyl)-1H-pyrrolo[2,3-b]pyridin-6-yl)cyclopropanecarboxamide
13) N-(4-(4-((4-fluorophenyl)sulfonamido)phenyl)-1H-pyrrolo[2,3-b]pyridin-6-yl)cyclopropanecarboxamide
14) N-(4-(4-((4-chlorophenyl)sulfonamido)phenyl)-1H-pyrrolo[2,3-b]pyridin-6-yl)cyclopropanecarboxamide
15) N-(4-(4-((1-methyl-1H-imidazole)-5-sulfonamido)phenyl)-1H-pyrrolo[2,3-b]pyridin-6-yl)cyclopropanecarboxamide
16) N-(4-(4-((1-methyl-1H-pyrazole)-4-sulfonamido)phenyl)-1H-pyrrolo[2,3-b]pyridin-6-yl)cyclopropanecarboxamide
17) 4-(N-(4-(6-(cyclopropanecarboxamido)-1H-pyrrolo[2,3-b]pyridin-4-yl)phenyl)sulfamoyl)benzamide
18) N-(4-(4-((1-acetylpiperidine)-4-sulfonamido)phenyl)-1H-pyrrolo[2,3-b]pyridin-6-yl)cyclopropanecarboxamide
19) N-(4-(4-((4-isopropoxyphenyl)sulfonamido)phenyl)-1H-pyrrolo[2,3-b]pyridin-6-yl)cyclopropanecarboxamide
20) N-(4-(4-((4-bromophenyl)sulfonamido)phenyl)-1H-pyrrolo[2,3-b]pyridin-6-yl)cyclopropanecarboxamide
21) N-(4-(4-((4-cyanophenyl)sulfonamido)phenyl)-1H-pyrrolo[2,3-b]pyridin-6-yl)cyclopropanecarboxamide
22) N-(4-(4-((2,3-dihydrobenzofuran)-5-sulfonamido)phenyl)-1H-pyrrolo[2,3-b]pyridin-6-yl)cyclopropanecarboxamide
23) N-(4-(4-((6-methoxypyridine)-3-sulfonamido)phenyl)-1H-pyrrolo[2,3-b]pyridin-6-yl)cyclopropanecarboxamide
24) N-(4-(4-(phenylsulfonamido)phenyl)-1H-pyrrolo[2,3-b]pyridin-6-yl)cyclopropanecarboxamide
25) N-(4-(4-((3-fluorophenyl)sulfonamido)phenyl)-1H-pyrrolo[2,3-b]pyridin-6-yl)cyclopropanecarboxamide
26) N-(4-(4-((3-chlorophenyl)sulfonamido)phenyl)-1H-pyrrolo[2,3-b]pyridin-6-yl)cyclopropanecarboxamide
27) N-(4-(4-((4-methylphenyl)sulfonamido)phenyl)-1H-pyrrolo[2,3-b]pyridin-6-yl)cyclopropanecarboxamide
28) N-(4-(4-((4-(methylthio)phenyl)sulfonamido)phenyl)-1H-pyrrolo[2,3-b]pyridin-6-yl)cyclopropanecarboxamide
29) N-(4-(4-(ethylsulfonamido)-2-methylphenyl)-1H-pyrrolo[2,3-b]pyridin-6-yl)cyclopropanecarboxamide
30) N-(4-(4-(ethylsulfonamido)-2-fluorophenyl)-1H-pyrrolo[2,3-b]pyridin-6-yl)cyclopropanecarboxamide
31) N-(4-(4-((4-bromo-3-fluorophenyl)sulfonamido)phenyl)-1H-pyrrolo[2,3-b]pyridin-6-yl)cyclopropanecarboxamide
32) N-(4-(4-((4-bromo-2-fluorophenyl)sulfonamido)phenyl)-1H-pyrrolo[2,3-b]pyridin-6-yl)cyclopropanecarboxamide
33) N-(4-(4-((4-chloro-3-(trifluoromethyl)phenyl)sulfonamido)phenyl)-1H-pyrrolo[2,3-b]pyridin-6-yl)cyclopropanecarboxamide -continued 34) N-(4-(4-(benzo[d][1,3]dioxole-5-sulfonamido)phenyl)-1H-pyrrolo[2,3-b]pyridin-6-yl)cyclopropanecarboxamide
35) N-(4-(4-(ethylsulfonamido)phenyl)-1H-pyrrolo[2,3-b]pyridin-6-yl)-2-methylcyclopropane-1-carboxamide
36) N-(4-(4-(((4-fluorophenyl)methyl)sulfonamido)phenyl)-1H-pyrrolo[2,3-b]pyridin-6-yl)cyclopropanecarboxamide
37) N-(4-(4-((4-(N,N-dimethylsulfamoyl)phenyl)sulfonamido)phenyl)-1H-pyrrolo[2,3-b]pyridin-6-yl)cyclopropanecarboxamide
38) N-(4-(4-((2,3-dihydrobenzo[b][1,4]dioxine)-6-sulfonamido)phenyl)-1H-pyrrolo[2,3-b]pyridin-6-yl)cyclopropanecarboxamide
39) N-(4-(4-((4-(1H-tetrazol-1-yl)phenyl)sulfonamido)phenyl)-1H-pyrrolo[2,3-b]pyridin-6-yl)cyclopropanecarboxamide
40) N-(4-(4-((6-cyanopyridine)-3-sulfonamido)phenyl)-1H-pyrrolo[2,3-b]pyridin-6-yl)cyclopropanecarboxamide
41) N-(4-(4-((1-methylethyl)sulfonamido)phenyl)-1H-pyrrolo[2,3-b]pyridin-6-yl)cyclopropanecarboxamide
42) N-(4-(4-((1-ethylpropyl)sulfonamido)phenyl)-1H-pyrrolo[2,3-b]pyridin-6-yl)cyclopropanecarboxamide
43) N-(4-(4-((2-methylpropyl)sulfonamido)phenyl)-1H-pyrrolo[2,3-b]pyridin-6-yl)cyclopropanecarboxamide
44) N-(4-(4-((2,2-dimethylpropyl)sulfonamido)phenyl)-1H-pyrrolo[2,3-b]pyridin-6-yl)cyclopropanecarboxamide
45) N-(4-(4-((3-methylbutyl)sulfonamido)phenyl)-1H-pyrrolo[2,3-b]pyridin-6-yl)cyclopropanecarboxamide
46) N-(4-(4-((cyclopropylmethyl)sulfonamido)phenyl)-1H-pyrrolo[2,3-b]pyridin-6-yl)cyclopropanecarboxamide
47) N-(4-(4-((cyclohexylmethyl)sulfonamido)phenyl)-1H-pyrrolo[2,3-b]pyridin-6-yl)cyclopropanecarboxamide
48) N-(4-(4-(allylsulfonamido)phenyl)-1H-pyrrolo[2,3-b]pyridin-6-yl)cyclopropanecarboxamide
49) N-(4-(4-((fluoromethyl)sulfonamido)phenyl)-1H-pyrrolo[2,3-b]pyridin-6-yl)cyclopropanecarboxamide
50) N-(4-(4-((difluoromethyl)sulfonamido)phenyl)-1H-pyrrolo[2,3-b]pyridin-6-yl)cyclopropanecarboxamide
51) N-(4-(4-((2,2-difluoroethyl)sulfonamido)phenyl)-1H-pyrrolo[2,3-b]pyridin-6-yl)cyclopropanecarboxamide
52) N-(4-(4-((3-cyanopropyl)sulfonamido)phenyl)-1H-pyrrolo[2,3-b]pyridin-6-yl)cyclopropanecarboxamide
53) N-(4-(4-((2-ethoxyethyl)sulfonamido)phenyl)-1H-pyrrolo[2,3-b]pyridin-6-yl)cyclopropanecarboxamide
54) N-(4-(4-(((tetrahydrofuran-3-yl)methyl)sulfonamido)phenyl)-1H-pyrrolo[2,3-b]pyridin-6-yl)cyclopropanecarboxamide
55) N-(4-(4-(((tetrahydro-2H-pyran-4-yl)methyl)sulfonamido)phenyl)-1H-pyrrolo[2,3-b]pyridin-6-yl)cyclopropanecarboxamide
56) N-(4-(4-((2-(methylsulfonyl)ethyl)sulfonamido)phenyl)-1H-pyrrolo[2,3-b]pyridin-6-yl)cyclopropanecarboxamide
57) N-(4-(4-(cyclopropanesulfonamido)phenyl)-1H-pyrrolo[2,3-b]pyridin-6-yl)cyclopropanecarboxamide
58) N-(4-(4-(cyclobutanesulfonamido)phenyl)-1H-pyrrolo[2,3-b]pyridin-6-yl)cyclopropanecarboxamide
59) N-(4-(3-cyano-4-(ethylsulfonamido)phenyl)-1H-pyrrolo[2,3-b]pyridin-6-yl)cyclopropanecarboxamide
60) N-(4-(4-(ethylsulfonamido)-3-fluorophenyl)-1-methyl-1H-pyrrolo[2,3-b]pyridin-6-yl)cyclopropanecarboxamide
61) N-(4-(4-(ethylsulfonamido)-3-fluorophenyl)-1-propyl-1H-pyrrolo[2,3-b]pyridin-6-yl)cyclopropanecarboxamide
62) N-(1-(cyanomethyl)-4-(4-(ethylsulfonamido)-3-fluorophenyl)-1H-pyrrolo[2,3-b]pyridin-6-yl)cyclopropanecarboxamide
63) N-(4-(3-chloro-4-(propylsulfonamido)phenyl)-1H-pyrrolo[2,3-b]pyridin-6-yl)cyclopropanecarboxamide
64) N-(4-(4-(ethylsulfonamido)-3-methylphenyl)-1H-pyrrolo[2,3-b]pyridin-6-yl)cyclopropanecarboxamide
65) N-(4-(3-methyl-4-(propylsulfonamido)phenyl)-1H-pyrrolo[2,3-b]pyridin-6-yl)cyclopropanecarboxamide
66) N-(4-(3-fluoro-4-(propylsulfonamido)phenyl)-1H-pyrrolo[2,3-b]pyridin-6-yl)cyclopropanecarboxamide
67) N-(4-(4-(butylsulfonamido)-3-fluorophenyl)-1H-pyrrolo[2,3-b]pyridin-6-yl)cyclopropanecarboxamide
68) N-(4-(4-(cyclohexanesulfonamido)-3-fluorophenyl)-1H-pyrrolo[2,3-b]pyridin-6-yl)cyclopropanecarboxamide
69) N-(4-(4-(cyclopropanesulfonamido)-3-fluorophenyl)-1H-pyrrolo[2,3-b]pyridin-6-yl)cyclopropanecarboxamide
70) N-(4-(4-((cyclohexylmethyl)sulfonamido)-3-fluorophenyl)-1H-pyrrolo[2,3-b]pyridin-6-yl)cyclopropanecarboxamide
71) N-(4-(4-(allylsulfonamido)-3-fluorophenyl)-1H-pyrrolo[2,3-b]pyridin-6-yl)cyclopropanecarboxamide
72) N-(4-(3-fluoro-4-(((tetrahydrofuran-3-yl)methyl)sulfonamido)phenyl)-1H-pyrrolo[2,3-b]pyridin-6-yl)cyclopropanecarboxamide -continued 73) N-(4-(3-fluoro-4-(((tetrahydro-2H-pyran-4-yl)methyl)sulfonamido)phenyl)-1H-pyrrolo[2,3-b]pyridin-6-yl)cyclopropanecarboxamide
74) N-(4-(4-(ethylsulfonamido)phenyl)-2-methyl-1H-pyrrolo[2,3-b]pyridin-6-yl)cyclopropanecarboxamide
75) N-(4-(3-fluoro-4-((2-methylpropyl)sulfonamido)phenyl)-1H-pyrrolo[2,3-b]pyridin-6-yl)cyclopropanecarboxamide
76) N-(4-(3-fluoro-4-((3-fluoropropyl)sulfonamido)phenyl)-1H-pyrrolo[2,3-b]pyridin-6-yl)cyclopropanecarboxamide
77) N-(4-(4-((3-cyanopropyl)sulfonamido)-3-fluorophenyl)-1H-pyrrolo[2,3-b]pyridin-6-yl)cyclopropanecarboxamide
78) N-(4-(4-(cyclobutanesulfonamido)-3-fluorophenyl)-1H-pyrrolo[2,3-b]pyridin-6-yl)cyclopropanecarboxamide
79) N-(4-(4-((2,2-dimethylpropyl)sulfonamido)-3-fluorophenyl)-1H-pyrrolo[2,3-b]pyridin-6-yl)cyclopropanecarboxamide
80) N-(4-(4-((cyclopropylmethyl)sulfonamido)-3-fluorophenyl)-1H-pyrrolo[2,3-b]pyridin-6-yl)cyclopropanecarboxamide
81) N-(4-(4-(ethylsulfonamido)-3,5-difluorophenyl)-1H-pyrrolo[2,3-b]pyridin-6-yl)cyclopropanecarboxamide
82) N-(4-(3,5-difluoro-4-(propylsulfonamido)phenyl)-1H-pyrrolo[2,3-b]pyridin-6-yl)cyclopropanecarboxamide
83) N-(4-(4-(ethylsulfonamido)-2,5-difluorophenyl)-1H-pyrrolo[2,3-b]pyridin-6-yl)cyclopropanecarboxamide
84) N-(4-(2,5-difluoro-4-(propylsulfonamido)phenyl)-1H-pyrrolo[2,3-b]pyridin-6-yl)cyclopropanecarboxamide
85) N-(4-(4-(((1-cyanocyclopropyl)methyl)sulfonamido)-3-fluorophenyl)-1H-pyrrolo[2,3-b]pyridin-6-yl)cyclopropanecarboxamide
86) N-(4-(4-(((1-(cyanomethyl)cyclopropyl)methyl)sulfonamido)-3-fluorophenyl)-1H-pyrrolo[2,3-b]pyridin-6-yl)cyclopropanecarboxamide
87) N-(4-(4-((3-cyano-3-methylbutyl)sulfonamido)-3-fluorophenyl)-1H-pyrrolo[2,3-b]pyridin-6-yl)cyclopropanecarboxamide
88) N-(4-(4-(((1-cyanocyclopropyl)methyl)sulfonamido)phenyl)-1H-pyrrolo[2,3-b]pyridin-6-yl)cyclopropanecarboxamide
89) N-(4-(4-(((1-(cyanomethyl)cyclopropyl)methyl)sulfonamido)phenyl)-1H-pyrrolo[2,3-b]pyridin-6-yl)cyclopropanecarboxamide
90) N-(4-(4-(cyclopropanesulfonamido)-2-methylphenyl)-1H-pyrrolo[2,3-b]pyridin-6-yl)cyclopropanecarboxamide
91) N-(4-(4-(cyclobutanesulfonamido)-2-methylphenyl)-1H-pyrrolo[2,3-b]pyridin-6-yl)cyclopropanecarboxamide
92) N-(4-(4-((cyclopropylmethyl)sulfonamido)-2-methylphenyl)-1H-pyrrolo[2,3-b]pyridin-6-yl)cyclopropanecarboxamide
93) N-(4-(4-(ethylsulfonamido)phenyl)-3-methyl-1H-pyrrolo[2,3-b]pyridin-6-yl)cyclopropanecarboxamide
94) N-(3-methyl-4-(4-(propylsulfonamido)phenyl)-1H-pyrrolo[2,3-b]pyridin-6-yl)cyclopropanecarboxamide
95) N-(4-(2-methyl-4-(propylsulfonamido)phenyl)-1H-pyrrolo[2,3-b]pyridin-6-yl)cyclopropanecarboxamide
96) N-(4-(4-((3-cyanopropyl)sulfonamido)-2-methylphenyl)-1H-pyrrolo[2,3-b]pyridin-6-yl)cyclopropanecarboxamide
97) 6-(cyclopropanecarboxamido)-4-(4-(ethylsulfonamido)-3-fluorophenyl)-1H-pyrrolo[2,3-b]pyridine 7-oxide
98) N-(4-(4-(ethylsulfonamido)-3-(trifluoromethyl)phenyl)-1H-pyrrolo[2,3-b]pyridin-6-yl)cyclopropanecarboxamide
99) N-(4-(2-ethyl-4-(ethylsulfonamido)phenyl)-1H-pyrrolo[2,3-b]pyridin-6-yl)cyclopropanecarboxamide
100) N-(4-(3-fluoro-2-methyl-4-(propylsulfonamido)phenyl)-1H-pyrrolo[2,3-b]pyridin-6-yl)cyclopropanecarboxamide
101) N-(4-(4-(ethylsulfonamido)-3-fluoro-2-methylphenyl)-1H-pyrrolo[2,3-b]pyridin-6-yl)cyclopropanecarboxamide
102) N-(4-(4-(((1-cyanocyclopropyl)methyl)sulfonamido)-2-methylphenyl)-1H-pyrrolo[2,3-b]pyridin-6-yl)cyclopropanecarboxamide
103) N-(4-(4-(((1-(cyanomethyl)cyclopropyl)methyl)sulfonamido)-2-methylphenyl)-1H-pyrrolo[2,3-b]pyridin-6-yl)cyclopropanecarboxamide
104) N-(4-(4-((3-cyanopropyl)sulfonamido)-2,5-difluorophenyl)-1H-pyrrolo[2,3-b]pyridin-6-yl)cyclopropanecarboxamide
105) N-(4-(4-(((1-cyanocyclopropyl)methyl)sulfonamido)-2,5-difluorophenyl)-1H-pyrrolo[2,3-b]pyridin-6-yl)cyclopropanecarboxamide
106) N-(4-(4-(((1-(cyanomethyl)cyclopropyl)methyl)sulfonamido)-2,5-difluorophenyl)-1H-pyrrolo[2,3-b]pyridin-6-yl)cyclopropanecarboxamide
107) N-(4-(4-(((1-cyanocyclopropyl)methyl)sulfonamido)-3,5-difluorophenyl)-1H-pyrrolo[2,3-b]pyridin-6-yl)cyclopropanecarboxamide
108) N-(4-(4-(((1-(cyanomethyl)cyclopropyl)methyl)sulfonamido)-3,5-difluorophenyl)-1H-pyrrolo[2,3-b]pyridin-6-yl)cyclopropanecarboxamide
109) N-(4-(4-(((1-cyanocyclopropyl)methyl)sulfonamido)-2-ethylphenyl)-1H-pyrrolo[2,3-b]pyridin-6-yl)cyclopropanecarboxamide
110) N-(4-(4-(((1-(cyanomethyl)cyclopropyl)methyl)sulfonamido)-2-ethylphenyl)-1H-pyrrolo[2,3-b]pyridin-6-yl)cyclopropanecarboxamide
111) N-(4-(4-((3-cyanopropyl)sulfonamido)-2-ethylphenyl)-1H-pyrrolo[2,3-b]pyridin-6-yl)cyclopropanecarboxamide -continued 112) N-(4-(4-(cyclohexanesulfonamido)-2-ethylphenyl)-1H-pyrrolo[2,3-b]pyridin-6-yl)cyclopropanecarboxamide
113) N-(4-(4-(cyclopropanesulfonamido)-2-ethylphenyl)-1H-pyrrolo[2,3-b]pyridin-6-yl)cyclopropanecarboxamide
114) N-(4-(4-(cyclobutanesulfonamido)-2-ethylphenyl)-1H-pyrrolo[2,3-b]pyridin-6-yl)cyclopropanecarboxamide
115) N-(4-(2-ethyl-4-(propylsulfonamido)phenyl)-1H-pyrrolo[2,3-b]pyridin-6-yl)cyclopropanecarboxamide
116) N-(4-(4-(butylsulfonamido)-2-ethylphenyl)-1H-pyrrolo[2,3-b]pyridin-6-yl)cyclopropanecarboxamide
117) N-(4-(2-methyl-4-((4,4,4-trifluorobutyl)sulfonamido)phenyl)-1H-pyrrolo[2,3-b]pyridin-6-yl)cyclopropanecarboxamide
118) N-(4-(4-(cyclopropanesulfonamido)-2-(trifluoromethyl)phenyl)-1H-pyrrolo[2,3-b]pyridin-6-yl)cyclopropanecarboxamide
119) N-(4-(4-(propylsulfonamido)-2-(trifluoromethyl)phenyl)-1H-pyrrolo[2,3-b]pyridin-6-yl)cyclopropanecarboxamide
120) N-(4-(4-(cyclobutanesulfonamido)-2-(trifluoromethyl)phenyl)-1H-pyrrolo[2,3-b]pyridin-6-yl)cyclopropanecarboxamide
121) N-(4-(4-((3,4-difluorophenyl)sulfonamido)-2-(trifluoromethyl)phenyl)-1H-pyrrolo[2,3-b]pyridin-6-yl)cyclopropanecarboxamide
122) N-(4-(4-((3-fluorophenyl)sulfonamido)-2-(trifluoromethyl)phenyl)-1H-pyrrolo[2,3-b]pyridin-6-yl)cyclopropanecarboxamide
123) N-(4-(4-(((1-cyanocyclopropyl)methyl)sulfonamido)-3-ethylphenyl)-1H-pyrrolo[2,3-b]pyridin-6-yl)cyclopropanecarboxamide
124) N-(4-(3-ethyl-4-(ethylsulfonamido)phenyl)-1H-pyrrolo[2,3-b]pyridin-6-yl)cyclopropanecarboxamide
125) N-(4-(4-(cyclopropanesulfonamido)-3-ethylphenyl)-1H-pyrrolo[2,3-b]pyridin-6-yl)cyclopropanecarboxamide
126) N-(4-(3-ethyl-4-(propylsulfonamido)phenyl)-1H-pyrrolo[2,3-b]pyridin-6-yl)cyclopropanecarboxamide
127) N-(4-(4-(butylsulfonamido)-3-ethylphenyl)-1H-pyrrolo[2,3-b]pyridin-6-yl)cyclopropanecarboxamide
128) N-(4-(4-(cyclobutanesulfonamido)-3-ethylphenyl)-1H-pyrrolo[2,3-b]pyridin-6-yl)cyclopropanecarboxamide
129) N-(4-(6-(methylsulfonamido)-[1,1'-biphenyl]-3-yl)-1H-pyrrolo[2,3-b]pyridin-6-yl)cyclopropanecarboxamide
130) N-(4-(6-(cyclopropanesulfonamido)-[1,1'-biphenyl]-3-yl)-1H-pyrrolo[2,3-b]pyridin-6-yl)cyclopropanecarboxamide
131) N-(4-(4-(ethylsulfonamido)-2,3-dimethylphenyl)-1H-pyrrolo[2,3-b]pyridin-6-yl)cyclopropanecarboxamide
132) N-(4-(2,3-dimethyl-4-(propylsulfonamido)phenyl)-1H-pyrrolo[2,3-b]pyridin-6-yl)cyclopropanecarboxamide
133) N-(4-(4-(cyclopropanesulfonamido)-2,3-dimethylphenyl)-1H-pyrrolo[2,3-b]pyridin-6-yl)cyclopropanecarboxamide
134) 6-(cyclopropanecarboxamido)-4-(4-(ethylsulfonamido)-2-methylphenyl)-1H-pyrrolo[2,3-b]pyridine 7-oxide
135) 6-(cyclopropanecarboxamido)-4-(3-ethyl-4-(ethylsulfonamido)phenyl)-1H-pyrrolo[2,3-b]pyridine 7-oxide
136) 6-(cyclopropanecarboxamido)-4-(4-(cyclopropanesulfonamido)-2,3-dimethylphenyl)-1H-pyrrolo[2,3-b]pyridine 7-oxide
137) 4-(4-(((1-cyanocyclopropyl)methyl)sulfonamido)-2-ethylphenyl)-6-(cyclopropanecarboxamido)-1H-pyrrolo[2,3-b]pyridine 7-oxide
138) N-(4-(4-(((1-cyanocyclopropyl)methyl)sulfonamido)-3,5-diethylphenyl)-1H-pyrrolo[2,3-b]pyridin-6-yl)cyclopropanecarboxamide
139) N-(4-(4-((3,4-difluorophenyl)sulfonamido)-3,5-diethylphenyl)-1H-pyrrolo[2,3-b]pyridin-6-yl)cyclopropanecarboxamide
140) methyl 2-(6-(cyclopropanecarboxamido)-1H-pyrrolo[2,3-b]pyridin-4-yl)-5-(ethylsulfonamido)benzoate
141) methyl 2-(6-(cyclopropanecarboxamido)-1H-pyrrolo[2,3-b]pyridin-4-yl)-5-(propylsulfonamido)benzoate
142) methyl 5-(((1-cyanocyclopropyl)methyl)sulfonamido)-2-(6-(cyclopropanecarboxamido)-1H-pyrrolo[2,3-b]pyridin-4-yl)benzoate
143) 5-(((1-cyanocyclopropyl)methyl)sulfonamido)-2-(6-(cyclopropanecarboxamido)-1H-pyrrolo[2,3-b]pyridin-4-yl)benzoic acid
144) N-(4-(2-cyano-4-(ethylsulfonamido)phenyl)-1H-pyrrolo[2,3-b]pyridin-6-yl)cyclopropanecarboxamide
145) N-(4-(2-cyano-4-(propylsulfonamido)phenyl)-1H-pyrrolo[2,3-b]pyridin-6-yl)cyclopropanecarboxamide
146) N-(4-(2-cyano-4-((3,4-difluorophenyl)sulfonamido)phenyl)-1H-pyrrolo[2,3-b]pyridin-6-yl)cyclopropanecarboxamide
147) N-(4-(2-cyano-4-(((1-cyanocyclopropyl)methyl)sulfonamido)phenyl)-1H-pyrrolo[2,3-b]pyridin-6-yl)cyclopropanecarboxamide
148) N-(4-(6-(ethylsulfonamido)pyridin-3-yl)-1H-pyrrolo[2,3-b]pyridin-6-yl)cyclopropanecarboxamide
149) N-(4-(5-(ethylsulfonamido)-6-fluoropyridin-2-yl)-1H-pyrrolo[2,3-b]pyridin-6-yl)cyclopropanecarboxamide
150) N-(4-(6-fluoro-5-(propylsulfonamido)pyridin-2-yl)-1H-pyrrolo[2,3-b]pyridin-6-yl)cyclopropanecarboxamide -continued 151) N-(4-(4-(ethylsulfonamido)cyclohex-1-en-1-yl)-1H-pyrrolo[2,3-b]pyridin-6-yl)cyclopropanecarboxamide
152) N-(4-(4-(propylsulfonamido)cyclohex-1-en-1-yl)-1H-pyrrolo[2,3-b]pyridin-6-yl)cyclopropanecarboxamide
153) N-(4-(4-((trifluoromethyl)sulfonamido)cyclohex-1-en-1-yl)-1H-pyrrolo[2,3-b]pyridin-6-yl)cyclopropanecarboxamide
154) N-(4-(4-(cyclopropanesulfonamido)cyclohex-1-en-1-yl)-1H-pyrrolo[2,3-b]pyridin-6-yl)cyclopropanecarboxamide
155) N-(4-(4-((2-cyanoethyl)sulfonamido)cyclohex-1-en-1-yl)-1H-pyrrolo[2,3-b]pyridin-6-yl)cyclopropanecarboxamide
156) N-(4-(4-(((1-(cyanomethyl)cyclopropyl)methyl)sulfonamido)cyclohex-1-en-1-yl)-1H-pyrrolo[2,3-b]pyridin-6-yl)cyclopropanecarboxamide
157) N-(4-(4-(((1-cyanocyclopropyl)methyl)sulfonamido)cyclohex-1-en-1-yl)-1H-pyrrolo[2,3-b]pyridin-6-yl)cyclopropanecarboxamide
158) N-(4-(4-((3-cyanopropyl)sulfonamido)cyclohex-1-en-1-yl)-1H-pyrrolo[2,3-b]pyridin-6-yl)cyclopropanecarboxamide
159) N-(4-(4-((3-fluoropropyl)sulfonamido)cyclohex-1-en-1-yl)-1H-pyrrolo[2,3-b]pyridin-6-yl)cyclopropanecarboxamide
160) N-(4-(4-(allylsulfonamido)cyclohex-1-en-1-yl)-1H-pyrrolo[2,3-b]pyridin-6-yl)cyclopropanecarboxamide
161) N-(4-(4-((cyclopropylmethyl)sulfonamido)cyclohex-1-en-1-yl)-1H-pyrrolo[2,3-b]pyridin-6-yl)cyclopropanecarboxamide
162) N-(4-(4-((3,4-difluorophenyl)sulfonamido)cyclohex-1-en-1-yl)-1H-pyrrolo[2,3-b]pyridin-6-yl)cyclopropanecarboxamide
163) N-(4-(4-((3-fluorophenyl)sulfonamido)cyclohex-1-en-1-yl)-1H-pyrrolo[2,3-b]pyridin-6-yl)cyclopropanecarboxamide
164) N-(4-(4-((4-cyanophenyl)sulfonamido)cyclohex-1-en-1-yl)-1H-pyrrolo[2,3-b]pyridin-6-yl)cyclopropanecarboxamide
165) N-(4-(4-(cyclobutanesulfonamido)cyclohex-1-en-1-yl)-1H-pyrrolo[2,3-b]pyridin-6-yl)cyclopropanecarboxamide
166) N-(4-(1-(ethylsulfonyl)-1,2,3,6-tetrahydropyridin-4-yl)-1H-pyrrolo[2,3-b]pyridin-6-yl)cyclopropanecarboxamide
167) N-(4-(1-((3-fluoropropyl)sulfonyl)-1,2,3,6-tetrahydropyridin-4-yl)-1H-pyrrolo[2,3-b]pyridin-6-yl)cyclopropanecarboxamide
168) N-(4-(1-(cyclopropylsulfonyl)-1,2,3,6-tetrahydropyridin-4-yl)-1H-pyrrolo[2,3-b]pyridin-6-yl)cyclopropanecarboxamide
169) N-(4-(1-(((tetrahydro-2H-pyran-4-yl)methyl)sulfonyl)-1,2,3,6-tetrahydropyridin-4-yl)-1H-pyrrolo[2,3-b]pyridin-6-yl)cyclopropanecarboxamide
170) N-(4-(1-((3-cyanopropyl)sulfonyl)-1,2,3,6-tetrahydropyridin-4-yl)-1H-pyrrolo[2,3-b]pyridin-6-yl)cyclopropanecarboxamide
171) N-(4-(1-(((1-(cyanomethyl)cyclopropyl)methyl)sulfonyl)-1,2,3,6-tetrahydropyridin-4-yl)-1H-pyrrolo[2,3-b]pyridin-6-yl-cyclopropanecarboxamide
172) N-(4-(1-(((1-cyanocyclopropyl)methyl)sulfonyl)-1,2,3,6-tetrahydropyridin-4-yl)-1H-pyrrolo[2,3-b]pyridin-6-yl)cyclopropanecarboxamide
173) N-(4-(1-((3,4-difluorophenyl)sulfonyl)-1,2,3,6-tetrahydropyridin-4-yl)-1H-pyrrolo[2,3-b]pyridin-6-yl)cyclopropanecarboxamide
174) N-(4-(8-(ethylsulfonyl)-8-azabicyclo[3.2.1]oct-2-en-3-yl)-1H-pyrrolo[2,3-b]pyridin-6-yl)cyclopropanecarboxamide
175) N-(4-(8-((3-fluoropropyl)sulfonyl)-8-azabicyclo[3.2.1]oct-2-en-3-yl)-1H-pyrrolo[2,3-b]pyridin-6-yl)cyclopropanecarboxamide
176) N-(4-(8-(propylsulfonyl)-8-azabicyclo[3.2.1]oct-2-en-3-yl)-1H-pyrrolo[2,3-b]pyridin-6-yl)cyclopropanecarboxamide
177) N-(4-(8-(cyclopropylsulfonyl)-8-azabicyclo[3.2.1]oct-2-en-3-yl)-1H-pyrrolo[2,3-b]pyridin-6-yl)cyclopropanecarboxamide
178) N-(4-(8-((3,4-difluorophenyl)sulfonyl)-8-azabicyclo[3.2.1]oct-2-en-3-yl)-1H-pyrrolo[2,3-b]pyridin-6-yl)cyclopropanecarboxamide
179) N-(4-(1-(ethylsulfonyl)-3,3-dimethyl-1,2,3,6-tetrahydropyridin-4-yl)-1H-pyrrolo[2,3-b]pyridin-6-yl)cyclopropanecarboxamide
180) N-(4-(1-((3-cyanopropyl)sulfonyl)-3,3-dimethyl-1,2,3,6-tetrahydropyridin-4-yl)-1H-pyrrolo[2,3-b]pyridin-6-yl)cyclopropanecarboxamide
181) N-(4-(4-((3,4-difluorophenyl)sulfonamido)phenyl)-7H-pyrrolo[2,3-d]pyrimidin-2-yl)cyclopropanecarboxamide
182) N-(4-(4-(ethylsulfonamido)phenyl)-7H-pyrrolo[2,3-d]pyrimidin-2-yl)cyclopropanecarboxamide
183) N-(4-(4-(cyclohexanesulfonamido)phenyl)-7H-pyrrolo[2,3-d]pyrimidin-2-yl)cyclopropanecarboxamide
184) N-(4-(4-((4,4,4-trifluorobutyl)sulfonamido)phenyl)-7H-pyrrolo[2,3-d]pyrimidin-2-yl)cyclopropanecarboxamide
185) N-(4-(4-((3-fluoropropyl)sulfonamido)phenyl)-7H-pyrrolo[2,3-d]pyrimidin-2-yl)cyclopropanecarboxamide
186) N-(4-(4-((3-cyanopropyl)sulfonamido)phenyl)-7H-pyrrolo[2,3-d]pyrimidin-2-yl)cyclopropanecarboxamide
187) N-(4-(4-((4-chlorophenyl)sulfonamido)phenyl)-7H-pyrrolo[2,3-d]pyrimidin-2-yl)cyclopropanecarboxamide
188) N-(4-(4-((4-fluorophenyl)sulfonamido)phenyl)-7H-pyrrolo[2,3-d]pyrimidin-2-yl)cyclopropanecarboxamide
189) N-(4-(4-((4-bromophenyl)sulfonamido)phenyl)-7H-pyrrolo[2,3-d]pyrimidin-2-yl)cyclopropanecarboxamide -continued 190) N-(4-(4-(propylsulfonamido)phenyl)-7H-pyrrolo[2,3-d]pyrimidin-2-yl)cyclopropanecarboxamide
191) N-(4-(4-(butylsulfonamido)phenyl)-7H-pyrrolo[2,3-d]pyrimidin-2-yl)cyclopropanecarboxamide
192) N-(4-(4-((3-fluorophenyl)sulfonamido)phenyl)-7H-pyrrolo[2,3-d]pyrimidin-2-yl)cyclopropanecarboxamide
193) N-(4-(4-(3,4-difluoro-N-methylphenylsulfonamido)phenyl)-7H-pyrrolo[2,3-d]pyrimidin-2-yl)cyclopropanecarboxamide
194) N-(4-(4-((3,3,3-trifluoropropyl)sulfonamido)phenyl)-7H-pyrrolo[2,3-d]pyrimidin-2-yl)cyclopropanecarboxamide
195) N-(4-(4-((1,1-dioxidotetrahydro-2H-thiopyran)-4-sulfonamido)phenyl)-7H-pyrrolo[2,3-d]pyrimidin-2-yl)cyclopropanecarboxamide
196) N-(4-(4-((1,1-dioxidotetrahydrothiophene)-3-sulfonamido)phenyl)-7H-pyrrolo[2,3-d]pyrimidin-2-yl)cyclopropanecarboxamide
197) N-(4-(4-((6-cyanopyridine)-3-sulfonamido)phenyl)-7H-pyrrolo[2,3-d]pyrimidin-2-yl)cyclopropanecarboxamide
198) N-(4-(4-((1-methyl-1H-imidazole)-5-sulfonamido)phenyl)-7H-pyrrolo[2,3-d]pyrimidin-2-yl)cyclopropanecarboxamide
199) N-(4-(4-((1-methyl-1H-pyrazole)-4-sulfonamido)phenyl)-7H-pyrrolo[2,3-d]pyrimidin-2-yl)cyclopropanecarboxamide
200) 4-(N-(4-(2-(cyclopropanecarboxamido)-7H-pyrrolo[2,3-d]pyrimidin-4-yl)phenyl)sulfamoyl)benzamide
201) N-(4-(3-fluoro-4-(methylsulfonamido)phenyl)-7H-pyrrolo[2,3-d]pyrimidin-2-yl)cyclopropanecarboxamide
202) N-(4-(4-(ethylsulfonamido)-3-fluorophenyl)-7H-pyrrolo[2,3-d]pyrimidin-2-yl)cyclopropanecarboxamide
203) N-(4-(3-fluoro-4-((3-fluoropropyl)sulfonamido)phenyl)-7H-pyrrolo[2,3-d]pyrimidin-2-yl)cyclopropanecarboxamide
204) N-(4-(4-((3-cyanopropyl)sulfonamido)-3-fluorophenyl)-7H-pyrrolo[2,3-d]pyrimidin-2-yl)cyclopropanecarboxamide
205) N-(4-(4-((3,4-difluorophenyl)sulfonamido)-3-fluorophenyl)-7H-pyrrolo[2,3-d]pyrimidin-2-yl)cyclopropanecarboxamide
206) N-(4-(3-fluoro-4-(propylsulfonamido)phenyl)-7H-pyrrolo[2,3-d]pyrimidin-2-yl)cyclopropanecarboxamide
207) N-(7-(4-(ethylsulfonamido)phenyl)-3H-imidazo[4,5-b]pyridin-5-yl)cyclopropanecarboxamide
208) N-(6-(4-((3,4-difluorophenyl)sulfonamido)phenyl)-9H-purin-2-yl)cyclopropanecarboxamide
209) N-(6-(4-(ethylsulfonamido)phenyl)-9H-purin-2-yl)cyclopropanecarboxamide
210) N-(6-(4-((3-cyanopropyl)sulfonamido)phenyl)-9H-purin-2-yl)cyclopropanecarboxamide
211) N-(6-(4-((4,4,4-trifluorobutyl)sulfonamido)phenyl)-9H-purin-2-yl)cyclopropanecarboxamide
212) N-(4-(1-(propylsulfonyl)-2,5-dihydro-1H-pyrrol-3-yl)-1H-pyrrolo[2,3-b]pyridin-6-yl)cyclopropanecarboxamide
213) N-(4-(1-(((1-cyanocyclopropyl)methyl)sulfonyl)-2,5-dihydro-1H-pyrrol-3-yl)-1H-pyrrolo[2,3-b]pyridin-6-yl)cyclopropanecarboxamide
214) N-(4-(4-(morpholine-4-sulfonamido)phenyl)-1H-pyrrolo[2,3-b]pyridin-6-yl)cyclopropanecarboxamide
215) N-(4-(4-((N-ethyl-N-methylsulfamoyl)amino)phenyl)-1H-pyrrolo[2,3-b]pyridin-6-yl)cyclopropanecarboxamide
216) N-(4-(4-((N,N-diethylsulfamoyl)amino)phenyl)-1H-pyrrolo[2,3-b]pyridin-6-yl)cyclopropanecarboxamide
217) N-(4-(4-((N-cyclopropyl-N-methylsulfamoyl)amino)phenyl)-1H-pyrrolo[2,3-b]pyridin-6-yl)cyclopropanecarboxamide
218) N-(4-(4-(pyrrolidine-1-sulfonamido)phenyl)-1H-pyrrolo[2,3-b]pyridin-6-yl)cyclopropanecarboxamide
219) N-(4-(4-(piperidine-1-sulfonamido)phenyl)-1H-pyrrolo[2,3-b]pyridin-6-yl)cyclopropanecarboxamide
220) N-(4-(4-((2,6-dimethylmorpholine)-4-sulfonamido)phenyl)-1H-pyrrolo[2,3-b]pyridin-6-yl)cyclopropanecarboxamide
221) N-(4-(4-((3-cyanoazetidine)-1-sulfonamido)phenyl)-1H-pyrrolo[2,3-b]pyridin-6-yl)cyclopropanecarboxamide
222) N-(4-(4-((N-isopropyl-N-methylsulfamoyl)amino)phenyl)-1H-pyrrolo[2,3-b]pyridin-6-yl)cyclopropanecarboxamide
223) N-(4-(4-((N-(2-methoxyethyl)-N-methylsulfamoyl)amino)phenyl)-1H-pyrrolo[2,3-b]pyridin-6-yl)cyclopropanecarboxamide
224) N-(4-(3-fluoro-4-(piperidine-1-sulfonamido)phenyl)-1H-pyrrolo[2,3-b]pyridin-6-yl)cyclopropanecarboxamide
225) N-(4-(3-fluoro-4-(pyrrolidine-1-sulfonamido)phenyl)-1H-pyrrolo[2,3-b]pyridin-6-yl)cyclopropanecarboxamide
226) N-(4-(3-fluoro-4-(morpholine-4-sulfonamido)phenyl)-1H-pyrrolo[2,3-b]pyridin-6-yl)cyclopropanecarboxamide
227) N-(4-(2-methyl-4-((N-(2,2,2-trifluoroethyl)sulfamoyl)amino)phenyl)-1H-pyrrolo[2,3-b]pyridin-6-yl)cyclopropanecarboxamide
228) N-(4-(2-methyl-4-((N-methyl-N-(2,2,2-trifluoroethyl)sulfamoyl)amino)phenyl)-1H-pyrrolo[2,3-b]pyridin-6-yl)cyclopropanecarboxamide
229) N-(4-(4-((1,1-dioxidothiomorpholine)-4-sulfonamido)phenyl)-1H-pyrrolo[2,3-b]pyridin-6-yl)cyclopropanecarboxamide -continued 230) N-(4-(4-((4-(methylsulfonyl)piperazine)-1-sulfonamido)phenyl)-1H-pyrrolo[2,3-b]pyridin-6-yl)cyclopropanecarboxamide
231) N-(4-(4-(morpholine-4-sulfonamido)cyclohex-1-en-1-yl)-1H-pyrrolo[2,3-b]pyridin-6-yl)cyclopropanecarboxamide
232) N-(4-(1-(N-(2,2,2-trifluoroethyl)sulfamoyl)-1,2,3,6-tetrahydropyridin-4-yl)-1H-pyrrolo[2,3-b]pyridin-6-yl)cyclopropanecarboxamide
233) N-(4-(1-(N-methyl-N-(2,2,2-trifluoroethyl)sulfamoyl)-1,2,3,6-tetrahydropyridin-4-yl)-1H-pyrrolo[2,3-b]pyridin-6-yl)cyclopropanecarboxamide
234) N-(4-(1-(morpholinosulfonyl)-1,2,3,6-tetrahydropyridin-4-yl)-1H-pyrrolo[2,3-b]pyridin-6-yl)cyclopropanecarboxamide
235) N-(4-(4-(morpholine-4-sulfonamido)phenyl)-7H-pyrrolo[2,3-d]pyrimidin-2-yl)cyclopropanecarboxamide
236) N-(4-(4-((N,N-dimethylsulfamoyl)amino)phenyl)-7H-pyrrolo[2,3-d]pyrimidin-2-yl)cyclopropanecarboxamide
237) N-(4-(4-((2,6-dimethylmorpholine)-4-sulfonamido)phenyl)-7H-pyrrolo[2,3-d]pyrimidin-2-yl)cyclopropanecarboxamide
238) N-(6-(4-(morpholine-4-sulfonamido)phenyl)-9H-purin-2-yl)cyclopropanecarboxamide
239) N-(4-(4-(2-cyanoacetamido)phenyl)-1H-pyrrolo[2,3-b]pyridin-6-yl)cyclopropanecarboxamide
240) N-(4-(4-(2-cyanoacetamido)-2-methylphenyl)-1H-pyrrolo[2,3-b]pyridin-6-yl)cyclopropanecarboxamide
241) N-(4-(4-(2-(1-cyanocyclopropyl)acetamido)phenyl)-1H-pyrrolo[2,3-b]pyridin-6-yl)cyclopropanecarboxamide
242) N-(4-(4-propionamidocyclohex-1-en-1-yl)-1H-pyrrolo[2,3-b]pyridin-6-yl)cyclopropanecarboxamide
243) N-(4-(6-(cyclopropanecarboxamido)-1H-pyrrolo[2,3-b]pyridin-4-yl)cyclohex-3-en-1-yl)benzamide
244) N-(4-(6-(cyclopropanecarboxamido)-1H-pyrrolo[2,3-b]pyridin-4-yl)cyclohex-3-en-1-yl)-2-methylcyclopropane-1-carboxamide
245) N-(4-(6-(cyclopropanecarboxamido)-1H-pyrrolo[2,3-b]pyridin-4-yl)cyclohex-3-en-1-yl)cyclopentanecarboxamide
246) N-(4-(6-(cyclopropanecarboxamido)-1H-pyrrolo[2,3-b]pyridin-4-yl)cyclohex-3-en-1-yl)cyclopropanecarboxamide
247) N-(4-(4-(2-cyanoacetamido)cyclohex-1-en-1-yl)-1H-pyrrolo[2,3-b]pyridin-6-yl)cyclopropanecarboxamide
248) N-(4-(4-(4,4,4-trifluorobutanamido)cyclohex-1-en-1-yl)-1H-pyrrolo[2,3-b]pyridin-6-yl)cyclopropanecarboxamide
249) N-(4-(1-(1,1-dioxidotetrahydro-2H-thiopyran-4-carbonyl)-1,2,3,6-tetrahydropyridin-4-yl)-1H-pyrrolo[2,3-b]pyridin-6-yl)cyclopropanecarboxamide
250) N-(4-(1-(2-cyanoacetyl)-1,2,3,6-tetrahydropyridin-4-yl)-1H-pyrrolo[2,3-b]pyridin-6-yl)cyclopropanecarboxamide
251) N-(4-(1-(2-(1,1-dioxidothiomorpholino)acetyl)-1,2,3,6-tetrahydropyridin-4-yl)-1H-pyrrolo[2,3-b]pyridin-6-yl)cyclopropanecarboxamide
252) N-(4-(1-(3-cyanopropanoyl)-1,2,3,6-tetrahydropyridin-4-yl)-1H-pyrrolo[2,3-b]pyridin-6-yl)cyclopropanecarboxamide
253) N-(4-(1-(3,3,3-trifluoropropanoyl)-1,2,3,6-tetrahydropyridin-4-yl)-1H-pyrrolo[2,3-b]pyridin-6-yl)cyclopropanecarboxamide
254) N-(4-(1-(4,4,4-trifluorobutanoyl)-1,2,3,6-tetrahydropyridin-4-yl)-1H-pyrrolo[2,3-b]pyridin-6-yl)cyclopropanecarboxamide
255) N-(4-(8-(3-cyanopropanoyl)-8-azabicyclo[3.2.1]oct-2-en-3-yl)-1H-pyrrolo[2,3-b]pyridin-6-yl)cyclopropanecarboxamide
256) N-(4-(8-(cyclopropanecarbonyl)-8-azabicyclo[3.2.1]oct-2-en-3-yl)-1H-pyrrolo[2,3-b]pyridin-6-yl)cyclopropanecarboxamide
257) N-(4-(8-(2-cyanoacetyl)-8-azabicyclo[3.2.1]oct-2-en-3-yl)-1H-pyrrolo[2,3-b]pyridin-6-yl)cyclopropanecarboxamide
258) N-(4-(8-(4,4,4-trifluorobutanoyl)-8-azabicyclo[3.2.1]oct-2-en-3-yl)-1H-pyrrolo[2,3-b]pyridin-6-yl)cyclopropanecarboxamide
259) N-(4-(1-(1-cyanocyclopropane-1-carbonyl)-1,2,3,6-tetrahydropyridin-4-yl)-1H-pyrrolo[2,3-b]pyridin-6-yl)cyclopropanecarboxamide
260) N-(4-(1-(3,3-difluorocyclobutane-1-carbonyl)-1,2,3,6-tetrahydropyridin-4-yl)-1H-pyrrolo[2,3-b]pyridin-6-yl)cyclopropanecarboxamide
261) N-(4-(8-(3,3,3-trifluoropropanoyl)-8-azabicyclo[3.2.1]oct-2-en-3-yl)-1H-pyrrolo[2,3-b]pyridin-6-yl)cyclopropanecarboxamide
262) N-(4-((1S,5R)-8-(2-cyanoacetyl)-8-azabicyclo[3.2.1]oct-2-en-3-yl)-1H-pyrrolo[2,3-b]pyridin-6-yl)cyclopropanecarboxamide
263) N-(4-(1-(2,2-difluorocyclopropane-1-carbonyl)-1,2,3,6-tetrahydropyridin-4-yl)-1H-pyrrolo[2,3-b]pyridin-6-yl)cyclopropanecarboxamide
264) N-(4-(1-(cyclopropanecarbonyl)-1,2,3,6-tetrahydropyridin-4-yl)-1H-pyrrolo[2,3-b]pyridin-6-yl)cyclopropanecarboxamide
265) N-(4-(1-(4-cyanobutanoyl)-1,2,3,6-tetrahydropyridin-4-yl)-1H-pyrrolo[2,3-b]pyridin-6-yl)cyclopropanecarboxamide
266) N-(4-(1-acryloyl-1,2,3,6-tetrahydropyridin-4-yl)-1H-pyrrolo[2,3-b]pyridin-6-yl)cyclopropanecarboxamide
267) N-(4-(1-((1S,2S)-2-cyanocyclopropane-1-carbonyl)-1,2,3,6-tetrahydropyridin-4-yl)-1H-pyrrolo[2,3-b]pyridin-6-yl)cyclopropanecarboxamide
268) N-(4-(1-(2-(1-cyanocyclopropyl)acetyl)-1,2,3,6-tetrahydropyridin-4-yl)-1H-pyrrolo[2,3-b]pyridin-6-yl)cyclopropanecarboxamide -continued 269) N-(4-(1-(2-cyanopropanoyl)-1,2,3,6-tetrahydropyridin-4-yl)-1H-pyrrolo[2,3-b]pyridin-6-yl)cyclopropanecarboxamide
270) N-(4-(1-(but-3-enoyl)-1,2,3,6-tetrahydropyridin-4-yl)-1H-pyrrolo[2,3-b]pyridin-6-yl)cyclopropanecarboxamide
271) N-(4-(1-(2-cyanobutanoyl)-1,2,3,6-tetrahydropyridin-4-yl)-1H-pyrrolo[2,3-b]pyridin-6-yl)cyclopropanecarboxamide
272) N-(4-(1-(2,2,2-trifluoroacetyl)-1,2,3,6-tetrahydropyridin-4-yl)-1H-pyrrolo[2,3-b]pyridin-6-yl)cyclopropanecarboxamide
273) N-(4-(1-(2-methylcyclopropane-1-carbonyl)-1,2,3,6-tetrahydropyridin-4-yl)-1H-pyrrolo[2,3-b]pyridin-6-yl)cyclopropanecarboxamide
274) N-(4-(1-(2-fluorocyclopropane-1-carbonyl)-1,2,3,6-tetrahydropyridin-4-yl)-1H-pyrrolo[2,3-b]pyridin-6-yl)cyclopropanecarboxamide
275) 4-(1-(2-cyanoacetyl)-1,2,3,6-tetrahydropyridin-4-yl)-6-(cyclopropanecarboxamido)-1H-pyrrolo[2,3-b]pyridine 7-oxide
276) N-(4-(1-(2-(3,4-difluorophenyl)acetyl)-1,2,3,6-tetrahydropyridin-4-yl)-1H-pyrrolo[2,3-b]pyridin-6-yl)cyclopropanecarboxamide
277) N-(4-(1-isonicotinoyl-1,2,3,6-tetrahydropyridin-4-yl)-1H-pyrrolo[2,3-b]pyridin-6-yl)cyclopropanecarboxamide
278) N-(4-(1-(furan-3-carbonyl)-1,2,3,6-tetrahydropyridin-4-yl)-1H-pyrrolo[2,3-b]pyridin-6-yl)cyclopropanecarboxamide
279) N-(4-(1-(4-fluorobenzoyl)-1,2,3,6-tetrahydropyridin-4-yl)-1H-pyrrolo[2,3-b]pyridin-6-yl)cyclopropanecarboxamide
280) N-(4-(1-(1-methylpyrrolidine-3-carbonyl)-1,2,3,6-tetrahydropyridin-4-yl)-1H-pyrrolo[2,3-b]pyridin-6-yl)cyclopropanecarboxamide
281) N-(4-(1-(dimethylglycyl)-1,2,3,6-tetrahydropyridin-4-yl)-1H-pyrrolo[2,3-b]pyridin-6-yl)cyclopropanecarboxamide
282) N-(4-(1-(2-(trifluoromethyl)cyclopropane-1-carbonyl)-1,2,3,6-tetrahydropyridin-4-yl)-1H-pyrrolo[2,3-b]pyridin-6-yl)cyclopropanecarboxamide
283) N-(4-(1-(2-cyanoacetyl)-3-methyl-1,2,3,6-tetrahydropyridin-4-yl)-1H-pyrrolo[2,3-b]pyridin-6-yl)cyclopropanecarboxamide
284) N-(4-(1-(3-cyanopropanoyl)-3-methyl-1,2,3,6-tetrahydropyridin-4-yl)-1H-pyrrolo[2,3-b]pyridin-6-yl)cyclopropanecarboxamide
285) N-(4-(1-(4-cyanobutanoyl)-3-methyl-1,2,3,6-tetrahydropyridin-4-yl)-1H-pyrrolo[2,3-b]pyridin-6-yl)cyclopropanecarboxamide
286) N-(4-(1-(1,2,5-oxadiazole-3-carbonyl)-1,2,3,6-tetrahydropyridin-4-yl)-1H-pyrrolo[2,3-b]pyridin-6-yl)cyclopropanecarboxamide
287) N-(4-(1-(isoxazole-4-carbonyl)-1,2,3,6-tetrahydropyridin-4-yl)-1H-pyrrolo[2,3-b]pyridin-6-yl)cyclopropanecarboxamide
288) N-(4-(1-(isoxazole-5-carbonyl)-1,2,3,6-tetrahydropyridin-4-yl)-1H-pyrrolo[2,3-b]pyridin-6-yl)cyclopropanecarboxamide
289) N-(4-(1-(2-cyanoacetyl)-1,2,3,6-tetrahydropyridin-4-yl)-5-methyl-1H-pyrrolo[2,3-b]pyridin-6-yl)cyclopropanecarboxamide
290) N-(5-methyl-4-(1-(3,3,3-trifluoropropanoyl)-1,2,3,6-tetrahydropyridin-4-yl)-1H-pyrrolo[2,3-b]pyridin-6-yl)cyclopropanecarboxamide
291) N-(4-(1-(thiazole-4-carbonyl)-1,2,3,6-tetrahydropyridin-4-yl)-1H-pyrrolo[2,3-b]pyridin-6-yl)cyclopropanecarboxamide
292) N-(4-(1-(isothiazole-4-carbonyl)-1,2,3,6-tetrahydropyridin-4-yl)-1H-pyrrolo[2,3-b]pyridin-6-yl)cyclopropanecarboxamide
293) N-(4-(1-(4-cyanobenzoyl)-1,2,3,6-tetrahydropyridin-4-yl)-1H-pyrrolo[2,3-b]pyridin-6-yl)cyclopropanecarboxamide
294) N-(4-(1-(2-cyanoacetyl)-3-ethyl-1,2,3,6-tetrahydropyridin-4-yl)-1H-pyrrolo[2,3-b]pyridin-6-yl)cyclopropanecarboxamide
295) N-(4-(1-(3-cyanopropanoyl)-3-ethyl-1,2,3,6-tetrahydropyridin-4-yl)-1H-pyrrolo[2,3-b]pyridin-6-yl)cyclopropanecarboxamide
296) N-(4-(1-(2-cyanoacetyl)-5-methyl-1,2,3,6-tetrahydropyridin-4-yl)-1H-pyrrolo[2,3-b]pyridin-6-yl)cyclopropanecarboxamide
297) N-(4-(1-(2-bromoacetyl)-1,2,3,6-tetrahydropyridin-4-yl)-1H-pyrrolo[2,3-b]pyridin-6-yl)cyclopropanecarboxamide
298) N-(4-(1-(2-chloroacetyl)-1,2,3,6-tetrahydropyridin-4-yl)-1H-pyrrolo[2,3-b]pyridin-6-yl)cyclopropanecarboxamide
299) N-(4-(1-(2-cyanoacetyl)-3,3-dimethyl-1,2,3,6-tetrahydropyridin-4-yl)-1H-pyrrolo[2,3-b]pyridin-6-yl)cyclopropanecarboxamide
300) N-(4-(1-(3-cyanopropanoyl)-3,3-dimethyl-1,2,3,6-tetrahydropyridin-4-yl)-1H-pyrrolo[2,3-b]pyridin-6-yl)cyclopropanecarboxamide
301) N-(4-(1-(2-cyanoacetyl)-1,2,3,6-tetrahydropyridin-4-yl)-1H-pyrrolo[2,3-b]pyridin-6-yl)furan-2-carboxamide
302) N-(4-(5-(3-cyanopropanoyl)-5-azaspiro[2.5]oct-7-en-8-yl)-1H-pyrrolo[2,3-b]pyridin-6-yl)cyclopropanecarboxamide
303) N-(4-(5-(2-cyanoacetyl)-5-azaspiro[2.5]oct-7-en-8-yl)-1H-pyrrolo[2,3-b]pyridin-6-yl)cyclopropanecarboxamide
304) (S)-N-(4-(1-(2-cyanoacetyl)-3-methyl-1,2,3,6-tetrahydropyridin-4-yl)-1H-pyrrolo[2,3-b]pyridin-6-yl)cyclopropanecarboxamide
305) (R)-N-(4-(1-(2-cyanoacetyl)-3-methyl-1,2,3,6-tetrahydropyridin-4-yl)-1H-pyrrolo[2,3-b]pyridin-6-yl)cyclopropanecarboxamide
306) N-(4-(3-methyl-1-(2-methylthiazole-5-carbonyl)-1,2,3,6-tetrahydropyridin-4-yl)-1H-pyrrolo[2,3-b]pyridin-6-yl)cyclopropanecarboxamide
307) N-(4-(1-(2,4-dimethylthiazole-5-carbonyl)-3-methyl-1,2,3,6-tetrahydropyridin-4-yl)-1H-pyrrolo[2,3-b]pyridin-6-yl)cyclopropanecarboxamide 308) N-(4-(3-methyl-1-(4-methylthiazole-5-carbonyl)-1,2,3,6-tetrahydropyridin-4-yl)-1H-pyrrolo[2,3-b]pyridin-6-yl)cyclopropanecarboxamide
309) N-(4-(1-(2-fluoroisonicotinoyl)-3-methyl-1,2,3,6-tetrahydropyridin-4-yl)-1H-pyrrolo[2,3-b]pyridin-6-yl)cyclopropanecarboxamide
310) N-(4-(1-(2-chloroisonicotinoyl)-3-methyl-1,2,3,6-tetrahydropyridin-4-yl)-1H-pyrrolo[2,3-b]pyridin-6-yl)cyclopropanecarboxamide
311) N-(4-(1-(3,4-difluorobenzoyl)-3-methyl-1,2,3,6-tetrahydropyridin-4-yl)-1H-pyrrolo[2,3-b]pyridin-6-yl)cyclopropanecarboxamide
312) N-(4-(1-(3-fluoro-4-methoxybenzoyl)-3-methyl-1,2,3,6-tetrahydropyridin-4-yl)-1H-pyrrolo[2,3-b]pyridin-6-yl)cyclopropanecarboxamide
313) N-(4-(3-methyl-1-(1H-pyrrole-2-carbonyl)-1,2,3,6-tetrahydropyridin-4-yl)-1H-pyrrolo[2,3-b]pyridin-6-yl)cyclopropanecarboxamide
314) N-(4-(1-(3-fluoroisonicotinoyl)-3-methyl-1,2,3,6-tetrahydropyridin-4-yl)-1H-pyrrolo[2,3-b]pyridin-6-yl)cyclopropanecarboxamide
315) N-(4-(1-(3-(2-(3,5-dioxomorpholino)ethyl)benzoyl)-3-methyl-1,2,3,6-tetrahydropyridin-4-yl)-1H-pyrrolo[2,3-b]pyridin-6-yl)cyclopropanecarboxamide
316) N-(4-(3-methyl-1-(3-(phenylamino)benzoyl)-1,2,3,6-tetrahydropyridin-4-yl)-1H-pyrrolo[2,3-b]pyridin-6-yl)cyclopropanecarboxamide
317) N-(4-(1-(6-(2,4-difluorophenyl)-2-oxo-1,2-dihydropyridine-3-carbonyl)-3-methyl-1,2,3,6-tetrahydropyridin-4-yl)-1H-pyrrolo[2,3-b]pyridin-6-yl)cyclopropanecarboxamide
318) methyl 1-(4-(6-(cyclopropanecarboxamido)-1H-pyrrolo[2,3-b]pyridin-4-yl)-3-methyl-1,2,3,6-tetrahydropyridine-1-carbonyl)cyclobutane-1-carboxylate
319) methyl 1-(4-(6-(cyclopropanecarboxamido)-1H-pyrrolo[2,3-b]pyridin-4-yl)-3-methyl-1,2,3,6-tetrahydropyridine-1-carbonyl)cyclopropane-1-carboxylate
320) methyl 3-(4-(6-(cyclopropanecarboxamido)-1H-pyrrolo[2,3-b]pyridin-4-yl)-3-methyl-3,6-dihydropyridin-1(2H)-yl)-2-methyl-3-oxopropanoate
321) N-(4-(1-(6-(tert-butyl)-2-oxo-1,2-dihydropyridine-3-carbonyl)-3-methyl-1,2,3,6-tetrahydropyridin-4-yl)-1H-pyrrolo[2,3-b]pyridin-6-yl)cyclopropanecarboxamide
322) N-(4-(1-(6-(4-fluorophenyl)-2-oxo-1,2-dihydropyridine-3-carbonyl)-3-methyl-1,2,3,6-tetrahydropyridin-4-yl)-1H-pyrrolo[2,3-b]pyridin-6-yl)cyclopropanecarboxamide
323) N-(4-(1-(3-fluoro-4-((2-morpholinoethyl)amino)benzoyl)-3-methyl-1,2,3,6-tetrahydropyridin-4-yl)-1H-pyrrolo[2,3-b]pyridin-6-yl)cyclopropanecarboxamide
324) N-(4-(1-(5-bromonicotinoyl)-3-methyl-1,2,3,6-tetrahydropyridin-4-yl)-1H-pyrrolo[2,3-b]pyridin-6-yl)cyclopropanecarboxamide
325) N-(4-(1-(2,3-dihydrobenzo[b][1,4]dioxine-6-carbonyl)-3-methyl-1,2,3,6-tetrahydropyridin-4-yl)-1H-pyrrolo[2,3-b]pyridin-6-yl)cyclopropanecarboxamide
326) N-(4-(1-(benzo[d][1,3]dioxole-5-carbonyl)-3-methyl-1,2,3,6-tetrahydropyridin-4-yl)-1H-pyrrolo[2,3-b]pyridin-6-yl)cyclopropanecarboxamide
327) N-(4-(1-(1H-indole-6-carbonyl)-3-methyl-1,2,3,6-tetrahydropyridin-4-yl)-1H-pyrrolo[2,3-b]pyridin-6-yl)cyclopropanecarboxamide
328) N-(4-(3-methyl-1-(1H-pyrrolo[2,3-b]pyridine-4-carbonyl)-1,2,3,6-tetrahydropyridin-4-yl)-1H-pyrrolo[2,3-b]pyridin-6-yl)cyclopropanecarboxamide
329) N-(4-(1-(3,4-dimethoxybenzoyl)-3-methyl-1,2,3,6-tetrahydropyridin-4-yl)-1H-pyrrolo[2,3-b]pyridin-6-yl)cyclopropanecarboxamide
330) N-(4-(1-(3-methoxybenzoyl)-3-methyl-1,2,3,6-tetrahydropyridin-4-yl)-1H-pyrrolo[2,3-b]pyridin-6-yl)cyclopropanecarboxamide
331) N-(4-(3-methyl-1-(4-nitrobenzoyl)-1,2,3,6-tetrahydropyridin-4-yl)-1H-pyrrolo[2,3-b]pyridin-6-yl)cyclopropanecarboxamide
332) N-(4-(1-(3-acetylbenzoyl)-3-methyl-1,2,3,6-tetrahydropyridin-4-yl)-1H-pyrrolo[2,3-b]pyridin-6-yl)cyclopropanecarboxamide
333) N-(4-(1-(4-chlorobenzoyl)-3-methyl-1,2,3,6-tetrahydropyridin-4-yl)-1H-pyrrolo[2,3-b]pyridin-6-yl)cyclopropanecarboxamide
334) N-(4-(1-(3-bromobenzoyl)-3-methyl-1,2,3,6-tetrahydropyridin-4-yl)-1H-pyrrolo[2,3-b]pyridin-6-yl)cyclopropanecarboxamide
335) N-(4-(1-(6-chloronicotinoyl)-3-methyl-1,2,3,6-tetrahydropyridin-4-yl)-1H-pyrrolo[2,3-b]pyridin-6-yl)cyclopropanecarboxamide
336) N-(4-(1-isonicotinoyl-3-methyl-1,2,3,6-tetrahydropyridin-4-yl)-1H-pyrrolo[2,3-b]pyridin-6-yl)cyclopropanecarboxamide
337) N-(4-(1-(6-bromopicolinoyl)-3-methyl-1,2,3,6-tetrahydropyridin-4-yl)-1H-pyrrolo[2,3-b]pyridin-6-yl)cyclopropanecarboxamide
338) N-(4-(1-(3-bromobutanoyl)-3-methyl-1,2,3,6-tetrahydropyridin-4-yl)-1H-pyrrolo[2,3-b]pyridin-6-yl)cyclopropanecarboxamide
339) (E)-N-(4-(1-(5-bromopent-2-enoyl)-3-methyl-1,2,3,6-tetrahydropyridin-4-yl)-1H-pyrrolo[2,3-b]pyridin-6-yl)cyclopropanecarboxamide
340) N-(4-(1-(2-cyclopentylacetyl)-3-methyl-1,2,3,6-tetrahydropyridin-4-yl)-1H-pyrrolo[2,3-b]pyridin-6-yl)cyclopropanecarboxamide
341) N-(4-(1-(2-(4-methoxyphenyl)acetyl)-3-methyl-1,2,3,6-tetrahydropyridin-4-yl)-1H-pyrrolo[2,3-b]pyridin-6-yl)cyclopropanecarboxamide
342) N-(4-(3-methyl-1-(3-methylthiophene-2-carbonyl)-1,2,3,6-tetrahydropyridin-4-yl)-1H-pyrrolo[2,3-b]pyridin-6-yl)cyclopropanecarboxamide
343) N-(4-(3-methyl-1-(pyrazine-2-carbonyl)-1,2,3,6-tetrahydropyridin-4-yl)-1H-pyrrolo[2,3-b]pyridin-6-yl)cyclopropanecarboxamide
344) N-(4-(3-methyl-1-(5-methylpyrazine-2-carbonyl)-1,2,3,6-tetrahydropyridin-4-yl)-1H-pyrrolo[2,3-b]pyridin-6-yl)cyclopropanecarboxamide
345) N-(4-(3-methyl-1-(2-(thiophen-2-yl)acetyl)-1,2,3,6-tetrahydropyridin-4-yl)-1H-pyrrolo[2,3-b]pyridin-6-yl)cyclopropanecarboxamide -continued 346) N-(4-(1-(2-(3-fluorophenyl)acetyl)-3-methyl-1,2,3,6-tetrahydropyridin-4-yl)-1H-pyrrolo[2,3-b]pyridin-6-yl)cyclopropanecarboxamide
347) N-(4-(1-(2-(3-bromophenyl)acetyl)-3-methyl-1,2,3,6-tetrahydropyridin-4-yl)-1H-pyrrolo[2,3-b]pyridin-6-yl)cyclopropanecarboxamide
348) N-(4-(1-(2-chloroacetyl)-3-methyl-1,2,3,6-tetrahydropyridin-4-yl)-1H-pyrrolo[2,3-b]pyridin-6-yl)cyclopropanecarboxamide
349) N-(4-(1-(2-chloronicotinoyl)-3-methyl-1,2,3,6-tetrahydropyridin-4-yl)-1H-pyrrolo[2,3-b]pyridin-6-yl)cyclopropanecarboxamide
350) N-(4-(1-(4-hydroxybenzoyl)-3-methyl-1,2,3,6-tetrahydropyridin-4-yl)-1H-pyrrolo[2,3-b]pyridin-6-yl)cyclopropanecarboxamide
351) N-(4-(1-(3,5-dichloro-2-hydroxybenzoyl)-3-methyl-1,2,3,6-tetrahydropyridin-4-yl)-1H-pyrrolo[2,3-b]pyridin-6-yl)cyclopropanecarboxamide
352) N-(4-(1-(benzofuran-2-carbonyl)-3-methyl-1,2,3,6-tetrahydropyridin-4-yl)-1H-pyrrolo[2,3-b]pyridin-6-yl)cyclopropanecarboxamide
353) N-(4-(1-(3,4-dichlorobenzoyl)-3-methyl-1,2,3,6-tetrahydropyridin-4-yl)-1H-pyrrolo[2,3-b]pyridin-6-yl)cyclopropanecarboxamide
354) N-(4-(3-methyl-1-(4-(methylsulfonyl)benzoyl)-1,2,3,6-tetrahydropyridin-4-yl)-1H-pyrrolo[2,3-b]pyridin-6-yl)cyclopropanecarboxamide
355) N-(4-(1-(2-chloro-4-fluorobenzoyl)-3-methyl-1,2,3,6-tetrahydropyridin-4-yl)-1H-pyrrolo[2,3-b]pyridin-6-yl)cyclopropanecarboxamide
356) N-(4-(1-(2,4-dimethoxybenzoyl)-3-methyl-1,2,3,6-tetrahydropyridin-4-yl)-1H-pyrrolo[2,3-b]pyridin-6-yl)cyclopropanecarboxamide
357) N-(4-(3-methyl-1-(2-(methylthio)benzoyl)-1,2,3,6-tetrahydropyridin-4-yl)-1H-pyrrolo[2,3-b]pyridin-6-yl)cyclopropanecarboxamide
358) N-(4-(1-(3,5-difluorobenzoyl)-3-methyl-1,2,3,6-tetrahydropyridin-4-yl)-1H-pyrrolo[2,3-b]pyridin-6-yl)cyclopropanecarboxamide
359) N-(4-(1-(2-cyano-3-(4-fluorophenyl)propanoyl)-3-methyl-1,2,3,6-tetrahydropyridin-4-yl)-1H-pyrrolo[2,3-b]pyridin-6-yl)cyclopropanecarboxamide
360) N-(4-(1-(2-cyano-3-phenylpropanoyl)-3-methyl-1,2,3,6-tetrahydropyridin-4-yl)-1H-pyrrolo[2,3-b]pyridin-6-yl)cyclopropanecarboxamide
361) N-(4-(1-(1-cyanocyclopentane-1-carbonyl)-3-methyl-1,2,3,6-tetrahydropyridin-4-yl)-1H-pyrrolo[2,3-b]pyridin-6-yl)cyclopropanecarboxamide
362) N-(4-(3-methyl-1-(3-morpholino-3-oxopropanoyl)-1,2,3,6-tetrahydropyridin-4-yl)-1H-pyrrolo[2,3-b]pyridin-6-yl)cyclopropanecarboxamide
363) N-(4-(1-(2-cyanoacetyl)-2-methyl-1,2,3,6-tetrahydropyridin-4-yl)-1H-pyrrolo[2,3-b]pyridin-6-yl)cyclopropanecarboxamide
365) N-(4-(3-methyl-1-(2-phenylacetyl)-1,2,3,6-tetrahydropyridin-4-yl)-1H-pyrrolo[2,3-b]pyridin-6-yl)cyclopropanecarboxamide
366) N-(4-(9-(2-fluoroisonicotinoyl)-9-azabicyclo[3.3.1]non-2-en-3-yl)-1H-pyrrolo[2,3-b]pyridin-6-yl)cyclopropanecarboxamide
367) N-(4-(9-(2-chloroisonicotinoyl)-9-azabicyclo[3.3.1]non-2-en-3-yl)-1H-pyrrolo[2,3-b]pyridin-6-yl)cyclopropanecarboxamide
368) N-(4-(9-(6-chloronicotinoyl)-9-azabicyclo[3.3.1]non-2-en-3-yl)-1H-pyrrolo[2,3-b]pyridin-6-yl)cyclopropanecarboxamide
369) N-(4-(9-(3-fluoroisonicotinoyl)-9-azabicyclo[3.3.1]non-2-en-3-yl)-1H-pyrrolo[2,3-b]pyridin-6-yl)cyclopropanecarboxamide
370) N-(4-(9-(4-nitrobenzoyl)-9-azabicyclo[3.3.1]non-2-en-3-yl)-1H-pyrrolo[2,3-b]pyridin-6-yl)cyclopropanecarboxamide
371) N-(4-(9-(3-bromobenzoyl)-9-azabicyclo[3.3.1]non-2-en-3-yl)-1H-pyrrolo[2,3-b]pyridin-6-yl)cyclopropanecarboxamide
372) N-(4-(1-(2,6-dichloroisonicotinoyl)-3-methyl-1,2,3,6-tetrahydropyridin-4-yl)-1H-pyrrolo[2,3-b]pyridin-6-yl)cyclopropanecarboxamide
373) N-(4-(1-(2,5-dichloroisonicotinoyl)-3-methyl-1,2,3,6-tetrahydropyridin-4-yl)-1H-pyrrolo[2,3-b]pyridin-6-yl)cyclopropanecarboxamide
374) N-(4-(1-(3,5-dichloroisonicotinoyl)-3-methyl-1,2,3,6-tetrahydropyridin-4-yl)-1H-pyrrolo[2,3-b]pyridin-6-yl)cyclopropanecarboxamide
375) N-(4-(1-(2-chloro-6-methylisonicotinoyl)-3-methyl-1,2,3,6-tetrahydropyridin-4-yl)-1H-pyrrolo[2,3-b]pyridin-6-yl)cyclopropanecarboxamide
376) N-(4-(1-(3-chloroisonicotinoyl)-3-methyl-1,2,3,6-tetrahydropyridin-4-yl)-1H-pyrrolo[2,3-b]pyridin-6-yl)cyclopropanecarboxamide
377) N-(4-(1-(3-hydroxyisonicotinoyl)-3-methyl-1,2,3,6-tetrahydropyridin-4-yl)-1H-pyrrolo[2,3-b]pyridin-6-yl)cyclopropanecarboxamide
378) N-(4-(1-(2,3-difluorobenzoyl)-3-methyl-1,2,3,6-tetrahydropyridin-4-yl)-1H-pyrrolo[2,3-b]pyridin-6-yl)cyclopropanecarboxamide
379) N-(4-(3-methyl-1-(2-methylisonicotinoyl)-1,2,3,6-tetrahydropyridin-4-yl)-1H-pyrrolo[2,3-b]pyridin-6-yl)cyclopropanecarboxamide
380) N-(4-(1-(6-methoxynicotinoyl)-3-methyl-1,2,3,6-tetrahydropyridin-4-yl)-1H-pyrrolo[2,3-b]pyridin-6-yl)cyclopropanecarboxamide
381) N-(4-(1-(2-aminoisonicotinoyl)-3-methyl-1,2,3,6-tetrahydropyridin-4-yl)-1H-pyrrolo[2,3-b]pyridin-6-yl)cyclopropanecarboxamide
382) N-(4-(1-(2-bromoisonicotinoyl)-3-methyl-1,2,3,6-tetrahydropyridin-4-yl)-1H-pyrrolo[2,3-b]pyridin-6-yl)cyclopropanecarboxamide
383) N-(4-(1-(2-hydroxyisonicotinoyl)-3-methyl-1,2,3,6-tetrahydropyridin-4-yl)-1H-pyrrolo[2,3-b]pyridin-6-yl)cyclopropanecarboxamide
384) N-(4-(3-methyl-1-(2-(trifluoromethyl)isonicotinoyl)-1,2,3,6-tetrahydropyridin-4-yl)-1H-pyrrolo[2,3-b]pyridin-6-yl)cyclopropanecarboxamide
385) N-(4-(1-(2-fluoroisonicotinoyl)-2,2-dimethyl-1,2,3,6-tetrahydropyridin-4-yl)-1H-pyrrolo[2,3-b]pyridin-6-yl)cyclopropanecarboxamide -continued 386) N-(4-(1-(2-chloroisonicotinoyl)-2,2-dimethyl-1,2,3,6-tetrahydropyridin-4-yl)-1H-pyrrolo[2,3-b]pyridin-6-yl)cyclopropanecarboxamide
387) N-(4-(1-(2-cyanoacetyl)-2,2-dimethyl-1,2,3,6-tetrahydropyridin-4-yl)-1H-pyrrolo[2,3-b]pyridin-6-yl)cyclopropanecarboxamide
388) (R)-N-(4-(1-(2-cyanoacetyl)-6-methyl-1,2,3,6-tetrahydropyridin-4-yl)-1H-pyrrolo[2,3-b]pyridin-6-yl)cyclopropanecarboxamide
389) (R)-N-(4-(1-(2-cyanoacetyl)-2-methyl-1,2,3,6-tetrahydropyridin-4-yl)-1H-pyrrolo[2,3-b]pyridin-6-yl)cyclopropanecarboxamide
390) (S)-N-(4-(1-(2-cyanoacetyl)-6-methyl-1,2,3,6-tetrahydropyridin-4-yl)-1H-pyrrolo[2,3-b]pyridin-6-yl)cyclopropanecarboxamide
391) (S)-N-(4-(1-(2-cyanoacetyl)-2-methyl-1,2,3,6-tetrahydropyridin-4-yl)-1H-pyrrolo[2,3-b]pyridin-6-yl)cyclopropanecarboxamide
392) N-(4-(1-(2-cyanoisonicotinoyl)-3-methyl-1,2,3,6-tetrahydropyridin-4-yl)-1H-pyrrolo[2,3-b]pyridin-6-yl)cyclopropanecarboxamide
393) N-(4-(1-(2-cyanoacetyl)-2-(trifluoromethyl)-1,2,3,6-tetrahydropyridin-4-yl)-1H-pyrrolo[2,3-b]pyridin-6-yl)cyclopropanecarboxamide
394) N-(4-(9-(2-cyanoacetyl)-9-azabicyclo[3.3.1]non-2-en-3-yl)-1H-pyrrolo[2,3-b]pyridin-6-yl)cyclopropanecarboxamide
395) (S)-N-(4-(1-(2-fluoroisonicotinoyl)-3-methyl-1,2,3,6-tetrahydropyridin-4-yl)-1H-pyrrolo[2,3-b]pyridin-6-yl)cyclopropanecarboxamide
396) (S)-N-(4-(1-(2,3-difluoroisonicotinoyl)-3-methyl-1,2,3,6-tetrahydropyridin-4-yl)-1H-pyrrolo[2,3-b]pyridin-6-yl)cyclopropanecarboxamide
397) (S)-N-(4-(1-(3-bromobenzoyl)-3-methyl-1,2,3,6-tetrahydropyridin-4-yl)-1H-pyrrolo[2,3-b]pyridin-6-yl)cyclopropanecarboxamide
398) (S)-N-(4-(3-methyl-1-(4-nitrobenzoyl)-1,2,3,6-tetrahydropyridin-4-yl)-1H-pyrrolo[2,3-b]pyridin-6-yl)cyclopropanecarboxamide
399) (S)-N-(4-(1-(2-chloroisonicotinoyl)-3-methyl-1,2,3,6-tetrahydropyridin-4-yl)-1H-pyrrolo[2,3-b]pyridin-6-yl)cyclopropanecarboxamide
400) (S)-N-(4-(1-(6-chloronicotinoyl)-3-methyl-1,2,3,6-tetrahydropyridin-4-yl)-1H-pyrrolo[2,3-b]pyridin-6-yl)cyclopropanecarboxamide
401) (S)-N-(4-(1-(2-chloroacetyl)-3-methyl-1,2,3,6-tetrahydropyridin-4-yl)-1H-pyrrolo[2,3-b]pyridin-6-yl)cyclopropanecarboxamide
402) (S)-N-(4-(1-(3-fluoroisonicotinoyl)-3-methyl-1,2,3,6-tetrahydropyridin-4-yl)-1H-pyrrolo[2,3-b]pyridin-6-yl)cyclopropanecarboxamide
403) (S)-N-(4-(1-(2-cyano-3-(thiophen-2-yl)acryloyl)-3-methyl-1,2,3,6-tetrahydropyridin-4-yl)-1H-pyrrolo[2,3-b]pyridin-6-yl)cyclopropanecarboxamide
404) (S)-N-(4-(1-(2-(cyanomethyl)-3-phenylacryloyl)-3-methyl-1,2,3,6-tetrahydropyridin-4-yl)-1H-pyrrolo[2,3-b]pyridin-6-yl)cyclopropanecarboxamide
405) (S)-N-(4-(3-methyl-1-(1-methyl-2-oxo-1,2-dihydropyridine-3-carbonyl)-1,2,3,6-tetrahydropyridin-4-yl)-1H-pyrrolo[2,3-b]pyridin-6-yl)cyclopropanecarboxamide
406) (S)-N-(4-(1-(2-(1-cyanocyclohexyl)acetyl)-3-methyl-1,2,3,6-tetrahydropyridin-4-yl)-1H-pyrrolo[2,3-b]pyridin-6-yl)cyclopropanecarboxamide
407) (S)-N-(4-(1-(4-cyanotetrahydro-2H-pyran-4-carbonyl)-3-methyl-1,2,3,6-tetrahydropyridin-4-yl)-1H-pyrrolo[2,3-b]pyridin-6-yl)cyclopropanecarboxamide
408) (S)-N-(4-(1-(2-cyano-3-methylbut-2-enoyl)-3-methyl-1,2,3,6-tetrahydropyridin-4-yl)-1H-pyrrolo[2,3-b]pyridin-6-yl)cyclopropanecarboxamide
409) N-(4-(1-(2-cyanoacetyl)-2,6-diethyl-1,2,3,6-tetrahydropyridin-4-yl)-1H-pyrrolo[2,3-b]pyridin-6-yl)cyclopropanecarboxamide
410) N-(4-(1-(2-cyanoacetyl)-2-isopropyl-1,2,3,6-tetrahydropyridin-4-yl)-1H-pyrrolo[2,3-b]pyridin-6-yl)cyclopropanecarboxamide
411) N-(4-(1-(2-cyanoacetyl)-6-propyl-1,2,3,6-tetrahydropyridin-4-yl)-1H-pyrrolo[2,3-b]pyridin-6-yl)cyclopropanecarboxamide
412) N-(4-(6-(tert-butyl)-1-(2-cyanoacetyl)-1,2,3,6-tetrahydropyridin-4-yl)-1H-pyrrolo[2,3-b]pyridin-6-yl)cyclopropanecarboxamide
413) N-(4-(1-(2-cyanoacetyl)-2-ethyl-1,2,3,6-tetrahydropyridin-4-yl)-1H-pyrrolo[2,3-b]pyridin-6-yl)cyclopropanecarboxamide
414) N-(4-(5-(2-cyanoacetyl)-5-azaspiro[3.5]non-7-en-8-yl)-1H-pyrrolo[2,3-b]pyridin-6-yl)cyclopropanecarboxamide
415) (S)-N-(4-(1-(2-(1-cyanocyclopropyl)acetyl)-3-methyl-1,2,3,6-tetrahydropyridin-4-yl)-1H-pyrrolo[2,3-b]pyridin-6-yl)cyclopropanecarboxamide
416) (R)-N-(4-(1-(2-cyanoacetyl)-6-ethyl-1,2,3,6-tetrahydropyridin-4-yl)-1H-pyrrolo[2,3-b]pyridin-6-yl)cyclopropanecarboxamide
417) (R)-N-(4-(1-(2-cyanoacetyl)-2-ethyl-1,2,3,6-tetrahydropyridin-4-yl)-1H-pyrrolo[2,3-b]pyridin-6-yl)cyclopropanecarboxamide
418) N-(4-(1-(3-cyanopropanoyl)-1,4,5,6-tetrahydropyridin-3-yl)-1H-pyrrolo[2,3-b]pyridin-6-yl)cyclopropanecarboxamide
419) N-(4-(1-(2-cyanoacetyl)-1,4,5,6-tetrahydropyridin-3-yl)-1H-pyrrolo[2,3-b]pyridin-6-yl)cyclopropanecarboxamide
420) N-(4-(1-(2-cyanoacetyl)-1,2,5,6-tetrahydropyridin-3-yl)-1H-pyrrolo[2,3-b]pyridin-6-yl)cyclopropanecarboxamide
421) N-(4-(1-(3-cyanopropanoyl)-1,2,5,6-tetrahydropyridin-3-yl)-1H-pyrrolo[2,3-b]pyridin-6-yl)cyclopropanecarboxamide
422) N-(4-(1-(2-cyanoacetyl)-2,5,6,7-tetrahydro-1H-azepin-4-yl)-1H-pyrrolo[2,3-b]pyridin-6-yl)cyclopropanecarboxamide
423) N-(4-(1-(2-fluoroisonicotinoyl)-2,5,6,7-tetrahydro-1H-azepin-4-yl)-1H-pyrrolo[2,3-b]pyridin-6-yl)cyclopropanecarboxamide
424) N-(4-(1-(2,3-difluoroisonicotinoyl)-2,5,6,7-tetrahydro-1H-azepin-4-yl)-1H-pyrrolo[2,3-b]pyridin-6-yl)cyclopropanecarboxamide 425) N-(4-(1-(2-cyanoacetyl)-1,2,3,6-tetrahydropyridin-4-yl)-7H-pyrrolo[2,3-d]pyrimidin-2-yl)cyclopropanecarboxamide
426) N-(4-(1-(2-cyanoacetyl)-2,5-dihydro-1H-pyrrol-3-yl)-1H-pyrrolo[2,3-b]pyridin-6-yl)cyclopropanecarboxamide
427) N-(4-(1-(3-cyanopropanoyl)-2,5-dihydro-1H-pyrrol-3-yl)-1H-pyrrolo[2,3-b]pyridin-6-yl)cyclopropanecarboxamide
428) N-(4-(1-(3,3,3-trifluoropropanoyl)-2,5-dihydro-1H-pyrrol-3-yl)-1H-pyrrolo[2,3-b]pyridin-6-yl)cyclopropanecarboxamide
429) N-(4-(1-(4,4,4-trifluorobutanoyl)-2,5-dihydro-1H-pyrrol-3-yl)-1H-pyrrolo[2,3-b]pyridin-6-yl)cyclopropanecarboxamide
430) N-(4-(1-(1-cyanocyclopropane-1-carbonyl)-2,5-dihydro-1H-pyrrol-3-yl)-1H-pyrrolo[2,3-b]pyridin-6-yl)cyclopropanecarboxamide
431) N-(4-(4-(3-ethylureido)phenyl)-1H-pyrrolo[2,3-b]pyridin-6-yl)cyclopropanecarboxamide
432) N-(4-(6-(cyclopropanecarboxamido)-1H-pyrrolo[2,3-b]pyridin-4-yl)phenyl)morpholine-4-carboxamide
433) N-(4-(4-(3-butylureido)phenyl)-1H-pyrrolo[2,3-b]pyridin-6-yl)cyclopropanecarboxamide
434) N-(4-(4-(3-(4-fluorophenyl)ureido)phenyl)-1H-pyrrolo[2,3-b]pyridin-6-yl)cyclopropanecarboxamide
435) N-(4-(4-(3-(2,2,2-trifluoroethyl)ureido)phenyl)-1H-pyrrolo[2,3-b]pyridin-6-yl)cyclopropanecarboxamide
436) N-(4-(2-methyl-4-(3-(2,2,2-trifluoroethyl)ureido)phenyl)-1H-pyrrolo[2,3-b]pyridin-6-yl)cyclopropanecarboxamide
437) N-(4-(4-(3-cyclopropylureido)phenyl)-7H-pyrrolo[2,3-d]pyrimidin-2-yl)cyclopropanecarboxamide
438) N-(4-(4-(3-ethylureido)phenyl)-7H-pyrrolo[2,3-d]pyrimidin-2-yl)cyclopropanecarboxamide
439) N-(4-(4-(3-butylureido)phenyl)-7H-pyrrolo[2,3-d]pyrimidin-2-yl)cyclopropanecarboxamide
440) N-(4-(4-(3-(3,4-difluorophenyl)ureido)phenyl)-7H-pyrrolo[2,3-d]pyrimidin-2-yl)cyclopropanecarboxamide
441) N-(4-(4-(3-(4-fluorophenyl)ureido)phenyl)-7H-pyrrolo[2,3-d]pyrimidin-2-yl)cyclopropanecarboxamide
442) N-(4-(4-(3-(2,2,2-trifluoroethyl)ureido)cyclohex-1-en-1-yl)-1H-pyrrolo[2,3-b]pyridin-6-yl)cyclopropanecarboxamide
443) 4-(6-(cyclopropanecarboxamido)-1H-pyrrolo[2,3-b]pyridin-4-yl)-N-(2,2,2-trifluoroethyl)-3,6-dihydropyridine-1(2H)-carboxamide
444) N-butyl-4-(6-(cyclopropanecarboxamido)-1H-pyrrolo[2,3-b]pyridin-4-yl)-3,6-dihydropyridine-1(2H)-carboxamide
445) N-(4-(1-(1,1-dioxidothiomorpholine-4-carbonyl)-1,2,3,6-tetrahydropyridin-4-yl)-1H-pyrrolo[2,3-b]pyridin-6-yl)cyclopropanecarboxamide
446) N-(4-(1-(morpholine-4-carbonyl)-1,2,3,6-tetrahydropyridin-4-yl)-1H-pyrrolo[2,3-b]pyridin-6-yl)cyclopropanecarboxamide
447) N-cyanomethyl)-4-(6-(cyclopropanecarboxamido)-1H-pyrrolo[2,3-b]pyridin-4-yl)-3,6-dihydropyridine-1(2H)-carboxamide
448) 3-(6-(cyclopropanecarboxamido)-1H-pyrrolo[2,3-b]pyridin-4-yl)-N-(2,2,2-trifluoroethyl)-8-azabicyclo[3.2.1]oct-2-ene-8-carboxamide
449) N-butyl-3-(6-(cyclopropanecarboxamido)-1H-pyrrolo[2,3-b]pyridin-4-yl)-8-azabicyclo[3.2.1]oct-2-ene-8-carboxamide
450) 4-(6-(cyclopropanecarboxamido)-1H-pyrrolo[2,3-b]pyridin-4-yl)-N-(1-cyclopropyl-2,2,2-trifluoroethyl)-3,6-dihydropyridine-1(2H)-carboxamide
451) N-(4-(1-(1H-imidazole-1-carbonyl)-1,2,3,6-tetrahydropyridin-4-yl)-1H-pyrrolo[2,3-b]pyridin-6-yl)cyclopropanecarboxamide
452) N-(4-(1-(1H-imidazole-1-carbonyl)-3-methyl-1,2,3,6-tetrahydropyridin-4-yl)-1H-pyrrolo[2,3-b]pyridin-6-yl)cyclopropanecarboxamide
453) 4-(6-(cyclopropanecarboxamido)-1H-pyrrolo[2,3-b]pyridin-4-yl)-3-methyl-N-(2,2,2-trifluoroethyl)-3,6-dihydropyridine-1(2H)-carboxamide
454) tert-butyl 4-(6-(cyclopropanecarboxamido)-1H-pyrrolo[2,3-b]pyridin-4-yl)-3,6-dihydropyridine-1(2H)-carboxylate
455) cyanomethyl 4-(6-(cyclopropanecarboxamido)-1H-pyrrolo[2,3-b]pyridin-4-yl)-3,6-dihydropyridine-1(2H)-carboxylate
456) tert-butyl 4-(6-(cyclopropanecarboxamido)-1H-pyrrolo[2,3-b]pyridin-4-yl)-3-methyl-3,6-dihydropyridine-1(2H)-carboxylate
457) tert-butyl 4-(6-(cyclopropanecarboxamido)-5-methyl-1H-pyrrolo[2,3-b]pyridin-4-yl)-3,6-dihydropyridine-1(2H)-carboxylate
458) tert-butyl 4-(6-(cyclopropanecarboxamido)-1H-pyrrolo[2,3-b]pyridin-4-yl)-3-ethyl-3,6-dihydropyridine-1(2H)-carboxylate
459) tert-butyl 5-(6-(cyclopropanecarboxamido)-1H-pyrrolo[2,3-b]pyridin-4-yl)-3,4-dihydropyridine-1(2H)-carboxylate
460) tert-butyl 5-(6-(cyclopropanecarboxamido)-1H-pyrrolo[2,3-b]pyridin-4-yl)-3,6-dihydropyridine-1(2H)-carboxylate
461) tert-butyl 3-(6-(cyclopropanecarboxamido)-1H-pyrrolo[2,3-b]pyridin-4-yl)-2,5-dihydro-1H-pyrrole-1-carboxylate
462) N-(4-(4-(3-ethylthioureido)phenyl)-1H-pyrrolo[2,3-b]pyridin-6-yl)cyclopropanecarboxamide
463) N-(4-(4-(3-butylthioureido)phenyl)-1H-pyrrolo[2,3-b]pyridin-6-yl)cyclopropanecarboxamide -continued 464) N-(4-(3-cyclohexylthioureido)phenyl)-7H-pyrrolo[2,3-d]pyrimidin-2-yl)cyclopropanecarboxamide
465) N-(4-(3-butylthioureido)phenyl)-7H-pyrrolo[2,3-d]pyrimidin-2-yl)cyclopropanecarboxamide
466) N-(4-(3-ethylthioureido)phenyl)-7H-pyrrolo[2,3-d]pyrimidin-2-yl)cyclopropanecarboxamide
467) N-(4-(3-propylthioureido)phenyl)-7H-pyrrolo[2,3-d]pyrimidin-2-yl)cyclopropanecarboxamide
468) N-(4-(1-(ethylcarbamothioyl)-1,2,3,6-tetrahydropyridin-4-yl)-1H-pyrrolo[2,3-b]pyridin-6-yl)cyclopropanecarboxamide
469) N-(4-(8-(ethylcarbamothioyl)-8-azabicyclo[3.2.1]oct-2-en-3-yl)-1H-pyrrolo[2,3-b]pyridin-6-yl)cyclopropanecarboxamide
470) N-(4-(4-((cyclopropylmethyl)amino)phenyl)-1H-pyrrolo[2,3-b]pyridin-6-yl)cyclopropanecarboxamide
471) N-(4-(4-((cyclohexylmethyl)amino)phenyl)-1H-pyrrolo[2,3-b]pyridin-6-yl)cyclopropanecarboxamide
472) N-(4-(4-(benzylamino)phenyl)-1H-pyrrolo[2,3-b]pyridin-6-yl)cyclopropanecarboxamide
473) N-(4-(4-((4-fluorobenzyl)amino)phenyl)-7H-pyrrolo[2,3-d]pyrimidin-2-yl)cyclopropanecarboxamide
474) N-(4-(4-((3-fluorobenzyl)amino)phenyl)-7H-pyrrolo[2,3-d]pyrimidin-2-yl)cyclopropanecarboxamide
475) N-(4-(4-((4-chlorobenzyl)amino)phenyl)-7H-pyrrolo[2,3-d]pyrimidin-2-yl)cyclopropanecarboxamide
476) N-(4-(4-((3-hydroxypropyl)amino)phenyl)-7H-pyrrolo[2,3-d]pyrimidin-2-yl)cyclopropanecarboxamide
477) N-(4-(1-(2-cyanoethyl)-1H-pyrazol-4-yl)-1H-pyrrolo[2,3-b]pyridin-6-yl)cyclopropanecarboxamide
478) N-(4-(1-(cyclopropylmethyl)-1H-pyrazol-4-yl)-1H-pyrrolo[2,3-b]pyridin-6-yl)cyclopropanecarboxamide
479) N-(4-(1-benzyl-1H-pyrazol-4-yl)-1H-pyrrolo[2,3-b]pyridin-6-yl)cyclopropanecarboxamide
480) N-(4-(1-(2-cyanoethyl)-3,5-dimethyl-1H-pyrazol-4-yl)-1H-pyrrolo[2,3-b]pyridin-6-yl)cyclopropanecarboxamide
481) N-(4-(1-benzyl-1H-1,2,3-triazol-4-yl)-1H-pyrrolo[2,3-b]pyridin-6-yl)cyclopropanecarboxamide
482) N-(4-(1-((6-cyanopyridin-3-yl)methyl)-1H-pyrazol-4-yl)-7H-pyrrolo[2,3-d]pyrimidin-2-yl)cyclopropanecarboxamide
483) N-(4-(1-(2-cyanoethyl)-1H-pyrrol-3-yl)-1H-pyrrolo[2,3-b]pyridin-6-yl)cyclopropanecarboxamide
484) N-(4-(1-(2-morpholinoethyl)-2,5-dihydro-1H-pyrrol-3-yl)-1H-pyrrolo[2,3-b]pyridin-6-yl)cyclopropanecarboxamide
485) N-(4-(1-(2-cyanoethyl)-2,5-dihydro-1H-pyrrol-3-yl)-1H-pyrrolo[2,3-b]pyridin-6-yl)cyclopropanecarboxamide
486) N-(4-(1-(2-cyanoethyl)-1,2,3,6-tetrahydropyridin-4-yl)-1H-pyrrolo[2,3-b]pyridin-6-yl)cyclopropanecarboxamide
487) N-(4-(1-((3-methyloxetan-3-yl)methyl)-1,2,3,6-tetrahydropyridin-4-yl)-1H-pyrrolo[2,3-b]pyridin-6-yl)cyclopropanecarboxamide
488) N-(4-(1-(isothiazol-5-ylmethyl)-1,2,3,6-tetrahydropyridin-4-yl)-1H-pyrrolo[2,3-b]pyridin-6-yl)cyclopropanecarboxamide
489) N-(4-(1-((2,2-difluorocyclopropyl)methyl)-1,2,3,6-tetrahydropyridin-4-yl)-1H-pyrrolo[2,3-b]pyridin-6-yl)cyclopropanecarboxamide
490) N-(4-(1-(3-cyanocyclobutyl)-1,2,3,6-tetrahydropyridin-4-yl)-1H-pyrrolo[2,3-b]pyridin-6-yl)cyclopropanecarboxamide
491) N-(4-(4-((1-(3,5-difluorobenzoyl)piperidin-4-yl)amino)cyclohex-1-en-1-yl)-1H-pyrrolo[2,3-b]pyridin-6-yl)cyclopropanecarboxamide
492) N-(4-(4-((1-(cyclohexanecarbonyl)piperidin-4-yl)amino)cyclohex-1-en-1-yl)-1H-pyrrolo[2,3-b]pyridin-6-yl)cyclopropanecarboxamide
493) N-(4-(4-((1-(2-fluoroisonicotinoyl)piperidin-4-yl)amino)cyclohex-1-en-1-yl)-1H-pyrrolo[2,3-b]pyridin-6-yl)cyclopropanecarboxamide
494) N-(4-(4-((1-(4-nitrobenzoyl)piperidin-4-yl)amino)cyclohex-1-en-1-yl)-1H-pyrrolo[2,3-b]pyridin-6-yl)cyclopropanecarboxamide
495) N-(4-(4-((1-(3,5-difluorobenzoyl)azetidin-3-yl)amino)cyclohex-1-en-1-yl)-1H-pyrrolo[2,3-b]pyridin-6-yl)cyclopropanecarboxamide
496) N-(4-(4-((1-(2-fluoroisonicotinoyl)azetidin-3-yl)amino)cyclohex-1-en-1-yl)-1H-pyrrolo[2,3-b]pyridin-6-yl)cyclopropanecarboxamide
497) N-(4-(4-((1-(2-methoxyisonicotinoyl)azetidin-3-yl)amino)cyclohex-1-en-1-yl)-1H-pyrrolo[2,3-b]pyridin-6-yl)cyclopropanecarboxamide
498) 4-((4-(6-(cyclopropanecarboxamido)-1H-pyrrolo[2,3-b]pyridin-4-yl)-2-fluorophenyl)amino)-N-phenylpiperidine-1-carboxamide
499) N-(4-(4-((1-(3,5-difluorobenzoyl)piperidin-4-yl)amino)-3-fluorophenyl)-1H-pyrrolo[2,3-b]pyridin-6-yl)cyclopropanecarboxamide
500) N-(4-(3-fluoro-4-((1-(2-fluoroisonicotinoyl)piperidin-4-yl)amino)phenyl)-1H-pyrrolo[2,3-b]pyridin-6-yl)cyclopropanecarboxamide
501) 4-((4-(6-(cyclopropanecarboxamido)-1H-pyrrolo[2,3-b]pyridin-4-yl)-2-fluorophenyl)amino)-N-(2,4-difluorophenyl)piperidine-1-carboxamide
502) N-(4-(4-(((2S)-1-(3,5-difluorobenzoyl)-2-methylpiperidin-4-yl)amino)phenyl)-1H-pyrrolo[2,3-b]pyridin-6-yl)cyclopropanecarboxamide -continued 503) N-(4-(4-(((2S)-1-(2-fluoroisonicotinoyl)-2-methylpiperidin-4-yl)amino)phenyl)-1H-pyrrolo[2,3-b]pyridin-6-yl)cyclopropanecarboxamide
504) (2S)-4-((4-(6-(cyclopropanecarboxamido)-1H-pyrrolo[2,3-b]pyridin-4-yl)phenyl)amino)-2-methyl-N-(2,2,2-trifluoroethyl)piperidine-1-carboxamide
505) 4-((4-(6-(cyclopropanecarboxamido)-1H-pyrrolo[2,3-b]pyridin-4-yl)-2-fluorophenyl)amino)-N-(2,2,2-trifluoroethyl)piperidine-1-carboxamide
506) (2S)-4-((4-(6-(cyclopropanecarboxamido)-1H-pyrrolo[2,3-b]pyridin-4-yl)phenyl)amino)-N-(2,4-difluorophenyl)-2-methylpiperidine-1-carboxamide
507) N-(4-(4-((1-isonicotinoylpiperidin-4-yl)amino)phenyl)-1H-pyrrolo[2,3-b]pyridin-6-yl)cyclopropanecarboxamide
508) N-(4-(4-((1-(3,5-difluorobenzoyl)piperidin-4-yl)amino)phenyl)-1H-pyrrolo[2,3-b]pyridin-6-yl)cyclopropanecarboxamide
509) N-(4-(4-((1-(2-fluoroisonicotinoyl)piperidin-4-yl)amino)phenyl)-1H-pyrrolo[2,3-b]pyridin-6-yl)cyclopropanecarboxamide
510) N-(4-(4-((1-(3,5-difluorobenzoyl)azetidin-3-yl)amino)phenyl)-1H-pyrrolo[2,3-b]pyridin-6-yl)cyclopropanecarboxamide
511) 4-((4-(6-(cyclopropanecarboxamido)-1H-pyrrolo[2,3-b]pyridin-4-yl)phenyl)amino)-N-(2,4-difluorophenyl)piperidine-1-carboxamide
512) 4-((4-(6-(cyclopropanecarboxamido)-1H-pyrrolo[2,3-b]pyridin-4-yl)phenyl)amino)-N-(2,2,2-trifluoroethyl)piperidine-1-carboxamide
513) 3-((4-(6-(cyclopropanecarboxamido)-1H-pyrrolo[2,3-b]pyridin-4-yl)phenyl)amino)-N-(2,4-difluorophenyl)azetidine-1-carboxamide
514) 3-((4-(6-(cyclopropanecarboxamido)-1H-pyrrolo[2,3-b]pyridin-4-yl)phenyl)amino)-N-(2,2,2-trifluoroethyl)azetidine-1-carboxamide
515) N-(4-(4-((1-(2-cyanoacetyl)azetidin-3-yl)amino)phenyl)-1H-pyrrolo[2,3-b]pyridin-6-yl)cyclopropanecarboxamide
516) N-(4-(4-((1-(2-cyanoacetyl)piperidin-4-yl)amino)phenyl)-1H-pyrrolo[2,3-b]pyridin-6-yl)cyclopropanecarboxamide
517) N-(4-(4-((1-(3,3,3-trifluoropropanoyl)azetidin-3-yl)amino)phenyl)-1H-pyrrolo[2,3-b]pyridin-6-yl)cyclopropanecarboxamide
518) N-(4-(4-((1-(3,3,3-trifluoropropanoyl)piperidin-4-yl)amino)phenyl)-1H-pyrrolo[2,3-b]pyridin-6-yl)cyclopropanecarboxamide
519) N-(4-(4-(2-cyanoacetyl)phenyl)-1H-pyrrolo[2,3-b]pyridin-6-yl)cyclopropanecarboxamide
520) N-(4-(4-(1,1-dioxidothiomorpholine-4-carbonyl)phenyl)-1H-pyrrolo[2,3-b]pyridin-6-yl)cyclopropanecarboxamide
521) N-(4-(4-(thiomorpholine-4-carbonyl)phenyl)-1H-pyrrolo[2,3-b]pyridin-6-yl)cyclopropanecarboxamide
522) N-(4-(2-methyl-4-(morpholine-4-carbonyl)phenyl)-1H-pyrrolo[2,3-b]pyridin-6-yl)cyclopropanecarboxamide
523) N-(cyanomethyl)-4-(6-(cyclopropanecarboxamido)-1H-pyrrolo[2,3-b]pyridin-4-yl)benzamide
524) 4-(6-(cyclopropanecarboxamido)-1H-pyrrolo[2,3-b]pyridin-4-yl)-N-(2,2,2-trifluoroethyl)benzamide
525) 4-(6-(cyclopropanecarboxamido)-1H-pyrrolo[2,3-b]pyridin-4-yl)-3-methyl-N-(2,2,2-trifluoroethyl)benzamide
526) N-(cyanomethyl)-4-(6-(cyclopropanecarboxamido)-1H-pyrrolo[2,3-b]pyridin-4-yl)-3-methylbenzamide
527) N-(cyanomethyl)-4-(6-(cyclopropanecarboxamido)-1H-pyrrolo[2,3-b]pyridin-4-yl)-N,3-dimethylbenzamide
528) N-(cyanomethyl)-4-(6-(cyclopropanecarboxamido)-1H-pyrrolo[2,3-b]pyridin-4-yl)-2-fluorobenzamide
529) N-(cyanomethyl)-4-(6-(cyclopropanecarboxamido)-1H-pyrrolo[2,3-b]pyridin-4-yl)-2,6-difluorobenzamide
530) N-(cyanomethyl)-4-(6-(cyclopropanecarboxamido)-1H-pyrrolo[2,3-b]pyridin-4-yl)cyclohex-3-ene-1-carboxamide
531) 4-(6-(cyclopropanecarboxamido)-1H-pyrrolo[2,3-b]pyridin-4-yl)-N-(2,2,2-trifluoroethyl)cyclohex-3-ene-1-carboxamide
532) N-(2-cyanoethyl)-4-(6-(cyclopropanecarboxamido)-1H-pyrrolo[2,3-b]pyridin-4-yl)cyclohex-3-ene-1-carboxamide
533) N-(4-(4-((N-methylsulfamoyl)methyl)phenyl)-1H-pyrrolo[2,3-b]pyridin-6-yl)cyclopropanecarboxamide
534) N-(4-(4-((morpholinosulfonyl)methyl)phenyl)-1H-pyrrolo[2,3-b]pyridin-6-yl)cyclopropanecarboxamide
535) N-(4-(4-(2-(1,1-dioxidothiomorpholino)-2-oxoethyl)phenyl)-1H-pyrrolo[2,3-b]pyridin-6-yl)cyclopropanecarboxamide
536) N-(4-(4-(2-morpholino-2-oxoethyl)phenyl)-1H-pyrrolo[2,3-b]pyridin-6-yl)cyclopropanecarboxamide
537) N-(4-(4-(2-oxo-2-((2,2,2-trifluoroethyl)amino)ethyl)phenyl)-1H-pyrrolo[2,3-b]pyridin-6-yl)cyclopropanecarboxamide
538) N-(4-(4-(2-((1,1-dioxidotetrahydrothiophen-3-yl)amino)-2-oxoethyl)phenyl)-1H-pyrrolo[2,3-b]pyridin-6-yl)cyclopropanecarboxamide
539) N-(4-(4-(2-(methylamino)-2-oxoethyl)phenyl)-1H-pyrrolo[2,3-b]pyridin-6-yl)cyclopropanecarboxamide
540) N-(4-(4-(2-(dimethylamino)-2-oxoethyl)phenyl)-1H-pyrrolo[2,3-b]pyridin-6-yl)cyclopropanecarboxamide
541) N-(4-(4-(2-(ethylamino)-2-oxoethyl)phenyl)-1H-pyrrolo[2,3-b]pyridin-6-yl)cyclopropanecarboxamide 542) N-(4-(2-(4-(methylsulfonyl)piperazin-1-yl)-2-oxoethyl)phenyl)-1H-pyrrolo[2,3-b]pyridin-6-yl)cyclopropanecarboxamide
543) N-(4-(2-(4-acetylpiperazin-1-yl)-2-oxoethyl)phenyl)-1H-pyrrolo[2,3-b]pyridin-6-yl)cyclopropanecarboxamide
544) N-(4-(4-(2-(isoxazol-3-ylamino)-2-oxoethyl)phenyl)-1H-pyrrolo[2,3-b]pyridin-6-yl)cyclopropanecarboxamide
545) N-(4-(4-(2-(1,1-dioxidothiomorpholino)-2-oxoethyl)-2-methylphenyl)-1H-pyrrolo[2,3-b]pyridin-6-yl)cyclopropanecarboxamide
546) N-(4-(4-(2-(azetidin-1-yl)-2-oxoethyl)phenyl)-1H-pyrrolo[2,3-b]pyridin-6-yl)cyclopropanecarboxamide
547) N-(4-(4-(2-oxo-2-(pyrrolidin-1-yl)ethyl)phenyl)-1H-pyrrolo[2,3-b]pyridin-6-yl)cyclopropanecarboxamide
548) N-(4-(4-(2-(4-cyanopiperidin-1-yl)-2-oxoethyl)phenyl)-1H-pyrrolo[2,3-b]pyridin-6-yl)cyclopropanecarboxamide
549) N-(4-(4-(2-oxo-2-(4-oxopiperidin-1-yl)ethyl)phenyl)-1H-pyrrolo[2,3-b]pyridin-6-yl)cyclopropanecarboxamide
550) N-(4-(4-(2-(4-methylpiperazin-1-yl)-2-oxoethyl)phenyl)-1H-pyrrolo[2,3-b]pyridin-6-yl)cyclopropanecarboxamide
551) N-(4-(4-(2-(4-ethylpiperazin-1-yl)-2-oxoethyl)phenyl)-1H-pyrrolo[2,3-b]pyridin-6-yl)cyclopropanecarboxamide
552) N-(4-(4-(2-(4-isopropylpiperazin-1-yl)-2-oxoethyl)phenyl)-1H-pyrrolo[2,3-b]pyridin-6-yl)cyclopropanecarboxamide
553) N-(4-(4-(2-((2-cyanoethyl)amino)-2-oxoethyl)phenyl)-1H-pyrrolo[2,3-b]pyridin-6-yl)cyclopropanecarboxamide
554) tert-butyl 4-(2-(4-(6-(cyclopropanecarboxamido)-1H-pyrrolo[2,3-b]pyridin-4-yl)phenyl)acetyl)piperazine-1-carboxylate
555) tert-butyl 3-(2-(4-(6-(cyclopropanecarboxamido)-1H-pyrrolo[2,3-b]pyridin-4-yl)phenyl)acetamido)piperidine-1-carboxylate
556) N-(4-(4-(2-((1-methyl-1H-pyrazol-3-yl)amino)-2-oxoethyl)phenyl)-1H-pyrrolo[2,3-b]pyridin-6-yl)cyclopropanecarboxamide
557) N-(4-(4-(2-oxo-2-(piperidin-1-yl)ethyl)phenyl)-1H-pyrrolo[2,3-b]pyridin-6-yl)cyclopropanecarboxamide
558) N-(4-(4-(2-oxo-2-(piperazin-1-yl)ethyl)phenyl)-1H-pyrrolo[2,3-b]pyridin-6-yl)cyclopropanecarboxamide
559) N-(4-(4-(2-(1,1-dioxidothiomorpholino)-2-oxoethyl)-3-fluorophenyl)-1H-pyrrolo[2,3-b]pyridin-6-yl)cyclopropanecarboxamide
560) N-(4-(4-(2-oxo-2-thiomorpholinoethyl)phenyl)-1H-pyrrolo[2,3-b]pyridin-6-yl)cyclopropanecarboxamide
561) N-(4-(4-(2-(4,4-difluoropiperidin-1-yl)-2-oxoethyl)phenyl)-1H-pyrrolo[2,3-b]pyridin-6-yl)cyclopropanecarboxamide
562) N-(4-(4-(2-oxo-2-(4-(trifluoromethylsulfonyl)piperazin-1-yl)ethyl)phenyl)-1H-pyrrolo[2,3-b]pyridin-6-yl)cyclopropanecarboxamide
563) N-(4-(4-(2-(4-(ethylsulfonyl)piperazin-1-yl)-2-oxoethyl)phenyl)-1H-pyrrolo[2,3-b]pyridin-6-yl)cyclopropanecarboxamide
564) N-(4-(4-(2-oxo-2-(4-(propylsulfonyl)piperazin-1-yl)ethyl)phenyl)-1H-pyrrolo[2,3-b]pyridin-6-yl)cyclopropanecarboxamide
565) ethyl 4-(2-(4-(6-(cyclopropanecarboxamido)-1H-pyrrolo[2,3-b]pyridin-4-yl)phenyl)acetyl)piperazine-1-carboxylate
566) N-(4-(4-(2-oxo-2-(4-(N-(2,2,2-trifluoroethyl)sulfamoyl)piperazin-1-yl)ethyl)phenyl)-1H-pyrrolo[2,3-b]pyridin-6-yl)cyclopropanecarboxamide
567) N-(4-(4-(2-(3-cyanopyrrolidin-1-yl)-2-oxoethyl)phenyl)-1H-pyrrolo[2,3-b]pyridin-6-yl)cyclopropanecarboxamide
568) N-(4-(4-(2-(3-cyanoazetidin-1-yl)-2-oxoethyl)phenyl)-1H-pyrrolo[2,3-b]pyridin-6-yl)cyclopropanecarboxamide
569) N-(4-(4-(2-(3,3-difluoropyrrolidin-1-yl)-2-oxoethyl)phenyl)-1H-pyrrolo[2,3-b]pyridin-6-yl)cyclopropanecarboxamide
570) N-(4-(4-(2-oxo-2-(4-(trifluoromethyl)piperidin-1-yl)ethyl)phenyl)-1H-pyrrolo[2,3-b]pyridin-6-yl)cyclopropanecarboxamide
571) N-(4-(4-(2-(1,1-dioxidothiomorpholino)-1,1-difluoro-2-oxoethyl)phenyl)-1H-pyrrolo[2,3-b]pyridin-6-yl)cyclopropanecarboxamide
572) N-(4-(4-(1,1-difluoro-2-morpholino-2-oxoethyl)phenyl)-1H-pyrrolo[2,3-b]pyridin-6-yl)cyclopropanecarboxamide
573) N-(4-(4-(2-((cyanomethyl)(methyl)amino)-2-oxoethyl)phenyl)-1H-pyrrolo[2,3-b]pyridin-6-yl)cyclopropanecarboxamide
574) N-(4-(4-(2-(1-oxidothiomorpholino)-2-oxoethyl)phenyl)-1H-pyrrolo[2,3-b]pyridin-6-yl)cyclopropanecarboxamide
575) N-(4-(4-(2-(4-cyanopiperidin-1-yl)-1,1-difluoro-2-oxoethyl)phenyl)-1H-pyrrolo[2,3-b]pyridin-6-yl)cyclopropanecarboxamide
576) N-(4-(4-(2-(3-cyanomorpholino)-2-oxoethyl)phenyl)-1H-pyrrolo[2,3-b]pyridin-6-yl)cyclopropanecarboxamide
577) N-(4-(4-(1-(1,1-dioxidothiomorpholine-4-carbonyl)cyclopropyl)phenyl)-1H-pyrrolo[2,3-b]pyridin-6-yl)cyclopropanecarboxamide
578) N-(4-(1-(2-(1,1-dioxidothiomorpholino)-2-oxoethyl)-1,2,3,6-tetrahydropyridin-4-yl)-1H-pyrrolo[2,3-b]pyridin-6-yl)cyclopropanecarboxamide
579) N-(4-(6-(cyclopropanecarboxamido)-1H-pyrrolo[2,3-b]pyridin-4-yl)benzyl)morpholine-4-carboxamide
580) N-(4-(6-(cyclopropanecarboxamido)-1H-pyrrolo[2,3-b]pyridin-4-yl)benzyl)thiomorpholine-4-carboxamide 1,1-dioxide -continued 581) N-(4-(4-((3-(2,2,2-trifluoroethyl)ureido)methyl)phenyl)-1H-pyrrolo[2,3-b]pyridin-6-yl)cyclopropanecarboxamide
582) N-(4-(4-(((3,4-difluorophenyl)sulfonamido)methyl)phenyl)-1H-pyrrolo[2,3-b]pyridin-6-yl)cyclopropanecarboxamide
583) N-(4-(4-(propylsulfonamidomethyl)phenyl)-1H-pyrrolo[2,3-b]pyridin-6-yl)cyclopropanecarboxamide
584) N-(4-(4-((1,1-dioxidothiomorpholino)methyl)phenyl)-1H-pyrrolo[2,3-b]pyridin-6-yl)cyclopropanecarboxamide
585) N-(4-(4-((4-oxopiperidin-1-yl)methyl)phenyl)-1H-pyrrolo[2,3-b]pyridin-6-yl)cyclopropanecarboxamide
586) N-(4-(4-((3-cyanoazetidin-1-yl)methyl)phenyl)-1H-pyrrolo[2,3-b]pyridin-6-yl)cyclopropanecarboxamide
587) N-(4-(4-((4-(methylsulfonyl)piperazin-1-yl)methyl)phenyl)-1H-pyrrolo[2,3-b]pyridin-6-yl)cyclopropanecarboxamide
588) N-(4-(4-((1,1-dioxidothiomorpholino)methyl)phenyl)-1H-pyrrolo[2,3-b]pyridin-6-yl)-2-methylcyclopropane-1-carboxamide
589) N-(4-(4-(1-(1,1-dioxidothiomorpholino)ethyl)phenyl)-1H-pyrrolo[2,3-b]pyridin-6-yl)cyclopropanecarboxamide
590) N-(4-(3,5-difluoro-4-(morpholinomethyl)phenyl)-1H-pyrrolo[2,3-b]pyridin-6-yl)cyclopropanecarboxamide
591) N-(4-(4-(2-(1,1-dioxidothiomorpholino)ethyl)phenyl)-1H-pyrrolo[2,3-b]pyridin-6-yl)cyclopropanecarboxamide
592) N-(6-(4-((1,1-dioxidothiomorpholino)methyl)phenyl)-9H-purin-2-yl)cyclopropanecarboxamide
593) N-(7-(4-((5-methyl-2H-tetrazol-2-yl)methyl)phenyl)-3H-imidazo[4,5-b]pyridin-5-yl)cyclopropanecarboxamide
594) N-(7-(4-((5-methyl-1H-tetrazol-1-yl)methyl)phenyl)-3H-imidazo[4,5-b]pyridin-5-yl)cyclopropanecarboxamide
595) N-(4-(4-(((1,1-dioxidotetrahydrothiophen-3-yl)amino)methyl)phenyl)-1H-pyrrolo[2,3-b]pyridin-6-yl)cyclopropanecarboxamide
596) N-(4-(4-(((1,1-dioxidotetrahydro-2H-thiopyran-4-yl)amino)methyl)phenyl)-1H-pyrrolo[2,3-b]pyridin-6-yl)cyclopropanecarboxamide
597) N-(6-(4-(((4-fluorophenyl)amino)methyl)phenyl)-9H-purin-2-yl)cyclopropanecarboxamide
598) N-(6-(4-(((3-fluorophenyl)amino)methyl)phenyl)-9H-purin-2-yl)cyclopropanecarboxamide
599) N-(4-(1-(1-((trifluoromethyl)sulfonyl)azetidin-3-yl)-1H-pyrazol-4-yl)-1H-pyrrolo[2,3-b]pyridin-6-yl)cyclopropanecarboxamide
600) N-(4-(1-(azetidin-3-yl)-1H-pyrazol-4-yl)-1H-pyrrolo[2,3-b]pyridin-6-yl)cyclopropanecarboxamide
601) N-(4-(1-(1-(ethylsulfonyl)azetidin-3-yl)-1H-pyrazol-4-yl)-1H-pyrrolo[2,3-b]pyridin-6-yl)cyclopropanecarboxamide
602) N-(4-(1-(1-(butylsulfonyl)azetidin-3-yl)-1H-pyrazol-4-yl)-1H-pyrrolo[2,3-b]pyridin-6-yl)cyclopropanecarboxamide
603) N-(4-(1-(1-(methylsulfonyl)azetidin-3-yl)-1H-pyrazol-4-yl)-1H-pyrrolo[2,3-b]pyridin-6-yl)cyclopropanecarboxamide
604) N-(4-(1-(1-(phenylsulfonyl)azetidin-3-yl)-1H-pyrazol-4-yl)-1H-pyrrolo[2,3-b]pyridin-6-yl)cyclopropanecarboxamide
605) N-(4-(1-(1-((3,4-difluorophenyl)sulfonyl)azetidin-3-yl)-1H-pyrazol-4-yl)-1H-pyrrolo[2,3-b]pyridin-6-yl)cyclopropanecarboxamide
606) N-(4-(1-(1-(cyclohexylsulfonyl)azetidin-3-yl)-1H-pyrazol-4-yl)-1H-pyrrolo[2,3-b]pyridin-6-yl)cyclopropanecarboxamide
607) N-(4-(1-(1-(methylsulfonyl)piperidin-4-yl)-1H-pyrazol-4-yl)-1H-pyrrolo[2,3-b]pyridin-6-yl)cyclopropanecarboxamide
608) N-(4-(1-(1-(ethylsulfonyl)piperidin-4-yl)-1H-pyrazol-4-yl)-1H-pyrrolo[2,3-b]pyridin-6-yl)cyclopropanecarboxamide
609) N-(4-(1-(1-((trifluoromethyl)sulfonyl)piperidin-4-yl)-1H-pyrazol-4-yl)-1H-pyrrolo[2,3-b]pyridin-6-yl)cyclopropanecarboxamide
610) N-(4-(1-(1-(2-cyanoacetyl)azetidin-3-yl)-1H-pyrazol-4-yl)-1H-pyrrolo[2,3-b]pyridin-6-yl)cyclopropanecarboxamide
611) N-(4-(1-(1-(cyanomethyl)piperidin-4-yl)-1H-pyrazol-4-yl)-1H-pyrrolo[2,3-b]pyridin-6-yl)cyclopropanecarboxamide
612) N-(4-(1-(3-(cyanomethyl)oxetan-3-yl)-1,2,3,6-tetrahydropyridin-4-yl)-1H-pyrrolo[2,3-b]pyridin-6-yl)cyclopropanecarboxamide
613) N-(4-(1-(3-(cyanomethyl)oxetan-3-yl)-3-methyl-1,2,3,6-tetrahydropyridin-4-yl)-1H-pyrrolo[2,3-b]pyridin-6-yl)cyclopropanecarboxamide
614) tert-butyl 3-(cyanomethyl)-3-(4-(6-(cyclopropanecarboxamido)-1H-pyrrolo[2,3-b]pyridin-4-yl)-3,6-dihydropyridin-1(2H)-yl)azetidine-1-carboxylate
615) N-(4-(1-(3-(cyanomethyl)azetidin-3-yl)-1,2,3,6-tetrahydropyridin-4-yl)-1H-pyrrolo[2,3-b]pyridin-6-yl)cyclopropanecarboxamide
616) N-(4-(1-(3-(cyanomethyl)-1-(ethylsulfonyl)azetidin-3-yl)-1,2,3,6-tetrahydropyridin-4-yl)-1H-pyrrolo[2,3-b]pyridin-6-yl)cyclopropanecarboxamide
617) N-(4-(1-(3-(cyanomethyl)-1-(isopropylsulfonyl)azetidin-3-yl)-1,2,3,6-tetrahydropyridin-4-yl)-1H-pyrrolo[2,3-b]pyridin-6-yl)cyclopropanecarboxamide
618) N-(4-(1-(3-(cyanomethyl)-1-((3-cyanopropyl)sulfonyl)azetidin-3-yl)-1,2,3,6-tetrahydropyridin-4-yl)-1H-pyrrolo[2,3-b]pyridin-6-yl)cyclopropanecarboxamide
619) N-(4-(1-(3-(cyanomethyl)-1-((trifluoromethyl)sulfonyl)azetidin-3-yl)-1,2,3,6-tetrahydropyridin-4-yl)-1H-pyrrolo[2,3-b]pyridin-6-yl)cyclopropanecarboxamide 620) N-(4-(1-(3-(cyanomethyl)-1-(piperidin-4-yl)azetidin-3-yl)-1,2,3,6-tetrahydropyridin-4-yl)-1H-pyrrolo[2,3-b]pyridin-6-yl)cyclopropanecarboxamide
621) N-(4-(1-(3-(cyanomethyl)-1-(1-(4-(trifluoromethyl)thiazole-2-carbonyl)piperidin-4-yl)azetidin-3-yl)-1,2,3,6-tetrahydropyridin-4-yl)-1H-pyrrolo[2,3-b]pyridin-6-yl)cyclopropanecarboxamide
622) N-(4-(1-(1-(1-(2-cyanoacetyl)piperidin-4-yl)-3-(cyanomethyl)azetidin-3-yl)-1,2,3,6-tetrahydropyridin-4-yl)-1H-pyrrolo[2,3-b]pyridin-6-yl)cyclopropanecarboxamide
623) N-(4-(1-(3-(cyanomethyl)-1-((4-fluorophenyl)sulfonyl)azetidin-3-yl)-1,2,3,6-tetrahydropyridin-4-yl)-1H-pyrrolo[2,3-b]pyridin-6-yl)cyclopropanecarboxamide
624) 3-(cyanomethyl)-3-(4-(6-(cyclopropanecarboxamido)-1H-pyrrolo[2,3-b]pyridin-4-yl)-3,6-dihydropyridin-1(2H)-yl)-N-(2,2,2-trifluoroethyl)azetidine-1-carboxamide
625) N-(4-(1-(3-(cyanomethyl)-1-(3,3,3-trifluoropropanoyl)azetidin-3-yl)-1,2,3,6-tetrahydropyridin-4-yl)-1H-pyrrolo[2,3-b]pyridin-6-yl)cyclopropanecarboxamide
626) N-(4-(1-(3-(cyanomethyl)-1-(ethylsulfonyl)azetidin-3-yl)-3-methyl-1,2,3,6-tetrahydropyridin-4-yl)-1H-pyrrolo[2,3-b]pyridin-6-yl)cyclopropanecarboxamide
627) (S)-N-(4-(1-(3-(cyanomethyl)-1-(ethylsulfonyl)azetidin-3-yl)-3-methyl-1,2,3,6-tetrahydropyridin-4-yl)-1H-pyrrolo[2,3-b]pyridin-6-yl)cyclopropanecarboxamide
628) (S)-N-(4-(1-(3-(cyanomethyl)-1-((trifluoromethyl)sulfonyl)azetidin-3-yl)-3-methyl-1,2,3,6-tetrahydropyridin-4-yl)-1H-pyrrolo[2,3-b]pyridin-6-yl)cyclopropanecarboxamide
629) 4-(6-(cyclopropanecarboxamido)-1H-pyrrolo[2,3-b]pyridin-4-yl)phenyl ethanesulfonate
630) 4-(6-(cyclopropanecarboxamido)-1H-pyrrolo[2,3-b]pyridin-4-yl)phenyl 4-fluorobenzenesulfonate
631) 4-(6-(cyclopropanecarboxamido)-1H-pyrrolo[2,3-b]pyridin-4-yl)phenyl propane-1-sulfonate
632) 4-(6-(cyclopropanecarboxamido)-1H-pyrrolo[2,3-b]pyridin-4-yl)phenyl butane-1-sulfonate
633) 4-(6-(cyclopropanecarboxamido)-1H-pyrrolo[2,3-b]pyridin-4-yl)phenyl propane-2-sulfonate
634) 4-(6-(cyclopropanecarboxamido)-1H-pyrrolo[2,3-b]pyridin-4-yl)phenyl cyclohexanesulfonate
635) 4-(6-(cyclopropanecarboxamido)-1H-pyrrolo[2,3-b]pyridin-4-yl)phenyl 3-fluoropropane-1-sulfonate
636) 4-(6-(cyclopropanecarboxamido)-1H-pyrrolo[2,3-b]pyridin-4-yl)phenyl prop-2-ene-1-sulfonate
637) 4-(6-(cyclopropanecarboxamido)-1H-pyrrolo[2,3-b]pyridin-4-yl)phenyl cyclohexylmethanesulfonate
638) 4-(6-(cyclopropanecarboxamido)-1H-pyrrolo[2,3-b]pyridin-4-yl)phenyl (tetrahydrofuran-3-yl)methanesulfonate
639) 4-(6-(cyclopropanecarboxamido)-1H-pyrrolo[2,3-b]pyridin-4-yl)phenyl 3-cyanopropane-1-sulfonate
640) 4-(1-(3-cyanopropyl)-6-(cyclopropanecarboxamido)-1H-pyrrolo[2,3-b]pyridin-4-yl)phenyl 3-cyanopropane-1-sulfonate
641) N-(4-(4-((4-fluorobenzyl)oxy)phenyl)-1H-pyrrolo[2,3-b]pyridin-6-yl)cyclopropanecarboxamide
642) N-(4-(4-(2-morpholinoethoxy)phenyl)-1H-pyrrolo[2,3-b]pyridin-6-yl)cyclopropanecarboxamide
643) N-(4-(4-butoxyphenyl)-1H-pyrrolo[2,3-b]pyridin-6-yl)cyclopropanecarboxamide
644) N-(6-(4-((6-cyanopyridin-3-yl)methoxy)phenyl)-9H-purin-2-yl)cyclopropanecarboxamide
645) N-(4-(4-(ethylsulfonamido)cyclohexyl)-1H-pyrrolo[2,3-b]pyridin-6-yl)cyclopropanecarboxamide
646) N-(4-(8-(ethylsulfonyl)-8-azabicyclo[3.2.1]octan-3-yl)-1H-pyrrolo[2,3-b]pyridin-6-yl)cyclopropanecarboxamide
647) N-(4-(8-(cyclopropylsulfonyl)-8-azabicyclo[3.2.1]octan-3-yl)-1H-pyrrolo[2,3-b]pyridin-6-yl)cyclopropanecarboxamide
648) N-(4-(8-((3-fluoropropyl)sulfonyl)-8-azabicyclo[3.2.1]octan-3-yl)-1H-pyrrolo[2,3-b]pyridin-6-yl)cyclopropanecarboxamide
649) N-(4-(8-((3,4-difluorophenyl)sulfonyl)-8-azabicyclo[3.2.1]octan-3-yl)-1H-pyrrolo[2,3-b]pyridin-6-yl)cyclopropanecarboxamide
650) N-(4-(8-(cyclopropanecarbonyl)-8-azabicyclo[3.2.1]octan-3-yl)-1H-pyrrolo[2,3-b]pyridin-6-yl)cyclopropanecarboxamide
651) N-(4-(8-pentanoyl-8-azabicyclo[3.2.1]octan-3-yl)-1H-pyrrolo[2,3-b]pyridin-6-yl)cyclopropanecarboxamide
652) N-(4-(1-(2-cyanoacetyl)piperidin-4-yl)-1H-pyrrolo[2,3-b]pyridin-6-yl)cyclopropanecarboxamide
653) N-butyl-4-(6-(cyclopropanecarboxamido)-1H-pyrrolo[2,3-b]pyridin-4-yl)piperidine-1-carboxamide
654) 4-(6-(cyclopropanecarboxamido)-1H-pyrrolo[2,3-b]pyridin-4-yl)-N-(2,2,2-trifluoroethyl)piperidine-1-carboxamide
655) tert-butyl 4-(6-(cyclopropanecarboxamido)-1H-pyrrolo[2,3-b]pyridin-4-yl)-3-hydroxypiperidine-1-carboxylate
656) tert-butyl 4-(6-(cyclopropanecarboxamido)-1H-pyrrolo[2,3-b]pyridin-4-yl)-3-fluoropiperidine-1-carboxylate
657) N-(4-(8-(ethylcarbamothioyl)-8-azabicyclo[3.2.1]octan-3-yl)-1H-pyrrolo[2,3-b]pyridin-6-yl)cyclopropanecarboxamide -continued 658) N-(4-(1-(ethylcarbamothioyl)piperidin-4-yl)-1H-pyrrolo[2,3-b]pyridin-6-yl)cyclopropanecarboxamide
659) N-(4-(1-(butylcarbamothioyl)piperidin-4-yl)-1H-pyrrolo[2,3-b]pyridin-6-yl)cyclopropanecarboxamide
660) N-(4-(4-(methylsulfonyl)piperazin-1-yl)-1H-pyrrolo[2,3-b]pyridin-6-yl)cyclopropanecarboxamide
661) N-(4-(8-(methylsulfonyl)-3,8-diazabicyclo[3.2.1]octan-3-yl)-1H-pyrrolo[2,3-b]pyridin-6-yl)cyclopropanecarboxamide
662) N-(4-(((1-cyanocyclopropyl)methyl)sulfonyl)piperazin-1-yl)-1H-pyrrolo[2,3-b]pyridin-6-yl)cyclopropanecarboxamide
663) N-(4-(4-((3-fluoropropyl)sulfonyl)piperazin-1-yl)-1H-pyrrolo[2,3-b]pyridin-6-yl)cyclopropanecarboxamide
664) N-(4-(8-((3-cyanopropyl)sulfonyl)-3,8-diazabicyclo[3.2.1]octan-3-yl)-1H-pyrrolo[2,3-b]pyridin-6-yl)cyclopropanecarboxamide
665) N-(4-(8-(((1-(cyanomethyl)cyclopropyl)methyl)sulfonyl)-3,8-diazabicyclo[3.2.1]octan-3-yl)-1H-pyrrolo[2,3-b]pyridin-6-yl)cyclopropanecarboxamide
666) N-(4-(8-((4,4,4-trifluorobutyl)sulfonyl)-3,8-diazabicyclo[3.2.1]octan-3-yl)-1H-pyrrolo[2,3-b]pyridin-6-yl)cyclopropanecarboxamide
667) N-(4-(8-(((1-cyanocyclopropyl)methyl)sulfonyl)-3,8-diazabicyclo[3.2.1]octan-3-yl)-1H-pyrrolo[2,3-b]pyridin-6-yl)cyclopropanecarboxamide
668) N-(4-(4-(propylsulfonyl)piperazin-1-yl)-7H-pyrrolo[2,3-d]pyrimidin-2-yl)cyclopropanecarboxamide
669) N-(4-(8-(ethylsulfonyl)-3,8-diazabicyclo[3.2.1]octan-3-yl)-7H-pyrrolo[2,3-d]pyrimidin-2-yl)cyclopropanecarboxamide
670) (S)-N-(4-(3-(propylsulfonamido)pyrrolidin-1-yl)-7H-pyrrolo[2,3-d]pyrimidin-2-yl)cyclopropanecarboxamide
671) (S)-N-(4-(3-(allylsulfonamido)pyrrolidin-1-yl)-7H-pyrrolo[2,3-d]pyrimidin-2-yl)cyclopropanecarboxamide
672) (S)-N-(4-(3-(N-methylethylsulfonamido)pyrrolidin-1-yl)-1H-pyrrolo[2,3-b]pyridin-6-yl)cyclopropanecarboxamide
673) N-(4-(4-(morpholinosulfonyl)piperazin-1-yl)-1H-pyrrolo[2,3-b]pyridin-6-yl)cyclopropanecarboxamide
674) N-(4-(4-(N,N-dimethylsulfamoyl)piperazin-1-yl)-1H-pyrrolo[2,3-b]pyridin-6-yl)cyclopropanecarboxamide
675) N-(4-(4-(2-cyanoacetamido)piperidin-1-yl)-1H-pyrrolo[2,3-b]pyridin-6-yl)cyclopropanecarboxamide
676) N-(4-(4-(2-cyanoacetyl)piperazin-1-yl)-1H-pyrrolo[2,3-b]pyridin-6-yl)cyclopropanecarboxamide
677) N-(4-(8-(2-cyanoacetyl)-3,8-diazabicyclo[3.2.1]octan-3-yl)-1H-pyrrolo[2,3-b]pyridin-6-yl)cyclopropanecarboxamide
678) N-(4-(3-(2-cyanoacetyl)-3,8-diazabicyclo[3.2.1]octan-8-yl)-1H-pyrrolo[2,3-b]pyridin-6-yl)cyclopropanecarboxamide
679) N-(4-((1S,4S)-5-(2-cyanoacetyl)-2,5-diazabicyclo[2.2.1]heptan-2-yl)-1H-pyrrolo[2,3-b]pyridin-6-yl)cyclopropanecarboxamide
680) N-(4-((1S,4S)-5-(3-cyanopropanoyl)-2,5-diazabicyclo[2.2.1]heptan-2-yl)-1H-pyrrolo[2,3-b]pyridin-6-yl)cyclopropanecarboxamide
681) N-(4-((1R,4R)-5-(2-cyanoacetyl)-2,5-diazabicyclo[2.2.1]heptan-2-yl)-1H-pyrrolo[2,3-b]pyridin-6-yl)cyclopropanecarboxamide
682) N-(4-((1R,4R)-5-(3-cyanopropanoyl)-2,5-diazabicyclo[2.2.1]heptan-2-yl)-1H-pyrrolo[2,3-b]pyridin-6-yl)cyclopropanecarboxamide
683) N-(4-(4-(2-(1-cyanocyclopropyl)acetyl)piperazin-1-yl)-1H-pyrrolo[2,3-b]pyridin-6-yl)cyclopropanecarboxamide
684) N-(4-(4-(3-cyanopropanoyl)piperazin-1-yl)-1H-pyrrolo[2,3-b]pyridin-6-yl)cyclopropanecarboxamide
685) N-(4-(6-(2-cyanoacetyl)-3,6-diazabicyclo[3.1.1]heptan-3-yl)-1H-pyrrolo[2,3-b]pyridin-6-yl)cyclopropanecarboxamide
686) N-(4-(8-(3-cyanobenzoyl)-3,8-diazabicyclo[3.2.1]octan-3-yl)-1H-pyrrolo[2,3-b]pyridin-6-yl)cyclopropanecarboxamide
687) N-(4-(4-(2-cyanoacetyl)piperazin-1-yl)-7H-pyrrolo[2,3-d]pyrimidin-2-yl)cyclopropanecarboxamide
688) N-(4-(8-(2-cyanoacetyl)-3,8-diazabicyclo[3.2.1]octan-3-yl)-7H-pyrrolo[2,3-d]pyrimidin-2-yl)cyclopropanecarboxamide
689) N-(4-(8-(2-(1-cyanocyclopropyl)acetyl)-3,8-diazabicyclo[3.2.1]octan-3-yl)-7H-pyrrolo[2,3-d]pyrimidin-2-yl)cyclopropanecarboxamide
690) 4-(6-(cyclopropanecarboxamido)-1H-pyrrolo[2,3-b]pyridin-4-yl)-N-(2,2,2-trifluoroethyl)piperazine-1-carboxamide
691) 3-(6-(cyclopropanecarboxamido)-1H-pyrrolo[2,3-b]pyridin-4-yl)-N-(2,2,2-trifluoroethyl)-3,8-diazabicyclo[3.2.1]octane-8-carboxamide
692) tert-butyl 4-(6-(cyclopropanecarboxamido)-1H-pyrrolo[2,3-b]pyridine-4-yl)piperazin-1-carboxylate
693) tert-butyl 3-(6-(cyclopropanecarboxamido)-1H-pyrrolo[2,3-b]pyridin-4-yl)-3,8-diazabicyclo[3.2.1]octane-8-carboxylate
694) tert-butyl 8-(6-(cyclopropanecarboxamido)-1H-pyrrolo[2,3-b]pyridin-4-yl)-3,8-diazabicyclo[3.2.1]octane-3-carboxylate
695) tert-butyl 3-(2-(cyclopropanecarboxamido)-7H-pyrrolo[2,3-d]pyrimidin-4-yl)-3,8-diazabicyclo[3.2.1]octane-8-carboxylate
696) tert-butyl (S)-(1-(2-(cyclopropanecarboxamido)-7H-pyrrolo[2,3-d]pyrimidin-4-yl)pyrrolidin-3-yl)carbamate 697) tert-butyl (S)-(1-(6-(cyclopropanecarboxamido)-1H-pyrrolo[2,3-b]pyridin-4-yl)pyrrolidin-3-yl)carbamate
698) N-(4-(4-(isothiazol-5-ylmethyl)piperazin-1-yl)-1H-pyrrolo[2,3-b]pyridin-6-yl)cyclopropanecarboxamide
699) (S)-N-(4-(4-((2,2-difluorocyclopropyl)methyl)piperazin-1-yl)-1H-pyrrolo[2,3-b]pyridin-6-yl)cyclopropanecarboxamide
700) N-(4-(4-(3-(cyanomethyl)-1-(ethylsulfonyl)azetidin-3-yl)piperazin-1-yl)-1H-pyrrolo[2,3-b]pyridin-6-yl)cyclopropanecarboxamide
701) N-(4-(8-(3-(cyanomethyl)-1-(ethylsulfonyl)azetidin-3-yl)-3,8-diazabicyclo[3.2.1]octan-3-yl)-1H-pyrrolo[2,3-b]pyridin-6-yl)cyclopropanecarboxamide
702) N-(4-(4-(2-(1,1-dioxidothiomorpholino)-2-oxoethyl)piperazin-1-yl)-1H-pyrrolo[2,3-b]pyridin-6-yl)cyclopropanecarboxamide
703) N-(4-(8-(2-((R)-2-cyanopyrrolidin-1-yl)-2-oxoethyl)-3,8-diazabicyclo[3.2.1]octan-3-yl)-1H-pyrrolo[2,3-b]pyridin-6-yl)cyclopropanecarboxamide
704) N-(4-(8-(2-(1,1-dioxidothiomorpholino)-2-oxoethyl)-3,8-diazabicyclo[3.2.1]octan-3-yl)-7H-pyrrolo[2,3-d]pyrimidin-2-yl)cyclopropanecarboxamide
705) (S)-3-(4-(6-amino-1H-pyrrolo[2,3-b]pyridin-4-yl)-3-methyl-3,6-dihydropyridin-1(2H)-yl)-3-oxopropanenitrile
706) N-(4-(4-(ethylsulfonamido)-3-fluorophenyl)-1H-pyrrolo[2,3-b]pyridin-6-yl)cyclopentanecarboxamide
707) N-(4-(4-(ethylsulfonamido)-3-fluorophenyl)-1H-pyrrolo[2,3-b]pyridin-6-yl)cyclohexanecarboxamide
708) N-(4-(4-(ethylsulfonamido)-3-fluorophenyl)-1H-pyrrolo[2,3-b]pyridin-6-yl)propionamide
709) N-(4-(4-(ethylsulfonamido)-3-fluorophenyl)-1H-pyrrolo[2,3-b]pyridin-6-yl)-2-phenylacetamide
710) N-(4-(4-(ethylsulfonamido)-3-fluorophenyl)-1H-pyrrolo[2,3-b]pyridin-6-yl)acetamide
711) N-(4-(4-(ethylsulfonamido)-3-fluorophenyl)-1H-pyrrolo[2,3-b]pyridin-6-yl)isobutyramide
712) N-(4-(4-(ethylsulfonamido)-3-fluorophenyl)-1H-pyrrolo[2,3-b]pyridin-6-yl)butyramide
713) N-(4-(6-((cyclopropylmethyl)amino)-1H-pyrrolo[2,3-b]pyridin-4-yl)-2-fluorophenyl)ethanesulfonamide
714) (Z)-N-(4-(4-(ethylsulfonamido)phenyl)-1H-pyrrolo[2,3-b]pyridin-6-yl)-N'-methylcyclopropanecarboximidamide
715) N-(4-(4-(ethylsulfonamido)phenyl)-1H-pyrrolo[2,3-b]pyridin-6-yl)cyclopropanecarbothioamide
716) N-(4-(4-(ethylsulfonamido)-3-fluorophenyl)-1H-pyrrolo[2,3-b]pyridin-6-yl)cyclopropanesulfonamide
717) 1-cyclopropyl-3-(4-(4-((1,1-dioxidothiomorpholino)methyl)phenyl)-1H-pyrrolo[2,3-b]pyridin-6-yl)urea
718) N-(4-(2-(dimethylamino)-7H-pyrrolo[2,3-d]pyrimidin-4-yl)phenyl)-3,4-difluorobenzenesulfonamide
719) N-(2-fluoro-4-(2-(phenylamino)-7H-pyrrolo[2,3-d]pyrimidin-4-yl)phenyl)ethanesulfonamide
720) N-(4-(2-(phenylamino)-7H-pyrrolo[2,3-d]pyrimidin-4-yl)phenyl)ethanesulfonamide
721) 3-oxo-3-(3-(2-(phenylamino)-7H-pyrrolo[2,3-d]pyrimidin-4-yl)-3,8-diazabicyclo[3.2.1]octan-8-yl)propanenitrile.

7. A pharmaceutical composition for treating a disease related to JAK protein kinase activity,
wherein the pharmaceutical composition comprises a compound, a stereoisomer thereof or a pharmaceutically acceptable salt thereof according to claim 1 as an effective component, and
the disease related to JAK protein kinase activity is selected from cancer, autoimmune disease, neurological disease, metabolic disease and infection.

8. A method for treating a disease related to JAK protein kinase activity,
wherein the method comprises administering to a subject a therapeutically effective dose of a compound, a stereoisomer thereof or a pharmaceutically acceptable salt thereof according to claim 1, and
the disease related to JAK protein kinase activity is selected from cancer, autoimmune disease, neurological disease, metabolic disease and infection.

9. A method for inhibiting JAK protein kinase, wherein the method comprises administering to a subject a therapeutically effective dose of a compound, a stereoisomer thereof or a pharmaceutically acceptable salt thereof according to claim 1.

10. A pharmaceutical composition for treating a disease related to JAK protein kinase activity,
wherein the pharmaceutical composition comprises a compound, a stereoisomer thereof or a pharmaceutically acceptable salt thereof according to claim 6 as an effective component, and
the disease related to JAK protein kinase activity is selected from cancer, autoimmune disease, neurological disease, metabolic disease and infection.

11. A method for treating a disease related to JAK protein kinase activity,
wherein the method comprises administering to a subject a therapeutically effective dose of a compound, a stereoisomer thereof or a pharmaceutically acceptable salt thereof according to claim 6, and
the disease related to JAK protein kinase activity is selected from cancer, autoimmune disease, neurological disease, metabolic disease and infection.

12. A method for inhibiting JAK protein kinase, wherein the method comprises administering to a subject a therapeutically effective dose of a compound, a stereoisomer thereof or a pharmaceutically acceptable salt thereof according to claim 6.

* * * * *